(12) United States Patent
Juneja et al.

(10) Patent No.: US 12,331,097 B2
(45) Date of Patent: Jun. 17, 2025

(54) T CELL RECEPTOR CONSTRUCTS AND USES THEREOF

(71) Applicant: BIONTECH US INC., Cambridge, MA (US)

(72) Inventors: Vikram Juneja, Waltham, MA (US); Jaewon Choi, Jamaica Plain, MA (US)

(73) Assignee: BIONTECH US INC., Cambridge, MA (US)

( * ) Notice: Subject to any disclaimer, the term of this patent is extended or adjusted under 35 U.S.C. 154(b) by 1094 days.

(21) Appl. No.: 17/268,915

(22) PCT Filed: Aug. 16, 2019

(86) PCT No.: PCT/US2019/046876
§ 371 (c)(1),
(2) Date: Jun. 29, 2021

(87) PCT Pub. No.: WO2020/037239
PCT Pub. Date: Feb. 20, 2020

(65) Prior Publication Data
US 2021/0340215 A1    Nov. 4, 2021

Related U.S. Application Data

(60) Provisional application No. 62/810,112, filed on Feb. 25, 2019, provisional application No. 62/764,817, filed on Aug. 16, 2018.

(51) Int. Cl.
| | | |
|---|---|---|
| A61K 40/10 | (2025.01) | |
| A61K 40/32 | (2025.01) | |
| A61K 40/42 | (2025.01) | |
| C07K 14/74 | (2006.01) | |
| C12N 5/0783 | (2010.01) | |
| A61K 38/00 | (2006.01) | |

(52) U.S. Cl.
CPC ........ *C07K 14/70539* (2013.01); *A61K 40/10* (2025.01); *A61K 40/32* (2025.01); *A61K 40/4201* (2025.01); *C12N 5/0636* (2013.01); *A61K 38/00* (2013.01); *A61K 2239/50* (2023.05); *C07K 2319/30* (2013.01)

(58) Field of Classification Search
None
See application file for complete search history.

(56) References Cited

U.S. PATENT DOCUMENTS

| | | | |
|---|---|---|---|
| 5,391,377 A | 2/1995 | Barnwell | |
| 5,849,589 A | 12/1998 | Tedder et al. | |
| 6,406,705 B1 | 6/2002 | Davis et al. | |
| 8,119,772 B2 | 2/2012 | Yang et al. | |
| 2015/0104441 A1 | 4/2015 | Olweus et al. | |

FOREIGN PATENT DOCUMENTS

| | | |
|---|---|---|
| CN | 108395479 A | 8/2018 |
| TW | 201738378 A | 11/2017 |
| WO | WO-9311161 A1 | 6/1993 |
| WO | WO-9403205 A1 | 2/1994 |
| WO | WO-9420127 A1 | 9/1994 |
| WO | WO-03020763 A2 | 3/2003 |
| WO | WO-2004033685 A1 | 4/2004 |
| WO | WO-2011044186 A1 | 4/2011 |
| WO | WO-2015095811 A2 | 6/2015 |
| WO | WO-2016085904 A1 | 6/2016 |
| WO | WO-2016154246 A1 | 9/2016 |
| WO | WO-2017044661 A1 | 3/2017 |
| WO | WO-2017048593 A1 | 3/2017 |
| WO | WO-2017173321 A1 | 10/2017 |
| WO | WO-2020037239 A1 | 2/2020 |

OTHER PUBLICATIONS

Wong et al., Comparative analysis of the CDR loops of antigen receptors; 2019, Frontiers in Immunology, 10:2454. (Year: 2019).*
Robbins et al., Single and dual amino acid substitutions in TCR CDRs can enhance antigen-specific T cell functions; 2008, Journal of Immunology, 180(9): 6116-6131. (Year: 2008).*
Japanese Patent Application No. 2021-507743 Office Action dated Jul. 28, 2023.
Taiwan Patent Application No. 108129290 Search Report dated Oct. 13, 2023.
"International Search Report and Written Opinion for corresponding PCT Application No. PCT/US2019/046876 issued Jan. 21, 2020".
Busch, R. et al., "Degenerate binding of immunogenic peptides to HLA-DR proteins on B Cell surface," Int. Immunol., 1990, vol. 2, No. 5, pp. 443-451.
Ceppellini, R. et al., "Binding of labelled influenza matrix peptide to HLA DR in living B lymphoid cells," Nature, 1989, vol. 339, pp. 392-394.
Cerundolo, V. et al., "The binding affinity and dissociation rates of peptides for class I major histocompatibility complex molecules," J. Immunol., 1991, vol. 21, No. 9, pp. 2069-2075.
Christinck, E. R. et al., "Peptide binding to class I MHC on living cells and quantitation of complexes required for CTL lysis," Nature, 1991, vol. 352, No. 6330, pp. 67-70.
Del Guercio, M. F. et al., "Binding of peptide antigen to multiple HLA alleles allows definition of an A2-like supertype," J. Immunol., 1995, vol. 154, No. 2, pp. 685-693.

(Continued)

*Primary Examiner* — Daniel E Kolker
*Assistant Examiner* — James Ryland Melchior
(74) *Attorney, Agent, or Firm* — Wilson Sonsini Goodrich & Rosati

(57) ABSTRACT

The present disclosure provides T cell receptors (TCRs) against peptide-MHC complexes, isolated nucleic acid molecules encoding TCRs against peptide-MHC complexes, T cells expressing TCRs against peptide-MHC complexes, and pharmaceutical compositions for use in the treatment of diseases.

17 Claims, 30 Drawing Sheets
Specification includes a Sequence Listing.

(56) References Cited

OTHER PUBLICATIONS

Dupuis, M, et al., "Dendritic Cells Internalize Vaccine Adjuvant after Intramuscular Injection," Cell Immunol., 1998, vol. 186, No. 1, pp. 18-27.
Engels, B. et al., "Retroviral Vectors for High-Level Transgene Expression in T Lymphocytes," Hum. Gene Ther., 2003, vol. 14, pp. 1155-1168.
Exam Report and Translation issued in Russian Patent Application No. 2021106561/10 on Dec. 29, 2021.
Exam Report and Translation issued in Russian Patent Application No. 2021106561/10 on May 26, 2022.
Extended European Search Report issued in European Patent Application No. 19849341.3 on Apr. 8, 2022.
Fix, J. A., "Oral controlled release technology for peptides: status and future prospects," Pharm Res., 1996, vol. 13, No. 12, pp. 1760-1764.
Frecha, C. et al., "Advances in the Field of Lentivector-based Transduction of T and B Lymphocytes for Gene Therapy," Mol. Ther., 2010, vol. 18, No. 10, pp. 1748-1757.
Fujii, S. et al., "Clinical significance of KRAS gene mutation and epidermal growth factor receptor expression in Japanese patients with squamous cell carcinoma of the larynx, oropharynx and hypopharynx," Int J Clin Oncol., Jun. 2013;18(3):454-63.
Gamvrellis, A. et al., "Vaccines that facilitate antigen entry into dendritic cells," Immunol & Cell Biol., 2004, vol. 82, pp. 506-516.
Gjertsen, M.K. et al., "Cytotoxic CD4+ and CD8+ T lymphocytes, generated by mutant p21-ras (12Val) peptide vaccination of a patient, recognize 12Val-dependent nested epitopes present within the vaccine peptide and kill autologous tumour cells carrying this mutation," Int J Cancer, Sep. 4, 1997;72(5):784-90.
Hammer, J. et al., "Precise prediction of major histocompatibility complex class II-peptide interaction based on peptide side chain scanning," J. Exp. Med., 1994, vol. 180, No. 6, pp. 2353-2358.
He, L.Z. et al., "RAS gene mutations in Chinese leukaemia patients and members of a family with high incidence of leukaemia," Leuk Res., Nov.-Dec. 1996;20(11-12):901-3.
Hill, C. M. et al., "Conformational and structural characteristics of peptides binding to HLA-DR molecules," J. Immunol., 1991, vol. 147, No. 1, pp. 189-197.
Hill, C. M. et al., "Exploration of requirements for peptide binding to HLA DRB1*0101 and DRB1*0401," J. Immunol., 1994, vol. 152, No. 6, pp. 2890-2898.
Khilko, S. N. et al., "Direct detection of major histocompatibility complex class I binding to antigenic peptides using surface plasmon resonance. Peptide immobilization and characterization of binding specificity," J. Biol. Chem., 1993, vol. 268, No. 21, pp. 15425-15434.
Krieg, A.M. et al., "Therapeutic potential of Toll-like receptor 9 activation," Nature Reviews, Drug Discovery, 2006, vol. 5, pp. 471-484.
Krisky, D.M. et al., "Development of herpes simplex virus replication defective multigene vectors for combination gene therapy applications," Gene Therapy, 1998, vol. 5, pp. 1517-1530.
Lefort, C.T. et al., "Human T lymphocyte isolation, culture and analysis of migration in vitro." J Vis Exp., 2010, vol. 40, 2017.
Li, H. et al., "TCRβ repertoire of CD4+ and CD8+ T cells is distinct in richness, distribution, and CDR3 amino acid composition," J Leukoc Biol., 2016, vol. 99, No. 3, pp. 505-513.
Ljunggren, H. G. et al., "Empty MHC class I molecules come out in the cold," Nature, 1990, vol. 346, pp. 476-480.
Marshall, K. W. et al., "Role of the polymorphic residues in HLA-DR molecules in allele-specific binding of peptide ligands," J. Immunol., 1994, vol. 152, No. 10, pp. 4946-4957.
Mosca, P.J. et al., "Dendritic cell vaccines," Frontiers in Bioscience, 2007, vol. 12, pp. 4050-4060.
Muller, S. et al., "Spliceosomal peptide P140 for immunotherapy of systemic lupus erythematosus: results of an early phase II clinical trial," Arthritis Rheum, Dec. 2008;58(12):3873-83.

Obenaus, M. et al., "Identification of human T-cell receptors with optimal affinity to cancer antigens using antigen-negative humanized mice," Nature Biotechnology, 2015, vol. 33, No. 4, pp. 402-407.
Parker, K. C. et al., "The beta 2-microglobulin dissociation rate is an accurate measure of the stability of MHC class I heterotrimers and depends on which peptide is bound," J. Immunol., 1992, vol. 149, No. 6, pp. 1896-1904.
Pfeifer, A. et al., "Gene therapy: promises and problems," Ann. Rev. Genomics Hum. Genet., 2001, vol. 2, pp. 177-211.
Reay, P. A. et al., "pH dependence and exchange of high and low responder peptides binding to a class II MHC molecule," EMBO J., 1992, vol. 11, No. 8, pp. 2829-2839.
Samanen, J. et al., "Chemical Approaches to Improve the Oral Bioavailability of Peptidergic Molecules," J. Pharm. Pharmacol., 1996, vol. 48, pp. 119 135.
Schumacher, T. N. M. et al., "Direct binding of peptide to empty MHC class I molecules on intact cells and in vitro," Cell, 1990, vol. 62, No. 3, pp. 563-567.
Sette, A. et al., "Peptide binding to the most frequent HLA-A class I alleles measured by quantitative molecular binding assays," Mol. Immunol, 1994, vol. 31, No. 11, pp. 813-822.
Sidney, J. et al., "Measurement of MHC/Peptide interactions by Gel Filtration or Monoclonal Antibody Capture," Current Protocols in Immunology, 1998, 18.3.1.
Singapore Patent Application No. 11202101524R Search Report issued on Oct. 30, 2022.
Townsend, A. et al., "Assembly of MHC class I molecules analyzed in vitro," Cell, 1990, vol. 62, No. 2, pp. 285-295.
Verhoef, J.C. et al., "Des-enkephalin-γ-endorphin (DEγE): Biotransformation in rat, dog and human plasma," Eur. J. Drug Metab. Pharmacokinetics, 1986, vol. 11, No. 4, pp. 291-302.
Verhoeyen, E. et al., "Lentiviral Vector Gene Transfer into Human T Cells," Methods Mol. Biol., 2009, vol. 506, pp. 97-114.
Walchli, S. et al., "A Practical Approach to T-Cell Receptor Cloning and Expression," PLoS One, 2011,vol. 6, No. 11, 327930.
Wang, Q.J. et al., "Identification of T-cell Receptors Targeting KRAS-Mutated Human Tumors," Cancer Immunol Res., Mar. 2016;4(3):204-14.
Ward, E. S. et al., "Binding activities of a repertoire of single immunoglobulin variable domains secreted from *Escherichia coli*," Nature, 1989, vol. 341, pp. 544 546.
Zhao, Y. et al., "Primary Human Lymphocytes Transduced with NY-ESO-1 Antigen-Specific TCR Genes Recognize and Kill Diverse Human Tumor Cell Lines," J. Immunol., 2005, vol. 174, No. 7, pp. 4415-4423.
International Preliminary Report on Patentability issued in PCT/US2019/046876, dated Feb. 16, 2021.
International Search Report and Written Opinion issued in PCT/US2019/046876, mailed Jan. 21, 2020.
Choi, J. et al., "Systematic discovery and validation of T Cell targeting directed against oncogenic KRAS mutations," Cell Reports Methods, 2021, vol. 1, No. 5.
Leidner, R. et al., "Neoantigen T-cell receptor Gene Therapy in Pancreatic Cancer," The New England Journal of Medicine, 2022, vol. 386, No. 22, pp. 2112-2119.
Levin, N. et al., "Identification and Validation of T-cell Receptors Targeting RAS Hotspot Mutations in Human Cancer for Use in Cell-based Immunotherapy," Clinical Cancer Research, 2021, vol. 27, pp. 5084-5095.
Lowery, F.J. et al., "Molecular signatures of antitumor neoantigen-reactive T cells from metastatic human cancers," Science, 2022, vol. 375, No. 6583, pp. 877-884.
Restifo, N.P. et al., "Adoptive immunotherapy for cancer: harnessing the T cell response," Nat Rev Immunol, 2018, vol. 12, No. 4, pp. 269-281.
Rosenberg, S.A. et al., "Adoptive cell transfer as personalized immunotherapy for human cancer," Science, 2015, vol. 348, No. 6230, pp. 62-68.
Tran, E. et al., "T-Cell Transfer Therapy Targeting Mutant KRAS in Cancer," N Engl J Med., 2017, vol. 375, No. 23, pp. 2255-2262.
Yossef, R. et al., "Enhanced detection of neoantigen-reactive T cells targeting unique and shared oncogenes for personalized cancer immunotherapy," JCI Insight, 2018, vol. 3, No. 19.

(56) References Cited

OTHER PUBLICATIONS

Choi, J. et al., "Systematic discovery and validation of T Cell targeting directed against oncogenic KRAS mutations," Cell Reports Methods 1:5 (2021).
International Preliminary Report on Patentability issued in PCT/US2019/040592, dated Feb. 16, 2021.
Leidner, R. et al., "Neoantigen T-cell receptor Gene Therapy in Pancreatic Cancer," The New England Journal of Medicine 386(22):2112-2119 (2022).
Levin, N. et al., "Identification and Validation of T-cell Receptors Targeting RAS Hotspot Mutations in Human Cancer for Use in Cell-based Immunotherapy," Clinical Cancer Research, 27:5084-5095 (2021).
Lowery, F.J. et al., "Molecular signatures of antitumor neoantigen-reactive T cells from metastatic human cancers," Science 375(6583):877-884 (2022).
Restifo, N.P. et al., "Adoptive immunotherapy for cancer: harnessing the T cell response," Nat Rev Immunol 12(4):269-281 (2018).
Rosenberg, S.A. et al., "Adoptive cell transfer as personalized immunotherapy for human cancer," Science 348(6230):62-68 (2015).
Tran, E. et al., "T-Cell Transfer Therapy Targeting Mutant KRAS in Cancer," N. Engl. J. Med. 375(23):2255-2262 (2017).
Yossef, R. et al., "Enhanced detection of neoantigen-reactive T cells targeting unique and shared oncogenes for personalized cancer immunotherapy," JCI Insight 3:19 (2018).

\* cited by examiner

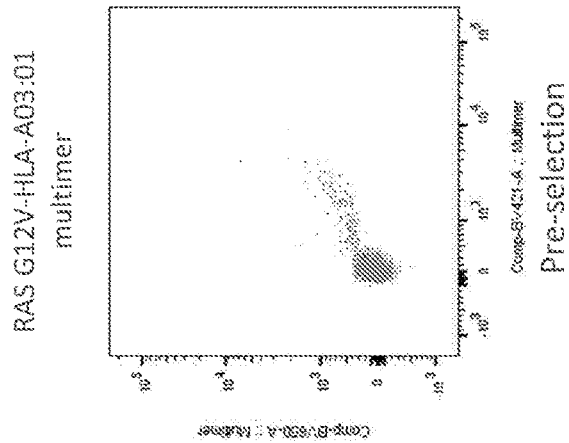
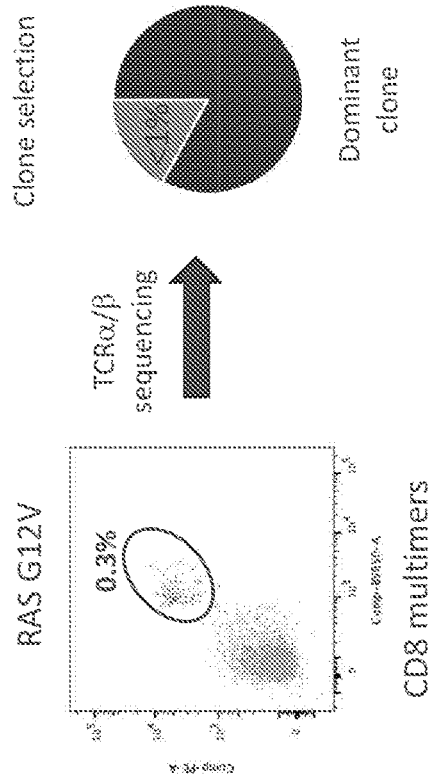
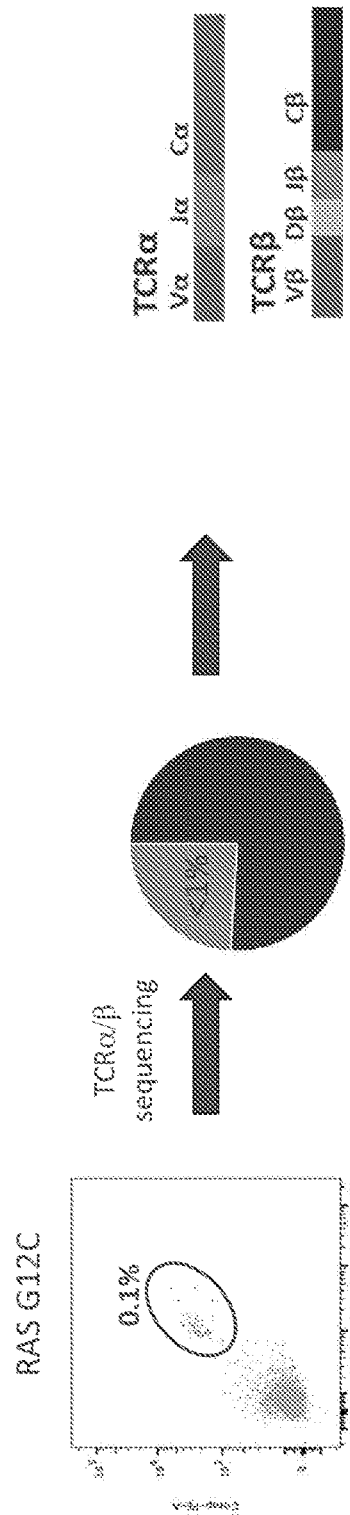
FIG. 10A
FIG. 10B

SEQUENCE LISTING

<160> NUMBER OF SEQ ID NOS: 621

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Ile Phe Asn Thr
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Leu Tyr Lys Ala Gly Glu Leu
1               5

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Ala Gly Arg Asn Phe Gly Asn Glu Lys Leu Thr Phe

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Phe Gln Ala Thr Thr
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Asn Glu Gly Ser Lys Ala
1               5

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Ala Arg Asp Arg Gly Leu Val Ser Leu Pro Ser Val Glu Ala Phe
1               5                   10                  15

Phe

<210> SEQ ID NO 7
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
atgctccttg aacatttatt aataatcttg tggatgcagc tgacatgggt cagtggtcaa      60
cagctgaatc agagtcctca atctatgttt atccaggaag agaagatgt ctccatgaac      120 tgcacttctt caagcatatt taacacctgg ctatggtaca agcaggaccc tgggaaggt      180 cctgtcctct tgatagcctt atataaggct ggtgaattga cctcaaatgg aagactgact      240
gctcagtttg gtataaccag aaaggacagc ttcctgaata tctcagcatc catacctagt      300
gatgtaggca tctacttctg tgctgggaga aactttggaa atgagaaatt aacctttggg      360
actggaacaa gactcaccat cataccc                                         387

<210> SEQ ID NO 8
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
atgctccttg aacatttatt aataatcttg tggatgcagc tgacatgggt cagtggtcaa    60
cagctgaatc agagtcctca atctatgttt atccaggaag agaagatgt ctccatgaac    120 tgcacttctt caagcatatt taacacctgg ctatggtaca agcaggaccc tggggaaggt    180
cctgtcctct tgatagcctt atataaggct ggtgaattga cctcaaatgg aagactgact    240
gctcagtttg gtataaccag aaaggacagc ttcctgaata tctcagcatc catacctagt    300
gatgtaggca tctacttctg tgctgggaga aactttggaa atgagaaatt aacctttggg    360
actggaacaa gactcaccat catacccc                                      387
```

<210> SEQ ID NO 9
<211> LENGTH: 129
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

```
Met Leu Leu Glu His Leu Leu Ile Ile Leu Trp Met Gln Leu Thr Trp
1               5                   10                  15

Val Ser Gly Gln Gln Leu Asn Gln Ser Pro Gln Ser Met Phe Ile Gln
            20                  25                  30

Glu Gly Glu Asp Val Ser Met Asn Cys Thr Ser Ser Ser Ile Phe Asn
        35                  40                  45

Thr Trp Leu Trp Tyr Lys Gln Asp Pro Gly Glu Gly Pro Val Leu Leu
    50                  55                  60

Ile Ala Leu Tyr Lys Ala Gly Glu Leu Thr Ser Asn Gly Arg Leu Thr
65                  70                  75                  80

Ala Gln Phe Gly Ile Thr Arg Lys Asp Ser Phe Leu Asn Ile Ser Ala
                85                  90                  95

Ser Ile Pro Ser Asp Val Gly Ile Tyr Phe Cys Ala Gly Arg Asn Phe
            100                 105                 110

Gly Asn Glu Lys Leu Thr Phe Gly Thr Gly Thr Arg Leu Thr Ile Ile
        115                 120                 125

Pro
```

<210> SEQ ID NO 10
<211> LENGTH: 405
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
atgctgctgc ttctgctgct tctggggcca ggctccgggc ttggtgctgt cgtctctcaa    60
catccgagca gggttatctg taagagtgga acctctgtga agatcgagtg ccgttccctg    120
gactttcagg ccacaactat gttttggtat cgtcagttcc cgaaacagag tctcatgctg    180
atggcaactt ccaatgaggg ctccaaggcc acatacgagc aaggcgtcga aggacaag     240 tttctcatca accatgcaag cctgaccttg tccactctga cagtgaccag tgcccatcct    300
gaagacagca gcttctacat ctgcagtgct cgcgacaggg ggcttgtatc gttgccgtcg    360
gtagaagctt tctttggaca aggcaccaga ctcacagttg tactg                    405
```

<210> SEQ ID NO 11
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
atgctgctgc ttctgctgct tctggggcca ggctccgggc ttggtgctgt cgtctctcaa    60
catccgagca gggttatctg taagagtgga acctctgtga agatcgagtg ccgttccctg   120
gactttcagg ccacaactat gttttggtat cgtcagttcc cgaaacagag tctcatgctg   180
atggcaactt ccaatgaggg ctccaaggcc acatacgagc aaggcgtcga aggacaag     240 tttctcatca accatgcaag cctgaccttg tccactctga cagtgaccag tgcccatcct   300
gaagacagca gcttctacat ctgcagtgct cgcgacaggg ggcttgtatc gttgccgtcg   360
gtagaagctt tctttggaca aggcaccaga ctcacagttg tactg                   405
```

<210> SEQ ID NO 12
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Met Leu Leu Leu Leu Leu Leu Gly Pro Gly Ser Gly Leu Gly Ala
1               5                   10                  15

Val Val Ser Gln His Pro Ser Arg Val Ile Cys Lys Ser Gly Thr Ser
            20                  25                  30

Val Lys Ile Glu Cys Arg Ser Leu Asp Phe Gln Ala Thr Thr Met Phe
        35                  40                  45

Trp Tyr Arg Gln Phe Pro Lys Gln Ser Leu Met Leu Met Ala Thr Ser
    50                  55                  60

Asn Glu Gly Ser Lys Ala Thr Tyr Glu Gln Gly Val Glu Lys Asp Lys
65                  70                  75                  80

Phe Leu Ile Asn His Ala Ser Leu Thr Leu Ser Thr Leu Thr Val Thr
                85                  90                  95

Ser Ala His Pro Glu Asp Ser Ser Phe Tyr Ile Cys Ser Ala Arg Asp
            100                 105                 110

Arg Gly Leu Val Ser Leu Pro Ser Val Glu Ala Phe Phe Gly Gln Gly
        115                 120                 125

Thr Arg Leu Thr Val Val
    130
```

<210> SEQ ID NO 13
<211> LENGTH: 270
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Met Leu Leu Glu His Leu Leu Ile Ile Leu Trp Met Gln Leu Thr Trp
1               5                   10                  15

Val Ser Gly Gln Gln Leu Asn Gln Ser Pro Gln Ser Met Phe Ile Gln
            20                  25                  30
```

```
Glu Gly Glu Asp Val Ser Met Asn Cys Thr Ser Ser Ile Phe Asn
            35                  40                  45
Thr Trp Leu Trp Tyr Lys Gln Asp Pro Gly Glu Gly Pro Val Leu Leu
 50                  55                  60
Ile Ala Leu Tyr Lys Ala Gly Glu Leu Thr Ser Asn Gly Arg Leu Thr
 65                  70                  75                  80
Ala Gln Phe Gly Ile Thr Arg Lys Asp Ser Phe Leu Asn Ile Ser Ala
                 85                  90                  95
Ser Ile Pro Ser Asp Val Gly Ile Tyr Phe Cys Ala Gly Arg Asn Phe
            100                 105                 110
Gly Asn Glu Lys Leu Thr Phe Gly Thr Gly Thr Arg Leu Thr Ile Ile
            115                 120                 125
Pro Asp Ile Gln Asn Pro Asp Pro Ala Val Tyr Gln Leu Arg Asp Ser
130                 135                 140
Lys Ser Ser Asp Lys Ser Val Cys Leu Phe Thr Asp Phe Asp Ser Gln
145                 150                 155                 160
Thr Asn Val Ser Gln Ser Lys Asp Ser Asp Val Tyr Ile Thr Asp Lys
                165                 170                 175
Thr Val Leu Asp Met Arg Ser Met Asp Phe Lys Ser Asn Ser Ala Val
            180                 185                 190
Ala Trp Ser Asn Lys Ser Asp Phe Ala Cys Ala Asn Ala Phe Asn Asn
            195                 200                 205
Ser Ile Ile Pro Glu Asp Thr Phe Phe Pro Ser Pro Glu Ser Ser Cys
210                 215                 220
Asp Val Lys Leu Val Glu Lys Ser Phe Glu Thr Asp Thr Asn Leu Asn
225                 230                 235                 240
Phe Gln Asn Leu Ser Val Ile Gly Phe Arg Ile Leu Leu Leu Lys Val
                245                 250                 255
Ala Gly Phe Asn Leu Leu Met Thr Leu Arg Leu Trp Ser Ser
            260                 265                 270

<210> SEQ ID NO 14
<211> LENGTH: 312
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Leu Leu Leu Leu Leu Leu Gly Pro Gly Ser Gly Leu Gly Ala
1               5                   10                  15
Val Val Ser Gln His Pro Ser Arg Val Ile Cys Lys Ser Gly Thr Ser
                 20                  25                  30
Val Lys Ile Glu Cys Arg Ser Leu Asp Phe Gln Ala Thr Thr Met Phe
             35                  40                  45
Trp Tyr Arg Gln Phe Pro Lys Gln Ser Leu Met Leu Met Ala Thr Ser
 50                  55                  60
Asn Glu Gly Ser Lys Ala Thr Tyr Glu Gln Gly Val Glu Lys Asp Lys
 65                  70                  75                  80
Phe Leu Ile Asn His Ala Ser Leu Thr Leu Ser Thr Leu Thr Val Thr
                 85                  90                  95
Ser Ala His Pro Glu Asp Ser Ser Phe Tyr Ile Cys Ser Ala Arg Asp
            100                 105                 110
Arg Gly Leu Val Ser Leu Pro Ser Val Glu Ala Phe Phe Gly Gln Gly
```

```
                    115                 120                 125
Thr Arg Leu Thr Val Val Leu Glu Asp Leu Asn Lys Val Phe Pro Pro
    130                 135                 140
Glu Val Ala Val Phe Glu Pro Ser Glu Ala Glu Ile Ser His Thr Gln
145                 150                 155                 160
Lys Ala Thr Leu Val Cys Leu Ala Thr Gly Phe Phe Pro Asp His Val
                165                 170                 175
Glu Leu Ser Trp Trp Val Asn Gly Lys Glu Val His Ser Gly Val Ser
                180                 185                 190
Thr Asp Pro Gln Pro Leu Lys Glu Gln Pro Ala Leu Asn Asp Ser Arg
            195                 200                 205
Tyr Cys Leu Ser Ser Arg Leu Arg Val Ser Ala Thr Phe Trp Gln Asn
210                 215                 220
Pro Arg Asn His Phe Arg Cys Gln Val Gln Phe Tyr Gly Leu Ser Glu
225                 230                 235                 240
Asn Asp Glu Trp Thr Gln Asp Arg Ala Lys Pro Val Thr Gln Ile Val
                245                 250                 255
Ser Ala Glu Ala Trp Gly Arg Ala Asp Cys Gly Phe Thr Ser Val Ser
                260                 265                 270
Tyr Gln Gln Gly Val Leu Ser Ala Thr Ile Leu Tyr Glu Ile Leu Leu
            275                 280                 285
Gly Lys Ala Thr Leu Tyr Ala Val Leu Val Ser Ala Leu Val Leu Met
    290                 295                 300
Ala Met Val Lys Arg Lys Asp Phe
305                 310

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Leu Val Val Val Gly Ala Cys Gly Val
1               5                   10

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Val Ser Gly Asn Pro Tyr
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Tyr Ile Thr Gly Asp Asn Leu Val
1               5
```

```
<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Cys Ala Val Arg Asp Gln Ser Gly Ala Asn Asn Leu Phe Phe
1               5                   10

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Glu His Asn Arg
1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Phe Gln Asn Glu Ala Gln
1               5

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Ser Tyr Leu Ser Gly Ser Ile Tyr Asn Glu Gln Phe Phe
1               5                   10

<210> SEQ ID NO 22
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
atggcctctg cacccatctc gatgcttgcg atgctcttca cattgagtgg gctgagagct      60
cagtcagtgg ctcagccgga agatcaggtc aacgttgctg aagggaatcc tctgactgtg     120
aaatgcacct attcagtctc tggaaaccct tatctttttt ggtatgttca ataccccaac     180
cgaggcctcc agttccttct gaaatacatc acagggggata acctggttaa aggcagctat     240
ggctttgaag ctgaatttaa caagagccaa acctccttcc acctgaagaa accatctgcc     300
cttgtgagcg actccgcttt gtacttctgt gctgtgagag accaaagtgg ggcaaacaac     360
```
ctcttctttg ggactggaac gagactcacc gttattccc         399

<210> SEQ ID NO 23
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
atggcttctg cgcctatatc aatgcttgcc atgctgttta cactgtccgg tctgagggct    60
caaagcgtgg cccaacctga ggatcaggtg aatgtagcgg agggcaatcc gttgacagtt   120
aagtgtacat actccgtatc aggcaatccg tacttgtttt ggtatgtgca gtacccaat    180 cgggggcttc aattcttgct gaagtacatt acaggcgata atctggtaaa aggtagttat   240
ggttttgagg ccgaattcaa caaatcacaa acatcatttc atcttaaaaa gccaagcgca   300
cttgtcagtg actcagcgct ttatttctgt gcagtcagag accaatcagg gcaaataat   360 ctgttctttg ggacagggac tagattgact gttataccc                         399

<210> SEQ ID NO 24
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
                20                  25                  30

Ala Glu Gly Asn Pro Leu Thr Val Lys Cys Thr Tyr Ser Val Ser Gly
            35                  40                  45

Asn Pro Tyr Leu Phe Trp Tyr Val Gln Tyr Pro Asn Arg Gly Leu Gln
        50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Asp Gln Ser Gly Ala Asn Asn Leu Phe Phe Gly Thr Gly Thr Arg
        115                 120                 125

Leu Thr Val Ile Pro
    130

<210> SEQ ID NO 25
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
atgggcacca gcctcctctg ctggatggcc ctgtgtctcc tgggggcaga tcacgcagat    60

```
actggagtct cccaggaccc cagacacaag atcacaaaga ggggacagaa tgtaactttc       120
aggtgtgatc caatttctga acacaaccgc ctttattggt accgacagac cctggggcag       180
ggcccagagt ttctgactta cttccagaat gaagctcaac tagaaaaatc aaggctgctc       240
agtgatcggt tctctgcaga gaggcctaag ggatctttct ccaccttgga gatccagcgc       300
acagagcagg gggactcggc catgtatctc tgtgccagct acctgagcgg ttccatttac       360
aatgagcagt tcttcgggcc agggacacgg ctcaccgtgc ta                         402
```

<210> SEQ ID NO 26
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
atgggcacta gcctcttgtg ttggatggca ctttgccttc ttggcgcgga tcacgccgat       60
acaggcgtct cccaagatcc cagacataaa atcacaaaac ggggccagaa cgttaccttt      120
cgctgcgatc cgatatcaga gcataatcga ctgtattggt ataggcaaac tctcgggcaa      180
gggcctgagt tcctcactta tttccaaaat gaggcgcaac tggaaaagag ccggttgttg      240
agtgataggt tttccgcaga gcgacccaag gggagcttct caacactgga gatacaaagg      300
accgaacaag gtgattccgc aatgtatctc tgtgctagtt atttgagcgg ctccatatat      360
aacgaacagt ttttcggacc gggcactcgc ctgaccgtac ta                        402
```

<210> SEQ ID NO 27
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Tyr Leu Ser Gly Ser Ile Tyr Asn Glu Gln Phe Phe Gly Pro Gly
        115                 120                 125

Thr Arg Leu Thr Val Leu
    130

<210> SEQ ID NO 28
<211> LENGTH: 274
<212> TYPE: PRT

-continued

<213> ORGANISM: Artificial Sequence
<220> FEATURE:
<223> OTHER INFORMATION: Description of Artificial Sequence: Synthetic
      polypeptide

<400> SEQUENCE: 28

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Asp Gln Ser Gly Ala Asn Asn Leu Phe Phe Gly Thr Gly Thr Arg
        115                 120                 125

Leu Thr Val Ile Pro Asp Ile Gln Asn Pro Asp Pro Ala Val Tyr Gln
130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 29
<211> LENGTH: 311
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
            50                  55                  60

Leu Thr Tyr Phe Gln Asn Glu Ala Gln Leu Glu Lys Ser Arg Leu Leu
 65                  70                  75                  80

Ser Asp Arg Phe Ser Ala Glu Arg Pro Lys Gly Ser Phe Ser Thr Leu
                 85                  90                  95

Glu Ile Gln Arg Thr Glu Gln Gly Asp Ser Ala Met Tyr Leu Cys Ala
                100                 105                 110

Ser Tyr Leu Ser Gly Ser Ile Tyr Asn Glu Gln Phe Phe Gly Pro Gly
                115                 120                 125

Thr Arg Leu Thr Val Leu Glu Asp Leu Asn Lys Val Phe Pro Pro Glu
            130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Phe Pro Asp His Val Glu
                165                 170                 175

Leu Ser Trp Trp Val Asn Gly Lys Glu Val His Ser Gly Val Ser Thr
                180                 185                 190

Asp Pro Gln Pro Leu Lys Glu Gln Pro Ala Leu Asn Asp Ser Arg Tyr
            195                 200                 205

Cys Leu Ser Ser Arg Leu Arg Val Ser Ala Thr Phe Trp Gln Asn Pro
210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Val Ser Tyr
                260                 265                 270

Gln Gln Gly Val Leu Ser Ala Thr Ile Leu Tyr Glu Ile Leu Leu Gly
            275                 280                 285

Lys Ala Thr Leu Tyr Ala Val Leu Val Ser Ala Leu Val Leu Met Ala
            290                 295                 300

Met Val Lys Arg Lys Asp Phe
305                 310

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Leu Val Val Val Gly Ala Cys Gly Val
1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asn Ser Met Phe Asp Tyr
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ile Ser Ser Ile Lys Asp Lys
1               5

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Ala Ser Gly Gly Gly Gly Ala Asp Gly Leu Thr
1               5                   10

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Met Asn His Asn Tyr
1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Val Gly Ala Gly Ile
1               5

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ala Ser Ser Tyr Ser Thr Glu Arg Gly Thr Ile Tyr
1               5                   10

<210> SEQ ID NO 37
<211> LENGTH: 417
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
atggccatgc tcctgggggc atcagtgctg attctgtggc ttcagccaga ctgggtaaac      60
agtcaacaga agaatgatga ccagcaagtt aagcaaaatt caccatccct gagcgtccag     120
gaaggaagaa tttctattct gaactgtgac tatactaaca gcatgtttga ttatttccta     180
tggtacaaaa ataccctgc tgaaggtcct acattcctga tatctataag ttccattaag     240
gataaaaatg aagatggaag attcactgtc ttcttaaaca aaagtgccaa gcacctctct     300
ctgcacattg tgccctccca gcctggagac tctgcagtgt acttctgtgc agcaagcggg     360
ggaggaggtg ctgacggact cacctttggc aaagggactc atctaatcat ccagccc       417
```

<210> SEQ ID NO 38
<211> LENGTH: 417
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38

```
atggccatgc tgctgggcgc cagcgtgctg attttatggc tgcagcccga ctgggtgaac      60
agccagcaga agaacgacga ccagcaagtg aagcagaact cccttctttt aagcgtgcaa     120
gaaggtcgta tcagcatttt aaactgcgac tacaccaaca gcatgttcga ctactttta      180
tggtacaaga agtaccccgc cgagggcccc acctttttaa tcagcatcag cagcatcaag     240
gacaagaacg aggacggtcg tttcaccgtg ttttaaaca agagcgccaa gcatttatct     300
ttacacatcg tgccctccca gcccggtgat agcgccgtgt acttctgcgc cgccagcgga     360
ggaggaggcg ccgatggact gacccttcggc aagggcaccc atttaatcat ccagccc       417
```

<210> SEQ ID NO 39
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

```
Met Ala Met Leu Leu Gly Ala Ser Val Leu Ile Leu Trp Leu Gln Pro
1               5                   10                  15

Asp Trp Val Asn Ser Gln Gln Lys Asn Asp Asp Gln Gln Val Lys Gln
            20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
    50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ala Ser Gly Gly Gly Gly Ala Asp Gly Leu Thr
        115                 120                 125

Phe Gly Lys Gly Thr His Leu Ile Ile Gln Pro
    130                 135
```

<210> SEQ ID NO 40
<211> LENGTH: 486
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

```
atgaggtctc agaatgactt ccttgagagt cctgttcccc tttcatcaat gcacagatac      60
agaagacccc tccgtcctgg agcacctgcc atgagcatca gcctcctgtg ctgtgcagcc     120
tttcctctcc tgtgggcagg tccagtgaat gctggtgtca ctcagacccc aaaattccgc     180
atcctgaaga taggacagag catgacactg cagtgtaccc aggatatgaa ccataactac     240
atgtactggt atcgacaaga cccaggcatg gggctgaagc tgatttatta ttcagttggt     300
gctggtatca ctgataaagg agaagtcccg aatggctaca acgtctccag atcaaccaca     360
gaggatttcc cgctcaggct ggagttggct gctccctccc agacatctgt gtacttctgt     420
gccagcagtt actcgacgga acgcgggacc atatattttg gagagggaag ttggctcact     480
gttgta                                                                 486
```

<210> SEQ ID NO 41
<211> LENGTH: 486
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

```
atgaggagcc agaacgactt tttagagagc cccgtgcctc tgagcagcat gcataggtat      60
aggaggcctc tgagacccgg tgcccccgct atgagcatct ctttactgtg ctgtgctgcc     120
tttcctttac tgtgggctgg ccccgttaac gctggcgtga cccagacccc caagtttagg     180
attttaaaga tcggccagtc catgactttc agtgcaccc aagatatgaa ccacaactac      240
atgtactggt atcgtcaaga tcccggcatg ggtttaaagc tgatttacta cagcgtggga     300
gccggcatca ccgacaaggg cgaggtgccc aacggctaca atgtgtctcg tagcaccacc     360
gaggacttcc ctctgagact ggagctggcc gcccctagcc agacaagcgt gtacttctgc     420
gcctcctcct acagcaccga gaggggcacc atctacttcg gcgagggcag ctggctgacc     480
gtggtg                                                                 486
```

<210> SEQ ID NO 42
<211> LENGTH: 162
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Met Arg Ser Gln Asn Asp Phe Leu Glu Ser Pro Val Pro Leu Ser Ser
1               5                   10                  15

Met His Arg Tyr Arg Arg Pro Leu Arg Pro Gly Ala Pro Ala Met Ser
            20                  25                  30

Ile Ser Leu Leu Cys Cys Ala Ala Phe Pro Leu Leu Trp Ala Gly Pro
        35                  40                  45
```

```
Val Asn Ala Gly Val Thr Gln Thr Pro Lys Phe Arg Ile Leu Lys Ile
 50                  55                  60

Gly Gln Ser Met Thr Leu Gln Cys Thr Gln Asp Met Asn His Asn Tyr
 65                  70                  75                  80

Met Tyr Trp Tyr Arg Gln Asp Pro Gly Met Gly Leu Lys Leu Ile Tyr
                 85                  90                  95

Tyr Ser Val Gly Ala Gly Ile Thr Asp Lys Gly Glu Val Pro Asn Gly
                100                 105                 110

Tyr Asn Val Ser Arg Ser Thr Thr Glu Asp Phe Pro Leu Arg Leu Glu
                115                 120                 125

Leu Ala Ala Pro Ser Gln Thr Ser Val Tyr Phe Cys Ala Ser Ser Tyr
130                 135                 140

Ser Thr Glu Arg Gly Thr Ile Tyr Phe Gly Glu Gly Ser Trp Leu Thr
145                 150                 155                 160

Val Val
```

<210> SEQ ID NO 43
<211> LENGTH: 280
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Met Ala Met Leu Leu Gly Ala Ser Val Leu Ile Leu Trp Leu Gln Pro
 1               5                  10                  15

Asp Trp Val Asn Ser Gln Gln Lys Asn Asp Asp Gln Gln Val Lys Gln
                 20                  25                  30

Asn Ser Pro Ser Leu Ser Val Gln Glu Gly Arg Ile Ser Ile Leu Asn
             35                  40                  45

Cys Asp Tyr Thr Asn Ser Met Phe Asp Tyr Phe Leu Trp Tyr Lys Lys
 50                  55                  60

Tyr Pro Ala Glu Gly Pro Thr Phe Leu Ile Ser Ile Ser Ser Ile Lys
 65                  70                  75                  80

Asp Lys Asn Glu Asp Gly Arg Phe Thr Val Phe Leu Asn Lys Ser Ala
                 85                  90                  95

Lys His Leu Ser Leu His Ile Val Pro Ser Gln Pro Gly Asp Ser Ala
                100                 105                 110

Val Tyr Phe Cys Ala Ala Ser Gly Gly Gly Ala Asp Gly Leu Thr
                115                 120                 125

Phe Gly Lys Gly Thr His Leu Ile Ile Gln Pro Asp Ile Gln Asn Pro
130                 135                 140

Asp Pro Ala Val Tyr Gln Leu Arg Asp Ser Lys Ser Ser Asp Lys Ser
145                 150                 155                 160

Val Cys Leu Phe Thr Asp Phe Asp Ser Gln Thr Asn Val Ser Gln Ser
                165                 170                 175

Lys Asp Ser Asp Val Tyr Ile Thr Asp Lys Thr Val Leu Asp Met Arg
                180                 185                 190

Ser Met Asp Phe Lys Ser Asn Ser Ala Val Ala Trp Ser Asn Lys Ser
                195                 200                 205

Asp Phe Ala Cys Ala Asn Ala Phe Asn Asn Ser Ile Ile Pro Glu Asp
                210                 215                 220

Thr Phe Phe Pro Ser Pro Glu Ser Ser Cys Asp Val Lys Leu Val Glu
225                 230                 235                 240
```

```
Lys Ser Phe Glu Thr Asp Thr Asn Leu Asn Phe Gln Asn Leu Ser Val
                245                 250                 255

Ile Gly Phe Arg Ile Leu Leu Lys Val Ala Gly Phe Asn Leu Leu
            260                 265                 270

Met Thr Leu Arg Leu Trp Ser Ser
        275                 280

<210> SEQ ID NO 44
<211> LENGTH: 339
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Arg Ser Gln Asn Asp Phe Leu Glu Ser Pro Val Pro Leu Ser Ser
1               5                   10                  15

Met His Arg Tyr Arg Arg Pro Leu Arg Pro Gly Ala Pro Ala Met Ser
            20                  25                  30

Ile Ser Leu Leu Cys Cys Ala Ala Phe Pro Leu Leu Trp Ala Gly Pro
        35                  40                  45

Val Asn Ala Gly Val Thr Gln Thr Pro Lys Phe Arg Ile Leu Lys Ile
    50                  55                  60

Gly Gln Ser Met Thr Leu Gln Cys Thr Gln Asp Met Asn His Asn Tyr
65                  70                  75                  80

Met Tyr Trp Tyr Arg Gln Asp Pro Gly Met Gly Leu Lys Leu Ile Tyr
                85                  90                  95

Tyr Ser Val Gly Ala Gly Ile Thr Asp Lys Gly Glu Val Pro Asn Gly
            100                 105                 110

Tyr Asn Val Ser Arg Ser Thr Thr Glu Asp Phe Pro Leu Arg Leu Glu
        115                 120                 125

Leu Ala Ala Pro Ser Gln Thr Ser Val Tyr Phe Cys Ala Ser Ser Tyr
    130                 135                 140

Ser Thr Glu Arg Gly Thr Ile Tyr Phe Gly Glu Gly Ser Trp Leu Thr
145                 150                 155                 160

Val Val Glu Asp Leu Asn Lys Val Phe Pro Pro Glu Val Ala Val Phe
                165                 170                 175

Glu Pro Ser Glu Ala Glu Ile Ser His Thr Gln Lys Ala Thr Leu Val
            180                 185                 190

Cys Leu Ala Thr Gly Phe Phe Pro Asp His Val Glu Leu Ser Trp Trp
        195                 200                 205

Val Asn Gly Lys Glu Val His Ser Gly Val Ser Thr Asp Pro Gln Pro
    210                 215                 220

Leu Lys Glu Gln Pro Ala Leu Asn Asp Ser Arg Tyr Cys Leu Ser Ser
225                 230                 235                 240

Arg Leu Arg Val Ser Ala Thr Phe Trp Gln Asn Pro Arg Asn His Phe
                245                 250                 255

Arg Cys Gln Val Gln Phe Tyr Gly Leu Ser Glu Asn Asp Glu Trp Thr
            260                 265                 270

Gln Asp Arg Ala Lys Pro Val Thr Gln Ile Val Ser Ala Glu Ala Trp
        275                 280                 285

Gly Arg Ala Asp Cys Gly Phe Thr Ser Val Ser Tyr Gln Gln Gly Val
    290                 295                 300

Leu Ser Ala Thr Ile Leu Tyr Glu Ile Leu Leu Gly Lys Ala Thr Leu
305                 310                 315                 320
```

Tyr Ala Val Leu Val Ser Ala Leu Val Leu Met Ala Met Val Lys Arg
            325                 330                 335

Lys Asp Phe

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Val Val Gly Ala Val Gly Val Gly Lys
1               5

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Val Val Val Gly Ala Val Gly Val Gly Lys
1               5                   10

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Thr Ser Ile Asn Asn
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ile Arg Ser Asn Glu Arg Glu
1               5

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Thr Asp Arg Gln Ser Ser Gly Asp Lys Leu Thr
1               5                   10

<210> SEQ ID NO 50
<211> LENGTH: 5

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ser Gly His Ala Thr
1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Phe Gln Asn Asn Gly Val
1               5

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ala Ser Ser Leu Ala Asp Ile Tyr Glu Gln Tyr
1               5                   10

<210> SEQ ID NO 53
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
atggaaactc tcctgggagt gtctttggtg attctatggc ttcaactggc tagggtgaac      60
agtcaacagg gagaagagga tcctcaggcc ttgagcatcc aggagggtga aaatgccacc     120
atgaactgca gttacaaaac tagtataaac aatttacagt ggtatagaca aaattcaggt     180
agaggccttg tccacctaat tttaatacgt tcaaatgaaa gagagaaaca cagtggaaga     240
ttaagagtca cgcttgacac ttccaagaaa agcagttcct tgttgatcac ggcttcccgg     300
gcagcagaca ctgcttctta cttctgtgct acggaccgtc aaagcagcgg agacaagctg     360
acttttggga ccgggactcg tttagcagtt aggccc                              396

<210> SEQ ID NO 54
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
atggagactt tactgggcgt gtctttagtg attttatggc tgcagctggc tcgtgtgaat      60
agccagcaag gtgaagagga cccccaagct ttaagcatcc aagaaggcga aacgccacc     120
```

```
atgaactgct cctacaagac cagcatcaac aatttacagt ggtatcgtca gaacagcggt    180
cgtggtttag tgcatttaat tttaattcgt agcaacgaga gggagaagca cagcggtcgt    240
ctgagggtga ctttagacac cagcaagaag agcagctctt tactgatcac agcctctagg    300
gccgctgaca ccgctagcta cttctgcgcc accgacagac agagcagcgg cgacaagctg    360
accttcggca ccggcacaag actggccgtg agaccc                              396
```

<210> SEQ ID NO 55
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Leu Leu Ile
                85                  90                  95

Thr Ala Ser Arg Ala Ala Asp Thr Ala Ser Tyr Phe Cys Ala Thr Asp
            100                 105                 110

Arg Gln Ser Ser Gly Asp Lys Leu Thr Phe Gly Thr Gly Thr Arg Leu
        115                 120                 125

Ala Val Arg Pro
    130
```

<210> SEQ ID NO 56
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56

```
atgggcacca ggctcctctg ctgggcggcc ctctgtctcc tgggagcaga actcacagaa    60
gctggagttg cccagtctcc cagatataag attatagaga aaaggcagag tgtggctttt    120
tggtgcaatc ctatatctgg ccatgctacc ctttactggt accagcagat cctgggacag    180
ggcccaaagc ttctgattca gtttcagaat aacggtgtag tggatgattc acagttgcct    240
aaggatcgat tttctgcaga gaggctcaaa ggagtagact ccactctcaa gatccagcct    300
gcaaagcttg aggactcggc cgtgtatctc tgtgccagca gcttagccga catctacgag    360
cagtacttcg gccgggcac caggctcacg gtcaca                               396
```

<210> SEQ ID NO 57
<211> LENGTH: 396
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 57

```
atgggcacca gactgctgtg ctgggccgct ctgtgtctgc tgggcgctga gctgacagaa    60
gctggcgtgg cccagagccc tcgttacaag atcatcgaga gaggcagag cgtggccttc   120
tggtgcaacc ccatcagcgg ccacgccact ttatactggt accagcagat tttaggccaa   180
ggtcccaagc tgctgatcca gttccagaac aacggcgtgg tggacgacag ccagctgccc   240
aaggatcgtt tcagcgccga gaggctgaag ggcgtggaca gcactttaaa aatccagccc   300
gctaagctgg aggacagcgc cgtgtattta tgcgctagct ctttagccga catctacgag   360
cagtacttcg gccccggcac tcgtctgacc gtgacc                             396
```

<210> SEQ ID NO 58
<211> LENGTH: 132
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 58

```
Met Gly Thr Arg Leu Leu Cys Trp Ala Ala Leu Cys Leu Leu Gly Ala
1               5                   10                  15
Glu Leu Thr Glu Ala Gly Val Ala Gln Ser Pro Arg Tyr Lys Ile Ile
            20                  25                  30
Glu Lys Arg Gln Ser Val Ala Phe Trp Cys Asn Pro Ile Ser Gly His
        35                  40                  45
Ala Thr Leu Tyr Trp Tyr Gln Gln Ile Leu Gly Gln Gly Pro Lys Leu
    50                  55                  60
Leu Ile Gln Phe Gln Asn Asn Gly Val Val Asp Asp Ser Gln Leu Pro
65                  70                  75                  80
Lys Asp Arg Phe Ser Ala Glu Arg Leu Lys Gly Val Asp Ser Thr Leu
                85                  90                  95
Lys Ile Gln Pro Ala Lys Leu Glu Asp Ser Ala Val Tyr Leu Cys Ala
            100                 105                 110
Ser Ser Leu Ala Asp Ile Tyr Glu Gln Tyr Phe Gly Pro Gly Thr Arg
        115                 120                 125
Leu Thr Val Thr
    130
```

<210> SEQ ID NO 59
<211> LENGTH: 273
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 59

```
Met Glu Thr Leu Leu Gly Val Ser Leu Val Ile Leu Trp Leu Gln Leu
1               5                   10                  15
Ala Arg Val Asn Ser Gln Gln Gly Glu Glu Asp Pro Gln Ala Leu Ser
            20                  25                  30
Ile Gln Glu Gly Glu Asn Ala Thr Met Asn Cys Ser Tyr Lys Thr Ser
        35                  40                  45
Ile Asn Asn Leu Gln Trp Tyr Arg Gln Asn Ser Gly Arg Gly Leu Val
    50                  55                  60
```

```
His Leu Ile Leu Ile Arg Ser Asn Glu Arg Glu Lys His Ser Gly Arg
 65                  70                  75                  80

Leu Arg Val Thr Leu Asp Thr Ser Lys Lys Ser Ser Leu Leu Ile
             85                  90                  95

Thr Ala Ser Arg Ala Ala Asp Thr Ala Ser Tyr Phe Cys Ala Thr Asp
                100                 105                 110

Arg Gln Ser Ser Gly Asp Lys Leu Thr Phe Gly Thr Gly Thr Arg Leu
                115                 120                 125

Ala Val Arg Pro Asp Ile Gln Asn Pro Asp Pro Ala Val Tyr Gln Leu
130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
                180                 185                 190

Ser Ala Val Ala Trp Ser Asn Lys Ser Asp Phe Ala Cys Ala Asn Ala
                195                 200                 205

Phe Asn Asn Ser Ile Ile Pro Glu Asp Thr Phe Phe Pro Ser Pro Glu
210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
                260                 265                 270

Ser

<210> SEQ ID NO 60
<211> LENGTH: 309
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Met Gly Thr Arg Leu Leu Cys Trp Ala Ala Leu Cys Leu Leu Gly Ala
  1               5                  10                  15

Glu Leu Thr Glu Ala Gly Val Ala Gln Ser Pro Arg Tyr Lys Ile Ile
             20                  25                  30

Glu Lys Arg Gln Ser Val Ala Phe Trp Cys Asn Pro Ile Ser Gly His
             35                  40                  45

Ala Thr Leu Tyr Trp Tyr Gln Gln Ile Leu Gly Gln Gly Pro Lys Leu
         50                  55                  60

Leu Ile Gln Phe Gln Asn Asn Gly Val Val Asp Asp Ser Gln Leu Pro
 65                  70                  75                  80

Lys Asp Arg Phe Ser Ala Glu Arg Leu Lys Gly Val Asp Ser Thr Leu
                 85                  90                  95

Lys Ile Gln Pro Ala Lys Leu Glu Asp Ser Ala Val Tyr Leu Cys Ala
                100                 105                 110

Ser Ser Leu Ala Asp Ile Tyr Glu Gln Tyr Phe Gly Pro Gly Thr Arg
            115                 120                 125

Leu Thr Val Thr Glu Asp Leu Asn Lys Val Phe Pro Pro Glu Val Ala
130                 135                 140
```

```
Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
            165                 170                 175

Trp Trp Val Asn Gly Lys Glu Val His Ser Gly Val Ser Thr Asp Pro
        180                 185                 190

Gln Pro Leu Lys Glu Gln Pro Ala Leu Asn Asp Ser Arg Tyr Cys Leu
    195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
                260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
    290                 295                 300

Lys Arg Lys Asp Phe
305

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Val Val Gly Ala Val Gly Val Gly Lys
1               5

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Val Val Val Gly Ala Val Gly Val Gly Lys
1               5                   10

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Thr Ser Gly Phe Asn Gly
1               5

<210> SEQ ID NO 64
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asn Val Leu Asp Gly Leu
1               5

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Cys Ala Pro Gly Asp Asn Phe Asn Lys Phe Tyr Phe
1               5                   10

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ser Gly His Arg Ser
1               5

<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Tyr Phe Ser Glu Thr Gln
1               5

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Cys Ala Ser Ser Ala Arg Asn Asp Glu Ala Phe Phe
1               5                   10

<210> SEQ ID NO 69
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
atgtggggag ttttccttct ttatgtttcc atgaagatgg gaggcactac aggacaaaac    60
```

```
attgaccagc ccactgagat gacagctacg gaaggtgcca ttgtccagat caactgcacg    120
taccagacat ctgggttcaa cgggctgttc tggtaccagc aacatgctgg cgaagcaccc    180
acatttctgt cttacaatgt tctggatggt ttggaggaga aggtcgtttt ttcttcattc    240
cttagtcggt ctaaagggta cagttacctc cttttgaagg agctccagat gaaagactct    300
gcctcttacc tctgtgctcc cggggacaac ttcaacaaat tttactttgg atctgggacc    360
aaactcaatg taaaacca                                                  378
```

<210> SEQ ID NO 70
<211> LENGTH: 378
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 70

```
atgtggggcg tgtttctgct gtacgtgtcc atgaagatgg gcggcaccac aggccagaac     60
atcgaccagc caaccgagat gaccgccaca gagggcgcca tcgtgcagat caactgcacc    120
taccagacat ctggcttcaa tggcctgttt tggtatcagc agcacgcagg agaggcaccc    180
acattcctga gctataatgt gctggatggc ctggaggaga agggcaggtt ctcctctttt    240
ctgtctcgca gcaagggcta ctcctatctg ctgctgaagg agctgcagat gaaggactcc    300
gcctcttacc tgtgcgcccc tggcgataac tttaataagt tctatttcgg ctctggcacc    360
aagctgaatg tgaagcca                                                  378
```

<210> SEQ ID NO 71
<211> LENGTH: 126
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 71

```
Met Trp Gly Val Phe Leu Leu Tyr Val Ser Met Lys Met Gly Gly Thr
1               5                   10                  15

Thr Gly Gln Asn Ile Asp Gln Pro Thr Glu Met Thr Ala Thr Glu Gly
            20                  25                  30

Ala Ile Val Gln Ile Asn Cys Thr Tyr Gln Thr Ser Gly Phe Asn Gly
        35                  40                  45

Leu Phe Trp Tyr Gln Gln His Ala Gly Glu Ala Pro Thr Phe Leu Ser
    50                  55                  60

Tyr Asn Val Leu Asp Gly Leu Glu Glu Lys Gly Arg Phe Ser Ser Phe
65                  70                  75                  80

Leu Ser Arg Ser Lys Gly Tyr Ser Tyr Leu Leu Leu Lys Glu Leu Gln
                85                  90                  95

Met Lys Asp Ser Ala Ser Tyr Leu Cys Ala Pro Gly Asp Asn Phe Asn
            100                 105                 110

Lys Phe Tyr Phe Gly Ser Gly Thr Lys Leu Asn Val Lys Pro
        115                 120                 125
```

<210> SEQ ID NO 72
<211> LENGTH: 390
<212> TYPE: DNA
<213> ORGANISM: Artificial Sequence
<220> FEATURE:

<223> OTHER INFORMATION: Description of Artificial Sequence: Synthetic
    polynucleotide

<400> SEQUENCE: 72

```
atgggctcca ggctgctctg ttgggtgctg ctttgtctcc tgggagcagg cccagtaaag    60
gctggagtca ctcaaactcc aagatatctg atcaaaacga gaggacagca agtgacactg   120
agctgctccc ctatctctgg cataggagt gtatcctggt accaacagac cccaggacag    180
ggccttcagt tcctctttga atacttcagt gagacacaga aaacaaagg aaacttccct    240
ggtcgattct cagggcgcca gttctctaac tctcgctctg agatgaatgt gagcaccttg    300
gagctggggg actcggccct ttatctttgc gccagcagcg cgagaaatga tgaagctttc    360
tttggacaag gcaccagact cacagttgta                                     390
```

<210> SEQ ID NO 73
<211> LENGTH: 390
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 73

```
atgggcagcc ggctgctgtg ctgggtgctg ctgtgcctgc tgggagcagg accagtgaag    60
gcaggcgtga cccagacacc tcggtacctg atcaagacca gaggccagca ggtgacactg   120
agctgctccc caatctccgg ccacagatct gtgagctggt accagcagac cccaggacag    180
ggactgcagt tcctgtttga gtatttctcc gagacacaga ggaacaaggg caatttccct    240
ggccggtttt ctggcagaca gttttccaac tctcgcagcg agatgaatgt gagcaccctg    300
gagctgggcg actccgccct gtacctgtgc gccagctccg ccaggaacga tgaggccttc    360
tttggccagg gcacccggct gacagtggtg                                     390
```

<210> SEQ ID NO 74
<211> LENGTH: 130
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 74

Met Gly Ser Arg Leu Leu Cys Trp Val Leu Leu Cys Leu Leu Gly Ala
1               5                   10                  15

Gly Pro Val Lys Ala Gly Val Thr Gln Thr Pro Arg Tyr Leu Ile Lys
            20                  25                  30

Thr Arg Gly Gln Gln Val Thr Leu Ser Cys Ser Pro Ile Ser Gly His
        35                  40                  45

Arg Ser Val Ser Trp Tyr Gln Gln Thr Pro Gly Gln Gly Leu Gln Phe
    50                  55                  60

Leu Phe Glu Tyr Phe Ser Glu Thr Gln Arg Asn Lys Gly Asn Phe Pro
65                  70                  75                  80

Gly Arg Phe Ser Gly Arg Gln Phe Ser Asn Ser Arg Ser Glu Met Asn
                85                  90                  95

Val Ser Thr Leu Glu Leu Gly Asp Ser Ala Leu Tyr Leu Cys Ala Ser
            100                 105                 110

Ser Ala Arg Asn Asp Glu Ala Phe Phe Gly Gln Gly Thr Arg Leu Thr
        115                 120                 125

Val Val
    130

<210> SEQ ID NO 75
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Met Trp Gly Val Phe Leu Leu Tyr Val Ser Met Lys Met Gly Gly Thr
1               5                   10                  15

Thr Gly Gln Asn Ile Asp Gln Pro Thr Glu Met Thr Ala Thr Glu Gly
                20                  25                  30

Ala Ile Val Gln Ile Asn Cys Thr Tyr Gln Thr Ser Gly Phe Asn Gly
            35                  40                  45

Leu Phe Trp Tyr Gln Gln His Ala Gly Glu Ala Pro Thr Phe Leu Ser
    50                  55                  60

Tyr Asn Val Leu Asp Gly Leu Glu Glu Lys Gly Arg Phe Ser Ser Phe
65                  70                  75                  80

Leu Ser Arg Ser Lys Gly Tyr Ser Tyr Leu Leu Lys Glu Leu Gln
                85                  90                  95

Met Lys Asp Ser Ala Ser Tyr Leu Cys Ala Pro Gly Asp Asn Phe Asn
            100                 105                 110

Lys Phe Tyr Phe Gly Ser Gly Thr Lys Leu Asn Val Lys Pro Asp Ile
        115                 120                 125

Gln Asn Pro Asp Pro Ala Val Tyr Gln Leu Arg Asp Ser Lys Ser Ser
    130                 135                 140

Asp Lys Ser Val Cys Leu Phe Thr Asp Phe Asp Ser Gln Thr Asn Val
145                 150                 155                 160

Ser Gln Ser Lys Asp Ser Asp Val Tyr Ile Thr Asp Lys Thr Val Leu
                165                 170                 175

Asp Met Arg Ser Met Asp Phe Lys Ser Asn Ser Ala Val Ala Trp Ser
            180                 185                 190

Asn Lys Ser Asp Phe Ala Cys Ala Asn Ala Phe Asn Asn Ser Ile Ile
        195                 200                 205

Pro Glu Asp Thr Phe Phe Pro Ser Pro Glu Ser Ser Cys Asp Val Lys
    210                 215                 220

Leu Val Glu Lys Ser Phe Glu Thr Asp Thr Asn Leu Asn Phe Gln Asn
225                 230                 235                 240

Leu Ser Val Ile Gly Phe Arg Ile Leu Leu Leu Lys Val Ala Gly Phe
                245                 250                 255

Asn Leu Leu Met Thr Leu Arg Leu Trp Ser Ser
            260                 265

<210> SEQ ID NO 76
<211> LENGTH: 307
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Met Gly Ser Arg Leu Leu Cys Trp Val Leu Leu Cys Leu Leu Gly Ala
1               5                   10                  15

Gly Pro Val Lys Ala Gly Val Thr Gln Thr Pro Arg Tyr Leu Ile Lys
            20                  25                  30

Thr Arg Gly Gln Gln Val Thr Leu Ser Cys Ser Pro Ile Ser Gly His
        35                  40                  45

Arg Ser Val Ser Trp Tyr Gln Gln Thr Pro Gly Gln Gly Leu Gln Phe
50                  55                  60

Leu Phe Glu Tyr Phe Ser Glu Thr Gln Arg Asn Lys Gly Asn Phe Pro
65                  70                  75                  80

Gly Arg Phe Ser Gly Arg Gln Phe Ser Asn Ser Arg Ser Glu Met Asn
                85                  90                  95

Val Ser Thr Leu Glu Leu Gly Asp Ser Ala Leu Tyr Leu Cys Ala Ser
            100                 105                 110

Ser Ala Arg Asn Asp Glu Ala Phe Phe Gly Gln Gly Thr Arg Leu Thr
        115                 120                 125

Val Val Glu Asp Leu Asn Lys Val Phe Pro Pro Glu Val Ala Val Phe
130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Val Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
290                 295                 300

Lys Asp Phe
305

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Val Val Gly Ala Val Gly Val Gly Lys
1               5

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 78

Val Val Val Gly Ala Val Gly Val Gly Lys
1               5                   10

<210> SEQ ID NO 79
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Asp Arg Gly Ser Gln Ser
1               5

<210> SEQ ID NO 80
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ile Tyr Ser Asn Gly Asp
1               5

<210> SEQ ID NO 81
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Cys Ala Val Lys Ser Arg Ala Gly Ser Tyr Gln Leu Thr Phe
1               5                   10

<210> SEQ ID NO 82
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ser Gly His Asn Ser
1               5

<210> SEQ ID NO 83
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Phe Asn Asn Asn Val Pro
1               5

<210> SEQ ID NO 84
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Cys Ala Ser Ser Leu Gly Asp Ser Glu Gln Tyr Phe
1               5                   10

<210> SEQ ID NO 85
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
atgaaatcct tgagagtttt actagtgatc ctgtggcttc agttgagctg ggtttggagc      60
caacagaagg aggtggagca gaattctgga cccctcagtg ttccagaggg agccattgcc     120
tctctcaact gcacttacag tgaccgaggt tcccagtcct tcttctggta cagacaatat     180
tctgggaaaa gccctgagtt gataatgttc atatactcca atggtgacaa agaagatgga     240
aggtttacag cacagctcaa taaagccagc cagtatgttt ctctgctcat cagagactcc     300
cagcccagtg attcagccac ctacctctgt gccgtgaagt caagggctgg gagttaccaa     360
ctcactttcg ggaaggggac caaactctcg gtcatacca                            399

<210> SEQ ID NO 86
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
atgaagagcc tgcgggtgct gctggtcatc ctgtggctgc agctgtcctg ggtgtggtct      60
cagcagaagg aggtggagca gaatagcgga ccactgtccg tgccagaggg agccatcgcc     120
tccctgaact gcacatactc tgacaggggc tcccagtctt tcttttggta ccgccagtat     180
agcggcaagt cccccgagct gatcatgttc atctactcta tggcgacaa ggaggatggc     240 aggtttaccg cccagctgaa caaggcctct cagtatgtga gcctgctgat ccgcgacagc     300
cagcctagcg attccgccac ataccctgtgc gcagtgaagt cccgggcagg ctcttatcag     360
ctgacctttg gcaagggcac aaagctgagc gtgatccca                            399

<210> SEQ ID NO 87
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
```

```
                35                  40                  45
Arg Gly Ser Gln Ser Phe Phe Trp Tyr Arg Gln Tyr Ser Gly Lys Ser
         50                  55                  60
Pro Glu Leu Ile Met Phe Ile Tyr Ser Asn Gly Asp Lys Glu Asp Gly
 65                  70                  75                  80
Arg Phe Thr Ala Gln Leu Asn Lys Ala Ser Gln Tyr Val Ser Leu Leu
                 85                  90                  95
Ile Arg Asp Ser Gln Pro Ser Asp Ser Ala Thr Tyr Leu Cys Ala Val
            100                 105                 110
Lys Ser Arg Ala Gly Ser Tyr Gln Leu Thr Phe Gly Lys Gly Thr Lys
        115                 120                 125
Leu Ser Val Ile Pro
        130

<210> SEQ ID NO 88
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
atggactcct ggaccttctg ctgtgtgtcc ctttgcatcc tggtagcgaa gcatacagat      60
gctggagtta tccagtcacc ccgccatgag gtgacagaga tgggacaaga agtgactctg     120
agatgtaaac aatttcagg ccacaactcc cttttctggt acagacagac catgatgcgg      180
ggactggagt tgctcattta ctttaacaac aacgttccga tagatgattc agggatgccc     240
gaggatcgat tctcagctaa gatgcctaat gcatcattct ccactctgaa gatccagccc     300
tcagaaccca gggactcagc tgtgtacttc tgtgccagca gtctcgggga cagcgagcag     360
tacttcgggc cgggcaccag gctcacggtc aca                                 393

<210> SEQ ID NO 89
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
atggacagct ggaccttctg ctgcgtgagc ctgtgcatcc tggtggccaa gcacacagat      60
gcaggcgtga tccagtcccc aaggcacgag gtgaccgaga tgggacagga ggtgacactg     120
aggtgtaagc ctatctctgg ccacaatagc ctgttctggt acaggcagac catgatgcgc     180
ggcctggagc tgctgatcta cttcaacaat aacgtgccta tcgacgattc cggcatgcca     240
gaggacagat tctctgccaa gatgcccaac gcctccttt ctacactgaa gatccagcca     300
agcgagccta gggactccgc cgtgtacttc tgcgccagct ccctgggcga tagcgagcag     360
tattttggcc ctggcacccg gctgaccgtg aca                                 393

<210> SEQ ID NO 90
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 90

Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asn Ser Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Leu Gly Asp Ser Glu Gln Tyr Phe Gly Pro Gly Thr Arg Leu
            115                 120                 125

Thr Val Thr
        130

<210> SEQ ID NO 91
<211> LENGTH: 274
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Lys Ser Arg Ala Gly Ser Tyr Gln Leu Thr Phe Gly Lys Gly Thr Lys
            115                 120                 125

Leu Ser Val Ile Pro Asp Ile Gln Asn Pro Asp Pro Ala Val Tyr Gln
        130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205
```

```
Ala Phe Asn Asn Ser Ile Ile Pro Glu Asp Thr Phe Phe Pro Ser Pro
    210                 215                 220
Glu Ser Ser Cys Asp Val Lys Leu Val Glu Lys Ser Phe Glu Thr Asp
225                 230                 235                 240
Thr Asn Leu Asn Phe Gln Asn Leu Ser Val Ile Gly Phe Arg Ile Leu
                245                 250                 255
Leu Leu Lys Val Ala Gly Phe Asn Leu Leu Met Thr Leu Arg Leu Trp
                260                 265                 270
Ser Ser
```

<210> SEQ ID NO 92
<211> LENGTH: 308
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

```
Met Asp Ser Trp Thr Phe Cys Cys Val Ser Leu Cys Ile Leu Val Ala
1               5                   10                  15
Lys His Thr Asp Ala Gly Val Ile Gln Ser Pro Arg His Glu Val Thr
            20                  25                  30
Glu Met Gly Gln Glu Val Thr Leu Arg Cys Lys Pro Ile Ser Gly His
        35                  40                  45
Asn Ser Leu Phe Trp Tyr Arg Gln Thr Met Met Arg Gly Leu Glu Leu
    50                  55                  60
Leu Ile Tyr Phe Asn Asn Val Pro Ile Asp Ser Gly Met Pro
65                  70                  75                  80
Glu Asp Arg Phe Ser Ala Lys Met Pro Asn Ala Ser Phe Ser Thr Leu
                85                  90                  95
Lys Ile Gln Pro Ser Glu Pro Arg Asp Ser Ala Val Tyr Phe Cys Ala
            100                 105                 110
Ser Ser Leu Gly Asp Ser Glu Gln Tyr Phe Gly Pro Gly Thr Arg Leu
        115                 120                 125
Thr Val Thr Glu Asp Leu Asn Lys Val Phe Pro Pro Glu Val Ala Val
    130                 135                 140
Phe Glu Pro Ser Glu Ala Glu Ile Ser His Thr Gln Lys Ala Thr Leu
145                 150                 155                 160
Val Cys Leu Ala Thr Gly Phe Phe Pro Asp His Val Glu Leu Ser Trp
                165                 170                 175
Trp Val Asn Gly Lys Glu Val His Ser Gly Val Ser Thr Asp Pro Gln
            180                 185                 190
Pro Leu Lys Glu Gln Pro Ala Leu Asn Asp Ser Arg Tyr Cys Leu Ser
        195                 200                 205
Ser Arg Leu Arg Val Ser Ala Thr Phe Trp Gln Asn Pro Arg Asn His
    210                 215                 220
Phe Arg Cys Gln Val Gln Phe Tyr Gly Leu Ser Glu Asn Asp Glu Trp
225                 230                 235                 240
Thr Gln Asp Arg Ala Lys Pro Val Thr Gln Ile Val Ser Ala Glu Ala
                245                 250                 255
Trp Gly Arg Ala Asp Cys Gly Phe Thr Ser Val Ser Tyr Gln Gln Gly
            260                 265                 270
Val Leu Ser Ala Thr Ile Leu Tyr Glu Ile Leu Leu Gly Lys Ala Thr
        275                 280                 285
```

```
Leu Tyr Ala Val Leu Val Ser Ala Leu Val Leu Met Ala Met Val Lys
    290                 295                 300

Arg Lys Asp Phe
305

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Val Val Gly Ala Val Gly Val Gly Lys
1               5

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Val Val Val Gly Ala Val Gly Val Gly Lys
1               5                   10

<210> SEQ ID NO 95
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ser Ser Tyr Ser Pro Ser
1               5

<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Tyr Thr Ser Ala Ala Thr Leu Val
1               5

<210> SEQ ID NO 97
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Cys Val Val Ser Gly Gly Gly Ser Ser Asn Thr Gly Lys Leu Ile Phe
1               5                   10                  15

<210> SEQ ID NO 98
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ser Gly His Ala Thr
1               5

<210> SEQ ID NO 99
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Phe Gln Asn Asn Gly Val
1               5

<210> SEQ ID NO 100
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Cys Ala Ser Ser Gln Arg Ser Asn Thr Gly Glu Leu Phe Phe
1               5                   10

<210> SEQ ID NO 101
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
atgctcctgc tgctcgtccc agtgctcgag gtgattttta ctctgggagg aaccagagcc     60
cagtcggtga cccagcttga cagccacgtc tctgtctctg aaggaacccc ggtgctgctg    120
aggtgcaact actcatcttc ttattcacca tctctcttct ggtatgtgca acaccccaac    180
aaaggactcc agcttctcct gaagtacaca tcagcggcca ccctggttaa aggcatcaac    240
ggttttgagg ctgaatttaa aagagtgaa acctccttcc acctgacgaa accctcagcc    300
catatgagcg acgcggctga gtacttctgt gttgtgagtg ggggaggctc tagcaacaca    360 ggcaaaactaa tctttgggca agggacaact ttacaagtaa aacca                   405

<210> SEQ ID NO 102
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
atgctgctgc tgctggtgcc cgtgctggaa gtgatcttca cctgggagg aacaagggca      60 cagagcgtga cccagctgga ctcccacgtg tccgtgtctg agggcacacc cgtgctgctg    120
```

```
agatgcaact actcctctag ctatagcccc tccctgttct ggtacgtgca gcaccctaat    180
aagggcctgc agctgctgct gaagtatacc tccgccgcca cactggtgaa gggcatcaac    240
ggcttcgagg ccgagtttaa gaagagcgag acctccttcc acctgacaaa gccttctgcc    300
cacatgagcg atgccgccga gtactttgtc gtggtgagcg gcggcggctc ctctaatacc    360
ggcaagctga tcttcggcca gggcaccaca ctgcaggtga agcca                    405
```

<210> SEQ ID NO 103
<211> LENGTH: 135
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 103

```
Met Leu Leu Leu Leu Val Pro Val Leu Glu Val Ile Phe Thr Leu Gly
1               5                   10                  15

Gly Thr Arg Ala Gln Ser Val Thr Gln Leu Asp Ser His Val Ser Val
            20                  25                  30

Ser Glu Gly Thr Pro Val Leu Leu Arg Cys Asn Tyr Ser Ser Ser Tyr
        35                  40                  45

Ser Pro Ser Leu Phe Trp Tyr Val Gln His Pro Asn Lys Gly Leu Gln
    50                  55                  60

Leu Leu Leu Lys Tyr Thr Ser Ala Ala Thr Leu Val Lys Gly Ile Asn
65                  70                  75                  80

Gly Phe Glu Ala Glu Phe Lys Lys Ser Glu Thr Ser Phe His Leu Thr
                85                  90                  95

Lys Pro Ser Ala His Met Ser Asp Ala Ala Glu Tyr Phe Cys Val Val
            100                 105                 110

Ser Gly Gly Gly Ser Ser Asn Thr Gly Lys Leu Ile Phe Gly Gln Gly
        115                 120                 125

Thr Thr Leu Gln Val Lys Pro
    130                 135
```

<210> SEQ ID NO 104
<211> LENGTH: 399
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 104

```
atgggcacca ggctcctctg ctgggcggcc ctctgtctcc tgggagcaga actcacagaa    60
gctggagttg cccagtctcc cagatataag attatagaga aaaggcagag tgtggctttt    120
tggtgcaatc ctatatctgg ccatgctacc ctttactggt accagcagat cctgggacag    180
ggcccaaagc ttctgattca gtttcagaat aacggtgtag tggatgattc acagttgcct    240
aaggatcgat tttctgcaga gaggctcaaa ggagtagact ccactctcaa gatccaacct    300
gcaaagcttg aggactcggc cgtgtatctc tgtgccagca gccagaggtc gaacaccggg    360
gagctgtttt ttggagaagg ctctaggctg accgtactg                           399
```

<210> SEQ ID NO 105
<211> LENGTH: 399
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 105

```
atgggcaccc ggctgctgtg ctgggccgcc ctgtgcctgc tgggagcaga gctgacagag      60
gcaggagtgg cccagtcccc acggtacaag atcatcgaga gagacagtc cgtggccttt     120
tggtgcaacc ccatctctgg ccacgccacc ctgtactggt atcagcagat cctgggccag    180
ggccctaagc tgctgatcca gttccagaac aatggcgtgg tggacgattc tcagctgcca    240
aaggacaggt ttagcgccga cgcctgaag ggcgtggata gcaccctgaa gatccagcct     300
gccaagctgg aggacagcgc cgtgtatctg tgcgccagct cccagcggtc caatacaggc    360
gagctgttct ttggcgaggg ctctaggctg accgtgctg                           399
```

<210> SEQ ID NO 106
<211> LENGTH: 133
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 106

```
Met Gly Thr Arg Leu Leu Cys Trp Ala Ala Leu Cys Leu Leu Gly Ala
1               5                   10                  15
Glu Leu Thr Glu Ala Gly Val Ala Gln Ser Pro Arg Tyr Lys Ile Ile
            20                  25                  30
Glu Lys Arg Gln Ser Val Ala Phe Trp Cys Asn Pro Ile Ser Gly His
        35                  40                  45
Ala Thr Leu Tyr Trp Tyr Gln Gln Ile Leu Gly Gln Gly Pro Lys Leu
    50                  55                  60
Leu Ile Gln Phe Gln Asn Asn Gly Val Val Asp Asp Ser Gln Leu Pro
65                  70                  75                  80
Lys Asp Arg Phe Ser Ala Glu Arg Leu Lys Gly Val Asp Ser Thr Leu
                85                  90                  95
Lys Ile Gln Pro Ala Lys Leu Glu Asp Ser Ala Val Tyr Leu Cys Ala
            100                 105                 110
Ser Ser Gln Arg Ser Asn Thr Gly Glu Leu Phe Phe Gly Glu Gly Ser
        115                 120                 125
Arg Leu Thr Val Leu
    130
```

<210> SEQ ID NO 107
<211> LENGTH: 276
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 107

```
Met Leu Leu Leu Leu Val Pro Val Leu Glu Val Ile Phe Thr Leu Gly
1               5                   10                  15
Gly Thr Arg Ala Gln Ser Val Thr Gln Leu Asp Ser His Val Ser Val
            20                  25                  30
Ser Glu Gly Thr Pro Val Leu Leu Arg Cys Asn Tyr Ser Ser Ser Tyr
        35                  40                  45
Ser Pro Ser Leu Phe Trp Tyr Val Gln His Pro Asn Lys Gly Leu Gln
    50                  55                  60
```

```
Leu Leu Leu Lys Tyr Thr Ser Ala Ala Thr Leu Val Lys Gly Ile Asn
 65                  70                  75                  80

Gly Phe Glu Ala Glu Phe Lys Lys Ser Glu Thr Ser Phe His Leu Thr
                 85                  90                  95

Lys Pro Ser Ala His Met Ser Asp Ala Ala Glu Tyr Phe Cys Val Val
            100                 105                 110

Ser Gly Gly Gly Ser Ser Asn Thr Gly Lys Leu Ile Phe Gly Gln Gly
        115                 120                 125

Thr Thr Leu Gln Val Lys Pro Asp Ile Gln Asn Pro Asp Pro Ala Val
130                 135                 140

Tyr Gln Leu Arg Asp Ser Lys Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
    210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
        275

<210> SEQ ID NO 108
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Met Gly Thr Arg Leu Leu Cys Trp Ala Ala Leu Cys Leu Leu Gly Ala
 1               5                  10                  15

Glu Leu Thr Glu Ala Gly Val Ala Gln Ser Pro Arg Tyr Lys Ile Ile
                20                  25                  30

Glu Lys Arg Gln Ser Val Ala Phe Trp Cys Asn Pro Ile Ser Gly His
            35                  40                  45

Ala Thr Leu Tyr Trp Tyr Gln Gln Ile Leu Gly Gln Gly Pro Lys Leu
    50                  55                  60

Leu Ile Gln Phe Gln Asn Asn Gly Val Val Asp Asp Ser Gln Leu Pro
 65                  70                  75                  80

Lys Asp Arg Phe Ser Ala Glu Arg Leu Lys Gly Val Asp Ser Thr Leu
                 85                  90                  95

Lys Ile Gln Pro Ala Lys Leu Glu Asp Ser Ala Val Tyr Leu Cys Ala
            100                 105                 110

Ser Ser Gln Arg Ser Asn Thr Gly Glu Leu Phe Phe Gly Glu Gly Ser
        115                 120                 125

Arg Leu Thr Val Leu Glu Asp Leu Asn Lys Val Phe Pro Pro Glu Val
```

```
                130             135             140
Ala Val Phe Glu Pro Ser Glu Ala Glu Ile Ser His Thr Gln Lys Ala
145                 150                 155                 160

Thr Leu Val Cys Leu Ala Thr Gly Phe Phe Pro Asp His Val Glu Leu
                165                 170                 175

Ser Trp Trp Val Asn Gly Lys Glu Val His Ser Gly Val Ser Thr Asp
                180                 185                 190

Pro Gln Pro Leu Lys Glu Gln Pro Ala Leu Asn Asp Ser Arg Tyr Cys
            195                 200                 205

Leu Ser Ser Arg Leu Arg Val Ser Ala Thr Phe Trp Gln Asn Pro Arg
        210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Val Ser Tyr Gln
                260                 265                 270

Gln Gly Val Leu Ser Ala Thr Ile Leu Tyr Glu Ile Leu Leu Gly Lys
            275                 280                 285

Ala Thr Leu Tyr Ala Val Leu Val Ser Ala Leu Val Leu Met Ala Met
        290                 295                 300

Val Lys Arg Lys Asp Phe
305                 310

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Val Val Gly Ala Cys Gly Val Gly Lys
1               5

<210> SEQ ID NO 110
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Val Val Val Gly Ala Cys Gly Val Gly Lys
1               5                   10

<210> SEQ ID NO 111
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Thr Ser Ile Asn Asn
1               5

<210> SEQ ID NO 112
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ile Arg Ser Asn Glu Arg Glu
1               5

<210> SEQ ID NO 113
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Cys Ala Thr Asp Ala Gly Gly Gly Ala Asp Gly Leu Thr Phe
1               5                   10

<210> SEQ ID NO 114
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ser Gly Asp Leu Ser
1               5

<210> SEQ ID NO 115
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Tyr Tyr Asn Gly Glu Glu
1               5

<210> SEQ ID NO 116
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Cys Ala Ser Gly Gly Arg Asp Ser Thr Asp Thr Gln Tyr Phe
1               5                   10

<210> SEQ ID NO 117
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117
```

```
atggaaactc tcctgggagt gtctttggtg attctatggc ttcaactggc tagggtgaac     60
agtcaacagg gagaagagga tcctcaggcc ttgagcatcc aggagggtga aaatgccacc    120
atgaactgca gttacaaaac tagtataaac aatttacagt ggtatagaca aaattcaggt    180
agaggccttg tccacctaat tttaatacgt tcaaatgaaa gagagaaaca cagtggaaga    240
ttaagagtca cgcttgacac ttccaagaaa agcagttcct tgttgatcac ggcttcccgg    300
gcagcagaca ctgcttctta cttctgtgct acggacgccg gaggaggtgc tgacggactc    360
acctttggca aagggactca tctaatcatc cagccc                              396

<210> SEQ ID NO 118
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118
atggagacac tgctgggcgt gtccctggtc atcctgtggc tgcagctggc cagggtgaac     60
agccagcagg gagaggagga cccccaggcc ctgtctatcc aggagggcga gaacgccacc    120
atgaattgct cttacaagac aagcatcaac aatctgcagt ggtatagaca gaactccggc    180
aggggcctgg tgcacctgat cctgatccgc tccaatgagc gggagaagca ctctggccgg    240
ctgagagtga ccctggatac atctaagaag tcctctagcc tgctgatcac cgccagccgg    300
gcagcagaca cagcctccta cttttgtgcc accgatgccg ggggcggagc agacggactg    360
acattcggga aggggactca cctgattatc cagcca                              396

<210> SEQ ID NO 119
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Ser Leu Leu Ile
                85                  90                  95

Thr Ala Ser Arg Ala Ala Asp Thr Ala Ser Tyr Phe Cys Ala Thr Asp
            100                 105                 110

Ala Gly Gly Gly Ala Asp Gly Leu Thr Phe Gly Lys Gly Thr His Leu
        115                 120                 125

Ile Ile Gln Pro
    130

<210> SEQ ID NO 120
```

<210> SEQ ID NO 120
<211> LENGTH: 396
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 120

```
atgggcttca ggctcctctg ctgtgtggcc ttttgtctcc tgggagcagg cccagtggat      60
tctggagtca cacaaacccc aaagcacctg atcacagcaa ctggacagcg agtgacgctg     120
agatgctccc ctaggtctgg agacctctct gtgtactggt accaacagag cctggaccag     180
ggcctccagt tcctcattca gtattataat ggagaagaga gagcaaaagg aaacattctt     240
gaacgattct ccgcacaaca gttccctgac ttgcactctg aactaaacct gagctctctg     300
gagctggggg actcagcttt gtatttctgt gccagcgggg gacgggattc cacagatacg     360
cagtattttg gcccaggcac ccggctgaca gtgctc                              396
```

<210> SEQ ID NO 121
<211> LENGTH: 396
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 121

```
atgggctttc ggctgctgtg ctgcgtggct ttttgcctgc tggggctgg gcctgtggat       60
agcggggtca ctcagacacc taaacatctg atcaccgcaa caggacagag ggtgaccctg     120
aggtgctctc ctcggagcgg cgacctgagc gtgtactggt atcagcagag cctggatcag     180
ggcctgcagt tcctgatcca gtactataac ggcgaggagc gcgccaaggg caatatcctg     240
gagcggttct ctgcccagca gtttccagac ctgcacagcg agctgaacct gagctccctg     300
gagctgggcg atagcgccct gtacttctgc gcctccggcg gcagagactc taccgataca     360
cagtattttg gccccggcac cagactgaca gtgctg                              396
```

<210> SEQ ID NO 122
<211> LENGTH: 132
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 122

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

```
Gly Gly Arg Asp Ser Thr Asp Thr Gln Tyr Phe Gly Pro Gly Thr Arg
        115                 120                 125

Leu Thr Val Leu
    130

<210> SEQ ID NO 123
<211> LENGTH: 273
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Leu Leu Ile
                85                  90                  95

Thr Ala Ser Arg Ala Ala Asp Thr Ala Ser Tyr Phe Cys Ala Thr Asp
            100                 105                 110

Ala Gly Gly Gly Ala Asp Gly Leu Thr Phe Gly Lys Gly Thr His Leu
        115                 120                 125

Ile Ile Gln Pro Asp Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 124
<211> LENGTH: 309
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 124

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Gly Gly Arg Asp Ser Thr Asp Thr Gln Tyr Phe Gly Pro Gly Thr Arg
        115                 120                 125

Leu Thr Val Leu Glu Asp Leu Asn Lys Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Phe
305

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Val Val Gly Ala Val Gly Val Gly Lys
1               5

<210> SEQ ID NO 126
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Val Val Val Gly Ala Val Gly Val Gly Lys
1               5                   10

<210> SEQ ID NO 127
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Asn Tyr Ser Pro Ala Tyr
1               5

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ile Arg Glu Asn Glu Lys Glu
1               5

<210> SEQ ID NO 129
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ala Leu Asp Ile Tyr Gly Asn Asn Arg Leu Ala
1               5                   10

<210> SEQ ID NO 130
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Met Asp His Glu Asn
1               5

<210> SEQ ID NO 131
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131
```

Ser Tyr Asp Val Lys Met
1               5

<210> SEQ ID NO 132
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ala Ser Ser Leu Asp Phe Val Leu Ala Gly Ser Tyr Ser Tyr Asn Glu
1               5                   10                  15

Gln Phe

<210> SEQ ID NO 133
<211> LENGTH: 453
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 133
atggcttttt ggctgagaag gctgggtcta catttcaggc cacatttggg gagacgaatg      60
gagtcattcc tgggaggtgt tttgctgatt ttgtggcttc aagtggactg ggtgaagagc     120
caaaagatag aacagaattc cgaggccctg aacattcagg agggtaaaac ggccacccctg    180 acctgcaact atacaaacta ttctccagca tacttacagt ggtaccgaca agatccagga     240
agaggccctg ttttcttgct actcatacgt gaaaatgaga agaaaaaag gaaagaaaga      300 ctgaaggtca cctttgatac cacccttaaa cagagtttgt ttcatatcac agcctcccag     360
cctgcagact cagctaccta cctctgtgct ctagacattt atgggaacaa cagactcgct     420
tttgggaagg gaaccaagt ggtggtcata cca                                   453

<210> SEQ ID NO 134
<211> LENGTH: 453
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 134
atggccttct ggctgaggag actgggttta cacttcagac cccatttagg cagaagaatg      60
gagagctttt taggcggcgt gctgctgatt ttatggctgc aagttgactg ggtgaagagc     120
cagaagatcg agcagaacag cgaggcttta aacattcaag aaggcaagac agccactta     180 acttgtaact ataccaacta ctccccgct tatttacagt ggtacagaca agatcccggc      240
agaggccccg tgttttact gctgattcgt gagaacgaga aggagaagag aaggagaga      300 ctgaaggtga ccttcgacac cactttaaag cagtctttat tccacatcac cgccagccag     360
cccgctgata gcgccaccta tttatgcgct ttagacatct acggcaacaa tcgtctggcc     420
ttcggcaagg gcaaccaagt tgtggtgatc ccc                                  453

<210> SEQ ID NO 135
<211> LENGTH: 151
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 135

Met Ala Phe Trp Leu Arg Arg Leu Gly Leu His Phe Arg Pro His Leu
1               5                   10                  15

Gly Arg Arg Met Glu Ser Phe Leu Gly Val Leu Leu Ile Leu Trp
            20                  25                  30

Leu Gln Val Asp Trp Val Lys Ser Gln Lys Ile Glu Gln Asn Ser Glu
        35                  40                  45

Ala Leu Asn Ile Gln Glu Gly Lys Thr Ala Thr Leu Thr Cys Asn Tyr
    50                  55                  60

Thr Asn Tyr Ser Pro Ala Tyr Leu Gln Trp Tyr Arg Gln Asp Pro Gly
65                  70                  75                  80

Arg Gly Pro Val Phe Leu Leu Leu Ile Arg Glu Asn Glu Lys Glu Lys
                85                  90                  95

Arg Lys Glu Arg Leu Lys Val Thr Phe Asp Thr Thr Leu Lys Gln Ser
            100                 105                 110

Leu Phe His Ile Thr Ala Ser Gln Pro Ala Asp Ser Ala Thr Tyr Leu
        115                 120                 125

Cys Ala Leu Asp Ile Tyr Gly Asn Asn Arg Leu Ala Phe Gly Lys Gly
    130                 135                 140

Asn Gln Val Val Val Ile Pro
145                 150

<210> SEQ ID NO 136
<211> LENGTH: 414
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136
atgggaatca ggctcctctg tcgtgtggcc ttttgtttcc tggctgtagg cctcgtagat     60
gtgaaagtaa cccagagctc gagatatcta gtcaaaagga cgggagagaa agttttctg    120 gaatgtgtcc aggatatgga ccatgaaaat atgttctggt atcgacaaga cccaggtctg   180
gggctacggc tgatctatt ctcatatgat gttaaaatga agaaaaagg agatattcct     240 gagggtaca gtgtctctag agagaagaag gagcgcttct ccctgattct ggagtccgcc   300
agcaccaacc agacatctat gtacctctgt gccagcagtt tagattttgt gctagcgggg   360
tcctactcct acaatgagca gttcttcggg ccagggacac ggctcaccgt gcta         414

<210> SEQ ID NO 137
<211> LENGTH: 414
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137
atgggcattc gtctgctgtg tcgtgtggcc ttctgctttt tagccgtggg tttagtggac     60
gtgaaggtga cccagtcctc tcgttatta gtgaagagga ccggcgagaa ggtgttttta   120
gaatgcgtgc aagatatgga ccacgagaac atgttctggt acagacaaga tcccggactg   180
ggtttaaggc tgatctactt cagctacgac gtgaagatga aggagaaggg cgacatcccc   240

```
gagggctact ccgtgtctcg tgagaagaag gagaggttct ctttaatttt agagtccgcc    300
agcaccaacc agaccagcat gtatttatgc gccagctctt tagactttgt gctggccggc    360
agctacagct acaacgagca gttcttcggc cccggcacca gactgaccgt gctg          414
```

<210> SEQ ID NO 138
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

```
Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Leu Asp Phe Val Leu Ala Gly Ser Tyr Ser Tyr Asn Glu Gln Phe
        115                 120                 125

Phe Gly Pro Gly Thr Arg Leu Thr Val Leu
    130                 135
```

<210> SEQ ID NO 139
<211> LENGTH: 292
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

```
Met Ala Phe Trp Leu Arg Arg Leu Gly Leu His Phe Arg Pro His Leu
1               5                   10                  15

Gly Arg Arg Met Glu Ser Phe Leu Gly Val Leu Leu Ile Leu Trp
            20                  25                  30

Leu Gln Val Asp Trp Val Lys Ser Gln Lys Ile Glu Gln Asn Ser Glu
        35                  40                  45

Ala Leu Asn Ile Gln Glu Gly Lys Thr Ala Thr Leu Thr Cys Asn Tyr
    50                  55                  60

Thr Asn Tyr Ser Pro Ala Tyr Leu Gln Trp Tyr Arg Gln Asp Pro Gly
65                  70                  75                  80

Arg Gly Pro Val Phe Leu Leu Leu Ile Arg Glu Asn Glu Lys Glu Lys
                85                  90                  95

Arg Lys Glu Arg Leu Lys Val Thr Phe Asp Thr Thr Leu Lys Gln Ser
            100                 105                 110

Leu Phe His Ile Thr Ala Ser Gln Pro Ala Asp Ser Ala Thr Tyr Leu
        115                 120                 125
```

-continued

```
Cys Ala Leu Asp Ile Tyr Gly Asn Asn Arg Leu Ala Phe Gly Lys Gly
    130                 135                 140

Asn Gln Val Val Val Ile Pro Asp Ile Gln Asn Pro Asp Pro Ala Val
145                 150                 155                 160

Tyr Gln Leu Arg Asp Ser Lys Ser Ser Asp Lys Ser Val Cys Leu Phe
                165                 170                 175

Thr Asp Phe Asp Ser Gln Thr Asn Val Ser Gln Ser Lys Asp Ser Asp
                180                 185                 190

Val Tyr Ile Thr Asp Lys Thr Val Leu Asp Met Arg Ser Met Asp Phe
                195                 200                 205

Lys Ser Asn Ser Ala Val Ala Trp Ser Asn Lys Ser Asp Phe Ala Cys
    210                 215                 220

Ala Asn Ala Phe Asn Asn Ser Ile Ile Pro Glu Asp Thr Phe Phe Pro
225                 230                 235                 240

Ser Pro Glu Ser Ser Cys Asp Val Lys Leu Val Glu Lys Ser Phe Glu
                245                 250                 255

Thr Asp Thr Asn Leu Asn Phe Gln Asn Leu Ser Val Ile Gly Phe Arg
                260                 265                 270

Ile Leu Leu Leu Lys Val Ala Gly Phe Asn Leu Leu Met Thr Leu Arg
    275                 280                 285

Leu Trp Ser Ser
    290

<210> SEQ ID NO 140
<211> LENGTH: 315
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
                20                  25                  30

Arg Thr Gly Glu Lys Val Phe Leu Glu Cys Val Gln Asp Met Asp His
            35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
                100                 105                 110

Ser Leu Asp Phe Val Leu Ala Gly Ser Tyr Ser Tyr Asn Glu Gln Phe
            115                 120                 125

Phe Gly Pro Gly Thr Arg Leu Thr Val Leu Glu Asp Leu Asn Lys Val
    130                 135                 140

Phe Pro Pro Glu Val Ala Val Phe Glu Pro Ser Glu Ala Glu Ile Ser
145                 150                 155                 160

His Thr Gln Lys Ala Thr Leu Val Cys Leu Ala Thr Gly Phe Phe Pro
                165                 170                 175

Asp His Val Glu Leu Ser Trp Trp Val Asn Gly Lys Glu Val His Ser
                180                 185                 190
```

```
Gly Val Ser Thr Asp Pro Gln Pro Leu Lys Glu Gln Pro Ala Leu Asn
        195                 200                 205

Asp Ser Arg Tyr Cys Leu Ser Ser Arg Leu Arg Val Ser Ala Thr Phe
    210                 215                 220

Trp Gln Asn Pro Arg Asn His Phe Arg Cys Gln Val Gln Phe Tyr Gly
225                 230                 235                 240

Leu Ser Glu Asn Asp Glu Trp Thr Gln Asp Arg Ala Lys Pro Val Thr
                245                 250                 255

Gln Ile Val Ser Ala Glu Ala Trp Gly Arg Ala Asp Cys Gly Phe Thr
                260                 265                 270

Ser Val Ser Tyr Gln Gln Gly Val Leu Ser Ala Thr Ile Leu Tyr Glu
            275                 280                 285

Ile Leu Leu Gly Lys Ala Thr Leu Tyr Ala Val Leu Val Ser Ala Leu
            290                 295                 300

Val Leu Met Ala Met Val Lys Arg Lys Asp Phe
305                 310                 315

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Met Leu Thr Gly Pro Pro Ala Arg Val
1               5

<210> SEQ ID NO 142
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Thr Arg Asp Thr Thr Tyr Tyr
1               5

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Arg Asn Ser Phe Asp Glu Gln Asn
1               5

<210> SEQ ID NO 144
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ala Leu Ser Glu Ala Arg Val Phe Asn Gly Ala Asn Ser Lys Leu Thr
```

```
1               5                   10                  15
```

<210> SEQ ID NO 145
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ser Gly His Asp Asn
1               5

<210> SEQ ID NO 146
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Phe Val Lys Glu Ser Lys
1               5

<210> SEQ ID NO 147
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Ala Ser Ser Gln Ala Asp Ser Pro Leu His
1               5                   10

<210> SEQ ID NO 148
<211> LENGTH: 417
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 148
atgctgactg ccagcctgtt gagggcagtc atagcctcca tctgtgttgt atccagcatg      60
gctcagaagg taactcaagc gcagactgaa atttctgtgg tggagaagga ggatgtgacc     120
ttggactgtg tgtatgaaac ccgtgatact acttattact tattctggta caagcaacca     180
ccaagtggag aattggtttt ccttattcgt cggaactctt ttgatgagca aaatgaaata     240
agtggtcggt attcttggaa cttccagaaa tccaccagtt ccttcaactt caccatcaca     300
gcctcacaag tcgtggactc agcagtatac ttctgtgctc tgagtgaggc ccgcgttttc     360
aatggagcca atagtaagct gacatttgga aaaggaatac tctgagtgt tagacca       417

<210> SEQ ID NO 149
<211> LENGTH: 417
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 149

```
atgctgaccg ccagcctgct gagggctgtg atcgccagca tctgcgtcgt gtccagcatg    60
gctcaaaagg tcacacaggc ccagacagag atctccgtcg tcgagaaaga ggacgtgacc   120
ctcgactgcg tgtatgagac cagggacacc acatactacc tgttttggta caagcagccc   180
cccagcggag agctcgtgtt tctgatcaga aggaacagct tgatgaaca gaatgagatc    240 tccggcaggt actcctggaa cttccagaag agcacctcca gcttcaactt cacaattaca   300
gcttcccagg tggtggatag cgccgtgtat ttctgcgctc tcagcgaggc cagggtgttc   360
aacggcgcca attccaaact gaccttcggc aaaggcatca cactgtccgt gagaccc      417
```

<210> SEQ ID NO 150
<211> LENGTH: 139
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 150

```
Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
            20                  25                  30

Val Val Glu Lys Glu Asp Val Thr Leu Asp Cys Val Tyr Glu Thr Arg
        35                  40                  45

Asp Thr Thr Tyr Tyr Leu Phe Trp Tyr Lys Gln Pro Pro Ser Gly Glu
    50                  55                  60

Leu Val Phe Leu Ile Arg Arg Asn Ser Phe Asp Glu Gln Asn Glu Ile
65                  70                  75                  80

Ser Gly Arg Tyr Ser Trp Asn Phe Gln Lys Ser Thr Ser Ser Phe Asn
                85                  90                  95

Phe Thr Ile Thr Ala Ser Gln Val Val Asp Ser Ala Val Tyr Phe Cys
            100                 105                 110

Ala Leu Ser Glu Ala Arg Val Phe Asn Gly Ala Asn Ser Lys Leu Thr
        115                 120                 125

Phe Gly Lys Gly Ile Thr Leu Ser Val Arg Pro
    130                 135
```

<210> SEQ ID NO 151
<211> LENGTH: 393
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 151

```
atggtttcca ggcttctcag tttagtgtcc ctttgtctcc tgggagcaaa gcacatagaa    60
gctggagtta ctcagttccc cagccacagc gtaatagaga agggccagac tgtgactctg   120
agatgtgacc caatttctgg acatgataat ctttattggt atcgacgtgt tatgggaaaa   180
gaaataaaat ttctgttaca ttttgtgaaa gagtctaaac aggatgaatc cggtatgccc   240
aacaatcgat tcttagctga aaggactgga gggacgtatt ctactctgaa ggtgcagcct   300
gcagaactgg aggattctgg agtttatttc tgtgccagca gccaagcgga ttcacccctc   360
cactttggga atgggaccag gctcactgtg aca                                 393
```

<210> SEQ ID NO 152
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 152

```
atggtctcca ggctgctctc cctcgtgagc ctgtgtctcc tgggagccaa gcacattgag      60
gccggcgtga cccaattccc cagccacagc gtgattgaga agggacagac cgtcaccctg     120
aggtgtgatc ctatcagcgg ccacgacaac ctctactggt ataggagagt catgggcaag     180
gaaattaaat ttctgctgca tttcgtgaaa gagtccaaac aggacgaaag cggcatgccc     240
aataataggt tcctcgccga gaggaccggc ggcacatatt ccaccctgaa ggtccagccc     300
gctgagctcg aagactccgg cgtctatttc tgtgcctcca gccaggctga ctcccctctc     360
catttcggaa acggcaccag gctcaccgtg acc                                  393
```

<210> SEQ ID NO 153
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Met Val Ser Arg Leu Leu Ser Leu Val Ser Leu Cys Leu Leu Gly Ala
1               5                   10                  15

Lys His Ile Glu Ala Gly Val Thr Gln Phe Pro Ser His Ser Val Ile
            20                  25                  30

Glu Lys Gly Gln Thr Val Thr Leu Arg Cys Asp Pro Ile Ser Gly His
        35                  40                  45

Asp Asn Leu Tyr Trp Tyr Arg Arg Val Met Gly Lys Glu Ile Lys Phe
    50                  55                  60

Leu Leu His Phe Val Lys Glu Ser Lys Gln Asp Glu Ser Gly Met Pro
65                  70                  75                  80

Asn Asn Arg Phe Leu Ala Glu Arg Thr Gly Gly Thr Tyr Ser Thr Leu
                85                  90                  95

Lys Val Gln Pro Ala Glu Leu Glu Asp Ser Gly Val Tyr Phe Cys Ala
            100                 105                 110

Ser Ser Gln Ala Asp Ser Pro Leu His Phe Gly Asn Gly Thr Arg Leu
        115                 120                 125

Thr Val Thr
    130

<210> SEQ ID NO 154
<211> LENGTH: 280
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
            20                  25                  30

Val Val Glu Lys Glu Asp Val Thr Leu Asp Cys Val Tyr Glu Thr Arg
            35                  40                  45

Asp Thr Thr Tyr Tyr Leu Phe Trp Tyr Lys Gln Pro Pro Ser Gly Glu
 50                  55                  60

Leu Val Phe Leu Ile Arg Arg Asn Ser Phe Asp Glu Gln Asn Glu Ile
 65                  70                  75                  80

Ser Gly Arg Tyr Ser Trp Asn Phe Gln Lys Ser Thr Ser Ser Phe Asn
                 85                  90                  95

Phe Thr Ile Thr Ala Ser Gln Val Val Asp Ser Ala Val Tyr Phe Cys
                100                 105                 110

Ala Leu Ser Glu Ala Arg Val Phe Asn Gly Ala Asn Ser Lys Leu Thr
            115                 120                 125

Phe Gly Lys Gly Ile Thr Leu Ser Val Arg Pro Asp Ile Gln Asn Pro
            130                 135                 140

Asp Pro Ala Val Tyr Gln Leu Arg Asp Ser Lys Ser Ser Asp Lys Ser
145                 150                 155                 160

Val Cys Leu Phe Thr Asp Phe Asp Ser Gln Thr Asn Val Ser Gln Ser
                165                 170                 175

Lys Asp Ser Asp Val Tyr Ile Thr Asp Lys Thr Val Leu Asp Met Arg
                180                 185                 190

Ser Met Asp Phe Lys Ser Asn Ser Ala Val Ala Trp Ser Asn Lys Ser
            195                 200                 205

Asp Phe Ala Cys Ala Asn Ala Phe Asn Asn Ser Ile Ile Pro Glu Asp
            210                 215                 220

Thr Phe Phe Pro Ser Pro Glu Ser Ser Cys Asp Val Lys Leu Val Glu
225                 230                 235                 240

Lys Ser Phe Glu Thr Asp Thr Asn Leu Asn Phe Gln Asn Leu Ser Val
                245                 250                 255

Ile Gly Phe Arg Ile Leu Leu Leu Lys Val Ala Gly Phe Asn Leu Leu
                260                 265                 270

Met Thr Leu Arg Leu Trp Ser Ser
            275                 280

<210> SEQ ID NO 155
<211> LENGTH: 308
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Met Val Ser Arg Leu Leu Ser Leu Val Ser Leu Cys Leu Leu Gly Ala
 1               5                  10                  15

Lys His Ile Glu Ala Gly Val Thr Gln Phe Pro Ser His Ser Val Ile
             20                  25                  30

Glu Lys Gly Gln Thr Val Thr Leu Arg Cys Asp Pro Ile Ser Gly His
             35                  40                  45

Asp Asn Leu Tyr Trp Tyr Arg Arg Val Met Gly Lys Glu Ile Lys Phe
 50                  55                  60

Leu Leu His Phe Val Lys Glu Ser Lys Gln Asp Glu Ser Gly Met Pro
65                   70                  75                  80

Asn Asn Arg Phe Leu Ala Glu Arg Thr Gly Gly Thr Tyr Ser Thr Leu
                 85                  90                  95

Lys Val Gln Pro Ala Glu Leu Glu Asp Ser Gly Val Tyr Phe Cys Ala
            100                 105                 110

```
Ser Ser Gln Ala Asp Ser Pro Leu His Phe Gly Asn Gly Thr Arg Leu
        115                 120                 125

Thr Val Thr Glu Asp Leu Asn Lys Val Phe Pro Glu Val Ala Val
130                 135                 140

Phe Glu Pro Ser Glu Ala Glu Ile Ser His Thr Gln Lys Ala Thr Leu
145                 150                 155                 160

Val Cys Leu Ala Thr Gly Phe Phe Pro Asp His Val Glu Leu Ser Trp
                165                 170                 175

Trp Val Asn Gly Lys Glu Val His Ser Gly Val Ser Thr Asp Pro Gln
                180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
        210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Val Ser Tyr Gln Gln Gly
                260                 265                 270

Val Leu Ser Ala Thr Ile Leu Tyr Glu Ile Leu Leu Gly Lys Ala Thr
            275                 280                 285

Leu Tyr Ala Val Leu Val Ser Ala Leu Val Leu Met Ala Met Val Lys
        290                 295                 300

Arg Lys Asp Phe
305

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ala Leu Asn Ser Glu Ala Leu Ser Val
1               5

<210> SEQ ID NO 157
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Met Arg Arg Leu Ser Ala Ala Arg Arg Ala Gly Thr Ser Cys Ala Asn
1               5                   10                  15

Cys Gln Thr Thr Thr Thr Thr Leu Trp Arg Arg Asn Ala Asn Gly Asp
                20                  25                  30

Pro Val Cys Asn Ala Cys Gly Leu Tyr Tyr Lys Leu His Asn Ile Asn
            35                  40                  45

Arg Pro Leu Thr Met Lys Lys Glu Gly Ile Gln Thr Arg Asn Arg Lys
        50                  55                  60

Met Ser Ser Lys Ser Lys Lys Cys Lys Lys Val His Asp Ser Leu Glu
65                  70                  75                  80
```

```
Asp Phe Pro Lys Asn Ser Ser Phe Pro Gly Arg Pro Leu Gln Thr His
                85                  90                  95

Val Leu Pro Glu Pro His Leu Ala Leu Gln Pro Leu Gln Pro His Ala
            100                 105                 110

Asp His Ala His Ala Asp Ala Pro Ala Ile Gln Pro Val Leu Trp Thr
            115                 120                 125

Thr Pro Pro Leu Gln His Gly His Arg His Gly Leu Glu Pro Cys Ser
130                 135                 140

Met Leu Thr Gly Pro Pro Ala Arg Val Pro Ala Val Pro Phe Asp Leu
145                 150                 155                 160

His Phe Cys Arg Ser Ser Ile Met Lys Pro Lys Arg Asp Gly Tyr Met
                165                 170                 175

Phe Leu Lys Ala Glu Ser Lys Ile Met Phe Ala Thr Leu Gln Arg Ser
            180                 185                 190

Ser Leu Trp Cys Leu Cys Ser Asn His
        195                 200

<210> SEQ ID NO 158
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Pro Gly Arg Pro Leu Gln Thr His Val Leu Pro Glu Pro His Leu Ala
1               5                   10                  15

Leu Gln Pro Leu Gln Pro His Ala Asp His Ala His Ala Asp Ala Pro
            20                  25                  30

Ala Ile Gln Pro Val Leu Trp Thr Thr Pro Pro Leu Gln His Gly His
        35                  40                  45

Arg His Gly Leu Glu Pro Cys Ser Met Leu Thr Gly Pro Pro Ala Arg
    50                  55                  60

Val Pro Ala Val Pro Phe Asp Leu His Phe Cys Arg Ser Ser Ile Met
65                  70                  75                  80

Lys Pro Lys Arg Asp Gly Tyr Met Phe Leu Lys Ala Glu Ser Lys Ile
                85                  90                  95

Met Phe Ala Thr Leu Gln Arg Ser Ser Leu Trp Cys Leu Cys Ser Asn
            100                 105                 110

His

<210> SEQ ID NO 159
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Asp Arg Gly Ser Gln Ser
1               5

<210> SEQ ID NO 160
<211> LENGTH: 6
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 160

Ile Tyr Ser Asn Gly Asp
1               5

<210> SEQ ID NO 161
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ala Val Asn Asp Tyr Gly Gly Ser Gln Gly Asn Leu Ile Phe
1               5                   10

<210> SEQ ID NO 162
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ser Glu His Asn Arg
1               5

<210> SEQ ID NO 163
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Phe Gln Asn Glu Ala Gln
1               5

<210> SEQ ID NO 164
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ala Ser Ser Phe Gly Pro Asp Glu Lys Leu Phe Phe
1               5                   10

<210> SEQ ID NO 165
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 165
atgatgaaat ccttgagagt tttactagtg atcctgtggc ttcagttgag ctgggtttgg      60
agccaacaga aggaggtgga gcagaattct ggaccccctca gtgttccaga gggagccatt     120

```
gcctctctca actgcactta cagtgaccga ggttcccagt ccttcttctg gtacagacaa    180
tattctggga aaagccctga gttgataatg ttcatatact ccaatggtga caaagaagat    240
ggaaggttta cagcacagct caataaagcc agccagtatg tttctctgct catcagagac    300
tcccagccca gtgattcagc cacctacctc tgtgccgtga acgattatgg aggaagccaa    360
ggaaatctca tctttggaaa aggcactaaa ctctctgtta aacca                    405
```

<210> SEQ ID NO 166
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 166

```
atgatgaaga gcctgcgggt gctgctggtc atcctgtggc tgcagctgtc ttgggtgtgg    60
agccagcaga aggaggtgga gcagaactcc ggaccactgt ctgtgcctga gggagccatc    120
gccagcctga attgcaccta ctccgacaga ggctcccagt cttttctttg gtacaggcag    180
tatagcggca gtccccccga gctgatcatg ttcatctact ccaacggcga caaggaggat    240
ggccgcttta cagcccagct gaataaggcc agccagtacg tgagcctgct gatccgggac    300
tctcagccaa gcgattccgc cacctacctg tgcgccgtga acgattatgg cggcagccag    360
ggcaatctga tctttggcaa gggcacaaag ctgtccgtga agccc                    405
```

<210> SEQ ID NO 167
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

```
Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asn Ser Gly Pro
            20                  25                  30

Leu Ser Val Pro Glu Gly Ala Ile Ala Ser Leu Asn Cys Thr Tyr Ser
        35                  40                  45

Asp Arg Gly Ser Gln Ser Phe Phe Trp Tyr Arg Gln Tyr Ser Gly Lys
    50                  55                  60

Ser Pro Glu Leu Ile Met Phe Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Val Asn Asp Tyr Gly Gly Ser Gln Gly Asn Leu Ile Phe Gly Lys Gly
        115                 120                 125

Thr Lys Leu Ser Val Lys Pro
    130                 135
```

<210> SEQ ID NO 168
<211> LENGTH: 396
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 168

```
atgggcacca gcctcctctg ctggatggcc ctgtgtctcc tgggggcaga tcacgcagat    60
actggagtct cccagaaccc cagacacaag atcacaaaga ggggacagaa tgtaactttc   120
aggtgtgatc caatttctga acacaaccgc ctttattggt accgacagac cctggggcag   180
ggcccagagt ttctgactta cttccagaat gaagctcaac tagaaaaatc aaggctgctc   240
agtgatcggt tctctgcaga gaggcctaag ggatctttct ccaccttgga gatccagcgc   300
acagagcagg gggactcggc catgtatctc tgtgccagca gcttcggacc tgatgaaaaa   360
ctgttttttg gcagtggaac ccagctctct gtcttg                              396
```

<210> SEQ ID NO 169
<211> LENGTH: 396
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 169

```
atgggcacct ctctgctgtg ctggatggca ctgtgcctgc tgggagcaga ccacgcagat    60
acaggcgtga gccagaaccc acgccacaag atcaccaagc ggggccagaa tgtgacattc   120
agatgcgacc ccatcagcga gcacaacagg ctgtactggt ataggcagac cctgggacag   180
ggaccagagt tcctgacata ctttcagaat gaggcccagc tggagaagtc tcggctgctg   240
agcgatagat tctccgccga gaggcctaag ggctcctttt ctaccctgga gatccagagg   300
acagagcagg gcgactccgc catgtatctg tgcgccagct ccttcggccc tgatgagaag   360
ctgttctttg gctctggcac ccagctgagc gtgctg                              396
```

<210> SEQ ID NO 170
<211> LENGTH: 132
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 170

Met Gly Thr Ser Leu Leu Cys Trp Met Ala Leu Cys Leu Leu Gly Ala
1               5                   10                  15

Asp His Ala Asp Thr Gly Val Ser Gln Asn Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Phe Gly Pro Asp Glu Lys Leu Phe Phe Gly Ser Gly Thr Gln
        115                 120                 125

```
Leu Ser Val Leu
    130

<210> SEQ ID NO 171
<211> LENGTH: 276
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Met Met Lys Ser Leu Arg Val Leu Val Ile Leu Trp Leu Gln Leu
1               5                   10                  15

Ser Trp Val Trp Ser Gln Gln Lys Glu Val Glu Gln Asn Ser Gly Pro
                20                  25                  30

Leu Ser Val Pro Glu Gly Ala Ile Ala Ser Leu Asn Cys Thr Tyr Ser
            35                  40                  45

Asp Arg Gly Ser Gln Ser Phe Phe Trp Tyr Arg Gln Tyr Ser Gly Lys
        50                  55                  60

Ser Pro Glu Leu Ile Met Phe Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Val Asn Asp Tyr Gly Gly Ser Gln Gly Asn Leu Ile Phe Gly Lys Gly
        115                 120                 125

Thr Lys Leu Ser Val Lys Pro Asp Ile Gln Asn Pro Asp Pro Ala Val
130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
    210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
        275

<210> SEQ ID NO 172
<211> LENGTH: 309
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172
```

```
Met Gly Thr Ser Leu Leu Cys Trp Met Ala Leu Cys Leu Leu Gly Ala
1               5                   10                  15

Asp His Ala Asp Thr Gly Val Ser Gln Asn Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Phe Gly Pro Asp Glu Lys Leu Phe Phe Gly Ser Gly Thr Gln
        115                 120                 125

Leu Ser Val Leu Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Phe
305

<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ser Leu Leu Asn Tyr Leu Arg Glu Met
1               5

<210> SEQ ID NO 174
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 174

Asp Arg Gly Ser Gln Ser
1               5

<210> SEQ ID NO 175
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ile Tyr Ser Asn Gly Asp
1               5

<210> SEQ ID NO 176
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ala Val Asn Glu Gly Asp Ser Ser Tyr Lys Leu Ile
1               5                   10

<210> SEQ ID NO 177
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ser Gly Asp Leu Ser
1               5

<210> SEQ ID NO 178
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Tyr Tyr Asn Gly Glu Glu
1               5

<210> SEQ ID NO 179
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ala Ser Ser Pro Gly Ala Asn Glu Lys Leu Phe
1               5                   10
```

<210> SEQ ID NO 180
<211> LENGTH: 402
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 180

```
atgatgaaat ccttgagagt tttactagtg atcctgtggc ttcagttgag ctgggtttgg      60
agccaacaga aggaggtgga gcagaattct ggacccctca gtgttccaga gggagccatt     120
gcctctctca actgcactta cagtgaccga ggttcccagt ccttcttctg gtacagacaa     180
tattctggga aaagccctga gttgataatg ttcatatact ccaatggtga caagaagat      240
ggaaggttta cagcacagct caataaagcc agccagtatg tttctctgct catcagagac     300
tcccagccca gtgattcagc cacctacctc tgtgccgtga acgaggggga tagcagctat     360
aaattgatct cgggagtgg accagactg ctggtcaggc ct                          402
```

<210> SEQ ID NO 181
<211> LENGTH: 402
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 181

```
atgatgaaga gcctgcgggt gctgctggtc atcctgtggc tgcagctgag ctgggtgtgg      60
tcccagcaga aggaggtgga gcagaactct ggaccactga gcgtgcctga gggagccatc     120
gcctccctga attgcaccta ctctgacaga ggcagccagt ccttcttttg gtacaggcag     180
tattccggca agtctcccga gctgatcatg ttcatctaca gcaacggcga caaggaggat     240
ggccgcttta cagcccagct gaataaggcc tcccagtacg tgagcctgct gatccgggac     300
tctcagccat ctgatagcgc cacctacctg tgcgccgtga acgagggcga tagctcctat     360
aagctgatct tggcagcgg cacaagactg ctggtgaggc cc                         402
```

<210> SEQ ID NO 182
<211> LENGTH: 134
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 182

```
Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asn Ser Gly Pro
            20                  25                  30

Leu Ser Val Pro Glu Gly Ala Ile Ala Ser Leu Asn Cys Thr Tyr Ser
        35                  40                  45

Asp Arg Gly Ser Gln Ser Phe Phe Trp Tyr Arg Gln Tyr Ser Gly Lys
    50                  55                  60

Ser Pro Glu Leu Ile Met Phe Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95
```

Leu Ile Arg Asp Ser Gln Pro Ser Asp Ser Ala Thr Tyr Leu Cys Ala
            100                 105                 110

Val Asn Glu Gly Asp Ser Ser Tyr Lys Leu Ile Phe Gly Ser Gly Thr
115                 120                 125

Arg Leu Leu Val Arg Pro
    130

<210> SEQ ID NO 183
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 183
atgggcttca ggctcctctg ctgtgtggcc ttttgtctcc tgggagcagg cccagtggat        60
tctggagtca cacaaacccc aaagcacctg atcacagcaa ctggacagcg agtgacgctg       120
agatgctccc ctaggtctgg agacctctct gtgtactggt accaacagag cctgaccag        180 ggcctccagt tcctcattca gtattataat ggagaagaga gagcaaaagg aaacattctt       240
gaacgattct ccgcacaaca gttccctgac ttgcactctg aactaaacct gagctctctg       300
gagctggggg actcagcttt gtatttctgt gccagcagcc gggggctaa tgaaaaactg       360 ttttttggca gtggaaccca gctctctgtc ttg                                   393

<210> SEQ ID NO 184
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 184
atgggcttcc ggctgctgtg ctgcgtggca ttttgcctgc tgggagcagg accagtggac        60
tccggcgtga cccagacacc caagcacctg atcaccgcaa caggacagag ggtgaccctg       120
agatgttccc ctaggtctgg cgacctgagc gtgtactggt atcagcagtc cctggatcag       180
ggcctgcagt tcctgatcca gtactataac ggcgaggagc gcgccaaggg caatatcctg       240
gagcggttct ccgcccagca gtttcccgac ctgcactctg agctgaacct gagctccctg       300
gagctgggcg atagcgccct gtacttctgc gcctctagcc ctggcgccaa tgagaagctg       360
ttctttggca gcggcacccca gctgtccgtg ctg                                  393

<210> SEQ ID NO 185
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

```
Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Pro Gly Ala Asn Glu Lys Leu Phe Phe Gly Ser Gly Thr Gln Leu
        115                 120                 125

Ser Val Leu
    130

<210> SEQ ID NO 186
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asn Ser Gly Pro
            20                  25                  30

Leu Ser Val Pro Glu Gly Ala Ile Ala Ser Leu Asn Cys Thr Tyr Ser
        35                  40                  45

Asp Arg Gly Ser Gln Ser Phe Phe Trp Tyr Arg Gln Tyr Ser Gly Lys
    50                  55                  60

Ser Pro Glu Leu Ile Met Phe Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Val Asn Glu Gly Asp Ser Ser Tyr Lys Leu Ile Phe Gly Ser Gly Thr
        115                 120                 125

Arg Leu Leu Val Arg Pro Asp Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270
```

Trp Ser Ser
    275

<210> SEQ ID NO 187
<211> LENGTH: 308
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Pro Gly Ala Asn Glu Lys Leu Phe Phe Gly Ser Gly Thr Gln Leu
        115                 120                 125

Ser Val Leu Glu Asp Leu Asn Lys Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Phe Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Val Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Phe
305

<210> SEQ ID NO 188
<211> LENGTH: 9
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 188

Ser Leu Leu Asn Tyr Leu Arg Glu Met
1               5

<210> SEQ ID NO 189
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Asn Ser Met Phe Asp Tyr
1               5

<210> SEQ ID NO 190
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Ile Ser Ser Ile Lys Asp Lys
1               5

<210> SEQ ID NO 191
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ala Ala Ser Ala Ser Asn Asn Asp Met Arg
1               5                   10

<210> SEQ ID NO 192
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Ser Glu His Asn Arg
1               5

<210> SEQ ID NO 193
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Phe Gln Asn Glu Ala Gln
1               5
```

<210> SEQ ID NO 194
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ala Ser Ser Gln Ser Gly Gln Gly Pro Tyr Glu Gln Tyr
1               5                   10

<210> SEQ ID NO 195
<211> LENGTH: 411
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 195
atggccatgc tcctgggggc atcagtgctg attctgtggc ttcagccaga ctgggtaaac      60
agtcaacaga agaatgatga ccagcaagtt aagcaaaatt caccatccct gagcgtccag     120
gaaggaagaa tttctattct gaactgtgac tatactaaca gcatgtttga ttatttccta     180
tggtacaaaa ataccctgc tgaaggtcct acattcctga tatctataag ttccattaag      240
gataaaaatg aagatggaag attcactgtc ttcttaaaca aaagtgccaa gcacctctct     300
ctgcacattg tgccctccca gcctggagac tctgcagtgt acttctgtgc agcaagcgcg     360
tcaaacaatg acatgcgctt tggagcaggg accagactga cagtaaaacc a              411

<210> SEQ ID NO 196
<211> LENGTH: 411
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 196
atggcaatgc tgctgggagc ctctgtgctg atcctgtggc tgcagccaga ttgggtgaac      60
tcccagcaga agaatgacga tcagcaggtg aagcagaata gccctccct gtctgtgcag      120 gagggcagaa tcagcatcct gaactgcgac tacaccaatt ccatgttcga ttatttctg      180 tggtacaaga gtatccagc cgagggcccc acctttctga tcagcatctc ctctatcaag      240
gacaagaacg aggatggcag gttcacagtg tttctgaata gtctgccaa gcacctgagc      300 ctgcacatcg tgccatccca gcctggcgac tctgccgtgt acttctgtgc cgccagcgcc     360
tccaacaatg atatgagatt tggcgccggc accaggctga cagtgaagcc c              411

<210> SEQ ID NO 197
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Met Ala Met Leu Leu Gly Ala Ser Val Leu Ile Leu Trp Leu Gln Pro
1               5                   10                  15

Asp Trp Val Asn Ser Gln Gln Lys Asn Asp Gln Gln Val Lys Gln
            20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
    50                  55                  60

Tyr Pro Ala Glu Gly Pro Thr Phe Leu Ile Ser Ile Ser Ile Lys
65              70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ala Ser Ala Ser Asn Asn Asp Met Arg Phe Gly
        115                 120                 125

Ala Gly Thr Arg Leu Thr Val Lys Pro
    130                 135

<210> SEQ ID NO 198
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 198
atgggcacca gcctcctctg ctggatggcc ctgtgtctcc tgggggcaga tcacgcagat      60
actggagtct cccaggaccc cagacacaag atcacaaaga ggggacagaa tgtaactttc     120
aggtgtgatc aatttctga acacaaccgc ctttattggt accgacagac cctggggcag     180
ggcccagagt ttctgactta cttccagaat gaagctcaac tagaaaaatc aaggctgctc     240
agtgatcggt tctctgcaga gaggcctaag ggatctttct ccaccttgga gatccagcgc     300
acagagcagg gggactcggc catgtatctc tgtgccagca gccaatcggg acaggggccc     360
tacgagcagt acttcgggcc gggcaccagg ctcacggtca cagag                    405

<210> SEQ ID NO 199
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 199
atgggcacct ctctgctgtg ctggatggca ctgtgcctgc tgggagcaga ccacgcagat      60
acaggcgtga gccaggaccc ccgccacaag atcaccaagc ggggccagaa cgtgacattc     120
agatgcgatc ctatctccga gcacaatagg ctgtactggt ataggcagac cctgggacag     180
ggaccagagt tcctgacata ctttcagaac gaggcccagc tggagaagag ccggctgctg     240
tccgacagat ctctgccga gaggcctaag ggcagctttt ccaccctgga gatccagagg     300
acagagcagg gcgattctgc catgtatctg tgcgccagct cccagagcgg acagggacct     360
tacgagcagt atttcggacc aggaaccagg ctgaccgtga cagag                    405

<210> SEQ ID NO 200
<211> LENGTH: 135
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 200

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Gln Ser Gly Gln Gly Pro Tyr Glu Gln Tyr Phe Gly Pro Gly
        115                 120                 125

Thr Arg Leu Thr Val Thr Glu
    130                 135

<210> SEQ ID NO 201
<211> LENGTH: 278
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Met Ala Met Leu Leu Gly Ala Ser Val Leu Ile Leu Trp Leu Gln Pro
1               5                   10                  15

Asp Trp Val Asn Ser Gln Gln Lys Asn Asp Asp Gln Gln Val Lys Gln
            20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
    50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ala Ser Ala Ser Asn Asn Asp Met Arg Phe Gly
        115                 120                 125

Ala Gly Thr Arg Leu Thr Val Lys Pro Asp Ile Gln Asn Pro Asp Pro
    130                 135                 140

Ala Val Tyr Gln Leu Arg Asp Ser Lys Ser Ser Asp Lys Ser Val Cys
145                 150                 155                 160

Leu Phe Thr Asp Phe Asp Ser Gln Thr Asn Val Ser Gln Ser Lys Asp
                165                 170                 175

Ser Asp Val Tyr Ile Thr Asp Lys Thr Val Leu Asp Met Arg Ser Met
            180                 185                 190
```

```
Asp Phe Lys Ser Asn Ser Ala Val Ala Trp Ser Asn Lys Ser Asp Phe
        195                 200                 205

Ala Cys Ala Asn Ala Phe Asn Asn Ser Ile Ile Pro Glu Asp Thr Phe
    210                 215                 220

Phe Pro Ser Pro Glu Ser Ser Cys Asp Val Lys Leu Val Glu Lys Ser
225                 230                 235                 240

Phe Glu Thr Asp Thr Asn Leu Asn Phe Gln Asn Leu Ser Val Ile Gly
            245                 250                 255

Phe Arg Ile Leu Leu Leu Lys Val Ala Gly Phe Asn Leu Leu Met Thr
            260                 265                 270

Leu Arg Leu Trp Ser Ser
            275

<210> SEQ ID NO 202
<211> LENGTH: 312
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Gln Ser Gly Gln Gly Pro Tyr Glu Gln Tyr Phe Gly Pro Gly
        115                 120                 125

Thr Arg Leu Thr Val Thr Glu Glu Asp Leu Asn Lys Val Phe Pro Pro
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Phe Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Val Ser
```

```
                260                 265                 270
Tyr Gln Gln Gly Val Leu Ser Ala Thr Ile Leu Tyr Glu Ile Leu Leu
            275                 280                 285

Gly Lys Ala Thr Leu Tyr Ala Val Leu Val Ser Ala Leu Val Leu Met
        290                 295                 300

Ala Met Val Lys Arg Lys Asp Phe
305                 310
```

<210> SEQ ID NO 203
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

```
Lys Pro Lys Arg Asp Gly Tyr Met Phe
1               5
```

<210> SEQ ID NO 204
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

```
Tyr Gly Gly Thr Val Asn
1               5
```

<210> SEQ ID NO 205
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

```
Tyr Phe Ser Gly Asp Pro Leu Val
1               5
```

<210> SEQ ID NO 206
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

```
Ala Val Ile Ser Val Thr Gly Asn Asn Arg Lys Leu Ile
1               5                   10
```

<210> SEQ ID NO 207
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Leu Asn His Asp Ala

<210> SEQ ID NO 208
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Ser Gln Ile Val Asn Asp
1               5

<210> SEQ ID NO 209
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ala Ser Ser Arg Thr Ala Met Asn Thr Glu Ala Phe
1               5                   10

<210> SEQ ID NO 210
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 210

```
atgctcctgt tgctcatacc agtgctgggg atgatttttg ccctgagaga tgccagagcc    60
cagtctgtga gccagcataa ccaccacgta attctctctg aagcagcctc actggagttg   120
ggatgcaact attcctatgg tggaactgtt aatctcttct ggtatgtcca gtaccctggt   180
caacaccttc agcttctcct caagtacttt tcaggggatc cactggttaa aggcatcaag   240
ggctttgagg ctgaatttat aaagagtaaa ttctccttta tctgaggaa accctctgtg   300 cagtggagtg acacagctga gtacttctgt gccgtgatct ccgtgactgg caacaaccgt   360
aagctgattt ggggattggg aacaagcctg cagtaaatc cg                       402
```

<210> SEQ ID NO 211
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 211

```
atgctgctgc tgctgatccc tgtgctgggc atgatctttg cactgaggga cgcaagagca    60
cagtccgtgt ctcagcacaa ccaccacgtg atcctgagcg aggcagcctc cctggagctg   120
ggctgcaact actcttatgg cggcacagtg aatctgttct ggtacgtgca gtatccaggc   180
cagcacctgc agctgctgct gaagtacttt agcggcgacc ccctggtgaa gggcatcaag   240
ggcttcgagg ccgagtttat caagtccaag ttctctttta acctgcggaa gccatctgtg   300
cagtggagcg ataccgccga gtatttctgt gccgtgatca gcgtgacagg caacaataga   360
aagctgatct ggggactggg cacctccctg gccgtgaatc cc                      402
```

<210> SEQ ID NO 212
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Met Leu Leu Leu Leu Ile Pro Val Leu Gly Met Ile Phe Ala Leu Arg
1               5                   10                  15

Asp Ala Arg Ala Gln Ser Val Ser Gln His Asn His His Val Ile Leu
            20                  25                  30

Ser Glu Ala Ala Ser Leu Glu Leu Gly Cys Asn Tyr Ser Tyr Gly Gly
        35                  40                  45

Thr Val Asn Leu Phe Trp Tyr Val Gln Tyr Pro Gly Gln His Leu Gln
    50                  55                  60

Leu Leu Leu Lys Tyr Phe Ser Gly Asp Pro Leu Val Lys Gly Ile Lys
65                  70                  75                  80

Gly Phe Glu Ala Glu Phe Ile Lys Ser Lys Phe Ser Phe Asn Leu Arg
                85                  90                  95

Lys Pro Ser Val Gln Trp Ser Asp Thr Ala Glu Tyr Phe Cys Ala Val
            100                 105                 110

Ile Ser Val Thr Gly Asn Asn Arg Lys Leu Ile Trp Gly Leu Gly Thr
        115                 120                 125

Ser Leu Ala Val Asn Pro
    130

<210> SEQ ID NO 213
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 213
atgagcaacc aggtgctctg ctgtgtggtc ctttgtctcc tgggagcaaa caccgtggat      60
ggtggaatca ctcagtcccc gaagtacctg ttcagaaagg aaggacagaa tgtgaccctg     120
agttgtgaac agaatttgaa ccacgatgcc atgtactggt accgacagga cccagggcaa     180
gggctgagat tgatctacta ctcacagata gtaaatgact tcagaaagg agatatagct      240 gaagggtaca gcgtctctcg ggagaagaag gaatcctttc ctctcactgt gacatcggcc     300
caaaagaacc cgacagcttt ctatctctgt gccagtagtc ggactgcaat gaacactgaa     360
gctttctttg gacaaggcac cagactcaca gttgta                               396

<210> SEQ ID NO 214
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 214
atgtccaacc aggtgctgtg ctgcgtggtg ctgtgcctgc tgggagcaaa taccgtggac      60
ggaggcatca cacagtcccc caagtacctg ttcaggaagg agggccagaa cgtgaccctg     120

```
tcttgtgagc agaacctgaa tcacgacgcc atgtactggt ataggcagga ccccggacag    180
ggactgagac tgatctacta tagccagatc gtgaatgact ttcagaaggg cgacatcgcc    240
gagggctact ccgtgtctag ggagaagaag gagagcttcc ccctgaccgt gacatccgcc    300
cagaagaacc ctacagcctt ttatctgtgc gccagctccc gcaccgccat gaatacagag    360
gccttctttg gccagggcac caggctgaca gtggtg                              396
```

<210> SEQ ID NO 215
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide <400> SEQUENCE: 215

```
Met Ser Asn Gln Val Leu Cys Cys Val Val Leu Cys Leu Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Arg Thr Ala Met Asn Thr Glu Ala Phe Phe Gly Gln Gly Thr Arg
        115                 120                 125

Leu Thr Val Val
    130
```

<210> SEQ ID NO 216
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide <400> SEQUENCE: 216

```
Met Leu Leu Leu Leu Ile Pro Val Leu Gly Met Ile Phe Ala Leu Arg
1               5                   10                  15

Asp Ala Arg Ala Gln Ser Val Ser Gln His Asn His His Val Ile Leu
            20                  25                  30

Ser Glu Ala Ala Ser Leu Glu Leu Gly Cys Asn Tyr Ser Tyr Gly Gly
        35                  40                  45

Thr Val Asn Leu Phe Trp Tyr Val Gln Tyr Pro Gly Gln His Leu Gln
    50                  55                  60

Leu Leu Leu Lys Tyr Phe Ser Gly Asp Pro Leu Val Lys Gly Ile Lys
65                  70                  75                  80

Gly Phe Glu Ala Glu Phe Ile Lys Ser Lys Phe Ser Phe Asn Leu Arg
                85                  90                  95

Lys Pro Ser Val Gln Trp Ser Asp Thr Ala Glu Tyr Phe Cys Ala Val
            100                 105                 110
```

```
Ile Ser Val Thr Gly Asn Asn Arg Lys Leu Ile Trp Gly Leu Gly Thr
        115                 120                 125

Ser Leu Ala Val Asn Pro Asp Ile Gln Asn Pro Asp Pro Ala Val Tyr
    130                 135                 140

Gln Leu Arg Asp Ser Lys Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275

<210> SEQ ID NO 217
<211> LENGTH: 309
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Met Ser Asn Gln Val Leu Cys Cys Val Val Leu Cys Leu Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Arg Thr Ala Met Asn Thr Glu Ala Phe Phe Gly Gln Gly Thr Arg
        115                 120                 125

Leu Thr Val Val Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
```

```
                180                 185                 190
Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
        210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Phe
305

<210> SEQ ID NO 218
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Glu Ser Lys Ile Met Phe Ala Thr Leu
1               5

<210> SEQ ID NO 219
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Lys Leu Val Val Val Gly Ala Asp Gly Val
1               5                   10

<210> SEQ ID NO 220
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Leu Val Val Val Gly Ala Asp Gly Val
1               5

<210> SEQ ID NO 221
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221
```

```
Lys Leu Val Val Val Gly Ala Val Gly Val
1               5                   10

<210> SEQ ID NO 222
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Leu Val Val Val Gly Ala Val Gly Val
1               5

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000
```

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Ser Val Phe Ser Ser
1               5

<210> SEQ ID NO 240
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Val Val Thr Gly Gly Glu Val
1               5

```
<210> SEQ ID NO 241
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Ala Gly Gly Pro Asn Thr Gly Asn Gln Phe Tyr
1               5                   10

<210> SEQ ID NO 242
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Ser Gly His Asn Thr
1               5

<210> SEQ ID NO 243
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Tyr Tyr Arg Glu Glu Glu
1               5

<210> SEQ ID NO 244
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Ala Ser Ser Thr Ser Phe Trp Glu Val Asn Thr Glu Ala Phe
1               5                   10

<210> SEQ ID NO 245
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 245
atggtcctga aattctccgt gtccattctt tggattcagt tggcatgggt gagcacccag      60
ctgctggagc agagccctca gtttctaagc atccaagagg gagaaaatct cactgtgtac     120
tgcaactcct caagtgtttt ttccagctta caatggtaca gacaggagcc tgggaaggt     180 cctgtcctcc tggtgacagt agttacgggt ggagaagtga agaagctgaa gagactaacc     240
tttcagtttg gtgatgcaag aaaggacagt tctctccaca tcactgcggc ccagcctggt     300
gatacaggcc tctacctctg tgcaggaggg ccgaacaccg gtaaccagtt ctattttggg     360
acagggacaa gtttgacggt cattccaaat                                       390
```

<210> SEQ ID NO 246
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 246

```
atggtgctga agttttccgt gtctatcctg tggattcagc tggcctgggt gtctacccag      60
ctgctggagc agagccccca gttcctgtcc atccaggagg gcgagaacct gacagtgtac     120
tgcaattcta gctccgtgtt ttctagcctg cagtggtata ggcaggagcc aggagaggga     180
cccgtgctgc tggtgaccgt ggtgacaggc ggcgaggtga agaagctgaa gagactgacc     240
ttccagtttg gcgacgccag gaaggattcc tctctgcaca tcaccgcagc acagcctggc     300
gatacaggac tgtacctgtg cgcaggagga ccaaacaccg gcaatcagtt ctattttggc     360
accggcacat ccctgacagt gatccctaat                                      390
```

<210> SEQ ID NO 247
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

```
Met Val Leu Lys Phe Ser Val Ser Ile Leu Trp Ile Gln Leu Ala Trp
1               5                   10                  15

Val Ser Thr Gln Leu Leu Glu Gln Ser Pro Gln Phe Leu Ser Ile Gln
            20                  25                  30

Glu Gly Glu Asn Leu Thr Val Tyr Cys Asn Ser Ser Ser Val Phe Ser
        35                  40                  45

Ser Leu Gln Trp Tyr Arg Gln Glu Pro Gly Glu Gly Pro Val Leu Leu
    50                  55                  60

Val Thr Val Val Thr Gly Gly Glu Val Lys Lys Leu Lys Arg Leu Thr
65                  70                  75                  80

Phe Gln Phe Gly Asp Ala Arg Lys Asp Ser Ser Leu His Ile Thr Ala
                85                  90                  95

Ala Gln Pro Gly Asp Thr Gly Leu Tyr Leu Cys Ala Gly Gly Pro Asn
            100                 105                 110

Thr Gly Asn Gln Phe Tyr Phe Gly Thr Gly Thr Ser Leu Thr Val Ile
        115                 120                 125

Pro Asn
    130
```

<210> SEQ ID NO 248
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 248

```
atgggccctg ggctcctctg ctgggtgctg ctttgtctcc tgggagcagg ctcagtggag      60
actggagtca cccaaagtcc cacacacctg atcaaaacga gaggacagca agtgactctg     120
```

```
agatgctctt ctcagtctgg gcacaacact gtgtcctggt accaacaggc cctgggtcag    180
gggccccagt ttatctttca gtattatagg gaggaagaga atggcagagg aaacttccct    240
cctagattct caggtctcca gttccctaat tatagctctg agctgaatgt gaacgccttg    300
gagctggacg actcggccct gtatctctgt gccagcagca catctttttg ggaggtgaac    360
actgaagctt tctttggaca aggcaccaga ctcacagttg ta                      402
```

<210> SEQ ID NO 249
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 249

```
atgggaccag gactgctgtg ctgggtgctg ctgtgcctgc tgggagcagg ctccgtggag    60
accggcgtga cacagtctcc cacccacctg atcaagacaa gaggccagca ggtgaccctg    120
aggtgcagct cccagtctgg ccacaacaca gtgagctggt accagcaggc cctgggacag    180
ggacctcagt tcatctttca gtactatagg gaggaggaga acggccgcgg caatttcccc    240
cctcggttta gcggcctgca gttcccaaac tactctagcg agctgaacgt gaatgccctg    300
gagctggacg atagcgccct gtatctgtgc gcctcctcta cctccttttg ggaagtgaat    360
acagaggcct tctttggcca gggcacccgc ctgacagtgg tg                      402
```

<210> SEQ ID NO 250
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Met Gly Pro Gly Leu Leu Cys Trp Val Leu Leu Cys Leu Leu Gly Ala
1               5                   10                  15

Gly Ser Val Glu Thr Gly Val Thr Gln Ser Pro Thr His Leu Ile Lys
            20                  25                  30

Thr Arg Gly Gln Gln Val Thr Leu Arg Cys Ser Ser Gln Ser Gly His
        35                  40                  45

Asn Thr Val Ser Trp Tyr Gln Gln Ala Leu Gly Gln Gly Pro Gln Phe
    50                  55                  60

Ile Phe Gln Tyr Tyr Arg Glu Glu Glu Asn Arg Gly Asn Phe Pro
65                  70                  75                  80

Pro Arg Phe Ser Gly Leu Gln Phe Pro Asn Tyr Ser Ser Glu Leu Asn
                85                  90                  95

Val Asn Ala Leu Glu Leu Asp Asp Ser Ala Leu Tyr Leu Cys Ala Ser
            100                 105                 110

Ser Thr Ser Phe Trp Glu Val Asn Thr Glu Ala Phe Phe Gly Gln Gly
        115                 120                 125

Thr Arg Leu Thr Val Val
    130

<210> SEQ ID NO 251
<211> LENGTH: 267
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 251

Met Val Leu Lys Phe Ser Val Ser Ile Leu Trp Ile Gln Leu Ala Trp
1               5                   10                  15

Val Ser Thr Gln Leu Leu Glu Gln Ser Pro Gln Phe Leu Ser Ile Gln
            20                  25                  30

Glu Gly Glu Asn Leu Thr Val Tyr Cys Asn Ser Ser Ser Val Phe Ser
        35                  40                  45

Ser Leu Gln Trp Tyr Arg Gln Glu Pro Gly Glu Gly Pro Val Leu Leu
    50                  55                  60

Val Thr Val Val Thr Gly Gly Glu Val Lys Lys Leu Lys Arg Leu Thr
65                  70                  75                  80

Phe Gln Phe Gly Asp Ala Arg Lys Asp Ser Ser Leu His Ile Thr Ala
                85                  90                  95

Ala Gln Pro Gly Asp Thr Gly Leu Tyr Leu Cys Ala Gly Gly Pro Asn
            100                 105                 110

Thr Gly Asn Gln Phe Tyr Phe Gly Thr Gly Thr Ser Leu Thr Val Ile
        115                 120                 125

Pro Asn Asp Ile Gln Asn Pro Glu Pro Ala Val Tyr Gln Leu Lys Asp
    130                 135                 140

Pro Arg Ser Gln Asp Ser Thr Leu Cys Leu Phe Thr Asp Phe Asp Ser
145                 150                 155                 160

Gln Ile Asn Val Pro Lys Thr Met Glu Ser Gly Thr Phe Ile Thr Asp
                165                 170                 175

Lys Thr Val Leu Asp Met Lys Ala Met Asp Ser Lys Ser Asn Gly Ala
            180                 185                 190

Ile Ala Trp Ser Asn Gln Thr Ser Phe Thr Cys Gln Asp Ile Phe Lys
        195                 200                 205

Glu Thr Asn Ala Thr Tyr Pro Ser Ser Asp Val Pro Cys Asp Ala Thr
    210                 215                 220

Leu Thr Glu Lys Ser Phe Glu Thr Asp Met Asn Leu Asn Phe Gln Asn
225                 230                 235                 240

Leu Ser Val Met Gly Leu Arg Ile Leu Leu Lys Val Ala Gly Phe
                245                 250                 255

Asn Leu Leu Met Thr Leu Arg Leu Trp Ser Ser
            260                 265

<210> SEQ ID NO 252
<211> LENGTH: 307
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Met Gly Pro Gly Leu Leu Cys Trp Val Leu Leu Cys Leu Leu Gly Ala
1               5                   10                  15

Gly Ser Val Glu Thr Gly Val Thr Gln Ser Pro Thr His Leu Ile Lys
            20                  25                  30

Thr Arg Gly Gln Gln Val Thr Leu Arg Cys Ser Ser Gln Ser Gly His
        35                  40                  45

Asn Thr Val Ser Trp Tyr Gln Gln Ala Leu Gly Gln Gly Pro Gln Phe
    50                  55                  60

```
Ile Phe Gln Tyr Tyr Arg Glu Glu Asn Gly Arg Gly Asn Phe Pro
 65                  70                  75                  80

Pro Arg Phe Ser Gly Leu Gln Phe Pro Asn Tyr Ser Ser Glu Leu Asn
                 85                  90                  95

Val Asn Ala Leu Glu Leu Asp Asp Ser Ala Leu Tyr Leu Cys Ala Ser
            100                 105                 110

Ser Thr Ser Phe Trp Glu Val Asn Thr Glu Ala Phe Phe Gly Gln Gly
        115                 120                 125

Thr Arg Leu Thr Val Val Lys Asp Leu Arg Asn Val Thr Pro Pro Lys
    130                 135                 140

Val Ser Leu Phe Glu Pro Ser Lys Ala Glu Ile Ala Asn Lys Gln Lys
145                 150                 155                 160

Ala Thr Leu Val Cys Leu Ala Arg Gly Phe Phe Pro Asp His Val Glu
                165                 170                 175

Leu Ser Trp Trp Val Asn Gly Lys Glu Val His Ser Gly Val Ser Thr
            180                 185                 190

Asp Pro Gln Ala Tyr Lys Glu Ser Asn Tyr Ser Tyr Cys Leu Ser Ser
        195                 200                 205

Arg Leu Arg Val Ser Ala Thr Phe Trp His Asn Pro Arg Asn His Phe
    210                 215                 220

Arg Cys Gln Val Gln Phe His Gly Leu Ser Glu Glu Asp Lys Trp Pro
225                 230                 235                 240

Glu Gly Ser Pro Lys Pro Val Thr Gln Asn Ile Ser Ala Glu Ala Trp
                245                 250                 255

Gly Arg Ala Asp Cys Gly Ile Thr Ser Ala Ser Tyr His Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Gly Leu Val Leu Met Ala Met Val Lys Lys
    290                 295                 300

Lys Asn Ser
305

<210> SEQ ID NO 253
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Val Val Gly Ala Cys Gly Val Gly Lys
1               5

<210> SEQ ID NO 254
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Val Val Val Gly Ala Cys Gly Val Gly Lys
1               5                   10

<210> SEQ ID NO 255
<211> LENGTH: 6
```

<210> SEQ ID NO 255 (implied continuation)
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Thr Ser Gly Phe Asn Gly
1               5

<210> SEQ ID NO 256
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Asn Val Leu Asp Gly Leu
1               5

<210> SEQ ID NO 257
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Ala Val Arg Glu Glu Val Leu Tyr Asn Gln Gly Gly Lys Leu Ile
1               5                   10                  15

<210> SEQ ID NO 258
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Leu Asn His Asp Ala
1               5

<210> SEQ ID NO 259
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Ser Gln Ile Val Asn Asp
1               5

<210> SEQ ID NO 260
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Ala Ser Ser Lys Arg Gly Trp Pro Tyr Glu Gln Tyr

<210> SEQ ID NO 261
<211> LENGTH: 393
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 261

```
atgtggggag ttttccttct ttatgtttcc atgaagatgg gaggcactac aggacaaaac    60
attgaccagc ccactgagat gacagctacg gaaggtgcca ttgtccagat caactgcacg   120
taccagacat ctgggttcaa cgggctgttc tggtaccagc aacatgctgg cgaagcaccc   180
acatttctgt cttacaatgt tctggatggt ttggaggaga aggtcgtttt tcttcattc    240
cttagtcggt ctaaagggta cagttacctc cttttgaagg agctccagat gaaagactct   300
gcctcttacc tctgtgctgt gagagaggag gtcctttata accaggagg aaagcttatc    360
ttcggacagg gaacggagtt atctgtgaaa ccc                                393
```

<210> SEQ ID NO 262
<211> LENGTH: 393
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 262

```
atgtggggcg tgtttctgct gtacgtgagc atgaagatgg gcggcaccac aggccagaac    60
atcgaccagc caaccgagat gaccgccaca gagggcgcca tcgtgcagat caactgcacc   120
taccagacaa gcggcttcaa tggcctgttt tggtatcagc agcacgcagg agaggcaccc   180
acattcctgt cctataatgt gctggacggc ctggaggaga agggcaggtt ctcctctttt   240
ctgagccgct ccaagggcta ctcctatctg ctgctgaagg agctgcagat gaaggattct   300
gccagctacc tgtgcgccgt gcgggaggag gtgctgtata tcagggcgg caagctgatc    360
tttggccagg gcaccgagct gagcgtgaag cct                                393
```

<210> SEQ ID NO 263
<211> LENGTH: 131
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 263

```
Met Trp Gly Val Phe Leu Leu Tyr Val Ser Met Lys Met Gly Gly Thr
1               5                   10                  15

Thr Gly Gln Asn Ile Asp Gln Pro Thr Glu Met Thr Ala Thr Glu Gly
            20                  25                  30

Ala Ile Val Gln Ile Asn Cys Thr Tyr Gln Thr Ser Gly Phe Asn Gly
        35                  40                  45

Leu Phe Trp Tyr Gln Gln His Ala Gly Glu Ala Pro Thr Phe Leu Ser
    50                  55                  60

Tyr Asn Val Leu Asp Gly Leu Glu Glu Lys Gly Arg Phe Ser Ser Phe
65                  70                  75                  80

Leu Ser Arg Ser Lys Gly Tyr Ser Tyr Leu Leu Leu Lys Glu Leu Gln
```

```
                    85                  90                  95
Met Lys Asp Ser Ala Ser Tyr Leu Cys Ala Val Arg Glu Glu Val Leu
                100                 105                 110

Tyr Asn Gln Gly Gly Lys Leu Ile Phe Gly Gln Gly Thr Glu Leu Ser
            115                 120                 125

Val Lys Pro
        130

<210> SEQ ID NO 264
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 264
atgagcaacc aggtgctctg ctgtgtggtc ctttgtctcc tgggagcaaa caccgtggat      60
ggtggaatca ctcagtcccc gaagtacctg ttcagaaagg aaggacagaa tgtgaccctg     120
agttgtgaac agaatttgaa ccacgatgcc atgtactggt accgacagga cccagggcaa     180
gggctgagat tgatctacta ctcacagata gtaaatgact tcagaaagg agatatagct     240 gaagggtaca gcgtctctcg ggagaagaag gaatcctttc ctctcactgt gacatcggcc     300
caaaagaacc cgacagcttt ctatctctgt gccagtagta aaggggatg cccctacgag     360 cagtacttcg ggccgggcac caggctcacg gtcaca                              396

<210> SEQ ID NO 265
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 265
atgtccaacc aggtgctgtg ctgcgtggtg ctgtgcctgc tgggagcaaa taccgtggac      60
ggaggcatca cacagtcccc caagtacctg ttccggaagg agggccagaa cgtgaccctg     120
tcttgtgagc agaacctgaa tcacgacgcc atgtactggt ataggcagga ccccggacag     180
ggactgagac tgatctacta tagccagatc gtgaacgact tcagaaaggg cgacatcgcc     240
gagggctaca gcgtgtcccg ggagaagaag gagtccttcc cactgaccgt gacatctgcc     300
cagaagaatc ccaccgcctt ttatctgtgc gccagtccaa agagaggctg cccctacgag     360
cagtatttcg gccctggcac caggctgacc gtgaca                              396

<210> SEQ ID NO 266
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Met Ser Asn Gln Val Leu Cys Cys Val Val Leu Cys Leu Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
```

```
                35                  40                  45
Asp Ala Met Tyr Trp Tyr Arg Gln Asp Pro Gly Gln Gly Leu Arg Leu
     50                  55                  60

Ile Tyr Tyr Ser Gln Ile Val Asn Asp Phe Gln Lys Gly Asp Ile Ala
 65                  70                  75                  80

Glu Gly Tyr Ser Val Ser Arg Glu Lys Lys Glu Ser Phe Pro Leu Thr
                 85                  90                  95

Val Thr Ser Ala Gln Lys Asn Pro Thr Ala Phe Tyr Leu Cys Ala Ser
            100                 105                 110

Ser Lys Arg Gly Trp Pro Tyr Glu Gln Tyr Phe Gly Pro Gly Thr Arg
        115                 120                 125

Leu Thr Val Thr
        130

<210> SEQ ID NO 267
<211> LENGTH: 268
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Met Trp Gly Val Phe Leu Leu Tyr Val Ser Met Lys Met Gly Gly Thr
 1               5                  10                  15

Thr Gly Gln Asn Ile Asp Gln Pro Thr Glu Met Thr Ala Thr Glu Gly
                 20                  25                  30

Ala Ile Val Gln Ile Asn Cys Thr Tyr Gln Thr Ser Gly Phe Asn Gly
             35                  40                  45

Leu Phe Trp Tyr Gln Gln His Ala Gly Glu Ala Pro Thr Phe Leu Ser
     50                  55                  60

Tyr Asn Val Leu Asp Gly Leu Glu Glu Lys Gly Arg Phe Ser Ser Phe
 65                  70                  75                  80

Leu Ser Arg Ser Lys Gly Tyr Ser Tyr Leu Leu Lys Glu Leu Gln
                 85                  90                  95

Met Lys Asp Ser Ala Ser Tyr Leu Cys Ala Val Arg Glu Glu Val Leu
            100                 105                 110

Tyr Asn Gln Gly Gly Lys Leu Ile Phe Gly Gln Gly Thr Glu Leu Ser
        115                 120                 125

Val Lys Pro Asp Ile Gln Asn Pro Glu Pro Ala Val Tyr Gln Leu Lys
    130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
        195                 200                 205

Lys Glu Thr Asn Ala Thr Tyr Pro Ser Ser Asp Val Pro Cys Asp Ala
    210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Leu Lys Val Ala Gly
                245                 250                 255
```

```
Phe Asn Leu Leu Met Thr Leu Arg Leu Trp Ser Ser
            260                 265

<210> SEQ ID NO 268
<211> LENGTH: 305
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Met Ser Asn Gln Val Leu Cys Cys Val Val Leu Cys Leu Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Lys Arg Gly Trp Pro Tyr Glu Gln Tyr Phe Gly Pro Gly Thr Arg
        115                 120                 125

Leu Thr Val Thr Lys Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr His Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Gly Leu Val Leu Met Ala Met Val Lys Lys Lys Asn
    290                 295                 300

Ser
305

<210> SEQ ID NO 269
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 269

Val Val Gly Ala Cys Gly Val Gly Lys
1               5

<210> SEQ ID NO 270
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Val Val Val Gly Ala Cys Gly Val Gly Lys
1               5                   10

<210> SEQ ID NO 271
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Thr Ser Ile Asn Asn
1               5

<210> SEQ ID NO 272
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Ile Arg Ser Asn Glu Arg Glu
1               5

<210> SEQ ID NO 273
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Ala Thr Asp Arg Gln Ser Ser Gly Asp Lys Leu Thr
1               5                   10

<210> SEQ ID NO 274
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Ser Gly His Ala Thr
1               5
```

<210> SEQ ID NO 275
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 275

Phe Gln Asn Asn Gly Val
1               5

<210> SEQ ID NO 276
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 276

Ala Ser Ser Leu Ala Asp Ile Tyr Glu Gln Tyr
1               5                   10

<210> SEQ ID NO 277
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 277

```
atggaaactc tcctgggagt gtctttggtg attctatggc ttcaactggc tagggtgaac      60
agtcaacagg gagaagagga tcctcaggcc ttgagcatcc aggagggtga aaatgccacc     120
atgaactgca gttacaaaac tagtataaac aatttacagt ggtatagaca aaattcaggt     180
agaggccttg tccacctaat tttaatacgt tcaaatgaaa gagagaaaca cagtggaaga     240
ttaagagtca cgcttgacac ttccaagaaa agcagttcct tgttgatcac ggcttcccgg     300
gcagcagaca ctgcttctta cttctgtgct acggaccgtc aaagcagcgg agacaagctg     360
acttttggga ccgggactcg tttagcagtt aggccc                               396
```

<210> SEQ ID NO 278
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 278

```
atggagaccc tgctgggcgt gtccctggtc atcctgtggc tgcagctggc cagggtgaac      60
agccagcagg gagaggagga ccccaggcc ctgagcatcc aggagggcga aacgccacc      120
atgaattgct cttacaagac aagcatcaac aatctgcagt ggtataggca gaactccggc     180
cgcggactgg tgcacctgat cctgatccgg agcaatgaga gagagaagca ctccggccgg     240
ctgagagtga ccctggacac atctaagaag tcctctagcc tgctgatcac cgcctctcgg     300
gcagcagata cagccagcta cttctgtgcc accgacagac agtcctctgg cgataagctg     360
acctttggca ccggcacaag gctggccgtg cgcccc                               396
```

<210> SEQ ID NO 279
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 279

```
Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Leu Leu Ile
                85                  90                  95

Thr Ala Ser Arg Ala Ala Asp Thr Ala Ser Tyr Phe Cys Ala Thr Asp
            100                 105                 110

Arg Gln Ser Ser Gly Asp Lys Leu Thr Phe Gly Thr Gly Thr Arg Leu
        115                 120                 125

Ala Val Arg Pro
    130
```

<210> SEQ ID NO 280
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 280

```
atgggcacca ggctcctctg ctgggcggcc ctctgtctcc tgggagcaga actcacagaa      60
gctggagttg cccagtctcc cagatataag attatagaga aaaggcagag tgtggctttt    120
tggtgcaatc ctatatctgg ccatgctacc ctttactggt accagcagat cctgggacag    180
ggcccaaagc ttctgattca gtttcagaat aacggtgtag tggatgattc acagttgcct    240
aaggatcgat ttctgcaga gaggctcaaa ggagtagact ccactctcaa gatccagcct    300
gcaaagcttg aggactcggc cgtgtatctc tgtgccagca gcttagccga catctacgag    360
cagtacttcg gccgggcac caggctcacg gtcaca                               396
```

<210> SEQ ID NO 281
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 281

```
atgggaacaa ggctgctgtg ctgggccgcc ctgtgcctgc tgggagcaga gctgaccgag      60
gccggcgtgg cccagagccc ccggtacaag atcatcgaga agagacagag cgtggccttc    120
tggtgcaacc ctatctccgg ccacgccaca ctgtactggt atcagcagat cctgggccag    180
```

```
ggcccaaagc tgctgatcca gttccagaac aatggcgtgg tggacgattc ccagctgccc    240
aaggaccggt tttctgccga gagactgaag ggcgtggatt ccaccctgaa gatccagccc    300
gccaagctgg aggactctgc cgtgtatctg tgcgccagct ccctggccga catctacgag    360
cagtatttcg gccctggcac aaggctgacc gtgaca                              396
```

<210> SEQ ID NO 282
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide <400> SEQUENCE: 282

```
Met Gly Thr Arg Leu Leu Cys Trp Ala Ala Leu Cys Leu Leu Gly Ala
1               5                   10                  15

Glu Leu Thr Glu Ala Gly Val Ala Gln Ser Pro Arg Tyr Lys Ile Ile
            20                  25                  30

Glu Lys Arg Gln Ser Val Ala Phe Trp Cys Asn Pro Ile Ser Gly His
        35                  40                  45

Ala Thr Leu Tyr Trp Tyr Gln Gln Ile Leu Gly Gln Gly Pro Lys Leu
    50                  55                  60

Leu Ile Gln Phe Gln Asn Asn Gly Val Val Asp Asp Ser Gln Leu Pro
65                  70                  75                  80

Lys Asp Arg Phe Ser Ala Glu Arg Leu Lys Gly Val Asp Ser Thr Leu
                85                  90                  95

Lys Ile Gln Pro Ala Lys Leu Glu Asp Ser Ala Val Tyr Leu Cys Ala
            100                 105                 110

Ser Ser Leu Ala Asp Ile Tyr Glu Gln Tyr Phe Gly Pro Gly Thr Arg
        115                 120                 125

Leu Thr Val Thr
    130
```

<210> SEQ ID NO 283
<211> LENGTH: 269
<212> TYPE: PRT
<213> ORGANISM: Artificial Sequence
<220> FEATURE:
<223> OTHER INFORMATION: Description of Artificial Sequence: Synthetic
      polypeptide <400> SEQUENCE: 283

```
Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Leu Leu Ile
                85                  90                  95

Thr Ala Ser Arg Ala Ala Asp Thr Ala Ser Tyr Phe Cys Ala Thr Asp
            100                 105                 110

Arg Gln Ser Ser Gly Asp Lys Leu Thr Phe Gly Thr Gly Thr Arg Leu
```

```
            115                 120                 125
Ala Val Arg Pro Asp Ile Gln Asn Pro Glu Pro Ala Val Tyr Gln Leu
            130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175

Thr Asp Lys Thr Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
            195                 200                 205

Phe Lys Glu Thr Asn Ala Thr Tyr Pro Ser Ser Asp Val Pro Cys Asp
210                 215                 220

Ala Thr Leu Thr Glu Lys Ser Phe Glu Thr Asp Met Asn Leu Asn Phe
225                 230                 235                 240

Gln Asn Leu Ser Val Met Gly Leu Arg Ile Leu Leu Leu Lys Val Ala
            245                 250                 255

Gly Phe Asn Leu Leu Met Thr Leu Arg Leu Trp Ser Ser
            260                 265

<210> SEQ ID NO 284
<211> LENGTH: 305
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Met Gly Thr Arg Leu Leu Cys Trp Ala Ala Leu Cys Leu Leu Gly Ala
1               5                   10                  15

Glu Leu Thr Glu Ala Gly Val Ala Gln Ser Pro Arg Tyr Lys Ile Ile
            20                  25                  30

Glu Lys Arg Gln Ser Val Ala Phe Trp Cys Asn Pro Ile Ser Gly His
        35                  40                  45

Ala Thr Leu Tyr Trp Tyr Gln Gln Ile Leu Gly Gln Gly Pro Lys Leu
    50                  55                  60

Leu Ile Gln Phe Gln Asn Asn Gly Val Val Asp Asp Ser Gln Leu Pro
65                  70                  75                  80

Lys Asp Arg Phe Ser Ala Glu Arg Leu Lys Gly Val Asp Ser Thr Leu
                85                  90                  95

Lys Ile Gln Pro Ala Lys Leu Glu Asp Ser Ala Val Tyr Leu Cys Ala
            100                 105                 110

Ser Ser Leu Ala Asp Ile Tyr Glu Gln Tyr Phe Gly Pro Gly Thr Arg
        115                 120                 125

Leu Thr Val Thr Lys Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Ala Tyr Lys Glu Ser Asn Tyr Ser Tyr Cys Leu Ser Ser Arg Leu
        195                 200                 205
```

-continued

```
Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr His Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Gly Leu Val Leu Met Ala Met Val Lys Lys Lys Asn
    290                 295                 300

Ser
305

<210> SEQ ID NO 285
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Val Val Gly Ala Cys Gly Val Gly Lys
1               5

<210> SEQ ID NO 286
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Val Val Val Gly Ala Cys Gly Val Gly Lys
1               5                   10

<210> SEQ ID NO 287
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Thr Ser Glu Ser Asp Tyr Tyr
1               5

<210> SEQ ID NO 288
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Gln Glu Ala Tyr Lys Gln Gln Asn
1               5

<210> SEQ ID NO 289
```

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Ala Leu Tyr Ile Tyr Gly Gly Ser Gln Gly Asn Leu Ile
1               5                   10

<210> SEQ ID NO 290
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Ser Glu His Asn Arg
1               5

<210> SEQ ID NO 291
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Phe Gln Asn Glu Ala Gln
1               5

<210> SEQ ID NO 292
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Ala Ser Ser Ser Thr Asp Arg Ile Glu Ala Phe
1               5                   10

<210> SEQ ID NO 293
<211> LENGTH: 408
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 293
atggcatgcc ctggcttcct gtgggcactt gtgatctcca cctgtcttga atttagcatg      60
gctcagacag tcactcagtc tcaaccagag atgtctgtgc aggaggcaga gaccgtgacc     120
ctgagctgca catatgacac cagtgagagt gattattatt tattctgtat caagcagcct     180
cccagcaggc agatgattct cgttattcgc caagaagctt ataagcaaca gaatgcaaca     240
gagaatcgtt tctctgtgaa cttccagaaa gcagccaaat ccttcagtct caagatctca     300
gactcacagc tgggggatgc cgcgatgtat ttctgtgctc tctatattta tggaggaagc     360
caaggaaatc tcatctttgg aaaaggcact aaactctctg ttaaacca                  408
```

<210> SEQ ID NO 294
<211> LENGTH: 408
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 294
atggcatgcc caggcttcct gtgggcactg gtcatcagca catgtctgga gttttctatg      60
gcccagaccg tgacacagtc tcagcctgag atgagcgtgc aggaggccga gaccgtgaca     120
ctgagctgca cctacgacac atctgagagc gattactatc tgttctggta taagcagcca     180
ccctccagac agatgatcct ggtcatcagg caggaggcct acaagcagca gaacgccacc     240
gagaatcggt tctccgtgaa ctttcagaag gccgccaagt ccttttctct gaagatcagc     300
gactcccagc tgggcgatgc cgccatgtat ttctgtgccc tgtacatcta tggcggctct     360
cagggcaatc tgatctttgg caagggcacc aagctgagcg tgaagcct                  408

<210> SEQ ID NO 295
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asp Tyr Tyr Leu Phe Trp Tyr Lys Gln Pro Pro Ser Arg Gln
    50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Leu Tyr Ile Tyr Gly Gly Ser Gln Gly Asn Leu Ile Phe Gly Lys
        115                 120                 125

Gly Thr Lys Leu Ser Val Lys Pro
    130                 135

<210> SEQ ID NO 296
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 296
atgggcacca gcctcctctg ctggatggcc ctgtgtctcc tggggcaga tcacgcagat       60 actggagtct cccaggaccc cagacacaag atcacaaaga gggacagaa tgtaactttc      120 aggtgtgatc caatttctga acacaaccgc ctttattggt accgacagac cctggggcag     180
ggcccagagt tctgactta cttccagaat gaagctcaac tagaaaaatc aaggctgctc    240
agtgatcggt tctctgcaga gaggcctaag ggatctttct ccaccttgga gatccagcgc    300
acagagcagg gggactcggc catgtatctc tgtgccagca gctccaccga caggattgaa    360
gctttctttg gacaaggcac cagactcaca gttgta                             396

<210> SEQ ID NO 297
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 297
atgggcacct ccctgctgtg ctggatggca ctgtgcctgc tgggagcaga ccacgcagat    60
acaggcgtgt ctcaggaccc acgccacaag atcaccaagc ggggccagaa cgtgacattc    120
agatgcgatc ccatctccga gcacaatagg ctgtactggt ataggcagac cctgggacag    180
ggaccagagt cctgacata ctttcagaac gaggcccagc tggagaagag ccggctgctg     240
tccgacagat tctctgccga gaggcccaag ggctctttta gcaccctgga gatccagaga    300
acagagcagg gcgacagcgc catgtatctg tgcgccagct cctctaccga taggatcgag    360
gccttctttg gccagggcac ccgcctgaca gtggtg                              396

<210> SEQ ID NO 298
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Ser Thr Asp Arg Ile Glu Ala Phe Phe Gly Gln Gly Thr Arg
        115                 120                 125

Leu Thr Val Val
    130

<210> SEQ ID NO 299
<211> LENGTH: 273
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 299

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asp Tyr Tyr Leu Phe Trp Tyr Lys Gln Pro Pro Ser Arg Gln
    50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Leu Tyr Ile Tyr Gly Gly Ser Gln Gly Asn Leu Ile Phe Gly Lys
        115                 120                 125

Gly Thr Lys Leu Ser Val Lys Pro Asp Ile Gln Asn Pro Glu Pro Ala
    130                 135                 140

Val Tyr Gln Leu Lys Asp Pro Arg Ser Gln Asp Ser Thr Leu Cys Leu
145                 150                 155                 160

Phe Thr Asp Phe Asp Ser Gln Ile Asn Val Pro Lys Thr Met Glu Ser
                165                 170                 175

Gly Thr Phe Ile Thr Asp Lys Thr Val Leu Asp Met Lys Ala Met Asp
            180                 185                 190

Ser Lys Ser Asn Gly Ala Ile Ala Trp Ser Asn Gln Thr Ser Phe Thr
        195                 200                 205

Cys Gln Asp Ile Phe Lys Glu Thr Asn Ala Thr Tyr Pro Ser Ser Asp
    210                 215                 220

Val Pro Cys Asp Ala Thr Leu Thr Glu Lys Ser Phe Glu Thr Asp Met
225                 230                 235                 240

Asn Leu Asn Phe Gln Asn Leu Ser Val Met Gly Leu Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 300
<211> LENGTH: 305
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

-continued

```
Leu Thr Tyr Phe Gln Asn Glu Ala Gln Leu Glu Lys Ser Arg Leu Leu
 65                  70                  75                  80

Ser Asp Arg Phe Ser Ala Glu Arg Pro Lys Gly Ser Phe Ser Thr Leu
                 85                  90                  95

Glu Ile Gln Arg Thr Glu Gln Gly Asp Ser Ala Met Tyr Leu Cys Ala
            100                 105                 110

Ser Ser Ser Thr Asp Arg Ile Glu Ala Phe Phe Gly Gln Gly Thr Arg
        115                 120                 125

Leu Thr Val Val Lys Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr His Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Gly Leu Val Leu Met Ala Met Val Lys Lys Lys Asn
    290                 295                 300

Ser
305

<210> SEQ ID NO 301
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Val Val Gly Ala Asp Gly Val Gly Lys
1               5

<210> SEQ ID NO 302
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Val Val Val Gly Ala Asp Gly Val Gly Lys
1               5                   10

<210> SEQ ID NO 303
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Val Ser Asn Ala Tyr Asn
1               5

<210> SEQ ID NO 304
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Gly Ser Lys Pro
1

<210> SEQ ID NO 305
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Ala Thr Tyr Asn Phe Asn Lys Phe Tyr
1               5

<210> SEQ ID NO 306
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Ser Gly His Thr Ser
1               5

<210> SEQ ID NO 307
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Tyr Asp Glu Gly Glu Glu
1               5

<210> SEQ ID NO 308
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308
```

Ala Ser Thr Thr Phe Lys Thr Gly Arg Ala Ile Glu Lys Leu Phe
1               5                   10                  15

<210> SEQ ID NO 309
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 309
atggctttgc agagcactct gggggcggtg tggctagggc ttctcctcaa ctctctctgg    60
aaggttgcag aaagcaagga ccaagtgttt cagccttcca cagtggcatc ttcagaggga   120
gctgtggtgg aaatcttctg taatcactct gtgtccaatg cttacaactt cttctggtac   180
cttcacttcc cgggatgtgc accaagactc cttgttaaag gctcaaagcc ttctcagcag   240
ggacgataca acatgaccta tgaacggttc tcttcatcgc tgctcatcct ccaggtgcgg   300
gaggcagatg ctgctgttta ctactgtgct acgtacaact tcaacaaatt ttactttgga   360
tctgggacca aactcaatgt aaaacca                                       387

<210> SEQ ID NO 310
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 310
atggccctgc agtctacact gggagccgtg tggctgggac tgctgctgaa ctctctgtgg    60
aaggtggccg agagcaagga ccaggtgttc agcctagca ccgtggcctc ctctgaggga   120
gcagtggtgg agatcttttg caatcactcc gtgtctaacg cctacaattt cttttggtat   180
ctgcactttc caggatgtgc accaaggctg ctggtgaagg cagcaagcc atcccagcag   240 ggccggtaca acatgaccta tgagagattc agctcctctc tgctgatcct gcaggtgaga   300
gaggccgatg ccgccgtgta ctattgtgcc acctacaact taataagtt ctattttggc   360 tccggcacaa agctgaatgt gaagcct                                       387

<210> SEQ ID NO 311
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 311

Met Ala Leu Gln Ser Thr Leu Gly Ala Val Trp Leu Gly Leu Leu Leu
1               5                   10                  15

Asn Ser Leu Trp Lys Val Ala Glu Ser Lys Asp Gln Val Phe Gln Pro
                20                  25                  30

Ser Thr Val Ala Ser Ser Glu Gly Ala Val Val Glu Ile Phe Cys Asn
            35                  40                  45

His Ser Val Ser Asn Ala Tyr Asn Phe Phe Trp Tyr Leu His Phe Pro
        50                  55                  60

Gly Cys Ala Pro Arg Leu Leu Val Lys Gly Ser Lys Pro Ser Gln Gln
65                  70                  75                  80

Gly Arg Tyr Asn Met Thr Tyr Glu Arg Phe Ser Ser Leu Leu Ile
                85                  90                  95

Leu Gln Val Arg Glu Ala Asp Ala Ala Val Tyr Tyr Cys Ala Thr Tyr
            100                 105                 110

Asn Phe Asn Lys Phe Tyr Phe Gly Ser Gly Thr Lys Leu Asn Val Lys
        115                 120                 125

Pro

<210> SEQ ID NO 312
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 312
atgggaccca ggctcctctt ctgggcactg ctttgtctcc tcggaacagg cccagtggag    60
gctggagtca cacaaagtcc cacacacctg atcaaaacga gaggacagca agcgactctg   120
agatgctctc ctatctctgg cacaccagt gtgtactggt accaacaggc cctgggtctg    180
ggcctccagt tcctcctttg gtatgacgag ggtgaagaga gaaacagagg aaacttccct   240
cctagatttt caggtcgcca gttccctaat tatagctctg agctgaatgt gaacgccttg   300
gagctggagg actcggccct gtatctctgt gccagcacca cttttaagac gggacgggca   360
attgaaaaac tgttttttgg cagtggaacc cagctctctg tcttg                  405

<210> SEQ ID NO 313
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 313
atgggaccaa ggctgctgtt ctgggcactg ctgtgcctgc tgggaaccgg acctgtggag    60
gccggcgtga cccagtctcc aacacacctg atcaagacca gggacagca ggccacactg    120 aggtgtagcc ccatctccgg ccacacaagc gtgtactggt atcagcaggc cctgggactg   180
ggactgcagt tcctgctgtg gtacgacgag ggcgaggaga ggaaccgcgg caatttccca   240
cctcggttca gcggccggca gtttcccaac tacagctccg agctgaacgt gaatgccctg   300
gagctggagg acagcgccct gtatctgtgc gcctccacca cattcaagac cggcagggcc   360
atcgagaagc tgttctttgg ctctggcacc cagctgagcg tgctg                  405

<210> SEQ ID NO 314
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 314

Met Gly Pro Arg Leu Leu Phe Trp Ala Leu Leu Cys Leu Leu Gly Thr
1               5                   10                  15

Gly Pro Val Glu Ala Gly Val Thr Gln Ser Pro Thr His Leu Ile Lys
            20                  25                  30

Thr Arg Gly Gln Gln Ala Thr Leu Arg Cys Ser Pro Ile Ser Gly His

```
            35                  40                  45
Thr Ser Val Tyr Trp Tyr Gln Gln Ala Leu Gly Leu Gly Leu Gln Phe
         50                  55                  60

Leu Leu Trp Tyr Asp Glu Gly Glu Arg Asn Arg Gly Asn Phe Pro
 65                  70                  75                  80

Pro Arg Phe Ser Gly Arg Gln Phe Pro Asn Tyr Ser Glu Leu Asn
                 85                  90                  95

Val Asn Ala Leu Glu Leu Glu Asp Ser Ala Leu Tyr Leu Cys Ala Ser
                100                 105                 110

Thr Thr Phe Lys Thr Gly Arg Ala Ile Glu Lys Leu Phe Phe Gly Ser
                115                 120                 125

Gly Thr Gln Leu Ser Val Leu
                130                 135

<210> SEQ ID NO 315
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

Met Ala Leu Gln Ser Thr Leu Gly Ala Val Trp Leu Gly Leu Leu
 1               5                  10                  15

Asn Ser Leu Trp Lys Val Ala Glu Ser Lys Asp Gln Val Phe Gln Pro
                 20                  25                  30

Ser Thr Val Ala Ser Ser Glu Gly Ala Val Val Glu Ile Phe Cys Asn
                 35                  40                  45

His Ser Val Ser Asn Ala Tyr Asn Phe Phe Trp Tyr Leu His Phe Pro
         50                  55                  60

Gly Cys Ala Pro Arg Leu Leu Val Lys Gly Ser Lys Pro Ser Gln Gln
 65                  70                  75                  80

Gly Arg Tyr Asn Met Thr Tyr Glu Arg Phe Ser Ser Ser Leu Leu Ile
                 85                  90                  95

Leu Gln Val Arg Glu Ala Asp Ala Ala Val Tyr Tyr Cys Ala Thr Tyr
                100                 105                 110

Asn Phe Asn Lys Phe Tyr Phe Gly Ser Gly Thr Lys Leu Asn Val Lys
                115                 120                 125

Pro Asp Ile Gln Asn Pro Glu Pro Ala Val Tyr Gln Leu Lys Asp Pro
130                 135                 140

Arg Ser Gln Asp Ser Thr Leu Cys Leu Phe Thr Asp Phe Asp Ser Gln
145                 150                 155                 160

Ile Asn Val Pro Lys Thr Met Glu Ser Gly Thr Phe Ile Thr Asp Lys
                165                 170                 175

Thr Val Leu Asp Met Lys Ala Met Asp Ser Lys Ser Asn Gly Ala Ile
                180                 185                 190

Ala Trp Ser Asn Gln Thr Ser Phe Thr Cys Gln Asp Ile Phe Lys Glu
                195                 200                 205

Thr Asn Ala Thr Tyr Pro Ser Ser Asp Val Pro Cys Asp Ala Thr Leu
                210                 215                 220

Thr Glu Lys Ser Phe Glu Thr Asp Met Asn Leu Asn Phe Gln Asn Leu
225                 230                 235                 240

Ser Val Met Gly Leu Arg Ile Leu Leu Leu Lys Val Ala Gly Phe Asn
                245                 250                 255
```

```
Leu Leu Met Thr Leu Arg Leu Trp Ser Ser
        260                 265
```

<210> SEQ ID NO 316
<211> LENGTH: 308
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 316

```
Met Gly Pro Arg Leu Leu Phe Trp Ala Leu Leu Cys Leu Leu Gly Thr
1               5                   10                  15

Gly Pro Val Glu Ala Gly Val Thr Gln Ser Pro Thr His Leu Ile Lys
            20                  25                  30

Thr Arg Gly Gln Gln Ala Thr Leu Arg Cys Ser Pro Ile Ser Gly His
        35                  40                  45

Thr Ser Val Tyr Trp Tyr Gln Gln Ala Leu Gly Leu Gly Leu Gln Phe
    50                  55                  60

Leu Leu Trp Tyr Asp Glu Gly Glu Arg Asn Arg Gly Asn Phe Pro
65              70                  75                  80

Pro Arg Phe Ser Gly Arg Gln Phe Pro Asn Tyr Ser Glu Leu Asn
                85                  90                  95

Val Asn Ala Leu Glu Leu Glu Asp Ser Ala Leu Tyr Leu Cys Ala Ser
            100                 105                 110

Thr Thr Phe Lys Thr Gly Arg Ala Ile Glu Lys Leu Phe Phe Gly Ser
        115                 120                 125

Gly Thr Gln Leu Ser Val Leu Lys Asp Leu Arg Asn Val Thr Pro Pro
    130                 135                 140

Lys Val Ser Leu Phe Glu Pro Ser Lys Ala Glu Ile Ala Asn Lys Gln
145                 150                 155                 160

Lys Ala Thr Leu Val Cys Leu Ala Arg Gly Phe Phe Pro Asp His Val
                165                 170                 175

Glu Leu Ser Trp Trp Val Asn Gly Lys Glu Val His Ser Gly Val Ser
            180                 185                 190

Thr Asp Pro Gln Ala Tyr Lys Glu Ser Asn Tyr Ser Tyr Cys Leu Ser
        195                 200                 205

Ser Arg Leu Arg Val Ser Ala Thr Phe Trp His Asn Pro Arg Asn His
    210                 215                 220

Phe Arg Cys Gln Val Gln Phe His Gly Leu Ser Glu Glu Asp Lys Trp
225                 230                 235                 240

Pro Glu Gly Ser Pro Lys Pro Val Thr Gln Asn Ile Ser Ala Glu Ala
                245                 250                 255

Trp Gly Arg Ala Asp Cys Gly Ile Thr Ser Ala Ser Tyr His Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Gly Leu Val Leu Met Ala Met Val Lys
    290                 295                 300

Lys Lys Asn Ser
305
```

<210> SEQ ID NO 317
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 317

Val Val Gly Ala Asp Gly Val Gly Lys
1               5

<210> SEQ ID NO 318
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Val Val Val Gly Ala Asp Gly Val Gly Lys
1               5                   10

<210> SEQ ID NO 319
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Thr Ser Gly Phe Asn Gly
1               5

<210> SEQ ID NO 320
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Asn Val Leu Asp Gly Leu
1               5

<210> SEQ ID NO 321
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Ala Val Arg Asp Arg Gly Gly Ser Tyr Ile Pro Thr
1               5                   10

<210> SEQ ID NO 322
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Met Asn His Glu Tyr
1               5
```

<210> SEQ ID NO 323
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Ser Met Asn Val Glu Val
1               5

<210> SEQ ID NO 324
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Ala Ser Ser Ser Arg Gly His Ser Gly Thr Glu Ala Phe
1               5                   10

<210> SEQ ID NO 325
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 325
atgtggggag ttttccttct ttatgtttcc atgaagatgg gaggcactac aggacaaaac      60
attgaccagc ccactgagat gacagctacg gaaggtgcca ttgtccagat caactgcacg     120
taccagacat ctgggttcaa cgggctgttc tggtaccagc aacatgctgg cgaagcaccc     180
acatttctgt cttacaatgt tctggatggt ttggaggaga aggtcgtttt tcttcattc     240 cttagtcggt ctaaagggta cagttacctc cttttgaagg agctccagat gaaagactct     300
gcctcttacc tctgtgctgt gagagatcga ggaggaagct acatacctac atttggaaga     360
ggaaccagcc ttattgttca tccg                                            384

<210> SEQ ID NO 326
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 326
atgtggggcg tgtttctgct gtacgtgtct atgaagatgg gcggcaccac aggccagaac      60
atcgaccagc ctaccgagat gaccgccaca gagggcgcca tcgtgcagat caactgcacc     120
taccagacat ctggcttcaa tggcctgttt tggtatcagc agcacgccgg cgaggcccca     180
acattcctgt cctataatgt gctggatggc ctggaggaga agggcaggtt ctctagcttt     240
ctgtcccgct ctaagggcta cagctatctg ctgctgaagg agctgcagat gaaggacagc     300
gcctcctacc tgtgcgccgt gcgggataga ggaggctcct atatccctac ctttggccgg     360
ggcacatctc tgatcgtgca ccca                                            384

<210> SEQ ID NO 327
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 327

Met Trp Gly Val Phe Leu Leu Tyr Val Ser Met Lys Met Gly Gly Thr
1               5                   10                  15

Thr Gly Gln Asn Ile Asp Gln Pro Thr Glu Met Thr Ala Thr Glu Gly
                20                  25                  30

Ala Ile Val Gln Ile Asn Cys Thr Tyr Gln Thr Ser Gly Phe Asn Gly
            35                  40                  45

Leu Phe Trp Tyr Gln Gln His Ala Gly Glu Ala Pro Thr Phe Leu Ser
        50                  55                  60

Tyr Asn Val Leu Asp Gly Leu Glu Glu Lys Gly Arg Phe Ser Ser Phe
65                  70                  75                  80

Leu Ser Arg Ser Lys Gly Tyr Ser Tyr Leu Leu Lys Glu Leu Gln
                85                  90                  95

Met Lys Asp Ser Ala Ser Tyr Leu Cys Ala Val Arg Asp Arg Gly Gly
            100                 105                 110

Ser Tyr Ile Pro Thr Phe Gly Arg Gly Thr Ser Leu Ile Val His Pro
        115                 120                 125

<210> SEQ ID NO 328
<211> LENGTH: 399
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 328
atgggccccc agctccttgg ctatgtggtc ctttgccttc taggagcagg ccccctggaa      60
gcccaagtga cccagaaccc aagataccct atcacagtga ctggaaagaa gttaacagtg     120
acttgttctc agaatatgaa ccatgagtat atgtcctggt atcgacaaga cccagggctg     180
ggcttaaggc agatctacta ttcaatgaat gttgaggtga ctgataaggg agatgttcct     240
gaagggtaca agtctctcg aaaagagaag aggaatttcc ccctgatcct ggagtcgccc      300
agccccaacc agacctctct gtacttctgt gccagcagtt ccaggggca ttcgggcact      360 gaagctttct ttggacaagg caccagactc acagttgta                            399

<210> SEQ ID NO 329
<211> LENGTH: 399
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 329
atgggaccac agctgctggg atacgtggtg ctgtgcctgc tgggagcagg accactggag      60
gcacaggtga cccagaaccc acggtatctg atcaccgtga caggcaagaa gctgaccgtg     120
acatgttctc agaacatgaa tcacgagtac atgagctggt ataggcagga ccctggactg     180
ggactgagac agatctacta tagcatgaat gtggaggtga ccgacaaggg cgatgtgccc     240
gagggctaca aggtgtccag gaaggagaag cgcaacttcc ctctgatcct ggagtcccca     300

```
tctcccaatc agaccagcct gtattttgc gccagctcct ctaggggaca ctccggaaca    360
gaggccttct tggccaggg caccaggctg acagtggtg                            399
```

<210> SEQ ID NO 330
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 330

```
Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Ser Arg Gly His Ser Gly Thr Glu Ala Phe Phe Gly Gln Gly Thr
        115                 120                 125

Arg Leu Thr Val Val
    130
```

<210> SEQ ID NO 331
<211> LENGTH: 265
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 331

```
Met Trp Gly Val Phe Leu Leu Tyr Val Ser Met Lys Met Gly Gly Thr
1               5                   10                  15

Thr Gly Gln Asn Ile Asp Gln Pro Thr Glu Met Thr Ala Thr Glu Gly
            20                  25                  30

Ala Ile Val Gln Ile Asn Cys Thr Tyr Gln Thr Ser Gly Phe Asn Gly
        35                  40                  45

Leu Phe Trp Tyr Gln Gln His Ala Gly Glu Ala Pro Thr Phe Leu Ser
    50                  55                  60

Tyr Asn Val Leu Asp Gly Leu Glu Glu Lys Gly Arg Phe Ser Ser Phe
65                  70                  75                  80

Leu Ser Arg Ser Lys Gly Tyr Ser Tyr Leu Leu Leu Lys Glu Leu Gln
                85                  90                  95

Met Lys Asp Ser Ala Ser Tyr Leu Cys Ala Val Arg Asp Arg Gly Gly
            100                 105                 110

Ser Tyr Ile Pro Thr Phe Gly Arg Gly Thr Ser Leu Ile Val His Pro
        115                 120                 125

Asp Ile Gln Asn Pro Glu Pro Ala Val Tyr Gln Leu Lys Asp Pro Arg
```

```
                130                 135                 140
Ser Gln Asp Ser Thr Leu Cys Leu Phe Thr Asp Phe Asp Ser Gln Ile
145                 150                 155                 160

Asn Val Pro Lys Thr Met Glu Ser Gly Thr Phe Ile Thr Asp Lys Thr
                165                 170                 175

Val Leu Asp Met Lys Ala Met Asp Ser Lys Ser Asn Gly Ala Ile Ala
                180                 185                 190

Trp Ser Asn Gln Thr Ser Phe Thr Cys Gln Asp Ile Phe Lys Glu Thr
                195                 200                 205

Asn Ala Thr Tyr Pro Ser Ser Asp Val Pro Cys Asp Ala Thr Leu Thr
                210                 215                 220

Glu Lys Ser Phe Glu Thr Asp Met Asn Leu Asn Phe Gln Asn Leu Ser
225                 230                 235                 240

Val Met Gly Leu Arg Ile Leu Leu Leu Lys Val Ala Gly Phe Asn Leu
                245                 250                 255

Leu Met Thr Leu Arg Leu Trp Ser Ser
                260                 265

<210> SEQ ID NO 332
<211> LENGTH: 306
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 332

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
                20                  25                  30

Val Thr Gly Lys Lys Leu Thr Val Thr Cys Ser Gln Asn Met Asn His
            35                  40                  45

Glu Tyr Met Ser Trp Tyr Arg Gln Asp Pro Gly Leu Gly Leu Arg Gln
        50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
                100                 105                 110

Ser Ser Arg Gly His Ser Gly Thr Glu Ala Phe Phe Gly Gln Gly Thr
            115                 120                 125

Arg Leu Thr Val Val Lys Asp Leu Arg Asn Val Thr Pro Pro Lys Val
130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Ser Thr Asp
                180                 185                 190

Pro Gln Ala Tyr Lys Glu Ser Asn Tyr Ser Tyr Cys Leu Ser Ser Arg
            195                 200                 205

Leu Arg Val Ser Ala Thr Phe Trp His Asn Pro Arg Asn His Phe Arg
        210                 215                 220
```

```
Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
            245                 250                 255

Arg Ala Asp Cys Gly Ile Thr Ser Ala Ser Tyr His Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Gly Leu Val Leu Met Ala Met Val Lys Lys Lys
    290                 295                 300

Asn Ser
305

<210> SEQ ID NO 333
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Val Val Gly Ala Asp Gly Val Gly Lys
1               5

<210> SEQ ID NO 334
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Val Val Val Gly Ala Asp Gly Val Gly Lys
1               5                   10

<210> SEQ ID NO 335
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Thr Ser Ile Asn Asn
1               5

<210> SEQ ID NO 336
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Ile Arg Ser Asn Glu Arg Glu
1               5

<210> SEQ ID NO 337
<211> LENGTH: 11
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 337

Ala Gly Leu Tyr Ser Ser Ala Ser Lys Ile Ile
1               5                   10

<210> SEQ ID NO 338
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Met Asn His Glu Tyr
1               5

<210> SEQ ID NO 339
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Ser Met Asn Val Glu Val
1               5

<210> SEQ ID NO 340
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Ala Ser Ser Ser Arg Gly His Ser Gly Thr Glu Ala Phe
1               5                   10

<210> SEQ ID NO 341
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 341
atggaaactc tcctgggagt gtctttggtg attctatggc ttcaactggc tagggtgaac      60
agtcaacagg gagaagagga tcctcaggcc ttgagcatcc aggagggtga aaatgccacc     120
atgaactgca gttacaaaac tagtataaac aatttacagt ggtatagaca aaattcaggt     180
agaggccttg tccacctaat tttaatacgt tcaaatgaaa gagagaaaca cagtggaaga     240
ttaagagtca cgcttgacac ttccaagaaa agcagttcct tgttgatcac ggcttcccgg     300
gcagcagaca ctgcttctta cttctgtgct gggctgtaca gcagtgcttc caagataatc     360
tttggatcag ggaccagact cagcatccgg cca                                  393

<210> SEQ ID NO 342
<211> LENGTH: 393

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 342
atggagacac tgctgggcgt gtccctggtc atcctgtggc tgcagctggc cagagtgaac      60
agccagcagg gagaggagga ccctcaggcc ctgagcatcc aggagggcga gaacgccacc     120
atgaattgct cttacaagac aagcatcaac aatctgcagt ggtataggca gaactccggc     180
cgcggactgg tgcacctgat cctgatcagg tctaatgagc gcgagaagca cagcggccgg     240
ctgagagtga ccctggacac aagcaagaag tctagctccc tgctgatcac cgcctccaga     300
gcagcagata cagcctctta cttctgtgcc ggcctgtatt ctagcgcctc caagatcatc     360
tttggcagcg gcacccggct gtccatcaga ccc                                 393

<210> SEQ ID NO 343
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 343

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Ser Leu Leu Ile
                85                  90                  95

Thr Ala Ser Arg Ala Ala Asp Thr Ala Ser Tyr Phe Cys Ala Gly Leu
            100                 105                 110

Tyr Ser Ser Ala Ser Lys Ile Ile Phe Gly Ser Gly Thr Arg Leu Ser
        115                 120                 125

Ile Arg Pro
    130

<210> SEQ ID NO 344
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 344
atgggccccc agctccttgg ctatgtggtc ctttgccttc taggagcagg ccccctggaa      60
gcccaagtga cccagaaccc aagataccct atcacagtga ctggaaagaa gttaacagtg     120
acttgttctc agaatatgaa ccatgagtat atgtcctggt atcgacaaga cccagggctg     180
ggcttaaggc agatctacta ttcaatgaat gttgaggtga ctgataaggg agatgttcct     240
```

```
gaagggtaca aagtctctcg aaaagagaag aggaatttcc ccctgatcct ggagtcgccc      300
agccccaacc agacctctct gtacttctgt gccagcagtt ccagggggca ttcgggcact      360
gaagctttct ttggacaagg caccagactc acagttgta                              399
```

<210> SEQ ID NO 345
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 345

```
atgggcccac agctgctggg ctacgtggtg ctgtgcctgc tgggagcagg accactggag      60
gcacaggtga cccagaaccc caggtatctg atcaccgtga caggcaagaa gctgaccgtg      120
acatgtagcc agaacatgaa tcacgagtac atgtcctggt ataggcagga ccccggactg      180
ggactgagac agatctacta ttccatgaat gtggaggtga ccgacaaggg cgatgtgcct      240
gagggctaca aggtgtctag gaaggagaag cgcaacttcc cactgatcct ggagtcccca      300
tctcccaatc agacctccct gtattttgc gccagctcct ctaggggcca ctctggcaca      360
gaggccttct ttggccaggg caccaggctg acagtggtg                             399
```

<210> SEQ ID NO 346
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 346

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Ser Arg Gly His Ser Gly Thr Glu Ala Phe Phe Gly Gln Gly Thr
        115                 120                 125

Arg Leu Thr Val Val
        130

<210> SEQ ID NO 347
<211> LENGTH: 268
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 347

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Ser Leu Leu Ile
                85                  90                  95

Thr Ala Ser Arg Ala Ala Asp Thr Ala Ser Tyr Phe Cys Ala Gly Leu
            100                 105                 110

Tyr Ser Ser Ala Ser Lys Ile Ile Phe Gly Ser Gly Thr Arg Leu Ser
        115                 120                 125

Ile Arg Pro Asp Ile Gln Asn Pro Glu Pro Ala Val Tyr Gln Leu Lys
130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
        195                 200                 205

Lys Glu Thr Asn Ala Thr Tyr Pro Ser Ser Asp Val Pro Cys Asp Ala
210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Leu Lys Val Ala Gly
                245                 250                 255

Phe Asn Leu Leu Met Thr Leu Arg Leu Trp Ser Ser
            260                 265

<210> SEQ ID NO 348
<211> LENGTH: 306
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 348

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
        50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile

```
                 85                  90                  95

Leu Glu Ser Pro Ser Pro Asn Gln Thr Ser Leu Tyr Phe Cys Ala Ser
            100                 105                 110

Ser Ser Arg Gly His Ser Gly Thr Glu Ala Phe Phe Gly Gln Gly Thr
        115                 120                 125

Arg Leu Thr Val Val Lys Asp Leu Arg Asn Val Thr Pro Pro Lys Val
    130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
    210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr His Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Gly Leu Val Leu Met Ala Met Val Lys Lys Lys
    290                 295                 300

Asn Ser
305

<210> SEQ ID NO 349
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Val Val Gly Ala Asp Gly Val Gly Lys
1               5

<210> SEQ ID NO 350
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Val Val Val Gly Ala Asp Gly Val Gly Lys
1               5                   10

<210> SEQ ID NO 351
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 351

Asn Ile Ala Thr Asn Asp Tyr
1               5

<210> SEQ ID NO 352
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Gly Tyr Lys Thr Lys
1               5

<210> SEQ ID NO 353
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Leu Ala Asn Thr Gly Gly Phe Lys Thr Ile
1               5                   10

<210> SEQ ID NO 354
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Ser Gly His Val Ser
1               5

<210> SEQ ID NO 355
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Phe Gln Asn Glu Ala Gln
1               5

<210> SEQ ID NO 356
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Ala Thr Tyr Lys Val Gly Asp Glu Gln Phe
1               5                   10

<210> SEQ ID NO 357

<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 357

```
atgaggcaag tggcgagagt gatcgtgttc ctgaccctga gtactttgag ccttgctaag      60
accacccagc ccatctccat ggactcatat gaaggacaag aagtgaacat aacctgtagc     120
cacaacaaca ttgctacaaa tgattatatc acgtggtacc aacagtttcc cagccaagga    180
ccacgattta ttattcaagg atacaagaca aaagttacaa cgaagtggc ctccctgttt      240
atccctgccg acagaaagtc cagcactctg agcctgcccc gggtttccct gagcgacact    300
gctgtgtact actgcctcgc taatactgga ggcttcaaaa ctatctttgg agcaggaaca    360
agactatttg ttaaagca                                                  378
```

<210> SEQ ID NO 358
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 358

```
atgaggcagg tggcacgcgt gatcgtgttt ctgaccctga gcacactgtc cctggccaag      60
accacacagc ctatctctat ggacagctac gagggccagg aggtgaacat cacctgctct    120
cacaacaata tcgccaccaa tgattacatc acatggtatc agcagttccc cagccagggc    180
cctcggttta tcatccaggg ctataagacc aaggtgacaa cgaggtggc cagcctgttc      240
atccctgccg acaggaagtc tagcaccctg tccctgccac gcgtgagcct gtccgataca    300
gccgtgtact attgtctggc caataccggc ggcttcaaga caatctttgg cgccggcacc    360
agactgtttg tgaaggcc                                                  378
```

<210> SEQ ID NO 359
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 359

```
Met Arg Gln Val Ala Arg Val Ile Val Phe Leu Thr Leu Ser Thr Leu
1               5                   10                  15

Ser Leu Ala Lys Thr Thr Gln Pro Ile Ser Met Asp Ser Tyr Glu Gly
            20                  25                  30

Gln Glu Val Asn Ile Thr Cys Ser His Asn Asn Ile Ala Thr Asn Asp
        35                  40                  45

Tyr Ile Thr Trp Tyr Gln Gln Phe Pro Ser Gln Gly Pro Arg Phe Ile
    50                  55                  60

Ile Gln Gly Tyr Lys Thr Lys Val Thr Asn Glu Val Ala Ser Leu Phe
65                  70                  75                  80

Ile Pro Ala Asp Arg Lys Ser Ser Thr Leu Ser Leu Pro Arg Val Ser
                85                  90                  95

Leu Ser Asp Thr Ala Val Tyr Tyr Cys Leu Ala Asn Thr Gly Gly Phe
                100                 105                 110
```

Lys Thr Ile Phe Gly Ala Gly Thr Arg Leu Phe Val Lys Ala
            115                 120                 125

<210> SEQ ID NO 360
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 360
atgggcacca ggctcctctg ctgggtggtc ctgggtttcc tagggacaga tcacacaggt      60
gctggagtct cccagtcccc taggtacaaa gtcgcaaaga gaggacagga tgtagctctc     120
aggtgtgatc caatttcggg tcatgtatcc cttttttggt accaacaggc cctggggcag     180
gggccagagt ttctgactta tttccagaat gaagctcaac tagacaaatc ggggctgccc     240
agtgatcgct ctttgcaga aaggcctgag ggatccgtct ccactctgaa gatccagcgc      300
acacagcagg aggactccgc cgtgtatctc tgtgccacct ataaggtcgg ggatgagcag     360
ttcttcgggc agggacacg gctcaccgtg cta                                    393

<210> SEQ ID NO 361
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 361
atgggaacca ggctgctgtg ctgggtggtg ctgggcttcc tgggaaccga ccacacagga      60
gcaggcgtgt cccagtctcc aaggtacaag gtggcaaaga gggggacagga cgtggccctg    120 agatgtgatc ctatctccgg ccacgtgtct ctgttttggt accagcaggc cctgggacag     180
ggacctgagt tcctgaccta ttttcagaac gaggcacagc tggacaagag cggactgcca     240
tccgatcggt ctctttgcaga gagaccgag ggcagcgtgt ccaccctgaa gatccagagg      300
acacagcagg aggactccgc cgtgtacctg tgcgccacat ataaagtggg cgatgagcag     360 ttcttttggcc caggcacccg gctgacagtg ctg                                  393

<210> SEQ ID NO 362
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 362

Met Gly Thr Arg Leu Leu Cys Trp Val Val Leu Gly Phe Leu Gly Thr
1               5                   10                  15

Asp His Thr Gly Ala Gly Val Ser Gln Ser Pro Arg Tyr Lys Val Ala
            20                  25                  30

Lys Arg Gly Gln Asp Val Ala Leu Arg Cys Asp Pro Ile Ser Gly His
        35                  40                  45

Val Ser Leu Phe Trp Tyr Gln Gln Ala Leu Gly Gln Gly Pro Glu Phe
    50                  55                  60

Leu Thr Tyr Phe Gln Asn Glu Ala Gln Leu Asp Lys Ser Gly Leu Pro
65                  70                  75                  80

Ser Asp Arg Phe Phe Ala Glu Arg Pro Glu Gly Ser Val Ser Thr Leu
                85                      90                      95

Lys Ile Gln Arg Thr Gln Gln Glu Asp Ser Ala Val Tyr Leu Cys Ala
            100                    105                    110

Thr Tyr Lys Val Gly Asp Glu Gln Phe Phe Gly Pro Gly Thr Arg Leu
            115                    120                    125

Thr Val Leu
    130

<210> SEQ ID NO 363
<211> LENGTH: 263
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 363

Met Arg Gln Val Ala Arg Val Ile Val Phe Leu Thr Leu Ser Thr Leu
1               5                    10                      15

Ser Leu Ala Lys Thr Thr Gln Pro Ile Ser Met Asp Ser Tyr Glu Gly
            20                    25                    30

Gln Glu Val Asn Ile Thr Cys Ser His Asn Asn Ile Ala Thr Asn Asp
            35                    40                    45

Tyr Ile Thr Trp Tyr Gln Gln Phe Pro Ser Gln Gly Pro Arg Phe Ile
    50                    55                    60

Ile Gln Gly Tyr Lys Thr Lys Val Thr Asn Glu Val Ala Ser Leu Phe
65                    70                    75                    80

Ile Pro Ala Asp Arg Lys Ser Ser Thr Leu Ser Leu Pro Arg Val Ser
            85                    90                    95

Leu Ser Asp Thr Ala Val Tyr Tyr Cys Leu Ala Asn Thr Gly Gly Phe
            100                    105                    110

Lys Thr Ile Phe Gly Ala Gly Thr Arg Leu Phe Val Lys Ala Asp Ile
            115                    120                    125

Gln Asn Pro Glu Pro Ala Val Tyr Gln Leu Lys Asp Pro Arg Ser Gln
130                    135                    140

Asp Ser Thr Leu Cys Leu Phe Thr Asp Phe Asp Ser Gln Ile Asn Val
145                  150                    155                    160

Pro Lys Thr Met Glu Ser Gly Thr Phe Ile Thr Asp Lys Thr Val Leu
            165                    170                    175

Asp Met Lys Ala Met Asp Ser Lys Ser Asn Gly Ala Ile Ala Trp Ser
            180                    185                    190

Asn Gln Thr Ser Phe Thr Cys Gln Asp Ile Phe Lys Glu Thr Asn Ala
            195                    200                    205

Thr Tyr Pro Ser Ser Asp Val Pro Cys Asp Ala Thr Leu Thr Glu Lys
            210                    215                    220

Ser Phe Glu Thr Asp Met Asn Leu Asn Phe Gln Asn Leu Ser Val Met
225                  230                    235                    240

Gly Leu Arg Ile Leu Leu Leu Lys Val Ala Gly Phe Asn Leu Leu Met
            245                    250                    255

Thr Leu Arg Leu Trp Ser Ser
            260

<210> SEQ ID NO 364
<211> LENGTH: 304
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 364

Met Gly Thr Arg Leu Leu Cys Trp Val Val Leu Gly Phe Leu Gly Thr
1               5                   10                  15

Asp His Thr Gly Ala Gly Val Ser Gln Ser Pro Arg Tyr Lys Val Ala
            20                  25                  30

Lys Arg Gly Gln Asp Val Ala Leu Arg Cys Asp Pro Ile Ser Gly His
        35                  40                  45

Val Ser Leu Phe Trp Tyr Gln Gln Ala Leu Gly Gln Gly Pro Glu Phe
    50                  55                  60

Leu Thr Tyr Phe Gln Asn Glu Ala Gln Leu Asp Lys Ser Gly Leu Pro
65                  70                  75                  80

Ser Asp Arg Phe Phe Ala Glu Arg Pro Glu Gly Ser Val Ser Thr Leu
                85                  90                  95

Lys Ile Gln Arg Thr Gln Gln Glu Asp Ser Ala Val Tyr Leu Cys Ala
            100                 105                 110

Thr Tyr Lys Val Gly Asp Glu Gln Phe Phe Gly Pro Gly Thr Arg Leu
        115                 120                 125

Thr Val Leu Lys Asp Leu Arg Asn Val Thr Pro Pro Lys Val Ser Leu
130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Ser Thr Asp Pro Gln
            180                 185                 190

Ala Tyr Lys Glu Ser Asn Tyr Ser Tyr Cys Leu Ser Ser Arg Leu Arg
        195                 200                 205

Val Ser Ala Thr Phe Trp His Asn Pro Arg Asn His Phe Arg Cys Gln
210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr His Gln Gly Val Leu Ser Ala
            260                 265                 270

Thr Ile Leu Tyr Glu Ile Leu Leu Gly Lys Ala Thr Leu Tyr Ala Val
        275                 280                 285

Leu Val Ser Gly Leu Val Leu Met Ala Met Val Lys Lys Lys Asn Ser
    290                 295                 300

<210> SEQ ID NO 365
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Val Val Gly Ala Asp Gly Val Gly Lys
1               5

```
<210> SEQ ID NO 366
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Val Val Val Gly Ala Asp Gly Val Gly Lys
1               5                   10

<210> SEQ ID NO 367
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Asp Ser Ala Ser Asn Tyr
1               5

<210> SEQ ID NO 368
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Ile Arg Ser Asn Val Gly Glu
1               5

<210> SEQ ID NO 369
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Ala Glu Thr Gly Phe Gln Lys Leu Val
1               5

<210> SEQ ID NO 370
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Met Asp His Glu Asn
1               5

<210> SEQ ID NO 371
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371
```

Ser Tyr Asp Val Lys Met
1               5

<210> SEQ ID NO 372
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Ala Ser Ser Asp Trp Leu Ala Gly Ala Lys Asp Glu Gln Tyr
1               5                   10

<210> SEQ ID NO 373
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 373
atgacatcca ttcgagctgt atttatattc ctgtggctgc agctggactt ggtgaatgga      60
gagaatgtgg agcagcatcc ttcaaccctg agtgtccagg agggagacag cgctgttatc     120
aagtgtactt attcagacag tgcctcaaac tacttccctt ggtataagca agaacttgga     180
aaaagacctc agcttattat agacattcgt tcaaatgtgg gcgaaaagaa agaccaacga     240
attgctgtta cattgaacaa gacagccaaa catttctccc tgcacatcac agagacccaa     300
cctgaagact cggctgtcta cttctgtgca gaaacaggct tcagaaaact tgtatttgga     360
actggcaccc gacttctggt cagtcca                                         387

<210> SEQ ID NO 374
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 374
atgacatcta tccgcgccgt gttcatcttt ctgtggctgc agctggacct ggtgaacggc      60
gagaatgtgg agcagcaccc aagcaccctg tccgtgcagg agggcgacag cgccgtgatc     120
aagtgcacat actctgatag cgcctccaac tactttccct ggtataagca ggagctgggc     180
aagcggcctc agctgatcat cgacatcaga tccaacgtgg gcgagaagaa ggatcagcgg     240
atcgccgtga ccctgaataa gacagccaag cacttcagcc tgcacatcac cgagacacag     300
cccgaggatt ccgccgtgta ttttgtgcc gagaccggct ccagaagct ggtgtttggc       360 accggcacaa gactgctggt gtcccct                                         387

<210> SEQ ID NO 375
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 375

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
                35                  40                  45

Ser Asn Tyr Phe Pro Trp Tyr Lys Gln Glu Leu Gly Lys Arg Pro Gln
50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Glu Thr
                100                 105                 110

Gly Phe Gln Lys Leu Val Phe Gly Thr Gly Thr Arg Leu Leu Val Ser
                115                 120                 125

Pro

<210> SEQ ID NO 376
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 376
atgggaatca ggctcctctg tcgtgtggcc ttttgttcc tggctgtagg cctcgtagat    60
gtgaaagtaa cccagagctc gagatatcta gtcaaaagga cgggagagaa agttttctg   120 gaatgtgtcc aggatatgga ccatgaaaat atgttctggt atcgacaaga cccaggtctg   180
gggctacggc tgatctattt ctcatatgat gttaaaatga agaaaaagg agatattcct   240 gagggggtaca gtgtctctag agagaagaag gagcgcttct ccctgattct ggagtccgcc   300
agcaccaacc agacatctat gtacctctgt gccagcagtg actggctagc gggagcgaag   360
gacgagcagt acttcgggcc gggcaccagg ctcacggtca ca                     402

<210> SEQ ID NO 377
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 377
atgggcatcc ggctgctgtg cagagtggcc ttctgttttc tggccgtggg cctggtggac    60
gtgaaggtga cccagagctc ccggtacctg gtgaagagaa caggcgagaa ggtgttcctg   120
gagtgcgtgc aggacatgga tcacgagaac atgttttggt ataggcagga ccccggactg   180
ggactgagac tgatctactt cagctatgac gtgaagatga ggagaaaggg cgacatccca   240
gagggctaca gcgtgtccag ggagaagaag gagcggttca gcctgatcct ggagtctgcc   300
agcaccaatc agacaagcat gtacctgtgc gcctctagcg actggctggc cggagcaaag   360
gatgagcagt atttcggccc aggcaccagg ctgaccgtga ca                     402

<210> SEQ ID NO 378
<211> LENGTH: 134

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 378

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
                20                  25                  30

Arg Thr Gly Glu Lys Val Phe Leu Glu Cys Val Gln Asp Met Asp His
            35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
                100                 105                 110

Ser Asp Trp Leu Ala Gly Ala Lys Asp Glu Gln Tyr Phe Gly Pro Gly
            115                 120                 125

Thr Arg Leu Thr Val Thr
            130

<210> SEQ ID NO 379
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 379

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
                20                  25                  30

Gln Glu Gly Asp Ser Ala Val Ile Lys Cys Thr Tyr Ser Asp Ser Ala
            35                  40                  45

Ser Asn Tyr Phe Pro Trp Tyr Lys Gln Glu Leu Gly Lys Arg Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Glu Thr
            100                 105                 110

Gly Phe Gln Lys Leu Val Phe Gly Thr Gly Thr Arg Leu Leu Val Ser
            115                 120                 125

Pro Asp Ile Gln Asn Pro Glu Pro Ala Val Tyr Gln Leu Lys Asp Pro
    130                 135                 140

Arg Ser Gln Asp Ser Thr Leu Cys Leu Phe Thr Asp Phe Asp Ser Gln
145                 150                 155                 160

Ile Asn Val Pro Lys Thr Met Glu Ser Gly Thr Phe Ile Thr Asp Lys
                165                 170                 175
```

```
Thr Val Leu Asp Met Lys Ala Met Asp Ser Lys Ser Asn Gly Ala Ile
            180                 185                 190

Ala Trp Ser Asn Gln Thr Ser Phe Thr Cys Gln Asp Ile Phe Lys Glu
        195                 200                 205

Thr Asn Ala Thr Tyr Pro Ser Ser Asp Val Pro Cys Asp Ala Thr Leu
    210                 215                 220

Thr Glu Lys Ser Phe Glu Thr Asp Met Asn Leu Asn Phe Gln Asn Leu
225                 230                 235                 240

Ser Val Met Gly Leu Arg Ile Leu Leu Lys Val Ala Gly Phe Asn
                245                 250                 255

Leu Leu Met Thr Leu Arg Leu Trp Ser Ser
            260                 265
```

<210> SEQ ID NO 380
<211> LENGTH: 307
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 380

```
Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Asp Trp Leu Ala Gly Ala Lys Asp Glu Gln Tyr Phe Gly Pro Gly
        115                 120                 125

Thr Arg Leu Thr Val Thr Lys Asp Leu Arg Asn Val Thr Pro Pro Lys
    130                 135                 140

Val Ser Leu Phe Glu Pro Ser Lys Ala Glu Ile Ala Asn Lys Gln Lys
145                 150                 155                 160

Ala Thr Leu Val Cys Leu Ala Arg Gly Phe Phe Pro Asp His Val Glu
                165                 170                 175

Leu Ser Trp Trp Val Asn Gly Lys Glu Val His Ser Gly Val Ser Thr
            180                 185                 190

Asp Pro Gln Ala Tyr Lys Glu Ser Asn Tyr Ser Tyr Cys Leu Ser Ser
        195                 200                 205

Arg Leu Arg Val Ser Ala Thr Phe Trp His Asn Pro Arg Asn His Phe
    210                 215                 220

Arg Cys Gln Val Gln Phe His Gly Leu Ser Glu Glu Asp Lys Trp Pro
225                 230                 235                 240

Glu Gly Ser Pro Lys Pro Val Thr Gln Asn Ile Ser Ala Glu Ala Trp
                245                 250                 255

Gly Arg Ala Asp Cys Gly Ile Thr Ser Ala Ser Tyr His Gln Gly Val
            260                 265                 270
```

```
Leu Ser Ala Thr Ile Leu Tyr Glu Ile Leu Leu Gly Lys Ala Thr Leu
        275                 280                 285

Tyr Ala Val Leu Val Ser Gly Leu Val Leu Met Ala Met Val Lys Lys
        290                 295                 300

Lys Asn Ser
305

<210> SEQ ID NO 381
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Val Val Gly Ala Asp Gly Val Gly Lys
1               5

<210> SEQ ID NO 382
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Val Val Val Gly Ala Asp Gly Val Gly Lys
1               5                   10

<210> SEQ ID NO 383
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Thr Ser Ile Asn Asn
1               5

<210> SEQ ID NO 384
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Ile Arg Ser Asn Glu Arg Glu
1               5

<210> SEQ ID NO 385
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Ala Thr Asp Pro Leu Asp Tyr Lys Leu Ser
1               5                   10
```

<210> SEQ ID NO 386
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Met Asn His Glu Tyr
1               5

<210> SEQ ID NO 387
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Ser Met Asn Val Glu Val
1               5

<210> SEQ ID NO 388
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Ala Ser Ser Leu Val Ala Ser Asn Glu Gln Phe
1               5                   10

<210> SEQ ID NO 389
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 389
atggaaactc tcctgggagt gtctttggtg attctatggc ttcaactggc tagggtgaac     60
agtcaacagg gagaagagga tcctcaggcc ttgagcatcc aggagggtga aaatgccacc    120
atgaactgca gttacaaaac tagtataaac aatttacagt ggtatagaca aaattcaggt    180
agaggccttg tccacctaat tttaatacgt tcaaatgaaa gagagaaaca cagtggaaga    240
ttaagagtca cgcttgacac ttccaagaaa agcagttcct tgttgatcac ggcttcccgg    300
gcagcagaca ctgcttctta cttctgtgct acggacccct tagactacaa gctcagcttt    360
ggagccggaa ccacagtaac tgtaagagca                                     390

<210> SEQ ID NO 390
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 390

```
atggagaccc tgctgggcgt gtctctggtc atcctgtggc tgcagctggc cagagtgaac    60
tctcagcagg gagaggagga ccctcaggcc ctgagcatcc aggagggcga gaacgccacc   120
atgaattgct cttacaagac aagcatcaac aatctgcagt ggtatcggca gaactccggc   180
agaggcctgg tgcacctgat cctgatcagg agcaatgagc gcgagaagca ctccggccgg   240
ctgagagtga ccctggacac atctaagaag tcctctagcc tgctgatcac cgcctctagg   300
gcagcagata cagccagcta cttctgtgcc accgacccac tggattataa gctgtccttt   360
ggcgccggca ccacagtgac cgtgcgcgcc                                    390
```

<210> SEQ ID NO 391
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 391

```
Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Ser Leu Leu Ile
                85                  90                  95

Thr Ala Ser Arg Ala Ala Asp Thr Ala Ser Tyr Phe Cys Ala Thr Asp
            100                 105                 110

Pro Leu Asp Tyr Lys Leu Ser Phe Gly Ala Gly Thr Thr Val Thr Val
        115                 120                 125

Arg Ala
    130
```

<210> SEQ ID NO 392
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 392

```
atgggccccc agctccttgg ctatgtggtc ctttgccttc taggagcagg ccccctggaa    60
gcccaagtga cccagaaccc aagatacctc atcacagtga ctggaaagaa gttaacagtg   120
acttgttctc agaatatgaa ccatgagtat atgtcctggt atcgacaaga cccagggctg   180
ggcttaaggc agatctacta ttcaatgaat gttgaggtga ctgataaggg agatgttcct   240
gaagggtaca agtctctcg aaaagagaag aggaatttcc ccctgatcct ggagtcgccc   300
agccccaacc agacctctct gtacttctgt gccagcagtt tggtggctag caatgagcag   360
ttcttcgggc agggacacg gctcaccgtg cta                                 393
```

<210> SEQ ID NO 393

<211> LENGTH: 393
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 393

```
atgggcccac agctgctggg ctacgtggtg ctgtgcctgc tgggagcagg accactggag    60
gcacaggtga cccagaatcc ccggtatctg atcaccgtga caggcaagaa gctgaccgtg   120
acatgttccc agaacatgaa tcacgagtac atgtcttggt ataggcagga ccccggactg   180
ggactgaggc agatctacta ttctatgaac gtggaggtga cagacaaggg cgatgtgcct   240
gagggctaca aggtgagcag gaaggagaag cgcaacttcc cactgatcct ggagtcccca   300
tctcccaatc agaccagcct gtattttgc gccagctccc tggtggcctc caacgagcag   360
ttctttggcc ctggcacccg gctgacagtg ctg                                393
```

<210> SEQ ID NO 394
<211> LENGTH: 131
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 394

Met Gly Pro Gln Leu Leu Gly Tyr Val Val Leu Cys Leu Leu Gly Ala
1               5                   10                  15
Gly Pro Leu Glu Ala Gln Val Thr Gln Asn Pro Arg Tyr Leu Ile Thr
            20                  25                  30
Val Thr Gly Lys Lys Leu Thr Val Thr Cys Ser Gln Asn Met Asn His
        35                  40                  45
Glu Tyr Met Ser Trp Tyr Arg Gln Asp Pro Gly Leu Gly Leu Arg Gln
    50                  55                  60
Ile Tyr Tyr Ser Met Asn Val Glu Val Thr Asp Lys Gly Asp Val Pro
65                  70                  75                  80
Glu Gly Tyr Lys Val Ser Arg Lys Glu Lys Arg Asn Phe Pro Leu Ile
                85                  90                  95
Leu Glu Ser Pro Ser Pro Asn Gln Thr Ser Leu Tyr Phe Cys Ala Ser
            100                 105                 110
Ser Leu Val Ala Ser Asn Glu Gln Phe Phe Gly Pro Gly Thr Arg Leu
        115                 120                 125
Thr Val Leu
    130

<210> SEQ ID NO 395
<211> LENGTH: 267
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 395

Met Glu Thr Leu Leu Gly Val Ser Leu Val Ile Leu Trp Leu Gln Leu
1               5                   10                  15
Ala Arg Val Asn Ser Gln Gln Gly Glu Glu Asp Pro Gln Ala Leu Ser
            20                  25                  30
Ile Gln Glu Gly Glu Asn Ala Thr Met Asn Cys Ser Tyr Lys Thr Ser

```
            35                  40                  45
Ile Asn Asn Leu Gln Trp Tyr Arg Gln Asn Ser Gly Arg Gly Leu Val
 50                  55                  60
His Leu Ile Leu Ile Arg Ser Asn Glu Arg Glu Lys His Ser Gly Arg
 65                  70                  75                  80
Leu Arg Val Thr Leu Asp Thr Ser Lys Lys Ser Ser Leu Leu Ile
                 85                  90                  95
Thr Ala Ser Arg Ala Ala Asp Thr Ala Ser Tyr Phe Cys Ala Thr Asp
                100                 105                 110
Pro Leu Asp Tyr Lys Leu Ser Phe Gly Ala Gly Thr Thr Val Thr Val
                115                 120                 125
Arg Ala Asp Ile Gln Asn Pro Glu Pro Ala Val Tyr Gln Leu Lys Asp
                130                 135                 140
Pro Arg Ser Gln Asp Ser Thr Leu Cys Leu Phe Thr Asp Phe Asp Ser
145                 150                 155                 160
Gln Ile Asn Val Pro Lys Thr Met Glu Ser Gly Thr Phe Ile Thr Asp
                165                 170                 175
Lys Thr Val Leu Asp Met Lys Ala Met Asp Ser Lys Ser Asn Gly Ala
                180                 185                 190
Ile Ala Trp Ser Asn Gln Thr Ser Phe Thr Cys Gln Asp Ile Phe Lys
                195                 200                 205
Glu Thr Asn Ala Thr Tyr Pro Ser Ser Asp Val Pro Cys Asp Ala Thr
210                 215                 220
Leu Thr Glu Lys Ser Phe Glu Thr Asp Met Asn Leu Asn Phe Gln Asn
225                 230                 235                 240
Leu Ser Val Met Gly Leu Arg Ile Leu Leu Lys Val Ala Gly Phe
                245                 250                 255
Asn Leu Leu Met Thr Leu Arg Leu Trp Ser Ser
                260                 265

<210> SEQ ID NO 396
<211> LENGTH: 304
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 396

Met Gly Pro Gln Leu Leu Gly Tyr Val Val Leu Cys Leu Leu Gly Ala
 1               5                  10                  15
Gly Pro Leu Glu Ala Gln Val Thr Gln Asn Pro Arg Tyr Leu Ile Thr
                20                  25                  30
Val Thr Gly Lys Lys Leu Thr Val Thr Cys Ser Gln Asn Met Asn His
                35                  40                  45
Glu Tyr Met Ser Trp Tyr Arg Gln Asp Pro Gly Leu Gly Leu Arg Gln
 50                  55                  60
Ile Tyr Tyr Ser Met Asn Val Glu Val Thr Asp Lys Gly Asp Val Pro
 65                  70                  75                  80
Glu Gly Tyr Lys Val Ser Arg Lys Glu Lys Arg Asn Phe Pro Leu Ile
                 85                  90                  95
Leu Glu Ser Pro Ser Pro Asn Gln Thr Ser Leu Tyr Phe Cys Ala Ser
                100                 105                 110
Ser Leu Val Ala Ser Asn Glu Gln Phe Phe Gly Pro Gly Thr Arg Leu
                115                 120                 125
```

-continued

```
Thr Val Leu Lys Asp Leu Arg Asn Val Thr Pro Pro Lys Val Ser Leu
            130                 135                 140
Phe Glu Pro Ser Lys Ala Glu Ile Ala Asn Lys Gln Lys Ala Thr Leu
145                 150                 155                 160
Val Cys Leu Ala Arg Gly Phe Phe Pro Asp His Val Glu Leu Ser Trp
                165                 170                 175
Trp Val Asn Gly Lys Glu Val His Ser Gly Val Ser Thr Asp Pro Gln
            180                 185                 190
Ala Tyr Lys Glu Ser Asn Tyr Ser Tyr Cys Leu Ser Ser Arg Leu Arg
        195                 200                 205
Val Ser Ala Thr Phe Trp His Asn Pro Arg Asn His Phe Arg Cys Gln
210                 215                 220
Val Gln Phe His Gly Leu Ser Glu Glu Asp Lys Trp Pro Glu Gly Ser
225                 230                 235                 240
Pro Lys Pro Val Thr Gln Asn Ile Ser Ala Glu Ala Trp Gly Arg Ala
                245                 250                 255
Asp Cys Gly Ile Thr Ser Ala Ser Tyr His Gln Gly Val Leu Ser Ala
            260                 265                 270
Thr Ile Leu Tyr Glu Ile Leu Leu Gly Lys Ala Thr Leu Tyr Ala Val
        275                 280                 285
Leu Val Ser Gly Leu Val Leu Met Ala Met Val Lys Lys Lys Asn Ser
290                 295                 300

<210> SEQ ID NO 397
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Val Val Gly Ala Val Gly Val Gly Lys
1               5

<210> SEQ ID NO 398
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Val Val Val Gly Ala Val Gly Val Gly Lys
1               5                   10

<210> SEQ ID NO 399
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Thr Ser Glu Ser Asp Tyr Tyr
1               5

<210> SEQ ID NO 400
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 400

Gln Glu Ala Tyr Lys Gln Gln Asn
1               5

<210> SEQ ID NO 401
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Ala Cys Gln Gly Gly Ser Glu Lys Leu Val
1               5                   10

<210> SEQ ID NO 402
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Ser Gly His Asn Thr
1               5

<210> SEQ ID NO 403
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Tyr Tyr Arg Glu Glu Glu
1               5

<210> SEQ ID NO 404
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Ala Ser Ser Leu Gly Leu Leu Leu Tyr Asn Glu Gln Phe
1               5                   10

<210> SEQ ID NO 405
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 405
atggcatgcc ctggcttcct gtgggcactt gtgatctcca cctgtcttga atttagcatg      60
```

```
gctcagacag tcactcagtc tcaaccagag atgtctgtgc aggaggcaga gaccgtgacc    120
ctgagctgca catatgacac cagtgagagt gattattatt tattctggta caagcagcct    180
cccagcaggc agatgattct cgttattcgc caagaagctt ataagcaaca gaatgcaaca    240
gagaatcgtt tctctgtgaa cttccagaaa gcagccaaat ccttcagtct caagatctca    300
gactcacagc tgggggatgc cgcgatgtat ttctgtgctt gtcagggcgg atctgaaaag    360
ctggtctttg aaagggaac gaaactgaca gtaaaccca                           399
```

<210> SEQ ID NO 406
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 406

```
atggcatgcc caggcttcct gtgggcactg gtcatcagca cctgtctgga gttttctatg    60
gcccagaccg tgacacagag ccagccagag atgtccgtgc aggaggcaga gaccgtgaca    120
ctgtcctgta cctacgacac aagcgagtcc gattactatc tgttctggta taagcagcct    180
ccatctcgcc agatgatcct ggtcatccgg caggaggcct acaagcagca gaacgccacc    240
gagaatcggt tctctgtgaa ttttcagaag gccgccaagt cttttagcct gaagatctcc    300
gactctcagc tgggcgatgc cgccatgtat ttctgcgcat gtcagggagg cagcgagaag    360
ctggtgtttg gcaagggcac caagctgaca gtgaaccct                           399
```

<210> SEQ ID NO 407
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 407

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
                20                  25                  30

Val Gln Glu Ala Glu Thr Val Thr Leu Ser Cys Thr Tyr Asp Thr Ser
            35                  40                  45

Glu Ser Asp Tyr Tyr Leu Phe Trp Tyr Lys Gln Pro Pro Ser Arg Gln
        50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Cys Gln Gly Gly Ser Glu Lys Leu Val Phe Gly Lys Gly Thr Lys
        115                 120                 125

Leu Thr Val Asn Pro
    130

<210> SEQ ID NO 408
<211> LENGTH: 399
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 408

```
atgggccctg ggctcctctg ctgggtgctg ctttgtctcc tgggagcagg ctcagtggag    60
actggagtca cccaaagtcc cacacacctg atcaaaacga aggacagca agtgactctg   120
agatgctctt ctcagtctgg cacaacact gtgtcctggt accaacaggc cctgggtcag    180
gggccccagt ttatctttca gtattatagg aggaagaga atggcagagg aaacttccct    240
cctagattct caggtctcca gttccctaat tatagctctg agctgaatgt gaacgccttg    300
gagctggacg actcggccct gtatctctgt gccagcagct gggactcct cctctacaat    360
gagcagttct cgggccagg gacacggctc accgtgcta                           399
```

<210> SEQ ID NO 409
<211> LENGTH: 399
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 409

```
atgggaccag gactgctgtg ctgggtgctg ctgtgcctgc tgggagcagg cagcgtggag    60
accggcgtga cacagtcccc tacccacctg atcaagacaa gaggccagca ggtgaccctg   120
aggtgcagct cccagtctgg ccacaataca gtgagctggt accagcaggc cctgggacag   180
gacctcagt tcatctttca gtactatagg gaggaggaga acggccgcgg caatttcccc   240
cctcggttta gcggcctgca gttcccaaac tattctagcg agctgaacgt gaatgccctg   300
gagctggacg attccgccct gtacctgtgc gcctcctctc tgggcctgct gctgtataac   360
gagcagttct ttggccccgg caccagactg acagtgctg                          399
```

<210> SEQ ID NO 410
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 410

```
Met Gly Pro Gly Leu Leu Cys Trp Val Leu Cys Leu Leu Gly Ala
1               5                   10                  15

Gly Ser Val Glu Thr Gly Val Thr Gln Ser Pro Thr His Leu Ile Lys
            20                  25                  30

Thr Arg Gly Gln Gln Val Thr Leu Arg Cys Ser Ser Gln Ser Gly His
        35                  40                  45

Asn Thr Val Ser Trp Tyr Gln Gln Ala Leu Gly Gln Gly Pro Gln Phe
    50                  55                  60

Ile Phe Gln Tyr Tyr Arg Glu Glu Glu Asn Gly Arg Gly Asn Phe Pro
65                  70                  75                  80

Pro Arg Phe Ser Gly Leu Gln Phe Pro Asn Tyr Ser Ser Glu Leu Asn
                85                  90                  95

Val Asn Ala Leu Glu Leu Asp Asp Ser Ala Leu Tyr Leu Cys Ala Ser
            100                 105                 110

Ser Leu Gly Leu Leu Leu Tyr Asn Glu Gln Phe Phe Gly Pro Gly Thr
```

```
            115                 120                 125
Arg Leu Thr Val Leu
        130
```

<210> SEQ ID NO 411
<211> LENGTH: 270
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 411

```
Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asp Tyr Tyr Leu Phe Trp Tyr Lys Gln Pro Pro Ser Arg Gln
    50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Cys Gln Gly Gly Ser Glu Lys Leu Val Phe Gly Lys Gly Thr Lys
        115                 120                 125

Leu Thr Val Asn Pro Asp Ile Gln Asn Pro Glu Pro Ala Val Tyr Gln
    130                 135                 140

Leu Lys Asp Pro Arg Ser Gln Asp Ser Thr Leu Cys Leu Phe Thr Asp
145                 150                 155                 160

Phe Asp Ser Gln Ile Asn Val Pro Lys Thr Met Glu Ser Gly Thr Phe
                165                 170                 175

Ile Thr Asp Lys Thr Val Leu Asp Met Lys Ala Met Asp Ser Lys Ser
            180                 185                 190

Asn Gly Ala Ile Ala Trp Ser Asn Gln Thr Ser Phe Thr Cys Gln Asp
        195                 200                 205

Ile Phe Lys Glu Thr Asn Ala Thr Tyr Pro Ser Ser Asp Val Pro Cys
    210                 215                 220

Asp Ala Thr Leu Thr Glu Lys Ser Phe Glu Thr Asp Met Asn Leu Asn
225                 230                 235                 240

Phe Gln Asn Leu Ser Val Met Gly Leu Arg Ile Leu Leu Leu Lys Val
                245                 250                 255

Ala Gly Phe Asn Leu Leu Met Thr Leu Arg Leu Trp Ser Ser
            260                 265                 270
```

<210> SEQ ID NO 412
<211> LENGTH: 306
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 412

```
Met Gly Pro Gly Leu Leu Cys Trp Val Leu Leu Cys Leu Leu Gly Ala
```

-continued

```
               1               5                  10                 15
            Gly Ser Val Glu Thr Gly Val Thr Gln Ser Pro Thr His Leu Ile Lys
                           20                  25                 30
            Thr Arg Gly Gln Gln Val Thr Leu Arg Cys Ser Ser Gln Ser Gly His
                           35                  40                 45
            Asn Thr Val Ser Trp Tyr Gln Gln Ala Leu Gly Gln Gly Pro Gln Phe
                50                          55                  60
            Ile Phe Gln Tyr Tyr Arg Glu Glu Asn Gly Arg Gly Asn Phe Pro
            65                          70                  75                 80
            Pro Arg Phe Ser Gly Leu Gln Phe Pro Asn Tyr Ser Ser Glu Leu Asn
                           85                  90                 95
            Val Asn Ala Leu Glu Leu Asp Asp Ser Ala Leu Tyr Leu Cys Ala Ser
                          100                 105                110
            Ser Leu Gly Leu Leu Tyr Asn Glu Gln Phe Phe Gly Pro Gly Thr
                          115                 120                125
            Arg Leu Thr Val Leu Lys Asp Leu Arg Asn Val Thr Pro Pro Lys Val
            130                         135                 140
            Ser Leu Phe Glu Pro Ser Lys Ala Glu Ile Ala Asn Lys Gln Lys Ala
            145                         150                 155                160
            Thr Leu Val Cys Leu Ala Arg Gly Phe Phe Pro Asp His Val Glu Leu
                                    165                 170                 175
            Ser Trp Trp Val Asn Gly Lys Glu Val His Ser Gly Val Ser Thr Asp
                                    180                 185                 190
            Pro Gln Ala Tyr Lys Glu Ser Asn Tyr Ser Tyr Cys Leu Ser Ser Arg
                           195                 200                 205
            Leu Arg Val Ser Ala Thr Phe Trp His Asn Pro Arg Asn His Phe Arg
                 210                         215                 220
            Cys Gln Val Gln Phe His Gly Leu Ser Glu Glu Asp Lys Trp Pro Glu
            225                         230                 235                240
            Gly Ser Pro Lys Pro Val Thr Gln Asn Ile Ser Ala Glu Ala Trp Gly
                                    245                 250                 255
            Arg Ala Asp Cys Gly Ile Thr Ser Ala Ser Tyr His Gln Gly Val Leu
                                    260                 265                 270
            Ser Ala Thr Ile Leu Tyr Glu Ile Leu Leu Gly Lys Ala Thr Leu Tyr
                           275                 280                 285
            Ala Val Leu Val Ser Gly Leu Val Leu Met Ala Met Val Lys Lys Lys
                           290                 295                 300
            Asn Ser
            305

<210> SEQ ID NO 413
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

Val Val Gly Ala Val Gly Val Gly Lys
1               5

<210> SEQ ID NO 414
<211> LENGTH: 10
<212> TYPE: PRT
<213> ORGANISM: Artificial Sequence
<220> FEATURE:
```

<223> OTHER INFORMATION: Description of Artificial Sequence: Synthetic
     peptide

<400> SEQUENCE: 414

Val Val Val Gly Ala Val Gly Val Gly Lys
1               5                   10

<210> SEQ ID NO 415
<211> LENGTH: 5
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 415

Thr Ser Ile Asn Asn
1               5

<210> SEQ ID NO 416
<211> LENGTH: 7
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 416

Ile Arg Ser Asn Glu Arg Glu
1               5

<210> SEQ ID NO 417
<211> LENGTH: 12
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 417

Ala Thr Asp Ala Gln Thr Gly Ala Asn Asn Leu Phe
1               5                   10

<210> SEQ ID NO 418
<211> LENGTH: 5
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 418

Ser Gly His Ala Thr
1               5

<210> SEQ ID NO 419
<211> LENGTH: 6
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 419

Phe Gln Asn Asn Gly Val
1               5

-continued

<210> SEQ ID NO 420
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Ala Ser Ser Leu Gly Asp Ser Tyr Glu Gln Tyr Phe
1               5                   10

<210> SEQ ID NO 421
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 421
atggaaactc tcctgggagt gtctttggtg attctatggc ttcaactggc tagggtgaac      60
agtcaacagg gagaagagga tcctcaggcc ttgagcatcc aggagggtga aaatgccacc     120
atgaactgca gttacaaaac tagtataaac aatttacagt ggtatagaca aaattcaggt     180
agaggccttg tccacctaat tttaatacgt tcaaatgaaa gagagaaaca cagtggaaga     240
ttaagagtca cgcttgacac ttccaagaaa agcagttcct tgttgatcac ggcttcccgg     300
gcagcagaca ctgcttctta cttctgtgct acggacgctc aaactggggc aaacaacctc     360
ttctttggga ctggaacgag actcaccgtt attccc                               396

<210> SEQ ID NO 422
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 422
atggagacac tgctgggcgt gtctctggtc atcctgtggc tgcagctggc cagagtgaat      60
agccagcagg gagaggagga cccccaggcc ctgtccatcc aggagggcga aacgccacc      120 atgaattgca gctacaagac atccatcaac aatctgcagt ggtatcggca gaactctggc     180
agaggcctgg tgcacctgat cctgatccgg tccaatgaga gagaagca ctctggccgg       240 ctgagagtga ccctggatac atccaagaag tcctctagcc tgctgatcac cgccagccgg     300
gcagcagaca cagcctccta tttttgtgcc accgatgccc agacaggcgc caacaatctg     360
ttctttggca ccggcacaag actgaccgtg atccct                               396

<210> SEQ ID NO 423
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 423

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
                20                  25                  30

Ile Gln Glu Gly Glu Asn Ala Thr Met Asn Cys Ser Tyr Lys Thr Ser
            35                  40                  45

Ile Asn Asn Leu Gln Trp Tyr Arg Gln Asn Ser Gly Arg Gly Leu Val
     50                  55                  60

His Leu Ile Leu Ile Arg Ser Asn Glu Arg Glu Lys His Ser Gly Arg
 65                  70                  75                  80

Leu Arg Val Thr Leu Asp Thr Ser Lys Lys Ser Ser Leu Leu Ile
                 85                  90                  95

Thr Ala Ser Arg Ala Ala Asp Thr Ala Ser Tyr Phe Cys Ala Thr Asp
             100                 105                 110

Ala Gln Thr Gly Ala Asn Asn Leu Phe Phe Gly Thr Gly Thr Arg Leu
             115                 120                 125

Thr Val Ile Pro
    130

<210> SEQ ID NO 424
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 424
atgggcacca ggctcctctg ctgggcggcc ctctgtctcc tgggagcaga actcacagaa      60
gctggagttg cccagtctcc cagatataag attatagaga aaaggcagag tgtggctttt    120
tggtgcaatc ctatatctgg ccatgctacc ctttactggt accagcagat cctgggacag    180
ggcccaaagc ttctgattca gtttcagaat aacggtgtag tggatgattc acagttgcct    240
aaggatcgat tttctgcaga gaggctcaaa ggagtagact ccactctcaa gatccagcct    300
gcaaagcttg aggactcggc cgtgtatctc tgtgccagca gctta                    345

<210> SEQ ID NO 425
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 425
atgggcacca ggctgctgtg ctgggccgcc ctgtgcctgc tgggagcaga gctgacagag      60
gcaggagtgg cccagagccc caggtacaag atcatcgaga gcgccagtc cgtggccttc    120 tggtgcaacc ctatctctgg ccacgccacc ctgtactggt atcagcagat cctgggccag    180
ggcccaaagc tgctgatcca gttccagaac aatggcgtgg tggacgattc cagctgccc    240 aaggacaggt ttagcgccga gcgcctgaag ggcgtggatt ctaccctgaa gatccagcca    300
gcaaagctgg aggacagcgc cgtgtacctg tgcgccagct ccctg                    345

<210> SEQ ID NO 426
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 426

```
Met Gly Thr Arg Leu Leu Cys Trp Ala Ala Leu Cys Leu Leu Gly Ala
1               5                   10                  15
Glu Leu Thr Glu Ala Gly Val Ala Gln Ser Pro Arg Tyr Lys Ile Ile
            20                  25                  30
Glu Lys Arg Gln Ser Val Ala Phe Trp Cys Asn Pro Ile Ser Gly His
        35                  40                  45
Ala Thr Leu Tyr Trp Tyr Gln Gln Ile Leu Gly Gln Gly Pro Lys Leu
    50                  55                  60
Leu Ile Gln Phe Gln Asn Gly Val Val Asp Ser Gln Leu Pro
65                  70                  75                  80
Lys Asp Arg Phe Ser Ala Glu Arg Leu Lys Gly Val Asp Ser Thr Leu
            85                  90                  95
Lys Ile Gln Pro Ala Lys Leu Glu Asp Ser Ala Val Tyr Leu Cys Ala
            100                 105                 110
Ser Ser Leu
        115

<210> SEQ ID NO 427
<211> LENGTH: 269
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 427

Met Glu Thr Leu Leu Gly Val Ser Leu Val Ile Leu Trp Leu Gln Leu
1               5                   10                  15
Ala Arg Val Asn Ser Gln Gln Gly Glu Glu Asp Pro Gln Ala Leu Ser
            20                  25                  30
Ile Gln Glu Gly Glu Asn Ala Thr Met Asn Cys Ser Tyr Lys Thr Ser
        35                  40                  45
Ile Asn Asn Leu Gln Trp Tyr Arg Gln Asn Ser Gly Arg Gly Leu Val
    50                  55                  60
His Leu Ile Leu Ile Arg Ser Asn Glu Arg Glu Lys His Ser Gly Arg
65                  70                  75                  80
Leu Arg Val Thr Leu Asp Thr Ser Lys Lys Ser Ser Ser Leu Leu Ile
            85                  90                  95
Thr Ala Ser Arg Ala Ala Asp Thr Ala Ser Tyr Phe Cys Ala Thr Asp
            100                 105                 110
Ala Gln Thr Gly Ala Asn Asn Leu Phe Phe Gly Thr Gly Thr Arg Leu
            115                 120                 125
Thr Val Ile Pro Asp Ile Gln Asn Pro Glu Pro Ala Val Tyr Gln Leu
    130                 135                 140
Lys Asp Pro Arg Ser Gln Asp Ser Thr Leu Cys Leu Phe Thr Asp Phe
145                 150                 155                 160
Asp Ser Gln Ile Asn Val Pro Lys Thr Met Glu Ser Gly Thr Phe Ile
                165                 170                 175
Thr Asp Lys Thr Val Leu Asp Met Lys Ala Met Asp Ser Lys Ser Asn
            180                 185                 190
Gly Ala Ile Ala Trp Ser Asn Gln Thr Ser Phe Thr Cys Gln Asp Ile
        195                 200                 205
Phe Lys Glu Thr Asn Ala Thr Tyr Pro Ser Ser Asp Val Pro Cys Asp
    210                 215                 220
Ala Thr Leu Thr Glu Lys Ser Phe Glu Thr Asp Met Asn Leu Asn Phe
225                 230                 235                 240
```

Gln Asn Leu Ser Val Met Gly Leu Arg Ile Leu Leu Lys Val Ala
                245                 250                 255

Gly Phe Asn Leu Leu Met Thr Leu Arg Leu Trp Ser Ser
            260                 265

<210> SEQ ID NO 428
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 428

Met Gly Thr Arg Leu Leu Cys Trp Ala Ala Leu Cys Leu Leu Gly Ala
1               5                   10                  15

Glu Leu Thr Glu Ala Gly Val Ala Gln Ser Pro Arg Tyr Lys Ile Ile
                20                  25                  30

Glu Lys Arg Gln Ser Val Ala Phe Trp Cys Asn Pro Ile Ser Gly His
            35                  40                  45

Ala Thr Leu Tyr Trp Tyr Gln Gln Ile Leu Gly Gln Gly Pro Lys Leu
        50                  55                  60

Leu Ile Gln Phe Gln Asn Asn Gly Val Val Asp Asp Ser Gln Leu Pro
65                  70                  75                  80

Lys Asp Arg Phe Ser Ala Glu Arg Leu Lys Gly Val Asp Ser Thr Leu
                85                  90                  95

Lys Ile Gln Pro Ala Lys Leu Glu Asp Ser Ala Val Tyr Leu Cys Ala
            100                 105                 110

Ser Ser Leu Lys Asp Leu Arg Asn Val Thr Pro Pro Lys Val Ser Leu
        115                 120                 125

Phe Glu Pro Ser Lys Ala Glu Ile Ala Asn Lys Gln Lys Ala Thr Leu
130                 135                 140

Val Cys Leu Ala Arg Gly Phe Phe Pro Asp His Val Glu Leu Ser Trp
145                 150                 155                 160

Trp Val Asn Gly Lys Glu Val His Ser Gly Val Ser Thr Asp Pro Gln
                165                 170                 175

Ala Tyr Lys Glu Ser Asn Tyr Ser Tyr Cys Leu Ser Ser Arg Leu Arg
            180                 185                 190

Val Ser Ala Thr Phe Trp His Asn Pro Arg Asn His Phe Arg Cys Gln
        195                 200                 205

Val Gln Phe His Gly Leu Ser Glu Glu Asp Lys Trp Pro Glu Gly Ser
    210                 215                 220

Pro Lys Pro Val Thr Gln Asn Ile Ser Ala Glu Ala Trp Gly Arg Ala
225                 230                 235                 240

Asp Cys Gly Ile Thr Ser Ala Ser Tyr His Gln Gly Val Leu Ser Ala
                245                 250                 255

Thr Ile Leu Tyr Glu Ile Leu Leu Gly Lys Ala Thr Leu Tyr Ala Val
            260                 265                 270

Leu Val Ser Gly Leu Val Leu Met Ala Met Val Lys Lys Lys Asn Ser
        275                 280                 285

<210> SEQ ID NO 429
<211> LENGTH: 9
<212> TYPE: PRT
<213> ORGANISM: Artificial Sequence
<220> FEATURE:
<223> OTHER INFORMATION: Description of Artificial Sequence: Synthetic

```
            peptide

<400> SEQUENCE: 429

Val Val Gly Ala Val Gly Val Gly Lys
1               5

<210> SEQ ID NO 430
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Val Val Val Gly Ala Val Gly Val Gly Lys
1               5                   10

<210> SEQ ID NO 431

<400> SEQUENCE: 431

000

<210> SEQ ID NO 432

<400> SEQUENCE: 432

000

<210> SEQ ID NO 433

<400> SEQUENCE: 433

000

<210> SEQ ID NO 434

<400> SEQUENCE: 434

000

<210> SEQ ID NO 435

<400> SEQUENCE: 435

000

<210> SEQ ID NO 436

<400> SEQUENCE: 436

000

<210> SEQ ID NO 437

<400> SEQUENCE: 437

000

<210> SEQ ID NO 438

<400> SEQUENCE: 438

000

<210> SEQ ID NO 439
```

<400> SEQUENCE: 439

000

<210> SEQ ID NO 440

<400> SEQUENCE: 440

000

<210> SEQ ID NO 441

<400> SEQUENCE: 441

000

<210> SEQ ID NO 442

<400> SEQUENCE: 442

000

<210> SEQ ID NO 443

<400> SEQUENCE: 443

000

<210> SEQ ID NO 444

<400> SEQUENCE: 444

000

<210> SEQ ID NO 445

<400> SEQUENCE: 445

000

<210> SEQ ID NO 446

<400> SEQUENCE: 446

000

<210> SEQ ID NO 447
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 447

Thr Arg Asp Thr Thr Tyr Tyr
1               5

<210> SEQ ID NO 448
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 448

Arg Asn Ser Phe Asp Glu Gln Asn
1               5

<210> SEQ ID NO 449
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 449

Ala Leu Lys Gly Ala Asn Thr Gly Phe Gln Lys Leu Val
1               5                   10

<210> SEQ ID NO 450
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 450

Ser Gly His Asp Tyr
1               5

<210> SEQ ID NO 451
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 451

Phe Asn Asn Asn Val Pro
1               5

<210> SEQ ID NO 452
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 452

Ala Ser Gly Gly Gly Leu Gly Leu Phe Glu Thr Gln Tyr
1               5                   10

<210> SEQ ID NO 453
<211> LENGTH: 408
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 453
atgctgactg ccagcctgtt gagggcagtc atagcctcca tctgtgttgt atccagcatg      60
gctcagaagg taactcaagc gcagactgaa atttctgtgg tggagaagga ggatgtgacc     120
ttggactgtg tgtatgaaac ccgtgatact acttattact tattctggta caagcaacca     180
ccaagtggag aattggtttt ccttattcgt cggaactctt ttgatgagca aaatgaaata     240
agtggtcggt attcttggaa cttccagaaa tccaccagtt ccttcaactt caccatcaca     300

```
gcctcacaag tcgtggactc agcagtatac ttctgtgctc tgaaaggggc gaacacaggc    360
tttcagaaac ttgtatttgg aactggcacc cgacttctgg tcagtcca                 408
```

<210> SEQ ID NO 454
<211> LENGTH: 408
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 454

```
atgctgacag cctccctgct gagggccgtg atcgcctcta tctgcgtggt gtctagcatg    60
gcccagaagg tgacccaggc ccagacagag atcagcgtgg tggagaagga ggacgtgacc    120
ctggattgcg tgtacgagac acgggacacc acatactatc tgttttggta taagcagcca    180
cccagcggcg agctggtgtt cctgatcagg cgcaattcct ttgatgagca gaacgagatc    240
tccggcagat actcttggaa tttccagaag tccacctcct ctttcaactt taccatcaca    300
gcctcccagg tggtggactc tgccgtgtat ttttgtgccc tgaagggcgc caacacaggc    360
ttccagaagc tggtgtttgg caccggcaca agactgctgg tgagccct                 408
```

<210> SEQ ID NO 455
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 455

```
Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
            20                  25                  30

Val Val Glu Lys Glu Asp Val Thr Leu Asp Cys Val Tyr Glu Thr Arg
        35                  40                  45

Asp Thr Thr Tyr Tyr Leu Phe Trp Tyr Lys Gln Pro Pro Ser Gly Glu
    50                  55                  60

Leu Val Phe Leu Ile Arg Arg Asn Ser Phe Asp Glu Gln Asn Glu Ile
65                  70                  75                  80

Ser Gly Arg Tyr Ser Trp Asn Phe Gln Lys Ser Thr Ser Ser Phe Asn
                85                  90                  95

Phe Thr Ile Thr Ala Ser Gln Val Val Asp Ser Ala Val Tyr Phe Cys
            100                 105                 110

Ala Leu Lys Gly Ala Asn Thr Gly Phe Gln Lys Leu Val Phe Gly Thr
        115                 120                 125

Gly Thr Arg Leu Leu Val Ser Pro
    130                 135
```

<210> SEQ ID NO 456
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 456

```
atggactcct ggaccctctg ctgtgtgtcc ctttgcatcc tggtagcaaa gcacacagat      60
gctggagtta tccagtcacc ccggcacgag gtgacagaga gtgggacaaga agtgactctg    120 agatgtaaac caatttcagg acacgactac cttttctggt acagacagac catgatgcgg    180
ggactggagt tgctcattta ctttaacaac aacgttccga tagatgattc agggatgccc    240
gaggatcgat tctcagctaa gatgcctaat gcatcattct ccactctgaa gatccagccc    300
tcagaaccca gggactcagc tgtgtacttc tgtgccagcg agggggact  aggtctatt     360 gagacccagt acttcgggcc aggcacgcgg ctcctggtgc tc                        402
```

<210> SEQ ID NO 457
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 457

```
atggacagct ggaccctgtg ctgcgtgagc ctgtgcatcc tggtggccaa gcacacagat      60
gcaggcgtga tccagtcccc aaggcacgag gtgaccgaga tgggacagga ggtgacactg    120
aggtgtaagc ctatctctgg ccacgactac ctgttctggt atcggcagac catgatgaga    180
ggcctggagc tgctgatcta ctttaacaat aacgtgccta cgacgattc tggcatgcca    240 gaggacaggt tcagcgccaa gatgcctaat gccagctttt ccaccctgaa gatccagcca    300
agcgagccaa gggattccgc cgtgtacttc tgcgcctccg aggaggact  gggactgttc    360 gagacccagt attttggccc aggcacaagg ctgctggtgc tg                        402
```

<210> SEQ ID NO 458
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 458

```
Met Asp Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
                20                  25                  30

Glu Met Gly Gln Glu Val Thr Leu Arg Cys Lys Pro Ile Ser Gly His
            35                  40                  45

Asp Tyr Leu Phe Trp Tyr Arg Gln Thr Met Met Arg Gly Leu Glu Leu
        50                  55                  60

Leu Ile Tyr Phe Asn Asn Asn Val Pro Ile Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Gly Gly Gly Leu Gly Leu Phe Glu Thr Gln Tyr Phe Gly Pro Gly
        115                 120                 125

Thr Arg Leu Leu Val Leu
    130
```

<210> SEQ ID NO 459

```
<211> LENGTH: 273
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 459

Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
                20                  25                  30

Val Val Glu Lys Glu Asp Val Thr Leu Asp Cys Val Tyr Glu Thr Arg
            35                  40                  45

Asp Thr Thr Tyr Tyr Leu Phe Trp Tyr Lys Gln Pro Pro Ser Gly Glu
    50                  55                  60

Leu Val Phe Leu Ile Arg Arg Asn Ser Phe Asp Glu Gln Asn Glu Ile
65                  70                  75                  80

Ser Gly Arg Tyr Ser Trp Asn Phe Gln Lys Ser Thr Ser Ser Phe Asn
                85                  90                  95

Phe Thr Ile Thr Ala Ser Gln Val Val Asp Ser Ala Val Tyr Phe Cys
                100                 105                 110

Ala Leu Lys Gly Ala Asn Thr Gly Phe Gln Lys Leu Val Phe Gly Thr
            115                 120                 125

Gly Thr Arg Leu Leu Val Ser Pro Asp Ile Gln Asn Pro Glu Pro Ala
    130                 135                 140

Val Tyr Gln Leu Lys Asp Pro Arg Ser Gln Asp Ser Thr Leu Cys Leu
145                 150                 155                 160

Phe Thr Asp Phe Asp Ser Gln Ile Asn Val Pro Lys Thr Met Glu Ser
                165                 170                 175

Gly Thr Phe Ile Thr Asp Lys Thr Val Leu Asp Met Lys Ala Met Asp
                180                 185                 190

Ser Lys Ser Asn Gly Ala Ile Ala Trp Ser Asn Gln Thr Ser Phe Thr
            195                 200                 205

Cys Gln Asp Ile Phe Lys Glu Thr Asn Ala Thr Tyr Pro Ser Ser Asp
    210                 215                 220

Val Pro Cys Asp Ala Thr Leu Thr Glu Lys Ser Phe Glu Thr Asp Met
225                 230                 235                 240

Asn Leu Asn Phe Gln Asn Leu Ser Val Met Gly Leu Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 460
<211> LENGTH: 307
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 460

Met Asp Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
                20                  25                  30
```

Glu Met Gly Gln Glu Val Thr Leu Arg Cys Lys Pro Ile Ser Gly His
            35                  40                  45

Asp Tyr Leu Phe Trp Tyr Arg Gln Thr Met Met Arg Gly Leu Glu Leu
        50                  55                  60

Leu Ile Tyr Phe Asn Asn Asn Val Pro Ile Asp Asp Ser Gly Met Pro
 65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Gly Gly Gly Leu Gly Leu Phe Glu Thr Gln Tyr Phe Gly Pro Gly
            115                 120                 125

Thr Arg Leu Leu Val Leu Lys Asp Leu Arg Asn Val Thr Pro Pro Lys
130                 135                 140

Val Ser Leu Phe Glu Pro Ser Lys Ala Glu Ile Ala Asn Lys Gln Lys
145                 150                 155                 160

Ala Thr Leu Val Cys Leu Ala Arg Gly Phe Phe Pro Asp His Val Glu
                165                 170                 175

Leu Ser Trp Trp Val Asn Gly Lys Glu Val His Ser Gly Val Ser Thr
            180                 185                 190

Asp Pro Gln Ala Tyr Lys Glu Ser Asn Tyr Ser Tyr Cys Leu Ser Ser
        195                 200                 205

Arg Leu Arg Val Ser Ala Thr Phe Trp His Asn Pro Arg Asn His Phe
210                 215                 220

Arg Cys Gln Val Gln Phe His Gly Leu Ser Glu Glu Asp Lys Trp Pro
225                 230                 235                 240

Glu Gly Ser Pro Lys Pro Val Thr Gln Asn Ile Ser Ala Glu Ala Trp
                245                 250                 255

Gly Arg Ala Asp Cys Gly Ile Thr Ser Ala Ser Tyr His Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Gly Leu Val Leu Met Ala Met Val Lys Lys
290                 295                 300

Lys Asn Ser
305

<210> SEQ ID NO 461
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 461

Gln Leu Ile Met Gln Leu Met Pro Phe
1               5

<210> SEQ ID NO 462
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 462

```
Leu Ile Met Gln Leu Met Pro Phe Gly Cys
1               5                   10

<210> SEQ ID NO 463
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 463

Met Gln Leu Met Pro Phe Gly Cys Leu Leu
1               5                   10

<210> SEQ ID NO 464
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 464

Asp Ser Ser Ser Thr Tyr
1               5

<210> SEQ ID NO 465
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 465

Ile Phe Ser Asn Met Asp Met
1               5

<210> SEQ ID NO 466
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 466

Ala Glu Trp Ala Asn Thr Asp Lys Leu Ile
1               5                   10

<210> SEQ ID NO 467
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 467

Asp Phe Gln Ala Thr Thr
1               5

<210> SEQ ID NO 468
<211> LENGTH: 7
<212> TYPE: PRT
<213> ORGANISM: Artificial Sequence
<220> FEATURE:
```

<223> OTHER INFORMATION: Description of Artificial Sequence: Synthetic
peptide

<400> SEQUENCE: 468

Ser Asn Glu Gly Ser Lys Ala
1               5

<210> SEQ ID NO 469
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 469

Ser Ala Arg Arg Arg Glu Gly Glu Ile Glu Gln Tyr
1               5                   10

<210> SEQ ID NO 470
<211> LENGTH: 393
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 470

```
atgaagacat tgctggatt ttcgttcctg tttttgtggc tgcagctgga ctgtatgagt    60
agaggagagg atgtggagca gagtcttttc ctgagtgtcc gagagggaga cagctccgtt   120
ataaactgca cttacacaga cagctcctcc acctactat  actggtataa gcaagaacct   180
ggagcaggtc tccagttgct gacgtatatt ttttcaaata tggacatgaa acaagaccaa   240
agactcactg ttctattgaa taaaaaggat aaacatctgt ctctgcgcat tgcagacacc   300
cagactgggg actcagctat ctacttctgt gcagagtggg ctaacaccga caagctcatc   360
tttgggactg ggaccagatt acaagtcttt cca                                393
```

<210> SEQ ID NO 471
<211> LENGTH: 393
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 471

```
atgaagacct tcgccggctt ctcctttctg ttcctgtggc tgcagctgga ctgcatgagc    60
cggggagagg atgtggagca gtccctgttc ctgtctgtga gggagggcga ctcctctgtg   120
atcaactgta catataccga tagctcctct acctacctgt attggtacaa gcaggagcca   180
ggagcaggac tgcagctgct gacatacatc tttagcaaca tggacatgaa gcaggatcag   240
cgcctgaccg tgctgctgaa taagaaggac aagcacctgt ctctgcggat cgccgacaca   300
cagaccggcg atagcgccat ctacttctgt gccgagtggg ccaataccga taagctgatc   360
tttggcacag gcacccggct gcaggtgttc cct                                393
```

<210> SEQ ID NO 472
<211> LENGTH: 131
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 472

Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
            20                  25                  30

Val Arg Glu Gly Asp Ser Ser Val Ile Asn Cys Thr Tyr Thr Asp Ser
        35                  40                  45

Ser Ser Thr Tyr Leu Tyr Trp Tyr Lys Gln Glu Pro Gly Ala Gly Leu
    50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
            100                 105                 110

Trp Ala Asn Thr Asp Lys Leu Ile Phe Gly Thr Gly Thr Arg Leu Gln
        115                 120                 125

Val Phe Pro
    130

<210> SEQ ID NO 473
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 473
atgctgctgc ttctgctgct tctggggcca ggctccgggc ttggtgctgt cgtctctcaa      60
catccgagct gggttatctg taagagtgga acctctgtga agatcgagtg ccgttccctg     120
gactttcagg ccacaactat gttttggtat cgtcagttcc gaaacagag tctcatgctg      180 atggcaactt ccaatgaggg ctccaaggcc acatacgagc aaggcgtcga aaggacaag      240 tttctcatca accatgcaag cctgaccttg tccactctga cagtgaccag tgcccatcct     300
gaagacagca gcttctacat ctgcagtgct agaaggcggg aggggagat cgagcagtac      360 ttcgggccgg gcaccaggct cacggtcaca                                      390

<210> SEQ ID NO 474
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 474
atgttattac tgctgctgct gctgggacca ggctccggac tgggagccgt ggtgtcccag      60
cacccttctt gggtcatctg caagtccggc acatctgtga agatcgagtg tcgctctctg     120
gactttcagg ccaccacaat gttttggtat cggcagttcc ccaagcagag cctgatgctg     180
atggccacaa gcaacgaggg ctccaaggcc acctacgagc agggcgtgga aaggacaag      240 ttcctgatca atcacgcctc tctgaccctg agcaccctga cagtgacctc cgcccaccct     300
gaggatagct cctttatat ctgctctgcc cggagaaggg agggcgagat cgagcagtac      360
ttcggcccag gcacaagact gacagtgacc                                390

<210> SEQ ID NO 475
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 475

Met Leu Leu Leu Leu Leu Leu Gly Pro Gly Ser Gly Leu Gly Ala
1               5                   10                  15

Val Val Ser Gln His Pro Ser Trp Val Ile Cys Lys Ser Gly Thr Ser
                20                  25                  30

Val Lys Ile Glu Cys Arg Ser Leu Asp Phe Gln Ala Thr Thr Met Phe
            35                  40                  45

Trp Tyr Arg Gln Phe Pro Lys Gln Ser Leu Met Leu Met Ala Thr Ser
    50                  55                  60

Asn Glu Gly Ser Lys Ala Thr Tyr Glu Gln Gly Val Glu Lys Asp Lys
65                  70                  75                  80

Phe Leu Ile Asn His Ala Ser Leu Thr Leu Ser Thr Leu Thr Val Thr
                85                  90                  95

Ser Ala His Pro Glu Asp Ser Ser Phe Tyr Ile Cys Ser Ala Arg Arg
            100                 105                 110

Arg Glu Gly Glu Ile Glu Gln Tyr Phe Gly Pro Gly Thr Arg Leu Thr
        115                 120                 125

Val Thr
    130

<210> SEQ ID NO 476
<211> LENGTH: 268
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 476

Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
                20                  25                  30

Val Arg Glu Gly Asp Ser Ser Val Ile Asn Cys Thr Tyr Thr Asp Ser
            35                  40                  45

Ser Ser Thr Tyr Leu Tyr Trp Tyr Lys Gln Glu Pro Gly Ala Gly Leu
    50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
            100                 105                 110

Trp Ala Asn Thr Asp Lys Leu Ile Phe Gly Thr Gly Thr Arg Leu Gln
        115                 120                 125

Val Phe Pro Asp Ile Gln Asn Pro Glu Pro Ala Val Tyr Gln Leu Lys
    130                 135                 140

Asp Pro Arg Ser Gln Asp Ser Thr Leu Cys Leu Phe Thr Asp Phe Asp

```
                145                 150                 155                 160
Ser Gln Ile Asn Val Pro Lys Thr Met Glu Ser Gly Thr Phe Ile Thr
                    165                 170                 175

Asp Lys Thr Val Leu Asp Met Lys Ala Met Asp Ser Lys Ser Asn Gly
                    180                 185                 190

Ala Ile Ala Trp Ser Asn Gln Thr Ser Phe Thr Cys Gln Asp Ile Phe
                    195                 200                 205

Lys Glu Thr Asn Ala Thr Tyr Pro Ser Ser Asp Val Pro Cys Asp Ala
                    210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Leu Lys Val Ala Gly
                    245                 250                 255

Phe Asn Leu Leu Met Thr Leu Arg Leu Trp Ser Ser
                    260                 265

<210> SEQ ID NO 477
<211> LENGTH: 303
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 477

Met Leu Leu Leu Leu Leu Leu Gly Pro Gly Ser Gly Leu Gly Ala
1                   5                   10                  15

Val Val Ser Gln His Pro Ser Trp Val Ile Cys Lys Ser Gly Thr Ser
                    20                  25                  30

Val Lys Ile Glu Cys Arg Ser Leu Asp Phe Gln Ala Thr Thr Met Phe
                    35                  40                  45

Trp Tyr Arg Gln Phe Pro Lys Gln Ser Leu Met Leu Met Ala Thr Ser
                    50                  55                  60

Asn Glu Gly Ser Lys Ala Thr Tyr Glu Gln Gly Val Glu Lys Asp Lys
65                  70                  75                  80

Phe Leu Ile Asn His Ala Ser Leu Thr Leu Ser Thr Leu Thr Val Thr
                    85                  90                  95

Ser Ala His Pro Glu Asp Ser Ser Phe Tyr Ile Cys Ser Ala Arg Arg
                    100                 105                 110

Arg Glu Gly Glu Ile Glu Gln Tyr Phe Gly Pro Gly Thr Arg Leu Thr
                    115                 120                 125

Val Thr Lys Asp Leu Arg Asn Val Thr Pro Pro Lys Val Ser Leu Phe
                    130                 135                 140

Glu Pro Ser Lys Ala Glu Ile Ala Asn Lys Gln Lys Ala Thr Leu Val
145                 150                 155                 160

Cys Leu Ala Arg Gly Phe Phe Pro Asp His Val Glu Leu Ser Trp Trp
                    165                 170                 175

Val Asn Gly Lys Glu Val His Ser Gly Val Ser Thr Asp Pro Gln Ala
                    180                 185                 190

Tyr Lys Glu Ser Asn Tyr Ser Tyr Cys Leu Ser Ser Arg Leu Arg Val
                    195                 200                 205

Ser Ala Thr Phe Trp His Asn Pro Arg Asn His Phe Arg Cys Gln Val
                    210                 215                 220

Gln Phe His Gly Leu Ser Glu Glu Asp Lys Trp Pro Glu Gly Ser Pro
225                 230                 235                 240
```

```
Lys Pro Val Thr Gln Asn Ile Ser Ala Glu Ala Trp Gly Arg Ala Asp
                245                 250                 255

Cys Gly Ile Thr Ser Ala Ser Tyr His Gln Gly Val Leu Ser Ala Thr
            260                 265                 270

Ile Leu Tyr Glu Ile Leu Leu Gly Lys Ala Thr Leu Tyr Ala Val Leu
        275                 280                 285

Val Ser Gly Leu Val Leu Met Ala Met Val Lys Lys Lys Asn Ser
    290                 295                 300

<210> SEQ ID NO 478
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 478

Gln Leu Ile Met Gln Leu Met Pro Phe
1               5

<210> SEQ ID NO 479
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 479

Leu Ile Met Gln Leu Met Pro Phe Gly Cys
1               5                   10

<210> SEQ ID NO 480
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 480

Met Gln Leu Met Pro Phe Gly Cys Leu Leu
1               5                   10

<210> SEQ ID NO 481
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 481

Thr Arg Asp Thr Thr Tyr Tyr
1               5

<210> SEQ ID NO 482
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 482
```

Arg Asn Ser Phe Asp Glu Gln Asn
1               5

<210> SEQ ID NO 483
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 483

Ala Leu Thr Pro Phe Pro Asn Ala Gly Gly Thr Ser Tyr Gly Lys Leu
1               5                   10                  15

Thr

<210> SEQ ID NO 484
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 484

Ser Gly His Asn Ser
1               5

<210> SEQ ID NO 485
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 485

Phe Asn Asn Asn Val Pro
1               5

<210> SEQ ID NO 486
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

Ala Ser Ser Leu Ala Tyr Leu Thr Gly Arg Val Glu Ala Phe
1               5                   10

<210> SEQ ID NO 487
<211> LENGTH: 420
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 487
atgctgactg ccagcctgtt gagggcagtc atagcctcca tctgtgttgt atccagcatg      60
gctcagaagg taactcaagc gcagactgaa atttctgtgg tggagaagga ggatgtgacc     120
ttggactgtg tgtatgaaac ccgtgatact acttattact tattctgtgta caagcaacca    180 ccaagtggag aattggtttt ccttattcgt cggaactctt tgatgagca aaatgaaata     240

```
agtggtcggt attcttggaa cttccagaaa tccaccagtt ccttcaactt caccatcaca    300
gcctcacaag tcgtggactc agcagtatac ttctgtgctc tgactccctt ccccaatgct    360
ggtggtacta gctatggaaa gctgacattt ggacaaggga ccatcttgac tgtccatcca    420
```

<210> SEQ ID NO 488
<211> LENGTH: 420
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 488

```
atgctgacag cctctctgct gagggccgtg atcgccagca tctgcgtggt gtcctctatg     60
gcccagaagg tgacccaggc ccagacagag atcagcgtgg tggagaagga ggacgtgacc    120
ctggattgcg tgtacgagac acgggacacc acatactatc tgttctggta taagcagcca    180
ccctccggcg agctggtgtt cctgatcagg cgcaattctt ttgatgagca gaacgagatc    240
tctggcagat acagctggaa ttttcagaag tctaccagct ccttcaactt taccatcaca    300
gcctctcagg tggtggatag cgccgtgtac ttctgtgccc tgacaccatt tcccaatgcc    360
ggcggcacca gctatggcaa gctgacattc ggccagggca ccatcctgac agtgcaccct    420
```

<210> SEQ ID NO 489
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 489

```
Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
            20                  25                  30

Val Val Glu Lys Glu Asp Val Thr Leu Asp Cys Val Tyr Glu Thr Arg
        35                  40                  45

Asp Thr Thr Tyr Tyr Leu Phe Trp Tyr Lys Gln Pro Pro Ser Gly Glu
    50                  55                  60

Leu Val Phe Leu Ile Arg Arg Asn Ser Phe Asp Glu Gln Asn Glu Ile
65                  70                  75                  80

Ser Gly Arg Tyr Ser Trp Asn Phe Gln Lys Ser Thr Ser Ser Phe Asn
                85                  90                  95

Phe Thr Ile Thr Ala Ser Gln Val Val Asp Ser Ala Val Tyr Phe Cys
            100                 105                 110

Ala Leu Thr Pro Phe Pro Asn Ala Gly Gly Thr Ser Tyr Gly Lys Leu
        115                 120                 125

Thr Phe Gly Gln Gly Thr Ile Leu Thr Val His Pro
    130                 135                 140
```

<210> SEQ ID NO 490
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 490

```
atggactcct ggaccttctg ctgtgtgtcc ctttgcatcc tggtagcgaa gcatacagat      60
gctggagtta tccagtcacc ccgccatgag gtgacagaga tgggacaaga agtgactctg     120
agatgtaaac caatttcagg ccacaactcc cttttctggt acagacagac catgatgcgg     180
ggactggagt tgctcattta ctttaacaac aacgttccga tagatgattc agggatgccc     240
gaggatcgat tctcagctaa gatgcctaat gcatcattct ccactctgaa gatccagccc     300
tcagaaccca gggactcagc tgtgtacttc tgtgccagca gtttagccta cctgacaggg     360
agggttgaag ctttctttgg acaaggcacc agactcacag ttgta                     405
```

<210> SEQ ID NO 491
<211> LENGTH: 405
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 491

```
atggactcct ggaccttctg ctgcgtgagc ctgtgcatcc tggtggccaa gcacacagat      60
gcaggcgtga tccagtcccc aaggcacgag gtgaccgaga tgggacagga ggtgacactg     120
aggtgtaagc ccatcagcgg ccacaattcc ctgttctggt accggcagac catgatgaga     180
ggcctggagc tgctgatcta cttcaacaat aacgtgccca tcgacgatag cggcatgcct     240
gaggaccggt tctccgccaa gatgcccaac gcctcttttta gcaccctgaa gatccagcct     300
tccgagccaa gggattctgc cgtgtacttc tgcgccagct ccctggccta tctgaccgga     360
agggtggagg ccttctttgg acagggcacc aggctgacag tggtg                     405
```

<210> SEQ ID NO 492
<211> LENGTH: 135
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 492

```
Met Asp Ser Trp Thr Phe Cys Cys Val Ser Leu Cys Ile Leu Val Ala
1               5                   10                  15
Lys His Thr Asp Ala Gly Val Ile Gln Ser Pro Arg His Glu Val Thr
            20                  25                  30
Glu Met Gly Gln Glu Val Thr Leu Arg Cys Lys Pro Ile Ser Gly His
        35                  40                  45
Asn Ser Leu Phe Trp Tyr Arg Gln Thr Met Met Arg Gly Leu Glu Leu
    50                  55                  60
Leu Ile Tyr Phe Asn Asn Asn Val Pro Ile Asp Asp Ser Gly Met Pro
65                  70                  75                  80
Glu Asp Arg Phe Ser Ala Lys Met Pro Asn Ala Ser Phe Ser Thr Leu
                85                  90                  95
Lys Ile Gln Pro Ser Glu Pro Arg Asp Ser Ala Val Tyr Phe Cys Ala
            100                 105                 110
Ser Ser Leu Ala Tyr Leu Thr Gly Arg Val Glu Ala Phe Phe Gly Gln
        115                 120                 125
Gly Thr Arg Leu Thr Val Val
    130                 135
```

```
<210> SEQ ID NO 493
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 493

Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
            20                  25                  30

Val Val Glu Lys Glu Asp Val Thr Leu Asp Cys Val Tyr Glu Thr Arg
        35                  40                  45

Asp Thr Thr Tyr Tyr Leu Phe Trp Tyr Lys Gln Pro Pro Ser Gly Glu
    50                  55                  60

Leu Val Phe Leu Ile Arg Arg Asn Ser Phe Asp Glu Gln Asn Glu Ile
65                  70                  75                  80

Ser Gly Arg Tyr Ser Trp Asn Phe Gln Lys Ser Thr Ser Ser Phe Asn
                85                  90                  95

Phe Thr Ile Thr Ala Ser Gln Val Val Asp Ser Ala Val Tyr Phe Cys
                100                 105                 110

Ala Leu Thr Pro Phe Pro Asn Ala Gly Gly Thr Ser Tyr Gly Lys Leu
            115                 120                 125

Thr Phe Gly Gln Gly Thr Ile Leu Thr Val His Pro Asp Ile Gln Asn
    130                 135                 140

Pro Glu Pro Ala Val Tyr Gln Leu Lys Asp Pro Arg Ser Gln Asp Ser
145                 150                 155                 160

Thr Leu Cys Leu Phe Thr Asp Phe Asp Ser Gln Ile Asn Val Pro Lys
                165                 170                 175

Thr Met Glu Ser Gly Thr Phe Ile Thr Asp Lys Thr Val Leu Asp Met
                180                 185                 190

Lys Ala Met Asp Ser Lys Ser Asn Gly Ala Ile Ala Trp Ser Asn Gln
            195                 200                 205

Thr Ser Phe Thr Cys Gln Asp Ile Phe Lys Glu Thr Asn Ala Thr Tyr
    210                 215                 220

Pro Ser Ser Asp Val Pro Cys Asp Ala Thr Leu Thr Glu Lys Ser Phe
225                 230                 235                 240

Glu Thr Asp Met Asn Leu Asn Phe Gln Asn Leu Ser Val Met Gly Leu
                245                 250                 255

Arg Ile Leu Leu Leu Lys Val Ala Gly Phe Asn Leu Leu Met Thr Leu
                260                 265                 270

Arg Leu Trp Ser Ser
        275

<210> SEQ ID NO 494
<211> LENGTH: 308
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 494

Met Asp Ser Trp Thr Phe Cys Cys Val Ser Leu Cys Ile Leu Val Ala
1               5                   10                  15
```

```
Lys His Thr Asp Ala Gly Val Ile Gln Ser Pro Arg His Glu Val Thr
                20                  25                  30

Glu Met Gly Gln Glu Val Thr Leu Arg Cys Lys Pro Ile Ser Gly His
        35                  40                  45

Asn Ser Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Leu Ala Tyr Leu Thr Gly Arg Val Glu Ala Phe Phe Gly Gln
        115                 120                 125

Gly Thr Arg Leu Thr Val Val Lys Asp Leu Arg Asn Val Thr Pro Pro
    130                 135                 140

Lys Val Ser Leu Phe Glu Pro Ser Lys Ala Glu Ile Ala Asn Lys Gln
145                 150                 155                 160

Lys Ala Thr Leu Val Cys Leu Ala Arg Gly Phe Phe Pro Asp His Val
                165                 170                 175

Glu Leu Ser Trp Trp Val Asn Gly Lys Glu Val His Ser Gly Val Ser
            180                 185                 190

Thr Asp Pro Gln Ala Tyr Lys Glu Ser Asn Tyr Ser Tyr Cys Leu Ser
        195                 200                 205

Ser Arg Leu Arg Val Ser Ala Thr Phe Trp His Asn Pro Arg Asn His
    210                 215                 220

Phe Arg Cys Gln Val Gln Phe His Gly Leu Ser Glu Glu Asp Lys Trp
225                 230                 235                 240

Pro Glu Gly Ser Pro Lys Pro Val Thr Gln Asn Ile Ser Ala Glu Ala
                245                 250                 255

Trp Gly Arg Ala Asp Cys Gly Ile Thr Ser Ala Ser Tyr His Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Gly Leu Val Leu Met Ala Met Val Lys
    290                 295                 300

Lys Lys Asn Ser
305

<210> SEQ ID NO 495
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 495

Gln Leu Ile Met Gln Leu Met Pro Phe
1               5

<210> SEQ ID NO 496
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 496

Leu Ile Met Gln Leu Met Pro Phe Gly Cys
1               5                   10

<210> SEQ ID NO 497
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 497

Met Gln Leu Met Pro Phe Gly Cys Leu Leu
1               5                   10

<210> SEQ ID NO 498
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 498

Thr Arg Asp Thr Thr Tyr Tyr
1               5

<210> SEQ ID NO 499
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 499

Arg Asn Ser Phe Asp Glu Gln Asn
1               5

<210> SEQ ID NO 500
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 500

Ala Leu Ile Arg Gly Ser Tyr Gln Leu Ile
1               5                   10

<210> SEQ ID NO 501
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 501

Asp Phe Gln Ala Thr Thr
1               5

<210> SEQ ID NO 502
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 502

Ser Asn Glu Gly Ser Lys Ala
1               5

<210> SEQ ID NO 503
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 503

Ser Ala Gln Gly Ser Ser Gly Arg Ile Glu Gln Phe
1               5                   10

<210> SEQ ID NO 504
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 504
atgctgactg ccagcctgtt gagggcagtc atagcctcca tctgtgttgt atccagcatg      60
gctcagaagg taactcaagc gcagactgaa atttctgtgg tggagaagga ggatgtgacc     120
ttggactgtg tgtatgaaac ccgtgatact acttattact tattctgtta caagcaacca     180
ccaagtggag aattggtttt ccttattcgt cggaactctt ttgatgagca aaatgaaata     240
agtggtcggt attcttggaa cttccagaaa tccaccagtt ccttcaactt caccatcaca     300
gcctcacaag tcgtggactc agcagtatac ttctgtgctc tgattcgagg gagctatcag     360
ttaatctggg gcgctgggac caagctaatt ataaagcca                            399

<210> SEQ ID NO 505
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 505
atgctgaccg cctctctgct gagggccgtg atcgccagca tctgcgtggt gagctccatg      60
gcccagaagg tgacacaggc ccagaccgag atcagcgtgg tggagaagga ggacgtgaca     120
ctggattgcg tgtacgagac ccgcgacacc acatactatc tgttttggta taagcagcca     180
ccctccggcg agctggtgtt cctgatcagg cgcaactctt ttgatgagca gaatgagatc     240
tctggccggt acagctggaa cttccagaag agcacatcta gcttcaactt caccatcacc     300
gccagccagg tggtggactc cgccgtgtac ttttgtgccc tgatcagagg ctcctatcag     360
ctgatctggg gcgccggcac caagctgatc atcaagccc                            399

<210> SEQ ID NO 506
<211> LENGTH: 133
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 506

```
Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
                20                  25                  30

Val Val Glu Lys Glu Asp Val Thr Leu Asp Cys Val Tyr Glu Thr Arg
            35                  40                  45

Asp Thr Thr Tyr Tyr Leu Phe Trp Tyr Lys Gln Pro Pro Ser Gly Glu
    50                  55                  60

Leu Val Phe Leu Ile Arg Arg Asn Ser Phe Asp Glu Gln Asn Glu Ile
65                  70                  75                  80

Ser Gly Arg Tyr Ser Trp Asn Phe Gln Lys Ser Thr Ser Ser Phe Asn
                85                  90                  95

Phe Thr Ile Thr Ala Ser Gln Val Val Asp Ser Ala Val Tyr Phe Cys
                100                 105                 110

Ala Leu Ile Arg Gly Ser Tyr Gln Leu Ile Trp Gly Ala Gly Thr Lys
            115                 120                 125

Leu Ile Ile Lys Pro
        130
```

<210> SEQ ID NO 507
<211> LENGTH: 390
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 507

```
atgctgctgc ttctgctgct tctggggcca ggctccgggc ttggtgctgt cgtctctcaa        60
catccgagca gggttatctg taagagtgga acctctgtga agatcgagtg ccgttccctg       120
gactttcagg ccacaactat gttttggtat cgtcagttcc cgaaacagag tctcatgctg       180
atggcaactt ccaatgaggg ctccaaggcc acatacgagc aaggcgtcga aaggacaag        240
tttctcatca accatgcaag cctgaccttg tccactctga cagtgaccag tgcccatcct       300
gaagacagca gcttctacat ctgcagcgcc caggggagta gcggaggat gagcagttc         360
ttcgggccag ggacacggct caccgtgcta                                        390
```

<210> SEQ ID NO 508
<211> LENGTH: 390
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 508

```
atgttattac tgctgctgct gctgggacca ggctccggac tgggagcagt ggtgtctcag        60
cacccaagca gagtgatctg caagtctggc accagcgtga agatcgagtg taggtccctg       120
gacttccagg ccaccacaat gttctggtac cgccagtttc caaagcagtc tctgatgctg       180
atggccacat ccaacgaggg ctctaaggcc acctatgagc agggcgtgga aaggacaag        240
ttcctgatca atcacgccag cctgaccctg tccaccctga cagtgaccag cgcccaccca       300
```

```
gaggatagct cctttacat ctgctccgcc cagggctcta gcggccggat cgagcagttc    360
tttggccctg gcacacggct gaccgtgctg                                    390
```

<210> SEQ ID NO 509
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 509

Met Leu Leu Leu Leu Leu Leu Gly Pro Gly Ser Gly Leu Gly Ala
1               5                   10                  15

Val Val Ser Gln His Pro Ser Arg Val Ile Cys Lys Ser Gly Thr Ser
            20                  25                  30

Val Lys Ile Glu Cys Arg Ser Leu Asp Phe Gln Ala Thr Thr Met Phe
        35                  40                  45

Trp Tyr Arg Gln Phe Pro Lys Gln Ser Leu Met Leu Met Ala Thr Ser
    50                  55                  60

Asn Glu Gly Ser Lys Ala Thr Tyr Glu Gln Gly Val Glu Lys Asp Lys
65                  70                  75                  80

Phe Leu Ile Asn His Ala Ser Leu Thr Leu Ser Thr Leu Thr Val Thr
                85                  90                  95

Ser Ala His Pro Glu Asp Ser Ser Phe Tyr Ile Cys Ser Ala Gln Gly
            100                 105                 110

Ser Ser Gly Arg Ile Glu Gln Phe Phe Gly Pro Gly Thr Arg Leu Thr
        115                 120                 125

Val Leu
    130

<210> SEQ ID NO 510
<211> LENGTH: 270
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 510

Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
            20                  25                  30

Val Val Glu Lys Glu Asp Val Thr Leu Asp Cys Val Tyr Glu Thr Arg
        35                  40                  45

Asp Thr Thr Tyr Tyr Leu Phe Trp Tyr Lys Gln Pro Pro Ser Gly Glu
    50                  55                  60

Leu Val Phe Leu Ile Arg Arg Asn Ser Phe Asp Glu Gln Asn Glu Ile
65                  70                  75                  80

Ser Gly Arg Tyr Ser Trp Asn Phe Gln Lys Ser Thr Ser Ser Phe Asn
                85                  90                  95

Phe Thr Ile Thr Ala Ser Gln Val Val Asp Ser Ala Val Tyr Phe Cys
            100                 105                 110

Ala Leu Ile Arg Gly Ser Tyr Gln Leu Ile Trp Gly Ala Gly Thr Lys
        115                 120                 125

Leu Ile Ile Lys Pro Asp Ile Gln Asn Pro Glu Pro Ala Val Tyr Gln

```
                130             135             140
Leu Lys Asp Pro Arg Ser Gln Asp Ser Thr Leu Cys Leu Phe Thr Asp
145                 150                 155                 160

Phe Asp Ser Gln Ile Asn Val Pro Lys Thr Met Glu Ser Gly Thr Phe
                165                 170                 175

Ile Thr Asp Lys Thr Val Leu Asp Met Lys Ala Met Asp Ser Lys Ser
            180                 185                 190

Asn Gly Ala Ile Ala Trp Ser Asn Gln Thr Ser Phe Thr Cys Gln Asp
        195                 200                 205

Ile Phe Lys Glu Thr Asn Ala Thr Tyr Pro Ser Ser Asp Val Pro Cys
    210                 215                 220

Asp Ala Thr Leu Thr Glu Lys Ser Phe Glu Thr Asp Met Asn Leu Asn
225                 230                 235                 240

Phe Gln Asn Leu Ser Val Met Gly Leu Arg Ile Leu Leu Leu Lys Val
                245                 250                 255

Ala Gly Phe Asn Leu Leu Met Thr Leu Arg Leu Trp Ser Ser
                260                 265                 270

<210> SEQ ID NO 511
<211> LENGTH: 303
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 511

Met Leu Leu Leu Leu Leu Leu Gly Pro Gly Ser Gly Leu Gly Ala
1               5                   10                  15

Val Val Ser Gln His Pro Ser Arg Val Ile Cys Lys Ser Gly Thr Ser
                20                  25                  30

Val Lys Ile Glu Cys Arg Ser Leu Asp Phe Gln Ala Thr Thr Met Phe
            35                  40                  45

Trp Tyr Arg Gln Phe Pro Lys Gln Ser Leu Met Leu Met Ala Thr Ser
    50                  55                  60

Asn Glu Gly Ser Lys Ala Thr Tyr Glu Gln Gly Val Glu Lys Asp Lys
65                  70                  75                  80

Phe Leu Ile Asn His Ala Ser Leu Thr Leu Ser Thr Leu Thr Val Thr
                85                  90                  95

Ser Ala His Pro Glu Asp Ser Ser Phe Tyr Ile Cys Ser Ala Gln Gly
                100                 105                 110

Ser Ser Gly Arg Ile Glu Gln Phe Phe Gly Pro Gly Thr Arg Leu Thr
            115                 120                 125

Val Leu Lys Asp Leu Arg Asn Val Thr Pro Pro Lys Val Ser Leu Phe
    130                 135                 140

Glu Pro Ser Lys Ala Glu Ile Ala Asn Lys Gln Lys Ala Thr Leu Val
145                 150                 155                 160

Cys Leu Ala Arg Gly Phe Phe Pro Asp His Val Glu Leu Ser Trp Trp
                165                 170                 175

Val Asn Gly Lys Glu Val His Ser Gly Val Ser Thr Asp Pro Gln Ala
                180                 185                 190

Tyr Lys Glu Ser Asn Tyr Ser Tyr Cys Leu Ser Ser Arg Leu Arg Val
            195                 200                 205

Ser Ala Thr Phe Trp His Asn Pro Arg Asn His Phe Arg Cys Gln Val
    210                 215                 220
```

```
Gln Phe His Gly Leu Ser Glu Glu Asp Lys Trp Pro Glu Gly Ser Pro
225                 230                 235                 240

Lys Pro Val Thr Gln Asn Ile Ser Ala Glu Ala Trp Gly Arg Ala Asp
                245                 250                 255

Cys Gly Ile Thr Ser Ala Ser Tyr His Gln Gly Val Leu Ser Ala Thr
                260                 265                 270

Ile Leu Tyr Glu Ile Leu Leu Gly Lys Ala Thr Leu Tyr Ala Val Leu
            275                 280                 285

Val Ser Gly Leu Val Leu Met Ala Met Val Lys Lys Lys Asn Ser
        290                 295                 300

<210> SEQ ID NO 512
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 512

Gln Leu Ile Met Gln Leu Met Pro Phe
1               5

<210> SEQ ID NO 513
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 513

Leu Ile Met Gln Leu Met Pro Phe Gly Cys
1               5                   10

<210> SEQ ID NO 514
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 514

Met Gln Leu Met Pro Phe Gly Cys Leu Leu
1               5                   10

<210> SEQ ID NO 515
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 515

Asp Ser Val Asn Asn
1               5

<210> SEQ ID NO 516
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 516

Ile Pro Ser Gly Thr
1               5

<210> SEQ ID NO 517
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 517

Ala Val Met Asp Ser Ser Tyr Lys Leu Ile
1               5                   10

<210> SEQ ID NO 518
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 518

Asp Phe Gln Ala Thr Thr
1               5

<210> SEQ ID NO 519
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 519

Ser Asn Glu Gly Ser Lys Ala
1               5

<210> SEQ ID NO 520
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 520

Ser Ala Leu Pro Gly Phe Ser Tyr Glu Gln Tyr
1               5                   10

<210> SEQ ID NO 521
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 521
atgaagagga tattgggagc tctgctgggg ctcttgagtg cccaggtttg ctgtgtgaga    60
ggaatacaag tggagcagag tcctccagac ctgattctcc aggagggagc caattccacg   120
ctgcggtgca attttctga ctctgtgaac aatttgcagt ggtttcatca aaacccttgg   180

```
ggacagctca tcaacctgtt ttacattccc tcagggacaa aacagaatgg aagattaagc    240
gccacgactg tcgctacgga acgctacagc ttattgtaca tttcctcttc ccagaccaca    300
gactcaggcg tttatttctg tgctgtgatg gatagcagct ataaattgat cttcgggagt    360
gggaccagac tgctggtcag gcct                                           384
```

```
<210> SEQ ID NO 522
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 522
atgaagagaa tcctgggcgc cctgctggga ctgctgtccg cccaggtgtg ctgcgtgcgg    60
ggcatccagg tggagcagag cccaccagac ctgatcctgc aggagggagc caactccacc    120
ctgagatgca atttctccga ttctgtgaac aatctgcagt ggtttcacca gaacccttgg    180
ggccagctga tcaatctgtt ttacatccca tccggcacaa agcagaacgg caggctgtct    240
gccaccacag tggccaccga gcggtactct ctgctgtata tctcctctag ccagaccaca    300
gacagcggcg tgtacttctg tgccgtgatg gattcctctt ataagctgat ctttggcagc    360
ggcaccaggc tgctggtgcg ccct                                           384
```

```
<210> SEQ ID NO 523
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 523

Met Lys Arg Ile Leu Gly Ala Leu Leu Gly Leu Leu Ser Ala Gln Val
1               5                   10                  15

Cys Cys Val Arg Gly Ile Gln Val Glu Gln Ser Pro Pro Asp Leu Ile
            20                  25                  30

Leu Gln Glu Gly Ala Asn Ser Thr Leu Arg Cys Asn Phe Ser Asp Ser
        35                  40                  45

Val Asn Asn Leu Gln Trp Phe His Gln Asn Pro Trp Gly Gln Leu Ile
    50                  55                  60

Asn Leu Phe Tyr Ile Pro Ser Gly Thr Lys Gln Asn Gly Arg Leu Ser
65                  70                  75                  80

Ala Thr Thr Val Ala Thr Glu Arg Tyr Ser Leu Leu Tyr Ile Ser Ser
                85                  90                  95

Ser Gln Thr Thr Asp Ser Gly Val Tyr Phe Cys Ala Val Met Asp Ser
            100                 105                 110

Ser Tyr Lys Leu Ile Phe Gly Ser Gly Thr Arg Leu Leu Val Arg Pro
        115                 120                 125
```

```
<210> SEQ ID NO 524
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 524
```

```
atgctgctgc ttctgctgct tctggggcca ggctccgggc ttggtgctgt cgtctctcaa    60
catccgagct gggttatctg taagagtgga acctctgtga agatcgagtg ccgttccctg   120
gactttcagg ccacaactat gttttggtat cgtcagttcc cgaaacagag tctcatgctg   180
atggcaactt ccaatgaggg ctccaaggcc acatacgagc aaggcgtcga aaggacaag    240 tttctcatca accatgcaag cctgaccttg tccactctga cagtgaccag tgcccatcct   300
gaagacagca gcttctacat ctgcagtgct ctgcccggat ctcctacga gcagtacttc    360 gggccgggca ccaggctcac ggtcaca                                       387
```

<210> SEQ ID NO 525
<211> LENGTH: 387
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 525

```
atgttattac tgctgctgct gctgggacca ggcagcggac tgggagcagt ggtgagccag    60 caccttcct gggtcatctg caagagcggc acatccgtga agatcgagtg tcggtctctg    120
gacttccagg ccaccacaat gttctggtac agacagtttc ctaagcagtc cctgatgctg   180
atggccacat ctaacgaggg cagcaaggcc acctatgagc agggcgtgga aaggacaag    240 ttcctgatca atcacgcctc cctgaccctg tctaccctga cagtgacctc cgcccaccca   300
gaggatagct ccttttacat ctgctctgcc ctgccaggct tcagctacga gcagtatttt   360
ggccccggca cacggctgac agtgacc                                       387
```

<210> SEQ ID NO 526
<211> LENGTH: 129
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 526

```
Met Leu Leu Leu Leu Leu Leu Gly Pro Gly Ser Gly Leu Gly Ala
1               5                   10                  15

Val Val Ser Gln His Pro Ser Trp Val Ile Cys Lys Ser Gly Thr Ser
            20                  25                  30

Val Lys Ile Glu Cys Arg Ser Leu Asp Phe Gln Ala Thr Thr Met Phe
        35                  40                  45

Trp Tyr Arg Gln Phe Pro Lys Gln Ser Leu Met Leu Met Ala Thr Ser
    50                  55                  60

Asn Glu Gly Ser Lys Ala Thr Tyr Glu Gln Val Glu Lys Asp Lys
65                  70                  75                  80

Phe Leu Ile Asn His Ala Ser Leu Thr Leu Ser Thr Leu Thr Val Thr
                85                  90                  95

Ser Ala His Pro Glu Asp Ser Ser Phe Tyr Ile Cys Ser Ala Leu Pro
            100                 105                 110

Gly Phe Ser Tyr Glu Gln Tyr Phe Gly Pro Gly Thr Arg Leu Thr Val
        115                 120                 125

Thr
```

<210> SEQ ID NO 527
<211> LENGTH: 265

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 527

Met Lys Arg Ile Leu Gly Ala Leu Leu Gly Leu Leu Ser Ala Gln Val
1               5                   10                  15

Cys Cys Val Arg Gly Ile Gln Val Glu Gln Ser Pro Pro Asp Leu Ile
            20                  25                  30

Leu Gln Glu Gly Ala Asn Ser Thr Leu Arg Cys Asn Phe Ser Asp Ser
        35                  40                  45

Val Asn Asn Leu Gln Trp Phe His Gln Asn Pro Trp Gly Gln Leu Ile
    50                  55                  60

Asn Leu Phe Tyr Ile Pro Ser Gly Thr Lys Gln Asn Gly Arg Leu Ser
65                  70                  75                  80

Ala Thr Thr Val Ala Thr Glu Arg Tyr Ser Leu Leu Tyr Ile Ser Ser
                85                  90                  95

Ser Gln Thr Thr Asp Ser Gly Val Tyr Phe Cys Ala Val Met Asp Ser
            100                 105                 110

Ser Tyr Lys Leu Ile Phe Gly Ser Gly Thr Arg Leu Leu Val Arg Pro
        115                 120                 125

Asp Ile Gln Asn Pro Glu Pro Ala Val Tyr Gln Leu Lys Asp Pro Arg
    130                 135                 140

Ser Gln Asp Ser Thr Leu Cys Leu Phe Thr Asp Phe Asp Ser Gln Ile
145                 150                 155                 160

Asn Val Pro Lys Thr Met Glu Ser Gly Thr Phe Ile Thr Asp Lys Thr
                165                 170                 175

Val Leu Asp Met Lys Ala Met Asp Ser Lys Ser Asn Gly Ala Ile Ala
            180                 185                 190

Trp Ser Asn Gln Thr Ser Phe Thr Cys Gln Asp Ile Phe Lys Glu Thr
        195                 200                 205

Asn Ala Thr Tyr Pro Ser Ser Asp Val Pro Cys Asp Ala Thr Leu Thr
    210                 215                 220

Glu Lys Ser Phe Glu Thr Asp Met Asn Leu Asn Phe Gln Asn Leu Ser
225                 230                 235                 240

Val Met Gly Leu Arg Ile Leu Leu Leu Lys Val Ala Gly Phe Asn Leu
                245                 250                 255

Leu Met Thr Leu Arg Leu Trp Ser Ser
            260                 265

<210> SEQ ID NO 528
<211> LENGTH: 302
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 528

Met Leu Leu Leu Leu Leu Leu Gly Pro Gly Ser Gly Leu Gly Ala
1               5                   10                  15

Val Val Ser Gln His Pro Ser Trp Val Ile Cys Lys Ser Gly Thr Ser
            20                  25                  30

Val Lys Ile Glu Cys Arg Ser Leu Asp Phe Gln Ala Thr Thr Met Phe
        35                  40                  45

```
Trp Tyr Arg Gln Phe Pro Lys Gln Ser Leu Met Leu Met Ala Thr Ser
 50                  55                  60

Asn Glu Gly Ser Lys Ala Thr Tyr Glu Gln Gly Val Glu Lys Asp Lys
 65                  70                  75                  80

Phe Leu Ile Asn His Ala Ser Leu Thr Leu Ser Thr Leu Thr Val Thr
                 85                  90                  95

Ser Ala His Pro Glu Asp Ser Ser Phe Tyr Ile Cys Ser Ala Leu Pro
            100                 105                 110

Gly Phe Ser Tyr Glu Gln Tyr Phe Gly Pro Gly Thr Arg Leu Thr Val
        115                 120                 125

Thr Lys Asp Leu Arg Asn Val Thr Pro Pro Lys Val Ser Leu Phe Glu
130                 135                 140

Pro Ser Lys Ala Glu Ile Ala Asn Lys Gln Lys Ala Thr Leu Val Cys
145                 150                 155                 160

Leu Ala Arg Gly Phe Phe Pro Asp His Val Glu Leu Ser Trp Trp Val
                165                 170                 175

Asn Gly Lys Glu Val His Ser Gly Val Ser Thr Asp Pro Gln Ala Tyr
            180                 185                 190

Lys Glu Ser Asn Tyr Ser Tyr Cys Leu Ser Ser Arg Leu Arg Val Ser
        195                 200                 205

Ala Thr Phe Trp His Asn Pro Arg Asn His Phe Arg Cys Gln Val Gln
210                 215                 220

Phe His Gly Leu Ser Glu Glu Asp Lys Trp Pro Glu Gly Ser Pro Lys
225                 230                 235                 240

Pro Val Thr Gln Asn Ile Ser Ala Glu Ala Trp Gly Arg Ala Asp Cys
                245                 250                 255

Gly Ile Thr Ser Ala Ser Tyr His Gln Gly Val Leu Ser Ala Thr Ile
            260                 265                 270

Leu Tyr Glu Ile Leu Leu Gly Lys Ala Thr Leu Tyr Ala Val Leu Val
        275                 280                 285

Ser Gly Leu Val Leu Met Ala Met Val Lys Lys Asn Ser
290                 295                 300

<210> SEQ ID NO 529
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 529

Gln Leu Ile Met Gln Leu Met Pro Phe
1               5

<210> SEQ ID NO 530
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 530

Leu Ile Met Gln Leu Met Pro Phe Gly Cys
1               5                   10

<210> SEQ ID NO 531
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 531

Met Gln Leu Met Pro Phe Gly Cys Leu Leu
1               5                   10

<210> SEQ ID NO 532
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 532

Asn Ser Met Phe Asp Tyr
1               5

<210> SEQ ID NO 533
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 533

Ile Ser Ser Ile Lys Asp Lys
1               5

<210> SEQ ID NO 534
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 534

Ala Ala Asn Ala Gly Gly Thr Ser Tyr Gly Lys Leu Thr
1               5                   10

<210> SEQ ID NO 535
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 535

Ser Asn His Leu Tyr
1               5

<210> SEQ ID NO 536
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 536

Phe Tyr Asn Asn Glu Ile
```

<210> SEQ ID NO 537
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 537

Ala Ser Ser Glu Trp Gly Ser Thr Gly Glu Leu Phe
1               5                   10

<210> SEQ ID NO 538
<211> LENGTH: 421
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 538
atggccatgc tcctgggggc atcagtgctg attctgtggc ttcagccaga ctgggtaaac      60
agtcaacaga agaatgatga ccagcaagtt aagcaaaatt caccatccct gagcgtccag     120
gaaggaagaa tttctattct gaactgtgac tatactaaca gcatgtttga ttatttccta     180
tggtacaaaa ataccctgc tgaaggtcct acattcctga tatctataag ttccattaag     240
gataaaaatg aagatggaag attcactgtc ttcttaaaca aaagtgccaa gcacctctct     300
ctgcacattg tgccctccca gcctggagac tctgcagtgt acttctgtgc agcaaatgct     360
ggtggtacta gctatggaaa gctgacattt ggacaaggga ccatcttgac tgtccatcca     420
a                                                                     421

<210> SEQ ID NO 539
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 539

Met Ala Met Leu Leu Gly Ala Ser Val Leu Ile Leu Trp Leu Gln Pro
1               5                   10                  15

Asp Trp Val Asn Ser Gln Gln Lys Asn Asp Asp Gln Gln Val Lys Gln
            20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
    50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ala Asn Ala Gly Gly Thr Ser Tyr Gly Lys Leu
        115                 120                 125

Thr Phe Gly Gln Gly Thr Ile Leu Thr Val His Pro

<210> SEQ ID NO 540
<211> LENGTH: 400
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 540

```
atggatacct ggctcgtatg ctgggcaatt tttagtctct tgaaagcagg actcacagaa    60
cctgaagtca cccagactcc cagccatcag gtcacacaga tgggacagga agtgatcttg   120
cgctgtgtcc ccatctctaa tcacttatac ttctattggt acagacaaat cttggggcag   180
aaagtcgagt ttctggtttc cttttataat aatgaaatct cagagaagtc tgaaatattc   240
gatgatcaat tctcagttga aaggcctgat ggatcaaatt tcactctgaa gatccggtcc   300
acaaagctgg aggactcagc catgtacttc tgtgccagca gtgaatgggg aagcaccggg   360
gagctgtttt ttggagaagg ctctaggctg accgtactgg                          400
```

<210> SEQ ID NO 541
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 541

```
Met Asp Thr Trp Leu Val Cys Trp Ala Ile Phe Ser Leu Leu Lys Ala
1               5                   10                  15
Gly Leu Thr Glu Pro Glu Val Thr Gln Thr Pro Ser His Gln Val Thr
            20                  25                  30
Gln Met Gly Gln Glu Val Ile Leu Arg Cys Val Pro Ile Ser Asn His
        35                  40                  45
Leu Tyr Phe Tyr Trp Tyr Arg Gln Ile Leu Gly Gln Lys Val Glu Phe
    50                  55                  60
Leu Val Ser Phe Tyr Asn Asn Glu Ile Ser Glu Lys Ser Glu Ile Phe
65                  70                  75                  80
Asp Asp Gln Phe Ser Val Glu Arg Pro Asp Gly Ser Asn Phe Thr Leu
                85                  90                  95
Lys Ile Arg Ser Thr Lys Leu Glu Asp Ser Ala Met Tyr Phe Cys Ala
            100                 105                 110
Ser Ser Glu Trp Gly Ser Thr Gly Glu Leu Phe Phe Gly Glu Gly Ser
        115                 120                 125
Arg Leu Thr Val Leu
    130
```

<210> SEQ ID NO 542
<211> LENGTH: 277
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 542

```
Met Ala Met Leu Leu Gly Ala Ser Val Leu Ile Leu Trp Leu Gln Pro
1               5                   10                  15
```

```
Asp Trp Val Asn Ser Gln Gln Lys Asn Asp Gln Gln Val Lys Gln
            20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
 50                  55                  60

Tyr Pro Ala Glu Gly Pro Thr Phe Leu Ile Ser Ile Ser Ile Lys
 65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ala Asn Ala Gly Gly Thr Ser Tyr Gly Lys Leu
        115                 120                 125

Thr Phe Gly Gln Gly Thr Ile Leu Thr Val His Pro Asp Ile Gln Asn
    130                 135                 140

Pro Glu Pro Ala Val Tyr Gln Leu Lys Asp Pro Arg Ser Gln Asp Ser
145                 150                 155                 160

Thr Leu Cys Leu Phe Thr Asp Phe Asp Ser Gln Ile Asn Val Pro Lys
                165                 170                 175

Thr Met Glu Ser Gly Thr Phe Ile Thr Asp Lys Thr Val Leu Asp Met
            180                 185                 190

Lys Ala Met Asp Ser Lys Ser Asn Gly Ala Ile Ala Trp Ser Asn Gln
        195                 200                 205

Thr Ser Phe Thr Cys Gln Asp Ile Phe Lys Glu Thr Asn Ala Thr Tyr
    210                 215                 220

Pro Ser Ser Asp Val Pro Cys Asp Ala Thr Leu Thr Glu Lys Ser Phe
225                 230                 235                 240

Glu Thr Asp Met Asn Leu Asn Phe Gln Asn Leu Ser Val Met Gly Leu
                245                 250                 255

Arg Ile Leu Leu Leu Lys Val Ala Gly Phe Asn Leu Leu Met Thr Leu
            260                 265                 270

Arg Leu Trp Ser Ser
        275

<210> SEQ ID NO 543
<211> LENGTH: 306
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 543

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95
```

```
Lys Ile Arg Ser Thr Lys Leu Glu Asp Ser Ala Met Tyr Phe Cys Ala
            100                 105                 110

Ser Ser Glu Trp Gly Ser Thr Gly Glu Leu Phe Gly Glu Gly Ser
        115                 120                 125

Arg Leu Thr Val Leu Lys Asp Leu Arg Asn Val Thr Pro Pro Lys Val
    130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
    210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr His Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Gly Leu Val Leu Met Ala Met Val Lys Lys Lys
    290                 295                 300

Asn Ser
305

<210> SEQ ID NO 544
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 544

Val Val Gly Ala Val Gly Val Gly Lys
1               5

<210> SEQ ID NO 545
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 545

Thr Thr Ser Asp Arg
1               5

<210> SEQ ID NO 546
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 546

Leu Leu Ser Asn Gly Ala Val
1               5

<210> SEQ ID NO 547
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 547

Ala Val Asp Ile Ile Gly Gly Lys Ser Thr
1               5                   10

<210> SEQ ID NO 548
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 548

Ser Asn His Leu Tyr
1               5

<210> SEQ ID NO 549
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 549

Phe Tyr Asn Asn Glu Ile
1               5

<210> SEQ ID NO 550
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 550

Ala Ser Ser Glu Trp Gly Ser Thr Gly Glu Leu Phe
1               5                   10

<210> SEQ ID NO 551
<211> LENGTH: 385
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 551
atgaagaagc tactagcaat gattctgtgg cttcaactag accggttaag tggagagctg     60
aaagtggaac aaaaccctct gttcctgagc atgcaggagg gaaaaaacta ccatctctac    120
tgcaattatt caaccacttc agacagactg tattggtaca ggcaggatcc tgggaaaagt    180

```
ctggaatctc tgtttgtgtt gctatcaaat ggagcagtga agcaggaggg acgattaatg    240
gcctcacttg ataccaaagc ccgtctcagc accctccaca tcacagctgc cgtgcatgac    300
ctctctgcca cctacttctg tgccgtggac atcatcggag gcaaatcaac ctttggggat    360
gggactacgc tcactgtgaa gccaa                                          385
```

<210> SEQ ID NO 552
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 552

```
Met Lys Lys Leu Leu Ala Met Ile Leu Trp Leu Gln Leu Asp Arg Leu
1               5                   10                  15

Ser Gly Glu Leu Lys Val Glu Gln Asn Pro Leu Phe Leu Ser Met Gln
                20                  25                  30

Glu Gly Lys Asn Tyr Thr Ile Tyr Cys Asn Tyr Ser Thr Thr Ser Asp
            35                  40                  45

Arg Leu Tyr Trp Tyr Arg Gln Asp Pro Gly Lys Ser Leu Glu Ser Leu
        50                  55                  60

Phe Val Leu Leu Ser Asn Gly Ala Val Lys Gln Glu Gly Arg Leu Met
65                  70                  75                  80

Ala Ser Leu Asp Thr Lys Ala Arg Leu Ser Thr Leu His Ile Thr Ala
                85                  90                  95

Ala Val His Asp Leu Ser Ala Thr Tyr Phe Cys Ala Val Asp Ile Ile
            100                 105                 110

Gly Gly Lys Ser Thr Phe Gly Asp Gly Thr Thr Leu Thr Val Lys Pro
        115                 120                 125
```

<210> SEQ ID NO 553
<211> LENGTH: 400
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 553

```
atggatacct ggctcgtatg ctgggcaatt tttagtctct tgaaagcagg actcacagaa    60
cctgaagtca cccagactcc cagccatcag gtcacacaga tgggacagga agtgatcttg    120
cgctgtgtcc ccatctctaa tcacttatac ttctattggt acagacaaat cttggggcag    180
aaagtcgagt ttctggtttc cttttataat aatgaaatct cagagaagtc tgaaatattc    240
gatgatcaat tctcagttga aaggcctgat ggatcaaatt tcactctgaa gatccggtcc    300
acaaagctgg aggactcagc catgtacttc tgtgccagca gtgaatgggg aagcaccggg    360
gagctgtttt ttggagaagg ctctaggctg accgtactgg                          400
```

<210> SEQ ID NO 554
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 554

```
Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Glu Trp Gly Ser Thr Gly Glu Leu Phe Phe Gly Glu Gly Ser
        115                 120                 125

Arg Leu Thr Val Leu
    130
```

<210> SEQ ID NO 555
<211> LENGTH: 265
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 555

```
Met Lys Lys Leu Leu Ala Met Ile Leu Trp Leu Gln Leu Asp Arg Leu
1               5                   10                  15

Ser Gly Glu Leu Lys Val Glu Gln Asn Pro Leu Phe Leu Ser Met Gln
            20                  25                  30

Glu Gly Lys Asn Tyr Thr Ile Tyr Cys Asn Tyr Ser Thr Thr Ser Asp
        35                  40                  45

Arg Leu Tyr Trp Tyr Arg Gln Asp Pro Gly Lys Ser Leu Glu Ser Leu
    50                  55                  60

Phe Val Leu Leu Ser Asn Gly Ala Val Lys Gln Glu Gly Arg Leu Met
65                  70                  75                  80

Ala Ser Leu Asp Thr Lys Ala Arg Leu Ser Thr Leu His Ile Thr Ala
                85                  90                  95

Ala Val His Asp Leu Ser Ala Thr Tyr Phe Cys Ala Val Asp Ile Ile
            100                 105                 110

Gly Gly Lys Ser Thr Phe Gly Asp Gly Thr Thr Leu Thr Val Lys Pro
        115                 120                 125

Asp Ile Gln Asn Pro Glu Pro Ala Val Tyr Gln Leu Lys Asp Pro Arg
    130                 135                 140

Ser Gln Asp Ser Thr Leu Cys Leu Phe Thr Asp Phe Asp Ser Gln Ile
145                 150                 155                 160

Asn Val Pro Lys Thr Met Glu Ser Gly Thr Phe Ile Thr Asp Lys Thr
                165                 170                 175

Val Leu Asp Met Lys Ala Met Asp Ser Lys Ser Asn Gly Ala Ile Ala
            180                 185                 190

Trp Ser Asn Gln Thr Ser Phe Thr Cys Gln Asp Ile Phe Lys Glu Thr
        195                 200                 205

Asn Ala Thr Tyr Pro Ser Ser Asp Val Pro Cys Asp Ala Thr Leu Thr
    210                 215                 220
```

Glu Lys Ser Phe Glu Thr Asp Met Asn Leu Asn Phe Gln Asn Leu Ser
225                 230                 235                 240

Val Met Gly Leu Arg Ile Leu Leu Lys Val Ala Gly Phe Asn Leu
                245                 250                 255

Leu Met Thr Leu Arg Leu Trp Ser Ser
            260                 265

<210> SEQ ID NO 556
<211> LENGTH: 306
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 556

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Glu Trp Gly Ser Thr Gly Glu Leu Phe Phe Gly Glu Gly Ser
        115                 120                 125

Arg Leu Thr Val Leu Lys Asp Leu Arg Asn Val Thr Pro Pro Lys Val
    130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
    210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr His Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Gly Leu Val Leu Met Ala Met Val Lys Lys Lys
    290                 295                 300

Asn Ser

-continued

```
<210> SEQ ID NO 557
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 557

Val Val Gly Ala Val Gly Val Gly Lys
1               5

<210> SEQ ID NO 558
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 558

Asn Ser Met Phe Asp Tyr
1               5

<210> SEQ ID NO 559
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 559

Ile Ser Ser Ile Lys Asp Lys
1               5

<210> SEQ ID NO 560
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 560

Ala Ala Ser Ala Val Gly Gln Glu Tyr Gly Asn Lys Leu Val
1               5                   10

<210> SEQ ID NO 561
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 561

Ser Glu His Asn Arg
1               5

<210> SEQ ID NO 562
<211> LENGTH: 6
<212> TYPE: PRT
<213> ORGANISM: Artificial Sequence
<220> FEATURE:
<223> OTHER INFORMATION: Description of Artificial Sequence: Synthetic
```

-continued

```
      peptide

<400> SEQUENCE: 562

Phe Gln Asn Glu Ala Gln
1               5

<210> SEQ ID NO 563
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 563

Ala Ser Ser Glu Tyr Thr Met Gly Thr Gln Tyr
1               5                   10

<210> SEQ ID NO 564
<211> LENGTH: 424
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 564
atggccatgc tcctgggggc atcagtgctg attctgtggc ttcagccaga ctgggtaaac      60
agtcaacaga gaatgatga ccagcaagtt aagcaaaatt caccatccct gagcgtccag     120
gaaggaagaa tttctattct gaactgtgac atactaaca gcatgtttga ttatttccta     180
tggtacaaaa ataccctgc tgaaggtcct acattcctga tatctataag ttccattaag     240
gataaaaatg aagatggaag attcactgtc ttcttaaaca aaagtgccaa gcacctctct     300
ctgcacattg tgccctccca gcctggagac tctgcagtgt acttctgtgc agcaagcgca     360
gtaggtcagg aatatggaaa caagctggtc tttggcgcag gaaccattct gagagtcaag     420
tcct                                                                  424

<210> SEQ ID NO 565
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 565

Met Ala Met Leu Leu Gly Ala Ser Val Leu Ile Leu Trp Leu Gln Pro
1               5                   10                  15

Asp Trp Val Asn Ser Gln Gln Lys Asn Asp Gln Gln Val Lys Gln
            20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
    50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110
```

Val Tyr Phe Cys Ala Ala Ser Ala Val Gly Gln Glu Tyr Gly Asn Lys
            115                 120                 125

Leu Val Phe Gly Ala Gly Thr Ile Leu Arg Val Lys Ser
    130                 135                 140

<210> SEQ ID NO 566
<211> LENGTH: 397
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 566
atgggcacca gcctcctctg ctggatggcc ctgtgtctcc tgggggcaga tcacgcagat     60
actggagtct cccagaaccc cagacacaag atcacaaaga ggggacagaa tgtaactttc    120
aggtgtgatc caatttctga acacaaccgc ctttattggt accgacagac cctggggcag    180
ggcccagagt ttctgactta cttccagaat gaagctcaac tagaaaaatc aaggctgctc    240
agtgatcggt tctctgcaga gaggcctaag ggatctttct ccaccttgga gatccagcgc    300
acagagcagg gggactcggc catgtatctc tgtgccagca gtaatatac tatggggacc     360 cagtacttcg ggccaggcac gcggctcctg gtgctcg                             397

<210> SEQ ID NO 567
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 567

Met Gly Thr Ser Leu Leu Cys Trp Met Ala Leu Cys Leu Leu Gly Ala
1               5                   10                  15

Asp His Ala Asp Thr Gly Val Ser Gln Asn Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Glu Tyr Thr Met Gly Thr Gln Tyr Phe Gly Pro Gly Thr Arg
        115                 120                 125

Leu Leu Val Leu
    130

<210> SEQ ID NO 568
<211> LENGTH: 278
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 568

Met Ala Met Leu Leu Gly Ala Ser Val Leu Ile Leu Trp Leu Gln Pro
1               5                   10                  15

Asp Trp Val Asn Ser Gln Gln Lys Asn Asp Gln Gln Val Lys Gln
            20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ala Ser Ala Val Gly Gln Glu Tyr Gly Asn Lys
        115                 120                 125

Leu Val Phe Gly Ala Gly Thr Ile Leu Arg Val Lys Ser Asp Ile Gln
130                 135                 140

Asn Pro Glu Pro Ala Val Tyr Gln Leu Lys Asp Pro Arg Ser Gln Asp
145                 150                 155                 160

Ser Thr Leu Cys Leu Phe Thr Asp Phe Asp Ser Gln Ile Asn Val Pro
                165                 170                 175

Lys Thr Met Glu Ser Gly Thr Phe Ile Thr Asp Lys Thr Val Leu Asp
            180                 185                 190

Met Lys Ala Met Asp Ser Lys Ser Asn Gly Ala Ile Ala Trp Ser Asn
        195                 200                 205

Gln Thr Ser Phe Thr Cys Gln Asp Ile Phe Lys Glu Thr Asn Ala Thr
210                 215                 220

Tyr Pro Ser Ser Asp Val Pro Cys Asp Ala Thr Leu Thr Glu Lys Ser
225                 230                 235                 240

Phe Glu Thr Asp Met Asn Leu Asn Phe Gln Asn Leu Ser Val Met Gly
                245                 250                 255

Leu Arg Ile Leu Leu Leu Lys Val Ala Gly Phe Asn Leu Leu Met Thr
            260                 265                 270

Leu Arg Leu Trp Ser Ser
        275

<210> SEQ ID NO 569
<211> LENGTH: 305
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 569

Met Gly Thr Ser Leu Leu Cys Trp Met Ala Leu Cys Leu Leu Gly Ala
1               5                   10                  15

Asp His Ala Asp Thr Gly Val Ser Gln Asn Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
50                  55                  60

```
Leu Thr Tyr Phe Gln Asn Glu Ala Gln Leu Glu Lys Ser Arg Leu Leu
 65                  70                  75                  80

Ser Asp Arg Phe Ser Ala Glu Arg Pro Lys Gly Ser Phe Ser Thr Leu
                 85                  90                  95

Glu Ile Gln Arg Thr Glu Gln Gly Asp Ser Ala Met Tyr Leu Cys Ala
            100                 105                 110

Ser Ser Glu Tyr Thr Met Gly Thr Gln Tyr Phe Gly Pro Gly Thr Arg
        115                 120                 125

Leu Leu Val Leu Lys Asp Leu Arg Asn Val Thr Pro Pro Lys Val Ser
130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr His Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Gly Leu Val Leu Met Ala Met Val Lys Lys Lys Asn
290                 295                 300

Ser
305

<210> SEQ ID NO 570

<400> SEQUENCE: 570

000

<210> SEQ ID NO 571

<400> SEQUENCE: 571

000

<210> SEQ ID NO 572

<400> SEQUENCE: 572

000

<210> SEQ ID NO 573

<400> SEQUENCE: 573

000

<210> SEQ ID NO 574
```

-continued

<400> SEQUENCE: 574

000

<210> SEQ ID NO 575

<400> SEQUENCE: 575

000

<210> SEQ ID NO 576

<400> SEQUENCE: 576

000

<210> SEQ ID NO 577

<400> SEQUENCE: 577

000

<210> SEQ ID NO 578

<400> SEQUENCE: 578

000

<210> SEQ ID NO 579

<400> SEQUENCE: 579

000

<210> SEQ ID NO 580

<400> SEQUENCE: 580

000

<210> SEQ ID NO 581

<400> SEQUENCE: 581

000

<210> SEQ ID NO 582

<400> SEQUENCE: 582

000

<210> SEQ ID NO 583

<400> SEQUENCE: 583

000

<210> SEQ ID NO 584

<400> SEQUENCE: 584

000

<210> SEQ ID NO 585

<400> SEQUENCE: 585

000

<210> SEQ ID NO 586

<400> SEQUENCE: 586

000

<210> SEQ ID NO 587

<400> SEQUENCE: 587

000

<210> SEQ ID NO 588

<400> SEQUENCE: 588

000

<210> SEQ ID NO 589

<400> SEQUENCE: 589

000

<210> SEQ ID NO 590

<400> SEQUENCE: 590

000

<210> SEQ ID NO 591

<400> SEQUENCE: 591

000

<210> SEQ ID NO 592

<400> SEQUENCE: 592

000

<210> SEQ ID NO 593

<400> SEQUENCE: 593

000

<210> SEQ ID NO 594

<400> SEQUENCE: 594

000

<210> SEQ ID NO 595

<400> SEQUENCE: 595

000

<210> SEQ ID NO 596

<400> SEQUENCE: 596

000

```
<210> SEQ ID NO 597

<400> SEQUENCE: 597

000

<210> SEQ ID NO 598

<400> SEQUENCE: 598

000

<210> SEQ ID NO 599

<400> SEQUENCE: 599

000

<210> SEQ ID NO 600
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 600

Val Val Gly Ala Val Gly Val Gly Lys
1               5

<210> SEQ ID NO 601
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 601

Ser Gly Ser Gly
1

<210> SEQ ID NO 602
<211> LENGTH: 8
<212> TYPE: PRT
<213> ORGANISM: Influenza virus

<400> SEQUENCE: 602

Gly Ile Leu Gly Phe Val Thr Leu
1               5

<210> SEQ ID NO 603
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 603

Cys Ala Val Lys Gly Gly Gly Ser Gly Thr Tyr Lys Tyr Ile Phe
1               5                   10                  15

<210> SEQ ID NO 604
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 604

Cys Ala Val Gly Asn Asn Gln Gly Gly Lys Leu Ile Phe
1               5                   10

<210> SEQ ID NO 605
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 605

Cys Ala Gly Pro Asn Thr Asn Ala Gly Lys Ser Thr Phe
1               5                   10

<210> SEQ ID NO 606
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 606

Cys Ala Ala Ser Ile Ala Asp Gly Gln Lys Leu Leu Phe
1               5                   10

<210> SEQ ID NO 607
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 607

Cys Ala Tyr Ile Asp Ala Gly Asn Gln Phe Tyr Phe
1               5                   10

<210> SEQ ID NO 608
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 608

Cys Ala Val Arg Gly Asp Ser Gly Gly Gly Ala Asp Gly Leu Thr Phe
1               5                   10                  15

<210> SEQ ID NO 609
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 609

Cys Ala Val Asp Ile Ile Gly Gly Lys Ser Thr Phe
1               5                   10
```

<210> SEQ ID NO 610
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 610

Cys Ala Ala Asn Ala Gly Gly Thr Ser Tyr Gly Lys Leu Thr Phe
1               5                   10                  15

<210> SEQ ID NO 611
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 611

Cys Ala Ser Ser Phe Phe Pro Thr Ser Thr Gly Arg Thr Asp Thr Gln
1               5                   10                  15

Tyr Phe

<210> SEQ ID NO 612
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 612

Cys Ala Ser Ser Gly Pro Gly Pro Arg Gly Phe Asn Glu Gln Phe Phe
1               5                   10                  15

<210> SEQ ID NO 613
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 613

Cys Ala Ser Ser Leu Gly Gln Asp Thr Glu Ala Phe Phe
1               5                   10

<210> SEQ ID NO 614
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 614

Cys Ala Ser Ser Glu Ser Gly Ser Gly Glu Lys Leu Phe Phe
1               5                   10

<210> SEQ ID NO 615
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 615

Cys Ala Ser Ile Thr Pro Arg Asp Glu Gln Phe Phe
1               5                   10

<210> SEQ ID NO 616
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 616

Cys Ala Ser Ser Glu Trp Gly Ser Thr Gly Glu Leu Phe Phe
1               5                   10

<210> SEQ ID NO 617
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 617

Cys Ala Met Arg Glu Gly Arg Gly Ala Gly Asn Asn Arg Lys Leu Ile
1               5                   10                  15

Trp

<210> SEQ ID NO 618
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 618

Cys Ala Leu Ser Glu Ala Gly Leu Gly Gly Gly Lys Leu Ile Phe
1               5                   10                  15

<210> SEQ ID NO 619
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 619

Cys Ala Ala Ser Ala Val Gly Gln Glu Tyr Gly Asn Lys Leu Val Phe
1               5                   10                  15

<210> SEQ ID NO 620
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 620

Cys Ala Ser Ser Gln Asp Arg Leu Ala Gly Asp Tyr Glu Gln Tyr Phe
1               5                   10                  15

```
<210> SEQ ID NO 621
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 621

Cys Ala Ser Ser Glu Tyr Thr Met Gly Thr Gln Tyr Phe
1               5                   10
```

T CELL RECEPTOR CONSTRUCTS AND USES THEREOF

CROSS REFERENCE

This application is a U.S. National Phase Application of International Patent Application No. PCT/US2019/046876, filed Aug. 16, 2019, which claims the benefit of U.S. Provisional Application No. 62/764,817, filed on Aug. 16, 2018, and U.S. Provisional Application No. 62/810,112, filed on Feb. 25, 2019, each of which is hereby incorporated by reference in its entirety.

BACKGROUND

T cell receptors (TCRs) are members of the immunoglobulin superfamily and usually consist of two subunits, namely the α- and β-subunits. These possess one N-terminal immunoglobulin (Ig)-variable (V) domain, one Ig-constant (C) domain, a transmembrane/cell membrane-spanning region, and a short cytoplasmic tail at the C-terminal end. The variable domains of both the TCR α-chain and β-chain have three hypervariable or complementarity determining regions (CDRs), whereas the variable region of the β-chain has an additional area of hypervariability (HV4) that does not normally contact antigen and therefore is not considered a CDR.

CDR3 is the principle CDR responsible for recognizing processed antigen, although CDR1 of the alpha chain has also been shown to interact with the N-terminal part of the antigenic peptide, whereas CDR1 of the β-chain interacts with the C-terminal part of the peptide. CDR2 is thought to recognize the MHC. The constant domain of the TCR domain consists of short connecting sequences in which a cysteine residue forms disulfide bonds, which forms a link between the two chains. The affinity of TCR's for a specific antigen makes them valuable for several therapeutic approaches. For example, cancer patients, such as melanoma patients, can be effectively treated by using adoptive immunotherapy as TCRs are exquisitely sensitive for their antigen and can direct immune responses at tumor cells expressing their cognate antigen. Accordingly, there is a need for TCRs against peptide-MHC complexes for development of new and effective therapeutics.

SUMMARY

The instant application is based on development of TCRs against peptide-MHC complexes and effective therapeutics comprising the TCRs. Provided herein, isolated nucleic acid molecules encoding TCRs against peptide-MHC complexes, T cells expressing TCRs against peptide-MHC complexes, and pharmaceutical compositions for use in the treatment of diseases.

Provided herein is a recombinant nucleic acid encoding a T cell receptor (TCR) comprising a TCR beta chain construct comprising a complementarity determining region 3 (CDR3) having an amino acid sequence set forth in SEQ ID NO: 52. In some embodiments, the T cell receptor (TCR) construct further comprises a complementarity determining region 1 (CDR1) and a complementarity determining region 2 (CDR2), wherein the CDR1 has an amino acid sequence set forth in SEQ ID NO: 50; and the CDR2 has an amino acid sequence set forth in SEQ ID NO: 51. In some embodiments, the TCR beta chain construct comprises a variable region having at least 80% sequence identity to an amino acid sequence set forth in SEQ ID NO: 58. In some embodiments, the TCR beta chain construct comprises a variable region having at least 90% sequence identity to an amino acid sequence set forth in SEQ ID NO: 58. In some embodiments, the TCR beta chain construct comprises a variable region having at least 95%, 96%, 97%, 98% or 99% sequence identity to an amino acid sequence set forth in SEQ ID NO: 58. In some embodiments, the TCR beta chain construct comprises a variable region having an amino acid sequence set forth in SEQ ID NO: 58. In some embodiments, the recombinant nucleic acid encoding a T cell receptor (TCR) of any one of the preceding embodiments, further comprises a TCR alpha chain construct having a CDR1, a CDR2, and a CDR3, wherein, the CDR1 has an amino acid sequence set forth in SEQ ID NO: 47; the CDR2 has an amino acid sequence set forth in SEQ ID NO: 48; and, the CDR has an amino acid sequence set forth in SEQ ID NO: 49. In some embodiments, the recombinant nucleic acid of any one of the preceding embodiments, comprises: (a) a sequence having at least 80% sequence identity with SEQ ID NOs: 56 or 57, further comprising a sequence encoding at least SEQ ID NO: 52; and (b) a sequence having at least 80% sequence identity with SEQ ID NOs: 53 or 54, further comprising a sequence encoding at least SEQ ID NO: 49. In some embodiments, the recombinant nucleic acid encoding a T cell receptor (TCR) of any one of the preceding embodiments comprises the TCR alpha chain construct which comprises a variable region having at least 80% sequence identity to an amino acid sequence set forth in SEQ ID NO: 55. In some embodiments, the TCR alpha chain construct comprises a variable region having at least 90% sequence identity to an amino acid sequence set forth in SEQ ID NO: 55. In some embodiments, the TCR alpha chain construct comprises a variable region having at least 95%, 96%, 97%, 98% or 99% sequence identity to an amino acid sequence set forth in SEQ ID NO: 55. In some embodiments, the TCR alpha chain construct comprises a variable region having an amino acid sequence set forth in SEQ ID NO: 55. In some embodiments, the recombinant nucleic acid encoding a TCR described above comprises: (a) a beta chain having an amino acid sequence set forth in SEQ ID NO: 60, or an amino acid sequence that is at least 80% identical to SEQ ID NO: 60; and (b) an alpha chain having an amino acid sequence set forth in SEQ ID NO: 59, or an amino acid sequence that is at least 80% identical to SEQ ID NO: 59. In some embodiments, the recombinant nucleic acid encoding a TCR of any one of the preceding embodiments, binds to an epitope from human RAS comprising a mutation G12V.

Provided herein is a recombinant nucleic acid encoding a TCR comprising a TCR beta chain construct and a TCR alpha chain construct, the TCR beta chain construct comprising a complementarity determining region 3 (CDR3) having an amino acid sequence selected from SEQ ID NO: 537 and 563. In some embodiments, the TCR beta chain construct comprises a CDR3 having an amino acid sequence of SEQ ID NO: 537. In some embodiments, the TCR beta chain construct comprising a CDR3 having an amino acid sequence of SEQ ID NO: 537, comprises a variable region having at least 80%, 90%, 95%, 96%, 97%, 98%, 99% or 100% sequence identity to an amino acid sequence set forth in SEQ ID NO: 541. In some embodiments, the TCR beta chain construct has an amino acid sequence identity set forth in SEQ ID NO: 541. In some embodiments, the TCR comprising a TCR beta chain CDR3 having an amino acid sequence of SEQ ID NO: 537, further comprises a TCR alpha chain construct that comprises a variable region having at least 80%, 90%, 95%, 96%, 97%, 98%, 99% or 100% sequence identity to an amino acid sequence set forth in SEQ ID NO: 539 or SEQ ID NO: 552. In some embodiments, the TCR alpha chain construct has an amino acid sequence identity set forth in SEQ ID NO: 539. In some embodiments, the TCR alpha chain construct has an amino acid sequence identity set forth in SEQ ID NO: 552. In some embodiments, the recombinant nucleic acid described above encodes a TCR comprising a beta chain having an amino acid sequence set forth in SEQ ID NO: 543, or a sequence that has at least 80% sequence identity to SEQ ID NO: 543; and an alpha chain having an amino acid sequence set forth in SEQ ID NO: 542, or a sequence that has at least 80% sequence identity to SEQ ID NO: 542. In some embodiments, the recombinant nucleic acid described above encodes a TCR comprising a beta chain having an amino acid sequence set forth in SEQ ID NO: 543, or a sequence that has at least 80% sequence identity to SEQ ID NO: 543; and an alpha chain having an amino acid sequence set forth in SEQ ID NO: 555, or a sequence that has at least 80% sequence identity to SEQ ID NO: 555. In some embodiments, the recombinant nucleic acid described above encodes a TCR comprising a beta chain variable domain having an amino acid sequence set forth in SEQ ID NO: 541, or a sequence that has at least 80% sequence identity to SEQ ID NO: 541; and an alpha chain variable domain having an amino acid sequence set forth in SEQ ID NO: 539, or a sequence that has at least 80% sequence identity to SEQ ID NO: 539. In some embodiments, the recombinant nucleic acid described above encodes a TCR comprising a beta chain variable domain having an amino acid sequence set forth in SEQ ID NO: 541, or a sequence that has at least 80% sequence identity to SEQ ID NO: 541; and an alpha chain variable domain having an amino acid sequence set forth in SEQ ID NO: 552, or a sequence that has at least 80% sequence identity to SEQ ID NO: 552.

In some embodiments, the recombinant nucleic acid encoding a TCR comprising a TCR beta chain construct and a TCR alpha chain construct, the TCR beta chain construct TCR beta chain construct comprises a CDR3 having an amino acid sequence of SEQ ID NO: 563. In some embodiments the TCR beta chain construct comprises a variable region having at least 80%, 90%, 95%, 96%, 97%, 98%, 99% or 100% sequence identity to an amino acid sequence set forth in SEQ ID NO: 567. In some embodiments the TCR alpha chain construct comprises a variable region having at least 80%, 90%, 95%, 96%, 97%, 98%, 99% or 100% sequence identity to an amino acid sequence set forth in SEQ ID NO: 565. In some embodiments, the recombinant nucleic acid described above encodes a TCR comprising a beta chain having an amino acid sequence set forth in SEQ ID NO: 569, or a sequence that has at least 80% sequence identity to SEQ ID NO: 569; and an alpha chain variable domain having an amino acid sequence set forth in SEQ ID NO: 568, or a sequence that has at least 80% sequence identity to SEQ ID NO: 568. Disclosed herein is a vector comprising the recombinant nucleic acid of any one of the embodiments described above. Also disclosed herein is a cell comprising the recombinant nucleic acid of any one of the embodiments described above or the vector of as described above.

Provided herein is a recombinant nucleic acid encoding a TCR construct comprising: (a) a TCR beta chain construct, and (b) a TCR alpha chain construct; wherein the TCR recognizes and binds to an epitope from human RAS comprising a point mutation G12V or G12C, the epitope being in a human MHC-protein complex, wherein the human MHC-protein is an HLA antigen encoded by the HLA A03:01 allele. In some embodiments, the TCR beta chain construct comprises a CDR3 having an amino acid sequence set forth in SEQ ID NO: 68. In some embodiments, the TCR beta chain construct further comprises a complementary determining region 1 (CDR1) and a complementarity determining region 2 (CDR2), wherein the CDR1 has an amino acid sequence set forth in SEQ ID NO: 66; and the CDR2 has an amino acid sequence set forth in SEQ ID NO: 67. In some embodiments, the recombinant nucleic acid encoding a T cell receptor (TCR) described in this paragraph, further comprising a TCR alpha chain construct having a CDR1, a CDR2, and a CDR3, wherein, the CDR1 has an amino acid sequence set forth in SEQ ID NO: 63; the CDR2 has an amino acid sequence set forth in SEQ ID NO: 64; and, the CDR has an amino acid sequence set forth in SEQ ID NO: 65. In some embodiments, the TCR beta chain construct comprises a variable region having at least 80%, or at least 90%, 95%, 96%, 97%, 98%, or 99% sequence identity to an amino acid sequence set forth in SEQ ID NO: 74. In some embodiments, the TCR beta chain construct comprises a variable region having an amino acid sequence set forth in SEQ ID NO: 74. In some embodiments, T cell receptor (TCR) comprises a TCR alpha chain construct, wherein the TCR alpha chain construct comprises a variable region having at least 80%, or at least 90%, 95%, 96%, 97%, 98% or 99% sequence identity to an amino acid sequence set forth in SEQ ID NO: 71. In some embodiments, the TCR alpha chain construct comprises a variable region having an amino acid sequence set forth in SEQ ID NO: 71. In some embodiment, the TCR comprises a beta chain construct having an amino acid sequence set forth in SEQ ID NO: 76, or a sequence having at least 80% sequence identity to SEQ ID NO: 76; and an alpha chain construct having an amino acid sequence set forth in SEQ ID NO: 75, or a sequence having at least 80% sequence identity to SEQ ID NO: 75. Provided herein is a vector comprising a recombinant nucleic acid of any one of the embodiments described in this paragraph. Also provided herein is a cell comprising any one of the recombinant nucleic acid of any one of the embodiments described in this paragraph or the vector described in this paragraph.

In some embodiments, the TCR that recognizes and binds to an epitope from human RAS comprising a point mutation G12V in complex with an HLA antigen encoded by the HLA A03:01 allele, comprises a TCR beta chain construct comprises a CDR3 having an amino acid sequence set forth in SEQ ID NO: 84. In some embodiments, the TCR beta chain construct further comprises a complementarity determining region 1 (CDR1) and a complementarity determining region 2 (CDR2), wherein the CDR1 has an amino acid sequence set forth in SEQ ID NO: 82; and the CDR2 has an amino acid sequence set forth in SEQ ID NO: 83. In some embodiments, the TCR further comprises a TCR alpha construct having a CDR1, a CDR2, and a CDR3, wherein, the CDR1 has an amino acid sequence set forth in SEQ ID NO: 79; the CDR2 has an amino acid sequence set forth in SEQ ID NO: 80; and, the CDR3 has an amino acid sequence set forth in SEQ ID NO: 81. In some embodiments, the TCR beta chain construct comprises a variable region having at least 80%, or at least 90%, 95%, 96%, 97%, 98% or 99% sequence identity to an amino acid sequence set forth in SEQ ID NO: 90. In some embodiments, the TCR beta chain construct comprises a variable region having an amino acid sequence set forth in SEQ ID NO: 90. In some embodiments, the TCR described above further comprises a TCR alpha chain construct that comprises a variable region having at least 80%, or at least 90%, 95%, 96%, 97%, 98% or 99% sequence identity to an amino acid sequence set forth in SEQ ID NO: 87. In some embodiments, the TCR alpha chain construct comprises a variable region having an amino acid sequence set forth in SEQ ID NO: 71. In some embodiments, the TCR comprises a beta chain construct having an amino acid sequence of SEQ ID NO: 92, or a sequence that has at least 80% sequence identity to SEQ ID NO: 92; and an alpha chain construct having an amino acid sequence of SEQ ID NO: 91, or a sequence that has at least 80% sequence identity to SEQ ID NO: 91. Provided herein is a vector comprising the recombinant nucleic acid of any one of the embodiments described in this paragraph and a cell comprising any one of the recombinant nucleic acid of any one of the embodiments described herein.

In some embodiments, the recombinant nucleic acid of embodiment described in the preceding paragraph, the TCR that recognizes and binds to an epitope from human RAS comprising a point mutation G12V or G12C in complex with an HLA antigen encoded by the HLA A03:01 allele, comprises a TCR beta chain construct comprises a CDR3 having an amino acid sequence set forth in SEQ ID NO: 388. In some embodiments, the TCR beta chain construct further comprises a complementarity determining region 1 (CDR1) and a complementarity determining region 2 (CDR2), wherein the CDR1 has an amino acid sequence set forth in SEQ ID NO: 386; and the CDR2 has an amino acid sequence set forth in SEQ ID NO: 387. In some embodiments, the TCR further comprises a TCR alpha construct having a CDR1, a CDR2, and a CDR3, wherein, the CDR1 has an amino acid sequence set forth in SEQ ID NO: 383; the CDR2 has an amino acid sequence set forth in SEQ ID NO: 384; and, the CDR3 has an amino acid sequence set forth in SEQ ID NO: 385. In some embodiments, the TCR beta chain construct comprises a variable region having at least 80%, or at least 90%, 95%, 96%, 97%, 98% or 99% sequence identity to an amino acid sequence set forth in SEQ ID NO: 394. In some embodiments, the TCR beta chain construct comprises a variable region having an amino acid sequence set forth in SEQ ID NO: 394. In some embodiments, the TCR described above further comprises a TCR alpha chain construct that comprises a variable region having at least 80%, or at least 90%, 95%, 96%, 97%, 98% or 99% sequence identity to an amino acid sequence set forth in SEQ ID NO: 391. In some embodiments, the TCR alpha chain construct comprises a variable region having an amino acid sequence set forth in SEQ ID NO: 391. In some embodiments, the TCR comprises a beta chain construct having an amino acid sequence of SEQ ID NO: 396, or a sequence that has at least 80% sequence identity to SEQ ID NO: 396; and an alpha chain construct having an amino acid sequence of SEQ ID NO: 395, or a sequence that has at least 80% sequence identity to SEQ ID NO: 395. Provided herein is a vector comprising the recombinant nucleic acid of any one of the embodiments described in this paragraph and a cell comprising any one of the recombinant nucleic acid of any one of the embodiments described herein.

In some embodiments, the recombinant nucleic acid of embodiment described in the preceding paragraph, the TCR that recognizes and binds to an epitope from human RAS comprising a point mutation G12C in complex with an HLA antigen encoded by the HLA A03:01 allele, comprises a TCR beta chain construct comprises a CDR3 having an amino acid sequence set forth in SEQ ID NO: 100. In some embodiments, the TCR beta chain construct further comprises a complementarity determining region 1 (CDR1) and a complementarity determining region 2 (CDR2), wherein the CDR1 has an amino acid sequence set forth in SEQ ID NO: 98; and the CDR2 has an amino acid sequence set forth in SEQ ID NO: 99. In some embodiments, the TCR further comprises a TCR alpha construct having a CDR1, a CDR2, and a CDR3, wherein, the CDR1 has an amino acid sequence set forth in SEQ ID NO: 95; the CDR2 has an amino acid sequence set forth in SEQ ID NO: 96; and, the CDR3 has an amino acid sequence set forth in SEQ ID NO: 97. In some embodiments, the TCR beta chain construct comprises a variable region having at least 80%, or at least 90%, 95%, 96%, 97%, 98% or 99% sequence identity to an amino acid sequence set forth in SEQ ID NO: 106. In some embodiments, the TCR beta chain construct comprises a variable region having an amino acid sequence set forth in SEQ ID NO: 106. In some embodiments, the TCR described above further comprises a TCR alpha chain construct that comprises a variable region having at least 80%, or at least 90%, 95%, 96%, 97%, 98% or 99% sequence identity to an amino acid sequence set forth in SEQ ID NO: 103. In some embodiments, the TCR alpha chain construct comprises a variable region having an amino acid sequence set forth in SEQ ID NO: 103. In some embodiments, the TCR comprises a beta chain construct having an amino acid sequence of SEQ ID NO: 108, or a sequence that has at least 80% sequence identity to SEQ ID NO: 108; and an alpha chain construct having an amino acid sequence of SEQ ID NO: 107, or a sequence that has at least 80% sequence identity to SEQ ID NO: 107. Provided herein is a vector comprising the recombinant nucleic acid of any one of the embodiments described in this paragraph and a cell comprising any one of the recombinant nucleic acid of any one of the embodiments described herein.

In some embodiments, the epitope has a length of from 8-25 amino acids. In some embodiments the epitope comprises a mutation that differs from the wild type epitope by at least one amino acid. In some embodiments, the epitope binds to the human MHC with a greater affinity than a corresponding wild-type epitope. In some embodiments, the epitope binds to the human MHC with a $K_D$ or an $IC_{50}$ less than 500 nM, 250 nM, 150 nM, 100 nM, 50 nM, 25 nM or 10 nM. In some embodiments, the mutation is not present in non-cancer cells of a subject. In some embodiments, the TCR binds to an MHC-peptide complex with a $K_D$ or an $IC_{50}$ of less than 500 nM, 250 nM, 150 nM, 100 nM, 50 nM, 25 nM or 10 nM. In some embodiments, the nucleic acid is operably linked to a promoter. In some embodiments, the cell is a $CD4^+$ T cell. In some embodiments, the cell is a $CD8^+$ T cell. In some embodiments, the cell is isolated from a subject having a RAS mutation.

Provided herein is a pharmaceutical composition comprising: (a) the nucleic acid of any one of embodiments described above; or, the vector of any one of embodiments described above; or, the cell of any one of embodiments above; and, (b) a pharmaceutically acceptable excipient or diluent. In some embodiments, the pharmaceutical composition further comprising an immunomodulatory agent or an adjuvant. In some embodiments, the adjuvant is poly I:C. In some embodiments, the pharmaceutical composition of any one of embodiments described above is for use in treating an immune disease or cancer.

Provided herein is method of treating a subject having a disease or condition, comprising administering to the subject the pharmaceutical composition of any one of embodiments described above. In some embodiments, the method of treating a subject with cancer comprises administering to the subject the pharmaceutical composition of any one of embodiments described above.

Also provided herein is a method of identifying a subject with cancer as a candidate for a therapeutic, the method comprising determining the subject as a subject that expresses a protein encoded by an HLA-A03:01 allele or an HLA-A11:01 allele, wherein the therapeutic is the pharmaceutical composition selected from any one of embodiments described above.

Provided herein is a nucleic acid encoding at least one T cell receptor (TCR) comprising a TCR alpha chain construct and/or TCR beta chain construct capable of specifically binding to an epitope from RAS in complex with a human MHC, wherein the TCR alpha chain construct comprises a complementarity determining region 3 (CDR3) having at least 84% sequence identity to an amino acid sequence selected from SEQ ID NOs: 3, 18, 33, 49, 65, 81, 97, 113, 241, 257, 273, 289, 305, 321, 337, 353, 369, 385, 401, 417, and 433 and/or wherein the TCR beta chain construct comprises a complementarity determining region 3 (CDR3) having at least 84% sequence identity to an amino acid sequence selected from SEQ ID NOs: 6, 21, 36, 52, 68, 84, 100, 116, 244, 260, 276, 292, 308, 324, 340, 356, 372, 388, 404, 420, and 436.

Provided herein is a nucleic acid encoding at least one T cell receptor (TCR) comprising a TCR alpha chain construct and/or TCR beta chain construct capable of specifically binding to an epitope from RAS in complex with a human MHC, wherein the epitope from RAS comprises a region having at least 70% sequence identity to an amino acid sequence selected from SEQ ID NOs: 15, 30, 45, 46, 61, 62, 77, 78, 93, 94, 109, 110, 125, 126, 219-222, 253, 254, 269, 270, 285, 286, 301, 302, 317, 318, 333, 334, 349, 350, 365, 366, 381, 382, 397, 398, 413, 414, 429, 430, 445 and 446.

Provided herein is an isolated nucleic acid or a cell comprising a recombinant nucleic acid, wherein the nucleic acid encodes at least one T cell receptor (TCR) comprising a TCR alpha chain construct and/or a TCR beta chain construct; wherein the TCR specifically binds to an epitope from RAS in complex with a human MHC encoded by an HLA-A03:01 allele. In some embodiments, the alpha chain construct comprises a variable region having at least 80% sequence identity to an amino acid sequence selected from SEQ ID NOs: 71, 87, 103, 295, 311, 327, 343, 359 and 391, wherein the TCR specifically binds to an epitope from RAS in complex with a human MHC encoded by an HLA-A03:01 allele. In some embodiments, the TCR beta chain construct comprises a variable region having at least 80% sequence identity to an amino acid sequence selected from SEQ ID NOs: 74, 90, 106, 298, 314, 330, 346, 362 and 394, wherein the TCR specifically binds to an epitope from RAS in complex with a human MHC encoded by an HLA-A03:01 allele.

In some embodiments, the TCR alpha chain construct as described above comprises a complementarity determining region 1 (CDR1) having at least 90% sequence identity to an amino acid sequence selected from SEQ ID NOs: 63, 79, 95, 287, 303, 319, 335, 351 and 383. In some embodiments, the TCR beta chain construct as described above comprises a complementarity determining region 1 (CDR1) having at least 90% sequence identity to an amino acid sequence selected from SEQ ID NOs: 66, 82, 98, 290, 306, 322, 338, 354 and 386. In some embodiments, the TCR alpha chain construct comprises a complementarity determining region 2 (CDR2) having at least 90% sequence identity to an amino acid sequence selected from SEQ ID NOs: 64, 80, 96, 288, 304, 320, 336, 352 and 384. In some embodiments, the TCR beta chain construct comprises a complementarity determining region 2 (CDR2) having at least 90% sequence identity to an amino acid sequence selected from SEQ ID NOs: 67, 83, 99, 291, 307, 323, 339, 355 and 387. In some embodiments, the TCR alpha chain construct comprises a complementarity determining region 3 (CDR3) having at least 90% sequence identity to an amino acid sequence selected from SEQ ID NOs: 65, 81, 97, 289, 305, 321, 337, 353 and 385. In some embodiments, the TCR beta chain construct comprises a complementarity determining region 3 (CDR3) having at least 90% sequence identity to an amino acid sequence selected from SEQ ID NOs: 68, 84, 100, 292, 308, 324, 340, 356 and 388.

Provided herein is an isolated nucleic acid or a cell comprising a recombinant nucleic acid, wherein the nucleic acid encodes at least one T cell receptor (TCR) comprising a TCR alpha chain construct and/or a TCR beta chain construct; wherein the TCR specifically binds to an epitope from RAS in complex with a human MHC encoded by an HLA-A02:01 allele. In some embodiments, the alpha chain construct comprises a variable region having at least 80% sequence identity to an amino acid sequence selected from SEQ ID NOs: 9 and 24 wherein the TCR specifically binds to an epitope from RAS in complex with a human MHC encoded by an HLA-A02:01 allele. In some embodiments, the TCR beta chain construct comprises a variable region having at least 80% sequence identity to an amino acid sequence selected from SEQ ID NOs: 12 and 27, wherein the TCR specifically binds to an epitope from RAS in complex with a human MHC encoded by an HLA-A02:01 allele.

In some embodiments, the TCR alpha chain construct as described above comprises a complementarity determining region 1 (CDR1) having at least 90% sequence identity to an amino acid sequence selected from SEQ ID NOs: 1 and 16. In some embodiments, the TCR beta chain construct as described above comprises a complementarity determining region 1 (CDR1) having at least 90% sequence identity to an amino acid sequence selected from SEQ ID NOs: 4 and 19. In some embodiments, the TCR alpha chain construct comprises a complementarity determining region 2 (CDR2) having at least 90% sequence identity to an amino acid sequence selected from SEQ ID NOs: 2 and 17. In some embodiments TCR beta chain construct comprises a complementarity determining region 2 (CDR2) having at least 90% sequence identity to an amino acid sequence selected from SEQ ID NOs: 5 and 20. In some embodiments, the TCR alpha chain construct comprises a complementarity determining region 3 (CDR3) having at least 90% sequence identity to an amino acid sequence selected from SEQ ID NOs: 3 and 18. In some embodiments, the TCR beta chain construct comprises a complementarity determining region 3 (CDR3) having at least 90% sequence identity to an amino acid sequence selected from SEQ ID NOs: 6 and 21.

Provided herein is an isolated nucleic acid or a cell comprising a recombinant nucleic acid, wherein the nucleic acid encodes at least one T cell receptor (TCR) comprising a TCR alpha chain construct and/or a TCR beta chain construct; wherein the TCR specifically binds to an epitope from RAS in complex with a human MHC encoded by an HLA-A11:01 allele. In some embodiments, the TCR alpha chain construct comprises a variable region having at least 80% sequence identity to an amino acid sequence selected from SEQ ID NOs: 39, 55, 122, 247, 263, 279, 375, 407, and 423, wherein the TCR specifically binds to an epitope from RAS in complex with a human MHC encoded by an HLA-A11:01 allele. In some embodiments, the TCR beta chain construct comprises a variable region having at least 80% sequence identity to an amino acid sequence selected from SEQ ID NOs: 42, 58, 125, 250, 266, 282, 378, 413, and 426, wherein the TCR specifically binds to an epitope from RAS in complex with a human MHC encoded by an HLA-A11:01 allele.

In some embodiments, the TCR alpha chain construct as described above comprises a complementarity determining region 1 (CDR1) having at least 90% sequence identity to an amino acid sequence selected from SEQ ID NOs: 31, 47, 111, 239, 255, 271, 367, 399, and 415. In some embodiments, the TCR beta chain construct as described above comprises a complementarity determining region 1 (CDR1) having at least 90% sequence identity to an amino acid sequence selected from SEQ ID NOs: 34, 50, 114, 242, 258, 274, 370, 402, and 418. In some embodiments, the TCR alpha chain construct comprises a complementarity determining region 2 (CDR2) having at least 90% sequence identity to an amino acid sequence selected from SEQ ID NOs: 32, 48, 112, 240, 256, 272, 368, 400, and 416. In some embodiments, the TCR beta chain construct comprises a complementarity determining region 2 (CDR2) having at least 90% sequence identity to an amino acid sequence selected from SEQ ID NOs: 35, 51, 115, 243, 259, 275, 371, 403, and 419. In some embodiments, the TCR alpha chain construct comprises a complementarity determining region 3 (CDR3) having at least 90% sequence identity to an amino acid sequence selected from SEQ ID NOs: 33, 49, 113, 241, 257, 273, 369, 401, 417, and 433. In some embodiments, the TCR beta chain construct comprises a complementarity determining region 3 (CDR3) having at least 90% sequence identity to an amino acid sequence selected from SEQ ID NOs: 36, 52, 116, 244, 260, 276, 372, 404, and 420. In some embodiments, the TCR alpha chain construct comprises a variable region having at least 80% sequence identity to SEQ ID NO: 9; and the TCR beta chain construct comprises a variable region having at least 80% sequence identity to SEQ ID NO: 12. In some embodiments, the TCR alpha chain construct comprises a CDR1 of SEQ ID NO: 1, a CDR2 of SEQ ID NO: 2, and a CDR3 of SEQ ID NO: 3; and the TCR beta chain construct comprises a CDR1 of SEQ ID NO: 4, a CDR2 of SEQ ID NO: 5, and a CDR3 of SEQ ID NO: 6. In some embodiments, the TCR comprises an alpha chain having a sequence of SEQ ID NO: 13, or a sequence that has at least 80% identity to SEQ ID NO: 13. In some embodiments, the TCR comprises a beta chain having a sequence of SEQ ID NO: 14 or a sequence that has at least 80% identity to SEQ ID NO: 14 In some embodiments, the TCR alpha chain construct comprises a variable region having at least 80% sequence identity to SEQ ID NO: 24; and the TCR beta chain construct comprises a variable region having at least 80% sequence identity to SEQ ID NO: 27. In some embodiments, the TCR alpha chain construct comprises a CDR1 of SEQ ID NO: 16, a CDR2 of SEQ ID NO: 17, and a CDR3 of SEQ ID NO: 18; and the TCR beta chain construct comprises a CDR1 of SEQ ID NO: 19, a CDR2 of SEQ ID NO: 20, and a CDR3 of SEQ ID NO: 21. In some embodiments, the TCR comprises an alpha chain having a sequence of SEQ ID NO: 28, or a sequence that has at least 80% identity to SEQ ID NO: 28. In some embodiments, the TCR comprises a beta chain having a sequence of SEQ ID NO: 29 or a sequence that has at least 80% identity to SEQ ID NO: 29. In some embodiments, the TCR alpha chain construct comprises a variable region having at least 80% sequence identity to SEQ ID NO: 39; and the TCR beta chain construct comprises a variable region having at least 80% sequence identity to SEQ ID NO: 42. In some embodiments, the TCR alpha chain construct comprises a CDR1 of SEQ ID NO: 31, a CDR2 of SEQ ID NO: 32, and a CDR3 of SEQ ID NO: 33; and the TCR beta chain construct comprises a CDR1 of SEQ ID NO: 34, a CDR2 of SEQ ID NO: 35, and a CDR3 of SEQ ID NO: 36. In some embodiments, the TCR comprises an alpha chain having a sequence of SEQ ID NO: 43, or a sequence that has at least 80% identity to SEQ ID NO: 43. In some embodiments, the TCR comprises a beta chain having a sequence of SEQ ID NO: 44 or a sequence that has at least 80% identity to SEQ ID NO: 44. In some embodiments, the TCR alpha chain construct comprises a variable region having at least 80% sequence identity to SEQ ID NO: 55; and the TCR beta chain construct comprises a variable region having at least 80% sequence identity to SEQ ID NO: 58. In some embodiments, the TCR alpha chain construct comprises a CDR1 of SEQ ID NO: 47, a CDR2 of SEQ ID NO: 48, and a CDR3 of SEQ ID NO: 49; and the TCR beta chain construct comprises a CDR1 of SEQ ID NO: 50, a CDR2 of SEQ ID NO: 51, and a CDR3 of SEQ ID NO: 52. In some embodiments, the TCR alpha chain construct comprises a variable region having at least 80% sequence identity to SEQ ID NO: 71; and the TCR beta chain construct comprises a variable region having at least 80% sequence identity to SEQ ID NO: 74. In some embodiments, the TCR alpha chain construct comprises a CDR1 of SEQ ID NO: 63, a CDR2 of SEQ ID NO: 64, and a CDR3 of SEQ ID NO: 65; and the TCR beta chain construct comprises a CDR1 of SEQ ID NO: 66, a CDR2 of SEQ ID NO: 67, and a CDR3 of SEQ ID NO: 68. In some embodiments, the TCR comprises an alpha chain having a sequence of SEQ ID NO: 75, or a sequence that has at least 80% identity to SEQ ID NO: 75. In some embodiments, the TCR comprises a beta chain having a sequence of SEQ ID NO: 76 or a sequence that has at least 80% identity to SEQ ID NO: 76. In some embodiments, the TCR alpha chain construct comprises a variable region having at least 80% sequence identity to SEQ ID NO: 87; and the TCR beta chain construct comprises a variable region having at least 80% sequence identity to SEQ ID NO: 90. In some embodiments, the TCR alpha chain construct comprises a CDR1 of SEQ ID NO: 79, a CDR2 of SEQ ID NO: 80, and a CDR3 of SEQ ID NO: 81; and the TCR beta chain construct comprises a CDR1 of SEQ ID NO: 82, a CDR2 of SEQ ID NO: 83, and a CDR3 of SEQ ID NO: 84. In some embodiments, the TCR comprises an alpha chain having a sequence of SEQ ID NO: 91, or a sequence that has at least 80% identity to SEQ ID NO: 91. In some embodiments, the TCR comprises a beta chain having a sequence of SEQ ID NO: 92 or a sequence that has at least 80% identity to SEQ ID NO: 92. In some embodiments, the TCR alpha chain construct comprises a variable region having at least 80% sequence identity to SEQ ID NO: 103; and the TCR beta chain construct comprises a variable region having at least 80% sequence identity to SEQ ID NO: 106. In some embodiments, the TCR alpha chain construct comprises a CDR1 of SEQ ID NO: 95, a CDR2 of SEQ ID NO: 96, and a CDR3 of SEQ ID NO: 97; and the TCR beta chain construct comprises a CDR1 of SEQ ID NO: 98, a CDR2 of SEQ ID NO: 99, and a CDR3 of SEQ ID NO: 100. In some embodiments, the TCR comprises an alpha chain having a sequence of SEQ ID NO: 107, or a sequence that has at least 80% identity to SEQ ID NO: 107. In some embodiments, the TCR comprises a beta chain having a sequence of SEQ ID NO: 108 or a sequence that has at least 80% identity to SEQ ID NO: 108. In some embodiments, the TCR alpha chain construct comprises a variable region having at least 80% sequence identity to SEQ ID NO: 119; and the TCR beta chain construct comprises a variable region having at least 80% sequence identity to SEQ ID NO: 122. In some embodiments, the TCR alpha chain construct comprises a CDR1 of SEQ ID NO: 111, a CDR2 of SEQ ID NO: 112, and a CDR3 of SEQ ID NO: 113; and the TCR beta chain construct comprises a CDR1 of SEQ ID NO: 114, a CDR2 of SEQ ID NO: 115, and a CDR3 of SEQ ID NO: 116. In some embodiments, the TCR comprises an alpha chain having a sequence of SEQ ID NO: 123, or a sequence that has at least 80% identity to SEQ ID NO: 123. In some embodiments, the TCR comprises a beta chain having a sequence of SEQ ID NO: 124 or a sequence that has at least 80% identity to SEQ ID NO: 124. In some embodiments, the TCR alpha chain construct comprises a variable region having at least 80% sequence identity to SEQ ID NO: 247; and the TCR beta chain construct comprises a variable region having at least 80% sequence identity to SEQ ID NO: 250. In some embodiments, the TCR alpha chain construct comprises a CDR1 of SEQ ID NO: 239, a CDR2 of SEQ ID NO: 240, and a CDR3 of SEQ ID NO: 241; and the TCR beta chain construct comprises a CDR1 of SEQ ID NO: 242, a CDR2 of SEQ ID NO: 243, and a CDR3 of SEQ ID NO: 244. In some embodiments, the TCR comprises an alpha chain having a sequence of SEQ ID NO: 251, or a sequence that has at least 80% identity to SEQ ID NO: 251. In some embodiments, the TCR comprises a beta chain having a sequence of SEQ ID NO: 252 or a sequence that has at least 80% identity to SEQ ID NO: 252. In some embodiments, the TCR alpha chain construct comprises a variable region having at least 80% sequence identity to SEQ ID NO: 263; and the TCR beta chain construct comprises a variable region having at least 80% sequence identity to SEQ ID NO: 266. In some embodiments, the TCR alpha chain construct comprises a CDR1 of SEQ ID NO: 255, a CDR2 of SEQ ID NO: 256, and a CDR3 of SEQ ID NO: 257; and the TCR beta chain construct comprises a CDR1 of SEQ ID NO: 258, a CDR2 of SEQ ID NO: 259, and a CDR3 of SEQ ID NO: 260. In some embodiments, the TCR comprises an alpha chain having a sequence of SEQ ID NO: 267, or a sequence that has at least 80% identity to SEQ ID NO: 267. In some embodiments, the TCR comprises a beta chain having a sequence of SEQ ID NO: 268 or a sequence that has at least 80% identity to SEQ ID NO: 268. In some embodiments, the TCR alpha chain construct comprises a variable region having at least 80% sequence identity to SEQ ID NO: 279; and the TCR beta chain construct comprises a variable region having at least 80% sequence identity to SEQ ID NO: 282. In some embodiments, the TCR alpha chain construct comprises a CDR1 of SEQ ID NO: 271, a CDR2 of SEQ ID NO: 272, and a CDR3 of SEQ ID NO: 273; and the TCR beta chain construct comprises a CDR1 of SEQ ID NO: 274, a CDR2 of SEQ ID NO: 275, and a CDR3 of SEQ ID NO: 276. In some embodiments, the TCR comprises an alpha chain having a sequence of SEQ ID NO: 283, or a sequence that has at least 80% identity to SEQ ID NO: 283. In some embodiments, the TCR comprises a beta chain having a sequence of SEQ ID NO: 284 or a sequence that has at least 80% identity to SEQ ID NO: 284. In some embodiments, the TCR alpha chain construct comprises a variable region having at least 80% sequence identity to SEQ ID NO: 295; and the TCR beta chain construct comprises a variable region having at least 80% sequence identity to SEQ ID NO: 298. In some embodiments, the TCR alpha chain construct comprises a CDR1 of SEQ ID NO: 287, a CDR2 of SEQ ID NO: 288, and a CDR3 of SEQ ID NO: 289; and the TCR beta chain construct comprises a CDR1 of SEQ ID NO: 290, a CDR2 of SEQ ID NO: 291, and a CDR3 of SEQ ID NO: 292. In some embodiments, the TCR comprises an alpha chain having a sequence of SEQ ID NO: 299, or a sequence that has at least 80% identity to SEQ ID NO: 299. In some embodiments, the TCR comprises a beta chain having a sequence of SEQ ID NO: 300 or a sequence that has at least 80% identity to SEQ ID NO: 300. In some embodiments, the TCR alpha chain construct comprises a variable region having at least 80% sequence identity to SEQ ID NO: 311; and the TCR beta chain construct comprises a variable region having at least 80% sequence identity to SEQ ID NO: 314. In some embodiments, the TCR alpha chain construct comprises a CDR1 of SEQ ID NO: 303, a CDR2 of SEQ ID NO: 304, and a CDR3 of SEQ ID NO: 305; and the TCR beta chain construct comprises a CDR1 of SEQ ID NO: 306, a CDR2 of SEQ ID NO: 307, and a CDR3 of SEQ ID NO: 308. In some embodiments, the TCR comprises an alpha chain having a sequence of SEQ ID NO: 315, or a sequence that has at least 80% identity to SEQ ID NO: 315. In some embodiments, the TCR comprises a beta chain having a sequence of SEQ ID NO: 316 or a sequence that has at least 80% identity to SEQ ID NO: 316. In some embodiments, the TCR alpha chain construct comprises a variable region having at least 80% sequence identity to SEQ ID NO: 327; and the TCR beta chain construct comprises a variable region having at least 80% sequence identity to SEQ ID NO: 330. In some embodiments, the TCR alpha chain construct comprises a CDR1 of SEQ ID NO: 319, a CDR2 of SEQ ID NO: 320, and a CDR3 of SEQ ID NO: 321; and the TCR beta chain construct comprises a CDR1 of SEQ ID NO: 322, a CDR2 of SEQ ID NO: 323, and a CDR3 of SEQ ID NO: 324. In some embodiments, the TCR comprises an alpha chain having a sequence of SEQ ID NO: 331, or a sequence that has at least 80% identity to SEQ ID NO: 331. In some embodiments, the TCR comprises a beta chain having a sequence of SEQ ID NO: 332 or a sequence that has at least 80% identity to SEQ ID NO: 332. In some embodiments, the TCR alpha chain construct comprises a variable region having at least 80% sequence identity to SEQ ID NO: 343; and the TCR beta chain construct comprises a variable region having at least 80% sequence identity to SEQ ID NO: 346. In some embodiments, the TCR alpha chain construct comprises a CDR1 of SEQ ID NO: 335, a CDR2 of SEQ ID NO: 336, and a CDR3 of SEQ ID NO: 337; and the TCR beta chain construct comprises a CDR1 of SEQ ID NO: 338, a CDR2 of SEQ ID NO: 339, and a CDR3 of SEQ ID NO: 340. In some embodiments, the TCR comprises an alpha chain having a sequence of SEQ ID NO: 347, or a sequence that has at least 80% identity to SEQ ID NO: 347. In some embodiments, the TCR comprises a beta chain having a sequence of SEQ ID NO: 348 or a sequence that has at least 80% identity to SEQ ID NO: 348. In some embodiments, the TCR alpha chain construct comprises a variable region having at least 80% sequence identity to SEQ ID NO: 359; and the TCR beta chain construct comprises a variable region having at least 80% sequence identity to SEQ ID NO: 362. In some embodiments, the TCR alpha chain construct comprises a CDR1 of SEQ ID NO: 351, a CDR2 of SEQ ID NO: 352, and a CDR3 of SEQ ID NO: 353; and the TCR beta chain construct comprises a CDR1 of SEQ ID NO: 354, a CDR2 of SEQ ID NO: 355, and a CDR3 of SEQ ID NO: 356. In some embodiments, the TCR comprises an alpha chain having a sequence of SEQ ID NO: 363, or a sequence that has at least 80% identity to SEQ ID NO: 363. In some embodiments, the TCR comprises a beta chain having a sequence of SEQ ID NO: 364 or a sequence that has at least 80% identity to SEQ ID NO: 364. In some embodiments, the TCR alpha chain construct comprises a variable region having at least 80% sequence identity to SEQ ID NO: 375; and the TCR beta chain construct comprises a variable region having at least 80% sequence identity to SEQ ID NO: 378. In some embodiments, the TCR alpha chain construct comprises a CDR1 of SEQ ID NO: 367, a CDR2 of SEQ ID NO: 368, and a CDR3 of SEQ ID NO: 369; and the TCR beta chain construct comprises a CDR1 of SEQ ID NO: 370, a CDR2 of SEQ ID NO: 371, and a CDR3 of SEQ ID NO: 372. In some embodiments, the TCR comprises an alpha chain having a sequence of SEQ ID NO: 379, or a sequence that has at least 80% identity to SEQ ID NO: 379. In some embodiments, the TCR comprises a beta chain having a sequence of SEQ ID NO: 380 or a sequence that has at least 80% identity to SEQ ID NO: 380. In some embodiments, the TCR alpha chain construct comprises a variable region having at least 80% sequence identity to SEQ ID NO: 391; and the TCR beta chain construct comprises a variable region having at least 80% sequence identity to SEQ ID NO: 394. In some embodiments, the TCR alpha chain construct comprises a CDR1 of SEQ ID NO: 383, a CDR2 of SEQ ID NO: 384, and a CDR3 of SEQ ID NO: 385; the TCR beta chain construct comprises a CDR1 of SEQ ID NO: 386, a CDR2 of SEQ ID NO: 387, and a CDR3 of SEQ ID NO: 388. In some embodiments, the TCR comprises an alpha chain having a sequence of SEQ ID NO: 395, or a sequence that has at least 80% identity to SEQ ID NO: 395. In some embodiments, the TCR comprises a beta chain having a sequence of SEQ ID NO: 396 or a sequence that has at least 80% identity to SEQ ID NO: 396. In some embodiments, the TCR alpha chain construct comprises a variable region having at least 80% sequence identity to SEQ ID NO: 407; and the TCR beta chain construct comprises a variable region having at least 80% sequence identity to SEQ ID NO: 410. In some embodiments, the TCR alpha chain construct comprises a CDR1 of SEQ ID NO: 399, a CDR2 of SEQ ID NO: 400, and a CDR3 of SEQ ID NO: 401; and the TCR beta chain construct comprises a CDR1 of SEQ ID NO: 402, a CDR2 of SEQ ID NO: 403, and a CDR3 of SEQ ID NO: 404. In some embodiments, the TCR comprises an alpha chain having a sequence of SEQ ID NO: 411, or a sequence that has at least 80% identity to SEQ ID NO: 411. In some embodiments, the TCR comprises a beta chain having a sequence of SEQ ID NO: 412 or a sequence that has at least 80% identity to SEQ ID NO: 412. In some embodiments, the TCR alpha chain construct comprises a variable region having at least 80% sequence identity to SEQ ID NO: 423; and the TCR beta chain construct comprises a variable region having at least 80% sequence identity to SEQ ID NO: 426. In some embodiments, the TCR alpha chain construct comprises a CDR1 of SEQ ID NO: 415, a CDR2 of SEQ ID NO: 416, and a CDR3 of SEQ ID NO: 417; and the TCR beta chain construct comprises a CDR1 of SEQ ID NO: 418, a CDR2 of SEQ ID NO: 419, and a CDR3 of SEQ ID NO: 420. In some embodiments, the TCR comprises an alpha chain having a sequence of SEQ ID NO: 427, or a sequence that has at least 80% identity to SEQ ID NO: 427. In some embodiments, the TCR comprises a beta chain having a sequence of SEQ ID NO: 428 or a sequence that has at least 80% identity to SEQ ID NO: 428. In some embodiments, the TCR alpha chain construct comprises a variable region having at least 80% sequence identity to SEQ ID NO: 391; and the TCR beta chain construct comprises a variable region having at least 80% sequence identity to SEQ ID NO: 394.

Provided herein is a nucleic acid encoding at least one T cell receptor (TCR) comprising a TCR alpha chain construct and/or TCR beta chain construct capable of specifically binding to an epitope from TMPRSS2:ERG in complex with a human MHC, wherein the TCR alpha chain construct and/or the TCR beta chain construct comprises a complementarity determining region 3 (CDR3) having a sequence of SEQ ID NO: 144 and SEQ ID NO: 147 or a sequence having at least 90% sequence identity to an amino acid sequence selected from SEQ ID NO: 144 and SEQ ID NO: 147. In some embodiments, the TCR comprises an alpha chain having a sequence of SEQ ID NO: 154, or a sequence that has at least 80% identity to SEQ ID NO: 154. In some embodiments, the TCR comprises a beta chain having a sequence of SEQ ID NO: 155 or a sequence that has at least 80% identity to SEQ ID NO: 155.

Provided herein is a nucleic acid encoding at least one T cell receptor (TCR) comprising a TCR alpha chain construct and/or TCR beta chain construct capable of specifically binding to an epitope from TMPRSS2:ERG in complex with a human MHC, wherein the epitope from TMPRSS2:ERG comprises a region having at least 90% sequence identity to amino acid sequence SEQ ID NO: 156.

In some embodiments, the TCR alpha chain construct comprises a variable region having at least 80% sequence identity to SEQ ID NO: 150. In some embodiments, the TCR beta chain construct comprises a variable region having at least 80% sequence identity to SEQ ID NO: 153. In some embodiments, the TCR alpha chain construct and/or the TCR beta chain construct comprises a complementarity determining region 1 (CDR1) having a sequence of SEQ ID NO: 142 or a sequence having at least 90% sequence identity to SEQ ID NO: 142 and a sequence of SEQ ID NO: 145 or a sequence having at least 90% sequence identity to SEQ ID NO: 145 respectively. In some embodiments, the TCR alpha chain construct and/or the TCR beta chain construct comprises a complementarity determining region 2 (CDR2) having at least 90% sequence identity to SEQ ID NO: 143 or SEQ ID NO: 146 respectively. In some embodiments, the TCR alpha chain construct comprises a variable region having a sequence of SEQ ID NO: 150 or at least 80% sequence identity to SEQ ID NO: 150; and the TCR beta chain construct comprises a variable region having a sequence of SEQ ID NO: 153 or at least 80% sequence identity to SEQ ID NO: 153. In some embodiments, the TCR alpha chain construct comprises a CDR1 of SEQ ID NO: 142, a CDR2 of SEQ ID NO: 143, and a CDR3 of SEQ ID NO: 144; and the TCR beta chain construct comprises a CDR1 of SEQ ID NO: 145, a CDR2 of SEQ ID NO: 146, and a CDR3 of SEQ ID NO: 147.

Provided herein is a nucleic acid encoding at least one T cell receptor (TCR) comprising a TCR alpha chain construct and/or TCR beta chain construct capable of specifically binding to an epitope from GATA3 in complex with a human MHC, wherein the TCR alpha chain construct and/or the TCR beta chain construct comprises a complementarity determining region 3 (CDR3) having at least 90% sequence identity to an amino acid sequence selected from SEQ ID NOs: 129, 132, 191, 194, 206 and 209.

Provided herein is a nucleic acid encoding at least one T cell receptor (TCR) capable of specifically binding to a mutant GATA3 peptide in complex with a protein encoded by an HLA allele of a subject with cancer, wherein the TCR comprises a TCR alpha chain construct and/or a TCR beta chain construct.

Provided herein is an isolated nucleic acid or a cell comprising a recombinant nucleic acid, wherein the nucleic acid encodes a T cell receptor (TCR) comprising a TCR alpha chain construct and/or a TCR beta chain construct, wherein the TCR specifically binds to a mutant GATA3 peptide in complex with an HLA-A02:01, HLA-B07:02 or HLA-B08:01 protein; comprises a complementarity determining region 3 (CDR3) having at least 90% sequence identity to SEQ ID NOs: 129, 132, 191, 194, 206 or 209; and/or specifically binds to a mutant GATA3 peptide comprising a region having a sequence of or having a sequence with at least 70% sequence identity to SEQ ID NO: 141, 203 or 218.

Provided herein is a nucleic acid encoding at least one T cell receptor (TCR) comprising a TCR alpha chain construct and/or TCR beta chain construct capable of specifically binding to an epitope from GATA3 in complex with a human MHC, wherein the epitope from GATA3 comprises a region having at least 90% sequence identity to amino acid sequence SEQ ID NO: 141, 203 or 218.

In some embodiments, the TCR alpha chain construct comprises a variable region having a sequence of SEQ ID NO: 135, 197 or 212; or a sequence with at least 80% sequence identity to SEQ ID NO: 135, 197 or 212. In some embodiments, the TCR beta chain construct comprises a variable region having a sequence of SEQ ID NO: 138, 200 or 215; or a sequence having at least 80% sequence identity to SEQ ID NO: 138, 200 or 215. In some embodiments, the TCR alpha chain construct and/or the TCR beta chain construct comprises a complementarity determining region 1 (CDR1) having an amino acid sequence of, having or at least 90% sequence identity to an amino acid sequence selected from SEQ ID NOs: 127, 130, 189, 192, 204 and 207. In some embodiments, the TCR alpha chain construct and/or the TCR beta chain construct comprises a complementarity determining region 2 (CDR2) having an amino acid sequence of, or having at least 90% sequence identity to an amino acid sequence selected from SEQ ID NOs: 128, 131, 190, 193, 205 and 208. In some embodiments, the GATA3 binding TCR alpha chain comprises a variable region having a sequence of SEQ ID NO: 135, or a sequence having at least 80% identity to SEQ ID NO: 135; and a beta chain having a variable region having a sequence of SEQ ID NO: 138, or a sequence having at least 80% identity to SEQ ID NO: 138. In some embodiments, the TCR alpha chain construct comprises a CDR1 of SEQ ID NO: 127, a CDR2 of SEQ ID NO: 128, and a CDR3 of SEQ ID NO: 129; and the TCR beta chain construct comprises a CDR1 of SEQ ID NO: 130, a CDR2 of SEQ ID NO: 131, and a CDR3 of SEQ ID NO: 132. In some embodiments, the TCR has an alpha chain having a sequence of SEQ ID NO: 139, or a sequence having at least 80% identity to SEQ ID NO: 139. In some embodiments, the TCR has a beta chain having a sequence of SEQ ID NO: 140, or a sequence having at least 80% identity to SEQ ID NO: 140. In some embodiments, the TCR alpha chain construct comprises a variable region having an amino acid sequence of, or having at least 80% sequence identity to SEQ ID NO: 197; and the TCR beta chain construct comprises a variable region having at least 80% sequence identity to SEQ ID NO: 200. In some embodiments the TCR alpha chain has a sequence of SEQ ID NO: 201 or a sequence having at least 80% identity to SEQ ID NO: 201. In some embodiments the TCR beta chain has a sequence of SEQ ID NO: 202 or a sequence having at least 80% identity to SEQ ID NO: 202. In some embodiments, the TCR alpha chain construct comprises a CDR1 of SEQ ID NO: 189, a CDR2 of SEQ ID NO: 190, and a CDR3 of SEQ ID NO: 191; and the TCR beta chain construct comprises a CDR1 of SEQ ID NO: 192, a CDR2 of SEQ ID NO: 193, and a CDR3 of SEQ ID NO: 194. In some embodiments, the TCR alpha chain construct comprises a variable region having at least 80% sequence identity to SEQ ID NO: 212; and the TCR beta chain construct comprises a variable region having at least 80% sequence identity to SEQ ID NO: 215. In some embodiments, the TCR alpha chain construct comprises a CDR1 of SEQ ID NO: 204, a CDR2 of SEQ ID NO: 205, and a CDR3 of SEQ ID NO: 206; and the TCR beta chain construct comprises a CDR1 of SEQ ID NO: 207, a CDR2 of SEQ ID NO: 208, and a CDR3 of SEQ ID NO: 209. In some embodiments, the TCR comprises of an alpha chain having a sequence of SEQ ID NO: 216 or a sequence having at least 80% identity to SEQ ID NO: 216. In some embodiments, the TCR comprises of a beta chain having a sequence of SEQ ID NO: 217 or a sequence having at least 80% identity to SEQ ID NO: 217.

Provided herein is a nucleic acid encoding at least one T cell receptor (TCR) comprising a TCR alpha chain construct and/or TCR beta chain construct capable of specifically binding to an epitope from BTK in complex with a human MHC, wherein the TCR alpha chain construct comprises a complementarity determining region 3 (CDR3) having at least 90% sequence identity to an amino acid sequence selected from SEQ ID NO: 161 and SEQ ID NO: 176, or wherein the TCR beta chain construct comprises a complementarity determining region 3 (CDR3) having at least 90% sequence identity to an amino acid sequence selected from SEQ ID NO: 164 and SEQ ID NO: 179.

Provided herein is a nucleic acid encoding at least one T cell receptor (TCR) capable of specifically binding to a mutant BTK peptide in complex with a protein encoded by an HLA allele of a subject with cancer, wherein the TCR comprises a TCR alpha chain construct and/or a TCR beta chain construct.

Provided herein is an isolated nucleic acid or a cell comprising a recombinant nucleic acid, wherein the nucleic acid encodes a T cell receptor (TCR) comprising a TCR alpha chain construct and/or a TCR beta chain construct, wherein the TCR specifically binds to a mutant BTK peptide in complex with an HLA-A02:01 protein; comprises a complementarity determining region 3 (CDR3) having at least 90% sequence identity to SEQ ID NO: 161, 164, 176, or 179; and/or specifically binds to a mutant BTK peptide comprising a region with at least 70% sequence identity to SEQ ID NO: 173 or 188.

Provided herein is a nucleic acid encoding at least one T cell receptor (TCR) comprising a TCR alpha chain construct and/or TCR beta chain construct capable of specifically binding to an epitope from BTK in complex with a human MHC, wherein the epitope from BTK comprises a region having at least 90% sequence identity to amino acid sequence SEQ ID NO: 173 or 188.

In some embodiments, the TCR alpha chain construct comprises a variable region having at least 80% sequence identity to SEQ ID NO: 167 or 182. In some embodiments, the TCR beta chain construct comprises a variable region having at least 80% sequence identity to SEQ ID NO: 170 or 185. In some embodiments, the TCR alpha chain construct and/or the TCR beta chain construct comprises a complementarity determining region 1 (CDR1) having at least 90% sequence identity to an amino acid sequence selected from SEQ ID NOs: 159, 162, 174, and 177. In some embodiments, the TCR alpha chain construct and/or the TCR beta chain construct comprises a complementarity determining region 2 (CDR2) having at least 90% sequence identity to an amino acid sequence selected from SEQ ID NOs: 160, 163, 175 and 178. In some embodiments, the TCR alpha chain construct comprises a variable region having at least 80% sequence identity to SEQ ID NO: 167 or 182; and the TCR beta chain construct comprises a variable region having at least 80% sequence identity to SEQ ID NO: 170 or 185. In some embodiments, the TCR alpha chain construct comprises a CDR1 of SEQ ID NO: 159 or 174, a CDR2 of SEQ ID NO: 160 or 175, and a CDR3 of SEQ ID NO: 161 or 176; and the TCR beta chain construct comprises a CDR1 of SEQ ID NO: 162 or 177, a CDR2 of SEQ ID NO: 163 or 178, and a CDR3 of SEQ ID NO: 164 or 179.

Provided herein is a nucleic acid encoding at least one T cell receptor (TCR) comprising a TCR alpha chain construct and/or TCR beta chain construct capable of specifically binding to an epitope from EGFR in complex with a human MHC, wherein the TCR alpha chain construct comprises a complementarity determining region 3 (CDR3) having at least 90% sequence identity to an amino acid sequence selected from SEQ ID NO: 449, SEQ ID NO: 466, SEQ ID NO: 483, SEQ ID NO: 500, and SEQ ID NO: 517, or wherein the TCR beta chain construct comprises a complementarity determining region 3 (CDR3) having at least 90% sequence identity to an amino acid sequence selected from SEQ ID NO: 452, SEQ ID NO: 469, SEQ ID NO: 486, SEQ ID NO: 503, and SEQ ID NO: 520.

Provided herein is a nucleic acid encoding at least one T cell receptor (TCR) capable of specifically binding to a mutant EGFR peptide in complex with a protein encoded by an HLA allele of a subject with cancer, wherein the TCR comprises a TCR alpha chain construct and/or a TCR beta chain construct.

Provided herein is an isolated nucleic acid or a cell comprising a recombinant nucleic acid, wherein the nucleic acid encodes a T cell receptor (TCR) comprising a TCR alpha chain construct and/or a TCR beta chain construct, wherein the TCR specifically binds to a mutant EGFR peptide in complex with an HLA-A02:01 protein; comprises a complementarity determining region 3 (CDR3) having a sequence of, or a sequence having at least 90% sequence identity to SEQ ID NO: 449, 466, 483, 500, 517, 452, 469, 486, 503, or 520; and/or specifically binds to a mutant EGFR peptide comprising a region having a sequence of, or having a sequence with at least 70% sequence identity to SEQ ID NO: 461, 462, 463, 478, 479, 480, 495, 496, 497, 512, 513, 514, 529, 530 or 531.

Provided herein is a nucleic acid encoding at least one T cell receptor (TCR) comprising a TCR alpha chain construct and/or TCR beta chain construct capable of specifically binding to an epitope from EGFR in complex with a human MHC, wherein the epitope from EGFR comprises a region having at least 90% sequence identity to amino acid sequence SEQ ID NO: 461, 462, 463, 478, 479, 480, 495, 496, 497, 512, 513, 514, 529, 530 or 531.

In some embodiments, the TCR alpha chain construct comprises a variable region having a sequence of, or a sequence having at least 80% sequence identity to SEQ ID NO: 449, 466, 483, 500 or 517. In some embodiments, the TCR beta chain construct comprises a variable region having a sequence of, or a sequence having at least 80% sequence identity to SEQ ID NO: 452, 469, 486, 503, or 520. In some embodiments, the TCR alpha chain construct and/or the TCR beta chain construct comprises a complementarity determining region 1 (CDR1) having a sequence of, or a sequence having at least 90% sequence identity to an amino acid sequence selected from SEQ ID NOs: 447, 464, 481, 498, 515, 450, 467, 484, 501, and 518. In some embodiments, the TCR alpha chain construct and/or the TCR beta chain construct comprises a complementarity determining region 2 (CDR2) having a sequence of, or a sequence having at least 90% sequence identity to an amino acid sequence selected from SEQ ID NOs: 448, 465, 482, 499, 516, 451, 468, 485, 502, and 519. In some embodiments, the TCR alpha chain construct comprises a variable region having a sequence of, or a sequence having at least 80% sequence identity to SEQ ID NO: 455, 472, 489, 506, or 523; and the TCR beta chain construct comprises a variable region having a sequence of, or a sequence having at least 80% sequence identity to SEQ ID NO: 458, 475, 492, 509 or 526. In some embodiments, the TCR alpha chain construct comprises a CDR1 of SEQ ID NO: 447, 464, 481, 498 or 515, a CDR2 of SEQ ID NO: 448, 465, 482, 499 or 516, and a CDR3 of SEQ ID NO: 449, 466, 483, 500 or 517; and the TCR beta chain construct comprises a CDR1 of SEQ ID NO: 450, 467, 484, 501 or 518, a CDR2 of SEQ ID NO: 451, 468, 485, 502, or 519, and a CDR3 of SEQ ID NO: 452, 469, 486, 503, or 520.

In some embodiments, the epitope comprises a mutation selected from the group consisting of a point mutation, a splice-site mutation, a frameshift mutation, a read-through mutation, a resistance mutation, a gene fusion mutation and any combination thereof. In some embodiments, the human MHC is encoded by either HLA-A02:01 allele, or HLA-A03:01 allele or HLA-A11:01 allele. In some embodiments, the RAS epitope comprises a point mutation. In some embodiments, the point mutation is a G12V mutation. In some embodiments, the point mutation is a G12C mutation. In some embodiments, the point mutation is a G12D mutation. In some embodiments, the human MHC is encoded by HLA-A02:01 allele. In some embodiments, the TMPRSS2:ERG epitope comprises a gene fusion mutation. In some embodiments, the human MHC is encoded by HLA-A02:01, HLA-B07:02 or HLA-B08:01 allele. In some embodiments, the epitope comprises a frameshift mutation. In some embodiments, the human MHC is encoded by HLA-A02:01 allele. In some embodiments, the BTK epitope comprises a point mutation. In some embodiments, the point mutation is C481S mutation. In some embodiments, the human MHC is encoded by HLA-A02:01 allele. In some embodiments, the EGFR epitope comprises a point mutation. In some embodiments, the point mutation is T790M.

In some embodiments, the epitope has a length of at least 8 amino acids. In some embodiments, the epitope has a length of at least 16 amino acids. In some embodiments, the epitope has a length of from 8-25 amino acids. In some embodiments, the epitope has a length of from 8-12 amino acids. In some embodiments, the epitope has a length of from 16-25 amino acids. In some embodiments, the epitope has a length of 7, 8, 9, 10, 11, 12, 13, 14, 15, 16, 17, 18, 19, 20, 21, 22, 23, 24, or 25 amino acids.

In some embodiments, the epitope binds to the human MHC with a greater affinity than a corresponding wild-type epitope. In some embodiments, the epitope binds to the human MHC with a $K_D$ or an $IC_{50}$ less than 500 nM, 250 nM, 150 nM, 100 nM, 50 nM, 25 nM or 10 nM.

In some embodiments, the mutation is not present in non-cancer cells of a subject. In some embodiments, the epitope is encoded by a gene or an expressed gene of a subject's cancer cells.

In some embodiments, the TCR binds to a MHC-peptide complex with a $K_D$ or an $IC_{50}$ of less than 500 nM, 250 nM, 150 nM, 100 nM, 50 nM, 25 nM or 10 nM.

In some embodiments, the nucleic acid is operably linked to a promoter.

Provided herein is a vector comprising a nucleic acid described herein. In some embodiments, the vector is a self-amplifying RNA replicon, plasmid, phage, transposon, cosmid, virus, or virion. In some embodiments, wherein the vector is a viral vector. In some embodiments, wherein the vector is derived from a retrovirus, lentivirus, adenovirus, adeno-associated virus, herpes virus, pox virus, alpha virus, vaccinia virus, hepatitis B virus, human papillomavirus or a pseudotype thereof. In some embodiments, the vector is a non-viral vector. In some embodiments, the non-viral vector is a nanoparticle, a cationic lipid, a cationic polymer, a metallic nanopolymer, a nanorod, a liposome, a micelle, a microbubble, a cell-penetrating peptide, or a liposphere.

Provided herein is a protein encoded by the nucleic acid of any one sections described above.

Provided herein is a host cell comprising the nucleic acid described above, the vector of described above, or the protein described above. In some embodiments, the host cell is a $CD4^+$ T cell. In some embodiments, the host cell is a $CD8^+$ T cell. In some embodiments, the host cell is an autologous cell. In some embodiments, the host cell is an allogeneic cell. In some embodiments, the host cell is a natural killer cell, a B cell, or an immortalized cell line. In some embodiments, the host cell is a human cell.

Provided herein is a pharmaceutical composition comprising a nucleic acid described herein, a vector described herein, a protein described herein, or a host cell described herein; and a pharmaceutically acceptable excipient or diluent. In some embodiments, the pharmaceutical composition further comprises an immunomodulatory agent or an adjuvant. In some embodiments, the immunomodulatory agent in the pharmaceutical composition is a cytokine. In some embodiments, the adjuvant in the pharmaceutical composition is poly I:C. In some embodiments, the pharmaceutical compositions are for use in treating an immune disease or cancer.

Provided herein is the use of the pharmaceutical composition described above, for treating an immune disease or cancer.

Provided herein is a vector described herein, a protein described herein, or a host cell described herein for manufacture of a medicament for treating an immune disease or cancer. In some embodiments, the medicament is an adoptive T cell therapy or a TCR gene therapy.

Provided herein is a method of treating a subject with a disease or condition, comprising administering to the subject a pharmaceutical composition disclosed herein.

Provided herein is a method of treating a subject with cancer, comprising administering to the subject a pharmaceutical composition disclosed herein.

Provided herein is a method of treating a subject with cancer comprising administering to the subject a pharmaceutical composition In some embodiments, wherein the subject is identified as expressing or expresses a protein encoded by an HLA-A02:01 allele, an HLA-B07:02, an HLA-B08:01, an HLA-A03:01 allele, an HLA-A11:01 allele, an HLA-A03:02 allele, an HLA-A30:01 allele, an HLA-A31:01 allele, an HLA-A33:01 allele, an HLA-A33:03 allele, an HLA-A68:01 allele, or an HLA-A74:01 allele of the subject's genome.

Provided herein is a method of treating a subject with cancer comprising administering a TCR or T cell expressing the TCR to the subject, wherein the TCR specifically binds to a mutant RAS peptide in complex with a protein encoded by an HLA-A02:01, an HLA-A03:01 allele, an HLA-A11:01 allele, an HLA-A03:02 allele, an HLA-A30:01 allele, an HLA-A31:01 allele, an HLA-A33:01 allele, an HLA-A33:03 allele, an HLA-A68:01 allele, or an HLA-A74:01; wherein the subject is identified as expressing or expresses a protein encoded by an HLA-A03:01 allele, an HLA-A11:01 allele, an HLA-A03:02 allele, an HLA-A30:01 allele, an HLA-A31:01 allele, an HLA-A33:01 allele, an HLA-A33:03 allele, an HLA-A68:01 allele, or an HLA-A74:01 allele, wherein the subject expresses the HLA allele.

Provided herein is a method of treating a subject with cancer comprising administering to the subject a pharmaceutical composition described herein; wherein the TCR binds to a mutant RAS peptide comprising a mutation at G12 in complex with an HLA-A02:01. an HLA-A03:01 allele, an HLA-A11:01 allele, an HLA-A03:02 allele, an HLA-A30:01 allele, an HLA-A31:01 allele, an HLA-A33:01 allele, an HLA-A33:03 allele, an HLA-A68:01 allele, or an HLA-A74:01; wherein the subject is identified as expressing a protein encoded by an HLA-A03:01 allele, an HLA-A11:01 allele, an HLA-A03:02 allele, an HLA-A30:01 allele, an HLA-A31:01 allele, an HLA-A33:01 allele, an HLA-A33:03 allele, an HLA-A68:01 allele, or an HLA-A74:01 allele.

Provided herein is a method of treating a subject with cancer comprising administering to the subject a composition comprising a T cell receptor (TCR) specific for a mutant GATA3 peptide in complex with an HLA protein; wherein the mutant GATA3 peptide comprises at least one mutant amino acid and is fragment of at least 8 contiguous amino acids of a mutant GATA3 protein arising from a mutation in a GATA3 gene of a cancer cell; wherein the mutant GATA3 peptide binds to a protein encoded by an HLA-A02:01, HLA-B07:02 or HLA-B08:01 allele.

Provided herein is a method of treating a subject with cancer comprising administering to the subject a composition comprising a T cell receptor (TCR) specific for a mutant GATA3 peptide in complex with an HLA protein; wherein the mutant GATA3 peptide comprises one or more mutant GATA3 amino acids encoded by a GATA3 neoORF sequence, wherein the mutant GATA3 peptide binds to a protein encoded by an HLA-A02:01, HLA-B07:02 or HLA-B08:01 allele.

Provided herein is a method of treating a subject with cancer comprising administering a TCR or T cell expressing the TCR to the subject; wherein the TCR specifically binds to a mutant GATA3 peptide in complex with a protein encoded by an HLA-A02:01, HLA-B07:02 or HLA-B08:01 allele; wherein the subject is identified as expressing or expresses a protein encoded by an HLA-A02:01, HLA-B07:02 or HLA-B08:01 allele.

Provided herein is a method of treating a subject with cancer comprising administering to the subject a composition comprising a T cell receptor (TCR) specific for a mutant TMPRSS2:ERG peptide in complex with an HLA protein; wherein the mutant TMPRSS2:ERG peptide comprises at least one mutant amino acid and is a fragment of a TMPRSS2:ERG gene fusion mutation; wherein the mutant TMPRSS2:ERG peptide binds to a protein encoded by an HLA-A02:01 allele.

Provided herein is a method of treating a subject with cancer comprising administering to the subject a composition comprising a T cell receptor (TCR) specific for a mutant BTK peptide in complex with an HLA protein; wherein the mutant BTK peptide comprises at least one mutant amino acid; wherein the mutant BTK peptide binds to a protein encoded by an HLA-A02:01 allele.

Provided herein is a method of treating a subject with cancer comprising administering to the subject a composition comprising a T cell receptor (TCR) specific for a mutant BTK peptide in complex with an HLA protein; wherein the mutant BTK peptide comprises a resistance mutation or a point mutation; wherein the mutant BTK peptide binds to a protein encoded by an HLA-A02:01 allele.

Provided herein is a method of treating a subject with cancer comprising administering to the subject a composition comprising a T cell receptor (TCR) specific for a mutant BTK peptide in complex with an HLA protein; wherein the mutant BTK peptide comprises a C481S mutation; wherein the mutant BTK peptide binds to a protein encoded by an HLA-A02:01 allele.

Provided herein is a method of treating a subject with cancer comprising administering to the subject a composition comprising a T cell receptor (TCR) or a T cell expressing the TCR to the subject, wherein the TCR specifically binds to a mutant EGFR peptide in complex with a protein encoded by an HLA-A02:01; wherein the mutant EGFR peptide comprises a resistance mutation or a point mutation, wherein the subject is identified as expressing or expresses a protein encoded by an HLA-A02:01 allele. In some embodiments, the mutant EGFR peptide comprises a T790M mutation.

Provided herein is a method of preventing resistance to a cancer therapy, the method comprising administering to a subject in need thereof a pharmaceutical composition described herein.

Provided herein is a method of inducing an immune response, the method comprising administering to a subject in need thereof a pharmaceutical composition described herein.

Provided herein is a method of identifying a subject with cancer as a candidate for a therapeutic, the method comprising identifying the subject as a subject that expresses a protein encoded by an HLA-A02:01 allele, an HLA-A03:01 allele, an HLA-A11:01 allele, an HLA-A03:02 allele, an HLA-A30:01 allele, an HLA-A31:01 allele, an HLA-A33:01 allele, an HLA-A33:03 allele, an HLA-A68:01 allele, or an HLA-A74:01 allele, wherein the therapeutic is a pharmaceutical composition described herein.

Provided herein is a method of identifying a subject with cancer as a candidate for a therapeutic, the method comprising identifying the subject as one that expresses a protein encoded by an HLA-A02:01, HLA-B07:02 or HLA-B08:01 allele, wherein the therapeutic comprises a T cell receptor (TCR) specific for a mutant GATA3 peptide in complex with an HLA protein; wherein the mutant GATA3 peptide comprises at least one mutant amino acid and is fragment of at least 8 contiguous amino acids of a mutant GATA3 protein arising from a mutation in a GATA3 gene of a cancer cell; wherein the mutant GATA3 peptide binds to a protein encoded by an HLA-A02:01, HLA-B07:02 or HLA-B08:01 allele.

Provided herein is a method of identifying a subject with cancer as a candidate for a therapeutic, the method comprising identifying the subject as one that expresses a protein encoded by an HLA-A03:01 allele, an HLA-A11:01 allele, an HLA-A03:02 allele, an HLA-A30:01 allele, an HLA-A31:01 allele, an HLA-A33:01 allele, an HLA-A33:03 allele, an HLA-A68:01 allele, or an HLA-A74:01 allele, wherein the therapeutic comprises a T cell receptor (TCR) specific for a mutant RAS peptide comprising a mutation at G12 in complex with an HLA protein; wherein the mutant RAS peptide binds to a protein encoded by an HLA-A03:01 allele, an HLA-A11:01 allele, an HLA-A03:02 allele, an HLA-A30:01 allele, an HLA-A31:01 allele, an HLA-A33:01 allele, an HLA-A33:03 allele, an HLA-A68:01 allele, or an HLA-A74:01 allele.

Provided herein is a method of identifying a subject with cancer as a candidate for a therapeutic, the method comprising identifying the subject as one that expresses a protein encoded by an HLA-A02:01 allele, wherein the therapeutic comprises a T cell receptor (TCR) specific for a mutant TMPRSS2:ERG peptide in complex with an HLA protein; wherein the mutant TMPRSS2:ERG peptide comprises at least one mutant amino acid and is a fragment of a TMPRSS2:ERG gene fusion mutation; wherein the mutant TMPRSS2:ERG peptide binds to a protein encoded by an HLA-A02:01 allele.

Provided herein is a method of identifying a subject with cancer as a candidate for a therapeutic, the method comprising identifying the subject as one that expresses a protein encoded by an HLA-A02:01 allele, wherein the therapeutic comprises a T cell receptor (TCR) specific for a mutant BTK peptide in complex with an HLA protein; wherein the mutant BTK peptide comprises at least one mutant amino acid; wherein the mutant BTK peptide binds to a protein encoded by an HLA-A02:01 allele.

Provided herein is a method of identifying a subject with cancer as a candidate for a therapeutic, the method comprising identifying the subject as one that expresses a protein encoded by an HLA-A02:01 allele, wherein the therapeutic a T cell receptor (TCR) specific for a mutant BTK peptide in complex with an HLA protein; wherein the mutant BTK peptide comprises a resistance mutation or a point mutation; wherein the mutant BTK peptide binds to a protein encoded by an HLA-A02:01 allele.

Provided herein is a method of identifying a subject with cancer as a candidate for a therapeutic, the method comprising identifying the subject as one that expresses a protein encoded by an HLA-A02:01 allele, wherein the therapeutic a T cell receptor (TCR) specific for a mutant BTK peptide in complex with an HLA protein; wherein the mutant BTK peptide comprises a C481S mutation; wherein the mutant BTK peptide binds to a protein encoded by an HLA-A02:01 allele.

Provided herein is a method of identifying a subject with cancer as a candidate for a therapeutic, the method comprising identifying the subject as one that expresses a protein encoded by an HLA-A02:01 allele, wherein the therapeutic comprises a T cell receptor (TCR) specific for a mutant EGFR peptide in complex with an HLA protein; wherein the mutant EGFR peptide comprises at least one mutant amino acid T790M; wherein the mutant EGFR peptide binds to a protein encoded by an HLA-A02:01 allele.

In some embodiments, the cancer is selected from the group consisting of breast cancer, lung cancer, non-small cell lung cancer, pancreatic cancer, colorectal cancer, uterine cancer, melanoma, ovarian cancer, prostate cancer, endometrial cancer, chronic lymphocytic leukemia (CLL) and liver cancer. In some embodiments, the subject has a breast cancer that is resistant to anti-estrogen therapy, is an MSI breast cancer, is a metastatic breast cancer, is a Her2 negative breast cancer, is a Her2 positive breast cancer, is an ER negative breast cancer, is an ER positive breast cancer is a recurrent breast cancer, is a metastatic breast cancer, or any combination thereof. In some embodiments, the breast cancer expresses an estrogen receptor with a mutation.

In some embodiments, the subject has a breast cancer that is resistant to anti-estrogen therapy. In some embodiments, the breast cancer expresses an estrogen receptor with a mutation. In some embodiments, the subject has a CLL that is resistant to ibrutinib therapy. In some embodiments, the CLL expresses a Bruton tyrosine kinase (BTK) with a mutation, such as a C481S mutation. In some embodiments, the subject has a lung cancer that is resistant to a tyrosine kinase inhibitor. In some embodiments, the lung cancer expresses an epidermal growth factor receptor (EGFR) with a mutation, such as a T790M, L792F, or C797S mutation.

In some embodiments, an immune response is elicited in the subject. In some embodiments, the immune response is a humoral response. In some embodiments, the immune response is a cytotoxic T cell response.

In some embodiments, the method further comprises administering at least one additional therapeutic agent or modality. In some embodiments, the at least one additional therapeutic agent or modality is surgery, a checkpoint inhibitor, an antibody or fragment thereof, a chemotherapeutic agent, radiation, a vaccine, a small molecule, a T cell, a vector, and APC, a polynucleotide, an oncolytic virus or any combination thereof. In some embodiments, the at least one additional therapeutic agent is an anti-PD-1 agent and anti-PD-L1 agent, an anti-CTLA-4 agent, or an anti-CD40 agent. In some embodiments, the additional therapeutic agent is administered before, simultaneously, or after administering a pharmaceutical composition described herein.

In some embodiments, administering comprises administering subcutaneously or intravenously.

In some embodiments, the subject is a subject that has had disease progression following endocrine therapy in combination with a CDK 4/6 inhibitor.

Provided herein is a method comprising: identifying neoantigen-specific T cells from a sample comprising a population of T cells; identifying one or more peptides of a peptide-MHC complex that are presented by an antigen presenting cell (APC); identifying a variable sequence of a T cell receptor (TCR) from the neoantigen-specific T cells; expressing a recombinant TCR comprising the variable sequence of the TCR identified in a TCR cell; and performing a functional assay, wherein the functional assay comprises contacting the TCR cell to a peptide-MHC complex comprising a peptide of the one or more peptides identified.

In some embodiments, the method comprises obtaining the sample comprising the population of cells comprising the neoantigen-specific T cells. In some embodiments, obtaining the sample comprises obtaining a T cell sample from a healthy subject or from a subject with cancer. In some embodiments, the T cell sample is from a healthy donor. In some embodiments, the T cell sample is a peripheral blood mononuclear cell (PBMC) sample.

In some embodiments, in identifying neoantigen-specific T cells comprises contacting the population of T cells to at least one peptide-MHC multimer complex comprising a neoantigen peptide. In some embodiments, identifying neoantigen-specific T cells comprises contacting the population of T cells to a peptide-MHC complex comprising a neoantigen peptide. In some embodiments, identifying neoantigen-specific T cells comprises contacting the population of T cells to an APC comprising the peptide-MHC complex. In some embodiments, identifying neoantigen-specific T cells further comprises isolating T cells of the T cell population specific to the peptide-MHC complex. In some embodiments, identifying neoantigen-specific T cells further comprises identifying or predicting T cells of the of the T cell population specific to the peptide-MHC complex based on TCR clonality. In some embodiments, identifying a variable sequence of a TCR from the neoantigen-specific T cells is performed before identifying neoantigen-specific T cells. In some embodiments, identifying a variable sequence of a TCR from the neoantigen-specific T cells comprises sequencing DNA, RNA, or amplified products thereof from one or more neoantigen-specific T cells that encode the variable sequence. In some embodiments, identifying a variable sequence of a TCR from the neoantigen-specific T cells comprises sequencing DNA, RNA, or amplified products thereof from a single neoantigen-specific T cell that encodes the variable sequence. In some embodiments, identifying a variable sequence of a TCR from the neoantigen-specific T cells comprises sequencing barcoded DNA or barcoded RNA, or amplified products thereof, from one or more neoantigen-specific T cells that encode the variable sequence. In some embodiments, identifying a variable sequence of a TCR from the neoantigen-specific T cells comprises pairing a TCR-alpha chain with a TCR-beta chain.

In some embodiments, expressing a recombinant TCR comprises expressing the variable sequence identified from a polynucleotide comprising a sequence encoding the variable sequence identified. In some embodiments, the polynucleotide is a vector. In some embodiments, the vector is a viral vector. In some embodiments, the viral vector is a lentiviral vector. In some embodiments, expressing a recombinant TCR comprises transducing or transfecting the polynucleotide into cells. In some embodiments, the cells are a T cell line or healthy donor PMBCs.

In some embodiments, identifying one or more peptides of a peptide-MHC complex that are presented by an APC comprises expressing the one or more peptides in cells. In some embodiments, identifying one or more peptides of a peptide-MHC complex that are presented by an APC comprises loading the one or more peptides onto MHCs of cells. In some embodiments, identifying one or more peptides of a peptide-MHC complex that are presented by an APC comprises eluting or isolating a peptide of the one or more peptides from a peptide MHC complex. In some embodiments, identifying one or more peptides of a peptide-MHC complex that are presented by an APC comprises performing mass spectrometry on a peptide of the one or more peptides that was isolated or eluted from a peptide-MHC complex. In some embodiments, performing a functional assay comprises determining expression of one or more cell markers. In some embodiments, the one or more cell markers comprise TNF-α, IFN-γ, LAMP-1, 4-1BB, IL-2, IL-17A, Granzyme B, PD-1, CD25, CD69, TIM3, LAG3, CTLA-4, CD62L, CD45RA, CD45RO, FoxP3, or any combination thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 10A depicts a workflow for antigen-specific TCR identification and analysis of a sample depicted in FIG. 9.

FIG. 10B depicts a workflow for antigen-specific TCR identification of a sample depicted in FIG. 9.

DETAILED DESCRIPTION

Figure 1:
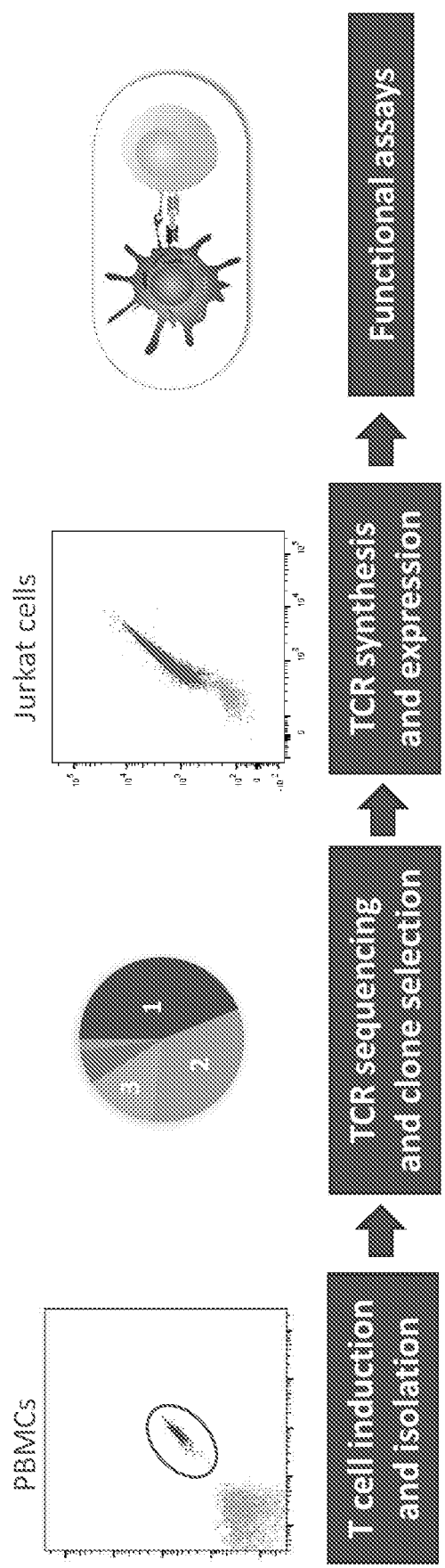
FIG. 1 depicts a workflow for antigen-specific TCR identification and analysis. PBMCs from healthy donors can be stimulated with the antigen of interest, after which antigen-specific T cells can be identified with peptide-MHC multimers (left). Antigen-specific T cells can be isolated and the TCR can be sequenced and analyzed (middle left). The TCR can be synthesized and expressed in a cell line or PBMCs, and the specificity can be again confirmed by peptide-MHC multimer (middle right). The TCR-expressing cell line or PBMCs can then be co-cultured with antigen-expressing cell lines to confirm the functionality of the TCR (right).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. The details of one or more particular embodiments are set forth in the description below.

I. Definitions

Unless otherwise stated, the term "TCR" should be understood to encompass full TCRs as well as antigen-binding portions or antigen-binding fragments (also called MHC-peptide binding fragments) thereof. In some embodiments, the TCR is an intact or full-length TCR. In some embodiments, the TCR is an antigen-binding portion that is less than a full-length TCR but that binds to a specific antigenic peptide bound to (i.e., in the context of) an MHC molecule, i.e., an MHC-peptide complex. In some cases, an antigen-binding portion or fragment of a TCR can contain only a portion of the structural domains of a full-length or intact TCR, but yet is able to bind the epitope (e.g., MHC-peptide complex) to which the full TCR binds. In some cases, an antigen-binding portion or fragment of a TCR contains the variable domains of a TCR, such as variable a chain and variable 13 chain of a TCR, sufficient to form a binding site for binding to a specific MHC-peptide complex, such as generally where each chain contains three complementarity determining regions. Polypeptides or proteins having a binding domain which is an antigen-binding domain or is homologous to an antigen-binding domain are included. Complementarity determining region (CDR) grafted TCRs and other humanized TCRs (including CDR modifications and framework region modifications) are also contemplated by these terms. It should be noted that while reference may be made only to immunoglobulin chains (e.g., heavy chains and lights chains), the disclosed invention can be applied to multiple other different types of paired sequences, e.g., T cell receptor chain pairs (TCRα and TCRβ chains and TCRγ and TCRδ chains), and is not limited to immunoglobulins.

The terms "complementarity determining region," and "CDR," synonymous with "hypervariable region" or "HVR," are known in the art to refer to non-contiguous sequences of amino acids within TCR variable regions, which confer specificity and/or binding affinity to an MHC-peptide complex. In general, there are three CDRs in each alpha chain variable region (CDR-H1, CDR-H2, CDR-H3) and three CDRs in each beta chain variable region (CDR-L1, CDR-L2, CDR-L3). "Framework regions" and "FR" are known in the art to refer to the non-CDR portions of the variable regions of the alpha and beta chains. In general, there are four FRs in each full-length alpha chain variable region (FR-H1, FR-H2, FR-H3, and FR-H4), and four FRs in each full-length beta chain variable region (FR-L1, FR-L2, FR-L3, and FR-L4).

The term "variable region" or "variable domain" refers to the domain of a TCR alpha, beta, gamma or delta chain, that is involved in binding the TCR to antigen-MHC complexes. The variable domains of the alpha chain and beta chain (Vα and Vβ, respectively), and the gamma chain and delta chain (Vγ and Vδ, respectively) of a native TCR generally have similar structures, with each domain comprising four conserved framework regions (FRs) and three CDRs. A single Vα or Vβ domain, or Vγ or Vδ domain, may be sufficient to confer binding specificity to a peptide-MHC complex.

Also provided herein are TCR fragments, including antigen-binding fragments. In some embodiments, the TCR is an antigen-binding portion thereof, such as a variant of a full-length TCR not containing the transmembrane and/or cytoplasmic region(s) thereof, which may be referred to as a full soluble TCR. In some embodiments, the TCR is a dimeric TCR (dTCR). In some embodiments, the TCR is a single-chain TCR (scTCR), such as a scTCR having a structure as described in PCT patent publication numbers WO2003/020763, WO2004/033685, or WO2011/044186. In certain embodiments, the TCR is a single-chain TCR fragment comprising an alpha chain variable region linked to a beta chain variable region, such as a scTv. In some embodiments, a scTv is also referred to as a scFv. A single-chain Tv or scTv refers in some aspects TCR fragments that comprise the variable alpha or gamma chain (Vα or Vγ) and variable beta or delta chain (Vβ or Vδ) domains of a TCR, wherein these domains are present in a single polypeptide chain. Generally, the Tv polypeptide further comprises a polypeptide linker between the Vα and Vβ domains or Vγ and Vδ domains which enables the scTv to form the desired structure for antigen binding. A diabody refers in some aspects to TCR fragments with two antigen-binding sites, which fragments comprise a Vα connected to a Vβ in the same polypeptide chain (Vα-Vβ) or a Vγ connected to a Vδ in the same polypeptide chain (Vγ-Vδ). By using a linker that is too short to allow pairing between the two domains on the same chain, the domains are forced to pair with the complementary domains of another chain and create two antigen-binding sites. Exemplary diabodies are described more fully in, for example, EP404097 and WO93111161. Fv refers in some aspects to a TCR fragment which contains a complete peptide-MHC complex recognition and peptide-MHC complex binding site. This region consists of a dimer of one TCRα chain and one TCRβ chain or one TCRγ chain and one TCRδ chain in tight, non-covalent association. It is in this configuration that the three CDRs of each variable domain interact to define a peptide-MHC complex binding site on the surface of the Vα-Vβ dimer or Vγ-Vδ dimer. Collectively, a combination of one or more of the CDRs from each of the Vα-Vβ chains or Vγ-Vδ chains confers peptide-MHC complex binding specificity to the TCR. For example, it would be understood that, for example, the CDRα3 and CDRβ3 or CDRγ3 and CDR63 could be sufficient to confer antigen-binding specificity to a TCR when transferred to Vα and Vβ chains or Vγ-Vδ chains of a recipient selected TCR or antigen-binding fragment thereof and this combination of CDRs can be tested for binding, affinity, etc. Furthermore, although the two domains of a Tv fragment (Vα and Vβ or Vγ and Vδ), are coded for by separate genes, they can be joined using recombinant methods by a synthetic linker that enables them to be made as a single protein chain in which the Vα and Vβ or Vγ and Vδ chain regions pair to form monovalent molecules (known as single chain Tv (scTv). Such scTvs are also intended to be encompassed within the peptide-MHC complex binding portion of a TCR.

A "bispecific TCR" refers in some aspects to a TCR that shows specificities to two different peptide-MHC complexes or two different types of peptide-MHC complexes. The terms as used herein specifically include, without limitation, TCRs which show binding specificity for a target peptide-MHC complex and to another peptide-MHC complex that facilitates delivery to a particular tissue. Similarly, multi-specific TCRs have two or more binding specificities. A linear TCR refers in some aspects to a pair of tandem Fd segments (e.g., Vα-Cα$_1$-Vα-Cα$_1$) which form a pair of antigen binding regions. Linear TCRs can be bispecific or monospecific.

An "antigen-binding domain" refers in some aspects to one or more fragments of a TCR that retain the ability to specifically bind to a peptide-MHC complex. Non-limiting examples of TCR fragments included within such terms include, but are not limited to, (i) a Tab fragment, a monovalent fragment consisting of the Vβ, Vα, C$_β$ and Cα domains; (ii) a T(ab')$_2$ fragment, a bivalent fragment containing two Tab fragments linked by a disulfide bridge at the hinge region; (iii) a Td fragment consisting of the Vα and Cα$_1$ domains; (iv) a Tv fragment containing the Vβ and Vα domains of a single arm of a TCR, including scTvs, (v) a dAb fragment (Ward et al., (1989) Nature 341:544 546), which contains a Vα domain; and (vi) an isolated CDR. Included in this definition are TCRs with a single alpha chain or a single beta chain.

Among the provided TCRs are humanized and human TCRs. A "humanized" TCR is a TCR in which all or substantially all CDR amino acid residues are derived from non-human CDRs and all or substantially all FR amino acid residues are derived from human FRs. A humanized TCR optionally may include at least a portion of a TCR constant region derived from a human TCR. A "humanized form" of a non-human TCR, refers to a variant of the non-human TCR that has undergone humanization, typically to reduce immunogenicity to humans, while retaining the specificity and affinity of the parental non-human TCR. In some embodiments, some FR residues in a humanized TCR are substituted with corresponding residues from a non-human TCR (e.g., the TCR from which the CDR residues are derived), e.g., to restore or improve TCR specificity or affinity. A "human TCR" is a TCR with an amino acid sequence corresponding to that of a TCR produced by a human or a human cell, or non-human source that utilizes human TCR repertoires or other human TCR-encoding sequences, including human TCR libraries. The term excludes humanized forms of non-human TCRs comprising non-human peptide-MHC complex binding regions, such as those in which all or substantially all CDRs are non-human. Human TCRs may be prepared by administering an immunogen to a transgenic animal that has been modified to produce intact human TCRs or intact TCRs with human variable regions in response to antigenic challenge. Such animals typically contain all or a portion of the human TCR loci, which replace the endogenous TCR loci, or which are present extrachromosomally or integrated randomly into the animal's chromosomes. In such transgenic animals, the endogenous TCR loci have generally been inactivated. Human TCRs also may be derived from human TCR libraries, including phage display and cell-free libraries, containing TCR-encoding sequences derived from a human repertoire.

The term "cancer neoantigen" or "neoantigen" or "neoepitope" can refer to antigens that are not encoded in a normal, non-mutated host genome. A neoantigen can relate to an antigen including one or more amino acid modifications compared to the parental antigen. For example, a neoantigen may be a tumor-associated neoantigen, wherein the term "tumor-associated neoantigen" can include a peptide or protein including amino acid modifications due to tumor-specific mutations. In some instances, a neoantigen represents either oncogenic viral proteins or abnormal proteins that arise as a consequence of somatic mutations. For example, a neoantigen can arise by the disruption of cellular mechanisms through the activity of viral proteins. Another example can be an exposure of a carcinogenic compound, which in some cases can lead to a somatic mutation. This somatic mutation can ultimately lead to the formation of a tumor/cancer. A neoantigen can be a class of tumor antigens which arise from tumor-specific changes in proteins. Neoantigens encompass, but are not limited to, tumor antigens which arise from, for example, a substitution in a protein sequence, a frame shift mutation, a fusion polypeptide, an in-frame deletion, an insertion, and expression of an endogenous retroviral polypeptide. A neoepitope can be an epitope that is not present in a reference, such as a non-diseased cell, e.g., a non-cancerous cell or a germline cell, but is found in a diseased cell, e.g., a cancer cell. This includes situations where a corresponding epitope is found in a normal non-diseased cell or a germline cell but, due to one or more mutations in a diseased cell, e.g., a cancer cell, the sequence of the epitope is changed so as to result in the neoepitope.

An "epitope" refers in some aspects to a portion of an antigen or other macromolecule capable of forming a binding interaction with the variable region binding pocket of a TCR. In some aspects, an epitope refers to a portion of a peptide-MHC complex capable of forming a binding interaction with the variable region binding pocket of a TCR. Such binding interactions can be manifested as an intermolecular contact with one or more amino acid residues of one or more CDRs. Peptide-MHC complex binding can involve, for example, a CDR3, a CDR3 pair, or in some instances, interactions of up to all six CDRs of the Vα and Vβ chains or Vγ or Vδ chains. An epitope can be a linear peptide sequence (i.e., "continuous") or can be composed of non-contiguous amino acid sequences (i.e., "conformational" or "discontinuous"). A TCR can recognize one or more amino acid sequences. Therefore an epitope can define more than one distinct amino acid sequence. In some aspects, a TCR can recognize one or more amino acid sequences or epitopes in the context of an MHC. Epitopes recognized by TCRs can be determined by peptide mapping and sequence analysis techniques well known to one of skill in the art. Binding interactions are manifested as intermolecular contacts with one or more amino acid residues of a CDR. An epitope can refer to an antigenic determinant in a molecule such as an antigen, i.e., to a part in or fragment of the molecule that is recognized by the immune system, for example, that is recognized by a T cell, in particular when presented in the context of MHC molecules. An epitope of a protein such as a tumor antigen can comprise a continuous or discontinuous portion of the protein and can be between 5 and 100, 5 and 50, 8 and 30, or 10 and 25 amino acids in length, for example, the epitope may be 9, 10, 11, 12, 13, 14, 15, 16, 17, 18, 19, 20 21, 22, 23, 24 or 25 amino acids in length.

The term "binding" refers to a direct association between two molecules, due to, for example, covalent, electrostatic, hydrophobic, and ionic and/or hydrogen-bond interactions under physiological conditions, and includes interactions such as salt bridges and water bridges, as well as any other conventional means of binding.

In some embodiments, reference to a TCR with "specific binding" refers to a situation in which a TCR will not show any significant binding to molecules other than the peptide-MHC complex containing the epitope recognized by the TCR. The term is also applicable where for example, an antigen binding domain is specific for a particular epitope which is carried by a number of peptide-MHC complexes, in which case the selected TCR or peptide-MHC complex binding fragment thereof carrying the peptide-MHC complex binding domain will be able to bind to the various peptide-MHC complexes carrying the epitope. The terms "preferentially binds" or "specifically binds" mean that the TCRs or fragments thereof bind to an epitope with greater affinity than it binds unrelated amino acid sequences, and, if cross-reactive to other polypeptides containing the epitope, are not toxic at the levels at which they are formulated for administration to human use. In one aspect, such affinity is at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater than the affinity of the TCR or fragment thereof for unrelated amino acid sequences.

The term "affinity" refers to a measure of the strength of binding between two members of a binding pair (e.g., a human leukocyte antigen (HLA)-binding peptide and a class I or II HLA, or a peptide-HLA complex and a T cell receptor (TCR)) Affinity can be expressed as an equilibrium constant of the reversible binding of two agents and can be expressed as $K_D$, $K_A$, $K_{off}$ or $K_{on}$. $K_D$ refers to the dissociation constant between two members of a binding pair and has units of molarity. $K_A$ refers to the affinity constant between two members of a binding pair is the inverse of the dissociation constant. Affinity may be determined experimentally, for example by surface plasmon resonance (SPR) using commercially available Biacore SPR units. $K_{off}$ refers to the off-rate constant of two members of a binding pair, (e.g., the off-rate constant of an HLA-binding peptide and a class I or II HLA, or a peptide-HLA complex and a TCR). $K_{on}$ refers to the on-rate constant of two members of a binding pair, (e.g., the on-rate constant of an HLA-binding peptide and a class I or II HLA, or a peptide-HLA complex and a TCR). Affinity of a binding protein to a ligand such as affinity of a TCR for an epitope can be, for example, from about 100 nanomolar (nM) to about 0.1 nM, from about 100 nM to about 1 picomolar (pM), or from about 100 nM to about 1 femtomolar (fM). The term "avidity" refers to the resistance of a complex of two or more agents to dissociation after dilution.

Throughout this disclosure, "binding data" results may be expressed in terms of an "$IC_{50}$." Affinity may also be expressed as the inhibitory concentration 50 ($IC_{50}$), or the concentration at which 50% of a first member of a binding pair (e.g., a peptide) is displaced. Likewise, $\ln(IC_{50})$ refers to the natural log of the $IC_{50}$. For example, an $IC_{50}$ may be the concentration of a tested peptide in a binding assay at which 50% inhibition of binding of a labeled reference peptide is observed. Given the conditions in which the assays are run (e.g., limiting HLA protein concentrations and/or labeled reference peptide concentrations), these values can approximate $K_D$ values. Assays for determining binding are well known in the art and are described in detail, for example, in PCT publications WO 94/20127 and WO 94/03205, and other publications such as Sidney et al., Current Protocols in Immunology 18.3.1 (1998); Sidney, et al., J. Immunol. 154:247 (1995); and Sette, et al., Mol. Immunol. 31:813 (1994). Alternatively, binding can be expressed relative to binding by a reference standard peptide. Binding can also be determined using other assay systems including those using: live cells (e.g., Ceppellini et al., Nature 339:392 (1989); Christnick et al., Nature 352:67 (1991); Busch et al., Int. Immunol. 2:443 (1990); Hill et al., J. Immunol. 147:189 (1991); del Guercio et al., J. Immunol. 154:685 (1995)), cell free systems using detergent lysates (e.g., Cerundolo et al., J. Immunol. 21:2069 (1991)), immobilized purified MHC (e.g., Hill et al., J. Immunol. 152, 2890 (1994); Marshall et al., J. Immunol. 152:4946 (1994)), ELISA systems (e.g., Reay et al., EMBO J. 11:2829 (1992)), surface plasmon resonance (e.g., Khilko et al., J. Biol. Chem. 268:15425 (1993)); high flux soluble phase assays (Hammer et al., J. Exp. Med. 180:2353 (1994)), and measurement of class I MHC stabilization or assembly (e.g., Ljunggren et al., Nature 346:476 (1990); Schumacher et al., Cell 62:563 (1990); Townsend et al., Cell 62:285 (1990); Parker et al., J. Immunol. 149:1896 (1992)).

The terms "major histocompatibility complex" and the abbreviation "MHC" can include MHC class I and MHC class II molecules and relate to a complex of genes which occurs in all vertebrates. MHC proteins or molecules can be important for signaling between lymphocytes and antigen presenting cells or diseased cells in immune reactions, wherein the MHC proteins or molecules bind peptides and present them for recognition by T cell receptors. The proteins encoded by the MHC can be expressed on the surface of cells, and display both self-antigens (peptide fragments from the cell itself) and non-self-antigens (e.g., fragments of invading microorganisms) to a T cell. The MHC region can be divided into three subgroups, class I, class II, and class III. MHC class I proteins can contain an α-chain and β2-microglobulin (not part of the MHC encoded by chromosome 15). They can present antigen fragments to cytotoxic T cells. MHC class II proteins can contain α- and β-chains and they can present antigen fragments to T-helper cells. MHC class III region can encode for other immune components, such as complement components and cytokines. The MHC can be both polygenic (there are several MHC class I and MHC class II genes) and polymorphic (there are multiple alleles of each gene).

The term "haplotype" can refer to the human leukocyte antigen (HLA) alleles found on one chromosome and the proteins encoded thereby. Haplotype may also refer to the allele present at any one locus within the MHC. Each class of MHC is represented by several loci: e.g., HLA-A (Human Leukocyte Antigen-A). HLA-B, HLA-C, HLA-E, HLA-F, HLA-G, HLA-H, HLA-J, HLA-K, HLA-L, HLA-P and HLA-V for class I and HLA-DRA, HLA-DRB1-9, HLA-DQA1, HLA-DQB1, HLA-DPA1, HLA-DPB1, HLA-DPB2, HLA-DMA, HLA-DMB, HLA-DOA, and HLA-DOB for class II. The terms "HLA allele" and "MHC allele" are used interchangeably herein.

The terms "polynucleotide", "nucleotide", "nucleotide sequence", "nucleic acid" and "oligonucleotide" are used interchangeably. They can refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. Polynucleotides can include nonstandard nucleotides, such as nucleotide analogs or modified nucleotides. In some embodiments, nonstandard nucleotides can stabilize hybrid formation. In some embodiments, nonstandard nucleotides can destabilize hybrid formation. In some embodiments, nonstandard nucleotides can enhance hybridization specificity. In some embodiments, nonstandard nucleotides can reduce hybridization specificity. Examples of nonstandard nucleotide modifications include 2' O-Me, 2' O-allyl, 2' O-propargyl, 2' O-alkyl, 2' fluoro, 2' arabino, 2' xylo, 2' fluoro arabino, phosphorothioate, phosphorodithioate, phosphoroamidates, 2' Amino, 5-alkyl-substituted pyrimidine, 3' deoxyguanosine, 5-halo-substituted pyrimidine, alkyl-substituted purine, halo-substituted purine, bicyclic nucleotides, 2'MOE, PNA molecules, LNA-molecules, LNA-like molecules, diaminopurine, S2T, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethyl-aminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, $N^6$-adenine, 7-methyl guanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxy acetic acid (v), 5-methyl-2-thiouracil, 3-(3-amino-3-N-2-carboxypropyl) uracil, (acp3)w, 2,6-diaminopurine, and derivatives thereof. The sequence of nucleotides may be interrupted by non-nucleotide components. A polynucleotide may be further modified after polymerization, such as by conjugation with a labeling component.

"Complementarity" can refer to the ability of a nucleic acid to form hydrogen bond(s) with another nucleic acid sequence by either traditional Watson-Crick or other non-traditional types. A percent complementarity can indicate the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). "Perfectly complementary" can mean that all the contiguous residues of a nucleic acid sequence will hydrogen bond with the same number of contiguous residues in a second nucleic acid sequence. "Substantially complementary" refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or can refer to two nucleic acids that hybridize under stringent conditions. Sequence identity, such as for the purpose of assessing percent complementarity, may be measured by any suitable alignment algorithm, including but not limited to the Needleman-Wunsch algorithm (e.g., the EMBOSS Needle aligner available at www.ebi.ac.uk/Tools/psa/embossneedle/nucleotide.html, optionally with default settings), the BLAST algorithm (see e.g., the BLAST alignment tool available at blast.ncbi.nlm.nih.gov/Blast.cgi, optionally with default settings), or the Smith-Waterman algorithm. Optimal alignment may be assessed using any suitable parameters of a chosen algorithm, including default parameters.

The terms "polypeptide" and "protein" are used interchangeably to refer to a polymer of amino acid residues, and, are not limited to a minimum length. For example, a polypeptide can comprise at least about 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000 peptides or amino acids. Examples of polypeptides include, but are not limited to, amino acid chains, proteins, peptides, hormones, polypeptide saccharides, lipids, glycolipids, phospholipids, antibodies, enzymes, kinases, receptors, transcription factors, and ligands. Polypeptides, including the provided TCRs and TCR chains and other peptides, e.g., linkers and binding peptides, may include amino acid residues including natural and/or non-natural amino acid residues. The terms also include post-expression modifications of the polypeptide, for example, glycosylation, sialylation, acetylation, phosphorylation, and the like. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

As used herein, the twenty conventional amino acids and their abbreviations known to one skilled in the art follow conventional usage. Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left hand direction is the amino terminal direction and the right hand direction is the carboxy-terminal direction, in accordance with standard usage and convention. Percent (%) sequence identity with respect to a reference polypeptide sequence (or nucleic acid sequence) is the percentage of amino acid residues (or nucleotides in case of nucleic acid sequence) in a candidate sequence that are identical with the amino acid residues (or nucleotides) in the reference polypeptide sequence (or nucleic acid sequence), after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

A "germline sequence" refers to a genetic sequence from the haploid gametes and those diploid cells from which they are formed. Germline DNA contains multiple gene segments that encode a single TCRα or TCRβ chain, or a single TCRγ or TCR chain. These gene segments are carried in the germ cells but cannot be transcribed and translated until they are arranged into functional genes. During T cell differentiation in the bone marrow, these gene segments are randomly shuffled by a dynamic genetic system capable of generating more than $10^8$ specificities.

Inhibition, "treatment" and "treating" are used interchangeably and refer to, for example, stasis of symptoms, prolongation of survival, partial or full amelioration of symptoms, and partial or full eradication of a condition, disease or disorder associated with excess levels of protein or correlated with protein activity. For example, treatment of cancer includes, but is not limited to, stasis, partial or total elimination of a cancerous growth or tumor. Treatment or partial elimination includes, for example, a fold reduction in growth or tumor size and/or volume such as about 2-fold, about 3-fold, about 4-fold, about 5-fold, about 10-fold, about 20-fold, about 50-fold, or any fold reduction in between. Similarly, treatment or partial elimination can include a percent reduction in growth or tumor size and/or volume of about 1%, 2%, 3%, 4%, 5%, 10%, 20%, 30%, 40%, 50%, 60%, 70%, 80%, 90%, 95% or any percentage reduction in between. Prevention refers to prophylaxis, prevention of onset of symptoms, prevention of progression of a disease or disorder associated with excess levels of protein or correlated with protein activity.

A "subject", "individual", "host" or "patient" refers to living organisms such as mammals. Examples of subjects and hosts include, but are not limited to, horses, cows, camels, sheep, pigs, goats, dogs, cats, rabbits, guinea pigs, rats, mice (e.g., humanized mice), gerbils, non-human primates (e.g., macaques), humans and the like, non-mammals, including, e.g., non-mammalian vertebrates, such as birds (e.g., chickens or ducks) fish (e.g., sharks) or frogs (e.g., Xenopus), and non-mammalian invertebrates, as well as transgenic species thereof. In certain aspects, a subject refers to a single organism (e.g., human). In certain aspects, or a group of individuals composing a small cohort having either a common immune factor to study and/or disease, and/or a cohort of individuals without the disease (e.g., negative/normal control) are provided. A subject from whom samples are obtained can either be inflicted with a disease and/or disorder (e.g., one or more allergies, infections, cancers or autoimmune disorders or the like) and can be compared against a negative control subject which is not affected by the disease.

A "kit" refers to a delivery system for delivering materials or reagents for carrying out a method disclosed herein. In some embodiments, kits include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains a plurality of primers. A packaging material refers to a physical structure housing the components of the kit. The packaging material can maintain the components sterilely and can be made of material commonly used for such purposes (e.g., paper, corrugated fiber, glass, plastic, foil, ampules, etc.). The label or packaging insert can include appropriate written instructions. Kits, therefore, can additionally include labels or instructions for using the kit components in any method of the invention. A kit can include a compound in a pack, or dispenser together with instructions for administering the compound in a method described herein.

The term "resistance mutation" refers to a mutation in a gene that allows the gene or the host cell containing the gene to become resistant to treatment with a drug. For example, BTK C481S mutation is a resistance mutation which can confer ibrutinib resistance.

II. Overview

The present disclosure provides T cell receptors (TCRs) against neoantigens, isolated nucleic acid molecules encoding TCRs against neoantigens, T cells expressing said TCRs, and pharmaceutical compositions for use in the treatment of diseases involving malignant cells expressing said neoantigens.

Provided herein is a nucleic acid encoding at least one T cell receptor (TCR) comprising a TCR alpha chain construct and/or TCR beta chain construct capable of specifically binding to an epitope from RAS in complex with a human MHC, wherein the TCR alpha chain construct comprises a complementarity determining region 3 (CDR3) having at least 84% sequence identity to an amino acid sequence selected from SEQ ID NOs: 3, 18, 33, 49, 65, 81, 97, and 113, and/or wherein the TCR beta chain construct comprises a complementarity determining region 3 (CDR3) having at least 84% sequence identity to an amino acid sequence selected from SEQ ID NOs: 6, 21, 36, 52, 68, 84, 100, and 116.

Provided herein is a nucleic acid encoding at least one T cell receptor (TCR) comprising a TCR alpha chain construct and/or TCR beta chain construct capable of specifically binding to an epitope from RAS in complex with a human MHC, wherein the epitope from RAS comprises a region having at least 70% sequence identity to an amino acid sequence selected from SEQ ID NOs: 15, 30, 45, 46, 61, 62, 77, 78, 93, 94, 109, 110, 125, 126 and 219-222.

Provided herein is an isolated nucleic acid or a cell comprising a recombinant nucleic acid, wherein the nucleic acid encodes at least one T cell receptor (TCR) comprising a TCR alpha chain construct and/or a TCR beta chain construct, wherein the TCR specifically binds to an epitope from RAS in complex with a human MHC encoded by an HLA-A03:01 allele.

In some embodiments, the TCR alpha chain construct comprises a variable region having at least 80% sequence identity an amino acid sequence selected from SEQ ID NOs: 9, 24, 39, 55, 71, 87, 103, and 119. In some embodiments, the TCR beta chain construct comprises a variable region having at least 80% sequence identity to an amino acid sequence selected from SEQ ID NOs: 12, 27, 42, 58, 74, 90, 106, and 122. In some embodiments, the TCR alpha chain construct and/or the TCR beta chain construct comprises a complementarity determining region 1 (CDR1) having at least 90% sequence identity to an amino acid sequence selected from SEQ ID NOs: 1, 16, 31, 47, 63, 79, 95, and 111. In some embodiments, the TCR beta chain construct comprises a complementarity determining region 1 (CDR1) having at least 90% sequence identity to an amino acid sequence selected from SEQ ID NOs: 4, 19, 34, 50, 66, 82, 98, and 114. In some embodiments, the TCR alpha chain construct comprises a complementarity determining region 2 (CDR2) having at least 90% sequence identity to an amino acid sequence selected from SEQ ID NOs: 2, 17, 32, 48, 64, 80, 96, and 112. In some embodiments, the TCR beta chain construct comprises a complementarity determining region 2 (CDR2) having at least 90% sequence identity to an amino acid sequence selected from SEQ ID NOs: 5, 20, 35, 51, 67, 83, 99, and 115. In some embodiments, the TCR alpha chain construct comprises a variable region having at least 80% sequence identity to SEQ ID NO: 9; and the TCR beta chain construct comprises a variable region having at least 80% sequence identity to SEQ ID NO: 12. In some embodiments, the TCR alpha chain construct comprises a CDR1 of SEQ ID NO: 1, a CDR2 of SEQ ID NO: 2, and a CDR3 of SEQ ID NO: 3; and the TCR beta chain construct comprises a CDR1 of SEQ ID NO: 4, a CDR2 of SEQ ID NO: 5, and a CDR3 of SEQ ID NO: 6. In some embodiments, the TCR alpha chain construct comprises a variable region having at least 80% sequence identity to SEQ ID NO: 24; and the TCR beta chain construct comprises a variable region having at least 80% sequence identity to SEQ ID NO: 27. In some embodiments, the TCR alpha chain construct comprises a CDR1 of SEQ ID NO: 16, a CDR2 of SEQ ID NO: 17, and a CDR3 of SEQ ID NO: 18; and the TCR beta chain construct comprises a CDR1 of SEQ ID NO: 19, a CDR2 of SEQ ID NO: 20, and a CDR3 of SEQ ID NO: 21. In some embodiments, the TCR alpha chain construct comprises a variable region having at least 80% sequence identity to SEQ ID NO: 39; and the TCR beta chain construct comprises a variable region having at least 80% sequence identity to SEQ ID NO: 42. In some embodiments, the TCR alpha chain construct comprises a CDR1 of SEQ ID NO: 31, a CDR2 of SEQ ID NO: 32, and a CDR3 of SEQ ID NO: 33; and the TCR beta chain construct comprises a CDR1 of SEQ ID NO: 34, a CDR2 of SEQ ID NO: 35, and a CDR3 of SEQ ID NO: 36. In some embodiments, the TCR alpha chain construct comprises a variable region having at least 80% sequence identity to SEQ ID NO: 55; and the TCR beta chain construct comprises a variable region having at least 80% sequence identity to SEQ ID NO: 58. In some embodiments, the TCR alpha chain construct comprises a CDR1 of SEQ ID NO: 47, a CDR2 of SEQ ID NO: 48, and a CDR3 of SEQ ID NO: 49; and the TCR beta chain construct comprises a CDR1 of SEQ ID NO: 50, a CDR2 of SEQ ID NO: 51, and a CDR3 of SEQ ID NO: 52.

Provided herein is a nucleic acid encoding at least one T cell receptor (TCR) comprising a TCR alpha chain construct and/or TCR beta chain construct capable of specifically binding to an epitope from TMPRSS2:ERG in complex with a human MHC, wherein the TCR alpha chain construct and/or the TCR beta chain construct comprises a complementarity determining region 3 (CDR3) having at least 90% sequence identity to an amino acid sequence selected from SEQ ID NO: 144 and SEQ ID NO: 147.

Provided herein is a nucleic acid encoding at least one T cell receptor (TCR) comprising a TCR alpha chain construct and/or TCR beta chain construct capable of specifically binding to an epitope from TMPRSS2:ERG in complex with a human MHC, wherein the epitope from TMPRSS2:ERG comprises a region having at least 90% sequence identity to amino acid sequence SEQ ID NO: 156.

In some embodiments, the TCR alpha chain construct comprises a variable region having at least 80% sequence identity to SEQ ID NO: 150. In some embodiments, the TCR beta chain construct comprises a variable region having at least 80% sequence identity to SEQ ID NO: 153. In some embodiments, the TCR alpha chain construct and/or the TCR beta chain construct comprises a complementarity determining region 1 (CDR1) having at least 90% sequence identity to SEQ ID NO: 142 or SEQ ID NO: 145. In some embodiments, the TCR alpha chain construct and/or the TCR beta chain construct comprises a complementarity determining region 2 (CDR2) having at least 90% sequence identity to SEQ ID NO: 143 or SEQ ID NO: 146. In some embodiments, the TCR alpha chain construct comprises a variable region having at least 80% sequence identity to SEQ ID NO: 150; and the TCR beta chain construct comprises a variable region having at least 80% sequence identity to SEQ ID NO: 153. In some embodiments, the TCR alpha chain construct comprises a CDR1 of SEQ ID NO: 142, a CDR2 of SEQ ID NO: 143, and a CDR3 of SEQ ID NO: 144; and the TCR beta chain construct comprises a CDR1 of SEQ ID NO: 145, a CDR2 of SEQ ID NO: 146, and a CDR3 of SEQ ID NO: 147.

Provided herein is a nucleic acid encoding at least one T cell receptor (TCR) comprising a TCR alpha chain construct and/or TCR beta chain construct capable of specifically binding to an epitope from GATA3 in complex with a human MHC, wherein the TCR alpha chain construct and/or the TCR beta chain construct comprises a complementarity determining region 3 (CDR3) having at least 90% sequence identity to an amino acid sequence selected from SEQ ID NO: 129 and SEQ ID NO: 132.

Provided herein is a nucleic acid encoding at least one T cell receptor (TCR) capable of specifically binding to a mutant GATA3 peptide in complex with a protein encoded by an HLA allele of a subject with cancer, wherein the TCR comprises a TCR alpha chain construct and/or a TCR beta chain construct.

Provided herein is an isolated nucleic acid or a cell comprising a recombinant nucleic acid, wherein the nucleic acid encodes a T cell receptor (TCR) comprising a TCR alpha chain construct and/or a TCR beta chain construct, wherein the TCR specifically binds to a mutant GATA3 peptide in complex with an HLA-A02:01 protein; comprises a complementarity determining region 3 (CDR3) having at least 90% sequence identity to SEQ ID NO: 129 or SEQ ID NO: 132; and/or specifically binds to a mutant GATA3 peptide comprising a region with at least 70% sequence identity to SEQ ID NO: 141.

Provided herein is a nucleic acid encoding at least one T cell receptor (TCR) comprising a TCR alpha chain construct and/or TCR beta chain construct capable of specifically binding to an epitope from GATA3 in complex with a human MHC, wherein the epitope from GATA3 comprises a region having at least 90% sequence identity to amino acid sequence SEQ ID NO: 141.

In some embodiments, the TCR alpha chain construct comprises a variable region having at least 80% sequence identity to SEQ ID NO: 135. In some embodiments, the TCR beta chain construct comprises a variable region having at least 80% sequence identity to SEQ ID NO: 138. In some embodiments, the TCR alpha chain construct and/or the TCR beta chain construct comprises a complementarity determining region 1 (CDR1) having at least 90% sequence identity to an amino acid sequence selected from SEQ ID NO: 127 and SEQ ID NO: 130. In some embodiments, the TCR alpha chain construct and/or the TCR beta chain construct comprises a complementarity determining region 2 (CDR2) having at least 90% sequence identity to an amino acid sequence selected from SEQ ID NO: 128 and SEQ ID NO:131. In some embodiments, the TCR alpha chain construct comprises a variable region having at least 80% sequence identity to SEQ ID NO: 135; and the TCR beta chain construct comprises a variable region having at least 80% sequence identity to SEQ ID NO: 138. In some embodiments, the TCR alpha chain construct comprises a CDR1 of SEQ ID NO: 127, a CDR2 of SEQ ID NO: 128, and a CDR3 of SEQ ID NO: 129; and the TCR beta chain construct comprises a CDR1 of SEQ ID NO: 130, a CDR2 of SEQ ID NO: 131, and a CDR3 of SEQ ID NO: 132.

In another aspect, provided herein is a nucleic acid encoding at least one T cell receptor (TCR) comprising a TCR alpha chain construct and/or TCR beta chain construct capable of specifically binding to an epitope from BTK in complex with a human MHC, wherein the TCR alpha chain construct comprises a complementarity determining region 3 (CDR3) having at least 90% sequence identity to an amino acid sequence selected from SEQ ID NO: 161 and SEQ ID NO: 176, or wherein the TCR beta chain construct comprises a complementarity determining region 3 (CDR3) having at least 90% sequence identity to an amino acid sequence selected from SEQ ID NO: 164 and SEQ ID NO: 179. In another aspect, provided herein is a nucleic acid encoding at least one T cell receptor (TCR) capable of specifically binding to a mutant BTK peptide in complex with a protein encoded by an HLA allele of a subject with cancer, wherein the TCR comprises a TCR alpha chain construct and/or a TCR beta chain construct. In another aspect, provided herein is an isolated nucleic acid or a cell comprising a recombinant nucleic acid, wherein the nucleic acid encodes a T cell receptor (TCR) comprising a TCR alpha chain construct and/or a TCR beta chain construct, wherein the TCR specifically binds to a mutant BTK peptide in complex with an HLA-A02:01 protein; comprises a complementarity determining region 3 (CDR3) having at least 90% sequence identity to SEQ ID NO: 161, 164, 176, or 179; and/or specifically binds to a mutant BTK peptide comprising a region with at least 70% sequence identity to SEQ ID NO: 173 or 188. In another aspect, provided herein is a nucleic acid encoding at least one T cell receptor (TCR) comprising a TCR alpha chain construct and/or TCR beta chain construct capable of specifically binding to an epitope from BTK in complex with a human MHC, wherein the epitope from BTK comprises a region having at least 90% sequence identity to amino acid sequence SEQ ID NO: 173 or 188. In some embodiments, the TCR alpha chain construct comprises a variable region having at least 80% sequence identity to SEQ ID NO: 167 or 182. In some embodiments, the TCR beta chain construct comprises a variable region having at least 80% sequence identity to SEQ ID NO: 170 or 185. In some embodiments, the TCR alpha chain construct and/or the TCR beta chain construct comprises a complementarity determining region 1 (CDR1) having at least 90% sequence identity to an amino acid sequence selected from SEQ ID NOs: 159, 162, 174, and 177. In some embodiments, the TCR alpha chain construct and/or the TCR beta chain construct comprises a complementarity determining region 2 (CDR2) having at least 90% sequence identity to an amino acid sequence selected from SEQ ID NOs: 160, 163, 175 and 178. In some embodiments, the TCR alpha chain construct comprises a variable region having at least 80% sequence identity to SEQ ID NO: 167 or 182; and the TCR beta chain construct comprises a variable region having at least 80% sequence identity to SEQ ID NO: 170 or 185. In some embodiments, the TCR alpha chain construct comprises a CDR1 of SEQ ID NO: 159 or 174, a CDR2 of SEQ ID NO: 160 or 175, and a CDR3 of SEQ ID NO: 161 or 176; and the TCR beta chain construct comprises a CDR1 of SEQ ID NO: 162 or 177, a CDR2 of SEQ ID NO: 163 or 178, and a CDR3 of SEQ ID NO: 164 or 179.

In yet another aspect, the present disclosure provides a host cell comprising the nucleic acid encoding a TCR against a neoantigen provided herein, a vector containing the nucleic acid sequence, or a protein encoded by the nucleic acid provided herein. In some embodiments, the host cell is a CD4+ T cell. In some embodiments, the host cell is a CD8+ T cell. The host cell may be a natural killer (NK) cell or a B cell. The host cell may be an immortalized cell line.

In yet another aspect, the present disclosure provides pharmaceutical compositions comprising the nucleic acid encoding a TCR against a neoantigen provided herein, a host cell comprising the nucleic acid encoding a TCR against a neoantigen provided herein, a vector containing the nucleic acid sequence, or a protein encoded by the nucleic acid provided herein. In some embodiments, provided herein also comprises a method of using the pharmaceutical compositions disclosed herein.

Also provided herein in an additional aspect is a method of treating a subject with a disease or condition, comprising administering to the subject a pharmaceutical composition disclosed herein. In some embodiments, the subject has cancer.

III. T Cell Receptors (TCRs)

The ability of T cells to recognize antigens associated with various cancers or infectious organisms is conferred by its TCR, which is made up of both an alpha (α) chain and a beta (β) chain or a gamma (γ) and a delta (δ) chain. The proteins which make up these chains are encoded by DNA, which employs a unique mechanism for generating the tremendous diversity of the TCR. This multi-subunit immune recognition receptor associates with the CD3 complex and binds peptides presented by the MHC class I and II proteins on the surface of antigen-presenting cells (APCs). Binding of a TCR to the antigenic peptide on the APC is a central event in T cell activation, which occurs at an immunological synapse at the point of contact between the T cell and the APC.

Each TCR contains variable complementarity determining regions (CDRs), as well as framework regions (FRs) and a constant region. The amino acid sequence of the third complementarity-determining region (CDR3) loops of the α and β chain variable domains largely determines the sequence diversity of αβ T cells arising from recombination between variable (Vβ), diversity (Dβ), and joining (Jβ) gene segments in the 13 chain locus, and between analogous Vα and Jα gene segments in the α chain locus, respectively. The existence of multiple such gene segments in the TCR α and β chain loci allows for a large number of distinct CDR3 sequences to be encoded. Independent addition and deletion of nucleotides at the Vβ-Dβ, Dβ-Jβ, and Vα-Jα junctions during the process of TCR gene rearrangement further increases CDR3 sequence diversity. In this respect, immunocompetence is reflected in the diversity of TCRs. The γδ TCR is distinctive from the αβ TCR in that it encodes a receptor that interacts closely with the innate immune system. TCRγδ, is expressed early in development, has specialized anatomical distribution, has unique pathogen and small-molecule specificities, and has a broad spectrum of innate and adaptive cellular interactions. Early in ontogeny, as the restricted subsets of TCRγδ cells populate various tissues prenatally, a biased pattern of TCRγ V and J segment expression is established.

The TCRs provided herein target may be engineered TCRs, for example, chimeric antigen receptors (CARs). CARS can be composed of three regions: an ectodomain, a transmembrane domain and an endodomain.

An ectodomain can be the region of the receptor that is exposed to the extracellular fluid and can consist of an antigen recognition region. In some embodiments, an ectodomain further comprises and a spacer. In some embodiments, an ectodomain further comprises and a signal peptide. A signal peptide can direct the nascent protein into the endoplasmic reticulum. A signal protein in a CAR may be a single-chain variable fragment (scFv). A fusion protein may be a protein that is formed by merging two or more genes that code originally for different proteins but when they are translated in the cell, the translation produces one or more polypeptides with functional properties derived for each of the original genes. A scFv is a chimeric protein made up of a light chain domain and heavy chain variable domain connected with a short linker peptide. The linker may comprise hydrophilic residues with stretches of glycine and/or serine residues. The linker may comprise stretches of glutamate and lysine residues, which can improve solubility.

A transmembrane domain can be a hydrophobic domain that spans the membrane. In some embodiments, a transmembrane domain comprises an alpha-helical domain. A transmembrane domain may be functional for the stability of the receptor as a whole. In some embodiments, a transmembrane domain comprises a transmembrane domain from the most membrane proximal component of an endodomain. In some embodiments, a transmembrane domain comprises a CD3-zeta transmembrane domain. In some embodiments, a transmembrane domain allows for incorporation of an artificial TCR into a native TCR complex. In some embodiments, a transmembrane domain comprises a CD28 transmembrane domain.

An endodomain can be a functional intracellular portion of a receptor, such as a TCR or CAR. After antigen recognition, receptors cluster and a signal may be transmitted to the cell. In some embodiments, an endodomain comprises a CD3-zeta intracellular domain. In some embodiments, an endodomain comprises at least one ITAM. In some embodiments, an endodomain comprises at least 3 or at least 3 ITAMs. In some embodiments, an endodomain comprises a CD28 intracellular domain. In some embodiments, an endodomain comprises an OX40 intracellular domain. In some embodiments, an endodomain comprises a chimeric intracellular domain. For example, an endodomain can comprises a CD28 intracellular domain, an OX40 intracellular domain and a CD3-zeta intracellular domain.

IV. T Cells

T cells belong to a group of white blood cells known as lymphocytes, and play a central role in cell-mediated immunity. T cells include CD4$^+$ T cells (helper T cells) and CD8$^+$ T cells (cytotoxic T cells). CD4$^+$ T cells can assist other white blood cells in immunologic processes, including maturation of B-cells and activation of cytotoxic T cells and macrophages. CD4$^+$ T cells are activated when presented with peptide antigens by MHC class II molecules expressed on the surface of antigen presenting cells (APCs). Once activated, the T cells can divide rapidly and secrete cytokines that regulate the active immune response. CD8$^+$ T cells can destroy virally infected cells and tumor cells, and, can also be implicated in transplant rejection. CD8$^+$ T cells can recognize their targets by binding to antigen associated with MHC class I, which is present on the surface of nearly every cell of the body. Most T cells have a T cell receptor (TCR). The ability of T cells to recognize antigens associated with various cancers or infectious organisms is conferred by its TCR, which is made up of both an alpha ($\alpha$) chain and a beta ($\beta$) chain or a gamma ($\gamma$) and a delta ($\delta$) chain. The proteins which make up these chains are encoded by DNA, which employs a unique mechanism for generating the diversity of the TCR. This multi-subunit immune recognition receptor can associate with the CD3 complex and bind peptides presented by the MHC class I and II proteins on the surface of antigen-presenting cells (APCs). The first signal in activation of T cells can be provided by binding of the T cell receptor to a short peptide presented by the MHC on another cell. This ensures that only a T cell with a TCR specific to that peptide is activated. The partner cell is usually an antigen presenting cell such as a professional antigen presenting cell, usually a dendritic cell in the case of naive responses, although B-cells and macrophages can be important APCs. Binding of a TCR to the antigenic peptide on the APC can be a central event in T cell activation, which occurs at an immunological synapse at the point of contact between the T cell and the APC.

T cells can be prepared according to methods known in the art. T cells can be an enriched T cell preparation, an APC-depleted cell preparation, or a substantially purified T cell preparation. T cells can be a mixed T cell population or a purified T cell subset. T cells can be an enriched T cell preparation containing a number or percentage of T cells that is increased with respect to an isolated population of T cells.

T cells, or a subset of T cells, can be obtained from various lymphoid tissues. T cells can be obtained from a number of sources, including peripheral blood mononuclear cells (PBMCs), bone marrow, thymus, tissue biopsy, tumor, lymph node tissue, gut associated lymphoid tissue, mucosa associated lymphoid tissue, spleen tissue, lymphoid tissue, and tumors. The term "peripheral blood lymphocytes" (PBL) and its grammatical equivalents as used herein can refer to lymphocytes that circulate in the blood (e.g., peripheral blood). Peripheral blood lymphocytes can refer to lymphocytes that are not localized to organs. Peripheral blood lymphocytes can comprise T cells, NK cells, B cell, or any combinations thereof.

The method can comprise isolating T cells from a subject. The method can comprise obtaining T cells isolated from a subject. T cells can be obtained from T cell lines. T cells can be obtained from autologous sources. T cells can be obtained from allogeneic sources. T cells may also be obtained from a xenogeneic source, for example, from mouse, rat, non-human primate, and pig.

T cells can be an APC-depleted cell preparation. T cells can be substantially free of APCs. For example, T cells can comprise T cells separated from over 75% of APCs. In an exemplary embodiment, peripheral blood mononuclear cells (PBMCs) can be obtained from blood, e.g., in heparinized vials. PBMCs can be separated from red blood cells by centrifugation and PBMCs recovered from the interface. The recovered PBMCs optionally can be washed (e.g., with PBS).

T cell purification can be achieved, for example, by positive or negative selection including, but not limited to, the use of antibodies directed to CD2, CD3, CD4, CD5, CD8, CD14, CD19, and/or MHC class II molecules. A specific T cell subset, such as CD28$^+$, CD4$^+$, CD8$^+$, CD45RA$^+$, and/or CD45RO$^+$ T cells, can be isolated by positive or negative selection techniques. For example, CD3$^+$, CD28$^+$ T cells can be positively selected using CD3/CD28 conjugated magnetic beads. In one aspect of the present invention, enrichment of a T cell population by negative selection can be accomplished with a combination of antibodies directed to surface markers unique to the negatively selected cells.

For example, a T cell sample can comprise cells from a subject's circulating blood and can be obtained by apheresis or leukopheresis. A T cell sample may contain lymphocytes, including T cells, monocytes, granulocytes, B cells, other nucleated white blood cells, red blood cells, and/or platelets. Undesirable components of the T cell sample can be removed and the remaining T cells can be suspended in culture media. For example, cells can be washed to remove the plasma fraction. For example, T cells can be isolated from peripheral blood lymphocytes by lysing the red blood cells and by centrifugation through a PERCOLL™ gradient.

In some embodiments, a T cell comprises at least one T cell receptor (TCR) comprising a TCR alpha chain construct and/or TCR beta chain construct capable of specifically binding to an epitope from RAS in complex with a human MHC. In some embodiments, a T cell comprises at least one T cell receptor (TCR) comprising a TCR alpha chain construct and/or TCR beta chain construct capable of specifically binding to an epitope from TMPRSS2:ERG in complex with a human MHC. In some embodiments, a T cell comprises at least one T cell receptor (TCR) comprising a TCR alpha chain construct and/or TCR beta chain construct capable of specifically binding to an epitope from GATA3 in complex with a human MHC. In some embodiments, a host cell comprises at least one TCR disclosed herein, wherein the host cell is a CD4$^+$ T cell. In some embodiments, the host cell is a CD8$^+$ T cell. In some embodiments, the host cell is an autologous cell. In some embodiments, the host cell is an allogeneic cell. In some embodiments, the host cell is a human cell. In some other cases, a host cell may be natural killer (NK) cell, a B cell, or an immortalized cell line.

In some embodiments, T cells can be obtained by positive selection and/or negative selection. In positive selection, an affinity agent (such as an antibody, an antibody fragment, and aptamer) can be used to bind a cell surface marker expressed on the population of cells, for example, CD3 for T cells. Using the affinity agent, the T cells can be labeled. The labeled T cells can then be enriched using various methods that are well-known in the art. Non-limiting examples of those methods include fluorescent-activated cell sorting (FACS) and (para)magnetic particle-based cell separation (e.g. MACS cell separation kits from Miltenyi Biotec).

In negative selection, affinity agents can be used to bind cell surface markers expressed on blood cells other than the desired population. For example, when attempting to isolate T cells, a cocktail of affinity agents can be used to label B cells, NK cells, monocytes, platelets, dendritic cells, granulocytes and erythrocytes. The labeled cells can then be depleted, leaving the T cells enriched. The exemplary methods to deplete labeled cells include FACS and (para)magnetic particle-based cell separation.

In addition to labeling-based isolation, special growth condition may be used to promote the growth of one particular cell population. For example, the special growth condition can be obtained using special cytokines or growth factors. For another example, in culture media containing phytohemagglutinin (PHA), IL-2, and/or IL-15, T cells may preferentially proliferate.

In some situations, non-functional markers may be used to isolate T cells since binding of functional markers such as binding of CD3 by anti-CD3 antibody (alone or conjugated to magnetic particles) may trigger unwanted signaling events on T cells. Therefore, a cocktail of antibodies against CD14, CD15, CD16, CD19, CD34, CD36, CD56, CD123, and CD235a (glycophorin A) can be used to isolate T cells.

Detailed protocol can be found in published literatures (e.g. see Lefort et al., J Vis Exp. 2010; (40): 2017) which are incorporated by reference herein. T cell isolation kits can be obtained from, for example, STEMCELL Technologies, Thermofisher, and Miltenyi Biotec.

The T cell described herein may be an allogeneic T cell.

In some embodiments, the T cell may be a genetically-modified cell comprising in its genome a modified human T cell receptor (TCR) alpha chain gene and/or a modified human TCR beta chain gene, wherein the cell has reduced cell-surface expression of the endogenous TCR.

Gene-editing nucleases may be employed in order to disrupt components of the TCR. The TCR alpha chain (TCRα) is encoded by a single TRAC gene and pairs with the TCR beta chain (TCRβ) encoded by two TCRB genes. Since the TCR α/β dimer can produce a fully functioning TCR complex, disrupting TCRα and/or TCRβ function may reduce (even eliminate) endogenous TCR expression.

Various methods may be used to disrupt endogenous TCRα or TCRβ genes. For example, four classes of gene editing proteins exist that share a common mode of action in binding a user defined sequence of DNA and mediating a double stranded DNA break (DSB). Zinc finger nucleases (ZFN) are heterodimeric arrays that co-localize at a target DNA site. ZFNs include individual finger subunits that bind DNA and are tethered to the FokI nuclease domain that cleaves DNA. Transcription activator-like effector nucleases (TALEN) include repeating units that bind DNA by virtue of a hypervariable two amino acid sequence (repeat variable diresidue; RVD) that governs DNA base recognition. Similar to ZFNS, TALENs function as dimeric proteins that are fused to the FokI endonuclease domain for DSB generation. Meganucleases (MN) are monomeric proteins with innate nuclease activity that are derived from bacterial homing endonucleases and engineered for a unique target site. The clustered regularly interspaced short palindromic repeats (CRISPR) and associated Cas9 nuclease platform involves a small guide RNA (gRNA) transcript that contacts a target DNA sequence via Watson-Crick base pairing and the Cas9 nuclease that cleaves the DNA.

In some embodiments, introducing the genome-editing nuclease into the T cell includes introducing into the T cell a polynucleotide that encodes the genome-editing nuclease.

In some embodiments, introducing the genome-editing nuclease into the T cell includes introducing into the T cell a Cas9 polypeptide. In some embodiments, the genome-editing nuclease includes a TALEN nuclease, a CRISPR/Cas9 nuclease, or a megaTAL nuclease.

In some embodiments, the CRISPR/Cas9 nuclease is derived from either *Streptococcus pyogenes* or *Staphylococcus aureus*. In some of these embodiments, the CRISPR/Cas9 nuclease includes a nuclease-resistant gRNA such as, for example, at least one 2'-OMe-phosphorothioate modified base, at least one 2'-O-methyl modified base, or at least one 2'-O-methyl 3' thioPACE modified base.

In some embodiments, the TALEN nuclease or the megaTAL nuclease is encoded by an RNA that has an exogenous polyadenylation signal.

In some embodiments, the method described herein may further include culturing the T cell under conditions effective for expanding the population of genome-modified T cells.

In some embodiments, disrupting expression of TCRα and/or TCRβ further disrupts assembly of TCRα and TCRβ. In some embodiments, disrupting expression of TCRα further disrupts formation of a complex between TCR and CD3. In some embodiments, disrupting expression of TCRα involves further disrupting assembly of TCRα and TCRβ.

In some embodiments, a genetically-modified T cell comprises a disrupted TCR alpha chain and/or beta chain and an inactivated gene encoding immune checkpoint protein such as PD1 and CTLA-4. This may be made possible by gene inactivation using specific TALE-nucleases directed against TCRalpha or TCRbeta coupled with inactivation of genes encoding immune checkpoint protein such as PD1 and CTLA-4.

In some embodiments, the genetic modification relies on the inactivation of one gene, or two genes selected from the group consisting of PD1, CTLA-4, LAG3, Tim3, BTLA, BY55, TIGIT, B7H5, LAIR1, SIGLEC10, 2B4, TCR alpha and TCR beta. In some embodiments, the genetic modification relies on the inactivation of two genes selected from the group consisting of PD1 and TCR alpha, PD1 and TCR beta, CTLA-4 and TCR alpha, CTLA-4 and TCR beta, LAG 3 and TCR alpha, LAG 3 and TCR beta, Tim3 and TCR alpha, Tim3 and TCR beta, BTLA and TCR alpha, BTLA and TCR beta, BY55 and TCR alpha, BY55 and TCR beta, TIGIT and TCR alpha, TIGIT and TCR beta, B7H5 and TCR alpha, B7H5 and TCR beta, LAIR' and TCR alpha, LAIR1 and TCR beta, SIGLEC10 and TCR alpha, SIGLEC10 and TCR beta, 2B4 and TCR alpha, 2B4 and TCR beta. In some embodiments, the genetic modification relies on the inactivation of more than two genes. The genetic modification may be operated ex-vivo.

V. TCRs Specific to RAS Peptide-MHC Complexes

Provided herein is a nucleic acid encoding at least one T cell receptor (TCR) comprising a TCR alpha chain construct and/or TCR beta chain construct capable of specifically binding to an epitope from RAS in complex with a human MHC, wherein the TCR alpha chain construct comprises a complementarity determining region 3 (CDR3) having at least 84% sequence identity to an amino acid sequence selected from SEQ ID NOs: 3, 18, 33, 49, 65, 81, 97, 113, 241, 257, 273, 289, 305, 321, 337, 353, 369, 385, 401, 417, and 433 and/or wherein the TCR beta chain construct comprises a complementarity determining region 3 (CDR3) having at least 84% sequence identity to an amino acid sequence selected from SEQ ID NOs: 6, 21, 36, 52, 68, 84, 100, 116, 244, 260, 276, 292, 308, 324, 340, 356, 372, 388, 404, 420, and 436.

Provided herein is a nucleic acid encoding at least one T cell receptor (TCR) comprising a TCR alpha chain construct and/or TCR beta chain construct capable of specifically binding to an epitope from RAS in complex with a human MHC, wherein the epitope from RAS comprises a region having at least 70% sequence identity to an amino acid sequence selected from SEQ ID NOs: 15, 30, 45, 46, 61, 62, 77, 78, 93, 94, 109, 110, 125, 126, 219-222, 253, 254, 269, 270, 285, 286, 301, 302, 317, 318, 333, 334, 349, 350, 365, 366, 381, 382, 397, 398, 413, 414, 429, 430, 445 and 446.

Provided herein is an isolated nucleic acid or a cell comprising a recombinant nucleic acid, wherein the nucleic acid encodes at least one T cell receptor (TCR) comprising a TCR alpha chain construct and/or a TCR beta chain construct; wherein the TCR specifically binds to an epitope from RAS in complex with a human MHC encoded by an HLA-A03:01 allele. In some embodiments, the alpha chain construct comprises a variable region having at least 80% sequence identity to an amino acid sequence selected from SEQ ID NOs: 71, 87, 103, 295, 311, 327, 343, 359 and 391, wherein the TCR specifically binds to an epitope from RAS in complex with a human MHC encoded by an HLA-A03:01 allele. In some embodiments, the TCR beta chain construct comprises a variable region having at least 80% sequence identity to an amino acid sequence selected from SEQ ID NOs: 74, 90, 106, 298, 314, 330, 346, 362 and 394, wherein the TCR specifically binds to an epitope from RAS in complex with a human MHC encoded by an HLA-A03:01 allele.

In some embodiments, the TCR alpha chain construct as described above comprises a complementarity determining region 1 (CDR1) having at least 90% sequence identity to an amino acid sequence selected from SEQ ID NOs: 63, 79, 95, 287, 303, 319, 335, 351 and 383. In some embodiments, the TCR beta chain construct as described above comprises a complementarity determining region 1 (CDR1) having at least 90% sequence identity to an amino acid sequence selected from SEQ ID NOs: 66, 82, 98, 290, 306, 322, 338, 354 and 386. In some embodiments, the TCR alpha chain construct comprises a complementarity determining region 2 (CDR2) having at least 90% sequence identity to an amino acid sequence selected from SEQ ID NOs: 64, 80, 96, 288, 304, 320, 336, 352 and 384. In some embodiments, the TCR beta chain construct comprises a complementarity determining region 2 (CDR2) having at least 90% sequence identity to an amino acid sequence selected from SEQ ID NOs: 67, 83, 99, 291, 307, 323, 339, 355 and 387. In some embodiments, the TCR alpha chain construct comprises a complementarity determining region 3 (CDR3) having at least 90% sequence identity to an amino acid sequence selected from SEQ ID NOs: 65, 81, 97, 289, 305, 321, 337, 353 and 385. In some embodiments, the TCR beta chain construct comprises a complementarity determining region 3 (CDR3) having at least 90% sequence identity to an amino acid sequence selected from SEQ ID NOs: 68, 84, 100, 292, 308, 324, 340, 356 and 388.

Provided herein is an isolated nucleic acid or a cell comprising a recombinant nucleic acid, wherein the nucleic acid encodes at least one T cell receptor (TCR) comprising a TCR alpha chain construct and/or a TCR beta chain construct; wherein the TCR specifically binds to an epitope from RAS in complex with a human MHC encoded by an HLA-A02:01 allele. In some embodiments, the alpha chain construct comprises a variable region having at least 80% sequence identity to an amino acid sequence selected from SEQ ID NOs: 9 and 24 wherein the TCR specifically binds to an epitope from RAS in complex with a human MHC encoded by an HLA-A02:01 allele. In some embodiments, the TCR beta chain construct comprises a variable region having at least 80% sequence identity to an amino acid sequence selected from SEQ ID NOs: 12 and 27, wherein the TCR specifically binds to an epitope from RAS in complex with a human MHC encoded by an HLA-A02:01 allele.

In some embodiments, the TCR alpha chain construct as described above comprises a complementarity determining region 1 (CDR1) having at least 90% sequence identity to an amino acid sequence selected from SEQ ID NOs: 1 and 16. In some embodiments, the TCR beta chain construct as described above comprises a complementarity determining region 1 (CDR1) having at least 90% sequence identity to an amino acid sequence selected from SEQ ID NOs: 4 and 19. In some embodiments, the TCR alpha chain construct comprises a complementarity determining region 2 (CDR2) having at least 90% sequence identity to an amino acid sequence selected from SEQ ID NOs: 2 and 17. In some embodiments TCR beta chain construct comprises a complementarity determining region 2 (CDR2) having at least 90% sequence identity to an amino acid sequence selected from SEQ ID NOs: 5 and 20. In some embodiments, the TCR alpha chain construct comprises a complementarity determining region 3 (CDR3) having at least 90% sequence identity to an amino acid sequence selected from SEQ ID NOs: 3 and 18. In some embodiments, the TCR beta chain construct comprises a complementarity determining region 3 (CDR3) having at least 90% sequence identity to an amino acid sequence selected from SEQ ID NOs: 6 and 21.

Provided herein is an isolated nucleic acid or a cell comprising a recombinant nucleic acid, wherein the nucleic acid encodes at least one T cell receptor (TCR) comprising a TCR alpha chain construct and/or a TCR beta chain construct; wherein the TCR specifically binds to an epitope from RAS in complex with a human MHC encoded by an HLA-A11:01 allele. In some embodiments, the TCR alpha chain construct comprises a variable region having at least 80% sequence identity to an amino acid sequence selected from SEQ ID NOs: 39, 55, 122, 247, 263, 279, 375, 407, 423 and 439, wherein the TCR specifically binds to an epitope from RAS in complex with a human MHC encoded by an HLA-A11:01 allele. In some embodiments, the TCR beta chain construct comprises a variable region having at least 80% sequence identity to an amino acid sequence selected from SEQ ID NOs: 42, 58, 125, 250, 266, 282, 378, 413, 426 and 442, wherein the TCR specifically binds to an epitope from RAS in complex with a human MHC encoded by an HLA-A11:01 allele.

In some embodiments, the TCR alpha chain construct as described above comprises a complementarity determining region 1 (CDR1) having at least 90% sequence identity to an amino acid sequence selected from SEQ ID NOs: 31, 47, 111, 239, 255, 271, 367, 399, 415, and 431. In some embodiments, the TCR beta chain construct as described above comprises a complementarity determining region 1 (CDR1) having at least 90% sequence identity to an amino acid sequence selected from SEQ ID NOs: 34, 50, 114, 242, 258, 274, 370, 402, 418, and 434. In some embodiments, the TCR alpha chain construct comprises a complementarity determining region 2 (CDR2) having at least 90% sequence identity to an amino acid sequence selected from SEQ ID NOs: 32, 48, 112, 240, 256, 272, 368, 400, 416, and 432. In some embodiments, the TCR beta chain construct comprises a complementarity determining region 2 (CDR2) having at least 90% sequence identity to an amino acid sequence selected from SEQ ID NOs: 35, 51, 115, 243, 259, 275, 371, 403, 419, and 435. In some embodiments, the TCR alpha chain construct comprises a complementarity determining region 3 (CDR3) having at least 90% sequence identity to an amino acid sequence selected from SEQ ID NOs: 33, 49, 113, 241, 257, 273, 369, 401, 417, and 433. In some embodiments, the TCR beta chain construct comprises a complementarity determining region 3 (CDR3) having at least 90% sequence identity to an amino acid sequence selected from SEQ ID NOs:36, 52, 116, 228, 244, 260, 276, 372, 404, 420, and 434. In some embodiments, the TCR alpha chain construct comprises a variable region having at least 80% sequence identity to SEQ ID NO: 9; and the TCR beta chain construct comprises a variable region having at least 80% sequence identity to SEQ ID NO: 12. In some embodiments, the TCR alpha chain construct comprises a CDR1 of SEQ ID NO: 1, a CDR2 of SEQ ID NO: 2, and a CDR3 of SEQ ID NO: 3; and the TCR beta chain construct comprises a CDR1 of SEQ ID NO: 4, a CDR2 of SEQ ID NO: 5, and a CDR3 of SEQ ID NO: 6. In some embodiments, the TCR alpha chain construct comprises a variable region having at least 80% sequence identity to SEQ ID NO: 24; and the TCR beta chain construct comprises a variable region having at least 80% sequence identity to SEQ ID NO: 27. In some embodiments, the TCR alpha chain construct comprises a CDR1 of SEQ ID NO: 16, a CDR2 of SEQ ID NO: 17, and a CDR3 of SEQ ID NO: 18; and the TCR beta chain construct comprises a CDR1 of SEQ ID NO: 19, a CDR2 of SEQ ID NO: 20, and a CDR3 of SEQ ID NO: 21. In some embodiments, the TCR alpha chain construct comprises a variable region having at least 80% sequence identity to SEQ ID NO: 39; and the TCR beta chain construct comprises a variable region having at least 80% sequence identity to SEQ ID NO: 42. In some embodiments, the TCR alpha chain construct comprises a CDR1 of SEQ ID NO: 31, a CDR2 of SEQ ID NO: 32, and a CDR3 of SEQ ID NO: 33; and the TCR beta chain construct comprises a CDR1 of SEQ ID NO: 34, a CDR2 of SEQ ID NO: 35, and a CDR3 of SEQ ID NO: 36. In some embodiments, the TCR alpha chain construct comprises a variable region having at least 80% sequence identity to SEQ ID NO: 55; and the TCR beta chain construct comprises a variable region having at least 80% sequence identity to SEQ ID NO: 58. In some embodiments, the TCR alpha chain construct comprises a CDR1 of SEQ ID NO: 47, a CDR2 of SEQ ID NO: 48, and a CDR3 of SEQ ID NO: 49; and the TCR beta chain construct comprises a CDR1 of SEQ ID NO: 50, a CDR2 of SEQ ID NO: 51, and a CDR3 of SEQ ID NO: 52. In some embodiments, the TCR alpha chain construct comprises a variable region having at least 80% sequence identity to SEQ ID NO: 71; and the TCR beta chain construct comprises a variable region having at least 80% sequence identity to SEQ ID NO: 74. In some embodiments, the TCR alpha chain construct comprises a CDR1 of SEQ ID NO: 63, a CDR2 of SEQ ID NO: 64, and a CDR3 of SEQ ID NO: 65; and the TCR beta chain construct comprises a CDR1 of SEQ ID NO: 66, a CDR2 of SEQ ID NO: 67, and a CDR3 of SEQ ID NO: 68. In some embodiments, the TCR alpha chain construct comprises a variable region having at least 80% sequence identity to SEQ ID NO: 87; and the TCR beta chain construct comprises a variable region having at least 80% sequence identity to SEQ ID NO: 90. In some embodiments, the TCR alpha chain construct comprises a CDR1 of SEQ ID NO: 79, a CDR2 of SEQ ID NO: 80, and a CDR3 of SEQ ID NO: 81; and the TCR beta chain construct comprises a CDR1 of SEQ ID NO: 82, a CDR2 of SEQ ID NO: 83, and a CDR3 of SEQ ID NO: 84. In some embodiments, the TCR alpha chain construct comprises a variable region having at least 80% sequence identity to SEQ ID NO: 103; and the TCR beta chain construct comprises a variable region having at least 80% sequence identity to SEQ ID NO: 106. In some embodiments, the TCR alpha chain construct comprises a CDR1 of SEQ ID NO: 95, a CDR2 of SEQ ID NO: 96, and a CDR3 of SEQ ID NO: 97; and the TCR beta chain construct comprises a CDR1 of SEQ ID NO: 98, a CDR2 of SEQ ID NO: 99, and a CDR3 of SEQ ID NO: 100. In some embodiments, the TCR alpha chain construct comprises a variable region having at least 80% sequence identity to SEQ ID NO: 119; and the TCR beta chain construct comprises a variable region having at least 80% sequence identity to SEQ ID NO: 122. In some embodiments, the TCR alpha chain construct comprises a CDR1 of SEQ ID NO: 111, a CDR2 of SEQ ID NO: 112, and a CDR3 of SEQ ID NO: 113; and the TCR beta chain construct comprises a CDR1 of SEQ ID NO: 114, a CDR2 of SEQ ID NO: 115, and a CDR3 of SEQ ID NO: 1161n some embodiments, the TCR alpha chain construct comprises a variable region having at least 80% sequence identity to SEQ ID NO: 263; and the TCR beta chain construct comprises a variable region having at least 80% sequence identity to SEQ ID NO: 266. In some embodiments, the TCR alpha chain construct comprises a CDR1 of SEQ ID NO: 255, a CDR2 of SEQ ID NO: 256, and a CDR3 of SEQ ID NO: 257; and the TCR beta chain construct comprises a CDR1 of SEQ ID NO: 258, a CDR2 of SEQ ID NO: 259, and a CDR3 of SEQ ID NO: 260. In some embodiments, the TCR alpha chain construct comprises a variable region having at least 80% sequence identity to SEQ ID NO: 279; and the TCR beta chain construct comprises a variable region having at least 80% sequence identity to SEQ ID NO: 282. In some embodiments, the TCR alpha chain construct comprises a CDR1 of SEQ ID NO: 271, a CDR2 of SEQ ID NO: 272, and a CDR3 of SEQ ID NO: 273; and the TCR beta chain construct comprises a CDR1 of SEQ ID NO: 274, a CDR2 of SEQ ID NO: 275, and a CDR3 of SEQ ID NO: 276. In some embodiments, the TCR alpha chain construct comprises a variable region having at least 80% sequence identity to SEQ ID NO: 295; and the TCR beta chain construct comprises a variable region having at least 80% sequence identity to SEQ ID NO: 298. In some embodiments, the TCR alpha chain construct comprises a CDR1 of SEQ ID NO: 287, a CDR2 of SEQ ID NO: 288, and a CDR3 of SEQ ID NO: 289; and the TCR beta chain construct comprises a CDR1 of SEQ ID NO: 290, a CDR2 of SEQ ID NO: 291, and a CDR3 of SEQ ID NO: 292. In some embodiments, the TCR alpha chain construct comprises a variable region having at least 80% sequence identity to SEQ ID NO: 311; and the TCR beta chain construct comprises a variable region having at least 80% sequence identity to SEQ ID NO: 314. In some embodiments, the TCR alpha chain construct comprises a CDR1 of SEQ ID NO: 303, a CDR2 of SEQ ID NO: 304, and a CDR3 of SEQ ID NO: 305; and the TCR beta chain construct comprises a CDR1 of SEQ ID NO: 306, a CDR2 of SEQ ID NO: 307, and a CDR3 of SEQ ID NO: 308. In some embodiments, the TCR alpha chain construct comprises a variable region having at least 80% sequence identity to SEQ ID NO: 327; and the TCR beta chain construct comprises a variable region having at least 80% sequence identity to SEQ ID NO: 330. In some embodiments, the TCR alpha chain construct comprises a CDR1 of SEQ ID NO: 319, a CDR2 of SEQ ID NO: 320, and a CDR3 of SEQ ID NO: 321; and the TCR beta chain construct comprises a CDR1 of SEQ ID NO: 322, a CDR2 of SEQ ID NO: 323, and a CDR3 of SEQ ID NO: 324. In some embodiments, the TCR alpha chain construct comprises a variable region having at least 80% sequence identity to SEQ ID NO: 343; and the TCR beta chain construct comprises a variable region having at least 80% sequence identity to SEQ ID NO: 346. In some embodiments, the TCR alpha chain construct comprises a CDR1 of SEQ ID NO: 335, a CDR2 of SEQ ID NO: 336, and a CDR3 of SEQ ID NO: 337; and the TCR beta chain construct comprises a CDR1 of SEQ ID NO: 338, a CDR2 of SEQ ID NO: 339, and a CDR3 of SEQ ID NO: 340. In some embodiments, the TCR alpha chain construct comprises a variable region having at least 80% sequence identity to SEQ ID NO: 343; and the TCR beta chain construct comprises a variable region having at least 80% sequence identity to SEQ ID NO: 346. In some embodiments, the TCR alpha chain construct comprises a CDR1 of SEQ ID NO: 351, a CDR2 of SEQ ID NO: 352, and a CDR3 of SEQ ID NO: 353; and the TCR beta chain construct comprises a CDR1 of SEQ ID NO: 354, a CDR2 of SEQ ID NO: 355, and a CDR3 of SEQ ID NO: 356. In some embodiments, the TCR alpha chain construct comprises a variable region having at least 80% sequence identity to SEQ ID NO: 343; and the TCR beta chain construct comprises a variable region having at least 80% sequence identity to SEQ ID NO: 346. In some embodiments, the TCR alpha chain construct comprises a CDR1 of SEQ ID NO: 367, a CDR2 of SEQ ID NO: 368, and a CDR3 of SEQ ID NO: 369; and the TCR beta chain construct comprises a CDR1 of SEQ ID NO: 370, a CDR2 of SEQ ID NO: 371, and a CDR3 of SEQ ID NO: 372. In some embodiments, the TCR alpha chain construct comprises a variable region having at least 80% sequence identity to SEQ ID NO: 391; and the TCR beta chain construct comprises a variable region having at least 80% sequence identity to SEQ ID NO: 394. In some embodiments, the TCR alpha chain construct comprises a CDR1 of SEQ ID NO: 383, a CDR2 of SEQ ID NO: 384, and a CDR3 of SEQ ID NO: 385; the TCR beta chain construct comprises a CDR1 of SEQ ID NO: 386, a CDR2 of SEQ ID NO: 387, and a CDR3 of SEQ ID NO: 388. In some embodiments, the TCR alpha chain construct comprises a variable region having at least 80% sequence identity to SEQ ID NO: 391; and the TCR beta chain construct comprises a variable region having at least 80% sequence identity to SEQ ID NO: 394. In some embodiments, the TCR alpha chain construct comprises a CDR1 of SEQ ID NO: 399, a CDR2 of SEQ ID NO: 400, and a CDR3 of SEQ ID NO: 401; and the TCR beta chain construct comprises a CDR1 of SEQ ID NO: 402, a CDR2 of SEQ ID NO: 403, and a CDR3 of SEQ ID NO: 404. In some embodiments, the TCR alpha chain construct comprises a variable region having at least 80% sequence identity to SEQ ID NO: 423; and the TCR beta chain construct comprises a variable region having at least 80% sequence identity to SEQ ID NO: 426. In some embodiments, the TCR alpha chain construct comprises a CDR1 of SEQ ID NO: 415, a CDR2 of SEQ ID NO: 416, and a CDR3 of SEQ ID NO: 417; and the TCR beta chain construct comprises a CDR1 of SEQ ID NO: 418, a CDR2 of SEQ ID NO: 419, and a CDR3 of SEQ ID NO: 420. In some embodiments, the TCR alpha chain construct comprises a variable region having at least 80% sequence identity to SEQ ID NO: 391; and the TCR beta chain construct comprises a variable region having at least 80% sequence identity to SEQ ID NO: 394. In some embodiments, the TCR alpha chain construct comprises a CDR1 of SEQ ID NO: 431, a CDR2 of SEQ ID NO: 432, and a CDR3 of SEQ ID NO: 433; and the TCR beta chain construct comprises a CDR1 of SEQ ID NO: 434, a CDR2 of SEQ ID NO: 435, and a CDR3 of SEQ ID NO: 426.

In various embodiments, the nucleic acid sequence encoding a TCR is codon optimized.

Mutations in any one of the three ras genes, H-ras, K-ras and N-ras are one of the most common events in human tumorigenesis. About 30% of all human tumors are found to carry at least one mutation in any of the canonical ras genes. Ras mutations are evident in, for example, adenocarcinoma of the biliary tract, transitional cell carcinoma of the bladder, breast carcinoma, cervical adenocarcinoma, colon adenocarcinoma, colon adenoma, neuroblastoma (autonomic ganglia), acute myeloid leukemia, chronic myeloid leukemia, chronic myelomonocytic leukemia, juvenile myelomonocytic leukemia, acute lymphoblastic leukemia, Burkitt's lymphoma, Hodgkin's lymphoma, plasma cell myeloma, hepatocellular carcinoma, large cell carcinoma, non-small cell carcinoma, ductal carcinoma, endocrine tumor, prostate adenocarcinoma, basal cell carcinoma, squamous cell carcinoma, malignant melanoma, angiosarcoma, leiomyosarcoma, liposarcoma, rhabdomyosarcoma, myxoma, malignant fibrous histiocytoma, pleomorphic sarcoma, germinoma, seminoma, anaplastic carcinoma, follicular carcinoma, papillary carcinoma and Hurthle cell carcinoma. Ras mutations are found in cancers affecting many tissues and organs of the body, for example, lung, liver, breast, bladder, colon, cervix, pancreas, prostate gland, stomach, thyroid, testis, soft tissue, skin and blood.

In various embodiments, the TCR binds to an MHC:RAS peptide complex, wherein the RAS peptide comprises a G12V mutation. In various embodiments, the TCR binds to an MHC:RAS peptide complex, wherein the RAS peptide comprises a G12C mutation. In various embodiments, the TCR binds to an MHC:RAS peptide complex, wherein the RAS peptide comprises a G12D mutation. In various embodiments, the TCR binds to an MHC:RAS peptide complex, wherein the RAS peptide comprises a mutation at Q61. In various embodiments, the TCR binds to an MHC: RAS peptide complex, wherein the RAS peptide comprises a sequence of VVGAVGVGK, VVVGAVGVGK, VVGADGVGK, VVVGADGVGK, VVGACGVGK, VVVGACGVGK, KLVVVGACGV, LVVVGACGV, KLVVVGADGV, LVVVGADGV, KLVVVGAVGV or LVVVGAVGV.

In various embodiments, the TCR binds to an MHC:RAS peptide complex, wherein the human MHC is encoded by an HLA-A02:01 allele. In various embodiments, the TCR binds to an MHC:RAS peptide complex, wherein the human MHC is encoded by an HLA-A03:01 allele. In various embodiments, the TCR binds to an MHC:RAS peptide complex, wherein the human MHC is encoded by an HLA-A11:01 allele.

In various embodiments, the TCR binds to an MHC:RAS peptide complex, wherein the human MHC is encoded by an HLA-A02:01 allele and wherein the RAS peptide comprises a sequence of VVGAVGVGK, VVVGAVGVGK, VVGADGVGK, VVVGADGVGK, VVGACGVGK, VVVGACGVGK, KLVVVGACGV, LVVVGACGV, KLVVVGADGV, LVVVGADGV, KLVVVGAVGV or LVVVGAVGV. In various embodiments, the TCR binds to an MHC:RAS peptide complex, wherein the human MHC is encoded by an HLA-A03:01 allele and wherein the RAS peptide comprises a sequence of VVGAVGVGK, VVVGAVGVGK, VVGADGVGK, VVVGADGVGK, VVGACGVGK, VVVGACGVGK, KLVVVGACGV, LVVVGACGV, KLVVVGADGV, LVVVGADGV, KLVVVGAVGV or LVVVGAVGV. In various embodiments, the TCR binds to an MHC:RAS peptide complex, wherein the human MHC is encoded by an HLA-A11:01 allele and wherein the RAS peptide comprises a sequence of VVGAVGVGK, VVVGAVGVGK, VVGADGVGK, VVVGADGVGK, VVGACGVGK, VVVGACGVGK, KLVVVGACGV, LVVVGACGV, KLVVVGADGV, LVVVGADGV, KLVVVGAVGV or LVVVGAVGV.

In some embodiments, one TCR as disclosed herein, exhibits a specific binding affinity to an epitope peptide containing a point mutation found in cancer when the epitope peptide is in complex with an MHC encoded by the specific allele; and additionally the TCR may exhibit a different binding affinity to another epitope peptide containing a different point mutation of the same cancer protein, when the epitope peptide is in complex with an MHC encoded by the specific allele, but do not exhibit binding affinity to the WT peptide which does not contain any mutation.

VI. TCRs Specific to TMPRSS2:ERG Peptide-MHC Complexes

Provided herein is a nucleic acid encoding at least one T cell receptor (TCR) comprising a TCR alpha chain construct and/or TCR beta chain construct capable of specifically binding to an epitope from TMPRSS2:ERG in complex with a human MHC, wherein the TCR alpha chain construct and/or the TCR beta chain construct comprises a complementarity determining region 3 (CDR3) having at least 90% sequence identity to an amino acid sequence selected from SEQ ID NO: 144 and SEQ ID NO: 147.

Provided herein is a nucleic acid encoding at least one T cell receptor (TCR) comprising a TCR alpha chain construct and/or TCR beta chain construct capable of specifically binding to an epitope from TMPRSS2:ERG in complex with a human MHC, wherein the epitope from TMPRSS2:ERG comprises a region having at least 90% sequence identity to amino acid sequence SEQ ID NO: 156.

In some embodiments, the TCR alpha chain construct comprises a variable region having at least 80% sequence identity to SEQ ID NO: 150. In some embodiments, the TCR beta chain construct comprises a variable region having at least 80% sequence identity to SEQ ID NO: 153. In some embodiments, the TCR alpha chain construct and/or the TCR beta chain construct comprises a complementarity determining region 1 (CDR1) having at least 90% sequence identity to SEQ ID NO: 142 or SEQ ID NO: 145. In some embodiments, the TCR alpha chain construct and/or the TCR beta chain construct comprises a complementarity determining region 2 (CDR2) having at least 90% sequence identity to SEQ ID NO: 143 or SEQ ID NO: 146. In some embodiments, the TCR alpha chain construct comprises a variable region having at least 80% sequence identity to SEQ ID NO: 150; and the TCR beta chain construct comprises a variable region having at least 80% sequence identity to SEQ ID NO: 153. In some embodiments, the TCR alpha chain construct comprises a CDR1 of SEQ ID NO: 142, a CDR2 of SEQ ID NO: 143, and a CDR3 of SEQ ID NO: 144; and the TCR beta chain construct comprises a CDR1 of SEQ ID NO: 145, a CDR2 of SEQ ID NO: 146, and a CDR3 of SEQ ID NO: 147.

In some embodiments, a TCR comprises a TCR alpha chain construct and/or TCR beta chain construct capable of specifically binding to an epitope from TMPRSS2:ERG in complex with a human MHC, wherein the TCR alpha chain construct and/or the TCR beta chain construct comprises a complementarity determining region 3 (CDR3) having at least 60%, at least 70%, at least 80%, at least 85%, at least 90%, at least 95%, or at least 98% sequence identity to SEQ ID NO: 144 or 147.

In some embodiments, a TCR comprises a TCR alpha chain construct and/or TCR beta chain construct capable of specifically binding to an epitope from TMPRSS2:ERG in complex with a human MHC, wherein the epitope from TMPRSS2:ERG comprises a region having at least 60%, at least 70%, at least 80%, at least 85%, at least 90%, at least 95%, or at least 98% sequence identity to SEQ ID NO: 156.

In some embodiments, the TCR alpha chain construct and or TCR beta chain construct comprises a variable region having at least 60%, at least 70%, at least 80%, at least 85%, at least 90%, at least 95%, or at least 98% sequence identity to SEQ ID NO: 150 or 153.

In some embodiments, the TCR alpha chain construct and/or the TCR beta chain construct comprises a complementarity determining region 1 (CDR1) having at least 60%, at least 70%, at least 80%, at least 85%, at least 90%, at least 95%, or at least 98% sequence identity to SEQ ID NO: 142 or 145.

In some embodiments, the TCR alpha chain construct and/or the TCR beta chain construct comprises a complementarity determining region 2 (CDR2) having at least 90% sequence identity to SEQ ID NO: 143 or 146.

In some embodiments, the nucleic acid encoding a TCR alpha chain construct and/or TCR beta chain comprises a nucleic acid sequence with at least 60%, at least 70%, at least 80%, at least 85%, at least 90%, at least 95%, or at least 98% sequence identity to any one of SEQ ID NOs: 148, 149, 151, and 152. In various embodiments, the nucleic acid sequence encoding a TCR is codon optimized.

In various embodiments, the TCR binds to an MHC: TMPRSS2::ERG peptide complex, wherein the TMPRSS2:: ERG peptide comprises a gene fusion mutation. In various embodiments, the TCR binds to an MHC:TMPRSS2::ERG peptide complex, wherein the TMPRSS2::ERG peptide comprises a gene fusion mutation comprising at least two consecutive amino acids wherein the at least two consecutive amino acids comprise at least one amino acid of TMPRSS2 and at least one amino acid of ERG. In various embodiments, the TCR binds to an MHC:TMPRSS2::ERG peptide complex, wherein the TMPRSS2::ERG peptide comprises a sequence of ALNSEALSV.

In various embodiments, the human MHC is encoded by an HLA-A02:01 allele. In various embodiments, the TCR binds to an MHC:TMPRSS2::ERG peptide complex, wherein the human MHC is encoded by an HLA-A02:01 allele.

In various embodiments, the human MHC is encoded by an HLA-A02:01 allele. In various embodiments, the TCR binds to an MHC:TMPRSS2::ERG peptide complex, wherein the human MHC is encoded by an HLA-A02:01 allele wherein the TMPRSS2::ERG peptide comprises a sequence of ALNSEALSV.

VII. TCRs Specific to GATA3 Peptide-MHC Complexes

In some other embodiments, a TCR comprises a TCR alpha chain construct and/or TCR beta chain construct capable of specifically binding to an epitope from GATA3 in complex with a human MHC, wherein the TCR alpha chain construct and/or the TCR beta chain construct comprises a complementarity determining region 3 (CDR3) having at least 60%, at least 70%, at least 80%, at least 85%, at least 90%, at least 95%, or at least 98% sequence identity to SEQ ID NO: 129, 132, 191, 194, 206 or 209.

In some embodiments, a TCR comprises a TCR alpha chain construct and/or TCR beta chain construct capable of specifically binding to an epitope from GATA3 in complex with a human MHC, wherein the epitope from GATA3 comprises a region having at least 60%, at least 70%, at least 80%, at least 85%, at least 90%, at least 95%, or at least 98% sequence identity to SEQ ID NO: 141, 203 or 218.

In some embodiments, the TCR alpha chain construct and or TCR beta chain construct comprises a variable region having at least 60%, at least 70%, at least 80%, at least 85%, at least 90%, at least 95%, or at least 98% sequence identity to SEQ ID NO: 135, 138, 197, 200, 212 or 215.

In some embodiments, the TCR alpha chain construct and/or the TCR beta chain construct comprises a complementarity determining region 1 (CDR1) having at least 60%, at least 70%, at least 80%, at least 85%, at least 90%, at least 95%, or at least 98% sequence identity to SEQ ID NO: 127, 130, 189, 192, 204 or 207.

In some embodiments, the TCR alpha chain construct and/or the TCR beta chain construct comprises a complementarity determining region 2 (CDR2) having at least 60%, at least 70%, at least 80%, at least 85%, at least 90%, at least 95%, or at least 98% sequence identity SEQ ID NO: 128, 131, 190, 193, 205 or 208.

Provided herein is a nucleic acid encoding at least one T cell receptor (TCR) comprising a TCR alpha chain construct and/or TCR beta chain construct capable of specifically binding to an epitope from GATA3 in complex with a human MHC, wherein the TCR alpha chain construct and/or the TCR beta chain construct comprises a complementarity determining region 3 (CDR3) having at least 90% sequence identity to an amino acid sequence selected from SEQ ID NO: 129, 132, 191, 194, 206 or 209.

Provided herein is a nucleic acid encoding at least one T cell receptor (TCR) capable of specifically binding to a mutant GATA3 peptide in complex with a protein encoded by an HLA-A02:01, HLA-B07:02 or HLA-B08:01 allele of a subject with cancer, wherein the TCR comprises a TCR alpha chain construct and/or a TCR beta chain construct.

Provided herein is an isolated nucleic acid or a cell comprising a recombinant nucleic acid, wherein the nucleic acid encodes a T cell receptor (TCR) comprising a TCR alpha chain construct and/or a TCR beta chain construct, wherein the TCR specifically binds to a mutant GATA3 peptide in complex with an HLA-A02:01, HLA-B07:02 or HLA-B08:01 protein; comprises a complementarity determining region 3 (CDR3) having at least 90% sequence identity to SEQ ID NO: 129, 132, 191, 194, 206 or 209; and/or specifically binds to a mutant GATA3 peptide comprising a region with at least 70% sequence identity to SEQ ID NO: 141, 203 or 218.

Provided herein is a nucleic acid encoding at least one T cell receptor (TCR) comprising a TCR alpha chain construct and/or TCR beta chain construct capable of specifically binding to an epitope from GATA3 in complex with a human MHC, wherein the epitope from GATA3 comprises a region having at least 90% sequence identity to amino acid sequence SEQ ID NO: 141, 203 or 218.

In some embodiments, the TCR alpha chain construct comprises a variable region having at least 80% sequence identity to SEQ ID NO: 135, 197 or 212. In some embodiments, the TCR beta chain construct comprises a variable region having at least 80% sequence identity to SEQ ID NO: 138, 200 or 215. In some embodiments, the TCR alpha chain construct and/or the TCR beta chain construct comprises a complementarity determining region 1 (CDR1) having at least 90% sequence identity to an amino acid sequence selected from SEQ ID NO: 127, 130, 189, 192, 204 and 207. In some embodiments, the TCR alpha chain construct and/or the TCR beta chain construct comprises a complementarity determining region 2 (CDR2) having at least 90% sequence identity to an amino acid sequence selected from SEQ ID NO: 128, 131, 190, 193, 205 and 208.

In some embodiments, the TCR alpha chain construct comprises a variable region having at least 80% sequence identity to SEQ ID NO: 135; and the TCR beta chain construct comprises a variable region having at least 80% sequence identity to SEQ ID NO: 138. In some embodiments, the TCR alpha chain construct comprises a variable region having at least 80% sequence identity to SEQ ID NO: 197; and the TCR beta chain construct comprises a variable region having at least 80% sequence identity to SEQ ID NO: 200. In some embodiments, the TCR alpha chain construct comprises a variable region having at least 80% sequence identity to SEQ ID NO: 212; and the TCR beta chain construct comprises a variable region having at least 80% sequence identity to SEQ ID NO: 215.

In some embodiments, the TCR alpha chain construct comprises a CDR1 of SEQ ID NO: 127, a CDR2 of SEQ ID NO: 128, and a CDR3 of SEQ ID NO: 129; and the TCR beta chain construct comprises a CDR1 of SEQ ID NO: 130, a CDR2 of SEQ ID NO: 131, and a CDR3 of SEQ ID NO: 132. In some embodiments, the TCR alpha chain construct comprises a CDR1 of SEQ ID NO: 189, a CDR2 of SEQ ID NO: 190, and a CDR3 of SEQ ID NO: 191; and the TCR beta chain construct comprises a CDR1 of SEQ ID NO: 192, a CDR2 of SEQ ID NO: 193, and a CDR3 of SEQ ID NO: 194. In some embodiments, the TCR alpha chain construct comprises a CDR1 of SEQ ID NO: 204, a CDR2 of SEQ ID NO: 205, and a CDR3 of SEQ ID NO: 206; and the TCR beta chain construct comprises a CDR1 of SEQ ID NO: 207, a CDR2 of SEQ ID NO: 208, and a CDR3 of SEQ ID NO: 209.

In some embodiments, the nucleic acid encoding a TCR alpha chain construct and/or TCR beta chain comprises a nucleic acid sequence with at least 60%, at least 70%, at least 80%, at least 85%, at least 90%, at least 95%, or at least 98% sequence identity to any one of SEQ ID NOs: 133, 134, 136 or 137. In some embodiments, the nucleic acid encoding a TCR alpha chain construct and/or TCR beta chain comprises a nucleic acid sequence with at least 60%, at least 70%, at least 80%, at least 85%, at least 90%, at least 95%, or at least 98% sequence identity to any one of SEQ ID NOs: 195, 196, 198 or 199. In some embodiments, the nucleic acid encoding a TCR alpha chain construct and/or TCR beta chain comprises a nucleic acid sequence with at least 60%, at least 70%, at least 80%, at least 85%, at least 90%, at least 95%, or at least 98% sequence identity to any one of SEQ ID NOs: 210, 211, 213 or 214.

In various embodiments, the nucleic acid sequence encoding a TCR is codon optimized.

In various embodiments, the TCR binds to an MHC:GATA3 peptide complex, wherein the GATA peptide comprises at least one amino acid encoded by a GATA3 neoORF sequence. In various embodiments, the TCR binds to an MHC:GATA3 peptide complex, wherein the GATA peptide comprises at least 2, 3, 4, 5, 6, 7, 8, 9, 10, 11, 12, 13, 14, 15, 16, 17, 18, 19, 20, 21, 22, 23, 24 or 25 amino acids encoded by a GATA3 neoORF sequence. In various embodiments, the TCR binds to an MHC:GATA3 peptide complex, wherein the GATA peptide comprises at least one amino acid encoded by a GATA3 neoORF sequence and at least one amino acid encoded by a GATA3 wild type sequence. In various embodiments, the TCR binds to an MHC:GATA3 peptide complex, wherein the GATA peptide comprises at least 2, 3, 4, 5, 6, 7, 8, 9, 10, 11, 12, 13, 14, 15, 16, 17, 18, 19, 20, 21, 22, 23, 24 or 25 amino acids encoded by a GATA3 neoORF sequence and at least 2, 3, 4, 5, 6, 7, 8, 9, 10, 11, 12, 13, 14, 15, 16, 17, 18, 19, 20, 21, 22, 23, 24 or 25 amino acids encoded by a GATA3 wild type sequence. In various embodiments, the TCR binds to an MHC:GATA3 peptide complex, wherein the GATA peptide comprises at least one amino acid encoded by a GATA3 neoORF sequence and at least one amino acid not encoded by a GATA3 neoORF sequence. In various embodiments, the TCR binds to an MHC:GATA3 peptide complex, wherein the GATA peptide comprises at least 2, 3, 4, 5, 6, 7, 8, 9, 10, 11, 12, 13, 14, 15, 16, 17, 18, 19, 20, 21, 22, 23, 24 or 25 amino acids encoded by a GATA3 neoORF sequence and at least 2, 3, 4, 5, 6, 7, 8, 9, 10, 11, 12, 13, 14, 15, 16, 17, 18, 19, 20, 21, 22, 23, 24 or 25 amino acids not encoded by a GATA3 neoORF sequence. In various embodiments, the TCR binds to an MHC:GATA3 peptide complex, wherein each amino acid of the GATA peptide is an amino acid encoded by a GATA3 neoORF sequence. In various embodiments, the TCR binds to an MHC:GATA3 peptide complex, wherein the GATA3 peptide comprises a sequence of MLTGPPARV, KPKRDGYMF or ESKIMFATL.

In various embodiments, the human MHC is encoded by an HLA-A02:01, HLA-B07:02 or HLA-B08:01 allele. In various embodiments, the TCR binds to an MHC:GATA3 peptide complex, wherein the human MHC is encoded by an HLA-A02:01 allele. In various embodiments, the TCR binds to an MHC:GATA3 peptide complex, wherein the human MHC is encoded by an HLA-B07:02 allele. In various embodiments, the TCR binds to an MHC:GATA3 peptide complex, wherein the human MHC is encoded by an HLA-B08:01 allele.

In various embodiments, the TCR binds to an MHC:GATA3 peptide complex, wherein the human MHC is encoded by an HLA-B08:01 allele and wherein the GATA3 peptide comprises a sequence of MLTGPPARV, KPKRDGYMF or ESKIMFATL.

VIII. TCRs Specific to BTK Peptide-MHC Complexes

The BTK gene can encode a Bruton tyrosine kinase (BTK) protein, which can be related to the development and maturation of B cells. The BTK protein can transmit chemical signals that instruct B cells to mature and produce antibodies.

Provided herein is a nucleic acid encoding at least one T cell receptor (TCR) comprising a TCR alpha chain construct and/or TCR beta chain construct capable of specifically binding to an epitope from BTK in complex with a human MHC, wherein the TCR alpha chain construct comprises a complementarity determining region 3 (CDR3) having at least 90% sequence identity to an amino acid sequence selected from SEQ ID NO: 161 and SEQ ID NO: 176, or wherein the TCR beta chain construct comprises a complementarity determining region 3 (CDR3) having at least 90% sequence identity to an amino acid sequence selected from SEQ ID NO: 164 and SEQ ID NO: 179.

Also provided herein is an isolated nucleic acid or a cell comprising a recombinant nucleic acid, wherein the nucleic acid encodes a T cell receptor (TCR) comprising a TCR alpha chain construct and/or a TCR beta chain construct, wherein the TCR specifically binds to a mutant BTK peptide in complex with an HLA-A02:01 protein; comprises a complementarity determining region 3 (CDR3) having at least 90% sequence identity to SEQ ID NO: 161, 164, 176, or 179; and/or specifically binds to a mutant BTK peptide comprising a region with at least 70% sequence identity to SEQ ID NO: 173 or 188.

Also provided herein is a nucleic acid encoding at least one T cell receptor (TCR) comprising a TCR alpha chain construct and/or TCR beta chain construct capable of specifically binding to an epitope from BTK in complex with a human MHC, wherein the epitope from BTK comprises a region having at least 90% sequence identity to amino acid sequence SEQ ID NO: 173 or 188.

In some embodiments, the TCR alpha chain construct comprises a variable region having at least 80% sequence identity to SEQ ID NO: 167 or 182.

In some embodiments, the TCR beta chain construct comprises a variable region having at least 80% sequence identity to SEQ ID NO: 170 or 185.

In some embodiments, the TCR alpha chain construct and/or the TCR beta chain construct comprises a complementarity determining region 1 (CDR1) having at least 90% sequence identity to an amino acid sequence selected from SEQ ID NOs: 159, 162, 174, and 177.

In some embodiments, the TCR alpha chain construct and/or the TCR beta chain construct comprises a complementarity determining region 2 (CDR2) having at least 90% sequence identity to an amino acid sequence selected from SEQ ID NOs: 160, 163, 175 and 178.

In some embodiments, the TCR alpha chain construct comprises a variable region having at least 80% sequence identity to SEQ ID NO: 167 or 182; and the TCR beta chain construct comprises a variable region having at least 80% sequence identity to SEQ ID NO: 170 or 185.

In some embodiments, the TCR alpha chain construct comprises a CDR1 of SEQ ID NO: 159 or 174, a CDR2 of SEQ ID NO: 160 or 175, and a CDR3 of SEQ ID NO: 161 or 176; and the TCR beta chain construct comprises a CDR1 of SEQ ID NO: 162 or 177, a CDR2 of SEQ ID NO: 163 or 178, and a CDR3 of SEQ ID NO: 164 or 179.

In some embodiments, the epitope comprises a point mutation. In some embodiments, the point mutation is C481S mutation.

In various embodiments, the nucleic acid sequence encoding a TCR is codon optimized.

In various embodiments, the TCR binds to an MHC:BTK peptide complex, wherein the BTK peptide comprises a point mutation. In various embodiments, the TCR binds to an MHC:BTK peptide complex, wherein the BTK peptide comprises a C481S point mutation. In various embodiments, the TCR binds to an MHC:BTK peptide complex, wherein the BTK peptide comprises a sequence of SLLNYLREM.

In some embodiments, the human MHC is encoded by HLA-A02:01 allele. In various embodiments, the human MHC is encoded by an HLA-A02:01 allele. In various embodiments, the TCR binds to an MHC:BTK peptide complex, wherein the human MHC is encoded by an HLA-A02:01 allele.

In various embodiments, the TCR binds to an MHC:BTK peptide complex, wherein the human MHC is encoded by an HLA-A02:01 allele and wherein the BTK peptide comprises a sequence of SLLNYLREM.

IX. TCRs Specific to EGFR Peptide-MHC Complexes

Provided herein is a nucleic acid encoding at least one T cell receptor (TCR) comprising a TCR alpha chain construct and/or TCR beta chain construct capable of specifically binding to an epitope from EGFR in complex with a human MHC, wherein the TCR alpha chain construct comprises a complementarity determining region 3 (CDR3) having at least 90% sequence identity to an amino acid sequence selected from SEQ ID NO: 449, SEQ ID NO: 466, SEQ ID NO: 483, SEQ ID NO: 500, and SEQ ID NO: 517, or wherein the TCR beta chain construct comprises a complementarity determining region 3 (CDR3) having at least 90% sequence identity to an amino acid sequence selected from SEQ ID NO: 452, SEQ ID NO: 469, SEQ ID NO: 486, SEQ ID NO: 503, and SEQ ID NO: 520.

Provided herein is a nucleic acid encoding at least one T cell receptor (TCR) capable of specifically binding to a mutant EGFR peptide in complex with a protein encoded by an HLA allele of a subject with cancer, wherein the TCR comprises a TCR alpha chain construct and/or a TCR beta chain construct.

Provided herein is an isolated nucleic acid or a cell comprising a recombinant nucleic acid, wherein the nucleic acid encodes a T cell receptor (TCR) comprising a TCR alpha chain construct and/or a TCR beta chain construct, wherein the TCR specifically binds to a mutant EGFR peptide in complex with an HLA-A02:01 protein; comprises a complementarity determining region 3 (CDR3) having at least 90% sequence identity to SEQ ID NO: 449, 466, 483, 500, 517, 452, 469, 486, 503, or 520; and/or specifically binds to a mutant EGFR peptide comprising a region with at least 70% sequence identity to SEQ ID NO: 461, 462, 463, 478, 479, 480, 495, 496, 497, 512, 513, 514, 529, 530 or 531.

Provided herein is a nucleic acid encoding at least one T cell receptor (TCR) comprising a TCR alpha chain construct and/or TCR beta chain construct capable of specifically binding to an epitope from EGFR in complex with a human MHC, wherein the epitope from EGFR comprises a region having at least 90% sequence identity to amino acid sequence SEQ ID NO: 461, 462, 463, 478, 479, 480, 495, 496, 497, 512, 513, 514, 529, 530 or 531.

In some embodiments, the TCR alpha chain construct comprises a variable region having at least 80% sequence identity to SEQ ID NO: 449, 466, 483, 500 or 517.

In some embodiments, the TCR beta chain construct comprises a variable region having at least 80% sequence identity to SEQ ID NO: 452, 469, 486, 503, or 520.

In some embodiments, the TCR alpha chain construct and/or the TCR beta chain construct comprises a complementarity determining region 1 (CDR1) having at least 90% sequence identity to an amino acid sequence selected from SEQ ID NOs: 447, 464, 481, 498, 515, 450, 467, 484, 501, and 518.

In some embodiments, the TCR alpha chain construct and/or the TCR beta chain construct comprises a complementarity determining region 2 (CDR2) having at least 90% sequence identity to an amino acid sequence selected from SEQ ID NOs: 448, 465, 482, 499, 516, 451, 468, 485, 502, and 519.

In some embodiments, the TCR alpha chain construct comprises a variable region having at least 80% sequence identity to SEQ ID NO: 455, 472, 489, 506, or 523; and the TCR beta chain construct comprises a variable region having at least 80% sequence identity to SEQ ID NO: 458, 475, 492, 509 or 526.

In some embodiments, the TCR alpha chain construct comprises a CDR1 of SEQ ID NO: 447, 464, 481, 498 or 515, a CDR2 of SEQ ID NO: 448, 465, 482, 499 or 516, and a CDR3 of SEQ ID NO: 449, 466, 483, 500 or 517; and the TCR beta chain construct comprises a CDR1 of SEQ ID NO: 450, 467, 484, 501 or 518, a CDR2 of SEQ ID NO: 451, 468, 485, 502, or 519, and a CDR3 of SEQ ID NO: 452, 469, 486, 503, or 520.

In some embodiments, the epitope comprises a point mutation. In some embodiments, the point mutation is a T790M mutation. In some embodiments, the human MHC is encoded by an HLA-A02:01 allele.

In various embodiments, the nucleic acid sequence encoding a TCR is codon optimized.

In various embodiments, the TCR binds to an MHC: EGFR peptide complex, wherein the EGFR peptide comprises a point mutation. In various embodiments, the TCR binds to an MHC:EGFR peptide complex, wherein the EGFR peptide comprises a T790M point mutation. In various embodiments, the TCR binds to an MHC:EGFR peptide complex, wherein the EGFR peptide comprises a sequence of QLIMQLMPF, LIMQLMPFGC or MQLMPFGCLL.

In various embodiments, the human MHC is encoded by an HLA-A02:01 allele. In various embodiments, the TCR binds to an MHC:EGFR peptide complex, wherein the human MHC is encoded by an HLA-A02:01 allele.

In various embodiments, the TCR binds to an MHC: EGFR peptide complex, wherein the human MHC is encoded by an HLA-A02:01 allele and wherein the EGFR peptide comprises a sequence of QLIMQLMPF, LIMQLMPFGC or MQLMPFGCLL.

Delivery of Nucleic Acid or Vector

Nucleic acids encoding TCRs or vectors containing such nucleic acids can be delivered to host cells for expression and processing.

Terms such as "transferring", "introducing" or "transfecting" are used interchangeably herein and relate to the introduction of nucleic acids, in particular exogenous or heterologous nucleic acids, into a cell.

Cells can be transfected with any carriers with which nucleic acid can be associated, e.g., by forming complexes with the nucleic acid or forming vesicles in which the nucleic acid is enclosed or encapsulated, resulting in increased stability of the nucleic acid compared to naked nucleic acid. Carriers useful according to the present disclosure include, for example, lipid-containing carriers such as cationic lipids, liposomes, in particular cationic liposomes, and micelles, and nanoparticles. Cationic lipids may form complexes with negatively charged nucleic acids. Any cationic lipid may be used according to the present disclosure.

In various embodiments, a nucleic acid encoding a TCR disclosed herein is operably linked to a promoter. Furthermore, the present disclosure provides a vector, e.g. a plasmid, shuttle vector, phagemide, cosmid, expression vector, retroviral vector, adenoviral vector or particle and/or vector to be used in gene therapy, which comprises one or more of the nucleic acids as disclosed above. A "vector" is a nucleic acid molecule that is capable of transporting another nucleic acid. The vector comprises the nucleic acid insert, which encodes the polypeptide or protein desired for expression in a cell, such as a host cell. For the purposes of the disclosure, an insert may be a nucleic acid encoding a TCR: an alpha chain or a beta chain or both of a TCR. The term "incorporating" a nucleic acid sequence in a vector may mean preparing a suitable expression vector with a insert comprising said nucleic acid sequence. An "expression vector" is a vector that can direct the expression of a protein encoded by one or more genes carried by the vector when it is present in the appropriate environment. "Retroviruses" are viruses having an RNA genome. "Gammaretrovirus" refers to a genus of the retroviridae family. Exemplary gammaretroviruses include, but are not limited to, mouse stem cell virus, murine leukemia virus, feline leukemia virus, feline sarcoma virus, and avian reticuloendotheliosis viruses. "Lentivirus" refers to a genus of retroviruses that are capable of infecting dividing and non-dividing cells. Several examples of lentiviruses include HIV (human immunodeficiency virus: including HIV type 1, and HIV type 2); equine infectious anemia virus, feline immunodeficiency virus (FIV); bovine immune deficiency virus (BIV); and simian immunodeficiency virus (SIV). A vector that encodes a core virus is also known as a "viral vector" There are a large number of available viral vectors that are suitable for use with the invention, including those identified for human gene therapy applications, such as those described by Pfeifer and Verma (Pfeifer, A. and I. M. Verma. 2001. Ann. Rev. Genomics Hum. Genet. 2:177-211). Suitable viral vectors include vectors based on RNA viruses, such as retrovirus-derived vectors, e.g., Moloney murine leukemia virus (MLV)-derived vectors, and include more complex retrovirus-derived vectors, e.g., lentivirus-derived vectors. HIV-1-derived vectors belong to this category. Other examples include lentivirus vectors derived from HIV-2, FIV, equine infectious anemia virus, SIV, and maedi/visna virus. Methods of using retroviral and lentiviral viral vectors and packaging cells for transducing mammalian target cells with viral particles containing TCRs transgenes are well known in the art and have been previous described, for example, in U.S. Pat. No. 8,119,772: Walchli et al., 2011, PLoS One 6-327930; Zhao et al., J. Immunol., 2005, 174:4415-4423: Engels et al., 2003, Hum. Gene Ther. 14:1155-68; Frecha et al., 2010, Mol. Ther. 18.1748-57: Verhoeyen et al., 2009, Methods Mol. Biol. 506:97-114. Retroviral and lentiviral vector constructs and expression systems are also commercially available. In some embodiments, a viral vector is used to introduce the non-endogenous nucleic acid sequence encoding TCRα chain specific for the peptide antigen into the hematopoietic progenitor cells. The viral vector may be a retroviral vector or a lentiviral vector. The viral vector may also include a nucleic acid sequence encoding a marker for transduction. Transduction markers for viral vectors are known in the art and include selection markers, which may confer drug resistance, or detectable markers, such as fluorescent markers or cell surface proteins that can be detected by methods such as flow cytometry. Where the viral vector genome comprises more than one nucleic acid sequence to be expressed in the host cell as separate transcripts, the viral vector may also comprise additional sequence between the two (or more) transcripts allowing bicistronic or multicistronic expression. Examples of such sequences used in viral vectors include internal ribosome entry sites (IRES), furin cleavage sites, viral 2A peptide. Other vectors also can be used for polynucleotide delivery including DNA viral vectors, including, for example adenovirus-based vectors and adeno-associated virus (AAV)-based vectors; vectors derived from herpes simplex viruses (HSVs), including amplicon vectors, replication-defective HSV and attenuated HSV (Krisky et al., 1998. Gene Ther. 5. 1517-30). Other vectors include those derived from baculoviruses and alphaviruses. (Jolly D J. 1999. Emerging viral vectors pp 209-40 in Friedmann T ed. 1999. The development of human gene therapy. New York: Cold Spring Harbor Lab).

A vector may include nucleic acid sequences that permit the nucleic acid to replicate in a host cell, such as an origin of replication. A vector may also include one or more selectable marker genes and other genetic elements known to those of ordinary skill in the art. A vector preferably is an expression vector that includes a nucleic acid according to the present invention operably linked to sequences allowing for the expression of said nucleic acid.

In some embodiments, provided herein is a vector comprising a nucleic acid encoding a TCR disclosed herein. In some embodiments, the vector is a self-amplifying RNA replicon, plasmid, phage, transposon, cosmid, virus, or virion. In some embodiments, the vector is a viral vector. In some embodiments, the vector is derived from a retrovirus, lentivirus, adenovirus, adeno-associated virus, herpes virus, pox virus, alpha virus, vaccina virus, hepatitis B virus, human papillomavirus or a pseudotype thereof. In some embodiments, the vector is a non-viral vector. In some embodiments, the non-viral vector is a nanoparticle, a cationic lipid, a cationic polymer, a metallic nanopolymer, a nanorod, a liposome, a micelle, a microbubble, a cell-penetrating peptide, or a liposphere.

Presented herein are constructs, for example, nucleic acid constructs that encode an alpha chain and a beta chain of a TCR for expression in a cell. In some embodiments, the constructs comprise one or more polynucleotides encoding a TCR alpha chain and a TCR beta chain. In some embodiments, the polynucleotides are incorporated in a suitable vector. In some embodiments, the polynucleotides encoding the alpha chain and the beta chain are incorporated in the same vector. In some embodiments, the polynucleotides encoding the alpha chain and the beta chain are incorporated in different vectors, and both vectors are delivered for expression in the single cell.

In some embodiments, a cell may be transduced or transfected with a nucleic acid encoding a TCR, wherein the cell is capable of expressing the TCR and the cell is used as a therapeutic. In some embodiments the cell is derived from a subject or a host, wherein the subject or the host is a human. In some embodiments, the subject or the host comprises a cell having a mutation in an epitope, and the TCR expressed in the cell is capable of binding specifically to the epitope having the mutation. In some embodiments, the cell is a lymphocyte cell. In some embodiments, the T-lymphocyte. In some embodiments, the cell is a lymphocytic precursor cell. In some embodiments, the cell is a T lymphocyte precursor cell. In some embodiments, the cell is a T lymphocyte progenitor cell. In some embodiments the cell is a thymocyte.

In some embodiments, the T cells are immature T cells. In some embodiments, the T cells are antigen naive T cells. The host cell may be cultured ex vivo for 1, 2, 3, 4, 5 or more days for monitoring and recover after transfection or transduction with the polynucleotide(s) encoding the TCR.

X. Neoantigens

The TCRs disclosed herein are specific to immunogenic neoantigens. In some embodiments, the neoantigen peptide is from RAS. In some embodiments, the neoantigen peptide is from GATA3. In some embodiments, the neoantigen peptide is from BTK. In some embodiments, the neoantigen peptide is from TMPRSS2:ERG. In some embodiments, one or more neoantigen peptides are loaded on to APCs, wherein the peptide loaded APCs are then used to stimulate T cells to produce antigen specific T cells. In some embodiments, the APCs used for peptide loading are dendritic cells. Immunogenic neoantigen sequences can be identified by any suitable method known in the art.

In various embodiments, the neoantigen comprises an epitope. In both animals and humans, mutated epitopes can be potentially effective in inducing an immune response or activating T cells. In some embodiments, the epitope comprises a mutation. In some embodiments, the mutation is selected from the group consisting of a point mutation, a splice-site mutation, a frameshift mutation, a read-through mutation, a gene fusion mutation and any combination thereof.

In some embodiments, the epitope has a length of at least 8 amino acids. In some embodiments, the epitope has a length of at least 16 amino acids. In some embodiments, the epitope has a length of from 8-25 amino acids. In some embodiments, the epitope has a length of from 8-12 amino acids. In some embodiments, the epitope has a length of from 16-25 amino acids. In some embodiments, the epitope has a length of 7, 8, 9, 10, 11, 12, 13, 14, 15, 16, 17, 18, 19, 20, 21, 22, 23, 24, or 25 amino acids.

In certain embodiments, a neoantigen or epitope thereof can comprise, but is not limited to, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 60, about 70, about 80, about 90, about 100, about 110, about 120 or greater amino acid residues, and any range derivable therein. In specific embodiments, a neoantigen or epitope thereof is equal to or less than 100 amino acids.

In some embodiments, a neoantigen or epitope thereof for MHC Class I is 13 residues or less in length and usually consists of between about 8 and about 11 residues, particularly 9 or 10 residues. In some embodiments, a neoantigen or epitope thereof for MHC Class II is 9-24 residues in length.

In some embodiments, neoantigens bind an HLA protein (e.g., HLA class I or HLA class II). In specific embodiments neoantigens bind an HLA protein with greater affinity than a corresponding wild-type peptide. In specific embodiments, the neoantigenic peptide or polypeptide has an IC50 of at least less than 5000 nM, at least less than 500 nM, at least less than 100 nM, at least less than 50 nM or less.

In some embodiments, the epitope binds to the human MHC with a greater affinity than a corresponding wild-type epitope. In some embodiments, the epitope binds to the human MHC with a $K_D$ or an $IC_{50}$ less than 500 nM, 250 nM, 150 nM, 100 nM, 50 nM, 25 nM or 10 nM. In some embodiments, the epitope comprises a mutation, wherein the mutation is not present in non-cancer cells of a subject. In some embodiments, the epitope is encoded by a gene or an expressed gene of a subject's cancer cells. In some embodiments, the TCR binds to an HLA-peptide complex with a $K_D$ or an $IC_{50}$ of less than 500 nM, 250 nM, 150 nM, 100 nM, 50 nM, 25 nM or 10 nM.

In some embodiments, the neoantigenic peptide can be from about 8 and about 50 amino acid residues in length, or from about 8 and about 30, from about 8 and about 20, from about 8 and about 18, from about 8 and about 15, or from about 8 and about 12 amino acid residues in length. In some embodiments, the neoantigenic peptide can be from about 8 and about 500 amino acid residues in length, or from about 8 and about 450, from about 8 and about 400, from about 8 and about 350, from about 8 and about 300, from about 8 and about 250, from about 8 and about 200, from about 8 and about 150, from about 8 and about 100, from about 8 and about 50, or from about 8 and about 30 amino acid residues in length.

In some embodiments, the neoantigenic peptide can be at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more amino acid residues in length. In some embodiments, the neoantigenic peptide can be at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 70, 80, 90, 100, 150, 200, 250, 300, 350, 400, 450, 500 or more amino acid residues in length. In some embodiments, the neoantigenic peptide can be at most 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or less amino acid residues in length. In some embodiments, the neoantigenic peptide can be at most 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 70, 80, 90, 100, 150, 200, 250, 300, 350, 400, 450, 500, or less amino acid residues in length.

In some embodiments, the neoantigenic peptide has a total length of at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 40, at least 50, at least 60, at least 70, at least 80, at least 90, at least 100, at least 150, at least 200, at least 250, at least 300, at least 350, at least 400, at least 450, or at least 500 amino acids.

In some embodiments, the neoantigenic peptide has a total length of at most 8, at most 9, at most 10, at most 11, at most 12, at most 13, at most 14, at most 15, at most 16, at most 17, at most 18, at most 19, at most 20, at most 21, at most 22, at most 23, at most 24, at most 25, at most 26, at most 27, at most 28, at most 29, at most 30, at most 40, at most 50, at most 60, at most 70, at most 80, at most 90, at most 100, at most 150, at most 200, at most 250, at most 300, at most 350, at most 400, at most 450, or at most 500 amino acids.

In some embodiments, the neoantigenic peptide can have a pI value of about 0.5 and about 12, about 2 and about 10, or about 4 and about 8. In some embodiments, the neoantigenic peptide can have a pI value of at least 4.5, 5, 5.5, 6, 6.5, 7, 7.5, or more. In some embodiments, the neoantigenic peptide can have a pI value of at most 4.5, 5, 5.5, 6, 6.5, 7, 7.5, or less.

In some embodiments, the neoantigenic peptide can have an HLA binding affinity of between about 1 pM and about 1 mM, about 100 pM and about 500 μM, about 500 pM and about 10 μM, about 1 nM and about 1 μM, or about 10 nM and about 1 μM. In some embodiments, the neoantigenic peptide can have an HLA binding affinity of at least 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 700, 800, 900 μM, or more. In some embodiments, the neoantigenic peptide can have an HLA binding affinity of at most 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 700, 800, 900 μM.

In some embodiments, a neoantigenic peptide described herein can comprise carriers such as those well known in the art, e.g., thyroglobulin, albumins such as human serum albumin, tetanus toxoid, polyamino acid residues such as poly L-lysine, poly L-glutamic acid, influenza virus proteins, hepatitis B virus core protein, and the like.

In some embodiments, a neoantigenic peptide described herein can be modified by terminal-NH2 acylation, e.g., by alkanoyl (C1-C20) or thioglycolyl acetylation, terminal-carboxyl amidation, e.g., ammonia, methylamine, etc. In some embodiments, these modifications can provide sites for linking to a support or other molecule.

In some embodiments, a neoantigenic peptide described herein can contain modifications such as but not limited to glycosylation, side chain oxidation, biotinylation, phosphorylation, addition of a surface active material, e.g. a lipid, or can be chemically modified, e.g., acetylation, etc. Moreover, bonds in the peptide can be other than peptide bonds, e.g., covalent bonds, ester or ether bonds, disulfide bonds, hydrogen bonds, ionic bonds, etc.

In some embodiments, a neoantigenic peptide described herein can contain substitutions to modify a physical property (e.g., stability or solubility) of the resulting peptide. For example, neoantigenic peptides can be modified by the substitution of a cysteine (C) with α-amino butyric acid ("B"). Due to its chemical nature, cysteine has the propensity to form disulfide bridges and sufficiently alter the peptide structurally so as to reduce binding capacity. Substituting α-amino butyric acid for C not only alleviates this problem, but actually improves binding and cross-binding capability in certain instances. Substitution of cysteine with α-amino butyric acid can occur at any residue of a neoantigenic peptide, e.g., at either anchor or non-anchor positions of an epitope or analog within a peptide, or at other positions of a peptide.

In some embodiments, a neoantigenic peptide described herein can comprise amino acid mimetics or unnatural amino acid residues, e.g. D- or L-naphylalanine; D- or L-phenylglycine; D- or L-2-thieneylalanine; D- or L-1, -2, 3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-.rho.-fluorophenylalanine; D- or L-.rho.-biphenyl-phenylalanine; D- or L-.rho.-methoxybiphenylphenylalanine; D- or L-2-indole(allyl)alanines; and, D- or L-alkylalanines, where the alkyl group can be a substituted or unsubstituted methyl, ethyl, propyl, hexyl, butyl, pentyl, isopropyl, iso-butyl, sec-isotyl, iso-pentyl, or a non-acidic amino acid residues. Aromatic rings of a non-natural amino acid include, e.g., thiazolyl, thiophenyl, pyrazolyl, benzimidazolyl, naphthyl, furanyl, pyrrolyl, and pyridyl aromatic rings. Modified peptides that have various amino acid mimetics or unnatural amino acid residues are particularly useful, as they tend to manifest increased stability in vivo. Such peptides can also possess improved shelf-life or manufacturing properties.

Peptide stability can be assayed in a number of ways. For instance, peptidases and various biological media, such as human plasma and serum, have been used to test stability. See, e.g., Verhoef, et al., Eur. J. Drug Metab. Pharmacokinetics 11:291 (1986). Half-life of the peptides described herein is conveniently determined using a 25% human serum (v/v) assay. The protocol is as follows: pooled human serum (Type AB, non-heat inactivated) is dilapidated by centrifugation before use. The serum is then diluted to 25% with RPMI-1640 or another suitable tissue culture medium. At predetermined time intervals, a small amount of reaction solution is removed and added to either 6% aqueous trichloroacetic acid (TCA) or ethanol. The cloudy reaction sample is cooled (4° C.) for 15 minutes and then spun to pellet the precipitated serum proteins. The presence of the peptides is then determined by reversed-phase HPLC using stability-specific chromatography conditions.

In some embodiments, a neoantigenic peptide described herein can be prepared synthetically, by recombinant DNA technology or chemical synthesis, or can be isolated from natural sources such as native tumors or pathogenic organisms. Epitopes can be synthesized individually or joined directly or indirectly in a peptide. Although a neoantigenic peptide described herein will be substantially free of other naturally occurring host cell proteins and fragments thereof, in some embodiments, the peptide can be synthetically conjugated to be joined to native fragments or particles.

In some embodiments, a neoantigenic peptide described herein can be prepared in a wide variety of ways. In some embodiments, the peptides can be synthesized in solution or on a solid support according to conventional techniques. Various automatic synthesizers are commercially available and can be used according to known protocols. (See, for example, Stewart & Young, SOLID PHASE PEPTIDE SYNTHESIS, 2D. ED., Pierce Chemical Co., 1984). Further, individual peptides can be joined using chemical ligation to produce larger peptides that are still within the bounds of the invention.

Alternatively, recombinant DNA technology can be employed wherein a nucleotide sequence which encodes a peptide inserted into an expression vector, transformed or transfected into an appropriate host cell and cultivated under conditions suitable for expression. These procedures are generally known in the art, as described generally in Sambrook et al., MOLECULAR CLONING, A LABORATORY MANUAL, Cold Spring Harbor Press, Cold Spring Harbor, N.Y. (1989). Thus, recombinant peptides, which comprise or consist of one or more epitopes described herein, can be used to present the appropriate T cell epitope.

XI. Pharmaceutical Compositions

Pharmaceutical compositions can be formulated using one or more physiologically acceptable carriers including excipients and auxiliaries which facilitate processing of the active agents into preparations which can be used pharmaceutically. Proper formulation can be dependent upon the route of administration chosen. Any of the well-known techniques, carriers, and excipients can be used as suitable and as understood in the art.

In some cases, a pharmaceutical composition is formulated as cell based therapeutic, e.g., a T cell therapeutics. In some embodiments, a pharmaceutical composition comprises a peptide-based therapy, a nucleic acid-based therapy, an antibody-based therapy, and/or a cell-based therapy. In some embodiments, a pharmaceutical composition comprises a peptide-based therapeutic, or nucleic acid based therapeutic in which the nucleic acid encodes the polypeptides. A composition can comprise T cells specific for two or more immunogenic antigen or neoantigen peptides. In some embodiments, the T cell specific therapeutic may be supplemented by one or more additional therapies.

In some embodiments, a pharmaceutical composition comprising: a nucleic acid encoding a TCR targeting a neoantigen disclosed herein, a vector containing the nucleic acid, the protein encoded by the nucleic acid, or a host cell comprising the nucleic acid, the protein or the vector; and a pharmaceutically acceptable excipient or diluent. In some embodiments, the pharmaceutical composition further comprises an immunomodulatory agent or an adjuvant. In some embodiments, the immunomodulatory agent is a cytokine. In some embodiments, the adjuvant is poly I:C.

Also provided herein is the use of the pharmaceutical compositions in treating an immune disease or cancer.

Pharmaceutical compositions can include, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration. Acceptable carriers, excipients, or stabilizers are those that are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, trehalose or sorbitol; salt-forming counter-ions such as sodium; metal complexes (e.g., Zn-protein complexes); and/or non-ionic surfactants such as TWEEN®, PLURONICS® or polyethylene glycol (PEG).

Acceptable carriers are physiologically acceptable to the administered patient and retain the therapeutic properties of the compounds with/in which it is administered. Acceptable carriers and their formulations are generally described in, for example, Remington's Pharmaceutical Sciences (18th ed. A. Gennaro, Mack Publishing Co., Easton, PA 1990). One example of carrier is physiological saline. A pharmaceutically acceptable carrier is a pharmaceutically acceptable material, composition or vehicle, such as a liquid or solid filler, diluent, excipient, solvent or encapsulating material, involved in carrying or transporting the subject compounds from the administration site of one organ, or portion of the body, to another organ, or portion of the body, or in an in vitro assay system. Acceptable carriers are compatible with the other ingredients of the formulation and not injurious to a subject to whom it is administered. Nor should an acceptable carrier alter the specific activity of the other ingredients.

In one aspect, provided herein are pharmaceutically acceptable or physiologically acceptable compositions including solvents (aqueous or non-aqueous), solutions, emulsions, dispersion media, coatings, isotonic and absorption promoting or delaying agents, compatible with pharmaceutical administration. Pharmaceutical compositions or pharmaceutical formulations therefore refer to a composition suitable for pharmaceutical use in a subject. Compositions can be formulated to be compatible with a particular route of administration (i.e., systemic or local). Thus, compositions include carriers, diluents, or excipients suitable for administration by various routes.

In some embodiments, a pharmaceutical composition can further comprise an acceptable additive in order to improve the stability of the composition. Acceptable additives may not alter the specific activity of the active agent, e.g. immune cells. Examples of acceptable additives include, but are not limited to, a sugar such as mannitol, sorbitol, glucose, xylitol, trehalose, sorbose, sucrose, galactose, dextran, dextrose, fructose, lactose and mixtures thereof. Acceptable additives can be combined with acceptable carriers and/or excipients such as dextrose. Alternatively, examples of acceptable additives include, but are not limited to, a surfactant such as polysorbate 20 or polysorbate 80 to increase stability of the peptide and decrease gelling of the solution. The surfactant can be added to the composition in an amount of 0.01% to 5% of the solution. Addition of such acceptable additives increases the stability and half-life of the composition in storage.

In some embodiments the pharmaceutical composition comprises a therapeutic which is a T cell expressing one or more polynucleotides, encoding a T cell receptor. In some embodiments, the pharmaceutical composition comprises physiologically acceptable carrier suitable for a cell suspension.

The pharmaceutical composition can be administered, for example, by injection. Pharmaceutical compositions for injection include aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). The carrier can be a solvent or dispersion medium containing, for example, water, ethanol, polyol (for example, glycerol, propylene glycol, and liquid polyethylene glycol, and the like), and suitable mixtures thereof. Fluidity can be maintained, for example, by the use of a coating such as lecithin, by the maintenance of the required particle size in the case of dispersion and by the use of surfactants. Antibacterial and antifungal agents include, for example, parabens, chlorobutanol, phenol, ascorbic acid and thimerosal. Isotonic agents, for example, sugars, polyalcohols such as mannitol, sorbitol, and sodium chloride can be included in the composition. The resulting solutions can be packaged for use as is, or lyophilized; the lyophilized preparation can later be combined with a sterile solution prior to administration. For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as needed. Sterile injectable solutions can be prepared by incorporating an active ingredient in the required amount in an appropriate solvent with one or a combination of ingredients enumerated above, as required, followed by filtered sterilization. Generally, dispersions are prepared by incorporating the active ingredient into a sterile vehicle which contains a basic dispersion medium and the required other ingredients from those enumerated above. In the case of sterile powders for the preparation of sterile injectable solutions, the preferred methods of preparation can be vacuum drying and freeze drying which yields a powder of the active ingredient plus any additional desired ingredient from a previously sterile-filtered solution thereof.

Pharmaceutical compositions can be conventionally administered intravenously, such as by injection of a unit dose, for example. For injection, an active ingredient can be in the form of a parenterally acceptable aqueous solution which is substantially pyrogen-free and has suitable pH, isotonicity and stability. One can prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required. Additionally, compositions can be administered via aerosolization.

When the pharmaceutical compositions are considered for use in medicaments or any of the methods provided herein, it is contemplated that the composition can be substantially free of pyrogens such that the composition will not cause an inflammatory reaction or an unsafe allergic reaction when administered to a human patient. Testing compositions for pyrogens and preparing compositions substantially free of pyrogens are well understood to one or ordinary skill of the art and can be accomplished using commercially available kits.

Acceptable carriers can contain a compound that stabilizes, increases or delays absorption, or increases or delays clearance. Such compounds include, for example, carbohydrates, such as glucose, sucrose, or dextrans; low molecular weight proteins; compositions that reduce the clearance or hydrolysis of peptides; or excipients or other stabilizers and/or buffers. Agents that delay absorption include, for example, aluminum monostearate and gelatin. Detergents can also be used to stabilize or to increase or decrease the absorption of the pharmaceutical composition, including liposomal carriers. To protect from digestion the compound can be complexed with a composition to render it resistant to acidic and enzymatic hydrolysis, or the compound can be complexed in an appropriately resistant carrier such as a liposome. Means of protecting compounds from digestion are known in the art (e.g., Fix (1996) Pharm Res. 13:1760 1764; Samanen (1996) J. Pharm. Pharmacol. 48:119 135; and U.S. Pat. No. 5,391,377).

The pharmaceutical compositions can be administered in a manner compatible with the dosage formulation, and in a therapeutically effective amount. The quantity to be administered depends on the subject to be treated, capacity of the subject's immune system to utilize the active ingredient, and degree of binding capacity desired. Precise amounts of active ingredient required to be administered depend on the judgment of the practitioner and are peculiar to each individual. Suitable regimes for initial administration and booster shots are also variable, but, are typified by an initial administration followed by repeated doses at one or more hour intervals by a subsequent injection or other administration. Alternatively, continuous intravenous infusions sufficient to maintain concentrations in the blood are contemplated.

In some embodiments, the present disclosure is directed to an immunogenic composition, e.g., a pharmaceutical composition capable of raising a neoantigen-specific response (e.g., a humoral or cell-mediated immune response). In some embodiments, the immunogenic composition comprises neoantigen therapeutics (e.g., peptides, polynucleotides, TCR, CAR, cells containing TCR or CAR, dendritic cell containing polypeptide, dendritic cell containing polynucleotide, antibody, etc.) described herein corresponding to a tumor specific antigen or neoantigen.

In some embodiments, a pharmaceutical composition described herein is capable of raising a specific cytotoxic T cells response, specific helper T cell response, or a B cell response.

In some embodiments, antigen polypeptides or polynucleotides can be provided as antigen presenting cells (e.g., dendritic cells) containing such polypeptides or polynucleotides. In other embodiments, such antigen presenting cells are used to stimulate T cells for use in patients. In some embodiments, the antigen presenting cells are dendritic cells. In related embodiments, the dendritic cells are autologous dendritic cells that are pulsed with the neoantigen peptide or nucleic acid. The neoantigen peptide can be any suitable peptide that gives rise to an appropriate T cell response. In some embodiments, the T cell is a CTL. In some embodiments, the T cell is an HTL. Thus, one embodiment of the present disclosure is an immunogenic composition containing at least one antigen presenting cell (e.g., a dendritic cell) that is pulsed or loaded with one or more neoantigen polypeptides or polynucleotides described herein. In some embodiments, such APCs are autologous (e.g., autologous dendritic cells). Alternatively, peripheral blood mononuclear cells (PBMCs) isolated from a patient can be loaded with neoantigen peptides or polynucleotides ex vivo. In related embodiments, such APCs or PBMCs are injected back into the patient. The polynucleotide can be any suitable polynucleotide that is capable of transducing the dendritic cell, thus resulting in the presentation of a neoantigen peptide and induction of immunity. In some embodiments, such antigen presenting cells (APCs) (e.g., dendritic cells) or peripheral blood mononuclear cells (PBMCs) are used to stimulate a T cell (e.g., an autologous T cell, or an allogeneic T cell). In related embodiments, the T cell is a CTL. In other related embodiments, the T cell is an HTL. In some embodiments, the T cells are $CD8^+$ T cells. In some embodiments, the T cells are $CD4^+$ T cells. Such T cells are then injected into the patient. In some embodiments, CTL is injected into the patient. In some embodiments, HTL is injected into the patient. In some embodiments, both CTL and HTL are injected into the patient. Administration of either therapeutic can be performed simultaneously or sequentially and in any order.

In some embodiments, pharmaceutical compositions (e.g., immunogenic compositions) described herein for therapeutic treatment can be formulated for parenteral, topical, nasal, oral or local administration. In some embodiments, the pharmaceutical compositions described herein are administered parenterally, e.g., intravenously, subcutaneously, intradermally, or intramuscularly. In some embodiments, the composition can be administered intratumorally. The compositions can be administered at the site of surgical excision to induce a local immune response to the tumor. In some embodiments, described herein are compositions for parenteral administration which comprise a solution of the neoantigen peptides and immunogenic compositions are dissolved or suspended in an acceptable carrier, for example, an aqueous carrier. A variety of aqueous carriers can be used, e.g., water, buffered water, 0.9% saline, 0.3% glycine, hyaluronic acid and the like. These compositions can be sterilized by conventional, well known sterilization techniques, or can be sterile filtered. The resulting aqueous solutions can be packaged for use as is, or lyophilized, the lyophilized preparation being combined with a sterile solution prior to administration. The compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The ability of an adjuvant to increase the immune response to an antigen is typically manifested by a significant increase in immune-mediated reaction, or reduction in disease symptoms. For example, an increase in humoral immunity can be manifested by a significant increase in the titer of antibodies raised to the antigen, and an increase in T cell activity can be manifested in increased cell proliferation, or cellular cytotoxicity, or cytokine secretion. An adjuvant can also alter an immune response, for example, by changing a primarily humoral or T helper 2 response into a primarily cellular, or T helper 1 response.

Suitable adjuvants are known in the art (see, WO 2015/095811) and include, but are not limited to poly(I:C), poly-ICLC, STING agonist, 1018 ISS, aluminum salts, Amplivax, AS15, BCG, CP-870,893, CpG7909, CyaA, dSLIM, GM-CSF, IC30, IC31, Imiquimod, ImuFact IMP321, IS Patch, ISS, ISCOMATRIX, JuvImmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PepTel® vector system, PLG microparticles, resiquimod, SRL172, virosomes and other virus-like particles, YF-17D, VEGF trap, R848, 13-glucan, Pam3Cys, Pam3CSK4, Aquila's QS21 stimulon (Aquila Biotech, Worcester, Mass., USA) which is derived from saponin, mycobacterial extracts and synthetic bacterial cell wall mimics, and other proprietary adjuvants such as Ribi's Detox. Quil or Superfos. Several immunological adjuvants (e.g., MF59) specific for dendritic cells and their preparation have been described (Dupuis M, et al., Cell Immunol. 1998; 186(1):18-27; Allison A C; Dev Biol Stand. 1998; 92:3-11) (Mosca et al. Frontiers in Bioscience, 2007; 12:4050-4060) (Gamvrellis et al. Immunol & Cell Biol. 2004; 82: 506-516). Also cytokines can be used. Several cytokines have been directly linked to influencing dendritic cell migration to lymphoid tissues (e.g., TNF-α), accelerating the maturation of dendritic cells into efficient antigen-presenting cells for T-lymphocytes (e.g., GM-CSF, PGE1, PGE2, IL-1, IL-113, IL-4, IL-6 and CD40L) (U.S. Pat. No. 5,849,589 incorporated herein by reference in its entirety) and acting as immunoadjuvants (e.g., IL-12) (Gabrilovich D I, et al., J Immunother Emphasis Tumor Immunol. 1996 (6):414-418).

CpG immunostimulatory oligonucleotides have also been reported to enhance the effects of adjuvants in a therapeutic setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell immunogenic pharmaceutical compositions, autologous cellular immunogenic pharmaceutical compositions and polysaccharide conjugates in both prophylactic and therapeutic immunogenic pharmaceutical compositions. Importantly, it enhances dendritic cell maturation and differentiation, resulting in enhanced activation of TH1 cells and strong cytotoxic T-lymphocyte (CTL) generation, even in the absence of CD4$^+$ T cell help. The TH1 bias induced by TLR9 stimulation is maintained even in the presence of adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially useful for inducing a strong response when the antigen is relatively weak. They can also accelerate the immune response and enabled the antigen doses to be reduced with comparable antibody responses to the full-dose immunogenic pharmaceutical composition without CpG in some experiments (Arthur M. Krieg, Nature Reviews, Drug Discovery, 5, Jun. 2006, 471-484). U.S. Pat. No. 6,406,705 describes the combined use of CpG oligonucleotides, non-nucleic acid adjuvants and an antigen to induce an antigen-specific immune response. A commercially available CpG TLR9 antagonist is dSLIM (double Stem Loop Immunomodulator) by Mologen (Berlin, DE), which is a component of the pharmaceutical composition described herein. Other TLR binding molecules such as RNA binding TLR7, TLR8 and/or TLR9 can also be used.

Other examples of useful adjuvants include, but are not limited to, chemically modified CpGs (e.g. CpR, Idera), Poly(I:C)(e.g., polyI:CI2U), polyIC:LC, non-CpG bacterial DNA or RNA, ssRNA40 for TLR8, as well as immunoactive small molecules and antibodies such as cyclophosphamide, sunitinib, bevacizumab, celebrex, NCX-4016, sildenafil, tadalafil, vardenafil, sorafinib, XL-999, CP-547632, pazopanib, ZD2171, AZD2171, ipilimumab, tremelimumab, and SC58175, which can act therapeutically and/or as an adjuvant. The amounts and concentrations of adjuvants and additives useful in the context of the present invention can readily be determined by the skilled artisan without undue experimentation. Additional adjuvants include colony-stimulating factors, such as Granulocyte Macrophage Colony Stimulating Factor (GM-CSF, sargramostim).

In some embodiments, an immunogenic composition according to the present disclosure can comprise more than one different adjuvant. Furthermore, the invention encompasses a pharmaceutical composition comprising any adjuvant substance including any of the above or combinations thereof. In some embodiments, the immunogenic composition comprises neoantigen therapeutics (e.g., peptides, polynucleotides, TCR, CAR, cells containing TCR or CAR, dendritic cell containing polypeptide, dendritic cell containing polynucleotide, antibody, etc.) and the adjuvant can be administered separately in any appropriate sequence.

Lipidation can be classified into several different types, such as N-myristoylation, palmitoylation, GPI-anchor addition, prenylation, and several additional types of modifications. N-myristoylation is the covalent attachment of myristate, a C14 saturated acid, to a glycine residue. Palmitoylation is thioester linkage of long-chain fatty acids (C16) to cysteine residues. GPI-anchor addition is glycosyl-phosphatidylinositol (GPI) linkage via amide bond. Prenylation is the thioether linkage of an isoprenoid lipid (e.g. farnesyl (C-15), geranylgeranyl (C-20)) to cysteine residues. Additional types of modifications can include attachment of S-diacylglycerol by a sulfur atom of cysteines, 0-octanoyl conjugation via serine or threonine residues, S-archaeol conjugation to cysteine residues, and cholesterol attachment.

Fatty acids for generating a lipidated peptides can include C2 to C30 saturated, monounsaturated, or polyunsaturated fatty acyl groups. Exemplary fatty acids can include palmitoyl, myristoyl, stearoyl and decanoyl groups. In some instances, a lipid moiety that has adjuvant property is attached to a polypeptide of interest to elicit or enhance immunogenicity in the absence of an extrinsic adjuvant. A lipidated peptide or lipopeptide can be referred to as a self-adjuvant lipopeptide. Any of the fatty acids described above and elsewhere herein can elicit or enhance immunogenicity of a polypeptide of interest. A fatty acid that can elicit or enhance immunogenicity can include palmitoyl, myristoyl, stearoyl, lauroyl, octanoyl, and decanoyl groups.

Polypeptides such as naked peptides or lipidated peptides can be incorporated into a liposome. Sometimes, lipidated peptides can be incorporated into a liposome. For example, the lipid portion of the lipidated peptide can spontaneously integrate into the lipid bilayer of a liposome. Thus, a lipopeptide can be presented on the "surface" of a liposome.

Liposome can also be used to deliver nucleic acids into a cell. The nucleic acid of interest comprises one or more sequences encoding a T cell receptor. Liposomes may be used to deliver a DNA or an RNA. Liposomes may be used to deliver a nucleic acid incorporated in a vector. The nucleic acid may be 50-200,000 nucleotides long, or may be 100-500,000 nucleotides long, or may be 20-500,000 nucleotides long. Exemplary liposomes suitable for incorporation in the formulations include, and are not limited to, multilamellar vesicles (MLV), oligolamellar vesicles (OLV), unilamellar vesicles (UV), small unilamellar vesicles (SUV), medium-sized unilamellar vesicles (MUV), large unilamellar vesicles (LUV), giant unilamellar vesicles (GUV), multivesicular vesicles (MVV), single or oligolamellar vesicles made by reverse-phase evaporation method (REV), multilamellar vesicles made by the reverse-phase evaporation method (MLV-REV), stable plurilamellar vesicles (SPLV), frozen and thawed MLV (FATMLV), vesicles prepared by extrusion methods (VET), vesicles prepared by French press (FPV), vesicles prepared by fusion (FUV), dehydration-rehydration vesicles (DRV), and bubblesomes (BSV).

Depending on the method of preparation, liposomes can be unilamellar or multilamellar, and can vary in size with diameters ranging from about 0.02 µm to greater than about 10 µm. Liposomes can adsorb many types of cells and then release an incorporated agent (e.g., a peptide described herein). In some cases, the liposomes fuse with the target cell, whereby the contents of the liposome then empty into the target cell. A liposome can be endocytosed by cells that are phagocytic. Endocytosis can be followed by intralysosomal degradation of liposomal lipids and release of the encapsulated agents.

The liposomes provided herein can also comprise carrier lipids. In some embodiments, the carrier lipids are phospholipids. Carrier lipids capable of forming liposomes include, but are not limited to dipalmitoylphosphatidylcholine (DPPC), phosphatidylcholine (PC; lecithin), phosphatidic acid (PA), phosphatidylglycerol (PG), phosphatidylethanolamine (PE), phosphatidylserine (PS). Other suitable phospholipids further include distearoylphosphatidylcholine (DSPC), dimyristoylphosphatidylcholine (DMPC), dipalmitoylphosphatidyglycerol (DPPG), distearoylphosphatidyglycerol (DSPG), dimyristoylphosphatidylglycerol (DMPG), dipalmitoylphosphatidic acid (DPPA); dimyristoylphosphatidic acid (DMPA), distearoylphosphatidic acid (DSPA), dipalmitoylphosphatidylserine (DPPS), dimyristoylphosphatidylserine (DMPS), distearoylphosphatidylserine (DSPS), dipalmitoylphosphatidyethanolamine (DPPE), dimyristoylphosphatidylethanolamine (DMPE), distearoylphosphatidylethanolamine (DSPE) and the like, or combinations thereof. In some embodiments, the liposomes further comprise a sterol (e.g., cholesterol) which modulates liposome formation. The carrier lipids can be any known non-phosphate polar lipids.

A pharmaceutical composition can be encapsulated within liposomes using well-known technology. Biodegradable microspheres can also be employed as carriers for the pharmaceutical compositions of this invention.

The pharmaceutical composition can be administered in liposomes or microspheres (or microparticles). Methods for preparing liposomes and microspheres for administration to a patient are well known to those of skill in the art. Essentially, material is dissolved in an aqueous solution, the appropriate phospholipids and lipids added, along with surfactants if required, and the material dialyzed or sonicated, as necessary.

Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months.

Cell-based immunogenic pharmaceutical compositions can also be administered to a subject. For example, an antigen presenting cell (APC) based immunogenic pharmaceutical composition can be formulated using any of the well-known techniques, carriers, and excipients as suitable and as understood in the art. APCs include monocytes, monocyte-derived cells, macrophages, and dendritic cells. Sometimes, an APC based immunogenic pharmaceutical composition can be a dendritic cell-based immunogenic pharmaceutical composition.

A dendritic cell-based immunogenic pharmaceutical composition can be prepared by any methods well known in the art. In some cases, dendritic cell-based immunogenic pharmaceutical compositions can be prepared through an ex vivo or in vivo method. The ex vivo method can comprise the use of autologous DCs pulsed ex vivo with the polypeptides described herein, to activate or load the DCs prior to administration into the patient. The in vivo method can comprise targeting specific DC receptors using antibodies coupled with the polypeptides described herein. The DC-based immunogenic pharmaceutical composition can further comprise DC activators such as TLR3, TLR-7-8, and CD40 agonists. The DC-based immunogenic pharmaceutical composition can further comprise adjuvants, and a pharmaceutically acceptable carrier.

An adjuvant can be used to enhance the immune response (humoral and/or cellular) elicited in a patient receiving the immunogenic pharmaceutical composition. Sometimes, adjuvants can elicit a Th1-type response. Other times, adjuvants can elicit a Th2-type response. A Th1-type response can be characterized by the production of cytokines such as IFN-γ as opposed to a Th2-type response which can be characterized by the production of cytokines such as IL-4, IL-5 and IL-10.

In some aspects, lipid-based adjuvants, such as MPLA and MDP, can be used with the immunogenic pharmaceutical compositions disclosed herein. Monophosphoryl lipid A (MPLA), for example, is an adjuvant that causes increased presentation of liposomal antigen to specific T Lymphocytes. In addition, a muramyl dipeptide (MDP) can also be used as a suitable adjuvant in conjunction with the immunogenic pharmaceutical formulations described herein.

Adjuvant can also comprise stimulatory molecules such as cytokines. Non-limiting examples of cytokines include: CCL20, α-interferon (IFNα), β-interferon (IFNβ), γ-interferon (IFNγ), platelet derived growth factor (PDGF), TNFα, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, IL-28, MHC, CD80, CD86, IL-1, IL-2, IL-4, IL-5, IL-6, IL-10, IL-18, MCP-1, MIP-1a, MIP-1-, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Fit, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IκB, Inactive NIK, SAP K, SAP-I, JNK, interferon response genes, NFκB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAPI, and TAP2.

Additional adjuvants include: MCP-1, MIP-la, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, IL-22, nerve growth factor, vascular endothelial growth factor, Fas, TNF receptor, Fit, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IκB, Inactive NIK, SAP K, SAP-1, JNK, interferon response genes, NFκB, Bax, TRAIL, TRAILrec, TRAIL-recDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

In some aspects, an adjuvant can be a modulator of a toll like receptor. Examples of modulators of toll-like receptors include TLR9 agonists and are not limited to small molecule modulators of toll-like receptors such as Imiquimod. Sometimes, an adjuvant is selected from bacteria toxoids, polyoxypropylene-polyoxyethylene block polymers, aluminum salts, liposomes, CpG polymers, oil-in-water emulsions, or a combination thereof. Sometimes, an adjuvant is an oil-in-water emulsion. The oil-in-water emulsion can include at least one oil and at least one surfactant, with the oil(s) and surfactant(s) being biodegradable (metabolizable) and biocompatible. The oil droplets in the emulsion can be less than 5 μm in diameter, and can even have a sub-micron diameter, with these small sizes being achieved with a microfluidiser to provide stable emulsions. Droplets with a size less than 220 nm can be subjected to filter sterilization.

In some instances, an immunogenic pharmaceutical composition can include carriers and excipients (including but not limited to buffers, carbohydrates, mannitol, proteins, polypeptides or amino acids such as glycine, antioxidants, bacteriostats, chelating agents, suspending agents, thickening agents and/or preservatives), water, oils including those of petroleum, animal, vegetable or synthetic origin, such as peanut oil, soybean oil, mineral oil, sesame oil and the like, saline solutions, aqueous dextrose and glycerol solutions, flavoring agents, coloring agents, and other acceptable additives, adjuvants, or binders, other pharmaceutically acceptable auxiliary substances as required to approximate physiological conditions, such as pH buffering agents, tonicity adjusting agents, emulsifying agents, wetting agents and the like. Examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In another instances, the pharmaceutical preparation is substantially free of preservatives. In other instances, the pharmaceutical preparation can contain at least one preservative. It will be recognized that, while any suitable carrier known to those of ordinary skill in the art can be employed to administer the pharmaceutical compositions described herein, the type of carrier will vary depending on the mode of administration.

An immunogenic pharmaceutical composition can include preservatives such as thiomersal or 2-phenoxyethanol. In some instances, the immunogenic pharmaceutical composition is substantially free from (e.g., <10 μg/mL) mercurial material e.g. thiomersal-free. α-Tocopherol succinate may be used as an alternative to mercurial compounds.

For controlling the tonicity, a physiological salt such as sodium salt can be included in the immunogenic pharmaceutical composition. Other salts can include potassium chloride, potassium dihydrogen phosphate, disodium phosphate, and/or magnesium chloride, or the like.

An immunogenic pharmaceutical composition can have an osmolality of between 200 mOsm/kg and 400 mOsm/kg, between 240-360 mOsm/kg, or within the range of 290-310 mOsm/kg.

An immunogenic pharmaceutical composition can comprise one or more buffers, such as a Tris buffer; a borate buffer; a succinate buffer; a histidine buffer (particularly with an aluminum hydroxide adjuvant); or a citrate buffer. Buffers, in some cases, are included in the 5-20 or 10-50 mM range.

The pH of the immunogenic pharmaceutical composition can be between about 5.0 and about 8.5, between about 6.0 and about 8.0, between about 6.5 and about 7.5, or between about 7.0 and about 7.8.

An immunogenic pharmaceutical composition can be sterile. The immunogenic pharmaceutical composition can be non-pyrogenic e.g. containing <1 EU (endotoxin unit, a standard measure) per dose, and can be <0.1 EU per dose. The composition can be gluten free.

An immunogenic pharmaceutical composition can include detergent e.g. a polyoxyethylene sorbitan ester surfactant (known as 'Tweens'), or an octoxynol (such as octoxynol-9 (Triton X-100) or t-octylphenoxypolyethoxyethanol). The detergent can be present only at trace amounts. The immunogenic pharmaceutical composition can include less than 1 mg/mL of each of octoxynol-10 and polysorbate 80. Other residual components in trace amounts can be antibiotics (e.g. neomycin, kanamycin, polymyxin B).

An immunogenic pharmaceutical composition can be formulated as a sterile solution or suspension, in suitable vehicles, well known in the art. The pharmaceutical compositions can be sterilized by conventional, well-known sterilization techniques, or can be sterile filtered. The resulting aqueous solutions can be packaged for use as is, or lyophilized, the lyophilized preparation being combined with a sterile solution prior to administration.

Pharmaceutical compositions comprising, for example, an active agent such as immune cells disclosed herein, in combination with one or more adjuvants can be formulated to comprise certain molar ratios. For example, molar ratios of about 99:1 to about 1:99 of an active agent such as an immune cell described herein, in combination with one or more adjuvants can be used. In some instances, the range of molar ratios of an active agent such as an immune cell described herein, in combination with one or more adjuvants can be selected from about 80:20 to about 20:80; about 75:25 to about 25:75, about 70:30 to about 30:70, about 66:33 to about 33:66, about 60:40 to about 40:60; about 50:50; and about 90:10 to about 10:90. The molar ratio of an active agent such as an immune cell described herein, in combination with one or more adjuvants can be about 1:9, and in some cases can be about 1:1. The active agent such as an immune cell described herein, in combination with one or more adjuvants can be formulated together, in the same dosage unit e.g., in one vial, suppository, tablet, capsule, an aerosol spray; or each agent, form, and/or compound can be formulated in separate units, e.g., two vials, suppositories, tablets, two capsules, a tablet and a vial, an aerosol spray, and the like.

In some instances, an immunogenic pharmaceutical composition can be administered with an additional agent. The choice of the additional agent can depend, at least in part, on the condition being treated. The additional agent can include, for example, a checkpoint inhibitor agent such as an anti-PD1, anti-CTLA4, anti-PD-L1, anti CD40, or anti-TIM3 agent (e.g., an anti-PD1, anti-CTLA4, anti-PD-L1, anti CD40, or anti-TIM3 antibody); or any agents having a therapeutic effect for a pathogen infection (e.g. viral infection), including, e.g., drugs used to treat inflammatory conditions such as an NSAID, e.g., ibuprofen, naproxen, acetaminophen, ketoprofen, or aspirin. For example, the checkpoint inhibitor can be a PD-1/PD-L1 antagonist selected from the group consisting of: nivolumab (ONO-4538/BMS-936558, MDX1 106, OPDIVO), pembrolizumab (MK-3475, KEYTRUDA), pidilizumab (CT-011), and MPDL328OA (ROCHE). As another example, formulations can additionally contain one or more supplements, such as vitamin C, E or other antioxidants.

A pharmaceutical composition comprising an active agent such as an immune cell described herein, in combination with one or more adjuvants can be formulated in conventional manner using one or more physiologically acceptable carriers, comprising excipients, diluents, and/or auxiliaries, e.g., which facilitate processing of the active agents into preparations that can be administered. Proper formulation can depend at least in part upon the route of administration chosen. The agent(s) described herein can be delivered to a patient using a number of routes or modes of administration, including oral, buccal, topical, rectal, transdermal, transmucosal, subcutaneous, intravenous, and intramuscular applications, as well as by inhalation.

The active agents can be formulated for parenteral administration (e.g., by injection, for example bolus injection or continuous infusion) and can be presented in unit dose form in ampoules, pre-filled syringes, small volume infusion or in multi-dose containers with an added preservative. The compositions can take such forms as suspensions, solutions, or emulsions in oily or aqueous vehicles, for example solutions in aqueous polyethylene glycol.

For injectable formulations, the vehicle can be chosen from those known in art to be suitable, including aqueous solutions or oil suspensions, or emulsions, with sesame oil, corn oil, cottonseed oil, or peanut oil, as well as elixirs, mannitol, dextrose, or a sterile aqueous solution, and similar pharmaceutical vehicles. The formulation can also comprise polymer compositions which are biocompatible, biodegradable, such as poly(lactic-co-glycolic)acid. These materials can be made into micro or nanospheres, loaded with drug and further coated or derivatized to provide superior sustained release performance. Vehicles suitable for periocular or intraocular injection include, for example, suspensions of therapeutic agent in injection grade water, liposomes and vehicles suitable for lipophilic substances. Other vehicles for periocular or intraocular injection are well known in the art.

In some instances, pharmaceutical composition is formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

When administration is by injection, the active agent can be formulated in aqueous solutions, specifically in physiologically compatible buffers such as Hanks solution, Ringer's solution, or physiological saline buffer. The solution can contain formulatory agents such as suspending, stabilizing and/or dispersing agents. In another embodiment, the pharmaceutical composition does not comprise an adjuvant or any other substance added to enhance the immune response.

In addition to the formulations described previously, the active agents can also be formulated as a depot preparation. Such long acting formulations can be administered by implantation or transcutaneous delivery (for example subcutaneously or intramuscularly), intramuscular injection or use of a transdermal patch. Thus, for example, the agents can be formulated with suitable polymeric or hydrophobic materials (for example as an emulsion in an acceptable oil) or ion exchange resins, or as sparingly soluble derivatives, for example, as a sparingly soluble salt.

In some cases, pharmaceutical compositions comprising one or more agents exert local and regional effects when administered topically or injected at or near particular sites of infection. Direct topical application, e.g., of a viscous liquid, solution, suspension, dimethylsulfoxide (DMSO)-based solutions, liposomal formulations, gel, jelly, cream, lotion, ointment, suppository, foam, or aerosol spray, can be used for local administration, to produce for example local and/or regional effects. Pharmaceutically appropriate vehicles for such formulation include, for example, lower aliphatic alcohols, polyglycols (e.g., glycerol or polyethylene glycol), esters of fatty acids, oils, fats, silicones, and the like. Such preparations can also include preservatives (e.g., p-hydroxybenzoic acid esters) and/or antioxidants (e.g., ascorbic acid and tocopherol). See also Dermatological Formulations: Percutaneous absorption, Barry (Ed.), Marcel Dekker Incl, 1983. In another embodiment, local/topical formulations comprising a transporter, carrier, or ion channel inhibitor are used to treat epidermal or mucosal viral infections.

Pharmaceutical compositions can contain adjuvants such as hydrophilic or lipophilic gelling agents, hydrophilic or lipophilic active agents, preserving agents, antioxidants, solvents, fragrances, fillers, sunscreens, odor-absorbers and dyestuffs. The amounts of these various adjuvants are those conventionally used in the fields considered and, for example, are from about 0.01% to about 20% of the total weight of the composition. Depending on their nature, these adjuvants can be introduced into the fatty phase, into the aqueous phase and/or into the lipid vesicles.

XII. Methods of Treatment

Provided herein are method of using any of the nucleic acid disclosed above, the vector containing any of the nucleic acid sequence disclosed above, the protein encoded by any of the nucleic acid disclosed above, or the host cell disclosed above, for manufacture of a medicament for treating an immune disease or cancer.

Also provided herein are methods of treating a subject with a disease, disorder or condition. A method of treatment can comprise administering a pharmaceutical composition disclosed herein to a subject with a disease, disorder or condition. The present disclosure provides methods of treatment comprising an immunogenic therapy. Methods of treatment for a disease (such as cancer or a viral infection) are provided. A method can comprise administering to a subject an effective amount of a pharmaceutical composition comprising an immunogenic antigen specific T cells. In some embodiments, the antigen comprises a tumor antigen.

In some embodiments, the method of treating a subject with a disease or condition comprises administering to the subject the pharmaceutical composition disclosed herein. In some embodiments, the method is a method of preventing resistance to a cancer therapy, wherein the method comprises administering to a subject in need thereof the pharmaceutical composition disclosed herein. In some embodiments, the method is a method of inducing an immune response, wherein the method comprises administering to a subject in need thereof the pharmaceutical composition disclosed herein. In some embodiments, the immune response is a humoral response. In some embodiments, the immune response is a cytotoxic T cell response.

In some embodiments, the subject has cancer, wherein the cancer is selected from the group consisting of melanoma, ovarian cancer, lung cancer, prostate cancer, breast cancer, colorectal cancer, endometrial cancer, and chronic lymphocytic leukemia (CLL).

In some embodiments, the subject has a breast cancer that is resistant to anti-estrogen therapy. In some embodiments, the breast cancer expresses an estrogen receptor with a mutation. In some embodiments, the subject has a CLL that is resistant to ibrutinib therapy. In some embodiments, the CLL expresses a Bruton tyrosine kinase with a mutation, such as a C481S mutation. In some embodiments, the subject has a lung cancer that is resistant to a tyrosine kinase inhibitor. In some embodiments, the lung cancer expresses an epidermal growth factor receptor (EGFR) with a mutation, such as a T790M, L792F, or C797S mutation.

In some embodiments, the method further comprises administering at least one additional therapeutic agent or modality. In some embodiments, the at least one additional therapeutic agent or modality is surgery, a checkpoint inhibitor, an antibody or fragment thereof, a chemotherapeutic agent, radiation, a vaccine, a small molecule, a T cell, a vector, and APC, a polynucleotide, an oncolytic virus or any combination thereof. In some embodiments, the at least one additional therapeutic agent is an anti-PD-1 agent and anti-PD-L1 agent, an anti-CTLA-4 agent, or an anti-CD40 agent. In some embodiments, the additional therapeutic agent is administered before, simultaneously, or after administering the pharmaceutical composition disclosed herein.

In some other aspects, provided here is use of a pharmaceutical composition for the manufacture of a medicament for use in therapy. In some embodiments, a method of treatment comprises administering to a subject an effective amount of T cells specifically recognizing an immunogenic neoantigen peptide. In some embodiments, a method of treatment comprises administering to a subject an effective amount of a TCR that specifically recognizes an immunogenic neoantigen peptide, such as a TCR expressed in a T cell.

In some embodiments, the cancer is selected from the group consisting of carcinoma, lymphoma, blastoma, sarcoma, leukemia, squamous cell cancer, lung cancer (including small cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, melanoma, endometrial or uterine carcinoma, salivary gland carcinoma, kidney or renal cancer, liver cancer, prostate cancer, vulval cancer, thyroid cancer, hepatic carcinoma, head and neck cancer, colorectal cancer, rectal cancer, soft-tissue sarcoma, Kaposi's sarcoma, B-cell lymphoma (including low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NEIL, bulky disease NHL, mantle cell lymphoma, AIDS-related lymphoma, and Waldenstrom's macroglobulinemia), chronic lymphocytic leukemia (CLL), acute lymphoblastic leukemia (ALL), myeloma, Hairy cell leukemia, chronic myeloblasts leukemia, and post-transplant lymphoproliferative disorder (PTLD), abnormal vascular proliferation associated with phakomatoses, edema, Meigs' syndrome, and combinations thereof.

The methods of the disclosure can be used to treat any type of cancer known in the art. Non-limiting examples of cancers to be treated by the methods of the present disclosure can include melanoma (e.g., metastatic malignant melanoma), renal cancer (e.g., clear cell carcinoma), prostate cancer (e.g., hormone refractory prostate adenocarcinoma), pancreatic adenocarcinoma, breast cancer, colon cancer, lung cancer (e.g., non-small cell lung cancer), esophageal cancer, squamous cell carcinoma of the head and neck, liver cancer, ovarian cancer, cervical cancer, thyroid cancer, glioblastoma, glioma, leukemia, lymphoma, and other neoplastic malignancies.

Additionally, the disease or condition provided herein includes refractory or recurrent malignancies whose growth may be inhibited using the methods of treatment of the present disclosure. In some embodiments, a cancer to be treated by the methods of treatment of the present disclosure is selected from the group consisting of carcinoma, squamous carcinoma, adenocarcinoma, sarcomata, endometrial cancer, breast cancer, ovarian cancer, cervical cancer, fallopian tube cancer, primary peritoneal cancer, colon cancer, colorectal cancer, squamous cell carcinoma of the anogenital region, melanoma, renal cell carcinoma, lung cancer, non-small cell lung cancer, squamous cell carcinoma of the lung, stomach cancer, bladder cancer, gall bladder cancer, liver cancer, thyroid cancer, laryngeal cancer, salivary gland cancer, esophageal cancer, head and neck cancer, glioblastoma, glioma, squamous cell carcinoma of the head and neck, prostate cancer, pancreatic cancer, mesothelioma, sarcoma, hematological cancer, leukemia, lymphoma, neuroma, and combinations thereof. In some embodiments, a cancer to be treated by the methods of the present disclosure include, for example, carcinoma, squamous carcinoma (for example, cervical canal, eyelid, tunica conjunctiva, vagina, lung, oral cavity, skin, urinary bladder, tongue, larynx, and gullet), and adenocarcinoma (for example, prostate, small intestine, endometrium, cervical canal, large intestine, lung, pancreas, gullet, rectum, uterus, stomach, mammary gland, and ovary). In some embodiments, a cancer to be treated by the methods of the present disclosure further include sarcomata (for example, myogenic sarcoma), leukosis, neuroma, melanoma, and lymphoma. In some embodiments, a cancer to be treated by the methods of the present disclosure is breast cancer. In some embodiments, a cancer to be treated by the methods of treatment of the present disclosure is triple negative breast cancer (TNBC). In some embodiments, a cancer to be treated by the methods of treatment of the present disclosure is ovarian cancer. In some embodiments, a cancer to be treated by the methods of treatment of the present disclosure is colorectal cancer.

In some embodiments, a patient or population of patients to be treated with a pharmaceutical composition of the present disclosure have a solid tumor. In some embodiments, a solid tumor is a melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, or Merkel cell carcinoma. In some embodiments, a patient or population of patients to be treated with a pharmaceutical composition of the present disclosure have a hematological cancer. In some embodiments, the patient has a hematological cancer such as Diffuse large B cell lymphoma ("DLBCL"), Hodgkin's lymphoma ("HL"), Non-Hodgkin's lymphoma ("NEIL"), Follicular lymphoma ("FL"), acute myeloid leukemia ("AML"), or Multiple myeloma ("MM"). In some embodiments, a patient or population of patients to be treated having the cancer selected from the group consisting of ovarian cancer, lung cancer and melanoma.

Specific examples of cancers that can be prevented and/or treated in accordance with present disclosure include, but are not limited to, the following: renal cancer, kidney cancer, glioblastoma multiforme, metastatic breast cancer; breast carcinoma; breast sarcoma; neurofibroma; neurofibromatosis; pediatric tumors; neuroblastoma; malignant melanoma; carcinomas of the epidermis; leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone cancer and connective tissue sarcomas such as but not limited to bone sarcoma, myeloma bone disease, multiple myeloma, cholesteatoma-induced bone osteosarcoma, Paget's disease of bone, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangio sarcoma, neurilemmoma, rhabdomyosarcoma, and synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease (including juvenile Paget's disease) and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; cervical carcinoma; esophageal cancers such as but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; colorectal cancer, KRAS mutated colorectal cancer; colon carcinoma; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as KRAS-mutated non-small cell lung cancer, non-small cell lung cancer, squamous cell carcinoma (epidermoid carcinoma), adenocarcinoma, large-cell carcinoma and small-cell lung cancer; lung carcinoma; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, androgen-independent prostate cancer, androgen-dependent prostate cancer, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acrallentiginous melanoma; kidney cancers such as but not limited to renal cell cancer, adenocarcinoma, hypernephroma, fibrosarcoma, transitional cell cancer (renal pelvis and/or uterus); renal carcinoma; Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas.

Cancers include, but are not limited to, B cell cancer, e.g., multiple myeloma, Waldenstrom's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer (e.g., metastatic, hormone refractory prostate cancer), pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. Other non-limiting examples of types of cancers applicable to the methods encompassed by the present disclosure include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, the cancer whose phenotype is determined by the method of the present disclosure is an epithelial cancer such as, but not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, brenner, or undifferentiated. In some embodiments, the present disclosure is used in the treatment, diagnosis, and/or prognosis of lymphoma or its subtypes, including, but not limited to, mantle cell lymphoma. Lymphoproliferative disorders are also considered to be proliferative diseases.

In some embodiments, the subject has a breast cancer that is resistant to anti-estrogen therapy, is an MSI breast cancer, is a metastatic breast cancer, is a Her2 negative breast cancer, is a Her2 positive breast cancer, is an ER negative breast cancer, is an ER positive breast cancer or any combination thereof.

In some embodiments, the breast cancer expresses an estrogen receptor with a mutation.

In some embodiments, the cancer is recurrent or metastatic breast cancer. In some embodiments, a cancer to be treated by the methods of treatment of the present disclosure is triple negative breast cancer (TNBC).

The pharmaceutical compositions provided herein may be used alone or in combination with conventional therapeutic regimens such as surgery, irradiation, chemotherapy and/or bone marrow transplantation (autologous, syngeneic, allogeneic or unrelated).

In some embodiments, at least one or more chemotherapeutic agents may be administered in addition to the pharmaceutical composition comprising an immunogenic therapy. In some embodiments, the one or more chemotherapeutic agents may belong to different classes of chemotherapeutic agents.

In practicing the methods of treatment or use provided herein, therapeutically-effective amounts of the pharmaceutical compositions can be administered to a subject having a disease or condition. A therapeutically-effective amount can vary widely depending on the severity of the disease, the age and relative health of the subject, the potency of the compounds used, and other factors.

Subjects can be, for example, mammal, humans, pregnant women, elderly adults, adults, adolescents, pre-adolescents, children, toddlers, infants, newborn, or neonates. A subject can be a patient. In some cases, a subject can be a human. In some cases, a subject can be a child (i.e. a young human being below the age of puberty). In some cases, a subject can be an infant. In some cases, the subject can be a formula-fed infant. In some cases, a subject can be an individual enrolled in a clinical study. In some cases, a subject can be a laboratory animal, for example, a mammal, or a rodent. In some cases, the subject can be a mouse. In some cases, the subject can be an obese or overweight subject.

In some embodiments, the subject has previously been treated with one or more different cancer treatment modalities. In some embodiments, the subject has previously been treated with one or more of radiotherapy, chemotherapy, or immunotherapy. In some embodiments, the subject has been treated with one, two, three, four, or five lines of prior therapy. In some embodiments, the prior therapy is a cytotoxic therapy.

In some embodiments, the disease or condition that can be treated with the methods disclosed herein is abnormal growth of cells. In some embodiments, the disease or condition that can be treated with the methods disclosed herein is cancer. In some embodiments, the cancer is a malignant cancer. In some embodiments, the cancer is a benign cancer. In some embodiments, the cancer is an invasive cancer. In some embodiments, the cancer is a solid tumor. In some embodiments, the cancer is a liquid cancer.

The methods of the disclosure can be used to treat any type of cancer known in the art. Non-limiting examples of cancers to be treated by the methods of the present disclosure include melanoma (e.g., metastatic malignant melanoma), renal cancer (e.g., clear cell carcinoma), prostate cancer (e.g., hormone refractory prostate adenocarcinoma), pancreatic adenocarcinoma, breast cancer, colon cancer, lung cancer (e.g., non-small cell lung cancer), esophageal cancer, squamous cell carcinoma of the head and neck, liver cancer, ovarian cancer, cervical cancer, thyroid cancer, glioblastoma, glioma, leukemia, lymphoma, and other neoplastic malignancies.

Additionally, the disease or condition provided herein includes refractory or recurrent malignancies whose growth may be inhibited using the methods of treatment of the present disclosure. In some embodiments, a cancer to be treated by the methods of treatment of the present disclosure is selected from the group consisting of carcinoma, squamous carcinoma, adenocarcinoma, sarcomata, endometrial cancer, breast cancer, ovarian cancer, cervical cancer, fallopian tube cancer, primary peritoneal cancer, colon cancer, colorectal cancer, squamous cell carcinoma of the anogenital region, melanoma, renal cell carcinoma, lung cancer, non-small cell lung cancer, squamous cell carcinoma of the lung, stomach cancer, bladder cancer, gall bladder cancer, liver cancer, thyroid cancer, laryngeal cancer, salivary gland cancer, esophageal cancer, head and neck cancer, glioblastoma, glioma, squamous cell carcinoma of the head and neck, prostate cancer, pancreatic cancer, mesothelioma, sarcoma, hematological cancer, leukemia, lymphoma, neuroma, and combinations thereof. In some embodiments, a cancer to be treated by the methods of the present disclosure include, for example, carcinoma, squamous carcinoma (for example, cervical canal, eyelid, tunica conjunctiva, vagina, lung, oral cavity, skin, urinary bladder, tongue, larynx, and gullet), and adenocarcinoma (for example, prostate, small intestine, endometrium, cervical canal, large intestine, lung, pancreas, gullet, rectum, uterus, stomach, mammary gland, and ovary). In some embodiments, a cancer to be treated by the methods of the present disclosure further include sarcomata (for example, myogenic sarcoma), leukosis, neuroma, melanoma, and lymphoma. In some embodiments, a cancer to be treated by the methods of the present disclosure is breast cancer. In some embodiments, a cancer to be treated by the methods of treatment of the present disclosure is triple negative breast cancer (TNBC). In some embodiments, a cancer to be treated by the methods of treatment of the present disclosure is ovarian cancer. In some embodiments, a cancer to be treated by the methods of treatment of the present disclosure is colorectal cancer.

In some embodiments, a patient or population of patients to be treated with a pharmaceutical composition of the present disclosure have a solid tumor. In some embodiments, a solid tumor is a melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, or Merkel cell carcinoma. In some embodiments, a patient or population of patients to be treated with a pharmaceutical composition of the present disclosure have a hematological cancer. In some embodiments, the patient has a hematological cancer such as Diffuse large B cell lymphoma ("DLBCL"), Hodgkin's lymphoma ("HL"), Non-Hodgkin's lymphoma ("NHL"), Follicular lymphoma ("FL"), acute myeloid leukemia ("AML"), or Multiple myeloma ("MM"). In some embodiments, a patient or population of patients to be treated having the cancer selected from the group consisting of ovarian cancer, lung cancer and melanoma.

Specific examples of cancers that can be prevented and/or treated in accordance with present disclosure include, but are not limited to, the following: renal cancer, kidney cancer, glioblastoma multiforme, metastatic breast cancer; breast carcinoma; breast sarcoma; neurofibroma; neurofibromatosis; pediatric tumors; neuroblastoma; malignant melanoma; carcinomas of the epidermis; leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone cancer and connective tissue sarcomas such as but not limited to bone sarcoma, myeloma bone disease, multiple myeloma, cholesteatoma-induced bone osteosarcoma, Paget's disease of bone, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangio sarcoma, neurilemmoma, rhabdomyosarcoma, and synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease (including juvenile Paget's disease) and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; cervical carcinoma; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; colorectal cancer, RAS mutated colorectal cancer; colon carcinoma; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as RAS-mutated non-small cell lung cancer, non-small cell lung cancer, squamous cell carcinoma (epidermoid carcinoma), adenocarcinoma, large-cell carcinoma and small-cell lung cancer; lung carcinoma; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, androgen-independent prostate cancer, androgen-dependent prostate cancer, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acrallentiginous melanoma; kidney cancers such as but not limited to renal cell cancer, adenocarcinoma, hypernephroma, fibrosarcoma, transitional cell cancer (renal pelvis and/or uterer); renal carcinoma; Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas.

In some embodiments, a subject with a mutation in a RAS gene is treated for cancer by administering a pharmaceutical composition comprising a TCR that recognizes a RAS mutant epitope in complex with an MHC protein encoded by the HLA allele of the subject, the TCR having a TCR alpha chain variable region and a TCR beta chain variable region having an amino acid sequence disclosed herein. In some embodiments, the pharmaceutical composition comprises a nucleic acid sequence encoding the TCR. In some embodiments, the nucleic acid is a DNA or an RNA. In some embodiments, the nucleic acid is a messenger RNA encoding the TCR having a TCR alpha chain variable region and a TCR beta chain variable region having an amino acid sequence disclosed herein. In some embodiments, the pharmaceutical composition comprises a vector that comprises a nucleic acid sequence encoding the TCR and is capable of driving the expression of the TCR, wherein the TCR recognizes a RAS mutant epitope in complex with an MHC protein encoded by the HLA allele of the subject, and wherein the TCR having a TCR alpha chain variable region and a TCR beta chain variable region having an amino acid sequence disclosed herein. In some embodiments, the pharmaceutical composition comprises a cell that comprises a nucleic acid sequence encoding the TCR that recognizes a RAS mutant epitope in complex with an MHC protein encoded by the HLA allele of the subject, the TCR having a TCR alpha chain variable region and a TCR beta chain variable region having an amino acid sequence disclosed herein. In some embodiments, the subject having a cancer is administered a pharmaceutical composition comprising a TCR that recognizes a RAS mutant epitope in complex with an MHC protein encoded by the HLA allele of the subject, the TCR having a TCR alpha chain variable region and a TCR beta chain variable region having an amino acid sequence disclosed herein, wherein the cancer is selected from adenocarcinoma of the biliary tract, transitional cell carcinoma of the bladder, breast carcinoma, cervical adenocarcinoma, colon adenocarcinoma, colon adenoma, neuroblastoma (autonomic ganglia), acute myeloid leukemia, chronic myeloid leukemia, chronic myelomonocytic leukemia, juvenile myelomonocytic leukemia, acute lymphoblastic leukemia, Burkitt's lymphoma, Hodgkin's lymphoma, plasma cell myeloma, hepatocellular carcinoma, large cell carcinoma, non-small cell carcinoma, ductal carcinoma, endocrine tumor, prostrate adenocarcinoma, basal cell carcinoma, squamous cell carcinoma, malignant melanoma, angiosarcoma, leiomyosarcoma, liposarcoma, rhabdomyosarcoma, myxoma, malignant fibrous histiocytoma, pleomorphic sarcoma, germinoma, seminoma, anaplastic carcinoma, follicular carcinoma, papillary carcinoma and Hurthle cell carcinoma.

In some embodiments, a subject with a mutation in a GATA3 gene is treated for cancer by administering a pharmaceutical composition comprising a TCR that recognizes a GATA3 mutant epitope in complex with an MHC protein encoded by the HLA allele of the subject, the TCR having a TCR alpha chain variable region and a TCR beta chain variable region having an amino acid sequence disclosed herein. In some embodiments, the subject with a mutation in a GATA3 gene is treated for breast cancer.

In some embodiments, a subject with a mutation in EGFR gene is treated for cancer by administering a pharmaceutical composition comprising a TCR that recognizes a EGFR mutant epitope in complex with an MHC protein encoded by the HLA allele of the subject, the TCR having a TCR alpha chain variable region and a TCR beta chain variable region having an amino acid sequence disclosed herein. In some embodiments, a subject with a mutation in TMPRSS2:ERG gene is treated for cancer by administering a pharmaceutical composition comprising a TCR that recognizes a TMPRSS2:ERG mutant epitope in complex with an MHC protein encoded by the HLA allele of the subject, the TCR having a TCR alpha chain variable region and a TCR beta chain variable region having an amino acid sequence disclosed herein.

In some embodiments, a subject with a mutation in BTK gene is treated for cancer by administering a pharmaceutical composition comprising a TCR that recognizes a BTK mutant epitope in complex with an MHC protein encoded by the HLA allele of the subject, the TCR having a TCR alpha chain variable region and a TCR beta chain variable region having an amino acid sequence disclosed herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1: Workflow for Antigen-Specific T Cell Identification and Validation

Figure 2:
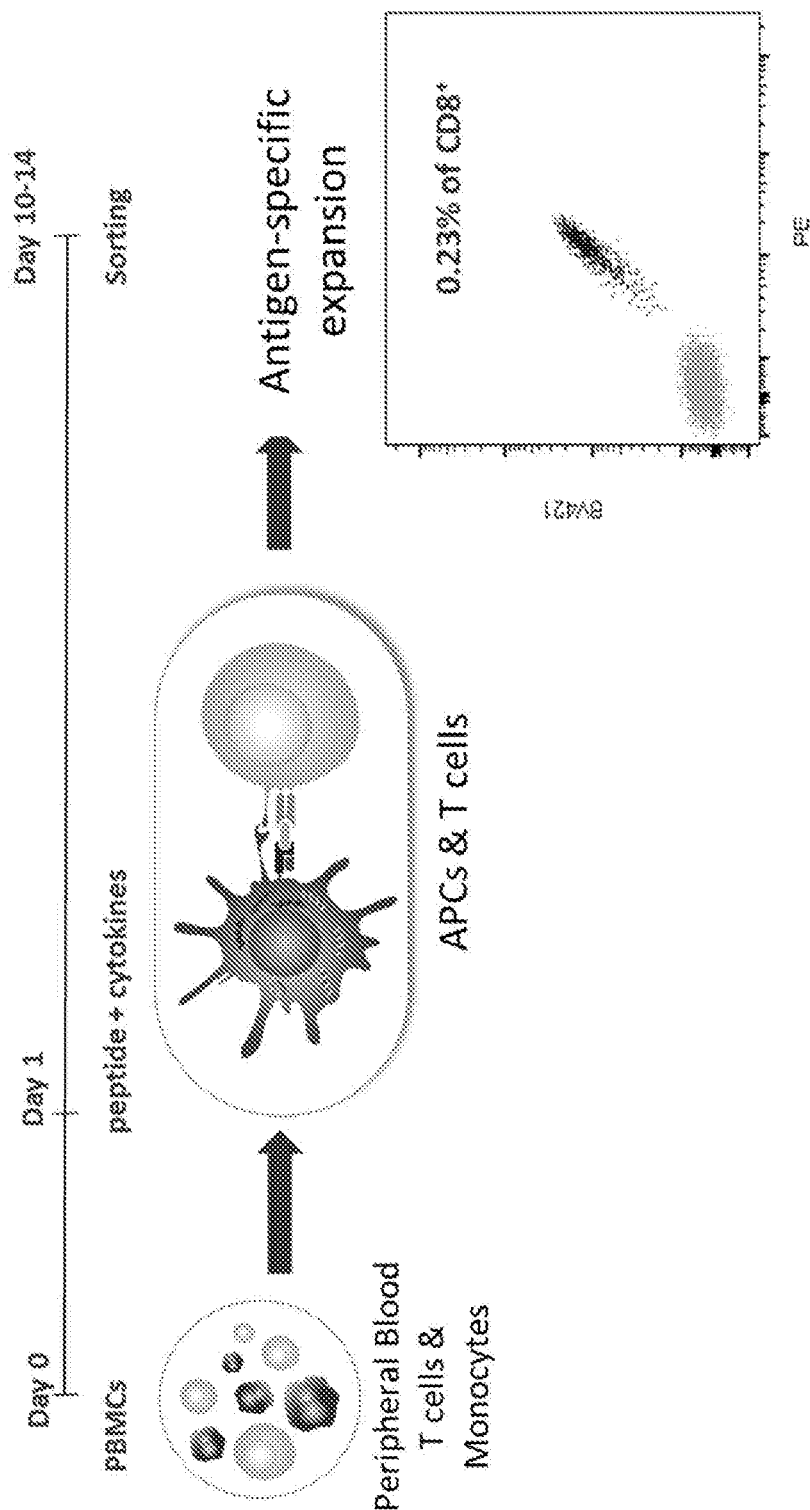
FIG. 2 an example schematic of an antigen-specific CD8+ T cell expansion. PBMCs can be stimulated with the antigen of interest and cytokines. After expansion antigen-specific CD8+ T cells can be identified with peptide-MHC multimers.

In this example, an exemplary workflow to generate and use antigen peptide specific TCRs is described. FIG. 1 demonstrates a graphical representation of the workflow. FIG. 2 details an exemplary timeline for the workflow process, starting with obtaining and culturing PBMCs from a subject, the PBMCs are then stabilized in overnight culture, and incubated in the presence of peptides and cytokines; the monocyte- and DC-derived antigen presenting cells (APCs) help induce T cells in response to the peptide antigens presented by the APCs; between 10 days to 2 weeks, antigen specific T cells expand and are sorted for antigen specificity and activation (for example, CD8+ marker expression indicating generation of cytotoxic T lymphocytes). The activated antigen responsive T cells contain antigen specific TCRs.

Briefly, Mutated peptides containing mutant target epitopes (e.g., mutant TMPRSS2:ERG, RAS, BTK and GATA3 peptides) were synthesized using a peptide synthesizer. The synthesized peptides were used to load APCs to stimulate T cells from a sample of healthy donor peripheral blood mononuclear cells (PBMCs). PBMCs from patients harboring neoantigens of interest can also be used to obtain neoantigen-specific T cells. After incubation with the peptide loaded APCs, T cell populations were analyzed by flow cytometry. Antigen-specific T cells were isolated using flow cytometry (FIGS. 1, 2, 4A, 5, 6, 8F, 8G, 9, 10A, 10B, 11, 13, 15, 16A and 16B). Single cell TCR sequencing was performed for the isolated antigen-specific T cells using 10× Genomics Single Cell V(D)J system to profile the sequences of isolated antigen-specific TCRs. Sequencing reads were analyzed using the Cell Ranger™ analysis pipeline, and candidate sequences of TCRs were selected for further analysis and functional assays (FIGS. 1, 6A, 10A, 10B, 11, 13, 15 and 16A and 16B).

For analysis of TCR functionality, vectors or mRNA encoding TMPRSS2:ERG, RAS, BTK or GATA3 peptides containing target mutant epitopes were transduced into HEK293T or A375 cells to produce antigen expressing cell lines. Jurkat cells, TCRβ deficient Jurkat cells or PBMCs from healthy donors were transduced with nucleic acids (FIG. 3A) encoding candidate TCRs in a lentiviral vector. An exemplary vector is shown in FIG. 3B. FIGS. 4B, 6A and 6B, 10C-10F, 11 and 13 show functional assays for TCR-expressing vector transduced cells. TMPRSS2:ERG, RAS, BTK and GATA3 antigen expressing cell lines were cocultured with TCR transduced Jurkat cells, TCRβ deficient Jurkat cells or PBMCs from healthy donors for antigen recognition assays to analyze the functionality of candidate TCRs (FIGS. 7A-7B, 8A-8E, 10A-10F, 12B and 14).

Example 2: Obtaining Antigen Specific T Cells

In vitro T cell inductions were used to expand antigen specific T cells. The healthy human donor PBMCs were seeded in each well of 24 well plate in AIM V media (Invitrogen). Mutant peptides (TMPRSS2:ERG, RAS, BTK or GATA3), TNF-α, IL-1β, PGE1, and IL-7 were added into wells after 24 hours incubation. The culture media was exchanged every 2 days with fresh media. The antigen specific T cells were evaluated and isolated at day 10 to 20 (FIG. 2).

Example 3: HLA-Multimer Staining and Sorting

Neoantigen specific T cells were detected by combining HLA-multimer staining with 2 different fluorochrome conjugated recombinant HLA (HLA-A02.01, HLA-A03.01, or HLA-A11.01) multimer with neoantigen peptides. Anti-CD8, anti-CD4, anti-CD19, anti-CD16, anti-CD14, anti-CD56 and antibodies and Live/Dead IR dye (Invitrogen) were used for cell surface staining. CD8$^+$ T cells were identified as CD8$^+$CD4$^-$CD19$^-$CD16$^-$CD14$^-$CD56$^-$IR$^-$ (FIGS. 1, 2, 4A, 5, 6A, 8F, 8G, 9, 10A, 10B, 11, 13, 15, 16A and 16B). For sorting, up to 5×10$^6$ cells were incubated with 1-20 μg multimer in 100 μL PBS+0.5% human serum. Antibodies and Live/Dead IR dye were used to stain the cells for an additional 30 min. After staining, cells were washed twice and diluted in PBS+0.5% human serum. Live/Dead IR dye-negative cells were gated and CD8$^+$/multimer$^+$ T cells were sorted on a FACSAria cell sorter (BD Biosciences).

Example 4: Deep Sequencing of Antigen-Specific TCRs

Antigen-specific T cells were sorted into a mixture of PBS and 2% FBS (Hyclone Defined), and 10× Genomics V(D)J kit was used to genetically barcode the RNAs from single T cells. RNA libraries were prepared according to the manufacturer's protocols. The resulting libraries were sequenced using ILLUMINA's MiSeq platform. 10× Genomics analysis software was then used to analyze the sequencing data to obtain paired TCR alpha and beta sequences. Dominant clones were identified based on the frequency of cells with a common TCR alpha and/or TCR beta (FIGS. 1, 6, 8F, 8G, 10A, 10B, 11, 13, 15 and 16A).

Example 5: Antigen-Specific TCR Gene Synthesis and Cloning

Figure 3A:
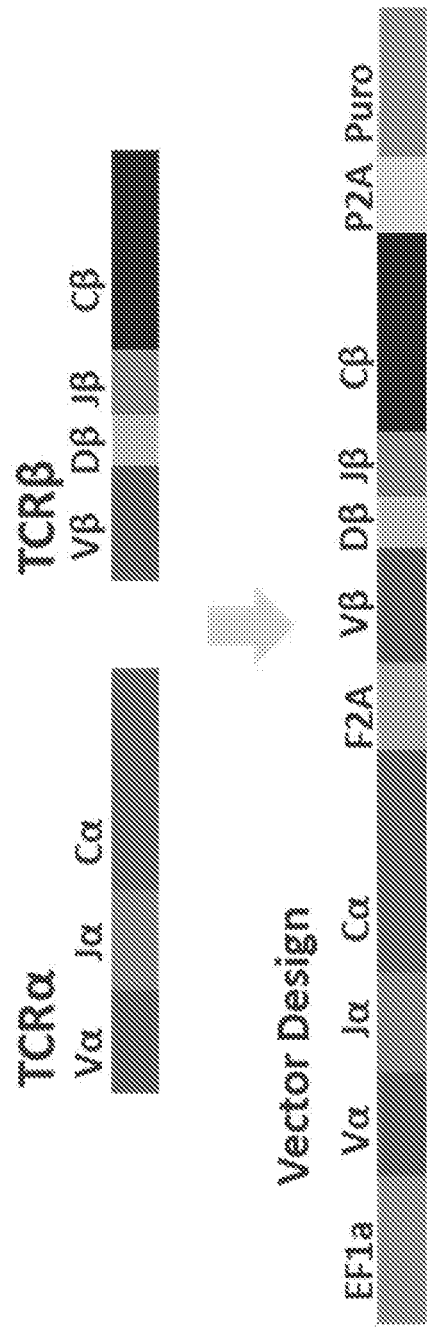
FIG. 3A is an example schematic of recombinant TCR constructs and vector design for expression of the TCR constructs in cells.
Figure 3B:
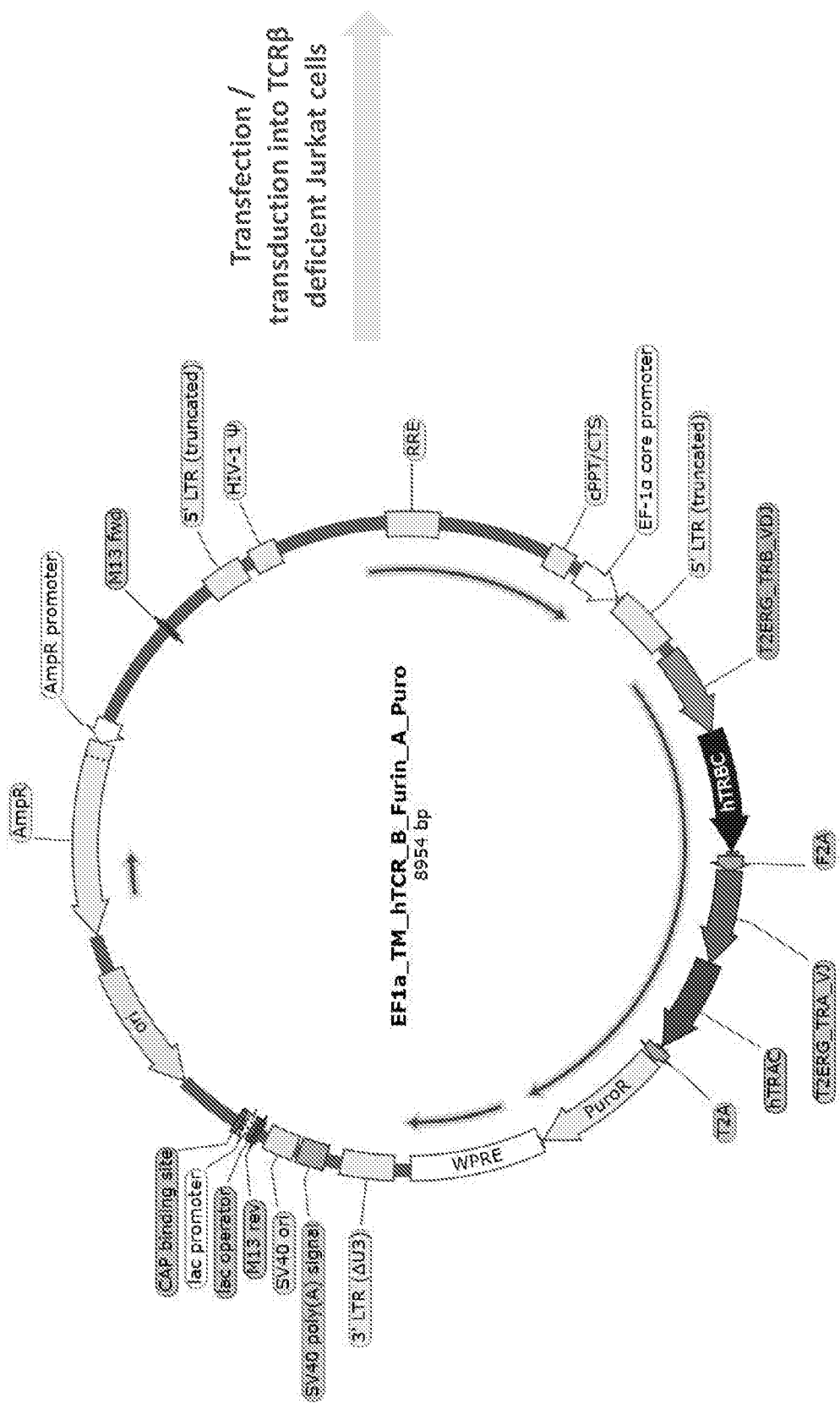
FIG. 3B is an example schematic of a viral vector encoding recombinant TCRs for transduction or transfection into cells.
Figure 4B:
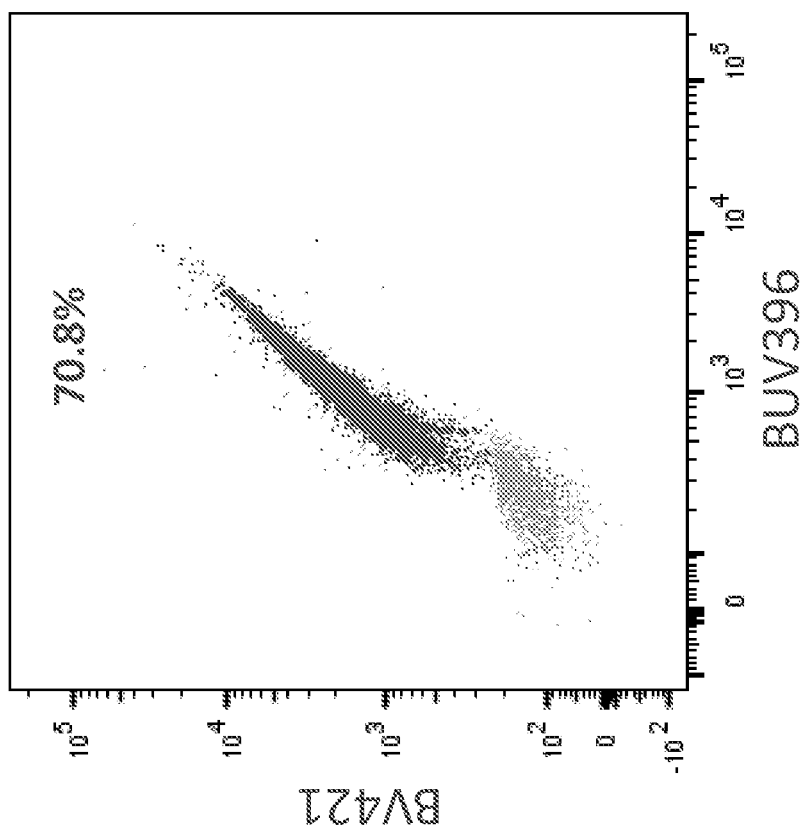
FIG. 4B depicts an example flow cytometry analysis of RAS antigen specific Jurkat cells after sorting of top 10% of multimer positive cells expressing a recombinant TCR after puromycin selection.
Figure 4A:
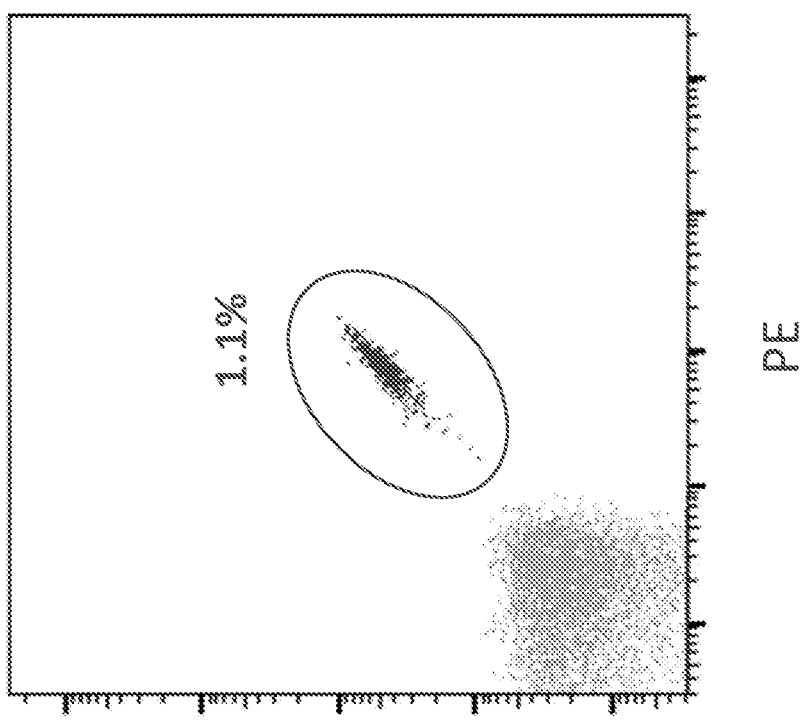
FIG. 4A depicts an example flow cytometry analysis of RAS antigen specific CD8+ T cell expansion in response to stimulation with a RAS peptide.
Figure 5:
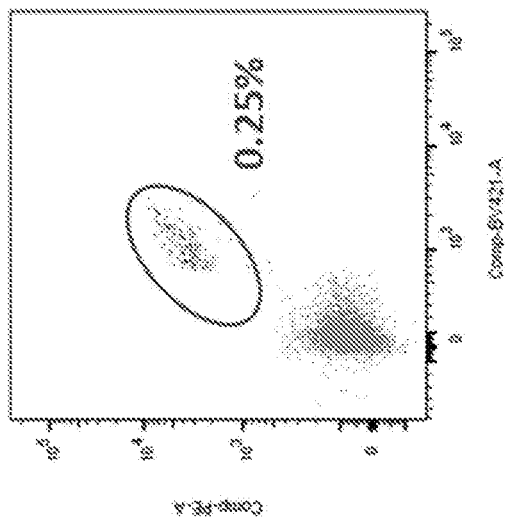
FIG. 5 depicts an example flow cytometry analysis of RAS-peptide-HLA-A11:01 complex specific CD8+ T cell expansion in response to stimulation with RAS G12V peptide (left), RAS-peptide-HLA-A11:01 complex specific CD8+ T cell expansion in response to stimulation with RAS G12C peptide (middle), and RAS-peptide-HLA-A11:01 complex specific CD8+ T cell expansion in response to stimulation with RAS G12D peptide (right).
Figure 5:
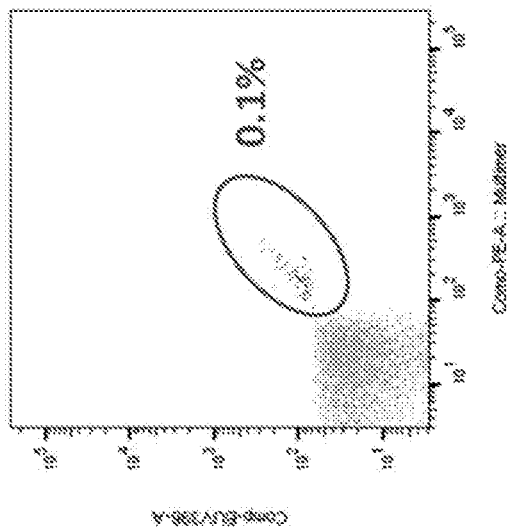
Figure 5:
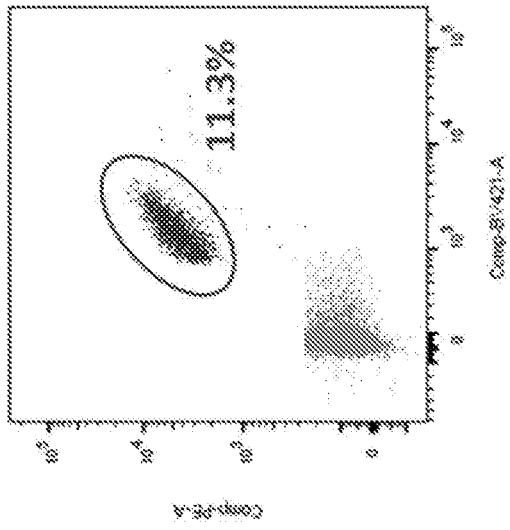
Figure 6A:
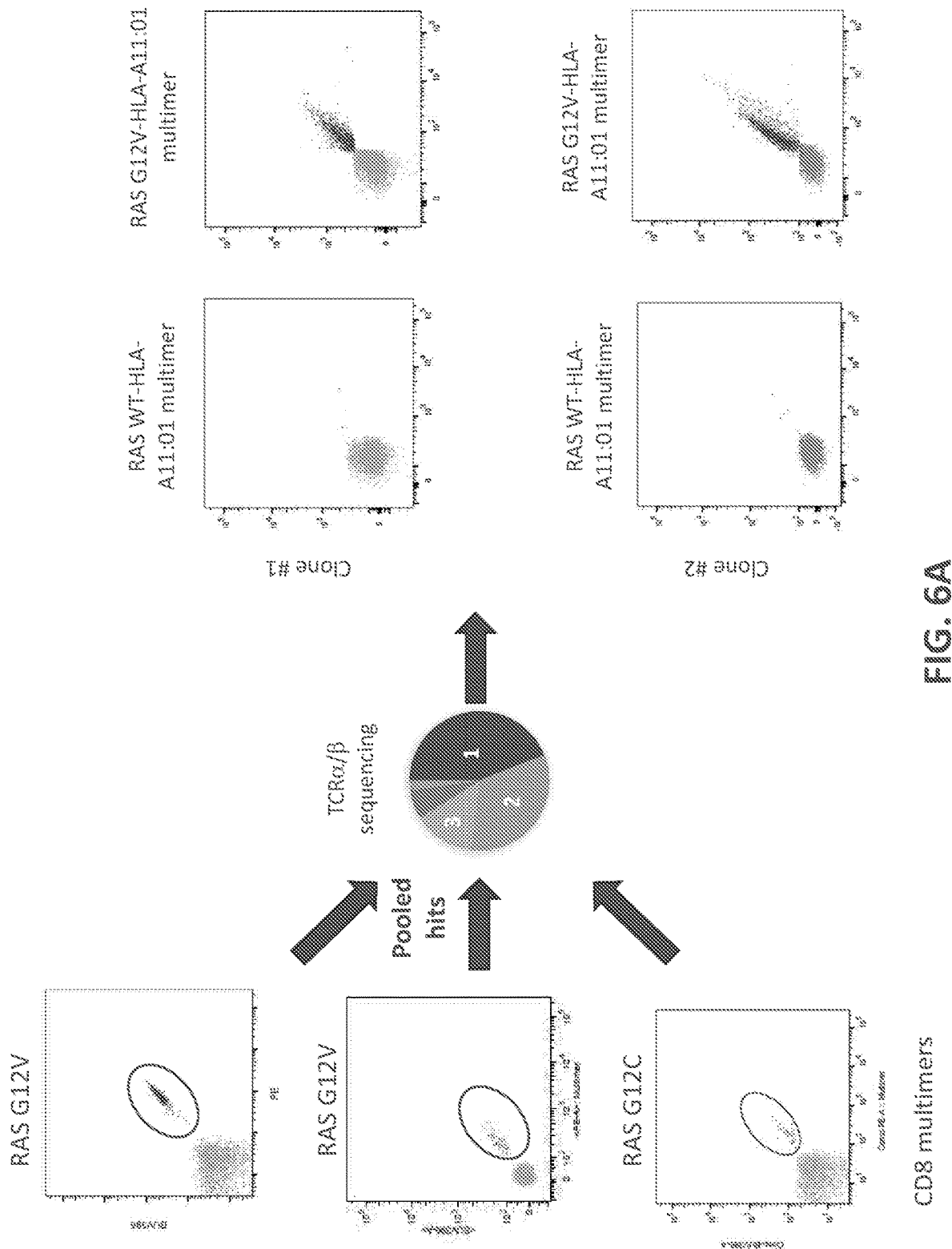
FIG. 6A depicts example flow cytometry analyses of RAS-peptide-HLA-A11:01 complex specific CD8+ T cell expansion in response to stimulation with a G12V or G12C mutant RAS peptides (left), TCR clone abundance analysis after sequencing the TCR from pooled hits (middle), and confirmation of mutant versus wild-type specificity of the top 2 retrieved clones after recombinant TCR expression in Jurkat cells (right).
Figure 6B:
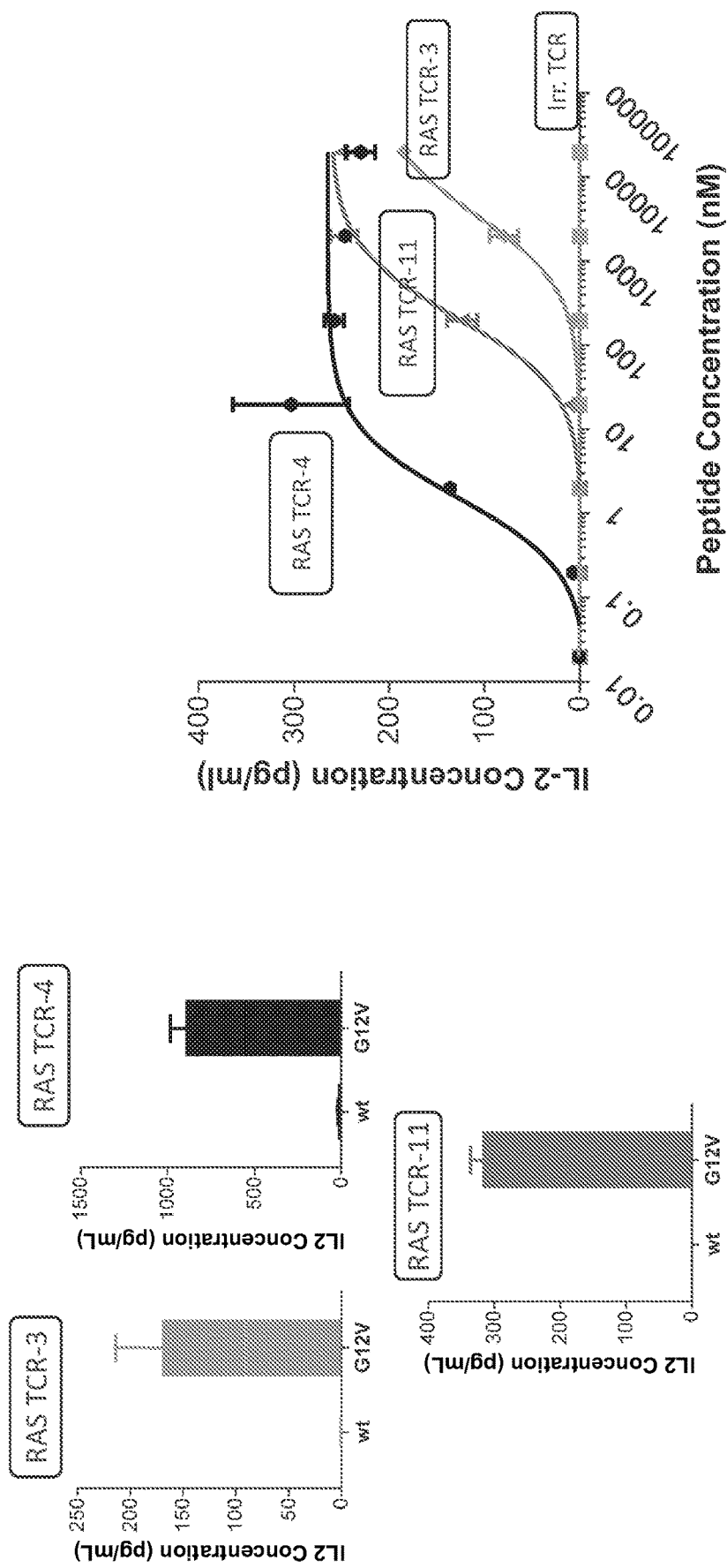
FIG. 6B depicts experimental results of TCR functional assays to assess the specificity (left) and avidity (right) of three RAS TCRs (RAS TCR-3, RAS TCR-4, RAS TCR-11). Graphs showing IL-2 production after co-culturing RAS TCR-transduced Jurkat cells with A375 cells expressing HLA-A11:01 loaded with either RAS wild-type or RAS-mutant peptide (left) or increasing amounts of RAS-mutant peptide (right).
Figures 7A, 7B:
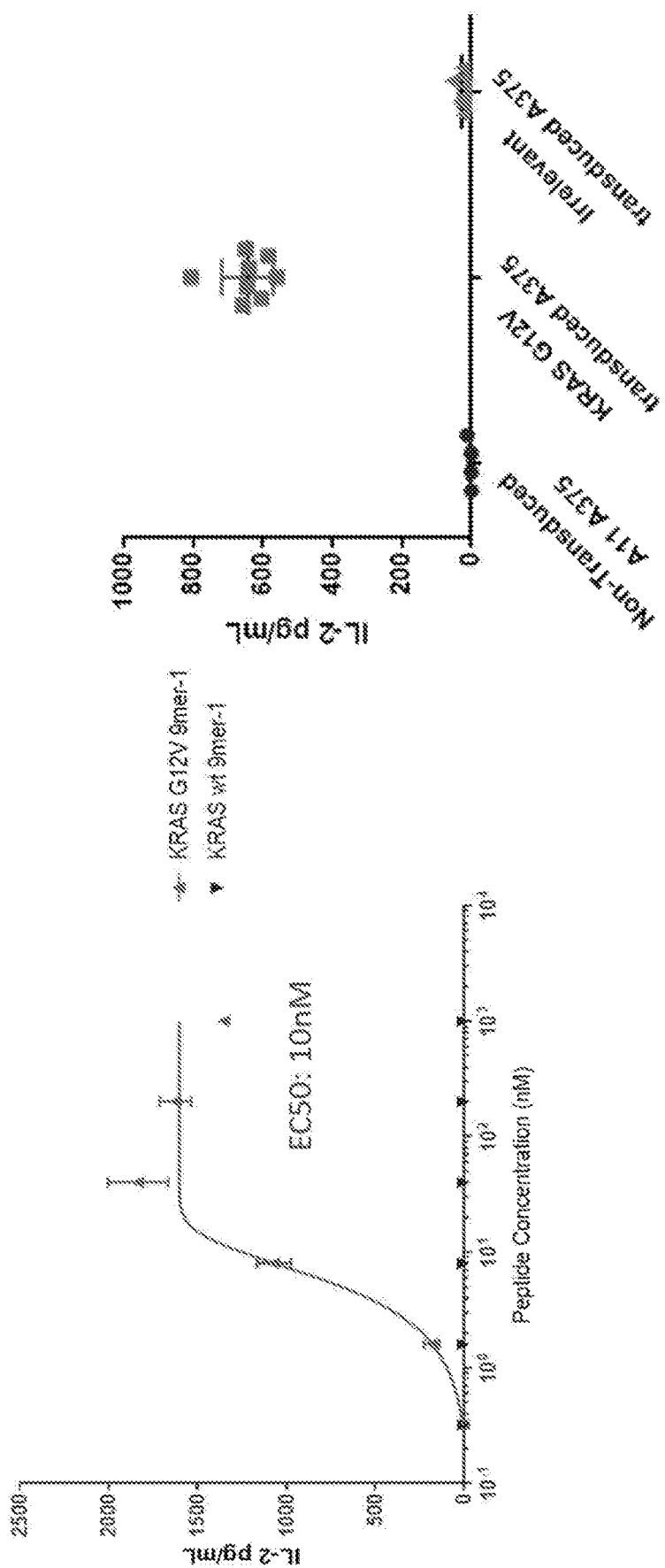
FIG. 7A depicts experimental results of a TCR functional avidity assay (peptide titration). A graph showing IL-2 production after co-culturing RAS TCR-transduced Jurkat cells with A375 cells expressing HLA-A11:01 loaded with increasing amounts of RAS-wild type or RAS-mutant peptide.
FIG. 7B depicts an example graph showing IL-2 production after co-culturing RAS TCR-4-transduced Jurkat cells with A375 cells modified to express HLA-A11:01 only, modified to express HLA-A11:01 and the KRAS G12V mutation, or modified to express HLA-A11:01 and an irrelevant mutation.

FIG. 3A represents a graphical diagram of an exemplary vector design, incorporating a TCR alpha chain and a TCR beta chain construct; wherein the TCR alpha- and beta-chain constructs comprise nucleic acid sequences encoding a variable (V), a diversity ((D), only in beta chain construct) a joining (J) and a constant (C) region for each of a TCR alpha (α) chain and a TCR beta (β) chain as shown in the diagram, in a vector with an upstream regulatory element comprising elements necessary for expression of the incorporated nucleic acid sequence, including, for example, a promoter (example EF1a region as shown in the diagram), further incorporating F2A and P2A proteolytic cleavage sites and a sequence encoding for Puromycin resistance (Puro) for Puromycin mediated selection. The lentiviral vectors were constructed from pCDH-EF1-T2A-Puro (SBI system bioscience). Antigen-specific TCR lentiviral vectors were generated by inserting a TCR beta variable region, followed by a TCR beta mouse constant region, furin cleavage site, SGSG linker, F2A site, a TCR alpha variable region, a TCR alpha constant region, a T2A site, and a puromycin resistance gene (FIGS. 3A and 3B).

Example 6: Transfection and Transduction

Lentivirus encoding antigen-specific TCRs was prepared by transient transfection of 293T cells. The cells were seeded on a 10 cm plate at $7 \times 10^6$ cells 16 hours before transfection with 7 µg of lentiviral vector, 7 µg of packaging plasmid mix (pPAX and pMD2.G), 28 µL of Fugene (Promega) and 1 mL of Opti-MEM (Gibco). The culture media was replaced a day after transfection. 72 hours after transfection, the supernatant was harvested concentrated 10-fold.

Jurkat cells or PBMCs were transduced with concentrated lentivirus encoding TCR sequences. Jurkat cells were washed and resuspended in RPMI-1640 containing polybrene and 10% FBS. $5 \times 10^5$ CD8-Jurkat cells in 100 µL of media were plated per well in 96-well plate and 25 µL of concentrated lentivirus was added. The cells were centrifuged at 2400 rotation per minute (rpm) for 1 hour and incubated in a $CO_2$ incubator. The cells were transduced again with fresh media with polybrene and FBS and 25 µL of concentrated lentivirus. The media was replaced with RPMI-1640 containing 10% FBS and Pen/Strep 24 hours after the second transduction. Puromycin treatment (1 µg/ml) started at day 4 after transduction.

Example 7: TCR Transduced Jurkat Binding to HLA-Peptide

To evaluate TCR transduction, transduced Jurkat cells were stained with fluorochrome conjugated multimer (HLA-neoantigen), anti-CD8 antibody, anti-mTCR constant region antibody, and Live/Dead IR dye. mTCR and multimer positive cells were measured by flow cytometry (FIGS. 4B, 6A, 6B, 10A-10F, 11 and 13).

Example 8: Peptide Loading of Target Cells

For exogenous peptide pulsing, $1 \times 10^6$ T2, 293T or A375 cells were incubated at 37° C. and 5% $CO_2$ for 2 h with 10 pg/mL human $β_2$-microglobulin (Calbiochem) and titrating amounts, ranging from $1 \times 10^{-5}$ M to $1 \times 10^{-12}$ M of the RAS or GATA3 peptides, T2 cells pulsed with $10^{-5}$M influenza peptide GIL (influenza matrix protein$_{58-66}$ GILGFVTL, Metabion) served as negative control. After washing, peptide-loaded T2 cells were used in IL-2 release assays (FIGS. 6B, 7, 8, 12E and 14).

Example 9: Neoantigen Expressing Target Cells

For endogenous antigen expressing target cells, $1 \times 10^6$ HEK293 or A375 cells were transduced with lentivirus vectors encoding TMPRSS2::ERG, BTK, GATA3 or KRAS mutated peptides. The transduced target cells were selected by puromycin (1 µg/ml) in culture media (DMEM with 10% FBS).

Example 10: IL-2 Release Assay

For investigation of specificity, T cell clones ($2.5 \times 10^5$ cells in 50 µL) can be incubated with HEK293T, HLA-A03.01 transduced A375 or HLA-A11.01 transduced A375 cell lines ($5 \times 10^4$ cells in 50 µL) and TMPRSS2::ERG, BTK, GATA3 or KRAS mutated peptide neoantigens. The following figures demonstrate IL2 release assay results in case of the respective TCRs as depicted within the figures: FIGS. 6B, 7A, 7B, 8E, 10C, 12A, 12B and 14). Culture supernatants were harvested after 24 h co-culture and assessed IL-2 concentration by a standard MSD using V-PLEX Human IL-2 assays (Meso Scale Discovery).

Example 11: IFN-γ Release Assay

For investigation of specificity, T cell clones ($2 \times 10^3$ cells in 100 µL) were incubated with cell lines expressing TMPRSS2::ERG, BTK, GATA3 or KRAS mutated peptide neoantigens. Culture supernatants were harvested after 24 h co-culture and assessed by a standard ELISA using the OptEJA™ Human IFN-γ Set (BD Biosciences Pharmingen).

Example 12: Cytotoxicity Assay

Cytotoxic activity of T cell clones can be analyzed in a standard 4 h 51-chromium release assay. Briefly, $1 \times 10^6$ target cells can be labeled with 100 µCi $Na_2^{51}CrO_4$(ICN Biochemicals) for 1-1.5 h. $^{51}$Cr-labeled target cells can be cultured with T cells in RPMI 1640 with 12% FCS. For determination of functional avidity $1 \times 10^4$T cells can be added to $1 \times 10^3$ peptide-pulsed T2 cells loaded with titrated amounts of TMPRSS2::ERG, BTK, GATA3 or KRAS mutated peptide neoantigens, giving a constant E:T of 10:1.

After 4 h co-culture at 37° C., 50 µL of supernatant can be collected and radioactivity can be measured in a gamma counter. The percentage of specific lysis can be calculated as: 100× (experimental release−spontaneous release)/(maximum release−spontaneous release). Spontaneous release can be assessed by incubating target cells in the absence of effector cells. For the calculation of percent relative lysis, the maximum percent specific lysis can be set to the reference value of 100% and corresponding values can be calculated corresponding to this reference. To determine half-maximum lysis, percent relative lysis can be plotted against peptide concentration. The peptide concentration at which the curve crossed 50% relative lysis can be taken as the value of half-maximum lysis.

Example 13: Cell Killing Assay

Figures 8A, 8B:
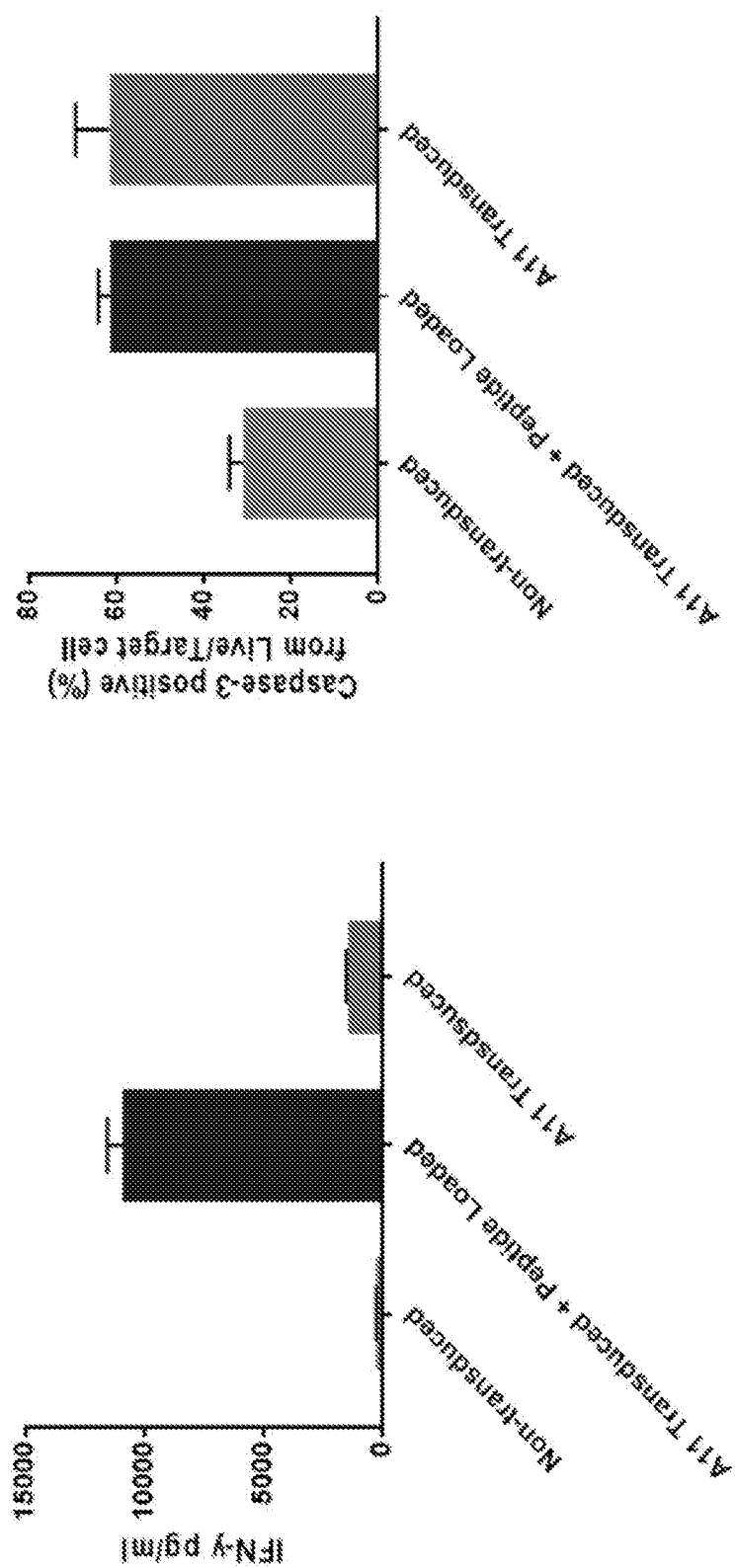
FIG. 8A depicts an example graph showing IFNγ secretion from RAS TCR-4-transduced PBMCs after co-culture with the naturally RAS G12V mutant SW620 colon cancer cell line without manipulation, with expression of HLA-A11:01 plus RAS G12V peptide added, and with expression of HLA-A11:01 only.
FIG. 8B depicts an example graph showing Caspase-3 activation after co-culture with RAS TCR-transduced PBMCs in the naturally RAS G12V mutant SW620 colon cancer cell line without manipulation, with expression of HLA-A11:01 plus RAS G12V peptide added, and with expression of HLA-A11:01 only.

A RAS-neoantigen specific recombinant TCR was transduced into PBMCs and their ability to kill a cancer cell line was analyzed (FIGS. 8A, 8B). The recombinant TCR expressing cells killed showed more than a 30% higher killing of cancer cell lines compared to control. A modified recombinant TCR (rTCR) with mouse constant regions was expressed from a SFFV promoter and a 30% neoantigen specific TCR transduction yield in PBMCs from a healthy donor was achieved. The SW620 cell line was used as target cell which naturally expresses the KRAS G12V mutation. HLA-A11:01 was introduced into the SW620 cell line by lentiviral transductions. The rTCR transduced PBMCs were co-cultured with two different SW620 cell lines with or without expression of HLA-A11:01 for 6 hours. Supernatant and cells were then harvested to analyze cytokine secretion and apoptosis.

After 6 hour co-culture, significantly higher levels of IFNγ, IL-2, and TNFα were detected for the groups of HLA-A11:01 transduced SW620 cell line (Ras$^{mut}$ cell line+ HLA-A11:01) compared to non-transduced SW620 (Ras$^{mut}$ cell line). This shows that the rTCR PBMC can specifically recognize a RAS peptide containing a G12V mutation on HLA-A11:01 of a cell line close to real tumor model. Also, a significantly higher percent of Caspase-3 (apoptosis marker) positive cells was observed in HLA-A11:01 transduced SW620 cell lines compared to control. Thus, the rTCR transduced PBMCs can not only secrete cytokine (IFNγ, IL-2, and TNFα) but also functionally kill target cells specifically.

Figure 8C:
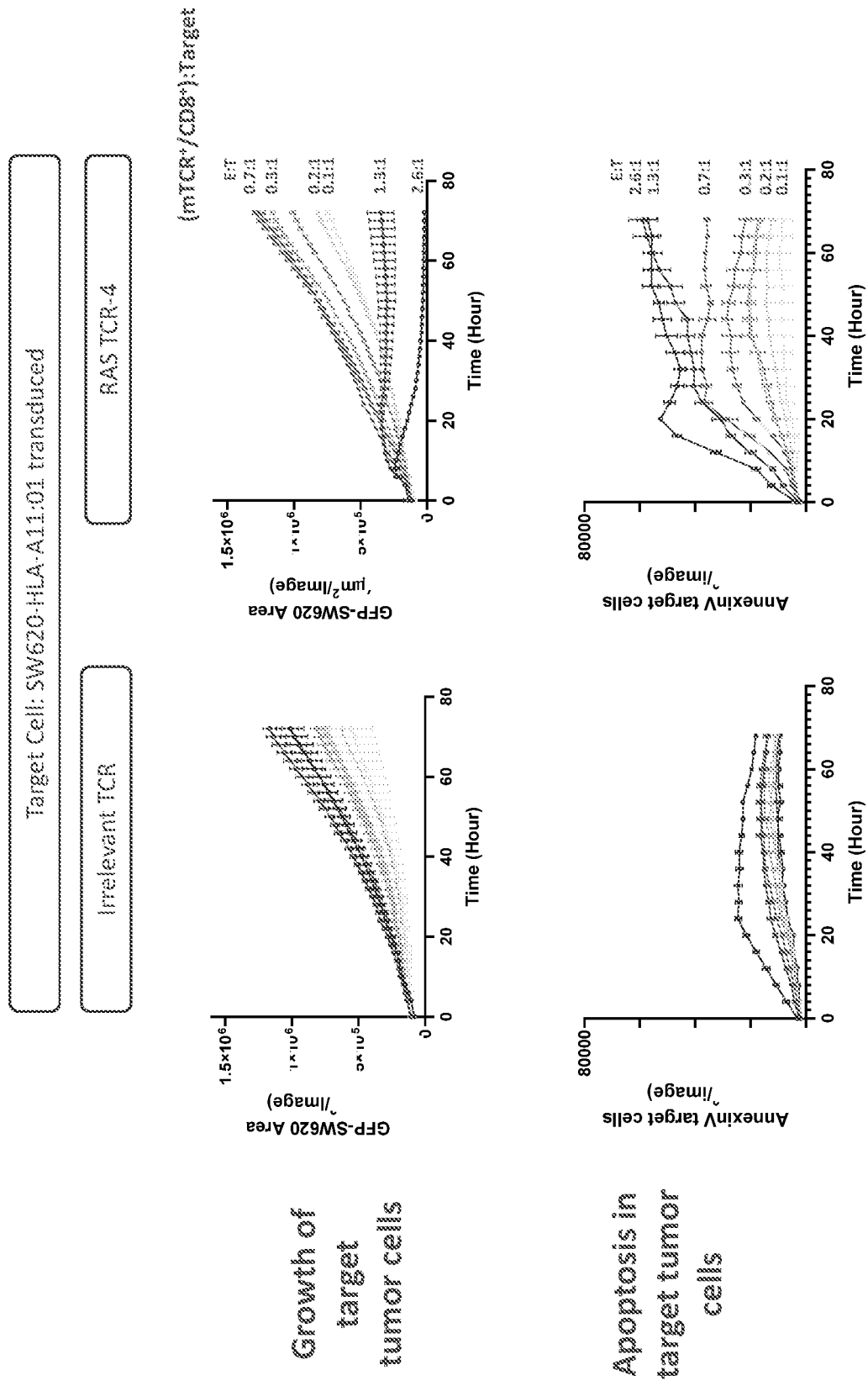
FIG. 8C depicts experimental results of a cytotoxicity assay in which PBMCs transduced with an irrelevant TCR (left) or RAS TCR-4 (right) are co-cultured with SW620 target tumor cells expressing HLA-A11:01 and GFP over an increasing range of PBMC to target ratios. Graphs depicting the growth of the target cells over 72 hours as measured by GFP signal (top) and the death of the target cells as measured by Annexin V signaling (bottom) show that the RAS TCR-transduced PBMCs kill the target cells effectively.
Figure 8D:
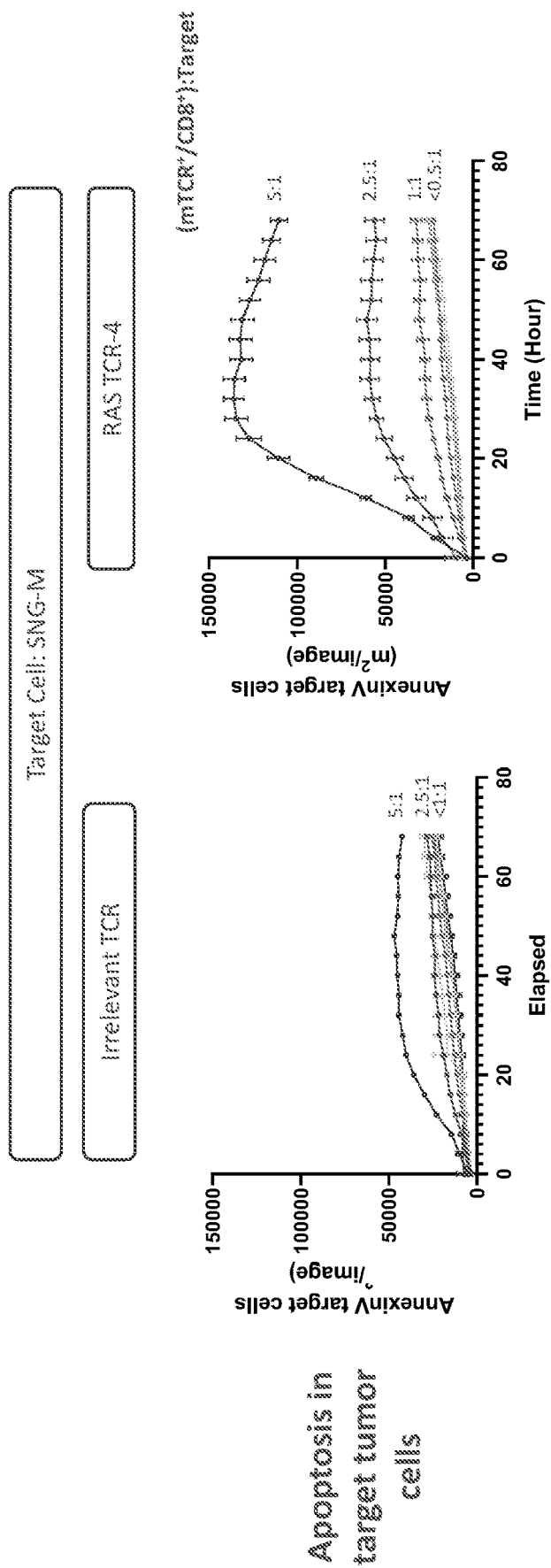
FIG. 8D depicts experimental results of a cytotoxicity assay in which PBMCs transduced with an irrelevant TCR (left) or RAS TCR-4 (right) are co-cultured with SNG-M target tumor cells over an increasing range of PBMC to target ratios. Graphs depicting the death of the target cells as measured by Annexin V signaling over 72 hours show that the RAS TCR-transduced PBMCs kill the target cells.
Figure 8E:
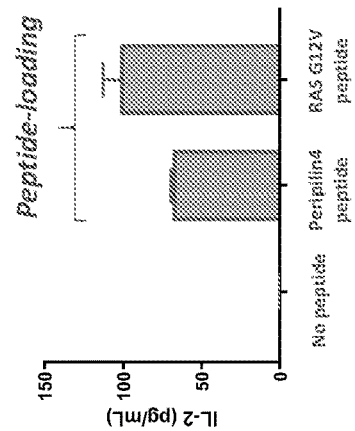
FIG. 8E depicts experimental results of a safety screen of RAS TCR-4. Depicted on the left is a graph showing IL-2 production after co-culturing RAS TCR-transduced Jurkat cells with A375 cells expressing HLA-A11:01 loaded with the cognate RAS G12V epitope or peptides in which one position of the cognate epitope is changed to an alanine. Depicted in the center is a graph showing IL-2 production after co-culturing RAS TCR-transduced Jurkat cells with A375 cells expressing HLA-A11:01 loaded with the RAS G12V epitope or peptides identified from the initial safety scree. Depicted on the right is a graph showing IL-2 production after co-culturing RAS TCR-transduced Jurkat cells with A375 cells expressing HLA-A11:01 transduced with Perilipin4 and loaded with RAS G12V peptide or Perilipin4 peptide or no peptide (right).
Figure 8E:
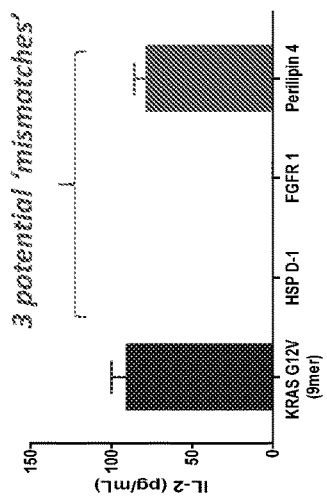
Figure 8E:
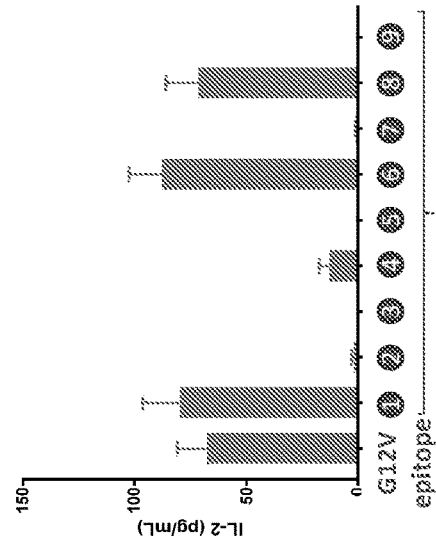
Figure 8E:

In some examples, cytotoxicity activity is assessed by co-culturing T cells expressing a TCR specific to a mutant RAS peptide on a specific HLA, with mutant RAS peptide-transduced target cancer cells expressing the corresponding HLA, and by determining the relative growth of the target cells, along with measuring the apoptotic marker Annexin V in the target cancer cells specifically (FIGS. 8C, 8D, 10D, 10E). Target cancer cells are engineered to express the mutant peptide along with the proper MHC-I allele. Mock-transduced target cells (i.e. not expressing the mutant peptide) are used as a negative control. The cells are also transduced to stably express GFP allowing the tracking of target cell growth. PBMCs from healthy donors, used as effector cells, are transduced to express a TCR specific to a mutant RAS peptide. Mock-transduced cells are used as a negative control. The target cells are cocultured with different amount of effector cells for 72 h in media containing Annexin V-detection reagent. The GFP signal and Annexin-V signal are measured over time with an IncuCyte S3 apparatus. Annexin V signal originating from effector cells is filtered out by size exclusion. Target cell growth and death is expressed as GFP and Annexin-V area (mm$^2$) over time, respectively. FIG. 8C demonstrate high degree of inverse correlation of the TCR levels as determined by the TCR/CD8+: target ratio with the growth of the target cells (upper panel). Similarly, higher TCR levels correlated with higher Annexin V positive target cells, indicating higher number of apoptotic target cells. This indicates high degree of specificity and efficiency in target cell destruction with RAS TCR4.

Figure 8F:
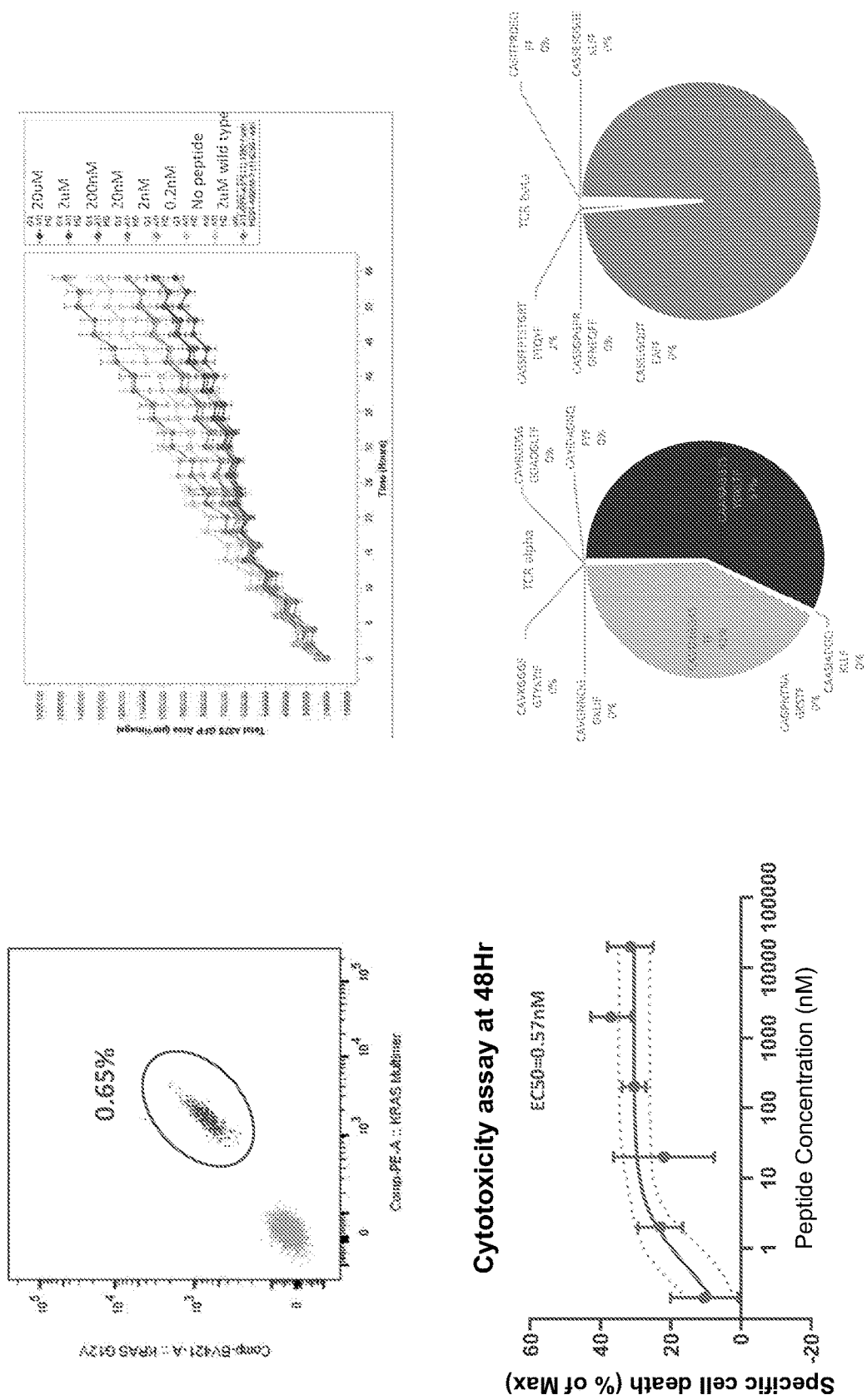
FIG. 8F depicts the workflow used to identify RAS TCR-26 and RAS TCR-27. Depicted on the top left is a flow cytometry analysis of RAS-peptide-HLA-A11:01 complex specific CD8+ T cell expansion in response to stimulation with RAS G12V peptide. Depicted on the top right is the measurement of the cell growth of target A375 cells expressing HLA-A11:01 and GFP over 54 hours after co-culture with the expanded CD8+ T cells. In this experiment, T cells expanded in the presence of the peptides were incubated with the A375 cells that were loaded with indicated amounts of peptides. Depicted on the bottom left is the specific cytotoxicity calculated at 48 hours comparing target cells loaded with increasing amounts or mutant-RAS peptide normalized to a control with wild-type peptide. Depicted on the bottom right are the relative abundances of TCR alpha and TCR beta CDR3 regions after single-cell TCR sequencing the multimer-positive cells.
Figure 8G:
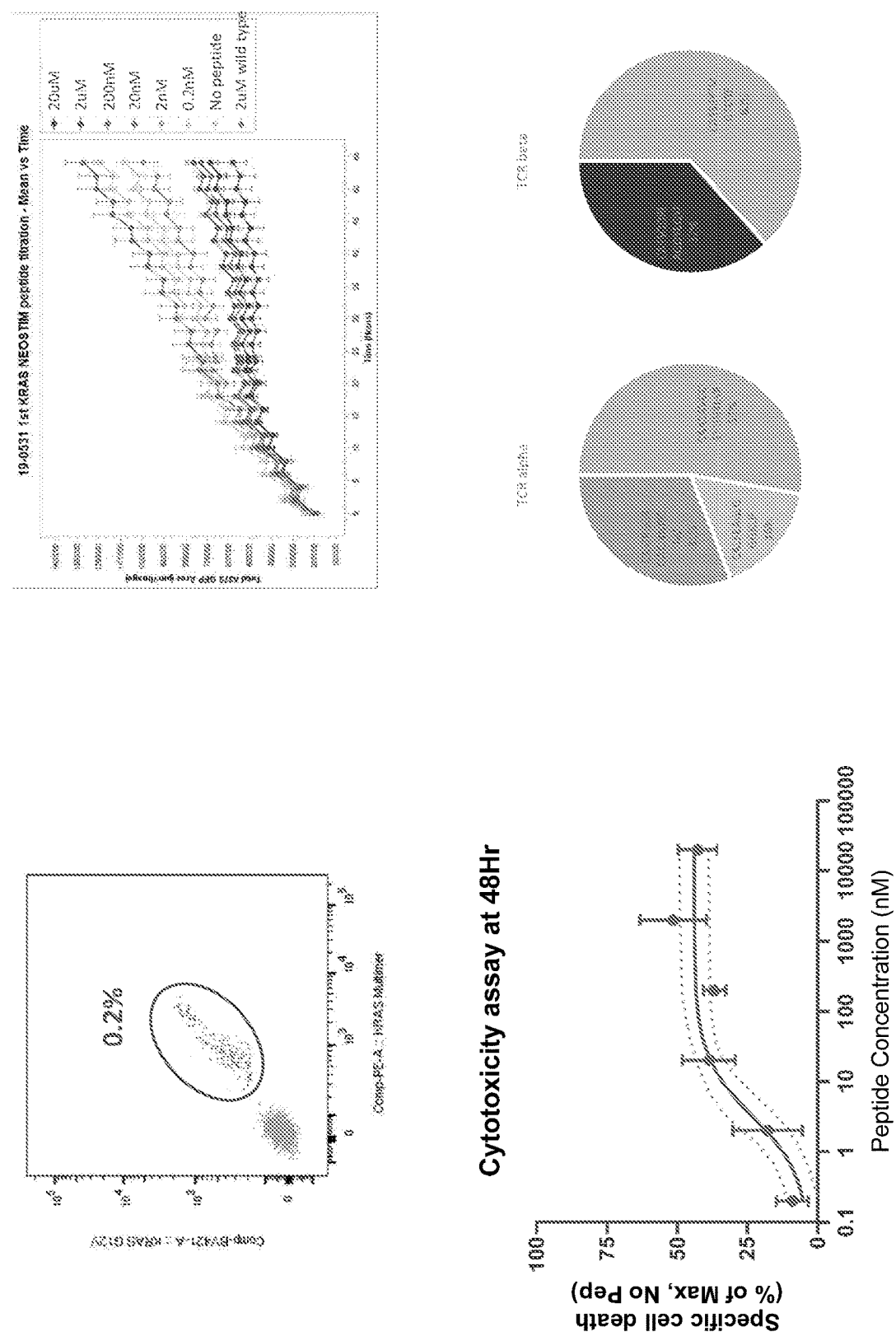
FIG. 8G depicts the workflow used to identify RAS TCR-28. Depicted on the top left is a flow cytometry analysis of RAS-peptide-HLA-A11:01 complex specific CD8+ T cell expansion in response to stimulation with RAS G12V peptide. Depicted on the top right is the measurement of the cell growth of target A375 cells expressing HLA-A11:01 and GFP and loaded with varying doses of the peptide, over 54 hours after co-culture with the expanded CD8+ T cells. The data show good inverse correlation of cell growth with peptide dose, which demonstrates the TCR specificity to the peptide. Depicted on the bottom left is the specific cytotoxicity calculated at 48 hours comparing target cells loaded with increasing amounts or mutant-RAS peptide normalized to a control with wild-type peptide. Depicted on the bottom right are the relative abundances of TCR alpha and TCR beta CDR3 regions after single-cell TCR sequencing the multimer-positive cells.
Figure 9:
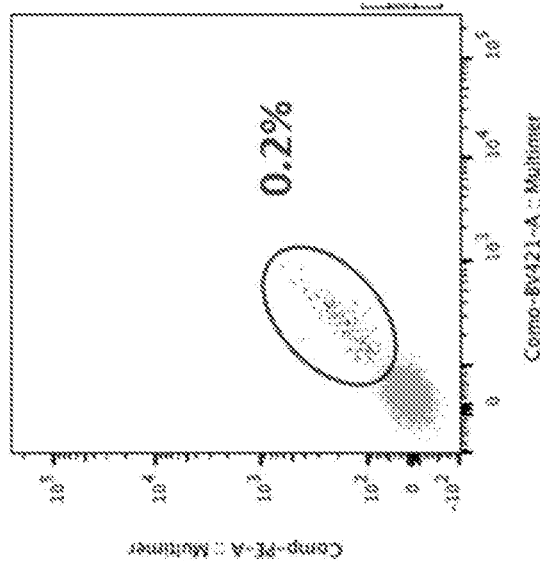
FIG. 9 depicts an example flow cytometry analysis of RAS-peptide-HLA-A03:01 complex specific CD8+ T cell expansion in response to stimulation with RAS G12V peptide (left) and RAS-peptide-HLA-A03:01 complex specific CD8+ T cell expansion in response to stimulation with RAS G12C peptide (right).
Figure 9:
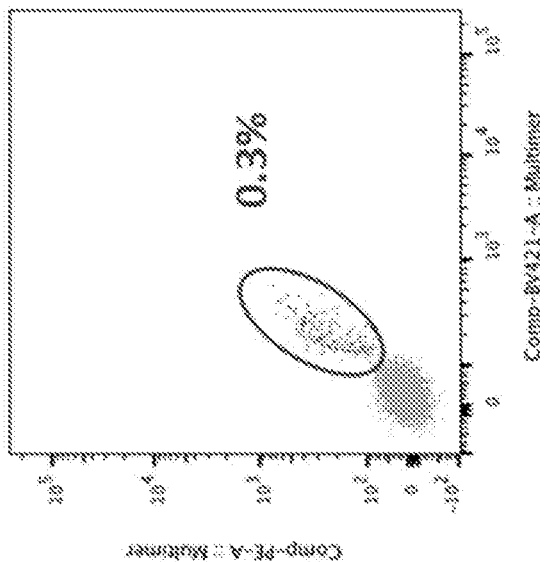
Figure 10C:
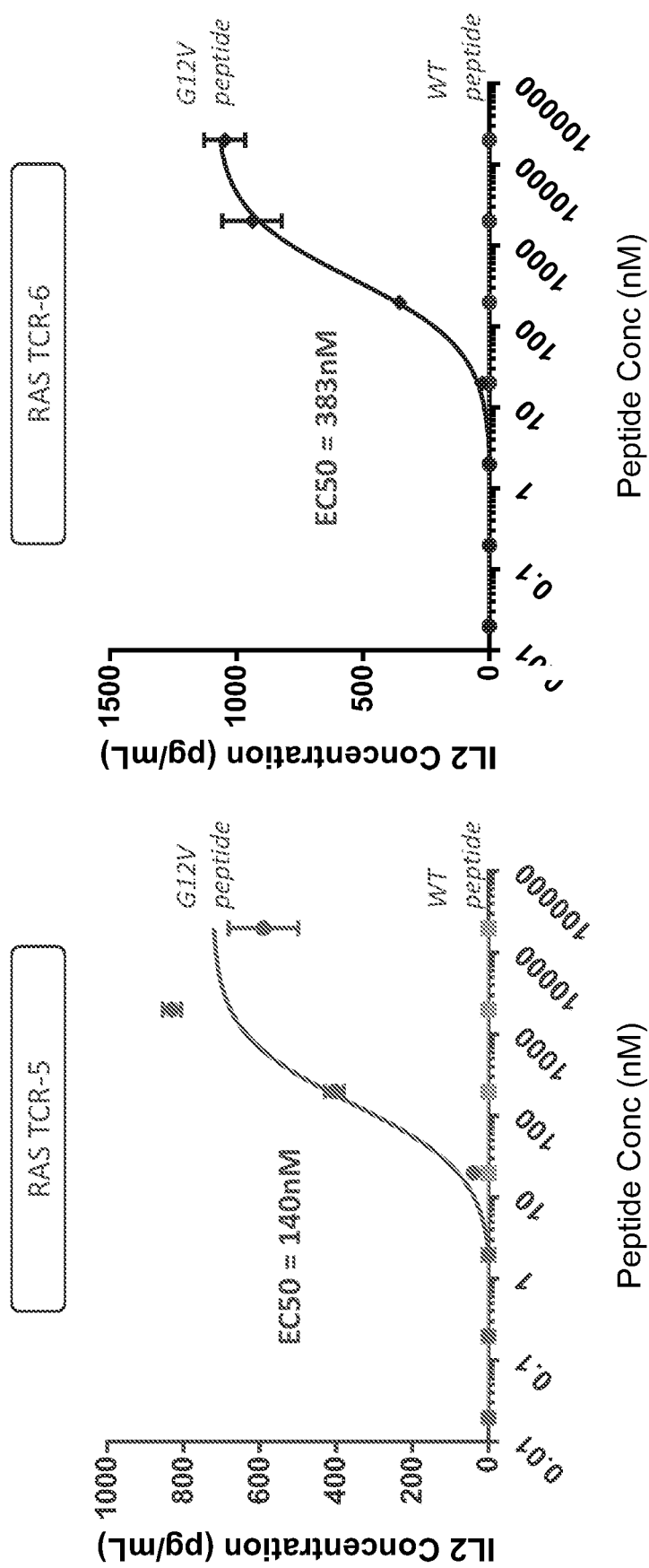
FIG. 10C depicts experimental results of TCR functional avidity assays (peptide titration). Depicted on the left is a graph showing IL-2 production after co-culturing RAS TCR-5-transduced Jurkat cells with A375 cells expressing HLA-A03:01 loaded with increasing amounts of RAS-wild type or RAS-mutant peptide. Depicted on the right is a graph showing IL-2 production after co-culturing RAS TCR-6-transduced Jurkat cells with A375 cells expressing HLA-A03:01 loaded with increasing amounts of RAS-wild type or RAS-mutant peptide.
Figure 10D:
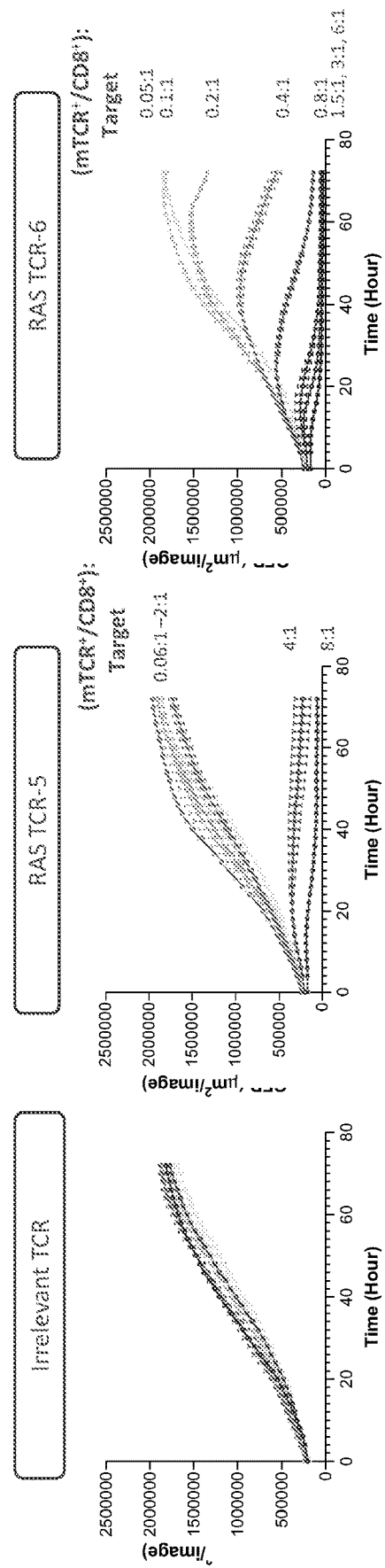
FIG. 10D depicts experimental results of a cytotoxicity assay in which PBMCs transduced with an irrelevant TCR (left), RAS TCR-5 (middle), or RAS TCR-6 (right) are co-cultured with A375 target tumor cells expressing HLA-A03:01 and GFP over an increasing range of PBMC to target ratios. Graphs of the growth of the target cells over 72 hours as measured by GFP signal show that the RAS TCR-transduced PBMCs kill the target cells effectively.
Figure 10E:
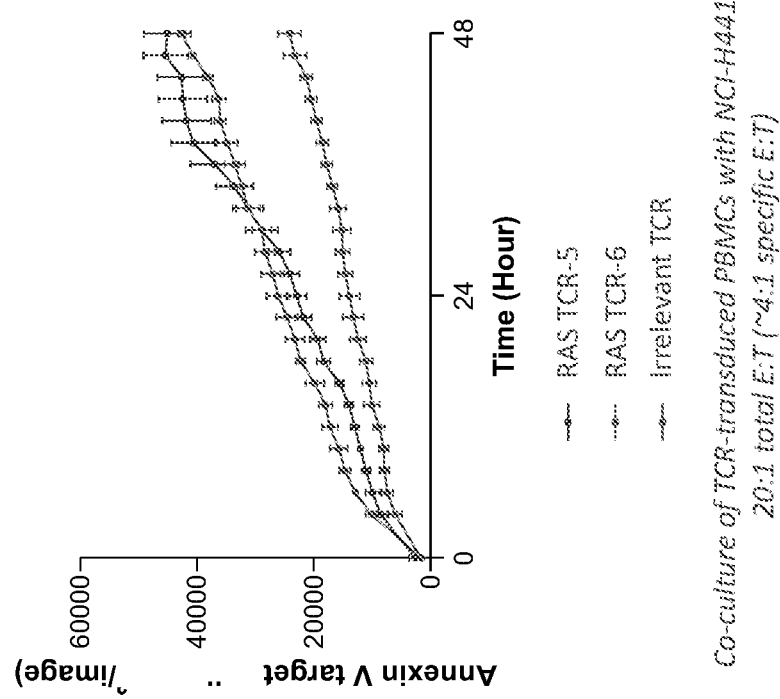
FIG. 10E depicts experimental results of a cytotoxicity assay in which PBMCs transduced with an irrelevant TCR, RAS TCR-5, or RAS TCR-6 are co-cultured with NCI-H441 target tumor cells. Increased Annexin V signal in target cells over 48 hours shows that the RAS TCRs are able to recognize and kill this target tumor cell.
Figure 10F:
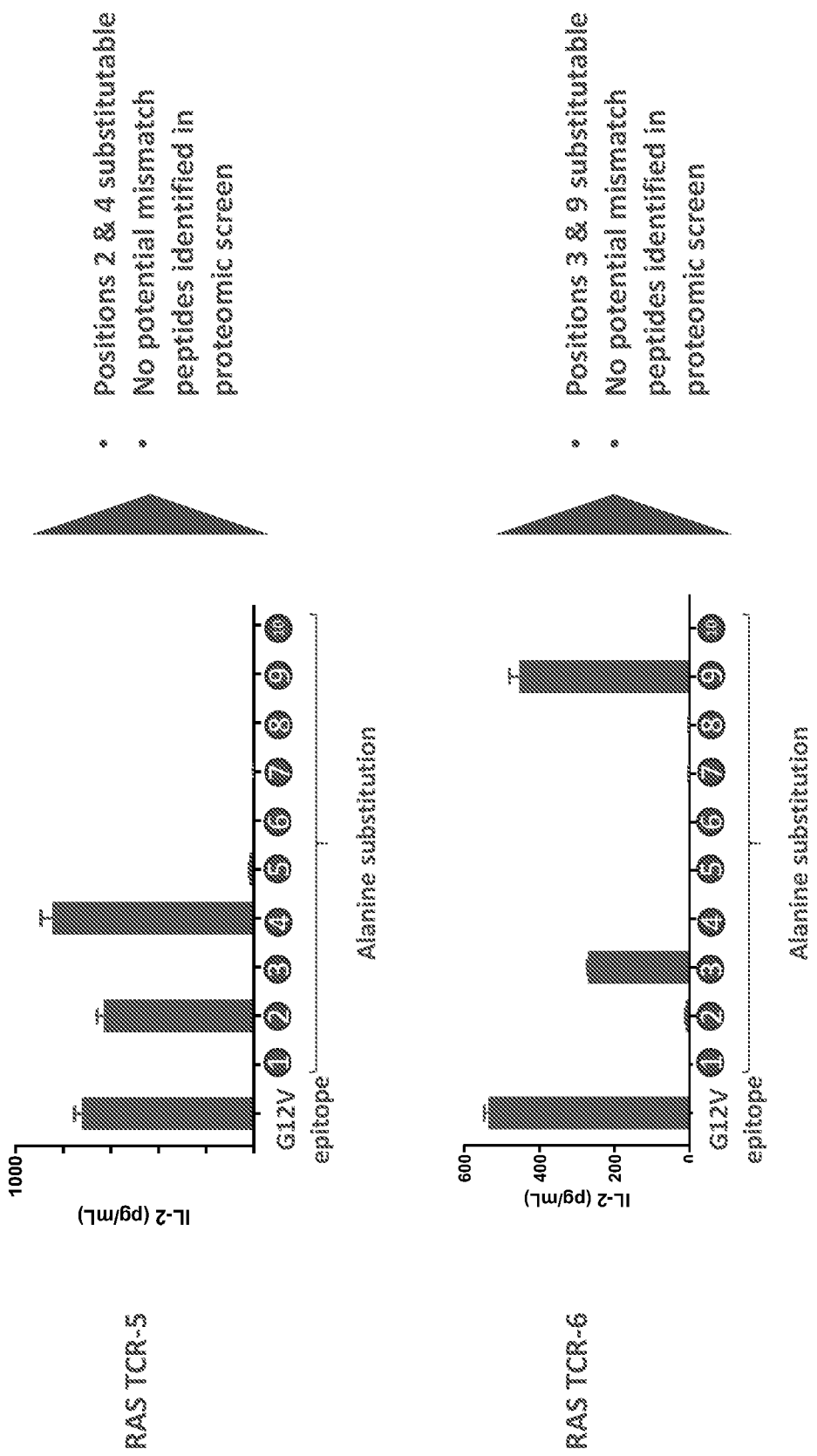
FIG. 10F depicts experimental results of a safety screen of RAS TCR-5 (top) and RAS TCR-6 (bottom). Graphs showing IL-2 production after co-culturing RAS TCR-transduced Jurkat cells with A375 cells expressing HLA-A11:01 loaded with the cognate RAS G12V epitope or peptides in which one position of the cognate epitope is changed to an alanine.
Figure 11:
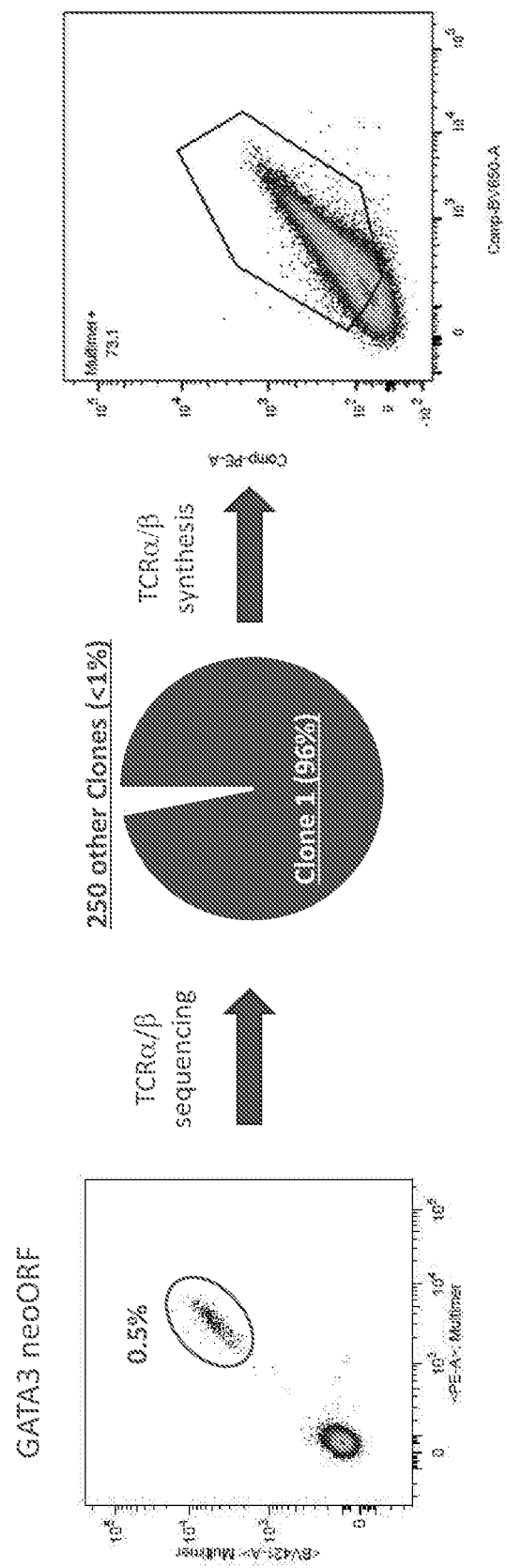
FIG. 11 depicts an example workflow for GATA3 antigen-specific TCR identification and analysis. Depicted on the left is an example flow cytometry analysis of GATA3-peptide-HLA-A02:01 complex specific CD8+ T cell expansion in response to stimulation with a GATA3 mutant peptide.
Figures 12A, 12B:
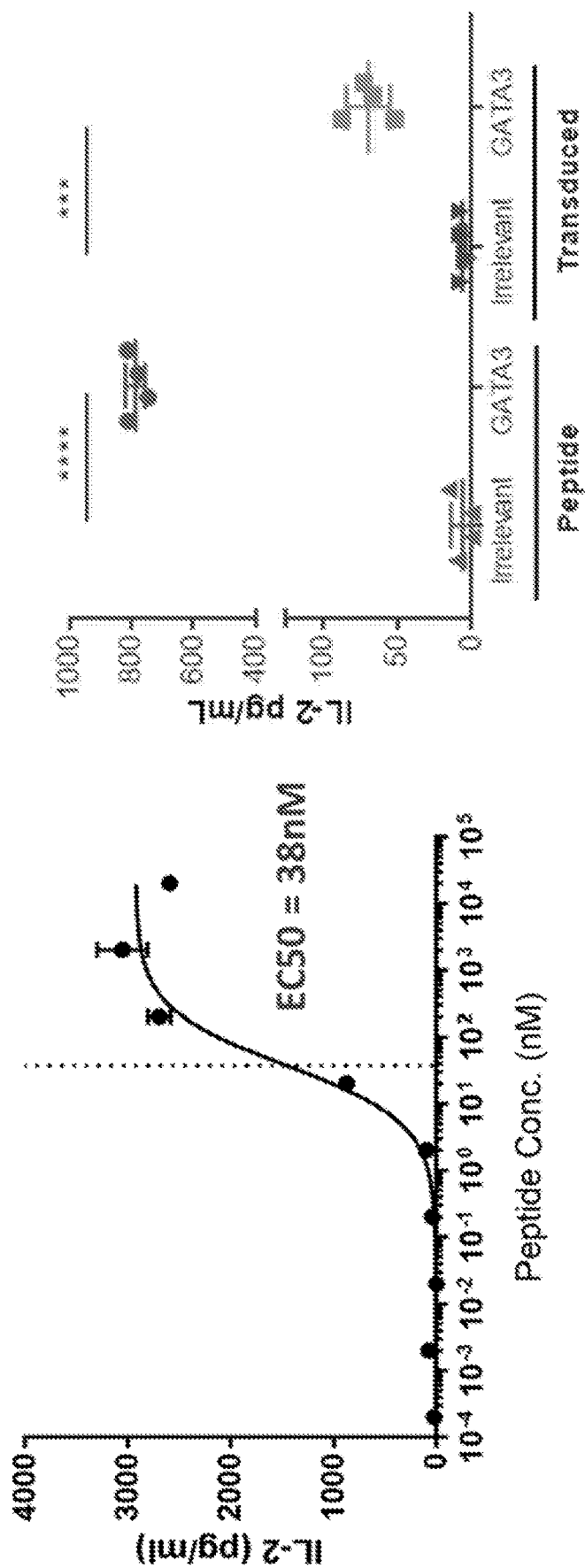
FIG. 12A depicts results of a TCR functional avidity assay (peptide titration). A graph showing IL-2 production after co-culturing GATA3 TCR-1-transduced T cells with cells loaded or transduced with increasing amounts of GATA3 mutant peptide.
FIG. 12B depicts a graph showing IL-2 production after co-culturing GATA3 TCR-transduced Jurkat cells with cells loaded with an irrelevant peptide or the mutant GATA3 peptide, and cells transduced with an irrelevant vector or a vector encoding the GATA3 neoORF mutation.
Figure 12D:
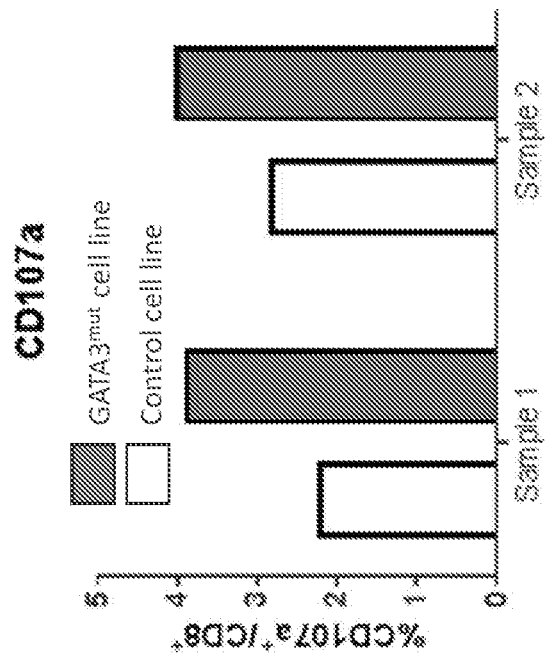
FIG. 12D depicts a graph showing percent CD8 and CD107a positive cells in 2 cell samples expressing control peptide or a GATA3 mutant peptide.
Figure 12C:
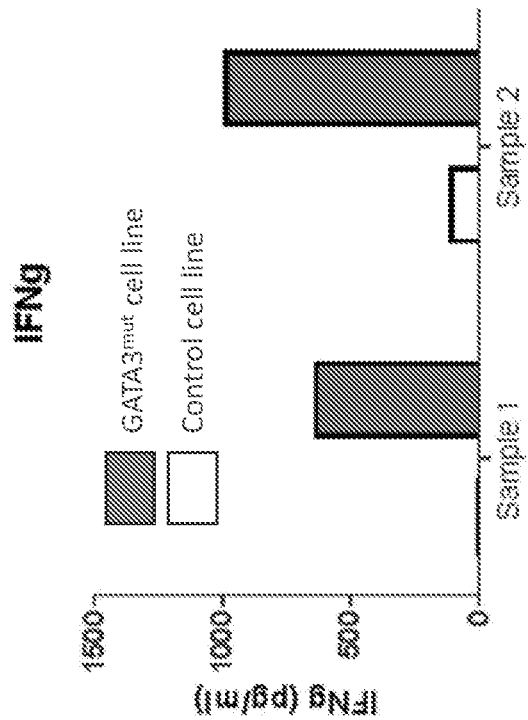
FIG. 12C depicts a graph showing upregulation of IFNγ production in 2 cell samples expressing control peptide or a GATA3 mutant peptide.
Figure 12E:
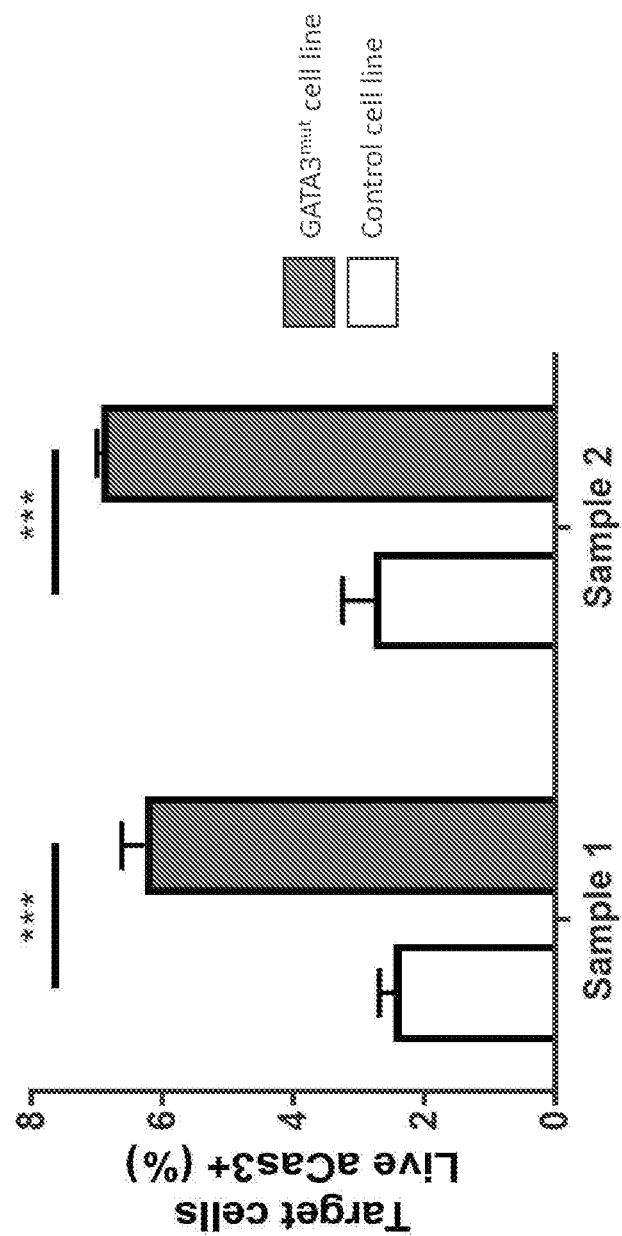
FIG. 12E depicts a graph showing percent live caspase 3 positive cells in 2 cell samples expressing control peptide or a GATA3 mutant peptide.
Figure 13:
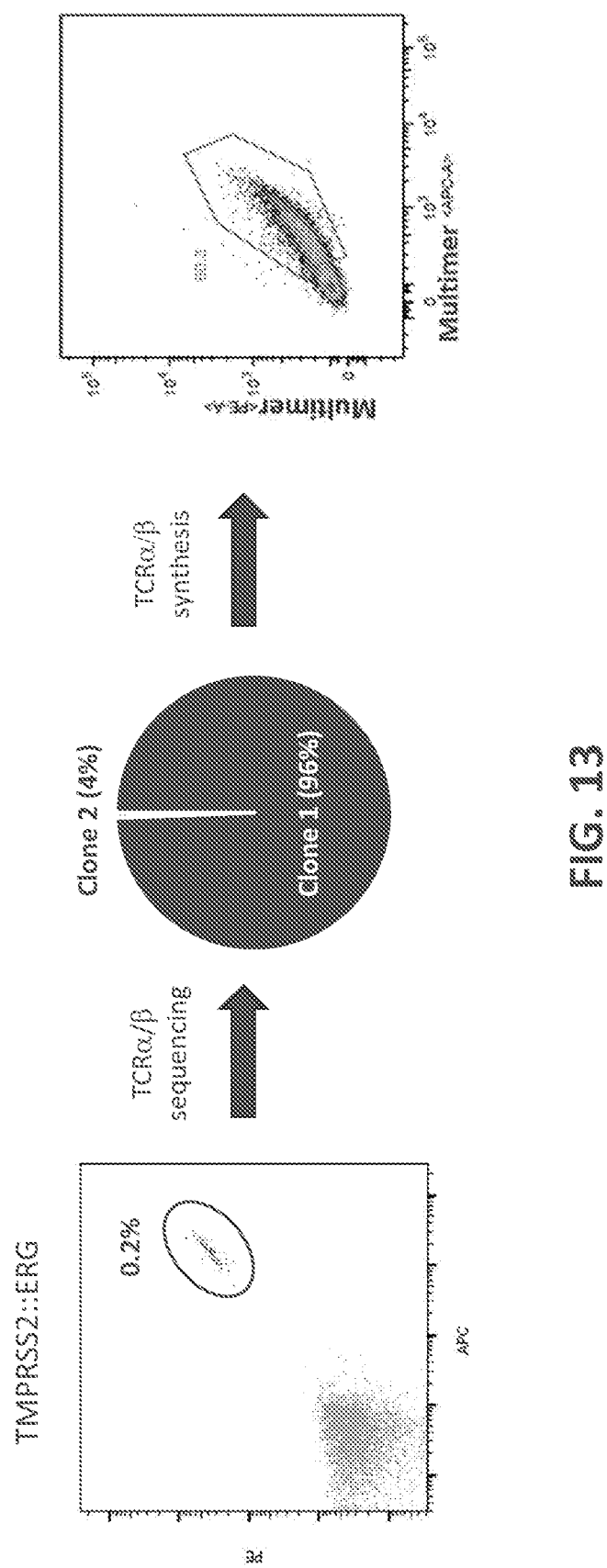
FIG. 13 depicts an example workflow for TMPRSS2:ERG antigen-specific TCR identification and analysis. Depicted on the left is an example flow cytometry analysis of TMPRSS2:ERG-peptide-HLA-A02:01 complex specific CD8+ T cell expansion in response to stimulation with a TMPRSS2:ERG mutant peptide.
Figure 14:
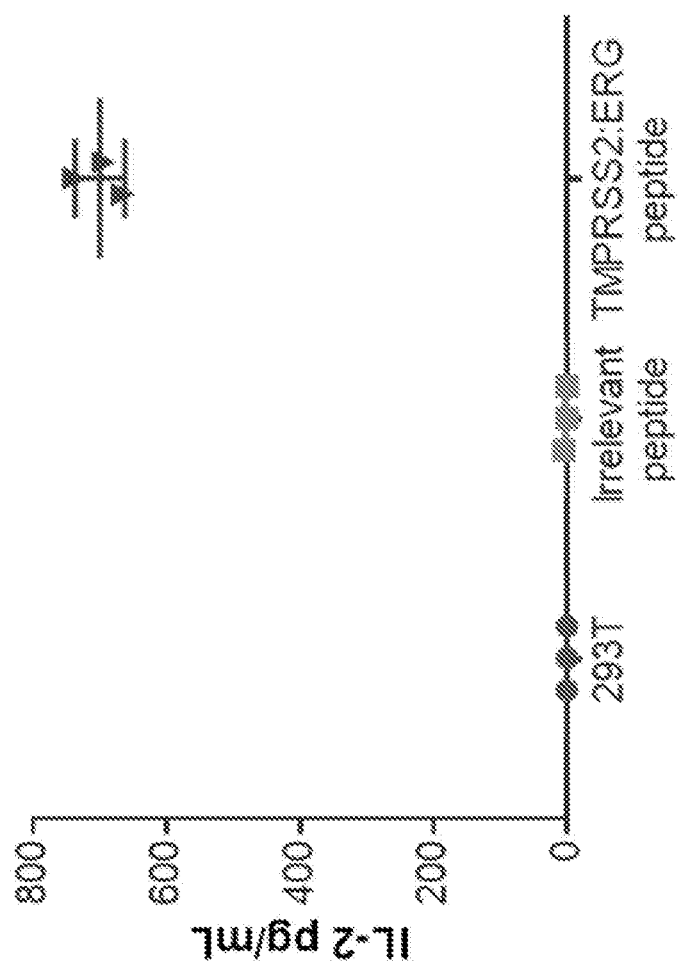
FIG. 14 depicts an example graph showing IL-2 production after co-culturing TMPRSS2:ERG TCR-1-transduced Jurkat cells with 293T cells either unmanipulated, loaded with irrelevant peptide, or loaded with the TMPRSS2:ERG peptide.
Figure 15:
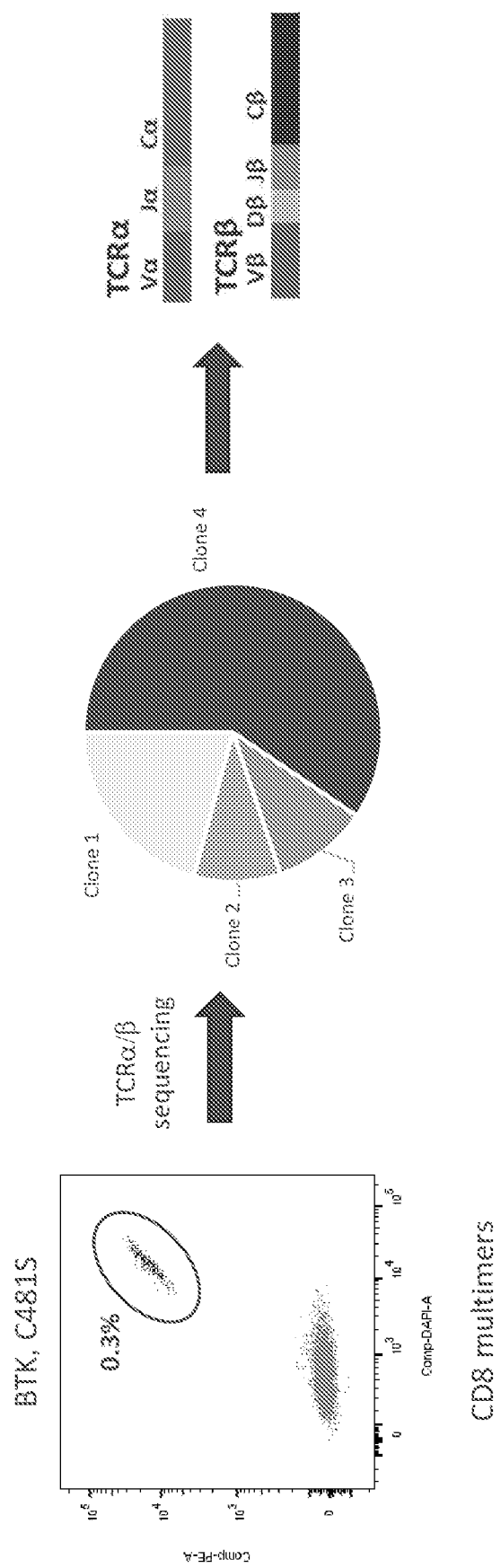
FIG. 15 depicts an example workflow for BTK antigen-specific TCR identification and analysis. Depicted on the left is an example flow cytometry analysis of BTK-peptide-HLA-A02:01 complex specific CD8+ T cell expansion in response to stimulation with a BTK mutant peptide.
Figure 16A:
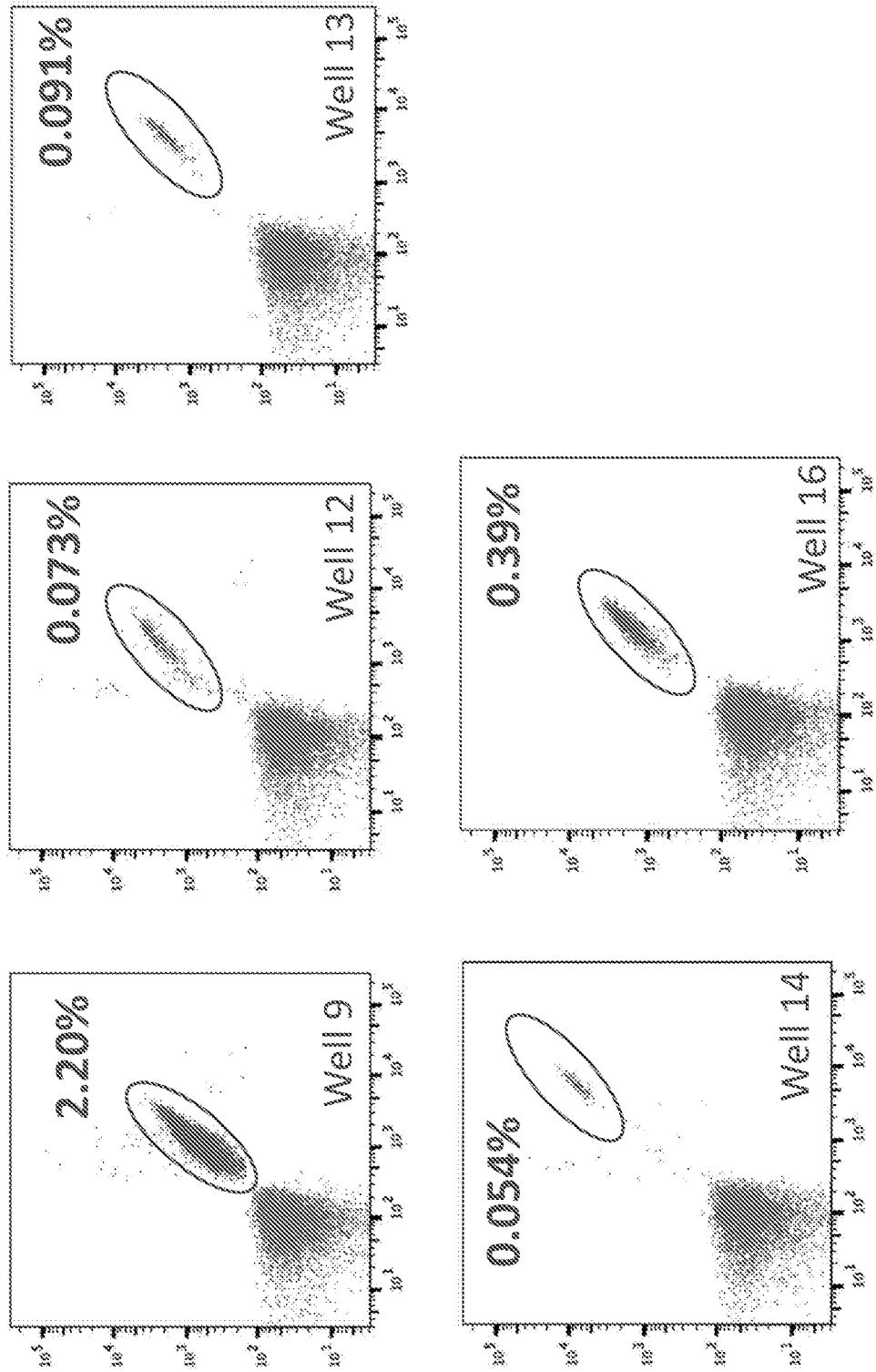
FIG. 16A depicts an example flow cytometry analysis of EGFR-peptide-HLA-A02:01 complex specific CD8+ T cell expansion in response to stimulation with EGFR T790M peptide. Each plot on FIG. 16A represents a representative T cell expansion sample (well) with the EGFR T790M peptide. The TCRs from the cells were sequenced.
Figure 16B:
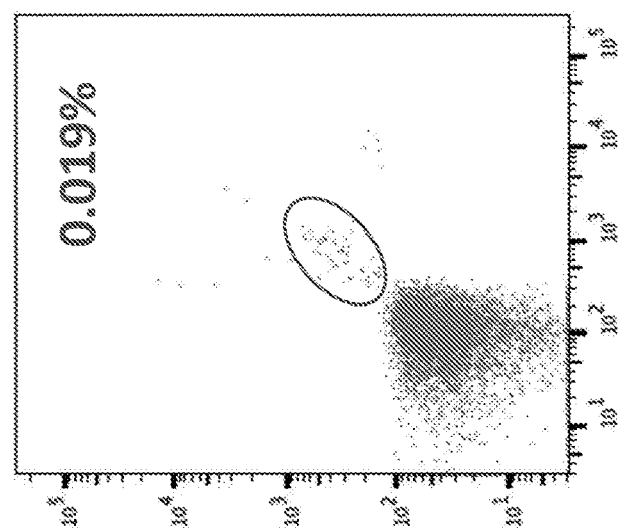
FIG. 16B depicts an example flow cytometry analysis of potential EGFR-peptide-HLA-A02:01 complex specific CD8+ T cell populations in response to stimulation with EGFR T790M peptide, the TCRs of which remain to be sequenced. Each plot on FIG. 16B represents a representative T cell expansion sample (well) in response to the EGFR T790M peptide.
Figure 16B:
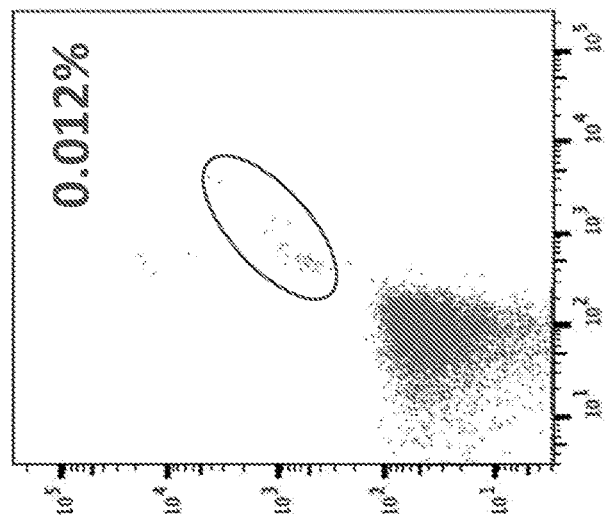
Figure 16B:
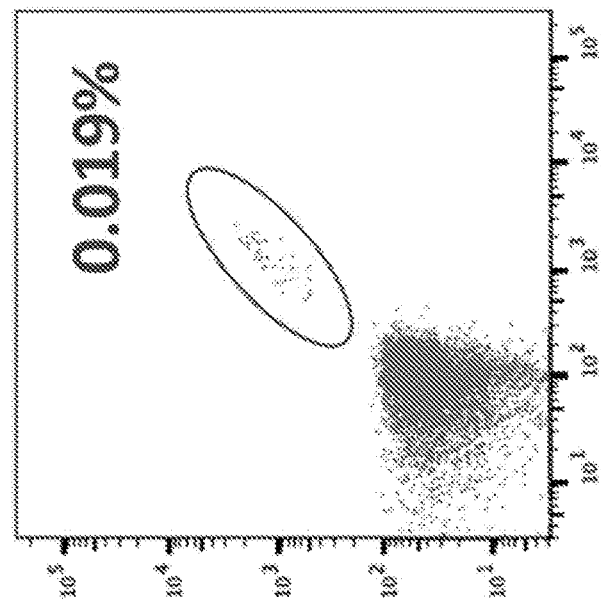

In some examples, cytotoxic activity is assessed before TCR cloning. T cells induced against a mutant RAS peptide on a specific HLA are co-cultured with mutant target cancer cells expressing the corresponding HLA loaded with a range of concentrations of the RAS mutant peptides (FIGS. 8F, 8G). The relative growth and the apoptotic marker Annexin V in the target cancer cells specifically are both measured. The target cells are also transduced to stably express GFP allowing the tracking of target cell growth. The GFP signal and Annexin-V signal are measured over time with an IncuCyte S3 apparatus. Annexin V signal originating from effector cells is filtered out by size exclusion. Target cell growth and death is expressed as GFP and Annexin-V area (mm$^2$) over time, respectively. For T cells demonstrating cytotoxicity at low peptide concentrations compared to no peptide and/or wild-type peptide, TCR sequencing can be performed as above. Regarding the data shown in experiments shown in FIGS. 8F and 8G, (figures on the upper right corner), the cytotoxicity of the T cells showed good dose responsiveness to the peptides as indicated by lower GFP-expressing cells with the higher dose of peptides over the indicated time. The inverse correlation depicts that with higher amounts of peptides for stimulating the TCR on the T cells, higher suppression of target cell growth was observed, as demonstrated by lower GFP-positive cells. This demonstrates that the T cells exhibit high TCR specificity and effectivity in limiting target cell progression.

Example 14: Summary of Recombinant TCRs Developed

This example provides the details of the TCRs developed. Table 1 provides a synopsis of the TCRs described herein and Table 2 provides the specific amino acid and coding sequences.

TABLE 1

| TCR name | Gene | Mutation | Allele | TCRbeta CDR3 | TCR binding to peptide-MHC | Method of determining TCR binding to peptide-MHC | |
|---|---|---|---|---|---|---|---|
| | | | | | | Multimer Hit | IL-2 by Jurkat and/or PBMC |
| RAS TCR-1 | KRAS | G12V, G12D, G12C | A02:01 | SARDRGLVSLPSVEAFF | — | — | — |
| RAS TCR-2 | KRAS | G12V, G12D, G12C | A02:01 | ASYLSGSIYNEQFF | — | — | — |
| RAS TCR-3 | KRAS | G12V | A11:01 | ASSYSTERGTIY | Yes | Yes | Yes |
| RAS TCR-4 | KRAS | G12V | A11:01 | ASSLADIYEQY | Yes | Yes | Yes |
| RAS TCR-5 | KRAS | G12V | A03:01 | CASSARNDEAFF | Yes | Yes | Yes |
| RAS TCR-6 | KRAS | G12V | A03:01 | CASSLGDSEQYF | Yes | Yes | IL-2 by Jurkat |
| RAS TCR-7 | KRAS | G12C | A03:01 | CASSQRSNTGELFF | Yes | Yes | Yes |

TABLE 1-continued

| TCR name | Gene | Mutation | Allele | TCRbeta CDR3 | TCR binding to peptide-MHC | Multimer Hit | IL-2 by Jurkat and/or PBMC |
|---|---|---|---|---|---|---|---|
| RAS TCR-8 | KRAS | G12V | A11:01 | CASGGRDSTDTQYF | Yes | Yes | IL-2 by Jurkat |
| RAS TCR-10 | KRAS | G12C | A11:01 | ASSTSFWEVNTEAF | Yes | — | IL-2 by Jurkat |
| RAS TCR-11 | KRAS | G12C | A11:01 | ASSKRGWPYEQY | Yes | — | IL-2 by Jurkat |
| RAS TCR-12 | KRAS | G12C | A11:01 | ASSLADIYEQY | — | — | — |
| RAS TCR-13 | KRAS | G12D | A03:01 | ASSSTDRIEAF | — | — | — |
| RAS TCR-14 | KRAS | G12D | A03:01 | ASTTFKTGRAIEKLF | — | — | — |
| RAS TCR-15 | KRAS | G12D | A03:01 | ASSSRGHSGTEAF | — | — | — |
| RAS TCR-16 | KRAS | G12D | A03:01 | ASSSRGHSGTEAF | — | — | — |
| RAS TCR-17 | KRAS | G12D | A03:01 | ATYKVGDEQF | — | — | — |
| RAS TCR-18 | KRAS | G12D | A11:01 | ASSDWLAGAKDEQY | — | — | — |
| RAS TCR-19 | KRAS | G12V | A03:01 | ASSLVASNEQF | — | — | — |
| RAS TCR-20 | KRAS | G12V | A11:01 | ASSLGLLLYNEQF | Yes | — | IL-2 by Jurkat |
| RAS TCR-21 | KRAS | G12V | A11:01 | ASSLGDSYEQYF | — | — | — |
| RAS TCR-26 | KRAS | G12V | A11:01 | ASSEWGSTGELF | — | — | — |
| RAS-TCR-27 | KRAS | G12V | A11:01 | ASSEWGSTGELF | — | — | — |
| RAS-TCR-28 | KRAS | G12V | A11:01 | ASSEYTMGTQY | — | — | — |
| GATA3 TCR-1 | GATA3 | neoORF (CSNH) | A02:01 | ASSLDFVLAGSYSYNEQF | Yes | Yes | IL-2 by Jurkat |
| GATA3 TCR-2 | GATA3 | neoORF (CSNH) | B07:02 | ASSQSGQGPYEQY | — | — | — |
| GATA3 TCR-3 | GATA3 | neoORF (CSNH) | B08:01 | ASSRTAMNTEAF | Yes | — | IL-2 by Jurkat |
| TMPRSS2::ERG TCR-1 | TMPRSS2::ERG | Fusion | A02:01 | ASSQADSPLH | Yes | Yes | IL-2 by Jurkat and PBMC |
| BTK TCR-1 | BTK | C481S | A02:01 | ASSFGPDEKLFF | Yes | Yes | IL-2 by Jurkat |
| BTK TCR-2 | BTK | C481S | A02:01 | ASSPGANEKLF | Yes | Yes | IL-2 by Jurkat |
| EGFR TCR-1 | EGFR | T790M | A02:01 | ASGGGLGLFETQY | — | — | — |
| EGFR TCR-2 | EGFR | T790M | A02:01 | SARRREGEIEQY | — | — | — |
| EGFR TCR-3 | EGFR | T790M | A02:01 | ASSLAYLTGRVEAF | — | — | — |
| EGFR TCR-4 | EGFR | T790M | A02:01 | SAQGSSGRIEQF | — | — | — |
| EGFR TCR-5 | EGFR | T790M | A02:01 | SALPGFSYEQY | — | — | — |

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

TABLE 2

SEQUENCES

| Name | SEQ ID NO | Sequence |
|---|---|---|
| RAS TCR-1 alpha chain CDR1 | 1 | SIFNT |
| RAS TCR-1 alpha chain CDR2 | 2 | LYKAGEL |
| RAS TCR-1 alpha chain CDR3 | 3 | CAGRNFGNEKLTF |
| RAS TCR-1 beta chain CDR1 | 4 | DFQATT |
| RAS TCR-1 beta chain CDR2 | 5 | SNEGSKA |
| RAS TCR-1 beta chain CDR3 | 6 | SARDRGLVSLPSVEAFF |
| RAS TCR-1 alpha chain variable domain | 7 | ATGCTCCTTGAACATTTATTAATAATCTTGTGGATGCAGCTGACATGGGTCAGTGGTCAACAGCTGAA TCAGAGTCCTCAATCTATGTTTATCCAGGAAGGAGAAGATGTCTCCATGAACTGCACTTCTTCAAGCA TATTTAACACCTGGCTATGGTACAAGCAGGACCCTGGGGAAGGTCCTGTCCTCTTGATAGCCTTATAT AAGGCTGGTGAATTGACCTCAAATGAAGACTGACTGCTCAGTTTGGTATAACCAGAAAGGACAGCTT CCTGAATATCTCAGCATCCATACCTAGTGATGTAGGCATCTACTTCTGTGCTGGGAGAAACTTTGGAA ATGAGAAATTAACCTTTGGGACTGGAACAAGACTCACCATCATACCC |
| | 8 | ATGCTCCTTGAACATTTATTAATAATCTTGTGGATGCAGCTGACATGGGTCAGTGGTCAACAGCTGAA TCAGAGTCCTCAATCTATGTTTATCCAGGAAGGAGAAGATGTCTCCATGAACTGCACTTCTTCAAGCA TATTTAACACCTGGCTATGGTACAAGCAGGACCCTGGGGAAGGTCCTGTCCTCTTGATAGCCTTATAT AAGGCTGGTGAATTGACCTCAAATGAAGACTGACTGCTCAGTTTGGTATAACCAGAAAGGACAGCTT CCTGAATATCTCAGCATCCATACCTAGTGATGTAGGCATCTACTTCTGTGCTGGGAGAAACTTTGGAA ATGAGAAATTAACCTTTGGGACTGGAACAAGACTCACCATCATACCC |
| | 9 | MLLEHLLIILWMQLTWVSGQQLNQSPQSMFIQEGEDVSMNCTSSSIFNTWLWYKQDPGEGPVLLIALY KAGELTSNGRLTAQFGITRKDSFLNISASIPSDVGIYFCAGRNFGNEKLTFGTGTRLTIIP |
| RAS TCR-1 beta chain variable domain | 10 | ATGCTGCTGCTTCTGCTGCTTCTGGGGCCAGGCTCCGGGCTTGGTGCTGTCGTCTCTCAACATCCGAG CAGGGTTATCTGTAAGAGTGGAACCTCTGTGAAGATCGAGTGCCGTTCCCTGGACTTTCAGGCCACAA CTATGTTTTGGTATCGTCAGTTCCCGAAACAGAGTCTCATGCTGATGGCAACTTCCAATGAGGGCTCC AAGGCCACATACGAGCAAGGCGTCGAGAAGGACAAGTTTCTCATCAACCATGCAAGCCTGACCTTGTC CACTCTGACAGTGACCAGTGCCCATCCTGAAGACAGCAGCTTCTACATCTGCAGTGCTCGCGACAGGG GGCTTGTATCGTTGCCGTCGGTAGAAGCTTTCTTTGGACAAGGCACCAGACTCACAGTTGTACTG |
| | 11 | ATGCTGCTGCTTCTGCTGCTTCTGGGGCCAGGCTCCGGGCTTGGTGCTGTCGTCTCTCAACATCCGAG CAGGGTTATCTGTAAGAGTGGAACCTCTGTGAAGATCGAGTGCCGTTCCCTGGACTTTCAGGCCACAA CTATGTTTTGGTATCGTCAGTTCCCGAAACAGAGTCTCATGCTGATGGCAACTTCCAATGAGGGCTCC AAGGCCACATACGAGCAAGGCGTCGAGAAGGACAAGTTTCTCATCAACCATGCAAGCCTGACCTTGTC CACTCTGACAGTGACCAGTGCCCATCCTGAAGACAGCAGCTTCTACATCTGCAGTGCTCGCGACAGGG GGCTTGTATCGTTGCCGTCGGTAGAAGCTTTCTTTGGACAAGGCACCAGACTCACAGTTGTACTG |
| | 12 | MLLLLLLLGPGSGLGAVVSQHPSRVICKSGTSVKIECRSLDFQATTMFWYRQFPKQSLMLMATSNEGS KATYEQGVEKDKFLINHASLTLSTLTVTSAHPEDSSFYICSARDRGLVSLPSVEAFFGQGTRLTVV |
| RAS TCR-1 alpha chain | 13 | MLLEHLLIILWMQLTWVSGQQLNQSPQSMFIQEGEDVSMNCTSSSIFNTWLWYKQDPGEGPVLLIALY KAGELTSNGRLTAQFGITRKDSFLNISASIPSDVGIYFCAGRNFGNEKLTFGTGTRLTIIPDIQNPDP AVYQLRDSKSSDKSVCLFTDFDSQTNVSQSKDSDVYITDKTVLDMRSMDFKSNSAVAWSNKSDFACAN AFNNSIIPEDTFFPSPESSCDVKLVEKSFETDTNLNFQNLSVIGFRILLLKVAGFNLLMTLRLWSS MLLLLLLLGPGSGLGAVVSQHPSRVICKSGTSVKIECRSLDFQATTMFWYRQFPKQSLMLMATSNEGS |
| RAS TCR-1 beta chain | 14 | KATYEQGVEKDKFLINHASLTLSTLTVTSAHPEDSSFYICSARDRGLVSLPSVEAFFGQGTRLTVVLE DLNKVFPPEVAVFEPSEAEISHTQKATLVCLATGFFPDHVELSWWVNGKEVHSGVSTDPQPLKEQPAL NDSRYCLSSRLRVSATFWQNPRNHFRCQVQFYGLSENDEWTQDRAKPVTQIVSAEAWGRADCGFTSVS YQQGVLSATILYEILLGKATLYAVLVSALVLMAMVKRKDF |

TABLE 2-continued

SEQUENCES

| Name | SEQ ID NO | Sequence |
| --- | --- | --- |
| RAS TCR-1/2 peptide | 15 | KLVVVGACGV |
| RAS TCR-2 alpha chain CDR1 | 16 | VSGNPY |
| RAS TCR-2 alpha chain CDR2 | 17 | YITGDNLV |
| RAS TCR-2 alpha chain CDR3 | 18 | CAVRDQSGANNLFF |
| RAS TCR-2 beta chain CDR1 | 19 | SEHNR |
| RAS TCR-2 beta chain CDR2 | 20 | FQNEAQ |
| Ras TCR-2 beta chain CDR3 | 21 | ASYLSGSIYNEQFF |
| RAS TCR-2 alpha chain variable domain | 22 | ATGGCCTCTGCACCCATCTCGATGCTTGCGATGCTCTTCACATTGAGTGGGCTGAGAGCTCAGTCAGT GGCTCAGCCGGAAGATCAGGTCAACGTTGCTGAAGGGAATCCTCTGACTGTGAAATGCACCTATTCAG TCTCTGGAAACCCTTATCTTTTTTGGTATGTTCAATACCCCAACCGAGGCCTCCAGTTCCTTCTGAAA TACATCACAGGGGATAACCTGGTTAAAGGCAGCTATGGCTTTGAAGCTGAATTTAACAAGAGCCAAAC CTCCTTCCACCTGAAGAAACCATCTGCCCTTGTGAGCGACTCCGCTTTGTACTTCTGTGCTGTGAGAG ACCAAAGTGGGGCAAACAACCTCTTCTTTGGGACTGGAACGAGACTCACCGTTATTCCC |
|  | 23 | ATGGCTTCTGCGCCTATATCAATGCTTGCCATGCTGTTTACACTGTCCGGTCTGAGGGCTCAAAGCGT GGCCCAACCTGAGGATCAGGTGAATGTAGCGGAGGGCAATCCGTTGACAGTTAAGTGTACATACTCCG TATCAGGCAATCCGTACTTGTTTTGGTATGTGCAGTACCCCAATCGGGGGCTTCAATTCTTGCTGAAG TACATTACAGGCGATAATCTGGTAAAAGGTAGTTATGGTTTTGAGGCCGAATTCAACAAATCACAAAC ATCATTTCATCTTAAAAAGCCAAGCGCACTTGTCAGTGACTCAGCGCTTTATTTCTGTGCAGTCAGAG ACCAATCAGGGGCAAATAATCTGTTCTTTGGGACAGGGACTAGATTGACTGTTATACCC |
|  | 24 | MASAPISMLAMLFTLSGLRAQSVAQPEDQVNVAEGNPLTVKCTYSVSGNPYLFWYVQYPNRGLQFLLK YITGDNLVKGSYGFEAEFNKSQTSFHLKKPSALVSDSALYFCAVRDQSGANNLFFGTGTRLTVIP |
| RAS TCR-2 beta chain variable domain | 25 | ATGGGCACCAGCCTCCTCTGCTGGATGGCCCTGTGTCTCCTGGGGGCAGATCACGCAGATACTGGAGT CTCCCAGGACCCCAGACACAAGATCACAAAGAGGGGACAGAATGTAACTTTCAGGTGTGATCCAATTT CTGAACACAACCGCCTTTATTGGTACCGACAGACCCTGGGGCAGGGCCCAGAGTTTCTGACTTACTTC CAGAATGAAGCTCAACTAGAAAATCAAGGCTGCTCAGTGATCGGTTCTCTGCAGAGAGGCCTAAGGG ATCTTTCTCCACCTTGGAGATCCAGCGCACAGAGCAGGGGACTCGGCCATGTATCTCTGTGCCAGCT ACCTGAGCGGTTCCATTTACAATGAGCAGTTCTTCGGGCCAGGGACACGGCTCACCGTGCTA |
|  | 26 | ATGGGCACTAGCCTCTTGTGTTGGATGGCACTTTGCCTTCTTGGCGCGGATCACGCCGATACAGGCGT CTCCCAAGATCCCAGACATAAAATCACAAAACGGGGCCAGAACGTTACCTTTCGCTGCGATCCGATAT CAGAGCATAATCGACTGTATTGGTATAGGCAAACTCTCGGGCAAGGGCCTGAGTTCCTCACTTATTTC CAAAATGAGGCGCAACTGGAAAAGAGCCGGTTGTTGAGTGATAGGTTTTCCGCAGAGCGACCCAAGGG GAGCTTCTCAACACTGGAGATACAAAGGACCGAACAAGGTGATTCCGCAATGTATCTCTGTGCTAGTT ATTTGAGCGGCTCCATATATAACGAACAGTTTTTCGGACCGGGCACTCGCCTGACCGTACTA |
|  | 27 | MGTSLLCWMALCLLGADHADTGVSQDPRHKITKRGQNVTFRCDPISEHNRLYWYRQTLGQGPEFLTYF QNEAQLEKSRLLSDRFSAERPKGSFSTLEIQRTEQGDSAMYLCASYLSGSIYNEQFFGPGTRLTVL |
| RAS TCR-2 alpha chain | 28 | MASAPISMLAMLFTLSGLRAQSVAQPEDQVNVAEGNPLTVKCTYSVSGNPYLFWYVQYPNRGLQFLLK YITGDNLVKGSYGFEAEFNKSQTSFHLKKPSALVSDSALYFCAVRDQSGANNLFFGTGTRLTVIPDIQ NPDPAVYQLRDSKSSDKSVCLFTDFDSQTNVSQSKDSDVYITDKTVLDMRSMDFKSNSAVAWSNKSDF ACANAFNNSIIPEDTFFPSPESSCDVKLVEKSFETDTNLNFQNLSVIGFRILLLKVAGFNLLMTLRLW SS |
| RAS TCR-2 beta chain | 29 | MGTSLLCWMALCLLGADHADTGVSQDPRHKITKRGQNVTFRCDPISEHNRLYWYRQTLGQGPEFLTYF QNEAQLEKSRLLSDRFSAERPKGSFSTLEIQRTEQGDSAMYLCASYLSGSIYNEQFFGPGTRLTVLED LNKVFPPEVAVFEPSEAEISHTQKATLVCLATGFFPDHVELSWWVNGKEVHSGVSTDPQPLKEQPALN DSRYCLSSRLRVSATFWQNPRNHFRCQVQFYGLSENDEWTQDRAKPVTQIVSAEAWGRADCGFTSVSY QQGVLSATILYEILLGKATLYAVLVSALVLMAMVKRKDF |
| RAS TCR-1/2 peptide | 30 | LVVVGACGV |

TABLE 2-continued

SEQUENCES

| Name | SEQ ID NO | Sequence |
|---|---|---|
| Ras TCR-3 alpha chain CDR1 | 31 | NSMFDY |
| RAS TCR-3 alpha chain CDR2 | 32 | ISSIKDK |
| RAS TCR-3 alpha chain CDR3 | 33 | AASGGGGADGLT |
| RAS TCR-3 beta chain CDR1 | 34 | MNHNY |
| RAS TCR-3 beta chain CDR2 | 35 | SVGAGI |
| RAS TCR-3 beta chain CDR3 | 36 | ASSYSTERGTIY |
| RAS TCR-3 alpha chain variable domain | 37 | ATGGCCATGCTCCTGGGGGCATCAGTGCTGATTCTGTGGCTTCAGCCAGACTGGGTAAACAGTCAACA GAAGAATGATGACCAGCAAGTTAAGCAAAATTCACCATCCCTGAGCGTCCAGGAAGGAAGAATTTCTA TTCTGAACTGTGACTATACTAACAGCATGTTTGATTATTTCCTATGGTACAAAAAATACCCTGCTGAA GGTCCTACATTCCTGATATCTATAAGTTCCATTAAGGATAAAAATGAAGATGGAAGATTCACTGTCTT CTTAAACAAAGTGCCAAGCACCTCTCTCTGCACATTGTGCCCTCCCAGCCTGGAGACTCTGCAGTGT ACTTCTGTGCAGCAAGCGGGGGAGGAGGTGCTGACGGACTCACCTTTGGCAAAGGGACTCATCTAATC ATCCAGCCC |
| | 38 | ATGGCCATGCTGCTGGGCGCCAGCGTGCTGATTTTATGGCTGCAGCCCGACTGGGTGAACAGCCAGCA GAAGAACGACGACCAGCAAGTGAAGCAGAACTCCCCCTTCTTTAAGCGTGCAAGAAGGTCGTATCAGCA TTTTAAACTGCGACTACACCAACAGCATGTTCGACTACTTTTTATGGTACAAGAAGTACCCCGCCGAG GGCCCCACCTTTTTAATCAGCATCAGCAGCATCAAGGACAAGAACGAGGACGGTCGTTTCACCGTGTT TTTAAACAAGAGCGCCAAGCATTTATCTTTACACATCGTGCCCTCCCAGCCGGTGATAGCGCCGTGT ACTTCTGCGCCGCCAGCGGAGGAGGAGGCGCCGATGGACTGACCTTCGGCAAGGGCACCCATTTAATC ATCCAGCCC |
| | 39 | MAMLLGASVLILWLQPDWVNSQQKNDDQQVKQNSPSLSVQEGRISILNCDYTNSMFDYFLWYKKYPAE GPTFLISISSIKDKNEDGRFTVFLNKSAKHLSLHIVPSQPGDSAVYFCAASGGGGADGLTFGKGTHLI IQP |
| RAS TCR-3 beta chain variable domain | 40 | ATGAGGTCTCAGAATGACTTCCTTGAGAGTCCTGTTCCCCTTTCATCAATGCACAGATACAGAAGACC CCTCCGTCCTGGAGCACCTGCCATGAGCATCAGCCTCCTGTGCTGTGCAGCCTTTCCTCTCCTGTGGG CAGGTCCAGTGAATGCTGGTGTCACTCAGACCCCAAAATTCCGCATCCTGAAGATAGGACAGAGCATG ACACTGCAGTGTACCCAGGATATGAACCATAACTACATGTACTGGTATCGACAAGACCCAGGCATGGG GCTGAAGCTGATTTATTATTCAGTTGGTGCTGGTATCACTGATAAAGGAGAAGTCCCGAATGGCTACA ACGTCTCCAGATCAACCACAGAGGATTTCCCGCTCAGGCTGGAGTTGGCTGCTCCCTCCCAGACATCT GTGTACTTCTGTGCCAGCAGTTACTCGACGGAACGCGGGACCATATATTTTGGAGAGGGAAGTTGGCT CACTGTTGTA |
| | 41 | ATGAGGAGCCAGAACGACTTTTTAGAGAGCCCCGTGCCTCTGAGCAGCATGCATAGGTATAGGAGGCC TCTGAGACCCGGTGCCCCCGCTATGAGCATCTCTTTACTGTGCTGTGCTGCCTTTCCTTTACTGTGGG CTGGCCCCGTTAACGCTGGCGTGACCCAGACCCCCAAGTTTAGGATTTTAAAGATCGGCCAGTCCATG ACTTTACAGTGCACCCAAGATATGAACCACAACTACATGTACTGGTATCGTCAAGATCCCGGCATGGG TTTAAAGCTGATTTACTACAGCGTGGGAGCCGGCATCACCGACAAGGGCGAGGTGCCCAACGGCTACA ATGTGTCTCGTAGCACCACCGAGGACTTCCCTCTGAGACTGGAGCTGGCCGCCCCTAGCCAGACAAGC GTGTACTTCTGCGCCTCCTCCTACAGCACCGAGAGGGGCACCATCTACTTCGGCGAGGGCAGCTGGCT GACCGTGGTG |
| | 42 | MRSQNDFLESPVPLSSMHRYRRPLRPGAPAMSISLLCCAAFPLLWAGPVNAGVTQTPKFRILKIGQSM TLQCTQDMNHNYMYWYRQDPGMGLKLIYYSVGAGITDKGEVPNGYNVSRSTTEDFPLRLELAAPSQTS VYFCASSYSTERGTIYFGEGSWLTVV |
| RAS TCR-3 alpha chain | 43 | MAMLLGASVLILWLQPDWVNSQQKNDDQQVKQNSPSLSVQEGRISILNCDYTNSMFDYFLWYKKYPAE GPTFLISISSIKDKNEDGRFTVFLNKSAKHLSLHIVPSQPGDSAVYFCAASGGGGADGLTFGKGTHLI IQPDIQNPDPAVYQLRDSKSSDKSVCLFTDFDSQTNVSQSKDSDVYITDKTVLDMRSMDFKSNSAVAW SNKSDFACANAFNNSIIPEDTFFPSPESSCDVKLVEKSFETDTNLNFQNLSVIGFRILLLKVAGFNLL MTLRLWSS |
| RAS TCR-3 beta chain | 44 | MRSQNDFLESPVPLSSMHRYRRPLRPGAPAMSISLLCCAAFPLLWAGPVNAGVTQTPKFRILKIGQSM TLQCTQDMNHNYMYWYRQDPGMGLKLIYYSVGAGITDKGEVPNGYNVSRSTTEDFPLRLELAAPSQTS VYFCASSYSTERGTIYFGEGSWLTVVEDLNKVFPPEVAVFEPSEAEISHTQKATLVCLATGFFPDHVE LSWWVNGKEVHSGVSTDPQPLKEQPALNDSRYCLSSRLRVSATFWQNPRNHFRCQVQFYGLSENDEWT QDRAKPVTQIVSAEAWGRADCGFTSVSYQQGVLSATILYEILLGKATLYAVLVSALVLMAMVKRKDF |

TABLE 2-continued

SEQUENCES

| Name | SEQ ID NO | Sequence |
|---|---|---|
| RAS TCR-3 peptide | 45 | VVGAVGVGK |
| | 46 | VVVGAVGVGK |
| RAS TCR-4 alpha chain CDR1 | 47 | TSINN |
| RAS TCR-4 alpha chain CDR2 | 48 | IRSNERE |
| RAS TCR-4 alpha chain CDR3 | 49 | ATDRQSSGDKLT |
| RAS TCR-4 beta chain CDR1 | 50 | SGHAT |
| RAS TCR-4 beta chain CDR2 | 51 | FQNNGV |
| RAS TCR-4 beta chain CDR3 | 52 | ASSLADIYEQY |
| RAS TCR-4 alpha chain variable domain | 53 | ATGGAAACTCTCCTGGGAGTGTCTTTGGTGATTCTATGGCTTCAACTGGCTAGGGTGAACAGTCAACA<br>GGGAGAAGAGGATCCTCAGGCCTTGAGCATCCAGGAGGGTGAAAATGCCACCATGAACTGCAGTTACA<br>AAACTAGTATAAACAATTTACAGTGGTATAGACAAAATTCAGGTAGAGGCCTTGTCCACCTAATTTTA<br>ATACGTTCAAATGAAAGAGAGAAACACAGTGGAAGATTAAGAGTCACGCTTGACACTTCCAAGAAAAG<br>CAGTTCCTTGTTGATCACGGCTTCCCGGGCAGCAGACACTGCTTCTTACTTCTGTGCTACGGACCGTC<br>AAAGCAGCGGAGACAAGCTGACTTTTGGGACCGGGACTCGTTTAGCAGTTAGGCCC |
| | 54 | ATGGAGACTTTACTGGGCGTGTCTTTAGTGATTTTATGGCTGCAGCTGGCTCGTGTGAATAGCCAGCA<br>AGGTGAAGAGGACCCCCAAGCTTTAAGCATCCAAGAAGGCGAGAACGCCACCATGAACTGCTCCTACA<br>AGACCAGCATCAACAATTTACAGTGGTATCGTCAGAACAGCGGTCGTGGTTTAGTGCATTTAATTTTA<br>ATTCGTAGCAACGAGAGGGAGAAGCACAGCGGTCGTCTGAGGGTGACTTTAGACACCAGCAAGAAGAG<br>CAGCTCTTTACTGATCACAGCCTCTAGGGCCGCTGACACCGCTAGCTACTTCTGCGCCACCGACAGAC<br>AGAGCAGCGGCGACAAGCTGACCTTCGGCACCGGCACAAGACTGGCCGTGAGACCC |
| | 55 | METLLGVSLVILWLQLARVNSQQGEEDPQALSIQEGENATMNCSYKTSINNLQWYRQNSGRGLVHLIL<br>IRSNEREKHSGRLRVTLDTSKKSSSLLITASRAADTASYFCATDRQSSGDKLTFGTGTRLAVRP |
| RAS TCR-4 beta chain variable domain | 56 | ATGGGCACCAGGCTCCTCTGCTGGGCGGCCCTCTGTCTCCTGGGAGCAGAACTCACAGAAGCTGGAGT<br>TGCCCAGTCTCCCAGATATAAGATTATAGAGAAAAGGCAGAGTGTGGCTTTTTGGTGCAATCCTATAT<br>CTGGCCATGCTACCCTTTACTGGTACCAGCAGATCCTGGGACAGGGCCCAAAGCTTCTGATTCAGTTT<br>CAGAATAACGGTGTAGTGGATGATTCACAGTTGCCTAAGGATCGATTTTCTGCAGAGAGGCTCAAAGG<br>AGTAGACTCCACTCTCAAGATCCAGCCTGCAAAGCTTGAGGACTCGGCCGTGTATCTCTGTGCCAGCA<br>GCTTAGCCGACATCTACGAGCAGTACTTCGGGCCGGGCACCAGGCTCACGGTCACA |
| | 57 | ATGGGCACCAGACTGCTGTGCTGGGCCGCTCTGTGTCTGCTGGGCGCTGAGCTGACAGAAGCTGGCGT<br>GGCCCAGAGCCCTCGTTACAAGATCATCGAGAAGAGGCAGAGCGTGGCCTTCTGGTGCAACCCCATCA<br>GCGGCCACGCCACTTTATACTGGTACCAGCAGATTTTAGGCCAAGGTCCCAAGCTGCTGATCCAGTTC<br>CAGAACAACGGCGTGGTGGACGACAGCCAGCTGCCCAAGGATCGTTTCAGCGCCGAGAGGCTGAAGGG<br>CGTGGACAGCACTTTAAAAATCCAGCCCGCTAAGCTGGAGGACAGCGCCGTGTATTTATGCGCTAGCT<br>CTTTAGCCGACATCTACGAGCAGTACTTCGGCCCCGGCACTCGTCTGACCGTGACC |
| | 58 | MGTRLLCWAALCLLGAELTEAGVAQSPRYKIIEKRQSVAFWCNPISGHATLYWYQQILGQGPKLLIQF<br>QNNGVVDDSQLPKDRFSAERLKGVDSTLKIQPAKLEDSAVYLCASSLADIYEQYFGPGTRLTVT |
| RAS TCR-4 alpha chain | 59 | METLLGVSLVILWLQLARVNSQQGEEDPQALSIQEGENATMNCSYKTSINNLQWYRQNSGRGLVHLIL<br>IRSNEREKHSGRLRVTLDTSKKSSSLLITASRAADTASYFCATDRQSSGDKLTFGTGTRLAVRPDIQN<br>PDPAVYQLRDSKSSDKSVCLFTDFDSQTNVSQSKDSDVYITDKTVLDMRSMDFKSNSAVAWSNKSDFA<br>CANAFNNSIIPEDTFFPSPESSCDVKLVEKSFETDTNLNFQNLSVIGFRILLLKVAGFNLLMTLRLWS<br>S |
| RAS TCR-4 beta chain | 60 | MGTRLLCWAALCLLGAELTEAGVAQSPRYKIIEKRQSVAFWCNPISGHATLYWYQQILGQGPKLLIQF<br>QNNGVVDDSQLPKDRFSAERLKGVDSTLKIQPAKLEDSAVYLCASSLADIYEQYFGPGTRLTVTEDLN<br>KVFPPEVAVFEPSEAEISHTQKATLVCLATGFFPDHVELSWWVNGKEVHSGVSTDPQPLKEQPALNDS<br>RYCLSSRLRVSATFWQNPRNHFRCQVQFYGLSENDEWTQDRAKPVTQIVSAEAWGRADCGFTSVSYQQ<br>GVLSATILYEILLGKATLYAVLVSALVLMAMVKRKDF |

TABLE 2-continued

SEQUENCES

| Name | SEQ ID NO | Sequence |
|---|---|---|
| RAS TCR-4 peptide | 61 | VVGAVGVGK |
|  | 62 | VVVGAVGVGK |
| RAS TCR-5 alpha chain CDR1 | 63 | TSGFNG |
| RAS TCR-5 alpha chain CDR2 | 64 | NVLDGL |
| RAS TCR-5 alpha chain CDR3 | 65 | CAPGDNFNKFYF |
| RAS TCR-5 beta chain CDR1 | 66 | SGHRS |
| RAS TCR-5 beta chain CDR2 | 67 | YFSETQ |
| RAS TCR-5 beta chain CDR3 | 68 | CASSARNDEAFF |
| RAS TCR-5 alpha chain variable domain | 69 | ATGTGGGAGTTTTCCTTCTTTATGTTTCCATGAAGATGGGAGGCACTACAGGACAAAACATTGACCA<br>GCCCACTGAGATGACAGCTACGGAAGGTGCCATTGTCCAGATCAACTGCACGTACCAGACATCTGGGT<br>TCAACGGGCTGTTCTGGTACCAGCAACATGCTGGCGAAGCACCCACATTTCTGTCTTACAATGTTCTG<br>GATGGTTTGGAGGAGAAAGGTCGTTTTTCTTCATTCCTTAGTCGGTCTAAAGGGTACAGTTACCTCCT<br>TTTGAAGGAGCTCCAGATGAAAGACTCTGCCTCTTACCTCTGTGCTCCCGGGGACAACTTCAACAAAT<br>TTTACTTTGGATCTGGGACCAAACTCAATGTAAAACCA |
|  | 70 | ATGTGGGGCGTGTTTCTGCTGTACGTGTCCATGAAGATGGGCGGCACCACAGGCCAGAACATCGACCA<br>GCCAACCGAGATGACCGCCACAGAGGGCGCCATCGTGCAGATCAACTGCACCTACCAGACATCTGGCT<br>TCAATGGCCTGTTTTGGTATCAGCAGCACGCAGGAGAGGCACCCACATTCCTGAGCTATAATGTGCTG<br>GATGGCCTGGAGGAGAAGGGCAGGTTCTCCTCTTTTCTGTCTCGCAGCAAGGGCTACTCCTATCTGCT<br>GCTGAAGGAGCTGCAGATGAAGGACTCCGCCTCTTACCTGTGCGCCCCTGGCGATAACTTTAATAAGT<br>TCTATTTCGGCTCTGGCACCAAGCTGAATGTGAAGCCA |
|  | 71 | MWGVFLLYVSMKMGGTTGQNIDQPTEMTATEGAIVQINCTYQTSGFNGLFWYQQHAGEAPTFLSYNVL<br>DGLEEKGRFSSFLSRSKGYSYLLLKELQMKDSASYLCAPGDNFNKFYFGSGTKLNVKP |
| RAS TCR-5 beta chain variable domain | 72 | ATGGGCTCCAGGCTGCTCTGTTGGGTGCTGCTTTGTCTCCTGGGAGCAGGCCCAGTAAAGGCTGGAGT<br>CACTCAAACTCCAAGATATCTGATCAAAACGAGAGGACAGCAAGTGACACTGAGCTGCTCCCCTATCT<br>CTGGGCATAGGAGTGTATCCTGGTACCAACAGACCCCAGGACAGGGCCTTCAGTTCCTCTTTGAATAC<br>TTCAGTGAGACACAGAGAAACAAAGGAAACTTCCCTGGTCGATTCTCAGGGCGCCAGTTCTCTAACTC<br>TCGCTCTGAGATGAATGTGAGCACCTTGGAGCTGGGGGACTCGGCCCTTTATCTTTGCGCCAGCAGCG<br>CGAGAAATGATGAAGCTTTCTTTGGACAAGGCACCAGACTCACAGTTGTA |
|  | 73 | ATGGGCAGCCGGCTGCTGTGCTGGGTGCTGCTGTGCCTGCTGGGAGCAGGACCAGTGAAGGCAGGCGT<br>GACCCAGACACCTCGGTACCTGATCAAGACCAGAGGCCAGCAGGTGACACTGAGCTGCTCCCCAATCT<br>CCGGCCACAGATCTGTGAGCTGGTACCAGCAGACCCCAGGACAGGGACTGCAGTTCCTGTTTGAGTAT<br>TTCTCCGAGACACAGAGGAACAAGGGCAATTTCCCTGGCCGGTTTTCTGGCAGACAGTTTTCCAACTC<br>TCGCAGCGAGATGAATGTGAGCACCCTGGAGCTGGGCGACTCCGCCCTGTACCTGTGCGCCAGCTCCG<br>CCAGGAACGATGAGGCCTTCTTTGGCCAGGGCACCCGGCTGACAGTGGTG |
|  | 74 | MGSRLLCWVLLCLLGAGPVKAGVTQTPRYLIKTRGQQVTLSCSPISGHRSVSWYQQTPGQGLQFLFEY<br>FSETQRNKGNFPGRFSGRQFSNSRSEMNVSTLELGDSALYLCASSARNDEAFFGQGTRLTVV |
| RAS TCR-5 alpha chain | 75 | MWGVFLLYVSMKMGGTTGQNIDQPTEMTATEGAIVQINCTYQTSGFNGLFWYQQHAGEAPTFLSYNVL<br>DGLEEKGRFSSFLSRSKGYSYLLLKELQMKDSASYLCAPGDNFNKFYFGSGTKLNVKPDIQNPDAVY<br>QLRDSKSSDKSVCLFTDFDSQTNVSQSKDSDVYITDKTVLDMRSMDFKSNSAVAWSNKSDFACANAFN<br>NSIIPEDTFFPSPESSCDVKLVEKSFETDTNLNFQNLSVIGFRILLLKVAGFNLLMTLRLWSS |
| RAS TCR-5 beta chain | 76 | MGSRLLCWVLLCLLGAGPVKAGVTQTPRYLIKTRGQQVTLSCSPISGHRSVSWYQQTPGQGLQFLFEY<br>FSETQRNKGNFPGRFSGRQFSNSRSEMNVSTLELGDSALYLCASSARNDEAFFGQGTRLTVVEDLNKV<br>FPPEVAVFEPSEAEISHTQKATLVCLATGFFPDHVELSWWVNGKEVHSGVSTDPQPLKEQPALNDSRY<br>CLSSRLRVSATFWQNPRNHFRCQVQFYGLSENDEWTQDRAKPVTQIVSAEAWGRADCGFTSVSYQQGV<br>LSATILYEILLGKATLYAVLVSALVLMAMVKRKDF |

TABLE 2-continued

SEQUENCES

| Name | SEQ ID NO | Sequence |
|---|---|---|
| RAS TCR-5 peptide | 77 | VVGAVGVGK |
|  | 78 | VVVGAVGVGK |
| RAS TCR-6 alpha chain CDR1 | 79 | DRGSQS |
| RAS TCR-6 alpha chain CDR2 | 80 | IYSNGD |
| RAS TCR-6 alpha chain CDR3 | 81 | CAVKSRAGSYQLTF |
| RAS TCR-6 beta chain CDR1 | 82 | SGHNS |
| RAS TCR-6 beta chain CDR2 | 83 | FNNNVP |
| RAS TCR-6 beta chain CDR3 | 84 | CASSLGDSEQYF |
| RAS TCR-6 alpha chain variable domain | 85 | ATGAAATCCTTGAGAGTTTTACTAGTGATCCTGTGGCTTCAGTTGAGCTGGGTTTGGAGCCAACAGAA<br>GGAGGTGGAGCAGAATTCTGGACCCCTCAGTGTTCCAGAGGGAGCCATTGCCTCTCTCAACTGCACTT<br>ACAGTGACCGAGGTTCCCAGTCCTTCTTCTGGTACAGACAATATTCTGGGAAAAGCCCTGAGTTGATA<br>ATGTTCATATACTCCAATGGTGACAAAGAAGATGGAAGGTTTACAGCACAGCTCAATAAAGCCAGCCA<br>GTATGTTTCTCTGCTCATCAGAGACTCCCAGCCCAGTGATTCAGCCACCTACCTCTGTGCCGTGAAGT<br>CAAGGGCTGGGAGTTACCAACTCACTTTCGGGAAGGGGACCAAACTCTCGGTCATACCA |
|  | 86 | ATGAAGAGCCTGCGGGTGCTGCTGGTCATCCTGTGGCTGCAGCTGTCCTGGGTGTGGTCTCAGCAGAA<br>GGAGGTGGAGCAGAATAGCGGACCACTGTCCGTGCCAGAGGGAGCCATCGCCTCCCTGAACTGCACAT<br>ACTCTGACAGGGGCTCCCAGTCTTTCTTTTGGTACCGCCAGTATAGCGGCAAGTCCCCCGAGCTGATC<br>ATGTTCATCTACTCTAATGGCGACAAGGAGGATGGCAGGTTTACCGCCCAGCTGAACAAGGCCTCTCA<br>GTATGTGAGCCTGCTGATCCGCGACAGCCAGCCTAGCGATTCCGCCACATACCTGTGCGCAGTGAAGT<br>CCCGGGCAGGCTCTTATCAGCTGACCTTTGGCAAGGGCACAAAGCTGAGCGTGATCCCA |
|  | 87 | MKSLRVLLVILWLQLSWVWSQQKEVEQNSGPLSVPEGAIASLNCTYSDRGSQSFFWYRQYSGKSPELI<br>MFIYSNGDKEDGRFTAQLNKASQYVSLLIRDSQPSDSATYLCAVKSRAGSYQLTFGKGTKLSVIP |
| RAS TCR-6 beta chain variable domain | 88 | ATGGACTCCTGGACCTTCTGCTGTGTGTCCCTTTGCATCCTGGTAGCGAAGCATACAGATGCTGAGT<br>TATCCAGTCACCCCGCCATGAGGTGACAGAGATGGGACAAGAAGTGACTCTGAGATGTAAACCAATTT<br>CAGGCCACAACTCCCTTTTCTGGTACAGACAGACCATGATGCGGGGACTGGAGTTGCTCATTTACTTT<br>AACAACAACGTTCCGATAGATGATTCAGGGATGCCCGAGGATCGATTCTCAGCTAAGATGCCTAATGC<br>ATCATTCTCCACTCTGAAGATCCAGCCCTCAGAACCCAGGGACTCAGCTGTGTACTTCTGTGCCAGCA<br>GTCTCGGGGACAGCGAGCAGTACTTCGGGCCGGGCACCAGGCTCACGGTCACA |
|  | 89 | ATGGACAGCTGGACCTTCTGCTGCGTGAGCCTGTGCATCCTGGTGGCCAAGCACACAGATGCAGGCGT<br>GATCCAGTCCCCAAGGCACGAGGTGACCGAGATGGGACAGGAGGTGACACTGAGGTGTAAGCCTATCT<br>CTGGCCACAATAGCCTGTTCTGGTACAGGCAGACCATGATGCGCGGCCTGGAGCTGCTGATCTACTTC<br>AACAATAACGTGCCTATCGACGATTCCGGCATGCCAGAGGACAGATTCTCTGCCAAGATGCCCAACGC<br>CTCCTTTTCTACACTGAAGATCCAGCCAAGCGAGCCTAGGGACTCCGCCGTGTACTTCTGCGCCAGCT<br>CCCTGGGCGATAGCGAGCAGTATTTTGGCCCTGGCACCCGGCTGACCGTGACA |
|  | 90 | MDSWTFCCVSLCILVAKHTDAGVIQSPRHEVTEMGQEVTLRCKPISGHNSLFWYRQTMMRGLELLIYF<br>NNNVPIDDSGMPEDRFSAKMPNASFSTLKIQPSEPRDSAVYFCASSLGDSEQYFGPGTRLTVT |
| RAS TCR-6 alpha chain | 91 | MKSLRVLLVILWLQLSWVWSQQKEVEQNSGPLSVPEGAIASLNCTYSDRGSQSFFWYRQYSGKSPELI<br>MFIYSNGDKEDGRFTAQLNKASQYVSLLIRDSQPSDSATYLCAVKSRAGSYQLTFGKGTKLSVIPDIQ<br>NPDPAVYQLRDSKSSDKSVCLFTDFDSQTNVSQSKDSDVYITDKTVLDMRSMDFKSNSAVAWSNKSDF<br>ACANAFNNSIIPEDTFFPSPESSCDVKLVEKSFETDTNLNFQNLSVIGFRILLLKVAGFNLLMTLRLW<br>SS |
| RAS TCR-6 beta chain | 92 | MDSWTFCCVSLCILVAKHTDAGVIQSPRHEVTEMGQEVTLRCKPISGHNSLFWYRQTMMRGLELLIYF<br>NNNVPIDDSGMPEDRFSAKMPNASFSTLKIQPSEPRDSAVYFCASSLGDSEQYFGPGTRLTVTEDLNK<br>VFPPEVAVFEPSEAEISHTQKATLVCLATGFFPDHVELSWWVNGKEVHSGVSTDPQPLKEQPALNDSR<br>YCLSSRLRVSATFWQNPRNHFRCQVQFYGLSENDEWTQDRAKPVTQIVSAEAWGRADCGFTSVSYQQG<br>VLSATILYEILLGKATLYAVLVSALVLMAMVKRKDF |

TABLE 2-continued

SEQUENCES

| Name | SEQ ID NO | Sequence |
|---|---|---|
| RAS TCR-6 peptide | 93 | VVGAVGVGK |
|  | 94 | VVVGAVGVGK |
| RAS TCR-7 alpha chain CDR1 | 95 | SSYSPS |
| RAS TCR-7 alpha chain CDR2 | 96 | YTSAATLV |
| RAS TCR-7 alpha chain CDR3 | 97 | CVVSGGGSSNTGKLIF |
| RAS TCR-7 beta chain CDR1 | 98 | SGHAT |
| RAS TCR-7 beta chain CDR2 | 99 | FQNNGV |
| RAS TCR-7 beta chain CDR3 | 100 | CASSQRSNTGELFF |
| RAS TCR-7 alpha chain variable domain | 101 | ATGCTCCTGCTGCTCGTCCCAGTGCTCGAGGTGATTTTTACTCTGGGAGGAACCAGAGCCCAGTCGGT GACCCAGCTTGACAGCCACGTCTCTGTCTCTGAAGGAACCCCGGTGCTGCTGAGGTGCAACTACTCAT CTTCTTATTCACCATCTCTCTTCTGGTATGTGCAACACCCCAACAAAGGACTCCAGCTTCTCCTGAAG TACACATCAGCGGCCACCCTGGTTAAAGGCATCAACGGTTTTGAGGCTGAATTTAAGAAGAGTGAAAC CTCCTTCCACCTGACGAAACCCTCAGCCCATATGAGCGACGCGGCTGAGTACTTCTGTGTTGTGAGTG GGGGAGGCTCTAGCAACACAGGCAAACTAATCTTTGGGCAAGGGACAACTTTACAAGTAAAACCA |
|  | 102 | ATGCTGCTGCTGCTGGTGCCCGTGCTGGAAGTGATCTTCACCCTGGGAGGAACAAGGGCACAGAGCGT GACCCAGCTGGACTCCCACGTGTCCGTGTCTGAGGGCACACCCGTGCTGCTGAGATGCAACTACTCCT CTAGCTATAGCCCCTCCCTGTTCTGGTACGTGCAGCACCCTAATAAGGGCCTGCAGCTGCTGCTGAAG TATACCTCCGCCGCCACACTGGTGAAGGGCATCAACGGCTTCGAGGCCGAGTTTAAGAAGAGCGAGAC CTCCTTCCACCTGACAAAGCCTTCTGCCCACATGAGCGATGCCGCCGAGTACTTTTGCGTGGTGAGCG GCGGCGGCTCCTCTAATACCGGCAAGCTGATCTTCGGCCAGGGCACCACACTGCAGGTGAAGCCA |
|  | 103 | MLLLLVPVLEVIFTLGGTRAQSVTQLDSHVSVSEGTPVLLRCNYSSSYSPSLFWYVQHPNKGLQLLLK YTSAATLVKGINGFEAEFKKSETSFHLTKPSAHMSDAAEYFCVVSGGGSSNTGKLIFGQGTTLQVKP |
| RAS TCR-7 beta chain variable domain | 104 | ATGGGCACCAGGCTCCTCTGCTGGGCGGCCCTCTGTCTCCTGGGAGCAGAACTCACAGAAGCTGGAGT TGCCCAGTCTCCCAGATATAAGATTATAGAGAAAAGGCAGAGTGTGGCTTTTTGGTGCAATCCTATAT CTGGCCATGCTACCCTTTACTGGTACCAGCAGATCCTGGACAGGGCCCAAAGCTTCTGATTCAGTTT CAGAATAACGGTGTAGTGGATGATTCACAGTTGCCTAAGGATCGATTTTCTGCAGAGAGGCTCAAAGG AGTAGACTCCACTCTCAAGATCCAACCTGCAAAGCTTGAGGACTCGGCCGTGTATCTCTGTGCCAGCA GCCAGAGGTCGAACACCGGGGAGCTGTTTTTTGGAGAAGGCTCTAGGCTGACCGTACTG |
|  | 105 | ATGGGCACCCGGCTGCTGTGCTGGGCCGCCCTGTGCCTGCTGGGAGCAGAGCTGACAGAGGCAGGAGT GGCCCAGTCCCCCACGGTACAAGATCATCGAGAAGAGACAGTCCGTGGCCTTTTGGTGCAACCCCATCT CTGGCCACGCCACCCTGTACTGGTATCAGCAGATCCTGGGCCAGGGCCCTAAGCTGCTGATCCAGTTC CAGAACAATGGCGTGGTGGACGATTCTCAGCTGCCAAAGGACAGGTTTAGCGCCGAGCGCCTGAAGGG CGTGGATAGCACCCTGAAGATCCAGCCTGCCAAGCTGGAGGACAGCGCCGTGTATCTGTGCGCCAGCT CCCAGCGGTCCAATACAGGCGAGCTGTTCTTTGGCGAGGGCTCTAGGCTGACCGTGCTG |
|  | 106 | MGTRLLCWAALCLLGAELTEAGVAQSPRYKIIEKRQSVAFWCNPISGHATLYWYQQILGQGPKLLIQF QNNGVVDDSQLPKDRFSAERLKGVDSTLKIQPAKLEDSAVYLCASSQRSNTGELFFGEGSRLTVL |
| RAS TCR-7 alpha chain | 107 | MLLLLVPVLEVIFTLGGTRAQSVTQLDSHVSVSEGTPVLLRCNYSSSYSPSLFWYVQHPNKGLQLLLK YTSAATLVKGINGFEAEFKKSETSFHLTKPSAHMSDAAEYFCVVSGGGSSNTGKLIFGQGTTLQVKPD IQNPDPAVYQLRDSKSSDKSVCLFTDFDSQTNVSQSKDSDVYITDKTVLDMRSMDFKSNSAVAWSNKS DFACANAFNNSIIPEDTFFPSPESSCDVKLVEKSFETDTNLNFQNLSVIGFRILLLKVAGFNLLMTLR LWSS |
| RAS TCR-7 beta chain | 108 | MGTRLLCWAALCLLGAELTEAGVAQSPRYKIIEKRQSVAFWCNPISGHATLYWYQQILGQGPKLLIQF QNNGVVDDSQLPKDRFSAERLKGVDSTLKIQPAKLEDSAVYLCASSQRSNTGELFFGEGSRLTVLEDL NKVFPPEVAVFEPSEAEISHTQKATLVCLATGFFPDHVELSWWVNGKEVHSGVSTDPQPLKEQPALND SRYCLSSRLRVSATFWQNPRNHFRCQVQFYGLSENDEWTQDRAKPVTQIVSAEAWGRADCGFTSVSYQ QGVLSATILYEILLGKATLYAVLVSALVLMAMVKRKDF |

TABLE 2-continued

SEQUENCES

| Name | SEQ ID NO | Sequence |
|---|---|---|
| RAS TCR-7 peptide | 109 | VVGACGVGK |
|  | 110 | VVVGACGVGK |
| RAS TCR-8 alpha chain CDR1 | 111 | TSINN |
| RAS TCR-8 alpha chain CDR2 | 112 | IRSNERE |
| RAS TCR-8 alpha chain CDR3 | 113 | CATDAGGGADGLTF |
| RAS TCR-8 beta chain CDR1 | 114 | SGDLS |
| RAS TCR-8 beta chain CDR2 | 115 | YYNGEE |
| RAS TCR-8 beta chain CDR3 | 116 | CASGGRDSTDTQYF |
| RAS TCR-8 alpha chain variable domain | 117 | ATGGAAACTCTCCTGGGAGTGTCTTTGGTGATTCTATGGCTTCAACTGGCTAGGGTGAACAGTCAACA GGGAGAAGAGGATCCTCAGGCCTTGAGCATCCAGGAGGGTGAAAATGCCACCATGAACTGCAGTTACA AAACTAGTATAAACAATTTACAGTGGTATAGACAAAATTCAGGTAGAGGCCTTGTCCACCTAATTTTA ATACGTTCAAATGAAAGAGAGAAACACAGTGGAAGATTAAGAGTCACGCTTGACACTTCCAAGAAAAG CAGTTCCTTGTTGATCACGGCTTCCCGGGCAGCAGACACTGCTTCTTACTTCTGTGCTACGGACGCCG GAGGAGGTGCTGACGGACTCACCTTTGGCAAAGGGACTCATCTAATCATCCAGCCC |
|  | 118 | ATGGAGACACTGCTGGGCGTGTCCCTGGTCATCCTGTGGCTGCAGCTGGCCAGGGTGAACAGCCAGCA GGGAGAGGAGGACCCCCAGGCCCTGTCTATCCAGGAGGGCGAGAACGCCACCATGAATTGCTCTTACA AGACAAGCATCAACAATCTGCAGTGGTATAGACAGAACTCCGGCAGGGGCCTGGTGCACCTGATCCTG ATCCGCTCCAATGAGCGGGAGAAGCACTCTGGCCGGCTGAGAGTGACCCTGGATACATCTAAGAAGTC CTCTAGCCTGCTGATCACCGCCAGCCGGGCAGCAGACACAGCCTCCTACTTTTGTGCCACCGATGCCG GGGGCGGAGCAGACGGACTGACATTCGGGAAGGGGACTCACCTGATTATCCAGCCA |
|  | 119 | METLLGVSLVILWLQLARVNSQQGEEDPQALSIQEGENATMNCSYKTSINNLQWYRQNSGRGLVHLIL IRSNEREKHSGRLRVTLDTSKKSSSLLITASRAADTASYFCATDAGGGADGLTFGKGTHLIIQP |
| RAS TCR-8 beta chain variable domain | 120 | ATGGGCTTCAGGCTCCTCTGCTGTGTGGCCTTTTGTCTCCTGGGAGCAGGCCCAGTGGATTCTGGAGT CACACAAACCCCAAAGCACCTGATCACAGCAACTGGACAGCAGGTGACGCTGAGATGCTCCCCTAGGT CTGGAGACCTCTCTGTGTACTGGTACCAACAGAGCCTGGACCAGGGCCTCCAGTTCCTCATTCAGTAT TATAATGGAGAAGAGAGAGCAAAAGGAAACATTCTTGAACGATTCTCCGCACAACAGTTCCCTGACTT GCACTCTGAACTAAACCTGAGCTCTCTGGAGCTGGGGGACTCAGCTTTGTATTTCTGTGCCAGCGGGG GACGGGATTCCACAGATACGCAGTATTTTGGCCCAGGCACCCGGCTGACAGTGCTC |
|  | 121 | ATGGGCTTTCGGCTGCTGTGCTGCGTGGCTTTTTGCCTGCTGGGGGCTGGGCCTGTGGATAGCGGGGT CACTCAGACACCTAAACATCTGATCACCGCAACAGGACAGAGGGTGACCCTGAGGTGCTCTCCTCGGA GCGGCGACCTGAGCGTGTACTGGTATCAGCAGAGCCTGGATCAGGGCCTGCAGTTCCTGATCCAGTAC TATAACGGCGAGGAGCGCGCCAAGGGCAATATCCTGGAGCGGTTCTCTGCCCAGCAGTTTCCAGACCT GCACAGCGAGCTGAACCTGAGCTCCCTGGAGCTGGGCGATAGCGCCCTGTACTTCTGCGCCTCCGGCG GCAGAGACTCTACCGATACACAGTATTTTGGCCCCGGCACCAGACTGACAGTGCTG |
|  | 122 | MGFRLLCCVAFCLLGAGPVDSGVTQTPKHLITATGQRVTLRCSPRSGDLSVYWYQQSLDQGLQFLIQY YNGEERAKGNILERFSAQQFPDLHSELNLSSLELGDSALYFCASGGRDSTDTQYFGPGTRLTVL |
| RAS TCR-8 alpha chain | 123 | METLLGVSLVILWLQLARVNSQQGEEDPQALSIQEGENATMNCSYKTSINNLQWYRQNSGRGLVHLIL IRSNEREKHSGRLRVTLDTSKKSSSLLITASRAADTASYFCATDAGGGADGLTFGKGTHLIIQPDIQN PDPAVYQLRDSKSSDKSVCLFTDFDSQTNVSQSKDSDVYITDKTVLDMRSMDFKSNSAVAWSNKSDFA CANAFNNSIIPEDTFFPSPESSCDVKLVEKSFETDTNLNFQNLSVIGFRILLLKVAGFNLLMTLRLWS S |
| RAS TCR-8 beta chain | 124 | MGFRLLCCVAFCLLGAGPVDSGVTQTPKHLITATGQRVTLRCSPRSGDLSVYWYQQSLDQGLQFLIQY YNGEERAKGNILERFSAQQFPDLHSELNLSSLELGDSALYFCASGGRDSTDTQYFGPGTRLTVLEDLN KVFPPEVAVFEPSEAEISHTQKATLVCLATGFFPDHVELSWWVNGKEVHSGVSTDPQPLKEQPALNDS RYCLSSRLRVSATFWQNPRNHFRCQVQFYGLSENDEWTQDRAKPVTQIVSAEAWGRADCGFTSVSYQQ GVLSATILYEILLGKATLYAVLVSALVLMAMVKRKDF |

TABLE 2-continued

SEQUENCES

| Name | SEQ ID NO | Sequence |
|---|---|---|
| RAS TCR-8 peptide | 125 | VVGAVGVGK |
| | 126 | VVVGAVGVGK |
| Ras TCR-1/2 peptide | 219 | KLVVVGADGV |
| Ras TCR-1/2 peptide | 220 | LVVVGADGV |
| Ras TCR-1/2 peptide | 221 | KLVVVGAVGV |
| Ras TCR-1/2 peptide | 222 | LVVVGAVGV |
| RAS TCR-10 alpha chain CDR1 | 239 | SVFSS |
| RAS TCR-10 alpha chain CDR2 | 240 | VVTGGEV |
| RAS TCR-10 alpha chain CDR3 | 241 | AGGPNTGNQFY |
| RAS TCR-10 beta chain CDR1 | 242 | SGHNT |
| RAS TCR-10 beta chain CDR2 | 243 | YYREEE |
| RAS TCR-10 beta chain CDR3 | 244 | ASSTSFWEVNTEAF |
| RAS TCR-10 alpha chain variable domains | 245 | ATGGTCCTGAAATTCTCCGTGTCCATTCTTTGGATTCAGTTGGCATGGGTGAGCACCCAGCTGCTGGA<br>GCAGAGCCCTCAGTTTCTAAGCATCCAAGAGGGAGAAAATCTCACTGTGTACTGCAACTCCTCAAGTG<br>TTTTTTCCAGCTTACAATGGTACAGACAGGAGCCTGGGGAAGGTCCTGTCCTCCTGGTGACAGTAGTT<br>ACGGGTGGAGAAGTGAAGAAGCTGAAGAGACTAACCTTTCAGTTTGGTGATGCAAGAAAGGACAGTTC<br>TCTCCACATCACTGCGGCCCAGCCTGGTGATACAGGCCTCTACCTCTGTGCAGGAGGGCCGAACACCG<br>GTAACCAGTTCTATTTTGGGACAGGGACAAGTTTGACGGTCATTCCAAAT |
| | 246 | ATGGTGCTGAAGTTTTCCGTGTCTATCCTGTGGATTCAGCTGGCCTGGGTGTCTACCCAGCTGCTGGA<br>GCAGAGCCCCAGTTCCTGTCCATCCAGGAGGGCGAGAACCTGACAGTGTACTGCAATTCTAGCTCCG<br>TGTTTTCTAGCCTGCAGTGGTATAGGCAGGAGCCAGGAGAGGGACCCGTGCTGCTGGTGACCGTGGTG<br>ACAGGCGGCGAGGTGAAGAAGCTGAAGAGACTGACCTTCCAGTTTGGCGACGCCAGGAAGGATTCCTC<br>TCTGCACATCACCGCAGCACAGCCTGGCGATACAGGACTGTACCTGTGCGCAGGAGGACCAAACACCG<br>GCAATCAGTTCTATTTTGGCACCGGCACATCCCTGACAGTGATCCCCTAAT |
| | 247 | MVLKFSVSILWIQLAWVSTQLLEQSPQFLSIQEGENLTVYCNSSSVFSSLQWYRQEPGEGPVLLVTVV<br>TGGEVKKLKRLTFQFGDARKDSSLHITAAQPGDTGLYLCAGGPNTGNQFYFGTGTSLTVIPN |
| RAS TCR-10 beta chain variable domain | 248 | ATGGGCCCTGGGCTCCTCTGCTGGGTGCTGCTTTGTCCTGGGAGCAGGCTCAGTGGAGACTGGAGT<br>CACCCAAAGTCCCACACACCTGATCAAAACGAGAGGACAGCAAGTGACTCTGAGATGCTCTTCTCAGT<br>CTGGGCACAACACTGTGTCCTGGTACCAACAGGCCCTGGGTCAGGGGCCCCAGTTTATCTTTCAGTAT<br>TATAGGGAGGAAGAGAATGGCAGAGGAAACTTCCCTCCTAGATTCTCAGGTCTCCAGTTCCCTAATTA<br>TAGCTCTGAGCTGAATGTGAACGCCTTGGAGCTGGACGACTCGGCCCTGTATCTCTGTGCCAGCAGCA<br>CATCTTTTTGGGAGGTGAACACTGAAGCTTTCTTTGGACAAGGCACCAGACTCACAGTTGTA |
| | 249 | ATGGGACCAGGACTGCTGTGCTGGGTGCTGCTGTGCCTGCTGGGAGCAGGCTCCGTGGAGACCGGCGT<br>GACACAGTCTCCCACCCACCTGATCAAGACAAGAGGCCAGCAGGTGACCCTGAGGTGCAGCTCCCAGT<br>CTGGCCACAACACAGTGAGCTGGTACCAGCAGGCCCTGGGACAGGGACCTCAGTTCATCTTTCAGTAC<br>TATAGGGAGGAGGAGAACGGCCGCGGCAATTTCCCCCCTCGGTTTAGCGGCCTGCAGTTCCCAAACTA<br>CTCTAGCGAGCTGAACGTGAATGCCCTGGAGCTGGACGATAGCGCCCTGTATCTGTGCGCCTCCTCTA<br>CCTCCTTTTGGGAAGTGAATACAGAGGCCTTCTTTGGCCAGGGCACCCGCCTGACAGTGGTG |

TABLE 2-continued

SEQUENCES

| Name | SEQ ID NO | Sequence |
|---|---|---|
| | 250 | MGPGLLCWVLLCLLGAGSVETGVTQSPTHLIKTRGQQVTLRCSSQSGHNTVSWYQQALGQGPQFIFQY YREEENGRGNFPPRFSGLQFPNYSSELNVNALELDDSALYLCASSTSFWEVNTEAFFGQGTRLTVV |
| RAS TCR-10 alpha chain | 251 | MVLKFSVSILWIQLAWVSTQLLEQSPQFLSIQEGENLTVYCNSSSVFSSLQWYRQEPGEGPVLLVTVV TGGEVKKLKRLTFQFGDARKDSSLHITAAQPGDTGLYLCAGGPNTGNQFYFGTGTSLTVIPNDIQNPE PAVYQLKDPRSQDSTLCLFTDFDSQINVPKTMESGTFITDKTVLDMKAMDSKSNGAIAWSNQTSFTCQ DIFKETNATYPSSDVPCDATLTEKSFETDMNLNFQNLSVMGLRILLLKVAGFNLLMTLRLWSS |
| RAS TCR-10 beta chain | 252 | MGPGLLCWVLLCLLGAGSVETGVTQSPTHLIKTRGQQVTLRCSSQSGHNTVSWYQQALGQGPQFIFQY YREEENGRGNFPPRFSGLQFPNYSSELNVNALELDDSALYLCASSTSFWEVNTEAFFGQGTRLTVVKD LRNVTPPKVSLFEPSKAEIANKQKATLVCLARGFFPDHVELSWWVNGKEVHSGVSTDPQAYKESNYSY CLSSRLRVSATFWHNPRNHFRCQVQFHGLSEEDKWPEGSPKPVTQNISAEAWGRADCGITSASYHQGV LSATILYEILLGKATLYAVLVSGLVLMAMVKKKNS |
| TCR peptide | 253 | VVGACGVGK |
| | 254 | VVVGACGVGK |
| RAS TCR-11 alpha chain CDR1 | 255 | TSGFNG |
| RAS TCR-11 alpha chain CDR2 | 256 | NVLDGL |
| RAS TCR-11 alpha chain CDR3 | 257 | AVREEVLYNQGGKLI |
| RAS TCR-11 beta chain CDR1 | 258 | LNHDA |
| RAS TCR-11 beta chain CDR2 | 259 | SQIVND |
| RAS TCR-11 beta chain CDR3 | 260 | ASSKRGWPYEQY |
| RAS TCR-11 alpha chain variable domain | 261 | ATGTGGGAGTTTTCCTTCTTTATGTTTCCATGAAGATGGGAGGCACTACAGGACAAAACATTGACCA GCCCACTGAGATGACAGCTACGGAAGGTGCCATTGTCCAGATCAACTGCACGTACCAGACATCTGGGT TCAACGGGCTGTTCTGGTACCAGCAACATGCTGGCGAAGCACCCACATTTCTGTCTTACAATGTTCTG GATGGTTTGGAGGAGAAAGGTCGTTTTTCTTCATTCCTTAGTCGGTCTAAAGGGTACAGTTACCTCCT TTTGAAGGAGCTCCAGATGAAAGACTCTGCCTCTTACCTCTGTGCTGTGAGAGAGGAGGTCCTTTATA ACCAGGGGAGGAAAGCTTATCTTCGGACAGGGAACGGAGTTATCTGTGAAACCC |
| | 262 | ATGTGGGGCGTGTTTCTGCTGTACGTGAGCATGAAGATGGGCGGCACCACAGGCCAGAACATCGACCA GCCCACCGAGATGACCGCCACAGAGGGCGCCATCGTGCAGATCAACTGCACCTACCAGACAAGCGGCT TCAATGGCCTGTTTTGGTATCAGCAGCACGCAGGAGAGGCACCCACATTCCTGTCCTATAATGTGCTG GACGGCCTGGAGGAGAAGGGCAGGTTCTCCTCTTTTCTGAGCCGCTCCAAGGGCTACTCCTATCTGCT GCTGAAGGAGCTGCAGATGAAGGATTCTGCCAGCTACCTGTGCGCCGTGCGGGAGGAGGTGCTGTATA ATCAGGGCGGCAAGCTGATCTTTGGCCAGGGCACCGAGCTGAGCGTGAAGCCT |
| | 263 | MWGVFLLYVSMKMGGTTGQNIDQPTEMTATEGAIVQINCTYQTSGFNGLFWYQQHAGEAPTFLSYNVL DGLEEKGRFSSFLSRSKGYSYLLLKELQMKDSASYLCAVREEVLYNQGGKLIFGQGTELSVKP |
| RAS TCR-11 beta chain variable domain | 264 | ATGAGCAACCAGGTGCTCTGCTGTGTGGTCCTTTGTCTCCTGGGAGCAAACACCGTGGATGGTGGAAT CACTCAGTCCCCGAAGTACCTGTTCAGAAAGGAAGGACAGAATGTGACCCTGAGTTGTGAACAGAATT TGAACCACGATGCCATGTACTGGTACCGACAGGACCCAGGGCAAGGGCTGAGATTGATCTACTACTCA CAGATAGTAAATGACTTTCAGAAGGAGATATAGCTGAAGGGTACAGCGTCTCTCGGGAGAAGAAGGA ATCCTTTCCTCTCACTGTGACATCGGCCCAAAAGAACCCCGACAGCTTTCTATCTCTGTGCCAGTAGTA AAAGGGGATGGCCCTACGAGCAGTACTTCGGGCCGGGCACCAGGCTCACGGTCACA |
| | 265 | ATGTCCAACCAGGTGCTGTGCTGCGTGGTGCTGTGCCTGCTGGGAGCAAATACCGTGGACGGAGGCAT CACACAGTCCCCCAAGTACCTGTTCCGGAAGGAGGGCCAGAACGTGACCCTGTCTTGTGAGCAGAACC TGAATCACGACGCCATGTACTGGTATAGGCAGGACCCCGGACAGGGACTGAGACTGATCTACTATAGC CAGATCGTGAACGACTTTCAGAAGGGCGACATCGCCGAGGGCTACAGCGTGTCCCGGGAGAAGAAGGA GTCCTTCCCACTGACCGTGACATCTGCCCAGAAGAATCCCACCGCCTTTTATCTGTGCGCCAGCTCCA AGAGAGGCTGGCCCTACGAGCAGTATTTCGGCCCTGGCACCAGGCTGACCGTGACA |
| | 266 | MSNQVLCCVVLCLLGANTVDGGITQSPKYLFRKEGQNVTLSCEQNLNHDAMYWYRQDPGQGLRLIYYS QIVNDFQKGDIAEGYSVSREKKESFPLTVTSAQKNPTAFYLCASSKRGWPYEQYFGPGTRLTVT |

TABLE 2-continued

SEQUENCES

| Name | SEQ ID NO | Sequence |
|---|---|---|
| RAS TCR-11 alpha chain | 267 | MWGVFLLYVSMKMGGTTGQNIDQPTEMTATEGAIVQINCTYQTSGFNGLFWYQQHAGEAPTFLSYNVL<br>DGLEEKGRFSSFLSRSKGYSYLLLKELQMKDSASYLCAVREEVLYNQGGKLIFGQGTELSVKPDIQNP<br>EPAVYQLKDPRSQDSTLCLFTDFDSQINVPKTMESGTFITDKTVLDMKAMDSKSNGAIAWSNQTSFTC<br>QDIFKETNATYPSSDVPCDATLTEKSFETDMNLNFQNLSVMGLRILLLKVAGFNLLMTLRLWSS |
| RAS TCR-11 beta chain | 268 | MSNQVLCCVVLCLLGANTVDGGITQSPKYLFRKEGQNVTLSCEQNLNHDAMYWYRQDPGQGLRLIYYS<br>QIVNDFQKGDIAEGYSVSREKKESFPLTVTSAQKNPTAFYLCASSKRGWPYEQYFGPGTRLTVTKDLR<br>NVTPPKVSLFEPSKAEIANKQKATLVCLARGFFPDHVELSWWVNGKEVHSGVSTDPQAYKESNYSYCL<br>SSRLRVSATFWHNPRNHFRCQVQFHGLSEEDKWPEGSPKPVTQNISAEAWGRADCGITSASYHQGVLS<br>ATILYEILLGKATLYAVLVSGLVLMAMVKKKNS |
| TCR peptide | 269 | VVGACGVGK |
|  | 270 | VVVGACGVGK |
| RAS TCR-12 alpha chain CDR1 | 271 | TSINN |
| RAS TCR-12 alpha chain CDR2 | 272 | IRSNERE |
| RAS TCR-12 alpha chain CDR3 | 273 | ATDRQSSGDKLT |
| RAS TCR-12 beta chain CDR1 | 274 | SGHAT |
| RAS TCR-12 beta chain CDR2 | 275 | FQNNGV |
| RAS TCR-12 beta chain CDR3 | 276 | ASSLADIYEQY |
| RAS TCR-12 alpha chain variable domain | 277 | ATGGAAACTCTCCTGGGAGTGTCTTTGGTGATTCTATGGCTTCAACTGGCTAGGGTGAACAGTCAACA<br>GGGAGAAGAGGATCCTCAGGCCTTGAGCATCCAGGAGGGTGAAAATGCCACCATGAACTGCAGTTACA<br>AAACTAGTATAAACAATTTACAGTGGTATAGACAAAATTCAGGTAGAGGCCTTGTCCACCTAATTTTA<br>ATACGTTCAAATGAAAGAGAGAAACACAGTGGAAGATTAAGAGTCACGCTTGACACTTCCAAGAAAAG<br>CAGTTCCTTGTTGATCACGGCTTCCCGGGCAGCAGACACTGCTTCTTACTTCTGTGCTACGGACCGTC<br>AAAGCAGCGGAGACAAGCTGACTTTTGGGACCGGGACTCGTTTAGCAGTTAGGCCC |
|  | 278 | ATGGAGACCCTGCTGGGCGTGTCCCTGGTCATCCTGTGGCTGCAGCTGGCCAGGGTGAACAGCCAGCA<br>GGGAGAGGAGGACCCCCAGGCCCTGAGCATCCAGGAGGGCGAGAACGCCACCATGAATTGCTCTTACA<br>AGACAAGCATCAACAATCTGCAGTGGTATAGGCAGAACTCCGGCCGCGGACTGGTGCACCTGATCCTG<br>ATCCGGAGCAATGAGAGAGAAGCACTCCGGCCGGCTGAGAGTGACCCTGGACACATCTAAGAAGTC<br>CTCTAGCCTGCTGATCACCGCCTCTCGGGCAGCAGATACAGCCAGCTACTTCTGTGCCACCGACAGAC<br>AGTCCTCTGGCGATAAGCTGACCTTTGGCACCGGCACAAGGCTGGCCGTGCGCCCC |
|  | 279 | METLLGVSLVILWLQLARVNSQQGEEDPQALSIQEGENATMNCSYKTSINNLQWYRQNSGRGLVHLIL<br>IRSNEREKHSGRLRVTLDTSKKSSSLLITASRAADTASYFCATDRQSSGDKLTFGTGTRLAVRP |
| RAS TCR-12 beta chain variable domain | 280 | ATGGGCACCAGGCTCCTCTGCTGGGCGGCCCTCTGTCTCCTGGGAGCAGAACTCACAGAAGCTGGAGT<br>TGCCCAGTCTCCCAGATATAAGATTATAGAGAAAAGGCAGAGTGTGGCTTTTTGGTGCAATCCTATAT<br>CTGGCCATGCTACCCTTTACTGGTACCAGCAGATCCTGGGACAGGGCCCAAAGCTTCTGATTCAGTTT<br>CAGAATAACGGTGTAGTGGATGATTCACAGTTGCCTAAGGATCGATTTTCTGCAGAGAGGCTCAAAGG<br>AGTAGACTCCACTCTCAAGATCCAGCCTGCAAAGCTTGAGGACTCGGCCGTGTATCTCTGTGCCAGCA<br>GCTTAGCCGACATCTACGAGCAGTACTTCGGGCCGGGCACCAGGCTCACGGTCACA |
|  | 281 | ATGGGAACAAGGCTGCTGTGCTGGGCCGCCCTGTGCCTGCTGGGAGCAGAGCTGACCGAGGCCGGCGT<br>GGCCCAGAGCCCCCGGTACAAGATCATCGAGAAGAGACAGAGCGTGGCCTTCTGGTGCAACCCTATCT<br>CCGGCCACGCCACACTGTACTGGTATCAGCAGATCCTGGGCCAGGGCCCAAAGCTGCTGATCCAGTTC<br>CAGAACAATGGCGTGGTGGACGATTCCCAGCTGCCCAAGGACCGGTTTTCTGCCGAGAGACTGAAGGG<br>CGTGGATTCCACCCTGAAGATCCAGCCCGCCAAGCTGGAGGACTCTGCCGTGTATCTGTGCGCCAGCT<br>CCCTGGCCGACATCTACGAGCAGTATTTCGGCCCTGGCACAAGGCTGACCGTGACA |
|  | 282 | MGTRLLCWAALCLLGAELTEAGVAQSPRYKIIEKRQSVAFWCNPISGHATLYWYQQILGQGPKLLIQF<br>QNNGVVDDSQLPKDRFSAERLKGVDSTLKIQPAKLEDSAVYLCASSLADIYEQYFGPGTRLTVT |

TABLE 2-continued

SEQUENCES

| Name | SEQ ID NO | Sequence |
|---|---|---|
| RAS TCR-12 alpha chain | 283 | METLLGVSLVILWLQLARVNSQQGEEDPQALSIQEGENATMNCSYKTSINNLQWYRQNSGRGLVHLIL<br>IRSNEREKHSGRLRVTLDTSKKSSSLLITASRAADTASYFCATDRQSSGDKLTFGTGTRLAVRPDIQN<br>PEPAVYQLKDPRSQDSTLCLFTDFDSQINVPKTMESGTFITDKTVLDMKAMDSKSNGAIAWSNQTSFT<br>CQDIFKETNATYPSSDVPCDATLTEKSFETDMNLNFQNLSVMGLRILLLKVAGFNLLMTLRLWSS |
| RAS TCR-12 beta chain | 284 | MGTRLLCWAALCLLGAELTEAGVAQSPRYKIIEKRQSVAFWCNPISGHATLYWYQQILGQGPKLLIQF<br>QNNGVVDDSQLPKDRFSAERLKGVDSTLKIQPAKLEDSAVYLCASSLADIYEQYFGPGTRLTVTKDLR<br>NVTPPKVSLFEPSKAEIANKQKATLVCLARGFFPDHVELSWWVNGKEVHSGVSTDPQAYKESNYSYCL<br>SSRLRVSATFWHNPRNHFRCQVQFHGLSEEDKWPEGSPKPVTQNISAEAWGRADCGITSASYHQGVLS<br>ATILYEILLGKATLYAVLVSGLVLMAMVKKKNS |
| TCR peptide | 285 | VVGACGVGK |
|  | 286 | VVVGACGVGK |
| RAS TCR-13 alpha chain CDR1 | 287 | TSESDYY |
| RAS TCR-13 alpha chain CDR2 | 288 | QEAYKQQN |
| RAS TCR-13 alpha chain CDR3 | 289 | ALYIYGGSQGNLI |
| RAS TCR-13 beta chain CDR1 | 290 | SEHNR |
| RAS TCR-13 beta chain CDR2 | 291 | FQNEAQ |
| RAS TCR-13 beta chain CDR3 | 292 | ASSSTDRIEAF |
| RAS TCR-13 alpha chain variable domain | 293 | ATGGCATGCCCTGGCTTCCTGTGGGCACTTGTGATCTCCACCTGTCTTGAATTTAGCATGGCTCAGAC<br>AGTCACTCAGTCTCAACCAGAGATGTCTGTGCAGGAGGCAGAGACCGTGACCCTGAGCTGCACATATG<br>ACACCAGTGAGAGTGATTATTATTTATTCTGGTACAAGCAGCCTCCCAGCAGGCAGATGATTCTCGTT<br>ATTCGCCAAGAAGCTTATAAGCAACAGAATGCAACAGAGAATCGTTTCTCTGTGAACTTCCAGAAAGC<br>AGCCAAATCCTTCAGTCTCAAGATCTCAGACTCACAGCTGGGGGATGCCGCATGTATTTCTGTGCTC<br>TCTATATTTATGGAGGAAGCCAAGGAAATCTCATCTTTGGAAAAGGCACTAAACTCTCTGTTAAACCA |
|  | 294 | ATGGCATGCCCAGGCTTCCTGTGGGCACTGGTCATCAGCACATGTCTGGAGTTTTCTATGGCCCAGAC<br>CGTGACACAGTCTCAGCCTGAGATGAGCGTGCAGGAGGCCGAGACCGTGACACTGAGCTGCACATACG<br>ACACATCTGAGAGCGATTACTATCTGTTCTGGTATAAGCAGCCACCCTCCAGACAGATGATCCTGGTC<br>ATCAGGCAGGAGGCCTACAAGCAGCAGAACGCCACCGAGAATCGGTTCTCCGTGAACTTTCAGAAGGC<br>CGCCAAGTCCTTTTCTCTGAAGATCAGCGACTCCCAGCTGGGCGATGCCGCCATGTATTTCTGTGCCC<br>TGTACATCTATGGCGGCTCTCAGGGCAATCTGATCTTTGGCAAGGGCACCAAGCTGAGCGTGAAGCCT |
|  | 295 | MACPGFLWALVISTCLEFSMAQTVTQSQPEMSVQEAETVTLSCTYDTSESDYYLFWYKQPPSRQMILV<br>IRQEAYKQQNATENRFSVNFQKAAKSFSLKISDSQLGDAAMYFCALYIYGGSQGNLIFGKGTKLSVKP |
| RAS TCR-13 beta chain variable domain | 296 | ATGGGCACCAGCCTCCTCTGCTGGATGGCCCTGTGTCTCCTGGGGGCAGATCACGCAGATACTGGAGT<br>CTCCCAGGACCCCAGACACAAGATCACAAAGAGGGGACAGAATGTAACTTTCAGGTGTGATCCAATTT<br>CTGAACACAACCGCCTTTATTGGTACCGACAGACCCTGGGCAGGGCCCAGAGTTTCTGACTTACTTC<br>CAGAATGAAGCTCAACTAGAAAAATCAAGGCTGCTCAGTGATCGGTTCTCTGCAGAGAGGCCTAAGGG<br>ATCTTTCTCCACCTTGGAGATCCAGCGCACAGAGCAGGGGACTCGGCCATGTATCTCTGTGCCAGCA<br>GCTCCACCGACAGGATTGAAGCTTTCTTTGGACAAGGCACCAGACTCACAGTTGTA |
|  | 297 | ATGGGCACCTCCCTGCTGTGCTGGATGGCACTGTGCCTGCTGGGAGCAGACCACGCAGATACAGGCGT<br>GTCTCAGGACCCACGCCACAAGATCACCAAGCGGGGCCAGAACGTGACATTCAGATGCGATCCCATCT<br>CCGAGCACAATAGGCTGTACTGGTATAGGCAGACCCTGGGACAGGGACCAGAGTTCCTGACATACTTT<br>CAGAACGAGGCCCAGCTGGAGAAGAGCCGGCTGCTGTCCGACAGATTCTCTGCCGAGAGGCCCAAGGG<br>CTCTTTTTAGCACCCTGGAGATCCAGAGAACAGAGCAGGGCGACAGCGCCATGTATCTGTGCGCCAGCT<br>CCTCTACCGATAGGATCGAGGCCTTCTTTGGCCAGGGCACCCGCCTGACAGTGGTG |
|  | 298 | MGTSLLCWMALCLLGADHADTGVSQDPRHKITKRGQNVTFRCDPISEHNRLYWYRQTLGQGPEFLTYF<br>QNEAQLEKSRLLSDRFSAERPKGSFSTLEIQRTEQGDSAMYLCASSSTDRIEAFFGQGTRLTVV |

TABLE 2-continued

SEQUENCES

| Name | SEQ ID NO | Sequence |
|---|---|---|
| RAS TCR-13 alpha chain | 299 | MACPGFLWALVISTCLEFSMAQTVTQSQPEMSVQEAETVTLSCTYDTSESDYYLFWYKQPPSRQMILV IRQEAYKQQNATENRFSVNFQKAAKSFSLKISDSQLGDAAMYFCALYIYGGSQGNLIFGKGTKLSVKP DIQNPEPAVYQLKDPRSQDSTLCLFTDFDSQINVPKTMESGTFITDKTVLDMKAMDSKSNGAIAWSNQ TSFTCQDIFKETNATYPSSDVPCDATLTEKSFETDMNLNFQNLSVMGLRILLLKVAGFNLLMTLRLWS S |
| RAS TCR-13 beta chain | 300 | MGTSLLCWMALCLLGADHADTGVSQDPRHKITKRGQNVTFRCDPISEHNRLYWYRQTLGQGPEFLTYF QNEAQLEKSRLLSDRFSAERPKGSFSTLEIQRTEQGDSAMYLCASSSTDRIEAFFGQGTRLTVVKDLR NVTPPKVSLFEPSKAEIANKQKATLVCLARGFFPDHVELSWWVNGKEVHSGVSTDPQAYKESNYSYCL SSRLRVSATFWHNPRNHFRCQVQFHGLSEEDKWPEGSPKPVTQNISAEAWGRADCGITSASYHQGVLS ATILYEILLGKATLYAVLVSGLVLMAMVKKKNS |
| TCR Peptides | 301 | VVGADGVGK |
|  | 302 | VVVGADGVGK |
| RAS TCR-14 alpha chain CDR1 | 303 | VSNAYN |
| RAS TCR-14 alpha chain CDR2 | 304 | GSKP |
| RAS TCR-14 alpha chain CDR3 | 305 | ATYNFNKFY |
| RAS TCR-14 beta chain CDR1 | 306 | SGHTS |
| RAS TCR-14 beta chain CDR2 | 307 | YDEGEE |
| RAS TCR-14 beta chain CDR3 | 308 | ASTTFKTGRAIEKLF |
| RAS TCR-14 alpha chain variable domain | 309 | ATGGCTTTGCAGAGCACTCTGGGGGCGGTGTGGCTAGGGCTTCTCCTCAACTCTCTCTGGAAGGTTGC AGAAAAGCAAGGACCAAGTGTTTCAGCCTTCCACAGTGGCATCTTCAGAGGGAGCTGTGGTGGAAATCT TCTGTAATCACTCTGTGTCCAATGCTTACAACTTCTTCTGGTACCTTCACTTCCCGGGATGTGCACCA AGACTCCTTGTTAAAGGCTCAAAGCCTTCTCAGCAGGGACGATACAACATGACCTATGAACGGTTCTC TTCATCGCTGCTCATCCTCCAGGTGCGGGAGGCAGATGCTGCTGTTTACTACTGTGCTACGTACAACT TCAACAAATTTTACTTTGGATCTGGGACCAAACTCAATGTAAAACCA |
|  | 310 | ATGGCCCTGCAGTCTACACTGGGAGCCGTGTGGCTGGGACTGCTGCTGAACTCTCTGTGGAAGGTGGC CGAGAGCAAGGACCAGGTGTTCCAGCCTAGCACCGTGGCCTCCTCTGAGGGAGCAGTGGTGGAGATCT TTTGCAATCACTCCGTGTCTAACGCCTACAATTTCTTTTGGTATCTGCACTTTCCAGGATGTGCACCA AGGCTGCTGGTGAAGGGCAGCAAGCCATCCCAGCAGGGCCGGTACAACATGACCTATGAGAGATTCAG CTCCTCTCTGCTGATCCTGCAGGTGAGAGAGGCCGATGCCGCCGTGTACTATTGTGCCACCTACAACT TTAATAAGTTCTATTTTGGCTCCGGCACAAAGCTGAATGTGAAGCCT |
|  | 311 | MALQSTLGAVWLGLLLNSLWKVAESKDQVFQPSTVASSEGAVVEIFCNHSVSNAYNFFWYLHFPGCAP RLLVKGSKPSQQGRYNMTYERFSSSLLILQVREADAAVYYCATYNFNKFYFGSGTKLNVKP |
| RAS TCR-14 beta chain variable domain | 312 | ATGGGACCCAGGCTCCTCTTCTGGGCACTGCTTTGTCTCCTCGGAACAGGCCCAGTGGAGGCTGGAGT CACACAAAGTCCCACACACCTGATCAAAACGAGAGGACAGCAAGCGACTCTGAGATGCTCTCCTATCT CTGGGCACACCAGTGTGTACTGGTACCAACAGGCCCTGGGTCTGGGCCTCCAGTTCCTCCTTTGGTAT GACGAGGGTGAAGAGAGAAACAGAGGAAACTTCCCTCCTAGATTTTCAGGTCGCCAGTTCCCTAATTA TAGCTCTGAGCTGAATGTGAACGCCTTGGAGCTGGAGGACTCGGCCCTGTATCTCTGTGCCAGCACCA CTTTTAAGACGGGACGGGCAATTGAAAAACTGTTTTTTGGCAGTGGAACCCAGCTCTCTGTCTTG |
|  | 313 | ATGGGACCAAGGCTGCTGTTCTGGGCACTGCTGTGCCTGCTGGGAACCGGACCTGTGGAGGCCGGCGT GACCCAGTCTCCAACACACCTGATCAAGACCAGGGGACAGCAGGCCACACTGAGGTGTAGCCCCATCT CCGGCCACACAAGCGTGTACTGGTATCAGCAGGCCCTGGGACTGGGACTGCAGTTCCTGCTGTGGTAC GACGAGGGCGAGGAGAGGAACCGCGGCAATTTCCCACCTCGGTTCAGCGGCCGGCAGTTTCCCAACTA CAGCTCCGAGCTGAACGTGAATGCCCTGGAGCTGGAGGACAGCGCCCTGTATCTGTGCGCCTCCACCA CATTCAAGACCGGCAGGGCCATCGAGAAGCTGTTCTTTGGCTCTGGCACCCAGCTGAGCGTGCTG |
|  | 314 | MGPRLLFWALLCLLGTGPVEAGVTQSPTHLIKTRGQQATLRCSPISGHTSVYWYQQALGLGLQFLLWY DEGEERNRGNFPPRFSGRQFPNYSSELNVNALELEDSALYLCASTTFKTGRAIEKLFFGSGTQLSVL |

TABLE 2-continued

SEQUENCES

| Name | SEQ ID NO | Sequence |
|---|---|---|
| RAS TCR-14 alpha chain | 315 | MALQSTLGAVWLGLLLNSLWKVAESKDQVFQPSTVASSEGAVVEIFCNHSVSNAYNFFWYLHFPGCAP RLLVKGSKPSQQGRYNMTYERFSSSLLILQVREADAAVYYCATYNFNKFYFGSGTKLNVKPDIQNPEP AVYQLKDPRSQDSTLCLFTDFDSQINVPKTMESGTFITDKTVLDMKAMDSKSNGAIAWSNQTSFTCQD IFKETNATYPSSDVPCDATLTEKSFETDMNLNFQNLSVMGLRILLLKVAGFNLLMTLRLWSS |
| RAS TCR-14 beta chain | 316 | MGPRLLFWALLCLLGTGPVEAGVTQSPTHLIKTRGQQATLRCSPISGHTSVYWYQQALGLGLQFLLWY DEGEERNRGNFPPRFSGRQFPNYSSELNVNALELEDSALYLCASTTFKTGRAIEKLFFGSGTQLSVLK DLRNVTPPKVSLFEPSKAEIANKQKATLVCLARGFFPDHVELSWWVNGKEVHSGVSTDPQAYKESNYS YCLSSRLRVSATFWHNPRNHFRCQVQFHGLSEEDKWPEGSPKPVTQNISAEAWGRADCGITSASYHQG VLSATILYEILLGKATLYAVLVSGLVLMAMVKKKNS |
| TCR peptide | 317 | VVGADGVGK |
|  | 318 | VVVGADGVGK |
| RAS TCR-15 alpha chain CDR1 | 319 | TSGFNG |
| RAS TCR-15 alpha chain CDR2 | 320 | NVLDGL |
| RAS TCR-15 alpha chain CDR3 | 321 | AVRDRGGSYIPT |
| RAS TCR-15 beta chain CDR1 | 322 | MNHEY |
| RAS TCR-15 beta chain CDR2 | 323 | SMNVEV |
| RAS TCR-15 beta chain CDR3 | 324 | ASSSRGHSGTEAF |
| RAS TCR-15 alpha chain variable domain | 325 | ATGTGGGGAGTTTTCCTTCTTTATGTTTCCATGAAGATGGGAGGCACTACAGGACAAAACATTGACCA GCCCACTGAGATGACAGCTACGGAAGGTGCCATTGTCCAGATCAACTGCTACGTACCAGACATCTGGGT TCAACGGGCTGTTCTGGTACCAGCAACATGCTGGCGAAGCACCCACATTTCTGTCTTACAATGTTCTG GATGGTTTGGAGGAGAAAGGTCGTTTTTCTTCATTCCTTAGTCGGTCTAAAGGGTACAGTTACCTCCT TTTGAAGGAGCTCCAGATGAAAGACTCTGCCTCTTACCTCTGTGCTGTGAGAGATCGAGGAGGAAGCT ACATACCTACATTTGGAAGAGGAACCAGCCTTATTGTTCATCCG |
|  | 326 | ATGTGGGGCGTGTTTCTGCTGTACGTGTCTATGAAGATGGGCGGCACCACAGGCCAGAACATCGACCA GCCTACCGAGATGACCGCCACAGAGGGCGCCATCGTGCAGATCAACTGCACCTACCAGACATCTGGCT TCAATGGCCTGTTTTGGTATCAGCAGCACGCCGGCGAGGCCCCAACATTCCTGTCCTATAATGTGCTG GATGGCCTGGAGGAGAAGGGCAGGTTCTCTAGCTTTCTGTCCCGCTCTAAGGGCTACAGCTATCTGCT GCTGAAGGAGCTGCAGATGAAGGACAGCGCCTCCTACCTGTGCGCCGTGCGGGATAGAGGAGGCTCCT ATATCCCTACCTTTGGCCGGGGCACATCTCTGATCGTGCACCCA |
|  | 327 | MWGVFLLYVSMKMGGTTGQNIDQPTEMTATEGAIVQINCTYQTSGFNGLFWYQQHAGEAPTFLSYNVL DGLEEKGRFSSFLSRSKGYSYLLLKELQMKDSASYLCAVRDRGGSYIPTFGRGTSLIVHP |
| RAS TCR-15 beta chain variable domain | 328 | ATGGGCCCCCAGCTCCTTGGCTATGTGGTCCTTTGCCTTCTAGGAGCAGGCCCCCTGGAAGCCCAAGT GACCCAGAACCCAAGATACCTCATCACAGTGACTGGAAAGAAGTTAACAGTGACTTGTTCTCAGAATA TGAACCATGAGTATATGTCCTGGTATCGACAAGACCCAGGGCTGGGCTTAAGGCAGATCTACTATTCA ATGAATGTTGAGGTGACTGATAAGGGAGATGTTCCTGAAGGGTACAAAGTCTCTCGAAAAGAGAAGAG GAATTTCCCCCTGATCCTGGAGTCGCCCAGCCCCAACCAGACCTCTCTGTACTTCTGTGCCAGCAGTT CCAGGGGGCATTCGGGCACTGAAGCTTTCTTTGGACAAGGCACCAGACTCACAGTTGTA |
|  | 329 | ATGGGACCACAGCTGCTGGGATACGTGGTGCTGTGCCTGCTGGGAGCAGGACCACTGGAGGCACAGGT GACCCAGAACCCACGGTATCTGATCACCGTGACAGGCAAGAAGCTGACCGTGACATGTTCTCAGAACA TGAATCACGAGTACATGAGCTGGTATAGGCAGGACCCTGGACTGGGACTGAGACAGATCTACTATAGC ATGAATGTGGAGGTGACCGACAAGGGCGATGTGCCCGAGGGCTACAAGGTGTCCAGGAAGGAGAAGCG CAACTTCCCTCTGATCCTGGAGTCCCCATCTCCCAATCAGACCAGCCTGTATTTTTGCGCCAGCTCCT CTAGGGGACACTCCGGAACAGAGGCCTTCTTTGGCCAGGGCACCAGGCTGACAGTGGTG |
|  | 330 | MGPQLLGYVVLCLLGAGPLEAQVTQNPRYLITVTGKKLTVTCSQNMNHEYMSWYRQDPGLGLRQTYYS MNVEVTDKGDVPEGYKVSRKEKRNFPLILESPSPNQTSLYFCASSSRGHSGTEAFFGQGTRLTVV |

TABLE 2-continued

SEQUENCES

| Name | SEQ ID NO | Sequence |
|---|---|---|
| RAS TCR-15 alpha chain | 331 | MWGVFLLYVSMKMGGTTGQNIDQPTEMTATEGAIVQINCTYQTSGFNGLFWYQQHAGEAPTFLSYNVL DGLEEKGRFSSFLSRSKGYSYLLLKELQMKDSASYLCAVRDRGGSYIPTFGRGTSLIVHPDIQNPEPA VYQLKDPRSQDSTLCLFTDFDSQINVPKTMESGTFITDKTVLDMKAMDSKSNGAIAWSNQTSFTCQDI FKETNATYPSSDVPCDATLTEKSFETDMNLNFQNLSVMGLRILLLKVAGFNLLMTLRLWSS |
| RAS TCR-15 beta chain | 332 | MGPQLLGYVVLCLLGAGPLEAQVTQNPRYLITVTGKKLTVTCSQNMNHEYMSWYRQDPGLGLRQTYYS MNVEVTDKGDVPEGYKVSRKEKRNFPLILESPSPNQTSLYFCASSSRGHSGTEAFFGQGTRLTVVKDL RNVTPPKVSLFEPSKAEIANKQKATLVCLARGFFPDHVELSWWVNGKEVHSGVSTDPQAYKESNYSYC LSSRLRVSATFWHNPRNHFRCQVQFHGLSEEDKWPEGSPKPVTQNISAEAWGRADCGITSASYHQGVL SATILYEILLGKATLYAVLVSGLVLMAMVKKKNS |
| TCR Peptides | 333 | VVGADGVGK |
|  | 334 | VVVGADGVGK |
| RAS TCR-16 alpha chain CDR1 | 335 | TSINN |
| RAS TCR-16 alpha chain CDR2 | 336 | IRSNERE |
| RAS TCR-16 alpha chain CDR3 | 337 | AGLYSSASKII |
| RAS TCR-16 beta chain CDR1 | 338 | MNHEY |
| RAS TCR-16 beta chain CDR2 | 339 | SMNVEV |
| RAS TCR-16 beta chain CDR3 | 340 | ASSSRGHSGTEAF |
| RAS TCR-16 alpha chain variable domain | 341 | ATGGAAACTCTCCTGGGAGTGTCTTTGGTGATTCTATGGCTTCAACTGGCTAGGGTGAACAGTCAACA GGGAGAAGAGGATCCTCAGGCCTTGAGCATCCAGGAGGGTGAAAATGCCACCATGAACTGCAGTTACA AAACTAGTATAAACAATTTACAGTGGTATAGACAAAATTCAGGTAGAGGCCTTGTCCACCTAATTTTA ATACGTTCAAATGAAAGAGAGAAACACAGTGGAAGATTAAGAGTCACGCTTGACACTTCCAAGAAAAG CAGTTCCTTGTTGATCACGGCTTCCCGGGCAGCAGACACTGCTTCTTACTTCTGTGCTGGGCTGTACA GCAGTGCTTCCAAGATAATCTTTGGATCAGGGACCAGACTCAGCATCCGGCCA |
|  | 342 | ATGGAGACACTGCTGGGCGTGTCCCTGGTCATCCTGTGGCTGCAGCTGGCCAGAGTGAACAGCCAGCA GGGAGAGGAGGACCCTCAGGCCCTGAGCATCCAGGAGGGCGAGAACGCCACCATGAATTGCTCTTACA AGACAAGCATCAACAATCTGCAGTGGTATAGGCAGAACTCCGGCCGCGGACTGGTGCACCTGATCCTG ATCAGGTCTAATGAGCGCGAGAAGCACAGCGGCCGGCTGAGAGTGACCCTGGACACAAGCAAGAAGTC TAGCTCCCTGCTGATCACCGCCTCCAGAGCAGCAGATACAGCCTCTTACTTCTGTGCCGGCCTGTATT CTAGCGCCTCCAAGATCATCTTTGGCAGCGGCACCCGGCTGTCCATCAGACCC |
|  | 343 | METLLGVSLVILWLQLARVNSQQGEEDPQALSIQEGENATMNCSYKTSINNLQWYRQNSGRGLVHLIL IRSNEREKHSGRLRVTLDTSKKSSSLLITASRAADTASYFCAGLYSSASKIIFGSGTRLSIRP |
| RAS TCR-16 beta chain variable domain | 344 | ATGGGCCCCCAGCTCCTTGGCTATGTGGTCCTTTGCCTTCTAGGAGCAGGCCCCCTGGAAGCCCAAGT GACCCAGAACCCAAGATACCTCATCACAGTGACTGGAAAGAAGTTAACAGTGACTTGTTCTCAGAATA TGAACCATGAGTATATGTCCTGGTATCGACAAGACCCAGGGCTGGGCTTAAGGCAGATCTACTATTCA ATGAATGTTGAGGTGACTGATAAGGGAGATGTTCCTGAAGGGTACAAAGTCTCTCGAAAAGAGAAGAG GAATTTCCCCCTGATCCTGGAGTCGCCCAGCCCCAACCAGACCTCTCTGTACTTCTGTGCCAGCAGTT CCAGGGGGCATTCGGGCACTGAAGCTTTCTTTGGACAAGGCACCAGACTCACAGTTGTA |
|  | 345 | ATGGGCCCACAGCTGCTGGGCTACGTGGTGCTGTGCCTGCTGGGAGCAGGACCACTGGAGGCACAGGT GACCCAGAACCCCAGGTATCTGATCACCGTGACAGGCAAGAAGCTGACCGTGACATGTAGCCAGAACA TGAATCACGAGTACATGTCCTGGTATAGGCAGGACCCCGGACTGGGACTGAGACAGATCTACTATTCC ATGAATGTGGAGGTGACCGACAAGGGCGATGTGCCTGAGGGCTACAAGGTGTCTAGGAAGGAGAAGCG CAACTTCCCCACTGATCCTGGAGTCCCCATCTCCCAATCAGACCTCCCTGTATTTTTGCGCCAGCTCCT CTAGGGGCCACTCTGGCACAGAGGCCTTCTTTGGCCAGGGCACCAGGCTGACAGTGGTG |
|  | 346 | MGPQLLGYVVLCLLGAGPLEAQVTQNPRYLITVTGKKLTVTCSQNMNHEYMSWYRQDPGLGLRQTYYS MNVEVTDKGDVPEGYKVSRKEKRNFPLILESPSPNQTSLYFCASSSRGHSGTEAFFGQGTRLTVV |

TABLE 2-continued

SEQUENCES

| Name | SEQ ID NO | Sequence |
|---|---|---|
| RAS TCR-16 alpha chain | 347 | METLLGVSLVILWLQLARVNSQQGEEDPQALSIQEGENATMNCSYKTSINNLQWYRQNSGRGLVHLIL<br>IRSNEREKHSGRLRVTLDTSKKSSSLLITASRAADTASYFCAGLYSSASKIIFGSGTRLSIRPDIQNP<br>EPAVYQLKDPRSQDSTLCLFTDFDSQINVPKTMESGTFITDKTVLDMKAMDSKSNGAIAWSNQTSFTC<br>QDIFKETNATYPSSDVPCDATLTEKSFETDMNLNFQNLSVMGLRILLLKVAGFNLLMTLRLWSS |
| RAS TCR-16 beta chain | 348 | MGPQLLGYVVLCLLGAGPLEAQVTQNPRYLITVTGKKLTVTCSQNMNHEYMSWYRQDPGLGLRQTYYS<br>MNVEVTDKGDVPEGYKVSRKEKRNFPLILESPSPNQTSLYFCASSSRGHSGTEAFFGQGTRLTVVKDL<br>RNVTPPKVSLFEPSKAEIANKQKATLVCLARGFFPDHVELSWWVNGKEVHSGVSTDPQAYKESNYSYC<br>LSSRLRVSATFWHNPRNHFRCQVQFHGLSEEDKWPEGSPKPVTQNISAEAWGRADCGITSASYHQGVL<br>SATILYEILLGKATLYAVLVSGLVLMAMVKKKNS |
| TCR Peptides | 349 | VVGADGVGK |
|  | 350 | VVVGADGVGK |
| RAS TCR-17 alpha chain CDR1 | 351 | NIATNDY |
| RAS TCR-17 alpha chain CDR2 | 352 | GYKTK |
| RAS TCR-17 alpha chain CDR3 | 353 | LANTGGFKTI |
| RAS TCR-17 beta chain CDR1 | 354 | SGHVS |
| RAS TCR-17 beta chain CDR2 | 355 | FQNEAQ |
| RAS TCR-17 beta chain CDR3 | 356 | ATYKVGDEQF |
| RAS TCR-17 alpha chain variable domains | 357 | ATGAGGCAAGTGGCGAGAGTGATCGTGTTCCTGACCCTGAGTACTTTGAGCCTTGCTAAGACCACCCA<br>GCCCATCTCCATGGACTCATATGAAGGACAAGAAGTGAACATAACCTGTAGCCACAACAACATTGCTA<br>CAAATGATTATATCACGTGGTACCAACAGTTTCCCAGCCAAGGACCACGATTTATTATTCAAGGATAC<br>AAGACAAAAGTTACAAACGAAGTGGCCTCCCTGTTTATCCCTGCCGACAGAAAGTCCAGCACTCTGAG<br>CCTGCCCCGGGTTTCCCTGAGCGACACTGCTGTGTACTACTGCCTCGCTAATACTGGAGGCTTCAAAA<br>CTATCTTTGGAGCAGGAACAAGACTATTTGTTAAAGCA |
|  | 358 | ATGAGGCAGGTGGCACGCGTGATCGTGTTTCTGACCCTGAGCACACTGTCCCTGGCCAAGACCACACA<br>GCCTATCTCTATGGACAGCTACGAGGGCCAGGAGGTGAACATCACCTGCTCTCACAACAATATCGCCA<br>CCAATGATTACATCACATGGTATCAGCAGTTCCCCAGCCAGGGCCCTCGGTTTATCATCCAGGGCTAT<br>AAGACCAAGGTGACAAACGAGGTGGCCAGCCTGTTCATCCCTGCCGACAGGAAGTCTAGCACCCTGTC<br>CCTGCCACGCGTGAGCCTGTCCGATACAGCCGTGTACTATTGTCTGGCCAATACCGGCGGCTTCAAGA<br>CAATCTTTGGCGCCGGCACCAGACTGTTTGTGAAGGCC |
|  | 359 | MRQVARVIVFLTLSTLSLAKTTQPISMDSYEGQEVNITCSHNNIATNDYITWYQQFPSQGPRFIIQGY<br>KTKVTNEVASLFIPADRKSSTLSLPRVSLSDTAVYYCLANTGGFKTIFGAGTRLFVKA |
| RAS TCR-17 beta chain variable domains | 360 | ATGGGCACCAGGCTCCTCTGCTGGGTGGTCCTGGGTTTCCTAGGGACAGATCACACAGGTGCTGGAGT<br>CTCCCAGTCCCCTAGGTACAAAGTCGCAAAGAGAGGACAGGATGTAGCTCTCAGGTGTGATCCAATTT<br>CGGGTCATGTATCCCTTTTTTGGTACCAACAGGCCCTGGGGCAGGGGCCAGAGTTTCTGACTTATTTC<br>CAGAATGAAGCTCAACTAGACAAATCGGGGCTGCCCAGTGATCGCTTCTTTGCAGAAAGGCCTGAGGG<br>ATCCGTCTCCACTCTGAAGATCCAGCGCACACAGCAGGAGGACTCCGCCGTGTATCTCTGTGCCACCT<br>ATAAGGTCGGGGATGAGCAGTTCTTCGGGCAGGGACACGGCTCACCGTGCTA |
|  | 361 | ATGGGAACCAGGCTGCTGTGCTGGGTGGTGCTGGGCTTCCTGGGAACCGACCACACAGGAGCAGGCGT<br>GTCCCAGTCTCCAAGGTACAAGGTGGCAAAGAGGGGACAGGACGTGGCCCTGAGATGTGATCCTATCT<br>CCGGCCACGTGTCTCTGTTTTGGTACCAGCAGCCCTGGGACAGGGACCTGAGTTCCTGACCTATTTT<br>CAGAACGAGGCACAGCTGGACAAGAGCGGACTGCCATCCGATCGGTTCTTTGCAGAGAGACCAGAGGG<br>CAGCGTGTCCACCCTGAAGATCCAGAGGACACAGCAGGAGGACTCCGCCGTGTACCTGTGCGCCACAT<br>ATAAAGTGGGCGATGAGCAGTTCTTTGGCCCAGGCACCCGGCTGACAGTGCTG |
|  | 362 | MGTRLLCWVVLGFLGTDHTGAGVSQSPRYKVAKRGQDVALRCDPISGHVSLFWYQQALGQGPEFLTYF<br>QNEAQLDKSGLPSDRFFAERPEGSVSTLKIQRTQQEDSAVYLCATYKVGDEQFFGPGTRLTVL |
| RAS TCR-17 alpha chain | 363 | MRQVARVIVFLTLSTLSLAKTTQPISMDSYEGQEVNITCSHNNIATNDYITWYQQFPSQGPRFIIQGY<br>KTKVTNEVASLFIPADRKSSTLSLPRVSLSDTAVYYCLANTGGFKTIFGAGTRLFVKADIQNPEPAVY |

TABLE 2-continued

SEQUENCES

| Name | SEQ ID NO | Sequence |
|---|---|---|
| | | QLKDPRSQDSTLCLFTDFDSQINVPKTMESGTFITDKTVLDMKAMDSKSNGAIAWSNQTSFTCQDIFK ETNATYPSSDVPCDATLTEKSFETDMNLNFQNLSVMGLRILLLKVAGFNLLMTLRLWSS |
| RAS TCR-17 beta chain | 364 | MGTRLLCWVVLGFLGTDHTGAGVSQSPRYKVAKRGQDVALRCDPISGHVSLFWYQQALGQGPEFLTYF QNEAQLDKSGLPSDRFFAERPEGSVSTLKIQRTQQEDSAVYLCATYKVGDEQFFGPGTRLTVLKDLRN VTPPKVSLFEPSKAEIANKQKATLVCLARGFFPDHVELSWWVNGKEVHSGVSTDPQAYKESNYSYCLS SRLRVSATFWHNPRNHFRCQVQFHGLSEEDKWPEGSPKPVTQNISAEAWGRADCGITSASYHQGVLSA TILYEILLGKATLYAVLVSGLVLMAMVKKKNS |
| TCR Peptides | 365 | VVGADGVGK |
| | 366 | VVVGADGVGK |
| RAS TCR-18 alpha chain CDR1 | 367 | DSASNY |
| RAS TCR-18 alpha chain CDR2 | 368 | IRSNVGE |
| RAS TCR-18 alpha chain CDR3 | 369 | AETGFQKLV |
| RAS TCR-18 beta chain CDR1 | 370 | MDHEN |
| RAS TCR-18 beta chain CDR2 | 371 | SYDVKM |
| RAS TCR-18 beta chain CDR3 | 372 | ASSDWLAGAKDEQY |
| RAS TCR-18 alpha chain variable domains | 373 | ATGACATCCATTCGAGCTGTATTTATATTCCTGTGGCTGCAGCTGGACTTGGTGAATGGAGAGAATGT GGAGCAGCATCCTTCAACCCTGAGTGTCCAGGAGGGAGACAGCGCTGTTATCAAGTGTACTTATTCAG ACAGTGCCCTCAAACTACTTTCCCTTGGTATAAGCAAGAACTTGGAAAAAGACCTCAGCTTATTATAGAC ATTCGTTCAAATGTGGGCGAAAAGAAAGACCAACGAATTGCTGTTACATTGAACAAGACAGCCAAACA TTTCTCCCTGCACATCACAGAGACCCAACCTGAAGACTCGGCTGTCTACTTCTGTGCAGAAACAGGCT TTCAGAAACTTGTATTTGGAACTGGCACCCGACTTCTGGTCAGTCCA |
| | 374 | ATGACATCTATCCGCGCCGTGTTCATCTTTCTGTGGCTGCAGCTGGACCTGGTGAACGGCGAGAATGT GGAGCAGCACCCAAGCACCCTGTCCGTGCAGGAGGGCGACAGCGCCGTGATCAAGTGCACATACTCTG ATAGCGCCTCCAACTACTTTCCCTGGTATAAGCAGGAGCTGGGCAAGCGGCCTCAGCTGATCATCGAC ATCAGATCCAACGTGGGCGAGAAGAAGGATCAGCGGATCGCCGTGACCCTGAATAAGACAGCCAAGCA CTTCAGCCTGCACATCACCGAGACACACCCGAGGATTCCGCCGTGTATTTTTGTGCCGAGACCGGCT TCCAGAAGCTGGTGTTTGGCACCGGCACAAGACTGCTGGTGTCCCCT |
| | 375 | MTSIRAVFIFLWLQLDLVNGENVEQHPSTLSVQEGDSAVIKCTYSDSASNYFPWYKQELGKRPQLIID IRSNVGEKKDQRIAVTLNKTAKHFSLHITETQPEDSAVYFCAETGFQKLVFGTGTRLLVSP |
| RAS TCR-18 beta chain variable domains | 376 | ATGGGAATCAGGCTCCTCTGTCGTGTGGCCTTTTGTTTCCTGGCTGTAGGCCTCGTAGATGTGAAAGT AACCCAGAGCTCGAGATATCTAGTCAAAAGGACGGGAGAGAAAGTTTTTCTGGAATGTGTCCAGGATA TGGACCATGAAAATATGTTCTGGTATCGACAAGACCCAGGTCTGGGGCTACGGCTGATCTATTTCTCA TATGATGTTAAAATGAAAGAAAAAGGAGATATTCCTGAGGGGTACAGTGTCTCTAGAGAGAAGAAGGA GCGCTTCTCCCTGATTCTGGAGTCCGCCAGCACCAACCAGACTATGTACCTCTGTGCCAGCAGTG ACTGGCTAGCGGGAGCGAAGGACGAGCAGTACTTCGGCCGGGCACCAGGCTCACGGTCACA |
| | 377 | ATGGGCATCCGGCTGCTGTGCAGAGTGGCCTTCTGTTTTCTGGCCGTGGGCCTGGTGGACGTGAAGGT GACCCAGAGCTCCCGGTACCTGGTGAAGAGAACAGGCGAGAAGGTGTTCCTGGAGTGCGTGCAGGACA TGGATCACGAGAACATGTTTTGGTATAGGCAGGACCCCGGACTGGGACTGAGACTGATCTACTTCAGC TATGACGTGAAGATGAAGGAGAAGGGCGACATCCCAGAGGGCTACAGCGTGTCCAGGGAGAAGAAGGA GCGGTTCAGCCTGATCCTGGAGTCTGCCAGCACCAATCAGACAAGCATGTACCTGTGCGCCTCTAGCG ACTGGCTGGCCGGAGCAAAGGATGAGCAGTATTTCGGCCCAGGCACCAGGCTGACCGTGACA |
| | 378 | MGIRLLCRVAFCFLAVGLVDVKVTQSSRYLVKRTGEKVFLECVQDMDHENMFWYRQDPGLGLRLIYFS YDVKMKEKGDIPEGYSVSREKKERFSLILESASTNQTSMYLCASSDWLAGAKDEQYFGPGTRLVT |
| RAS TCR-18 alpha chain | 379 | MTSIRAVFIFLWLQLDLVNGENVEQHPSTLSVQEGDSAVIKCTYSDSASNYFPWYKQELGKRPQLIID IRSNVGEKKDQRIAVTLNKTAKHFSLHITETQPEDSAVYFCAETGFQKLVFGTGTRLLVSPDIQNPEP AVYQLKDPRSQDSTLCLFTDFDSQINVPKTMESGTFITDKTVLDMKAMDSKSNGAIAWSNQTSFTCQD IFKETNATYPSSDVPCDATLTEKSFETDMNLNFQNLSVMGLRILLLKVAGFNLLMTLRLWSS |

TABLE 2-continued

SEQUENCES

| Name | SEQ ID NO | Sequence |
|---|---|---|
| RAS TCR-18 beta chain | 380 | MGIRLLCRVAFCFLAVGLVDVKVTQSSRYLVKRTGEKVFLECVQDMDHENMFWYRQDPGLGLRLIYFS<br>YDVKMKEKGDIPEGYSVSREKKERFSLILESASTNQTSMYLCASSDWLAGAKDEQYFGPGTRLTVTKD<br>LRNVTPPKVSLFEPSKAEIANKQKATLVCLARGFFPDHVELSWWVNGKEVHSGVSTDPQAYKESNYSY<br>CLSSRLRVSATFWHNPRNHFRCQVQFHGLSEEDKWPEGSPKPVTQNISAEAWGRADCGITSASYHQGV<br>LSATILYEILLGKATLYAVLVSGLVLMAMVKKKNS |
| TCR peptides | 381 | VVGADGVGK |
|  | 382 | VVVGADGVGK |
| RAS TCR-19 alpha chain CDR1 | 383 | TSINN |
| RAS TCR-19 alpha chain CDR2 | 384 | IRSNERE |
| RAS TCR-19 alpha chain CDR3 | 385 | ATDPLDYKLS |
| RAS TCR-19 beta chain CDR1 | 386 | MNHEY |
| RAS TCR-19 beta chain CDR2 | 387 | SMNVEV |
| RAS TCR-19 beta chain CDR3 | 388 | ASSLVASNEQF |
| RAS TCR-19 alpha chain variable domains | 389 | ATGGAAACTCTCCTGGGAGTGTCTTTGGTGATTCTATGGCTTCAACTGGCTAGGGTGAACAGTCAACA<br>GGGAGAAGAGGATCCTCAGCCTTGAGCATCCAGGAGGGTGAAAATGCCACCATGAACTGCAGTTACA<br>AAACTAGTATAAACAATTTACAGTGGTATAGACAAAATTCAGGTAGAGGCCTTGTCCACCTAATTTTA<br>ATACGTTCAAATGAAAGAGAGAAACACAGTGGAAGATTAAGAGTCACGCTTGACACTTCCAAGAAAG<br>CAGTTCCTTGTTGATCACGGCTTCCCGGGCAGCAGACACTGCTTCTTACTTCTGTGCTACGGACCCCT<br>TAGACTACAAGCTCAGCTTTGGAGCCGGAACCACAGTAACTGTAAGAGCA |
|  | 390 | ATGGAGACCCTGCTGGGCGTGTCTCTGGTCATCCTGTGGCTGCAGCTGGCCAGAGTGAACTCTCAGCA<br>GGGGAGAGGAGGACCCTCAGGCCCTGAGCATCCAGGAGGGCGAGAACGCCACCATGAATTGCTCTTACA<br>AGACAAGCATCAACAATCTGCAGTGGTATCGGCAACCTGCCGGCAGGGCTGGTGCACCTGATCCTG<br>ATCAGGAGCAATGAGCGCGAGAAGCACTCCGGCCGGCTGAGAGTGACCCTGGACACATCAAGAAGTC<br>CTCTAGCCTGCTGATCACCGCCTCTAGGGCAGCAGATACAGCCAGCTACTTCTGTGCCACCGACCCAC<br>TGGATTATAAGCTGTCCTTTGGCGCCGGCACCACAGTGACCGTGCGCGCC |
|  | 391 | METLLGVSLVILWLQLARVNSQQGEEDPQALSIQEGENATMNCSYKTSINNLQWYRQNSGRGLVHLIL<br>IRSNEREKHSGRLRVTLDTSKKSSSLLITASRAADTASYFCATDPLDYKLSFGAGTTVTVRA |
| RAS TCR-19 beta chain variable domains | 392 | ATGGGCCCCCAGCTCCTTGGCTATGTGGTCCTTTGCCTTCTAGGAGCAGGCCCCCTGGAAGCCCAAGT<br>GACCCAGAACCCAAGATACCTCATCACAGTGACTGGAAAGAAGTTAACAGTGACTTGTTCTCAGAATA<br>TGAACCATGAGTATATGTCCTGGTATCGACAAGACCCAGGGCTGGGCTTAAGGCAGATCTACTATTCA<br>ATGAATGTTGAGGTGACTGATAAGGGAGATGTTCCTGAAGGGTACAAAGTCTCTCGAAAAGAGAAGAG<br>GAATTTCCCCCTGATCCTGGAGTCGCCCAGCCCCAACCAGACCTCTCTGTACTTCTGTGCCAGCAGTT<br>TGGTGGCTAGCAATGAGCAGTTCTTCGGGCAGGGACACGGCTCACCGTGCTA |
|  | 393 | ATGGGCCCACAGCTGCTGGGCTACGTGGTGCTGTGCCTGCTGGGAGCAGGACCACTGGAGGCACAGGT<br>GACCCAGAATCCCCGGTATCTGATCACCGTGACAGGCAAGAAGCTGACCGTGACATGTTCCCAGAACA<br>TGAATCACGAGTACATGTCTTGGTATAGGCAGGACCCCGGACTGGGACTGAGGCAGATCTACTATTCT<br>ATGAACGTGGAGGTGACAGACAAGGGCGATGTGCCTGAGGGCTACAAGGTGAGCAGGAAGGAGAAGCG<br>CAACTTCCCACTGATCCTGGAGTCCCCATCTCCCAATCAGACCAGCCTGTATTTTTGCGCCAGCTCCC<br>TGGTGGCCTCCAACGAGCAGTTCTTTGGCCCTGGCACCCGGCTGACAGTGCTG |
|  | 394 | MGPQLLGYVVLCLLGAGPLEAQVTQNPRYLITVTGKKLTVTCSQNMNHEYMSWYRQDPGLGLRQTYYS<br>MNVEVTDKGDVPEGYKVSRKEKRNFPLILESPSPNQTSLYFCASSLVASNEQFFGPGTRLTVL |
| RAS TCR-19 alpha chain | 395 | METLLGVSLVILWLQLARVNSQQGEEDPQALSIQEGENATMNCSYKTSINNLQWYRQNSGRGLVHLIL<br>IRSNEREKHSGRLRVTLDTSKKSSSLLITASRAADTASYFCATDPLDYKLSFGAGTTVTVRADIQNPE<br>PAVYQLKDPRSQDSTLCLFTDFDSQINVPKTMESGTFITDKTVLDMKAMDSKSNGAIAWSNQTSFTCQ<br>DIFKETNATYPSSDVPCDATLTEKSFETDMNLNFQNLSVMGLRILLLKVAGFNLLMTLRLWSS |

TABLE 2-continued

SEQUENCES

| Name | SEQ ID NO | Sequence |
|---|---|---|
| RAS TCR-19 beta chain | 396 | MGPQLLGYVVLCLLGAGPLEAQVTQNPRYLITVTGKKLTVTCSQNMNHEYMSWYRQDPGLGLRQTYYS<br>MNVEVTDKGDVPEGYKVSRKEKRNFPLILESPSPNQTSLYFCASSLVASNEQFFGPGTRLTVLKDLRN<br>VTPPKVSLFEPSKAEIANKQKATLVCLARGFFPDHVELSWWVNGKEVHSGVSTDPQAYKESNYSYCLS<br>SRLRVSATFWHNPRNHFRCQVQPHGLSEEDKWPEGSPKPVTQNISAEAWGRADCGITSASYHQGVLSA<br>TILYEILLGKATLYAVLVSGLVLMAMVKKKNS |
| TCR Peptides | 397 | VVGAVGVGK |
|  | 398 | VVVGAVGVGK |
| RAS TCR-20 alpha chain CDR1 | 399 | TSESDYY |
| RAS TCR-20 alpha chain CDR2 | 400 | QEAYKQQN |
| RAS TCR-20 alpha chain CDR3 | 401 | ACQGGSEKLV |
| RAS TCR-20 beta chain CDR1 | 402 | SGHNT |
| RAS TCR-20 beta chain CDR2 | 403 | YYREEE |
| RAS TCR-20 beta chain CDR3 | 404 | ASSLGLLLYNEQF |
| RAS TCR-20 alpha chain variable domains | 405 | ATGGCATGCCCTGGCTTCCTGTGGGCACTTGTGATCTCCACCTGTCTTGAATTTAGCATGGCTCAGAC<br>AGTCACTCAGTCTCAACCAGAGATGTCTGTGCAGGAGGCAGAGACCGTGACCCTGAGCTGCACATATG<br>ACACCAGTGAGAGTGATTATTATTTATTCTGGTACAAGCAGCCTCCCAGCAGGCAGATGATTCTCGTT<br>ATTCGCCAAGAAGCTTATAAGCAACAGAATGCAACAGAGAATCGTTTCTCTGTGAACTTCCAGAAAGC<br>AGCCAAATCCTTCAGTCTCAAGATCTCAGACTCACAGCTGGGGATGCCGCGATGTATTTCTGTGCTT<br>GTCAGGGCGGATCTGAAAAGCTGGTCTTTGGAAAGGGAACGAAACTGACAGTAAACCCA |
|  | 406 | ATGGCATGCCCAGGCTTCCTGTGGGCACTGGTCATCAGCACCTGTCTGGAGTTTTCTATGGCCCAGAC<br>CGTGACACAGAGCCAGCCAGAGATGTCCGTGCAGGAGGCAGAGACCGTGACACTGTCCTGTACCTACG<br>ACACAAGCGAGTCCGATTACTATCTGTTCTGGTATAAGCAGCCTCCATCTCGCCAGATGATCCTGGTC<br>ATCCGGCAGGAGGCCTACAAGCAGCAGAACGCCACCGAGAATCGGTTCTCTGTGAATTTTCAGAAGGC<br>CGCCAAGTCTTTTAGCCTGAAGATCTCCGACTCTCAGCTGGGCGATGCCGCCATGTATTTCTGCGCAT<br>GTCAGGGAGGCAGCGAGAAGCTGGTGTTTGGCAAGGGCACCAAGCTGACAGTGAACCCT |
|  | 407 | MACPGFLWALVISTCLEFSMAQTVTQSQPEMSVQEAETVTLSCTYDTSESDYYLFWYKQPPSRQMILV<br>IRQEAYKQQNATENRFSVNFQKAAKSFSLKISDSQLGDAAMYFCACQGGSEKLVFGKGTKLTVNP |
| RAS TCR-20 beta chain variable domains | 408 | ATGGGCCCTGGGCTCCTCTGCTGGGTGCTGCTTTGTCTCCTGGGAGCAGGCTCAGTGGAGACTGGAGT<br>CACCCAAAGTCCCACACACCTGATCAAAACGAGAGGACAGCAAGTGACTCTGAGATGCTCTTCTCAGT<br>CTGGGCACAACACTGTGTCCTGGTACCAACAGGCCCTGGGTCAGGGGCCCCAGTTTATCTTTCAGTAT<br>TATAGGGAGGAAGAGAATGGCAGAGGAAACTTCCCTCCTAGATTCTCAGGTCTCCAGTTCCCTAATTA<br>TAGCTCTGAGCTGAATGTGAACGCCTTGGAGCTGGACGACTCGGCCCTGTATCTCTGTGCCAGCAGCT<br>TGGGACTCCTCCTCTACAATGAGCAGTTCTTCGGGCCAGGGACACGGCTCACCGTGCTA |
|  | 409 | ATGGGACCAGGACTGCTGTGCTGGGTGCTGCTGTGCCTGCTGGGAGCAGGCAGCGTGGAGACCGGCGT<br>GACACAGTCCCCTACCCACCTGATCAAGACAAGAGGCCAGCAGGTGACCCTGAGGTGCAGCTCCCAGT<br>CTGGCCACAATACAGTGAGCTGGTACCAGCAGGCCCTGGGACAGGGACCTCAGTTCATCTTTCAGTAC<br>TATAGGGAGGAGGAGAACGGCCGCGGCAATTTCCCCCCTCGGTTTAGCGGCCTGCAGTTCCCAAACTA<br>TTCTAGCGAGCTGAACGTGAATGCCCTGGAGCTGGACGATTCCGCCCTGTACCTGTGCGCCTCCTCTC<br>TGGGCCTGCTGCTGTATAACGAGCAGTTCTTTGGCCCCGGCACCAGACTGACAGTGCTG |
|  | 410 | MGPGLLCWVLLCLLGAGSVETGVTQSPTHLIKTRGQQVTLRCSSQSGHNTVSWYQQALGQGPQFIFQY<br>YREEENGRGNFPPRFSGLQFPNYSSELNVNALELDDSALYLCASSLGLLLYNEQFFGPGTRLTVL |
| RAS TCR-20 alpha chain | 411 | MACPGFLWALVISTCLEFSMAQTVTQSQPEMSVQEAETVTLSCTYDTSESDYYLFWYKQPPSRQMILV<br>IRQEAYKQQNATENRFSVNFQKAAKSFSLKISDSQLGDAAMYFCACQGGSEKLVFGKGTKLTVNPDIQ<br>NPEPAVYQLKDPRSQDSTLCLFTDFDSQINVPKTMESGTFITDKTVLDMKAMDSKSNGAIAWSNQTSF<br>TCQDIFKETNATYPSSDVPCDATLTEKSFETDMNLNFQNLSVMGLRILLLKVAGFNLLMTLRLWSS |
| RAS TCR-20 beta chain | 412 | MGPGLLCWVLLCLLGAGSVETGVTQSPTHLIKTRGQQVTLRCSSQSGHNTVSWYQQALGQGPQFIFQY<br>YREEENGRGNFPPRFSGLQFPNYSSELNVNALELDDSALYLCASSLGLLLYNEQFFGPGTRLTVLKDL |

TABLE 2-continued

SEQUENCES

| Name | SEQ ID NO | Sequence |
|---|---|---|
| | | RNVTPPKVSLFEPSKAEIANKQKATLVCLARGFFPDHVELSWWVNGKEVHSGVSTDPQAYKESNYSYC LSSRLRVSATFWHNPRNHFRCQVQFHGLSEEDKWPEGSPKPVTQNISAEAWGRADCGITSASYHQGVL SATILYEILLGKATLYAVLVSGLVLMAMVKKKNS |
| TCR Peptides | 413 | VVGAVGVGK |
| | 414 | VVVGAVGVGK |
| RAS TCR-21 alpha chain CDR1 | 415 | TSINN |
| RAS TCR-21 alpha chain CDR2 | 416 | IRSNERE |
| RAS TCR-21 alpha chain CDR3 | 417 | ATDAQTGANNLF |
| RAS TCR-21 beta chain CDR1 | 418 | SGHAT |
| RAS TCR-21 beta chain CDR2 | 419 | FQNNGV |
| RAS TCR-21 beta chain CDR3 | 420 | ASSLGDSYEQYF |
| RAS TCR-21 alpha chain variable domains | 421 | ATGGAAACTCTCCTGGGAGTGTCTTTGGTGATTCTATGGCTTCAACTGGCTAGGGTGAACAGTCAACA GGGAGAAGAGGATCCTCAGGCCTTGAGCATCCAGGAGGGTGAAAATGCCACCATGAACTGCAGTTACA AAACTAGTATAAACAATTTACAGTGGTATAGACAAAATTCAGGTAGAGGCCTTGTCCACCTAATTTTA ATACGTTCAAATGAAAGAGAGAAACACAGTGGAAGATTAAGAGTCACGCTTGACACTTCCAAGAAAAG CAGTTCCTTGTTGATCACGGCTTCCCGGGCAGCAGACACTGCTTCTTACTTCTGTGCTACGGACGCTC AAACTGGGGCAAACAACCTCTTCTTTGGGACTGGAACGAGACTCACCGTTATTCCC |
| | 422 | ATGGAGACACTGCTGGGCGTGTCTCTGGTCATCCTGTGGCTGCAGCTGGCCAGAGTGAATAGCCAGCA GGGAGAGGAGGACCCCCAGGCCCTGTCCATCCAGGAGGGCGAGAACGCCACCATGAATTGCAGCTACA AGACATCCATCAACAATCTGCAGTGGTATCGGCAGAACTCTGGCAGAGGCCTGGTGCACCTGATCCTG ATCCGGTCCAATGAGAGAGAGAAGCACTCTGGCCGGCTGAGAGTGACCCTGGATACATCCAAGAAGTC CTCTAGCCTGCTGATCACCGCCAGCCGGGCAGCAGACACAGCCTCCTATTTTTGTGCCACCGATGCCC AGACAGGCGCCAACAATCTGTTCTTTGGCACCGGCACAAGACTGACCGTGATCCCT |
| | 423 | METLLGVSLVILWLQLARVNSQQGEEDPQALSIQEGENATMNCSYKTSINNLQWYRQNSGRGLVHLIL IRSNEREKHSGRLRVTLDTSKKSSSLLITASRAADTASYFCATDAQTGANNLFFGTGTRLTVIP |
| RAS TCR-21 beta chain variable domains | 424 | ATGGGCACCAGGCTCCTCTGCTGGGCGGCCCTCTGTCTCCTGGGAGCAGAACTCACAGAAGCTGGAGT TGCCCAGTCTCCCAGATATAAGATTATAGAGAAAAGGCAGAGTGTGGCTTTTTGGTGCAATCCTATAT CTGGCCATGCTACCCTTTACTGGTACCAGCAGATCCTGGGACAGGGCCCAAAGCTTCTGATTCAGTTT CAGAATAACGGTGTAGTGGATGATTCACAGTTGCCTAAGGATCGATTTTCTGCAGAGAGGCTCAAAGG AGTAGACTCCACTCTCAAGATCCAGCCTGCAAAGCTTGAGGACTCGGCCGTGTATCTCTGTGCCAGCA GCTTA |
| | 425 | ATGGGCACCAGGCTGCTGTGCTGGGCCGCCCTGTGCCTGCTGGGAGCAGAGCTGACAGAGGCAGGAGT GGCCCAGAGCCCCAGGTACAAGATCATCGAGAAGCGCCAGTCCGTGGCCTTCTGGTGCAACCCTATCT CTGGCCACGCCACCCTGTACTGGTATCAGCAGATCCTGGGCCAGGGCCCAAAGCTGCTGATCCAGTTC CAGAATAATGGCGTGGTGGACGATTCTCAGCTGCCCAAGGACAGGTTTAGCGCCGAGCGCCTGAAGGG CGTGGATTCTACCCTGAAGATCCAGCCAGCAAAGCTGGAGGACAGCGCCGTGTACCTGTGCGCCAGCT CCCTG |
| | 426 | MGTRLLCWAALCLLGAELTEAGVAQSPRYKIIEKRQSVAFWCNPISGHATLYWYQQILGQGPKLLIQF QNNGVVDDSQLPKDRFSAERLKGVDSTLKIQPAKLEDSAVYLCASSL |
| RAS TCR-21 alpha chain | 427 | METLLGVSLVILWLQLARVNSQQGEEDPQALSIQEGENATMNCSYKTSINNLQWYRQNSGRGLVHLIL IRSNEREKHSGRLRVTLDTSKKSSSLLITASRAADTASYFCATDAQTGANNLFFGTGTRLTVIPDIQN PEPAVYQLKDPRSQDSTLCLFTDFDSQINVPKTMESGTFITDKTVLDMKAMDSKSNGAIAWSNQTSFT CQDIFKETNATYPSSDVPCDATLTEKSFETDMNLNFQNLSVMGLRILLLLKVAGFNLLMTLRLWSS |

TABLE 2-continued

SEQUENCES

| Name | SEQ ID NO | Sequence |
|---|---|---|
| RAS TCR-21 beta chain | 428 | MGTRLLCWAALCLLGAELTEAGVAQSPRYKIIEKRQSVAFWCNPISGHATLYWYQQILGQGPKLLIQF QNNGVVDDSQLPKDRFSAERLKGVDSTLKIQPAKLEDSAVYLCASSLKDLRNVTPPKVSLFEPSKAEI ANKQKATLVCLARGFFPDHVELSWWVNGKEVHSGVSTDPQAYKESNYSYCLSSRLRVSATFWHNPRNH FRCQVQFHGLSEEDKWPEGSPKVTQNISAEAWGRADCGITSASYHQGVLSATILYEILLGKATLYAV LVSGLVLMAMVKKKNS |
| TCR Peptides | 429 | VVGAVGVGK |
|  | 430 | VVVGAVGVGK |
| RAS TCR-26 alpha chain CDR1 | 532 | NSMFDY |
| RAS TCR-26 alpha chain CDR2 | 533 | ISSIKDK |
| RAS TCR-26 alpha chain CDR3 | 534 | AANAGGTSYGKLT |
| RAS TCR-26 beta chain CDR1 | 535 | SNHLY |
| RAS TCR-26 beta chain CDR2 | 536 | FYNNEI |
| RAS TCR-26 beta chain CDR3 | 537 | ASSEWGSTGELF |
| RAS TCR-26 alpha chain variable domain | 538 | atggccatgctcctgggggcatcagtgctgattctgtggcttcagccagactgggtaaacagtcaaca gaagaatgatgaccagcaagttaagcaaaattcaccatccctgagcgtccaggaaggaagaatttcta ttctgaactgtgactatactaacagcatgtttgattatttcctatggtacaaaaaatacccctgctgaa ggtcctacattcctgatatctataagttccattaaggataaaaatgaagatggaagattcactgtctt cttaaacaaaagtgccaagcacctctctctgcacattgtgccctcccagcctggagactctgcagtgt acttctgtgcagcaaatgctggtggtactagctatggaaagctgacatttggacaagggaccatcttg actgtccatccaa |
|  | 539 | MAMLLGASVLILWLQPDWVNSQQKNDDQQVKQNSPSLSVQEGRISILNCDYTNSMFDYFLWYKKYPAE GPTFLISISSIKDKNEDGRFTVFLNKSAKHLSLHIVPSQPGDSAVYFCAANAGGTSYGKLTFGQGTIL TVHP |
| RAS TCR-26 beta chain variable domain | 540 | atggatacctggctcgtatgctgggcaattttagtctcttgaaagcaggactcacagaacctgaagt cacccagactcccagccatcaggtcacacagatgggacaggaagtgatcttgcgctgtgtccccatct ctaatcacttatactttctattggtacagacaaattcttggggcagaaagtcgagtttctggtttcctttt tataataatgaaatctcagagaagtctgaaatattcgatgatcaattctcagttgaaaggcctgatgg atcaaatttcactctgaagatccggtccacaaaagctggaggactcagccatgtacttctgtgccagca gtgaatgggaagcaccggggagctgttttttggagaaggctctaggctgaccgtactgg |
|  | 541 | MDTWLVCWAIFSLLKAGLTEPEVTQTPSHQVTQMGQEVILRCVPISNHLYFYWYRQILGQKVEFLVSF YNNEISEKSEIFDDQFSVERPDGSNFTLKIRSTKLEDSAMYFCASSEWGSTGELFFGEGSRLTVL |
| RAS TCR-26 alpha chain | 542 | MAMLLGASVLILWLQPDWVNSQQKNDDQQVKQNSPSLSVQEGRISILNCDYTNSMFDYFLWYKKYPAE GPTFLISISSIKDKNEDGRFTVFLNKSAKHLSLHIVPSQPGDSAVYFCAANAGGTSYGKLTFGQGTIL TVHPDIQNPEPAVYQLKDPRSQDSTLCLFTDFDSQINVPKTMESGTFITDKTVLDMKAMDSKSNGAIA WSNQTSFTCQDIFKETNATYPSSDVPCDATLTEKSFETDMNLNFQNLSVMGLRILLLKVAGFNLLMTL RLWSS |
| RAS TCR-26 beta chain | 543 | MDTWLVCWAIFSLLKAGLTEPEVTQTPSHQVTQMGQEVILRCVPISNHLYFYWYRQILGQKVEFLVSF YNNEISEKSEIFDDQFSVERPDGSNFTLKIRSTKLEDSAMYFCASSEWGSTGELFFGEGSRLTVLKDL RNVTPPKVSLFEPSKAEIANKQKATLVCLARGFFPDHVELSWWVNGKEVHSGVSTDPQAYKESNYSYC LSSRLRVSATFWHNPRNHFRCQVQFHGLSEEDKWPEGSPKVTQNISAEAWGRADCGITSASYHQGVL SATILYEILLGKATLYAVLVSGLVLMAMVKKKNS |
| RAS TCR-26 peptide | 544 | VVGAVGVGK |
| RAS TCR-27 alpha chain CDR1 | 545 | TTSDR |

TABLE 2-continued

SEQUENCES

| Name | SEQ ID NO | Sequence |
|---|---|---|
| RAS TCR-27 alpha chain CDR2 | 546 | LLSNGAV |
| RAS TCR-27 alpha chain CDR3 | 547 | AVDIIGGKST |
| RAS TCR-27 beta chain CDR1 | 548 | SNHLY |
| RAS TCR-27 beta chain CDR2 | 549 | FYNNEI |
| RAS TCR-27 beta chain CDR3 | 550 | ASSEWGSTGELF |
| RAS TCR-27 alpha chain variable domain | 551 | atgaagaagctactagcaatgattctgtggcttcaactagaccggttaagtggagagctgaaagtgga acaaaaccctctgttcctgagcatgcaggagggaaaaaactataccatctactgcaattattcaacca cttcagacagactgtattggtacaggcaggatcctgggaaaagtctgaatctctgtttgtgttgcta tcaaatggagcagtgaagcaggagggacgattaatggcctcacttgataccaaagcccgtctcagcac cctccacatcacagctgccgtgcatgacctctctgccacctacttctgtgccgtggacatcatcggag gcaaatcaaccttgggatggggactacgctcactgtgaagccaa |
| | 552 | MKKLLAMILWLQLDRLSGELKVEQNPLFLSMQEGKNYTIYCNYSTTSDRLYWYRQDPGKSLESLFVLL SNGAVKQEGRLMASLDTKARLSTLHITAAVHDLSATYFCAVDIIGGKSTFGDGTTLTVKP |
| RAS TCR-27 beta chain variable domain | 553 | atggatacctggctcgtatgctgggcaattttagtctcttgaaagcaggactcacagaacctgaagt cacccagactcccagccatcaggtcacacagatgggacaggaagtgatcttgcgctgtgtccccatct ctaatcacttatacttctattggtacagacaaatcttggggcagaaagtcgagtttctggtttcctttt tataataatgaaatctcagagaagtctgaaatattcgatgatcaattctcagttgaaaggcctgatgg atcaaatttcactctgaagatccggtccacaaagctggaggactcagccatgtacttctgtgccagca gtgaatggggaagcaccggggagctgttttttggagaaggctctaggctgaccgtactgg |
| | 554 | MDTWLVCWAIFSLLKAGLTEPEVTQTPSHQVTQMGQEVILRCVPISNHLYFYWYRQILGQKVEFLVSF YNNEISEKSEIFDDQFSVERPDGSNFTLKIRSTKLEDSAMYFCASSEWGSTGELFFGEGSRLTVL |
| RAS TCR-27 alpha chain | 555 | MKKLLAMILWLQLDRLSGELKVEQNPLFLSMQEGKNYTIYCNYSTTSDRLYWYRQDPGKSLESLFVLL SNGAVKQEGRLMASLDTKARLSTLHITAAVHDLSATYFCAVDIIGGKSTFGDGTTLTVKPDIQNPEPA VYQLKDPRSQDSTLCLFTDFDSQINVPKTMESGTFITDKTVLDMKAMDSKSNGAIAWSNQTSFTCQDI FKETNATYPSSDVPCDATLTEKSFETDMNLNFQNLSVMGLRILLLKVAGFNLLMTLRLWSS |
| RAS TCR-27 beta chain | 556 | MDTWLVCWAIFSLLKAGLTEPEVTQTPSHQVTQMGQEVILRCVPISNHLYFYWYRQILGQKVEFLVSF YNNEISEKSEIFDDQFSVERPDGSNFTLKIRSTKLEDSAMYFCASSEWGSTGELFFGEGSRLTVLKDL RNVTPPKVSLFEPSKAEIANKQKATLVCLARGFFPDHVELSWWVNGKEVHSGVSTDPQAYKESNYSYC LSSRLRVSATFWHNPRNHFRCQVFHGLSEEDKWPEGSPKPVTQNISAEAWGRADCGITSASYHQGVL SATILYEILLGKATLYAVLVSGLVLMAMVKKKNS |
| RAS TCR-27 peptide | 557 | VVGAVGVGK |
| RAS TCR-28 alpha chain CDR1 | 558 | NSMFDY |
| RAS TCR-28 alpha chain CDR2 | 559 | ISSIKDK |
| RAS TCR-28 alpha chain CDR3 | 560 | AASAVGQEYGNKLV |
| RAS TCR-28 beta chain CDR1 | 561 | SEHNR |
| RAS TCR-28 beta chain CDR2 | 562 | FQNEAQ |

TABLE 2-continued

SEQUENCES

| Name | SEQ ID NO | Sequence |
| --- | --- | --- |
| RAS TCR-28 beta chain CDR3 | 563 | ASSEYTMGTQY |
| RAS TCR-28 alpha chain variable domain | 564 | atggccatgctcctgggggcatcagtgctgattctgtggcttcagccagactgggtaaacagtcaaca gaagaatgatgaccagcaagttaagcaaaattcaccatccctgagcgtccaggaaggaagaatttcta ttctgaactgtgactatactaacagcatgtttgattatttcctatggtacaaaaaatacctgctgaa ggtcctacattcctgatatctataagttccattaaggataaaaatgaagatggaagattcactgtctt cttaaacaaaagtgccaagcacctctctctgcacattgtgccctcccagcctggagactctgcagtgt acttctgtgcagcaagcgcagtaggtcaggaatatggaaacaagctggtctttggcgcaggaaccatt ctgagagtcaagtcct |
|  | 565 | MAMLLGASVLILWLQPDWVNSQQKNDDQQVKQNSPSLSVQEGRISILNCDYTNSMFDYFLWYKKYPAE GPTFLISISSIKDKNEDGRFTVFLNKSAKHLSLHIVPSQPGDSAVYFCAASAVGQEYGNKLVFGAGTI LRVKS |
| RAS TCR-28 beta chain variable domain | 566 | atgggcaccagcctcctctgctggatggccctgtgtcctgggggcagatcacgcagatactggagt ctcccagaacccagacacaagatcacaaagaggggacagaatgtaactttcaggtgtgatccaattt ctgaacacaaccgcctttattggtaccgacagaccctggggcagggcccagagtttctgacttacttc cagaatgaagctcaactagaaaaatcaaggctgctcagtgatcggttctctgcagagaggcctaaggg atctttctccaccttggagatccagcgcacagagcaggggactcggccatgtatctctgtgccagca gtgaatatactatggggacccagtacttcgggccaggcacgggctcctggtgctcg |
|  | 567 | MGTSLLCWMALCLLGADHADTGVSQNPRHKITKRGQNVTFRCDPISEHNRLYWYRQTLGQGPEFLTYF QNEAQLEKSRLLSDRFSAERPKGSFSTLEIQRTEQGDSAMYLCASSEYTMGTQYFGPGTRLLVL |
| RAS TCR-28 alpha chain | 568 | MAMLLGASVLILWLQPDWVNSQQKNDDQQVKQNSPSLSVQEGRISILNCDYTNSMFDYFLWYKKYPAE GPTFLISISSIKDKNEDGRFTVFLNKSAKHLSLHIVPSQPGDSAVYFCAASAVGQEYGNKLVFGAGTI LRVKSDIQNPEPAVYQLKDPRSQDSTLCLFTDFDSQINVPKTMESGTFITDKTVLDMKAMDSKSNGAI AWSNQTSFTCQDIFKETNATYPSSDVPCDATLTEKSFETDMNLNFQNLSVMGLRILLLKVAGFNLLMT LRLWSS |
| RAS TCR-28 beta chain | 569 | MGTSLLCWMALCLLGADHADTGVSQNPRHKITKRGQNVTFRCDPISEHNRLYWYRQTLGQGPEFLTYF QNEAQLEKSRLLSDRFSAERPKGSFSTLEIQRTEQGDSAMYLCASSEYTMGTQYFGPGTRLLVLKDLR NVTPPKVSLFEPSKAEIANKQKATLVCLARGFFPDHVELSWWVNGKEVHSGVSTDPQAYKESNYSYCL SSRLRVSATFWHNPRNHFRCQVQFHGLSEEDKWPEGSPKPVTQNISAEAWGRADCGITSASYHQGVLS ATILYEILLGKATLYAVLVSGLVLMAMVKKKNS |
| RAS TCR-28 peptide | 600 | VVGAVGVGK |
| GATA3 TCR-1 alpha chain CDR1 | 127 | NYSPAY |
| GATA3 TCR-1 alpha chain CDR2 | 128 | IRENEKE |
| GATA3 TCR-1 alpha chain CDR3 | 129 | ALDIYGNNRLA |
| GATA3 TCR-1 beta chain CDR1 | 130 | MDHEN |
| GATA3 TCR-1 beta chain CDR2 | 131 | SYDVKM |
| GATA3 TCR-1 beta chain CDR3 | 132 | ASSLDFVLAGSYSYNEQF |
| GATA3 TCR-1 alpha chain variable domain | 133 | ATGGCTTTTGGCTGAGAAGGCTGGGTCTACATTTCAGGCCACATTTGGGGAGACGAATGGAGTCATTC CTGGGAGGTGTTTTGCTGATTTTGTGGCTTCAAGTGGACTGGGTGAAGAGCCAAAAGATAGAACAGAAT TCCGAGGCCCTGAACATTCAGGAGGTAAAACGGCCACCCTGACCTGCAACTATACAAACTATTCTCCA GCATACTTACAGTGGTACCGACAAGATCCAGGAAGAGGCCCTGTTTTCTTGCTACTCATACGTGAAAAT GAGAAAGAAAAAGGAAAGAAAGACTGAAGGTCACTTTGATACACCCTTAAACAGAGTTTGTTTCAT ATCACAGCCTCCCAGCCTGCAGACTCAGCTACCTACCTCTGTGCTCTAGACATTTATGGGAACAACAGA CTCGCTTTTGGGAAGGGGAACCAAGTGGTGGTCATACCA |
|  | 134 | ATGGCCTTCTGGCTGAGGAGACTGGGTTTACACTTCAGACCCCATTTAGGCAGAAGAATGGAGAGCTTT TTAGGCGGCGTGCTGCTGATTTTATGGCTGCAAGTTGACTGGGTGAAGAGCCAGAAGATCGAGCAGAAC |

TABLE 2-continued

SEQUENCES

| Name | SEQ ID NO | Sequence |
|---|---|---|
| | | AGCGAGGCTTTAAACATTCAAGAAGGCAAGACAGCCACTTTAACTTGTAACTATACCAACTACTCCCCC<br>GCTTATTTACAGTGGTACAGACAAGATCCCGGCAGAGGCCCCGTGTTTTTACTGCTGATTCGTGAGAAC<br>GAGAAGGAGAAGAGGAAGGAGAGACTGAAGGTGACCTTCGACACCACTTTAAAGCAGTCTTTATTCCAC<br>ATCACCGCCAGCCAGCCCGCTGATAGCGCCACCTATTTATGCGCTTTAGACATCTACGGCAACAATCGT<br>CTGGCCTTCGGCAAGGGCAACCAAGTTGTGGTGATCCCC |
| | 135 | MAFWLRRLGLHFRPHLGRRMESFLGGVLLILWLQVDWVKSQKIEQNSEALNIQEGKTATLTCNYTNYSP<br>AYLQWYRQDPGRGPVFLLLIRENEKEKRKERLKVTFDTTLKQSLFHITASQPADSATYLCALDIYGNNR<br>LAFGKGNQVVVIP |
| GATA3 TCR-1 beta chain variable domain | 136 | ATGGGAATCAGGCTCCTCTGTCGTGTGGCCTTTTGTTTCCTGGCTGTAGGCCTCGTAGATGTGAAAGTA<br>ACCCAGAGCTCGAGATATCTAGTCAAAAGGACGGGAGAGAAAGTTTTTCTGGAATGTGTCCAGGATATG<br>GACCATGAAAATATGTTCTGGTATCGACAAGACCCAGGTCTGGGGCTACGGCTGATCTATTTCTCATAT<br>GATGTTAAAATGAAAGAAAAGGAGATATTCCTGAGGGGTACAGTGTCTCTAGAGAGAAGAAGGAGCGC<br>TTCTCCCTGATTCTGGAGTCCGCCAGCACCAACCAGACATCTATGTACCTCTGTGCCAGCAGTTTAGAT<br>TTTGTGCTAGCGGGGTCCTACTCCTACAATGAGCAGTTCTTCGGGCCAGGGACACGGCTCACCGTGCTA |
| | 137 | ATGGGCATTCGTCTGCTGTGTCGTGTGGCCTTCTGCTTTTTAGCCGTGGGTTTAGTGGACGTGAAGGTG<br>ACCCAGTCCTCTCGTTATTTAGTGAAGAGGACCGGCGAGAAGGTGTTTTTAGAATGCGTGCAAGATATG<br>GACCACGAGAACATGTTCTGGTACAGACAAGATCCCGGACTGGGTTTAAGGCTGATCTACTTCAGCTAC<br>GACGTGAAGATGAAGGAGAAGGGCGACATCCCCGAGGGCTACTCCGTGTCTCGTGAGAAGAAGGAGAGG<br>TTCTCTTTAATTTTAGAGTCCGCCAGCACCAACCAGACCAGCATGTATTTATGCGCCAGCTCTTTAGAC<br>TTTGTGCTGGCCGGCAGCTACAGCTACAACGAGCAGTTCTTCGGCCCCGGCACCAGACTGACCGTGCTG |
| | 138 | MGIRLLCRVAFCFLAVGLVDVKVTQSSRYLVKRTGEKVFLECVQDMDHENMFWYRQDPGLGLRLIYFSY<br>DVKMKEKGDIPEGYSVSREKKERFSLILESASTNQTSMYLCASSLDFVLAGSYSYNEQFFGPGTRLTVL |
| GATA3 TCR-1 alpha chain | 139 | MAFWLRRLGLHFRPHLGRRMESFLGGVLLILWLQVDWVKSQKIEQNSEALNIQEGKTATLTCNYTNYSP<br>AYLQWYRQDPGRGPVFLLLIRENEKEKRKERLKVTFDTTLKQSLFHITASQPADSATYLCALDIYGNNR<br>LAFGKGNQVVVIPDIQNPDPAVYQLRDSKSSDKSVCLFTDFDSQTNVSQSKDSDVYITDKTVLDMRSMD<br>FKSNSAVAWSNKSDFACANAFNNSIIPEDTFFPSPESSCDVKLVEKSFETDTNLNFQNLSVIGFRILLL<br>KVAGFNLLMTLRLWSS |
| GATA3 TCR-1 beta chain | 140 | MGIRLLCRVAFCFLAVGLVDVKVTQSSRYLVKRTGEKVFLECVQDMDHENMFWYRQDPGLGLRLIYFSY<br>DVKMKEKGDIPEGYSVSREKKERFSLILESASTNQTSMYLCASSLDFVLAGSYSYNEQFFGPGTRLTVL<br>EDLNKVFPPEVAVFEPSEAEISHTQKATLVCLATGFFPDHVELSWWVNGKEVHSGVSTDPQPLKEQPAL<br>NDSRYCLSSRLRVSATFWQNPRNHFRCQVQFYGLSENDEWTQDRAKPVTQIVSAEAWGRADCGFTSVSY<br>QQGVLSATILYEILLGKATLYAVLVSALVLMAMVKRKDF |
| GATA3 TCR-1 peptide | 141 | MLTGPPARV |
| GATA3 neoORF mutant protein | 157 | MRRLSAARRAGTSCANCQTTTTTLWRRNANGDPVCNACGLYYKLHNINRPLTMKKEGIQTRNRKMSSKS<br>KKCCKKVHDSLEDFPKNSSFPGRPLQTHVLPEPHLALQPLQPHADHAHADAPAIQPVLWTTPPLQHGHRH<br>GLEPCSMLTGPPARVPAVPFDLHFCRSSIMKPKRDGYMFLKAESKIMFATLQRSSLWCLCSNH |
| GATA3 neoORF sequence | 158 | PGRPLQTHVLPEPHLALQPLQPHADHAHADAPAIQPVLWTTPPLQHGHRHGLEPCSMLTGPPARVPAVP<br>FDLHFCRSSIMKPKRDGYMFLKAESKIMFATLQRSSLWCLCSNH |
| GATA3 TCR-2 alpha chain CDR1 | 189 | NSMFDY |
| GATA3 TCR-2 alpha chain CDR2 | 190 | ISSIKDK |
| GATA3 TCR-2 alpha chain CDR3 | 191 | AASASNNDMR |
| GATA3 TCR-2 beta chain CDR1 | 192 | SEHNR |
| GATA3 TCR-2 beta chain CDR2 | 193 | FQNEAQ |
| GATA3 TCR-2 beta chain CDR3 | 194 | ASSQSGQGPYEQY |

TABLE 2-continued

SEQUENCES

| Name | SEQ ID NO | Sequence |
|---|---|---|
| GATA3 TCR-2 alpha chain variable domain | 195 | ATGGCCATGCTCCTGGGGGCATCAGTGCTGATTCTGTGGCTTCAGCCAGACTGGGTAAACAGTCAACAG<br>AAGAATGATGACCAGCAAGTTAAGCAAAATTCACCATCCCTGAGCGTCCAGGAAGGAAGAATTTCTATT<br>CTGAACTGTGACTATACTAACAGCATGTTTGATTATTTCCTATGGTACAAAAAATACCCTGCTGAAGGT<br>CCTACATTCCTGATATCTATAAGTTCCATTAAGGATAAAAATGAAGATGGAAGATTCACTGTCTTCTTA<br>AACAAAAGTGCCAAGCACCTCTCTCTGCACATTGTGCCCTCCCAGCCTGGAGACTCTGCAGTGTACTTC<br>TGTGCAGCAAGCGCGTCAAACAATGACATGCGCTTTGGAGCAGGGACCAGACTGACAGTAAAACCA |
| | 196 | ATGGCAATGCTGCTGGGAGCCTCTGTGCTGATCCTGTGGCTGCAGCCAGATTGGGTGAACTCCCAGCAG<br>AAGAATGACGATCAGCAGGTGAAGCAGAATAGCCCCTCCCTGTCTGTGCAGGAGGGCAGAATCAGCATC<br>CTGAACTGCGACTACACCAATTCCATGTTCGATTATTTTCTGTGGTACAAGAAGTATCCAGCCGAGGGC<br>CCCACCTTTCTGATCAGCATCTCCTCTATCAAGGACAAGAACGAGGATGGCAGGTTCACAGTGTTTCTG<br>AATAAGTCTGCCAAGCACCTGAGCCTGCACATCGTGCCATCCCAGCCTGGCGACTCTGCCGTGTACTTC<br>TGTGCCGCCAGCGCCTCCAACAATGATATGAGATTTGGCGCCGGCACCAGGCTGACAGTGAAGCCC |
| | 197 | MAMLLGASVLILWLQPDWVNSQQKNDDQQVKQNSPSLSVQEGRISILNCDYTNSMFDYFLWYKKYPAEG<br>PTFLISISSIKDKNEDGRFTVFLNKSAKHLSLHIVPSQPGDSAVYFCAASASNNDMRFGAGTRLTVKP |
| GATA3 TCR-2 beta chain variable domain | 198 | ATGGGCACCAGCCTCCTCTGCTGGATGGCCCTGTGTCTCCTGGGGGCAGATCACGCAGATACTGGAGTC<br>TCCCAGGACCCCAGACACAAGATCACAAAGAGGGGACAGAATGTAACTTTCAGGTGTGATCCAATTTCT<br>GAACACAACCGCCTTTATTGGTACCGACAGACCCTGGGGCAGGGCCCAGAGTTTCTGACTTACTTCCAG<br>AATGAAGCTCAACTAGAAAAATCAAGGCTGCTCAGTGATCGGTTCTCTGCAGAGAGGCCTAAGGGATCT<br>TTCTCCACCTTGGAGATCCAGCGCACAGAGCAGGGGACTCGGCCATGTATCTCTGTGCCAGCAGCCAA<br>TCGGGACAGGGGCCCTACGAGCAGTACTTCGGGCCGGGCACCAGGCTCACGGTCACAGAG |
| | 199 | ATGGGCACCTCTCTGCTGTGCTGGATGGCACTGTGCCTGCTGGGAGCAGACCACGCAGATACAGGCGTG<br>AGCCAGGACCCCCGCCACAAGATCACCAAGCGGGGCCAGAACGTGACATTCAGATGCGATCCTATCTCC<br>GAGCACAATAGGCTGTACTGGTATAGGCAGACCCTGGGACAGGGACCAGAGTTCCTGACATACTTTCAG<br>AACGAGGCCCAGCTGGAAGAGAGCCGGCTGCTGTCCGACAGATTCTCTGCCGAGAGGCCTAAGGGCAGC<br>TTTTCCACCCTGGAGATCCAGAGGACAGAGCAGGGCGATTCTGCCATGTATCTGTGCGCCAGCTCCCAG<br>AGCGGACAGGGACCTTACGAGCAGTATTTCGGACCAGGAACCAGGCTGACCGTGACAGAG |
| | 200 | MGTSLLCWMALCLLGADHADTGVSQDPRHKITKRGQNVTFRCDPISEHNRLYWYRQTLGQGPEFLTYFQ<br>NEAQLEKSRLLSDRFSAERPKGSFSTLEIQRTEQGDSAMYLCASSQSGQGPYEQYFGPGTRLTVTE |
| GATA3 TCR-2 alpha chain | 201 | MAMLLGASVLILWLQPDWVNSQQKNDDQQVKQNSPSLSVQEGRISILNCDYTNSMFDYFLWYKKYPAEG<br>PTFLISISSIKDKNEDGRFTVFLNKSAKHLSLHIVPSQPGDSAVYFCAASASNNDMRFGAGTRLTVKPD<br>IQNPDPAVYQLRDSKSSDKSVCLFTDFDSQTNVSQSKDSDVYITDKTVLDMRSMDFKSNSAVAWSNKSD<br>FACANAFNNSIIPEDTFFPSPESSCDVKLVEKSFETDTNLNFQNLSVIGFRILLLKVAGFNLLMTLRLW<br>SS |
| GATA3 TCR-2 beta chain | 202 | MGTSLLCWMALCLLGADHADTGVSQDPRHKITKRGQNVTFRCDPISEHNRLYWYRQTLGQGPEFLTYFQ<br>NEAQLEKSRLLSDRFSAERPKGSFSTLEIQRTEQGDSAMYLCASSQSGQGPYEQYFGPGTRLTVTEEDL<br>NKVFPPEVAVFEPSEAEISHTQKATLVCLATGFFPDHVELSWWVNGKEVHSGVSTDPQPLKEQPALNDS<br>RYCLSSRLRVSATFWQNPRNHFRCQVQFYGLSENDEWTQDRAKPVTQIVSAEAWGRADCGFTSVSYQQG<br>VLSATILYEILLGKATLYAVLVSALVLMAMVKRKDF |
| GATA3 TCR-2 peptide | 203 | KPKRDGYMF |
| GATA3 TCR-3 alpha chain CDR1 | 204 | YGGTVN |
| GATA3 TCR-3 alpha chain CDR2 | 205 | YFSGDPLV |
| GATA3 TCR-3 alpha chain CDR3 | 206 | AVISVTGNNRKLI |
| GATA3 TCR-3 beta chain CDR1 | 207 | LNHDA |
| GATA3 TCR-3 beta chain CDR2 | 208 | SQIVND |
| GATA3 TCR-3 beta chain CDR3 | 209 | ASSRTAMNTEAF |

TABLE 2-continued

SEQUENCES

| Name | SEQ ID NO | Sequence |
|---|---|---|
| GATA3 TCR-3 alpha chain variable domain | 210 | ATGCTCCTGTTGCTCATACCAGTGCTGGGGATGATTTTTGCCCTGAGAGATGCCAGAGCCCAGTCTGTG AGCCAGCATAACCACCACGTAATTCTCTCTGAAGCAGCCTCACTGGAGTTGGGATGCAACTATTCCTAT GGTGGAACTGTTAATCTCTTCTGGTATGTCCAGTACCCTGGTCAACACCTTCAGCTTCTCCTCAAGTAC TTTTCAGGGGATCCACTGGTTAAAGGCATCAAGGGCTTTGAGGCTGAATTTATAAAGAGTAAATTCTCC TTTAATCTGAGGAAACCCTCTGTGCAGTGGAGTGACACAGCTGAGTACTTCTGTGCCGTGATCTCCGTG ACTGGCAACAACCGTAAGCTGATTTGGGGATTGGGAACAAGCCTGGCAGTAAATCCG |
|  | 211 | ATGCTGCTGCTGCTGATCCCTGTGCTGGGCATGATCTTTGCACTGAGGGACGCAAGAGCACAGTCCGTG TCTCAGCACAACCACCACGTGATCCTGAGCGAGGCAGCCTCCCTGGAGCTGGGCTGCAACTACTCTTAT GGCGGCACAGTGAATCTGTTCTGGTACGTGCAGTATCCAGGCCAGCACCTGCAGCTGCTGCTGAAGTAC TTTAGCGGCGACCCCCTGGTGAAGGGCATCAAGGGCTTCGAGGCCGAGTTTATCAAGTCCAAGTTCTCT TTTAACCTGCGGAAGCCATCTGTGCAGTGGAGCGATACCGCCGAGTATTTCTGTGCCGTGATCAGCGTG ACAGGCAACAATAGAAAGCTGATCTGGGGACTGGGCACCTCCCTGGCCGTGAATCCC |
|  | 212 | MLLLLIPVLGMIFALRDARAQSVSQHNHHVILSEAASLELGCNYSYGGTVNLFWYVQYPGQHLQLLLKY FSGDPLVKGIKGFEAEFIKSKFSFNLRKPSVQWSDTAEYFCAVISVTGNNRKLIWGLGTSLAVNP |
| GATA3 TCR-3 beta chain variable domain | 213 | ATGAGCAACCAGGTGCTCTGCTGTGTGGTCCTTTGTCTCCTGGGAGCAAACACCGTGGATGGTGGAATC ACTCAGTCCCCGAAGTACCTGTTCAGAAAGGAAGGACAGAATGTGACCCTGAGTTGTGAACAGAATTTG AACCACGATGCCATGTACTGGTACCGACAGGACCCAGGGCAAGGGCTGAGATTGATCTACTACTCACAG ATAGTAAATGACTTTCAGAAAGGAGATATAGCTGAAGGGTACAGCGTCTCTCGGGAGAAGAAGGAATCC TTTCCTCTCACTGTGACATCGGCCCAAAAGAACCCGACAGCTTTCTATCTCTGTGCCAGTAGTCGGACT GCAATGAACACTGAAGCTTTCTTTGGACAAGGCACCAGACTCACAGTTGTA |
|  | 214 | ATGTCCAACCAGGTGCTGTGCTGCGTGGTGCTGTGCCTGCTGGGAGCAAATACCGTGGACGGAGGCATC ACACAGTCCCCCAAGTACCTGTTCAGGAAGGAGGGCCAGAACGTGACCCTGTCTTGTGAGCAGAACCTG AATCACGACGCCATGTACTGGTATAGGCAGGACCCCGGACAGGGACTGAGACTGATCTACTATAGCCAG ATCGTGAATGACTTTCAGAAGGGCGACATCGCCGAGGGCTACTCCGTGTCTAGGGAGAAGAAGGAGAGC TTCCCCCTGACCGTGACATCCGCCCAGAAGAACCCTACAGCCTTTTATCTGTGCGCCAGCTCCCGCACC GCCATGAATACAGAGGCCTTCTTTGGCCAGGGCACCAGGCTGACAGTGGTG |
|  | 215 | MSNQVLCCVVLCLLGANTVDGGITQSPKYLFRKEGQNVTLSCEQNLNHDAMYWYRQDPGQGLRLIYYSQ IVNDFQKGDIAEGYSVSREKKESFPLTVTSAQKNPTAFYLCASSRTAMNTEAFFGQGTRLTVV |
| GATA3 TCR-3 alpha chain | 216 | MLLLLIPVLGMIFALRDARAQSVSQHNHHVILSEAASLELGCNYSYGGTVNLFWYVQYPGQHLQLLLKY FSGDPLVKGIKGFEAEFIKSKFSFNLRKPSVQWSDTAEYFCAVISVTGNNRKLIWGLGTSLAVNPDIQN PDPAVYQLRDSKSSDKSVCLFTDFDSQTNVSQSKDSDVYITDKTVLDMRSMDFKSNSAVAWSNKSDFAC ANAFNNSIIPEDTFFPSPESSCDVKLVEKSFETDTNLNFQNLSVIGFRILLLKVAGFNLLMTLRLWSS |
| GATA3 TCR-3 beta chain | 217 | MSNQVLCCVVLCLLGANTVDGGITQSPKYLFRKEGQNVTLSCEQNLNHDAMYWYRQDPGQGLRLIYYSQ IVNDFQKGDIAEGYSVSREKKESFPLTVTSAQKNPTAFYLCASSRTAMNTEAFFGQGTRLTVVEDLNKV FPPEVAVFEPSEAEISHTQKATLVCLATGFFPDHVELSWWVNGKEVHSGVSTDPQPLKEQPALNDSRYC LSSRLRVSATFWQNPRNHFRCQVQFYGLSENDEWTQDRAKPVTQIVSAEAWGRADCGFTSVSYQQGVLS ATILYEILLGKATLYAVLVSALVLMAMVKRKDF |
| GATA3 TCR-3 peptide | 218 | ESKIMFATL |
| TMPRSS2:ERG TCR-1 alpha chain CDR1 | 142 | TRDTTYY |
| TMPRSS2:ERG TCR-1 alpha chain CDR2 | 143 | RNSFDEQN |
| TMPRSS2:ERG TCR-1 alpha chain CDR3 | 144 | ALSEARVFNGANSKLT |
| TMPRSS2:ERG TCR-1 beta chain CDR1 | 145 | SGHDN |
| TMPRSS2:ERG TCR-1 beta chain CDR2 | 146 | FVKESK |
| TMPRSS2:ERG TCR-1 beta chain CDR3 | 147 | ASSQADSPLH |

TABLE 2-continued

SEQUENCES

| Name | SEQ ID NO | Sequence |
|---|---|---|
| TMPRSS2:ERG TCR-1 alpha chain variable domain | 148 | ATGCTGACTGCCAGCCTGTTGAGGGCAGTCATAGCCTCCATCTGTGTTGTATCCAGCATGGCTCAGAAG GTAACTCAAGCGCAGACTGAAATTTCTGTGGTGGAGAAGGAGGATGTGACCTTGGACTGTGTGTATGAA ACCCGTGATACTACTTATTACTTATTCTGGTACAAGCAACCACCAAGTGGAGAATTGGTTTTCCTTATT CGTCGGAACTCTTTTGATGAGCAAAATGAAATAAGTGGTCGGTATTCTTGGAACTTCCAGAAATCCACC AGTTCCTTCAACTTCACCATCACAGCCTCACAAGTCGTGGACTCAGCAGTATACTTCTGTGCTCTGAGT GAGGCCCGCGTTTTCAATGGAGCCAATAGTAAGCTGACATTTGGAAAAGGAATAACTCTGAGTGTTAGA CCA |
| | 149 | ATGCTGACCGCCAGCCTGCTGAGGGCTGTGATCGCCAGCATCTGCGTCGTGTCCAGCATGGCTCAAAAG GTCACACAGGCCCAGACAGAGATCTCCGTCGTCGAGAAGGAGGACGTGACCCTCGACTGCGTGTATGAG ACCAGGGACACCACATACTACCTGTTTTGGTACAAGCAGCCCCCCAGCGGAGAGCTCGTGTTTCTGATC AGAAGGAACAGCTTTGATGAACAGAATGAGATCTCCAGGGTACTCCTGGAACTTCCAGAAGAGCACC TCCAGCTTCAACTTCACAATTACAGCTTCCCAGGTGGTGGATAGCGCCGTGTATTTCTGCGCTCTCAGC GAGGCCAGGGTGTTCAACGGCGCCAATTCCAAACTGACCTTCGGCAAAGGCATCACACTGTCCGTGAGA CCC |
| | 150 | MLTASLLRAVIASICVVSSMAQKVTQAQTEISVVEKEDVTLDCVYETRDTTYYLFWYKQPPSGELVFLI RRNSFDEQNEISGRYSWNFQKSTSSFNFTITASQVVDSAVYFCALSEARVFNGANSKLTFGKGITLSVR P |
| TMPRSS2:ERG TCR-1 beta chain variable domain | 151 | ATGGTTTCCAGGCTTCTCAGTTTAGTGTCCCTTTGTCTCCTGGGAGCAAAGCACATAGAAGCTGGAGTT ACTCAGTTCCCCAGCCACAGCGTAATAGAGAAGGGCCAGACTGTGACTCTGAGATGTGACCCAATTTCT GGACATGATAATCTTTATTGGTATCGACGTGTTATGGGAAAAGAAATAAAATTTCTGTTACATTTTGTG AAAGAGTCTAAACAGGATGAATCCGGTATGCCCAACAATCGATTCTTAGCTGAAAGGACTGGAGGGACG TATTCTACTCTGAAGGTGCAGCCTGCAGAATGGAGGATTCTGGAGTTTATTTCTGTGCCAGCAGCCAA GCGGATTCACCCCTCCACTTTGGGAATGGGACCAGGCTCACTGTGACA |
| | 152 | ATGGTCTCCAGGCTGCTCTCCCTCGTGAGCCTGTGTCTCCTGGGAGCCAAGCACATTGAGGCCGGCGTG ACCCAATTCCCCAGCCACAGCGTGATTGAGAAGGGACAGACCGTCACCCTGAGGTGTGATCCTATCAGC GGCCACGACAACCTCTACTGGTATAGGAGAGTCATGGGCAAGGAAATTAAATTTCTGCTGCATTTCGTG AAAGAGTCCAAACAGGACGAAAGCGGCATGCCCAATAATAGGTTCCTCGCCGAGAGGACCGGCGGCACA TATTCCACCCTGAAGGTCCAGCCCGCTGAGCTCGAAGACTCCGGCGTCTATTTCTGTGCCTCCAGCCAG GCTGACTCCCCTCTCCATTTCGGAAACGGCACCAGGCTCACCGTGACC |
| | 153 | MVSRLLSLVSLCLLGAKHIEAGVTQFPSHSVIEKGQTVTLRCDPISGHDNLYWYRRVMGKEIKFLLHFV KESKQDESGMPNNRFLAERTGGTYSTLKVQPAELEDSGVYFCASSQADSPLHFGNGTRLTVT MLTASLLRAVIASICVVSSMAQKVTQAQTEISVVEKEDVTLDCVYETRDTTYYLFWYKQPPSGELVFLI |
| TMPRSS2:ERG TCR-1 alpha chain | 154 | RRNSFDEQNEISGRYSWNFQKSTSSFNFTITASQVVDSAVYFCALSEARVFNGANSKLTFGKGITLSVR PDIQNPDPAVYQLRDSKSSDKSVCLFTDFDSQTNVSQSKDSDVYITDKTVLDMRSMDFKSNSAVAWSNK SDFACANAFNNSIIPEDTFFPSPESSCDVKLVEKSFETDTNLNFQNLSVIGFRILLLKVAGFNLLMTLR LWSS |
| TMPRSS2:ERG TCR-1 beta chain | 155 | MVSRLLSLVSLCLLGAKHIEAGVTQFPSHSVIEKGQTVTLRCDPISGHDNLYWYRRVMGKEIKFLLHFV KESKQDESGMPNNRFLAERTGGTYSTLKVQPAELEDSGVYFCASSQADSPLHFGNGTRLTVTEDLNKVF PPEVAVFEPSEAEISHTQKATLVCLATGFFPDHVELSWWVNGKEVHSGVSTDPQPLKEQPALNDSRYCL SSRLRVSATFWQNPRNHFRCQVQFYGLSENDEWTQDRAKPVTQIVSAEAWGRADCGFTSVSYQQGVLSA TILYEILLGKATLYAVLVSALVLMAMVKRKDF |
| TMPRSS2:ERG TCR-1 peptide | 156 | ALNSEALSV |
| BTK TCR-1 alpha chain CDR1 | 159 | DRGSQS |
| BTK TCR-1 alpha chain CDR2 | 160 | IYSNGD |
| BTK TCR-1 alpha chain CDR3 | 161 | AVNDYGGSQGNLIF |
| BTK TCR-1 beta chain CDR1 | 162 | SEHNR |
| BTK TCR-1 beta chain CDR2 | 163 | FQNEAQ |
| BTK TCR-1 beta chain CDR3 | 164 | ASSFGPDEKLFF |

TABLE 2-continued

SEQUENCES

| Name | SEQ ID NO | Sequence |
|---|---|---|
| BTK TCR-1 alpha chain variable domain | 165 | ATGATGAAATCCTTGAGAGTTTTACTAGTGATCCTGTGGCTTCAGTTGAGCTGGGTTTGGAGCCAACAG<br>AAGGAGGTGGAGCAGAATTCTGGACCCCTCAGTGTTCCAGAGGGAGCCATTGCCTCTCTCAACTGCACT<br>TACAGTGACCGAGGTTCCCAGTCCTTCTTCTGGTACAGACAATATTCTGGGAAAAGCCCTGAGTTGATA<br>ATGTTCATATACTCCAATGGTGACAAAGAAGATGGAAGGTTTACAGCACAGCTCAATAAAGCCAGCCAG<br>TATGTTTCTCTGCTCATCAGAGACTCCCAGCCCAGTGATTCAGCCACCTACCTCTGTGCCGTGAACGAT<br>TATGGAGGAAGCCAAGGAAATCTCATCTTTGGAAAAGGCACTAAACTCTCTGTTAAACCA |
| | 166 | ATGATGAAGAGCCTGCGGGTGCTGCTGGTCATCCTGTGGCTGCAGCTGTCTTGGGTGTGGAGCCAGCAG<br>AAGGAGGTGGAGCAGAACTCCGGACCACTGTCTGTGCCTGAGGGAGCCATCGCCAGCCTGAATTGCACC<br>TACTCCGACAGAGGCTCCCAGTCTTTCTTTTGGTACAGGCAGTATAGCGGCAAGTCCCCCGAGCTGATC<br>ATGTTCATCTACTCCAACGGCGACAAGGAGGATGGCCGCTTTACAGCCCAGCTGAATAAGGCCAGCCAG<br>TACGTGAGCCTGCTGATCCGGGACTCTCAGCCAAGCGATTCCGCCACCTACCTGTGCGCCGTGAACGAT<br>TATGGCGGCAGCCAGGGCAATCTGATCTTTGGCAAGGGCACAAAGCTGTCCGTGAAGCCC |
| | 167 | MMKSLRVLLVILWLQLSWVWSQQKEVEQNSGPLSVPEGAIASLNCTYSDRGSQSFFWYRQYSGKSPELI<br>MFIYSNGDKEDGRFTAQLNKASQYVSLLIRDSQPSDSATYLCAVNDYGGSQGNLIFGKGTKLSVKP |
| BTK TCR-1 beta chain variable domain | 168 | ATGGGCACCAGCCTCCTCTGCTGGATGGCCCTGTGTCTCCTGGGGGCAGATCACGCAGATACTGGAGTC<br>TCCCAGAACCCCAGACACAAGATCACAAAGAGGGGACAGAATGTAACTTTCAGGTGTGATCCAATTTCT<br>GAACACAACCGCCTTTATTGGTACCGACAGACCCTGGGGCAGGGCCCAGAGTTTCTGACTTACTTCCAG<br>AATGAAGCTCAACTAGAAAAATCAAGGCTGCTCAGTGATCCGGTTCTTCTGCAGAGAGGCCTAAGGGATCT<br>TTCTCCACCTTGGAGATCCAGCGCACAGAGCAGGGGACTCCGGCCATGTATCTCTGTGCCAGCAGCTTC<br>GGACCTGATGAAAAACTGTTTTTTTGGCAGTGGAACCCAGCTCTCTGTCTTG |
| | 169 | ATGGGCACCTCTCTGCTGTGCTGGATGGCACTGTGCCTGCTGGGAGCAGACCACGCAGATACAGGCGTG<br>AGCCAGAACCCACGCCACAAGATCACCAAGCGGGGCCAGAATGTGACATTCAGATGCGACCCCATCAGC<br>GAGCACAACAGGCTGTACTGGTATAGGCAGACCCTGGGACAGGGACCAGAGTTCCTGACATACTTTCAG<br>AATGAGGCCCAGCTGGAGAAGTCTCGGCTGCTGAGCGATAGATTCTCCGCCGAGAGGCCTAAGGGCTCC<br>TTTTCTACCCTGGAGATCCAGAGGACAGAGCAGGGCGACTCCGCCATGTATCTGTGCGCCAGCTCCTTC<br>GGCCCTGATGAGAAGCTGTTCTTTGGCTCTGGCACCCAGCTGAGCGTGCTG |
| | 170 | MGTSLLCWMALCLLGADHADTGVSQNPRHKITKRGQNVTFRCDPISEHNRLYWYRQTLGQGPEFLTYFQ<br>NEAQLEKSRLLSDRFSAERPKGSFSTLEIQRTEQGDSAMYLCASSFGPDEKLFFGSGTQLSVL |
| BTK TCR-1 alpha chain | 171 | MMKSLRVLLVILWLQLSWVWSQQKEVEQNSGPLSVPEGAIASLNCTYSDRGSQSFFWYRQYSGKSPELI<br>MFIYSNGDKEDGRFTAQLNKASQYVSLLIRDSQPSDSATYLCAVNDYGGSQGNLIFGKGTKLSVKPDIQ<br>NPDPAVYQLRDSKSSDKSVCLFTDFDSQTNVSQSKDSDVYITDKTVLDMRSMDFKSNSAVAWSNKSDFA<br>CANAFNNSIIPEDTFFPSPESSCDVKLVEKSFETDTNLNFQNLSVIGFRILLLKVAGFNLLMTLRLWSS |
| BTK TCR-1 beta chain | 172 | MGTSLLCWMALCLLGADHADTGVSQNPRHKITKRGQNVTFRCDPISEHNRLYWYRQTLGQGPEFLTYFQ<br>NEAQLEKSRLLSDRFSAERPKGSFSTLEIQRTEQGDSAMYLCASSFGPDEKLFFGSGTQLSVLEDLNKV<br>FPPEVAVFEPSEAEISHTQKATLVCLATGFFPDHVELSWWVNGKEVHSGVSTDPQPLKEQPALNDSRYC<br>LSSRLRVSATFWQNPRNHFRCQVQFYGLSENDEWTQDRAKPVTQIVSAEAWGRADCGFTSVSYQQGVLS<br>ATILYEILLGKATLYAVLVSALVLMAMVKRKDF |
| BTK TCR-1 peptide | 173 | SLLNYLREM |
| BTK TCR-2 alpha chain CDR1 | 174 | DRGSQS |
| BTK TCR-2 alpha chain CDR2 | 175 | IYSNGD |
| BTK TCR-2 alpha chain CDR3 | 176 | AVNEGDSSYKLI |
| BTK TCR-2 beta chain CDR1 | 177 | SGDLS |
| BTK TCR-2 beta chain CDR2 | 178 | YNGEE |
| BTK TCR-2 beta chain CDR3 | 179 | ASSPGANEKLF |
| BTK TCR-2 alpha chain variable domain | 180 | ATGATGAAATCCTTGAGAGTTTTACTAGTGATCCTGTGGCTTCAGTTGAGCTGGGTTTGGAGCCAACAG<br>AAGGAGGTGGAGCAGAATTCTGGACCCCTCAGTGTTCCAGAGGGAGCCATTGCCTCTCTCAACTGCACT<br>TACAGTGACCGAGGTTCCCAGTCCTTCTTCTGGTACAGACAATATTCTGGGAAAAGCCCTGAGTTGATA<br>ATGTTCATATACTCCAATGGTGACAAAGAAGATGGAAGGTTTACAGCACAGCTCAATAAAGCCAGCCAG<br>TATGTTTCTCTGCTCATCAGAGACTCCCAGCCCAGTGATTCAGCCACCTACCTCTGTGCCGTGAACGAG<br>GGGGATAGCAGCTATAAATTGATCTTCGGGAGTGGGACCAGACTGCTGGTCAGGCCT |

TABLE 2-continued

SEQUENCES

| Name | SEQ ID NO | Sequence |
|---|---|---|
| | 181 | ATGATGAAGAGCCTGCGGGTGCTGCTGGTCATCCTGTGGCTGCAGCTGAGCTGGGTGTGGTCCCAGCAG<br>AAGGAGGTGGAGCAGAACTCTGGACCACTGAGCGTGCCTGAGGGAGCCATCGCCTCCCTGAATTGCACC<br>TACTCTGACAGAGGCAGCCAGTCCTTCTTTTGGTACAGGCAGTATTCCGGCAAGTCTCCCGAGCTGATC<br>ATGTTCATCTACAGCAACGGCGACAAGGAGGATGGCCGCTTTACAGCCCAGCTGAATAAGGCCTCCCAG<br>TACGTGAGCCTGCTGATCCGGGACTCTCAGCCATCTGATAGCGCCACCTACCTGTGCGCCGTGAACGAG<br>GGCGATAGCTCCTATAAGCTGATCTTTGGCAGCGGCACAAGACTGCTGGTGAGGCCC |
| | 182 | MMKSLRVLLVILWLQLSWVWSQQKEVEQNSGPLSVPEGAIASLNCTYSDRGSQSFFWYRQYSGKSPELI<br>MFIYSNGDKEDGRFTAQLNKASQYVSLLIRDSQPSDSATYLCAVNEGDSSYKLIFGSGTRLLVRP |
| BTK TCR-2 beta chain variable domain | 183 | ATGGGCTTCAGGCTCCTCTGCTGTGTGGCCTTTTGTCTCCTGGGAGCAGGCCCAGTGGATTCTGGAGTC<br>ACACAAACCCCAAAGCACCTGATCACAGCAACTGGACAGCGAGTGACGCTGAGATGCTCCCCTAGGTCT<br>GGAGACCTCTCTGTGTACTGGTACCAACAGAGCCTGGACCAGGGCCTCCAGTTCCTCATTCAGTATTAT<br>AATGGAGAAGAGAGAGCAAAAGGAAACATTCTTGAACGATTCTCCGCACAACAGTTCCCTGACTTGCAC<br>TCTGAACTAAACCTGAGCTCTCTGGAGCTGGGGGACTCAGCTTTGTATTTCTGTGCCAGCAGCCCGGGG<br>GCTAATGAAAAACTGTTTTTTGGCAGTGGAACCCAGCTCTCTGTCTTG |
| | 184 | ATGGGCTTCCGGCTGCTGTGCTGCGTGGCATTTTGCCTGCTGGGAGCAGGACCAGTGGACTCCGGCGTG<br>ACCCAGACACCCAAGCACCTGATCACCGCAACAGGACAGAGGGTGACCCTGAGATGTTCCCCTAGGTCT<br>GGCGACCTGAGCGTGTACTGGTATCAGCAGTCCCTGGATCAGGGCCTGCAGTTCCTGATCCAGTACTAT<br>AACGGCGAGGAGCGCGCCAAGGGCAATATCCTGGAGCGGTTCTCCGCCCAGCAGTTTCCCGACCTGCAC<br>TCTGAGCTGAACCTGAGCTCCCTGGAGCTGGGCGATAGCGCCCTGTACTTCTGCGCCTCTAGCCCTGGC<br>GCCAATGAGAAGCTGTTCTTTGGCAGCGGCACCCAGCTGTCCGTGCTG |
| | 185 | MGFRLLCCVAFCLLGAGPVDSGVTQTPKHLITATGQRVTLRCSPRSGDLSVYWYQQSLDQGLQFLIQYY<br>NGEERAKGNILERFSAQQFPDLHSELNLSSLELGDSALYFCASSPGANEKLFFGSGTQLSVL |
| BTK TCR-2 alpha chain | 186 | MMKSLRVLLVILWLQLSWVWSQQKEVEQNSGPLSVPEGAIASLNCTYSDRGSQSFFWYRQYSGKSPELI<br>MFIYSNGDKEDGRFTAQLNKASQYVSLLIRDSQPSDSATYLCAVNEGDSSYKLIFGSGTRLLVRPDIQN<br>PDPAVYQLRDSKSSDKSVCLFTDFDSQTNVSQSKDSDVYITDKTVLDMRSMDFKSNSAVAWSNKSDFAC<br>ANAFNNSIIPEDTFFPSPESSCDVKLVEKSFETDTNLNFQNLSVIGFRILLLKVAGFNLLMTLRLWSS |
| BTK TCR-2 beta chain | 187 | MGFRLLCCVAFCLLGAGPVDSGVTQTPKHLITATGQRVTLRCSPRSGDLSVYWYQQSLDQGLQFLIQYY<br>NGEERAKGNILERFSAQQFPDLHSELNLSSLELGDSALYFCASSPGANEKLFFGSGTQLSVLEDLNKVF<br>PPEVAVFEPSEAEISHTQKATLVCLATGFFPDHVELSWWVNGKEVHSGVSTDPQPLKEQPALNDSRYCL<br>SSRLRVSATFWQNPRNHFRCQVQFYGLSENDEWTQDRAKPVTQIVSAEAWGRADCGFTSVSYQQGVLSA<br>TILYEILLGKATLYAVLVSALVLMAMVKRKDF |
| BTK TCR-2 peptide | 188 | SLLNYLREM |
| EGFR TCR-1 alpha chain CDR1 | 447 | TRDTTYY |
| EGFR TCR-1 alpha chain CDR2 | 448 | RNSFDEQN |
| EGFR TCR-1 alpha chain CDR3 | 449 | ALKGANTGFQKLV |
| EGFR TCR-1 beta chain CDR1 | 450 | SGHDY |
| EGFR TCR-1 beta chain CDR2 | 451 | FNNNVP |
| EGFR TCR-1 beta chain CDR3 | 452 | ASGGGLGLFETQY |
| EGFR TCR-1 alpha chain variable domains | 453 | ATGCTGACTGCCAGCCTGTTGAGGGCAGTCATAGCCTCCATCTGTGTTGTATCCAGCATGGCTCAGAAG<br>GTAACTCAAGCGCAGACTGAAATTTCTGTGGTGGAGAAGGAGGATGTGACCTTGGACTGTGTGTATGAA<br>ACCCGTGATACTACTTATTACTTATTCTGGTACAAGCAACCACCAAGTGGAGAATTGGTTTTCCTTATT<br>CGTCGGAACTCTTTTGATGAGCAAAATGAAATAAGTGGTCGGTATTCTTGGAACTTCCAGAAATCCACC<br>AGTTCCTTCAACTTCACCATCACAGCCTCACAAGTCGTGGACTCAGCAGTATACTTCTGTGCTCTGAAA<br>GGGGCGAACACAGGCTTTCAGAAACTTGTATTTGGAACTGGCACCCGACTTCTGGTCAGTCCA |
| | 454 | ATGCTGACAGCCTCCCTGCTGAGGGCCGTGATCGCCTCTATCTGCGTGGTGTCTAGCATGGCCCAGAAG<br>GTGACCCAGGCCCAGACAGAGATCAGCGTGGTGGAGAAGGAGGACGTGACCCTGGATTGCGTGTACGAG<br>ACACGGGACACCACATACTATCTGTTTTGGTATAAGCAGCCACCCAGCGGCGAGCTGGTGTTCCTGATC |

TABLE 2-continued

SEQUENCES

| Name | SEQ ID NO | Sequence |
|---|---|---|
| | | AGGCGCAATTCCTTTGATGAGCAGAACGAGATCTCCGGCAGATACTCTTGGAATTTCCAGAAGTCCACC<br>TCCTCTTTCAACTTTACCATCACAGCCTCCCAGGTGGTGGACTCTGCCGTGTATTTTTGTGCCCTGAAG<br>GGCGCCAACACAGGCTTCCAGAAGCTGGTGTTTGGCACCGGCACAAGACTGCTGGTGAGCCCT |
| | 455 | MLTASLLRAVIASICVVSSMAQKVTQAQTEISVVEKEDVTLDCVYETRDTTYYLFWYKQPPSGELVFLI<br>RRNSFDEQNEISGRYSWNFQKSTSSFNFTITASQVVDSAVYFCALKGANTGFQKLVFGTGTRLLVSP |
| EGFR TCR-1 beta chain variable domains | 456 | ATGGACTCCTGGACCCTCTGCTGTGTGTCCCTTTGCATCCTGGTAGCAAAGCACACAGATGCTGGAGTT<br>ATCCAGTCACCCCGGCACGAGGTGACAGAGATGGGACAAGAAGTGACTCTGAGATGTAAACCAATTTCA<br>GGACACGACTACCTTTTCTGGTACAGACAGACCATGATGCGGGGACTGGAGTTGCTCATTTACTTTAAC<br>AACAACGTTCCGATAGATGATTCAGGGATGCCCGAGGATCGATTCTCAGCTAAGATGCCTAATGCATCA<br>TTCTCCACTCTGAAGATCCAGCCCTCAGAACCCAGGGACTCAGCTGTGTACTTCTGTGCCAGCGGAGGG<br>GGACTAGGTCTATTTGAGACCCAGTACTTCGGGCCAGGCACGCGGCTCCTGGTGCTC |
| | 457 | ATGGACAGCTGGACCCTGTGCTGCGTGAGCCTGTGCATCCTGGTGGCCAAGCACACAGATGCAGGCGTG<br>ATCCAGTCCCCAAGGCACGAGGTGACCGAGATGGGACAGGAGGTGACACTGAGGTGTAAGCCTATCTCT<br>GGCCACGACTACCTGTTCTGGTATCGGCAGACCATGATGAGAGGCCTGGAGCTGCTGATCTACTTTAAC<br>AATAACGTGCCTATCGACGATTCTGGCATGCCAGAGGACAGGTTCAGCGCCAAGATGCCTAATGCCAGC<br>TTTTCCACCCTGAAGATCCAGCCAAGCGAGCCAAGGGATTCCGCCGTGTACTTCTGCGCCTCCGGAGGA<br>GGACTGGGACTGTTCGAGACCCAGTATTTTGGCCCAGGCACAAGGCTGCTGGTGCTG |
| | 458 | MDSWTLCCVSLCILVAKHTDAGVIQSPRHEVTEMGQEVTLRCKPISGHDYLFWYRQTMMRGLELLIYFN<br>NNVPIDDSGMPEDRFSAKMPNASFSTLKIQPSEPRDSAVYFCASGGGLGLFETQYFGPGTRLLVL |
| EGFR TCR-1 alpha chain | 459 | MLTASLLRAVIASICVVSSMAQKVTQAQTEISVVEKEDVTLDCVYETRDTTYYLFWYKQPPS<br>GELVFLIRRNSFDEQNEISGRYSWNFQKSTSSFNFTITASQVVDSAVYFCALKGANTGFQKL<br>VFGTGTRLLVSPDIQNPEPAVYQLKDPRSQDSTLCLFTDFDSQINVPKTMESGTFITDKTVL<br>DMKAMDSKSNGAIAWSNQTSFTCQDIFKETNATYPSSDVPCDATLTEKSFETDMNLNFQNLS<br>VMGLRILLLKVAGFNLLMTLRLWSS |
| EGFR TCR-1 beta chain | 460 | MDSWTLCCVSLCILVAKHTDAGVIQSPRHEVTEMGQEVTLRCKPISGHDYLFWYRQTMMRGL<br>ELLIYFNNNVPIDDSGMPEDRFSAKMPNASFSTLKIQPSEPRDSAVYFCASGGGLGLFETQY<br>FGPGTRLLVLKDLRNVTPPKVSLFEPSKAEIANKQKATLVCLARGFFPDHVELSWWVNGKEV<br>HSGVSTDPQAYKESNYSYCLSSRLRVSATFWHNPRNHFRCQVQFHGLSEEDKWPEGSPKPVT<br>QNISAEAWGRADCGITSASYHQGVLSATILYEILLGKATLYAVLVSGLVLMAMVKKKNS |
| Peptides | 461 | QLIMQLMPF |
| | 462 | LIMQLMPFGC |
| | 463 | MQLMPFGCLL |
| EGFR TCR2 alpha chain CDR1 | 464 | DSSSTY |
| EGFR TCR2 alpha chain CDR2 | 465 | IFSNMDM |
| EGFR TCR2 alpha chain CDR3 | 466 | AEWANTDKLI |
| EGFR TCR2 beta chain CDR1 | 467 | DFQATT |
| EGFR TCR2 beta chain CDR2 | 468 | SNEGSKA |
| EGFR TCR2 beta chain CDR3 | 469 | SARRREGEIEQY |
| EGFR TCR2 alpha chain variable domains | 470 | ATGAAGACATTTGCTGGATTTTCGTTCCTGTTTTTGTGGCTGCAGCTGGACTGTATGAGTAGAGGAGAG<br>GATGTGGAGCAGAGTCTTTTCCTGAGTGTCCGAGAGGGAGACAGCTCCGTTATAAACTGCACTTACACA<br>GACAGCTCCTCCACCTACTTATACTGGTATAAGCAAGAACCTGGAGCAGGTCTCCAGTTGCTGACGTAT<br>ATTTTTTCAAATATGGACATGAAAACAAGACCAAAGACTCACTGTTCTATTGAATAAAAAGGATAAACAT<br>CTGTCTCTGCGCATTCAGACACCCAGACTGGGGACTCAGCTATCTACTTCTGTGCAGAGTGGGCTAAC<br>ACCGACAAGCTCATCTTTGGGACTGGGACCAGATTACAAGTCTTTCCA |
| | 471 | ATGAAGACCTTCGCCGGCTTCTCCTTTCTGTTCCTGTGGCTGCAGCTGGACTGCATGAGCCGGGGAGAG<br>GATGTGGAGCAGTCCCTGTTCCTGTCTGTGAGGGAGGGCGACTCCTCTGTGATCAACTGTACATATACC<br>GATAGCTCCTCTACCTACCTGTATTGGTACAAGCAGGAGCCAGGAGCAGGACTGCAGCTGCTGACATAC |

TABLE 2-continued

SEQUENCES

| Name | SEQ ID NO | Sequence |
|---|---|---|
| | | ATCTTTAGCAACATGGACATGAAGCAGGATCAGCGCCTGACCGTGCTGCTGAATAAGAAGGACAAGCAC<br>CTGTCTCTGCGGATCGCCGACACACAGACCGGCGATAGCGCCATCTACTTCTGTGCCGAGTGGGCCAAT<br>ACCGATAAGCTGATCTTTGGCACAGGCACCCGGCTGCAGGTGTTCCCT |
| | 472 | MKTFAGFSFLFLWLQLDCMSRGEDVEQSLFLSVREGDSSVINCTYTDSSSTYLYWYKQEPGAGLQLLTY<br>IFSNMDMKQDQRLTVLLNKKDKHLSLRIADTQTGDSAIYFCAEWANTDKLIFGTGTRLQVFP |
| EGFR TCR2 beta chain variable domains | 473 | ATGCTGCTGCTTCTGCTGCTTCTGGGGCCAGGCTCCGGGCTTGGTGCTGTCGTCTCTCAACATCCGAGC<br>TGGGTTATCTGTAAGAGTGGAACCTCTGTGAAGATCGAGTGCCGTTCCCTGGACTTTCAGGCCACAACT<br>ATGTTTTGGTATCGTCAGTTCCCGAAACAGAGTCTCATGCTGATGGCAACTTCCAATGAGGGCTCCAAG<br>GCCACATACGAGCAAGGCGTCGAGAAGGACAAGTTTCTCATCAACCATGCAAGCCTGACCTTGTCCACT<br>CTGACAGTGACCAGTGCCCATCCTGAAGACAGCAGCTTCTACATCTGCAGTGCTAGAAGGCGGGAGGGG<br>GAGATCGAGCAGTACTTCGGGCCGGGCACCAGGCTCACGGTCACA |
| | 474 | ATGTTATTACTGCTGCTGCTGGGACCAGGCTCCGGACTGGGAGCCGTGGTGTCCCAGCACCCTTCT<br>TGGGTCATCTGCAAGTCCGGCACATCTGTGAAGATCGAGTGTCGCTCTCTGGACTTTCAGGCCACCACA<br>ATGTTTTGGTATCGGCAGTTCCCCAAGCAGAGCCTGATGCTGATGGCCACAAGCAACGAGGGCTCCAAG<br>GCCACCTACGAGCAGGGCGTGGAGAAGGACAAGTTCCTGATCAATCACGCCTCTCTGACCCTGAGCACC<br>CTGACAGTGACCTCCGCCCACCCTGAGGATAGCTCCTTTTATATCTGCTCTGCCCGGAGAAGGGAGGGC<br>GAGATCGAGCAGTACTTCGGCCCAGGCACAAGACTGACAGTGACC |
| | 475 | MLLLLLLLGPGSGLGAVVSQHPSWVICKSGTSVKIECRSLDFQATTMFWYRQFPKQSLMLMATSNEGSK<br>ATYEQGVEKDKFLINHASLTLSTLTVTSAHPEDSSFYICSARRREGEIEQYFGPGTRLTVT |
| EGFR TCR2 alpha chain | 476 | MKTFAGFSFLFLWLQLDCMSRGEDVEQSLFLSVREGDSSVINCTYTDSSSTYLYWYKQEPGA<br>GLQLLTYIFSNMDMKQDQRLTVLLNKKDKHLSLRIADTQTGDSAIYFCAEWANTDKLIFGTG<br>TRLQVFPDIQNPEPAVYQLKDPRSQDSTLCLFTDFDSQINVPKTMESGTFITDKTVLDMKAM<br>DSKSNGAIAWSNQTSFTCQDIFKETNATYPSSDVPCDATLTEKSFETDMNLNFQNLSVMGLR<br>ILLLKVAGFNLLMTLRLWSS |
| EGFR TCR2 beta chain | 477 | MLLLLLLLGPGSGLGAVVSQHPSWVICKSGTSVKIECRSLDFQATTMFWYRQFPKQSLMLMA<br>TSNEGSKATYEQGVEKDKFLINHASLTLSTLTVTSAHPEDSSFYICSARRREGEIEQYFGPG<br>TRLTVTKDLRNVTPPKVSLFEPSKAEIANKQKATLVCLARGFFPDHVELSWWVNGKEVHSGV<br>STDPQAYKESNYSYCLSSRLRVSATFWHNPRNHFRCQVQFHGLSEEDKWPEGSPKPVTQNIS<br>AEAWGRADCGITSASYHQGVLSATILYEILLGKATLYAVLVSGLVLMAMVKKKNS |
| Peptides | 478 | QLIMQLMPF |
| | 479 | LIMQLMPFGC |
| | 480 | MQLMPFGCLL |
| EGFR TCR3 alpha chain CDR1 | 481 | TRDTTYY |
| EGFR TCR3 alpha chain CDR2 | 482 | RNSFDEQN |
| EGFR TCR3 alpha chain CDR3 | 483 | ALTPFPNAGGTSYGKLT |
| EGFR TCR3 beta chain CDR1 | 484 | SGHNS |
| EGFR TCR3 beta chain CDR2 | 485 | FNNNVP |
| EGFR TCR3 beta chain CDR3 | 486 | ASSLAYLTGRVEAF |
| EGFR TCR3 alpha chain variable domains | 487 | ATGCTGACTGCCAGCCTGTTGAGGGCAGTCATAGCCTCCATCTGTGTTGTATCCAGCATGGCTCAGAAG<br>GTAACTCAAGCGCAGACTGAAATTTCTGTGGTGGAGAAGGAGGATGTGACCTTGGACTGTGTGTATGAA<br>ACCCGTGATACTACTTATTACTTATTCTGGTACAAGCAACCACCAAGTGGAGAATTGGTTTTCCTTATT<br>CGTCGGAACTCTTTTGATGAGCAAAATGAAATAAGTGGTCGGTATTCTTGGAACTTCCAGAAATCCACC<br>AGTTCCTTCAACTTCACCATCACAGCCTCACAAGTCGTGGACTCAGCAGTATACTTCTGTGCTCTGACT<br>CCCTTCCCCAATGCTGGTGGTACTAGCTATGGAAAGCTGACATTTGGACAAGGGACCATCTTGACTGTC<br>CATCCA |
| | 488 | ATGCTGACAGCCTCTCTGCTGAGGGCCGTGATCGCCAGCATCTGCGTGGTGTCCTCTATGGCCCAGAAG<br>GTGACCCAGGCCCAGACAGAGATCAGCGTGGTGGAGAAGGAGGACGTGACCCTGGATTGCGTGTACGAG<br>ACACGGGACACCACATACTATCTGTTCTGGTATAAGCAGCCACCCTCCGGCGAGCTGGTGTTCCTGATC<br>AGGCGCAATTCTTTTGATGAGCAGAACGAGATCTCTGGCAGATACAGCTGGAATTTTCAGAAGTCTACC |

TABLE 2-continued

SEQUENCES

| Name | SEQ ID NO | Sequence |
|---|---|---|
| | | AGCTCCTTCAACTTTACCATCACAGCCTCTCAGGTGGTGGATAGCGCCGTGTACTTCTGTGCCCTGACA<br>CCATTTCCCAATGCCGGCGGCACCAGCTATGGCAAGCTGACATTCGGCCAGGGCACCATCCTGACAGTG<br>CACCCT |
| | 489 | MLTASLLRAVIASICVVSSMAQKVTQAQTEISVVEKEDVTLDCVYETRDTTYYLFWYKQPPSGELVFLI<br>RRNSFDEQNEISGRYSWNFQKSTSSFNFTITASQVVDSAVYFCALTPFPNAGGTSYGKLTFGQGTILTV<br>HP |
| EGFR TCR3 beta chain variable domains | 490 | ATGGACTCCTGGACCTTCTGCTGTGTGTCCCTTTGCATCCTGGTAGCGAAGCATACAGATGCTGGAGTT<br>ATCCAGTCACCCCGCCATGAGGTGACAGAGATGGGACAAGAAGTGACTCTGAGATGTAAACCAATTTCA<br>GGCCACAACTCCCTTTTCTGGTACAGACAGACCATGATGCGGGGACTGGAGTTGCTCATTTACTTTAAC<br>AACAACGTTCCGATAGATGATTCAGGGATGCCCGAGGATGCTTCAGCTAAGATGCCTAATGCATCA<br>TTCTCCACTCTGAAGATCCAGCCCTCAGAACCCAGGGACTCAGCTGTGTACTTCTGTGCCAGCAGTTTA<br>GCCTACCTGACAGGGAGGGTTGAAGCTTTCTTTGGACAAGGCACCAGACTCACAGTTGTA |
| | 491 | ATGGACTCCTGGACCTTCTGCTGCGTGAGCCTGTGCATCCTGGTGGCCAAGCACACAGATGCAGGCGTG<br>ATCCAGTCCCCAAGGCACGAGGTGACCGAGATGGGACAGGAGGTGACACTGAGGTGTAAGCCCATCAGC<br>GGCCACAATTCCCTGTTCTGGTACCGGCAGACCATGATGAGAGGCCTGGAGCTGCTGATCTACTTCAAC<br>AATAACGTGCCCATCGACGATAGCGGCATGCCTGAGGACCGGTTCTCCGCCAAGATGCCCAACGCCTCT<br>TTTAGCACCCTGAAGATCCAGCCTTCCGAGCCAAGGGATTCTGCCGTGTACTTCTGCGCCAGCTCCCTG<br>GCCTATCTGACCGGAAGGGTGGAGGCCTTCTTTGGACAGGGCACCAGGCTGACAGTGGTG |
| | 492 | MDSWTFCCVSLCILVAKHTDAGVIQSPRHEVTEMGQEVTLRCKPISGHNSLFWYRQTMMRGLELLIYFN<br>NNVPIDDSGMPEDRFSAKMPNASFSTLKIQPSEPRDSAVYFCASSLAYLTGRVEAFFGQGTRLTVV |
| EGFR TCR3 alpha chain | 493 | MLTASLLRAVIASICVVSSMAQKVTQAQTEISVVEKEDVTLDCVYETRDTTYYLFWYKQPPS<br>GELVFLIRRNSFDEQNEISGRYSWNFQKSTSSFNFTITASQVVDSAVYFCALTPFPNAGGTS<br>YGKLTFGQGTILTVHPDIQNPEPAVYQLKDPRSQDSTLCLFTDFDSQINVPKTMESGTFITD<br>KTVLDMKAMDSKSNGAIAWSNQTSFTCQDIFKETNATYPSSDVPCDATLTEKSFETDMNLNF<br>QNLSVMGLRILLLKVAGFNLLMTLRLWSS |
| EGFR TCR3 beta chain | 494 | MDSWTFCCVSLCILVAKHTDAGVIQSPRHEVTEMGQEVTLRCKPISGHNSLFWYRQTMMRGL<br>ELLIYFNNNVPIDDSGMPEDRFSAKMPNASFSTLKIQPSEPRDSAVYFCASSLAYLTGRVEA<br>FFGQGTRLTVVKDLRNVTPPKVSLFEPSKAEIANKQKATLVCLARGFFPDHVELSWWVNGKE<br>VHSGVSTDPQAYKESNYSYCLSSRLRVSATFWHNPRNHFRCQVQFHGLSEEDKWPEGSPKPV<br>TQNISAEAWGRADCGITSASYHQGVLSATILYEILLGKATLYAVLVSGLVLMAMVKKKNS |
| Peptides | 495 | QLIMQLMPF |
| | 496 | LIMQLMPFGC |
| | 497 | MQLMPFGCLL |
| EGFR TCR4 alpha chain CDR1 | 498 | TRDTTYY |
| EGFR TCR4 alpha chain CDR2 | 499 | RNSFDEQN |
| EGFR TCR4 alpha chain CDR3 | 500 | ALIRGSYQLI |
| EGFR TCR4 beta chain CDR1 | 501 | DFQATT |
| EGFR TCR4 beta chain CDR2 | 502 | SNEGSKA |
| EGFR TCR4 beta chain CDR3 | 503 | SAQGSSGRIEQF |
| EGFR TCR4 alpha chain variable domains | 504 | ATGCTGACTGCCAGCCTGTTGAGGGCAGTCATAGCCTCCATCTGTGTTGTATCCAGCATGGCTCAGAAG<br>GTAACTCAAGCGCAGACTGAAATTTCTGTGGTGGAGAAGGAGGATGTGACCTTGGACTGTGTGTATGAA<br>ACCCGTGATACTACTTATTACTTATTCTGGTACAAGCAACCACCAAGTGGAGAATTGGTTTTCCTTATT<br>CGTCGGAACTCTTTTGATGAGCAAAATGAAATAAGTGGTCGGTATTCTTGGAACTTCCAGAAATCCACC<br>AGTTCCTTCAACTTCACCATCACAGCCTCACAAGTCGTGGACTCAGCAGTATACTTCTGTGCTCTGATT<br>CGAGGGGAGCTATCAGTTAATCTGGGGCGCTGGGACCAAGCTAATTATAAAGCCA |
| | 505 | ATGCTGACCGCCTCTCTGCTGAGGGCCGTGATCGCCAGCATCTGCGTGGTGAGCTCCATGGCCCAGAAG<br>GTGACACAGGCCCAGACCGAGATCAGCGTGGTGGAAGGAGGACGTGACACTGGATTGCGTGTACGAG<br>ACCCGCGACACCACATACTATCTGTTTTGGTATAAGCAGCCACCCTCCGGCGAGCTGGTGTTCCTGATC<br>AGGCGCAACTCTTTTGATGAGCAGAATGAGATCTCTGGCCGGTACAGCTGGAACTTCCAGAAGAGCACA |

TABLE 2-continued

SEQUENCES

| Name | SEQ ID NO | Sequence |
|---|---|---|
| | | TCTAGCTTCAACTTCACCATCACCGCCAGCCAGGTGGTGGACTCCGCCGTGTACTTTTGTGCCCTGATC AGAGGCTCCTATCAGCTGATCTGGGGCGCCGGCACCAAGCTGATCATCAAGCCC |
| | 506 | MLTASLLRAVIASICVVSSMAQKVTQAQTEISVVEKEDVTLDCVYETRDTTYYLFWYKQPPSGELVFLI RRNSFDEQNEISGRYSWNFQKSTSSFNFTITASQVVDSAVYFCALIRGSYQLIWGAGTKLIIKP |
| EGFR TCR4 beta chain variable domains | 507 | ATGCTGCTGCTTCTGCTGCTTCTGGGGCCAGGCTCCGGGCTTGGTGCTGTCGTCTCTCAACATCCGAGC AGGGTTATCTGTAAGAGTGGAACCTCTGTGAAGATCGAGTGCCGTTCCCTGGACTTTCAGGCCACAACT ATGTTTTGGTATCGTCAGTTCCCGAAACAGAGTCTCATGCTGATGGCAACTTCCAATGAGGGCTCCAAG GCCACATACGAGCAAGGCGTCGAGAAGGACAAGTTTCTCATCAACCATGCAAGCCTGACCTTGTCCACT CTGACAGTGACCAGTGCCCATCCTGAAGACAGCAGCTTCTACATCTGCAGCGCCCAGGGGAGTAGCGGG AGGATTGAGCAGTTCTTCGGGCCAGGGACACGGCTCACCGTGCTA |
| | 508 | ATGTTATTACTGCTGCTGCTGCTGGGACCAGGCTCCGGACTGGGAGCAGTGGTGTCTCAGCACCCAAGC AGAGTGATCTGCAAGTCTGGCACCAGCGTGAAGATCGAGTGTAGGTCCCTGGACTTCCAGGCCACCACA ATGTTCTGGTACCGCCAGTTTCCAAAGCAGTCTCTGATGCTGATGGCCACATCCAACGAGGGCTCTAAG GCCACCTATGAGCAGGGCGTGGAGAAGGACAAGTTCCTGATCAATCACGCCAGCCTGACCCTGTCCACC CTGACAGTGACCAGCGCCCACCCAGAGGATAGCTCCTTTTACATCTGCTCCGCCCAGGGCTCTAGCGGC CGGATCGAGCAGTTCTTTGGCCCTGGCACACGGCTGACCGTGCTG |
| | 509 | MLLLLLLLGPGSGLGAVVSQHPSRVICKSGTSVKIECRSLDFQATTMFWYRQFPKQSLMLMATSNEGSK ATYEQGVEKDKFLINHASLTLSTLTVTSAHPEDSSFYICSAQGSSGRIEQFFGPGTRLTVL |
| EGFR TCR4 alpha chain | 510 | MLTASLLRAVIASICVVSSMAQKVTQAQTEISVVEKEDVTLDCVYETRDTTYYLFWYKQPPS GELVFLIRRNSFDEQNEISGRYSWNFQKSTSSFNFTITASQVVDSAVYFCALIRGSYQLIWG AGTKLIIKPDIQNPEPAVYQLKDPRSQDSTLCLFTDFDSQINVPKTMESGTFITDKTVLDMK AMDSKSNGAIAWSNQTSFTCQDIFKETNATYPSSDVPCDATLTEKSFETDMNLNFQNLSVMG LRILLLKVAGFNLLMTLRLWSS |
| EGFR TCR4 beta chain | 511 | MLLLLLLLGPGSGLGAVVSQHPSRVICKSGTSVKIECRSLDFQATTMFWYRQFPKQSLMLMA TSNEGSKATYEQGVEKDKFLINHASLTLSTLTVTSAHPEDSSFYICSAQGSSGRIEQFFGPG TRLTVLKDLRNVTPPKVSLFEPSKAEIANKQKATLVCLARGFFPDHVELSWWVNGKEVHSGV STDPQAYKESNYSYCLSSRLRVSATFWHNPRNHFRCQVQFHGLSEEDKWPEGSPKPVTQNIS AEAWGRADCGITSASYHQGVLSATILYEILLGKATLYAVLVSGLVLMAMVKKNS |
| Peptides | 512 | QLIMQLMPF |
| | 513 | LIMQLMPFGC |
| | 514 | MQLMPFGCLL |
| EGFR TCR5 alpha chain CDR1 | 515 | DSVNN |
| EGFR TCR5 alpha chain CDR2 | 516 | IPSGT |
| EGFR TCR5 alpha chain CDR3 | 517 | AVMDSSYKLI |
| EGFR TCR5 beta chain CDR1 | 518 | DFQATT |
| EGFR TCR5 beta chain CDR2 | 510 | SNEGSKA |
| EGFR TCR5 beta chain CDR3 | 520 | SALPGFSYEQY |
| EGFR TCR5 alpha chain variable domains | 521 | ATGAAGAGGATATTGGGAGCTCTGCTGGGGCTCTTGAGTGCCCAGGTTTGCTGTGTGAGAGGAATACAA GTGGAGCAGAGTCCTCCAGACCTGATTCTCCAGGAGGGAGCCAATTCCACGCTGCGGTGCAATTTTTCT GACTCTGTGAACAATTTGCAGTGGTTTCATCAAAACCCTTGGGGACAGCTCATCAACCTGTTTTACATT CCCTCAGGGACAAAACAGAATGGAAGATTAAGCGCCACGACTGTCGCTACGGAACGCTACAGCTTATTG TACATTTCCTCTTCCCAGACCACAGACTCAGGCGTTTATTTCTGTGCTGTGATGGATAGCAGCTATAAA TTGATCTTCGGGAGTGGGACCAGACTGCTGGTCAGGCCT |
| | 522 | ATGAAGAGAATCCTGGGCGCCCTGCTGGGACTGCTGTCCGCCCAGGTGTGCTGCGTGCGGGGCATCCAG GTGGAGCAGAGCCCACCAGACCTGATCCTGCAGGAGGGAGCCAACTCCACCCTGAGATGCAATTTCTCC GATTCTGTGAACAATCTGCAGTGGTTTCACCAGAACCCTTGGGGCCAGCTGATCAATCTGTTTTACATC CCATCCGGCACAAAGCAGAACGGCAGGCTGTCTGCCACCACAGTGGCCACCGAGCGGTACTCTCTGCTG TATATCTCCTCTAGCCAGACCACAGACAGCGGCGTGTACTTCTGTGCCGTGATGGATTCCTCTTATAAG CTGATCTTTGGCAGCGGCACCAGGCTGCTGGTGCGCCCT |

TABLE 2-continued

SEQUENCES

| Name | SEQ ID NO | Sequence |
|---|---|---|
| | 523 | MKRILGALLGLLSAQVCCVRGIQVEQSPPDLILQEGANSTLRCNFSDSVNNLQWFHQNPWGQLINLFYI PSGTKQNGRLSATTVATERYSLLYISSSQTTDSGVYFCAVMDSSYKLIFGSGTRLLVRP |
| EGFR TCR5 beta chain variable domains | 524 | ATGCTGCTGCTTCTGCTGCTTCTGGGGCCAGGCTCCGGGCTTGGTGCTGTCGTCTCTCAACATCCGAGC TGGGTTATCTGTAAGAGTGGAACCTCTGTGAAGATCGAGTGCCGTTCCCTGGACTTTCAGGCCACAACT ATGTTTTGGTATCGTCAGTTCCCGAAACAGAGTCTCATGCTGATGGCAACTTCCAATGAGGGCTCCAAG GCCACATACGAGCAAGGCGTCGAGAAGGACAAGTTTCTCATCAACCATGCAAGCCTGACCTTGTCCACT CTGACAGTGACCAGTGCCCATCCTGAAGACAGCAGCTTCTACATCTGCAGTGCTCTGCCCGGATTCTCC TACGAGCAGTACTTCGGGCCGGGCACCAGGCTCACGGTCACA |
| | 525 | ATGTTATTACTGCTGCTGCTGCTGGGACCAGGCAGCGGACTGGGAGCAGTGGTGAGCCAGCACCCTTCC TGGGTCATCTGCAAGAGCGGCACATCCGTGAAGATCGAGTGTCGGTCTCTGGACTTCCAGGCCACCACA ATGTTCTGGTACAGACAGTTTCCTAAGCAGTCCCTGATGCTGATGGCCACATCTAACGAGGGCAGCAAG GCCACCTATGAGCAGGGCGTGGAGAAGGACAAGTTCCTGATCAATCACGCCTCCCTGACCCTGTCTACC CTGACAGTGACCTCCGCCCACCCAGAGGATAGCTCCTTTTACATCTGCTCTGCCCTGCCAGGCTTCAGC TACGAGCAGTATTTTGGCCCCGGCACACGGCTGACAGTGACC |
| | 526 | MLLLLLLLGPGSGLGAVVSQHPSWVICKSGTSVKIECRSLDFQATTMFWYRQFPKQSLMLMATSNEGSK ATYEQGVEKDKFLINHASLTLSTLTVTSAHPEDSSFYICSALPGFSYEQYFGPGTRLTVT |
| EGFR TCR5 alpha chain | 527 | MKRILGALLGLLSAQVCCVRGIQVEQSPPDLILQEGANSTLRCNFSDSVNNLQWFHQNPWGQ LINLFYIPSGTKQNGRLSATTVATERYSLLYISSSQTTDSGVYFCAVMDSSYKLIFGSGTRL LVRPDIQNPEPAVYQLKDPRSQDSTLCLFTDFDSQINVPKTMESGTFITDKTVLDMKAMDSK SNGAIAWSNQTSFTCQDIFKETNATYPSSDVPCDATLTEKSFETDMNLNFQNLSVMGLRILL LKVAGFNLLMTLRLWSS |
| EGFR TCR5 beta chain | 528 | MLLLLLLLGPGSGLGAVVSQHPSWVICKSGTSVKIECRSLDFQATTMFWYRQFPKQSLMLMA TSNEGSKATYEQGVEKDKFLINHASLTLSTLTVTSAHPEDSSFYICSALPGFSYEQYFGPGT RLTVTKDLRNVTPPKVSLFEPSKAEIANKQKATLVCLARGFFPDHVELSWWVNGKEVHSGVS TDPQAYKESNYSYCLSSRLRVSATFWHNPRNHFRCQVQFHGLSEEDKWPEGSPKPVTQNISA EAWGRADCGITSASYHQGVLSATILYEILLGKATLYAVLVSGLVLMAMVKKKNS |
| Peptides | 529 | QLIMQLMPF |
| | 530 | LIMQLMPFGC |
| | 531 | MQLMPFGCLL |

EMBODIMENTS

The following embodiments are contemplated within the disclosure:

1. A nucleic acid encoding at least one T cell receptor (TCR) comprising a TCR alpha chain construct and/or TCR beta chain construct capable of specifically binding to an epitope from RAS in complex with a human MHC, wherein the TCR alpha chain construct comprises a complementarity determining region 3 (CDR3) having at least 84% sequence identity to or 100% sequence identity to an amino acid sequence selected from SEQ ID NOs: 3, 18, 33, 49, 65, 81, 97, 113, 241, 257, 273, 289, 305, 321, 337, 353, 369, 385, 401, 417, 534, 547 and 560 and/or wherein the TCR beta chain construct comprises a complementarity determining region 3 (CDR3) having at least 84% sequence identity to or 100% sequence identity to an amino acid sequence selected from SEQ ID NOs: 6, 21, 36, 52, 68, 84, 100, 116, 244, 260, 276, 292, 308, 324, 340, 356, 372, 388, 404, 420, 537, 550, and 563.
2. A nucleic acid encoding at least one T cell receptor (TCR) comprising a TCR alpha chain construct and/or TCR beta chain construct capable of specifically binding to an epitope from RAS in complex with a human MHC, wherein the epitope from RAS comprises a region having at least 70% sequence identity to or 100% sequence identity to an amino acid sequence selected from SEQ ID NOs: 15, 30, 45, 46, 61, 62, 77, 78, 93, 94, 109, 110, 125, 126, 219-222, 253, 254, 269, 270, 285, 286, 301, 302, 317, 318, 333, 334, 349, 350, 365, 366, 381, 382, 397, 398, 413, 414, 429, 430, 544, 557 and 600.
3. A nucleic acid or a cell comprising a recombinant nucleic acid, wherein the nucleic acid encodes at least one T cell receptor (TCR) comprising
   a. a TCR alpha chain construct and/or
   b. a TCR beta chain construct
   wherein the TCR specifically binds to an epitope from RAS in complex with a human MHC encoded by an HLA-A03:01 allele.
4. A nucleic acid or a cell comprising a recombinant nucleic acid, wherein the nucleic acid encodes at least one T cell receptor (TCR) comprising
   a. a TCR alpha chain construct and/or
   b. a TCR beta chain construct
   wherein the TCR specifically binds to an epitope from RAS in complex with a human MHC encoded by an HLA-A02:01 allele.
5. A nucleic acid or a cell comprising a recombinant nucleic acid, wherein the nucleic acid encodes at least one T cell receptor (TCR) comprising
   a. a TCR alpha chain construct and/or
   b. a TCR beta chain construct
   wherein the TCR specifically binds to an epitope from RAS in complex with a human MHC encoded by an HLA-A11:01 allele.

6. The nucleic acid of the embodiment in paragraph 3, wherein the TCR alpha chain construct comprises a variable region having at least 80%, or at least 90%, or 100% sequence identity to an amino acid sequence selected from SEQ ID NOs: 71, 87, 103, 295, 311, 327, 343, 359 and 391.
7. The nucleic acid of embodiment in paragraph 4, wherein the TCR alpha chain construct comprises a variable region having at least 80%, or at least 90%, or 100% sequence identity to an amino acid sequence selected from SEQ ID NOs: 9 and 24.
8. The nucleic acid of embodiment in paragraph 5, wherein the TCR alpha chain construct comprises a variable region having at least 80%, or at least 90%, or 100% sequence identity to an amino acid sequence selected from SEQ ID NOs:39, 55, 119, 247, 263, 279, 375, 407, 423, 539, 552, and 565.
9. The nucleic acid of embodiment in paragraph 3, wherein the TCR beta chain construct comprises a variable region having at least 80%, or at least 90%, or 100% sequence identity to an amino acid sequence selected from SEQ ID NOs: 74, 90, 106, 298, 314, 330, 346, 362 and 394.
10. The nucleic acid of embodiment 4, wherein the TCR beta chain construct comprises a variable region having at least 80%, or at least 90%, or 100% sequence identity to an amino acid sequence selected from SEQ ID NOs: 12 and 27.
11. The nucleic acid of embodiment 5, wherein the TCR beta chain construct comprises a variable region having at least 80%, or at least 90%, or 100% sequence identity to an amino acid sequence selected from SEQ ID NOs: 42, 58, 122, 250, 266, 282, 378, 410, 426, 541, 554, and 567.
12. The nucleic acid of the embodiments any one of the embodiments in paragraphs 1-3, and 6, wherein the TCR alpha chain construct comprises a complementarity determining region 1 (CDR1) having at least 90% sequence identity to or 100% sequence identity to an amino acid sequence selected from SEQ ID NOs: 63, 79, 95, 287, 303, 319, 335, 351 and 383.
13. The nucleic acid of the embodiments any one of the embodiments in paragraphs 1-3, and 6, wherein the TCR beta chain construct comprises a complementarity determining region 1 (CDR1) having at least 90% sequence identity to or 100% sequence identity to an amino acid sequence selected from SEQ ID NOs: 66, 82, 98, 290, 306, 322, 338, 354 and 386.
14. The nucleic acid of any one of the embodiments in paragraphs 1-2, 4 and 7, wherein the TCR alpha chain construct comprises a complementarity determining region 1 (CDR1) having at least 90% sequence identity to or 100% sequence identity to an amino acid sequence selected from SEQ ID NOs: 1 and 16.
15. The nucleic acid of any one of the embodiments in paragraphs 1-2, 4 and 10, wherein the TCR beta chain construct comprises a complementarity determining region 1 (CDR1) having at least 90% sequence identity to or 100% sequence identity to an amino acid sequence selected from SEQ ID NOs: 4 and 19.
16. The nucleic acid of any one of the embodiments in paragraphs 1-2, 5 and 8, wherein the TCR alpha chain construct comprises a complementarity determining region 1 (CDR1) having at least 90% sequence identity to or 100% sequence identity to an amino acid sequence selected from SEQ ID NOs: 31, 47, 111, 239, 255, 271, 367, 399, 415, 532, 545 and 558.
17. The nucleic acid of any one of the embodiments in paragraphs 1-2, 5 and 11, wherein the TCR beta chain construct comprises a complementarity determining region 1 (CDR1) having at least 90% sequence identity to or 100% sequence identity to an amino acid sequence selected from SEQ ID NOs:34, 50, 114, 242, 258, 274, 370, 402, 418, 53, 548 and 561.
18. The nucleic acid of the embodiments any one of the embodiments in paragraphs 1-3, 6, and 12, wherein the TCR alpha chain construct comprises a complementarity determining region 2 (CDR2) having at least 90% sequence identity to or 100% sequence identity to an amino acid sequence selected from SEQ ID NOs: 64, 80, 96, 288, 304, 320, 336, 352 and 384.
19. The nucleic acid of any one of the embodiments in paragraphs 1-3, 6, and 13 wherein the TCR beta chain construct comprises a complementarity determining region 2 (CDR2) having at least 90% sequence identity to or 100% sequence identity to an amino acid sequence selected from SEQ ID NOs: 67, 83, 99, 291, 307, 323, 339, 355 and 387.
20. The nucleic acid of the embodiments any one of the embodiments in paragraphs 1-2, 4, 7 and 14, wherein the TCR alpha chain construct comprises a complementarity determining region 2 (CDR2) having at least 90% sequence identity to or 100% sequence identity to an amino acid sequence selected from SEQ ID NOs: 2 and 17.
21. The nucleic acid of any one of the embodiments in paragraphs 1-2, 4, 10 and 15, wherein the TCR beta chain construct comprises a complementarity determining region 2 (CDR2) having at least 90% sequence identity to or 100% sequence identity to an amino acid sequence selected from SEQ ID NOs: 5 and 20.
22. The nucleic acid of any one of the embodiments in paragraphs 1-2, 5, 8, and 16 wherein the TCR alpha chain construct comprises a complementarity determining region 2 (CDR2) having at least 90% sequence identity to or 100% sequence identity to an amino acid sequence selected from SEQ ID NOs: 32, 48, 112, 240, 256, 272, 368, 400, 416, 533, 546, and 559.
23. The nucleic acid of any one of the embodiments in paragraphs 1-2, 5, 11 and 17 wherein the TCR beta chain construct comprises a complementarity determining region 2 (CDR2) having at least 90% sequence identity to or 100% sequence identity to an amino acid sequence selected from SEQ ID NOs: 35, 51, 115, 243, 259, 275, 371, 403, 419, 536, 549, and 562.
24. The nucleic acid of the embodiments any one of the in paragraphs 1-3, 6, 12 and 18 wherein the TCR alpha chain construct comprises a complementarity determining region 3 (CDR3) having at least 90% sequence identity to or 100% sequence identity to an amino acid sequence selected from SEQ ID NOs: 65, 81, 97, 289, 305, 321, 337, 353 and 385.
25. The nucleic acid of any one of the embodiments in paragraphs 1-3, 6, 13 and 19 wherein the TCR beta chain construct comprises a complementarity determining region 3 (CDR3) having at least 90% sequence identity to or 100% sequence identity to an amino acid sequence selected from SEQ ID NOs: 68, 84, 100, 292, 308, 324, 340, 356 and 388.
26. The nucleic acid of the embodiments any one of the embodiments 1-2, 4, 7 14 and 20 wherein the TCR alpha chain construct comprises a complementarity determining region 3 (CDR3) having at least 90% sequence identity to or 100% sequence identity to an amino acid sequence selected from SEQ ID NOs: 3 and 18.

27. The nucleic acid of any one of the embodiments in paragraphs 1-2, 4, 10, 15 and 21 wherein the TCR beta chain construct comprises a complementarity determining region 3 (CDR3) having at least 90% sequence identity to or 100% sequence identity to an amino acid sequence selected from SEQ ID NOs: 6 and 21.

28. The nucleic acid of any one of the embodiments in paragraphs 1-2, 5, 8, 16 and 22 wherein the TCR alpha chain construct comprises a complementarity determining region 3 (CDR3) having at least 90% sequence identity to or 100% sequence identity to an amino acid sequence selected from SEQ ID NOs:33, 49, 113, 241, 257, 273, 369, 401, 417, 534, 547, and 560.

29. The nucleic acid of any one of the embodiments in paragraphs 1-2, 5, 11, 17 and 23 wherein the TCR beta chain construct comprises a complementarity determining region 3 (CDR3) having at least 90% sequence identity to or 100% sequence identity to an amino acid sequence selected from SEQ ID NOs:36, 52, 116, 244, 260, 276, 372, 404, 420, 537, 550, and 563.

30. The nucleic acid of any one of the embodiments in paragraphs 1-5, wherein
    a. the TCR alpha chain construct comprises a variable region having at least 80% sequence identity to or 100% sequence identity to SEQ ID NO: 9; and
    b. the TCR beta chain construct comprises a variable region having at least 80% sequence identity to or 100% sequence identity to SEQ ID NO: 12.

31. The nucleic acid of any one of the embodiments in paragraphs 1-5 or 30, wherein
    a. the TCR alpha chain construct comprises
        i. a CDR1 of SEQ ID NO: 1,
        ii. a CDR2 of SEQ ID NO: 2, and
        iii. a CDR3 of SEQ ID NO: 3; and
    b. the TCR beta chain construct comprises
        i. a CDR1 of SEQ ID NO: 4,
        ii. a CDR2 of SEQ ID NO: 5, and
        iii. a CDR3 of SEQ ID NO: 6.

32. The nucleic acid of any one of the embodiments in paragraphs 1-5, wherein
    a. the TCR alpha chain construct comprises a variable region having at least 80% sequence identity to or 100% sequence identity to SEQ ID NO: 24; and
    b. the TCR beta chain construct comprises a variable region having at least 80% sequence identity to or 100% sequence identity to SEQ ID NO: 27.

33. The nucleic acid of any one of the embodiments in paragraphs 1-5 and 32, wherein
    a. the TCR alpha chain construct comprises
        i. a CDR1 of SEQ ID NO: 16,
        ii. a CDR2 of SEQ ID NO: 17, and
        iii. a CDR3 of SEQ ID NO: 18; and
    b. the TCR beta chain construct comprises
        i. a CDR1 of SEQ ID NO: 19,
        ii. a CDR2 of SEQ ID NO: 20, and
        iii. a CDR3 of SEQ ID NO: 21.

34. The nucleic acid of any one of the embodiments in paragraphs 1-5, wherein
    a. the TCR alpha chain construct comprises a variable region having at least 80% sequence identity to or 100% sequence identity to SEQ ID NO: 39; and
    b. the TCR beta chain construct comprises a variable region having at least 80% sequence identity to or 100% sequence identity to SEQ ID NO: 42.

35. The nucleic acid of any one of the embodiments in paragraphs 1-5 and 34, wherein
    a. the TCR alpha chain construct comprises
        i. a CDR1 of SEQ ID NO: 31,
        ii. a CDR2 of SEQ ID NO: 32, and
        iii. a CDR3 of SEQ ID NO: 33; and
    b. the TCR beta chain construct comprises
        i. a CDR1 of SEQ ID NO: 34,
        ii. a CDR2 of SEQ ID NO: 35, and
        iii. a CDR3 of SEQ ID NO: 36.

36. The nucleic acid of any one of the embodiments in paragraphs 1-5, wherein
    a. the TCR alpha chain construct comprises a variable region having at least 80% sequence identity to or 100% sequence identity to SEQ ID NO: 55; and
    b. the TCR beta chain construct comprises a variable region having at least 80% sequence identity to or 100% sequence identity to SEQ ID NO: 58.

37. The nucleic acid of any one of the embodiments in paragraphs 1-5 and 36, wherein
    a. the TCR alpha chain construct comprises
        i. a CDR1 of SEQ ID NO: 47,
        ii. a CDR2 of SEQ ID NO: 48, and
        iii. a CDR3 of SEQ ID NO: 49; and
    b. the TCR beta chain construct comprises
        i. a CDR1 of SEQ ID NO: 50,
        ii. a CDR2 of SEQ ID NO: 51, and
        iii. a CDR3 of SEQ ID NO: 52.

38. The nucleic acid of any one of the embodiments in paragraphs 1-5, wherein
    a. the TCR alpha chain construct comprises a variable region having at least 80% sequence identity to or 100% sequence identity to SEQ ID NO: 71; and
    b. the TCR beta chain construct comprises a variable region having at least 80% sequence identity to or 100% sequence identity to SEQ ID NO: 74.

39. The nucleic acid of any one of the embodiments in paragraphs 1-5 and 38, wherein
    a. the TCR alpha chain construct comprises
        i. a CDR1 of SEQ ID NO: 63,
        ii. a CDR2 of SEQ ID NO: 64, and
        iii. a CDR3 of SEQ ID NO: 65; and
    b. the TCR beta chain construct comprises
        i. a CDR1 of SEQ ID NO: 66,
        ii. a CDR2 of SEQ ID NO: 67, and
        iii. a CDR3 of SEQ ID NO: 68.

40. The nucleic acid of any one of the embodiments in paragraphs 1-5, wherein
    a. the TCR alpha chain construct comprises a variable region having at least 80% sequence identity to or 100% sequence identity to SEQ ID NO: 87; and
    b. the TCR beta chain construct comprises a variable region having at least 80% sequence identity to or 100% sequence identity to SEQ ID NO: 90.

41. The nucleic acid of any one of the embodiments in paragraphs 1-5 and 40, wherein
    a. the TCR alpha chain construct comprises
        i. a CDR1 of SEQ ID NO: 79,
        ii. a CDR2 of SEQ ID NO: 80, and
        iii. a CDR3 of SEQ ID NO: 81; and
    b. the TCR beta chain construct comprises
        i. a CDR1 of SEQ ID NO: 82,
        ii. a CDR2 of SEQ ID NO: 83, and
        iii. a CDR3 of SEQ ID NO: 84.

42. The nucleic acid of any one of the embodiments in paragraphs 1-5, wherein
   a. the TCR alpha chain construct comprises a variable region having at least 80% sequence identity to or 100% sequence identity to SEQ ID NO: 103; and
   b. the TCR beta chain construct comprises a variable region having at least 80% sequence identity to or 100% sequence identity to SEQ ID NO: 106.
43. The nucleic acid of any one of the embodiments in paragraphs 1-5 and 42, wherein
   a. the TCR alpha chain construct comprises
      i. a CDR1 of SEQ ID NO: 95,
      ii. a CDR2 of SEQ ID NO: 96, and
      iii. a CDR3 of SEQ ID NO: 97; and
   b. the TCR beta chain construct comprises
      i. a CDR1 of SEQ ID NO: 98,
      ii. a CDR2 of SEQ ID NO: 99, and
      iii. a CDR3 of SEQ ID NO: 100.
44. The nucleic acid of any one of the embodiments in paragraphs 1-5, wherein
   a. the TCR alpha chain construct comprises a variable region having at least 80% sequence identity to or 100% sequence identity to SEQ ID NO: 119; and
   b. the TCR beta chain construct comprises a variable region having at least 80% sequence identity to or 100% sequence identity to SEQ ID NO: 122.
45. The nucleic acid of any one of the embodiments in paragraphs 1-5 and 44, wherein
   a. the TCR alpha chain construct comprises
      i. a CDR1 of SEQ ID NO: 111,
      ii. a CDR2 of SEQ ID NO: 112, and
      iii. a CDR3 of SEQ ID NO: 113; and
   b. the TCR beta chain construct comprises
      i. a CDR1 of SEQ ID NO: 114,
      ii. a CDR2 of SEQ ID NO: 115, and
      iii. a CDR3 of SEQ ID NO: 116.
46. The nucleic acid of any one of the embodiments 1-5, wherein
   a. the TCR alpha chain construct comprises a variable region having at least 80% sequence identity to or 100% sequence identity to SEQ ID NO: 247; and
   b. the TCR beta chain construct comprises a variable region having at least 80% sequence identity to or 100% sequence identity to SEQ ID NO: 250.
47. The nucleic acid of any one of the embodiments in paragraphs 1-5 and 46, wherein
   a. the TCR alpha chain construct comprises
      i. a CDR1 of SEQ ID NO: 239,
      ii. a CDR2 of SEQ ID NO: 240, and
      iii. a CDR3 of SEQ ID NO: 241; and
   b. the TCR beta chain construct comprises
      i. a CDR1 of SEQ ID NO: 242,
      ii. a CDR2 of SEQ ID NO: 243, and
      iii. a CDR3 of SEQ ID NO: 244.
48. The nucleic acid of any one of the embodiments in paragraphs 1-5, wherein
   a. the TCR alpha chain construct comprises a variable region having at least 80% sequence identity to or 100% sequence identity to SEQ ID NO: 263; and
   b. the TCR beta chain construct comprises a variable region having at least 80% sequence identity to or 100% sequence identity to SEQ ID NO: 266.
49. The nucleic acid of any one of the embodiments in paragraphs 1-5 and 48, wherein
   a. the TCR alpha chain construct comprises
      i. a CDR1 of SEQ ID NO: 255,
      ii. a CDR2 of SEQ ID NO: 256, and
      iii. a CDR3 of SEQ ID NO: 257; and
   b. the TCR beta chain construct comprises
      i. a CDR1 of SEQ ID NO: 258,
      ii. a CDR2 of SEQ ID NO: 259, and
      iii. a CDR3 of SEQ ID NO: 260.
50. The nucleic acid of any one of the embodiments in paragraphs 1-5, wherein
   a. the TCR alpha chain construct comprises a variable region having at least 80% sequence identity to or 100% sequence identity to SEQ ID NO: 279; and
   b. the TCR beta chain construct comprises a variable region having at least 80% sequence identity to or 100% sequence identity to SEQ ID NO: 282.
51. The nucleic acid of any one of the embodiments in paragraphs 1-5 and 50, wherein
   a. the TCR alpha chain construct comprises
      i. a CDR1 of SEQ ID NO: 271,
      ii. a CDR2 of SEQ ID NO: 272, and
      iii. a CDR3 of SEQ ID NO: 273; and
   b. the TCR beta chain construct comprises
      i. a CDR1 of SEQ ID NO: 274,
      ii. a CDR2 of SEQ ID NO: 275, and
      iii. a CDR3 of SEQ ID NO: 276.
52. The nucleic acid of any one of the embodiments in paragraphs 1-5, wherein
   a. the TCR alpha chain construct comprises a variable region having at least 80% sequence identity to or 100% sequence identity to SEQ ID NO: 295; and
   b. the TCR beta chain construct comprises a variable region having at least 80% sequence identity to S or 100% sequence identity to EQ ID NO: 298.
53. The nucleic acid of any one of the embodiments in paragraphs 1-5 and 52, wherein
   a. the TCR alpha chain construct comprises
      i. a CDR1 of SEQ ID NO: 287,
      ii. a CDR2 of SEQ ID NO: 288, and
      iii. a CDR3 of SEQ ID NO: 289; and
   b. the TCR beta chain construct comprises
      i. a CDR1 of SEQ ID NO: 290,
      ii. a CDR2 of SEQ ID NO: 291, and
      iii. a CDR3 of SEQ ID NO: 292.
54. The nucleic acid of any one of the embodiments in paragraphs 1-5, wherein
   a. the TCR alpha chain construct comprises a variable region having at least 80% sequence identity to or 100% sequence identity to SEQ ID NO: 311; and
   b. the TCR beta chain construct comprises a variable region having at least 80% sequence identity to or 100% sequence identity to SEQ ID NO: 314.
55. The nucleic acid of any one of the embodiments in paragraphs 1-5 and 54, wherein
   a. the TCR alpha chain construct comprises
      i. a CDR1 of SEQ ID NO: 303,
      ii. a CDR2 of SEQ ID NO: 304, and
      iii. a CDR3 of SEQ ID NO: 305; and
   b. the TCR beta chain construct comprises
      i. a CDR1 of SEQ ID NO: 306,
      ii. a CDR2 of SEQ ID NO: 307, and
      iii. a CDR3 of SEQ ID NO: 308.
56. The nucleic acid of any one of the embodiments in paragraphs 1-5, wherein
   a. the TCR alpha chain construct comprises a variable region having at least 80% sequence identity to or 100% sequence identity to SEQ ID NO: 327; and
   b. the TCR beta chain construct comprises a variable region having at least 80% sequence identity to or 100% sequence identity to SEQ ID NO: 330.

57. The nucleic acid of any one of the embodiments in paragraphs 1-5 and 56, wherein
   a. the TCR alpha chain construct comprises
      i. a CDR1 of SEQ ID NO: 319,
      ii. a CDR2 of SEQ ID NO: 320, and
      iii. a CDR3 of SEQ ID NO: 321; and
   b. the TCR beta chain construct comprises
      i. a CDR1 of SEQ ID NO: 322,
      ii. a CDR2 of SEQ ID NO: 323, and
      iii. a CDR3 of SEQ ID NO: 324.

58. The nucleic acid of any one of the embodiments in paragraphs 1-5, wherein
   a. the TCR alpha chain construct comprises a variable region having at least 80% sequence identity to or 100% sequence identity to SEQ ID NO: 343; and
   b. the TCR beta chain construct comprises a variable region having at least 80% sequence identity to or 100% sequence identity to SEQ ID NO: 346.

59. The nucleic acid of any one of the embodiments in paragraphs 1-5 and 58, wherein
   a. the TCR alpha chain construct comprises
      i. a CDR1 of SEQ ID NO: 335,
      ii. a CDR2 of SEQ ID NO: 336, and
      iii. a CDR3 of SEQ ID NO: 337; and
   b. the TCR beta chain construct comprises
      i. a CDR1 of SEQ ID NO: 338,
      ii. a CDR2 of SEQ ID NO: 339, and
      iii. a CDR3 of SEQ ID NO: 340.

60. The nucleic acid of any one of the embodiments in paragraphs 1-5, wherein
   a. the TCR alpha chain construct comprises a variable region having at least 80% sequence identity to or 100% sequence identity to SEQ ID NO: 359; and
   b. the TCR beta chain construct comprises a variable region having at least 80% sequence identity to or 100% sequence identity to SEQ ID NO: 361.

61. The nucleic acid of any one of the embodiments in paragraphs 1-5 and 60, wherein
   a. the TCR alpha chain construct comprises
      i. a CDR1 of SEQ ID NO: 351,
      ii. a CDR2 of SEQ ID NO: 352, and
      iii. a CDR3 of SEQ ID NO: 353; and
   b. the TCR beta chain construct comprises
      i. a CDR1 of SEQ ID NO: 354,
      ii. a CDR2 of SEQ ID NO: 355, and
      iii. a CDR3 of SEQ ID NO: 356.

62. The nucleic acid of any one of the embodiments in paragraphs 1-5, wherein
   a. the TCR alpha chain construct comprises a variable region having at least 80% sequence identity to or 100% sequence identity to SEQ ID NO: 375; and
   b. the TCR beta chain construct comprises a variable region having at least 80% sequence identity to or 100% sequence identity to SEQ ID NO: 378.

63. The nucleic acid of any one of the embodiments in paragraphs 1-5 and 62, wherein
   a. the TCR alpha chain construct comprises
      i. a CDR1 of SEQ ID NO: 367,
      ii. a CDR2 of SEQ ID NO: 368, and
      iii. a CDR3 of SEQ ID NO: 369; and
   b. the TCR beta chain construct comprises
      i. a CDR1 of SEQ ID NO: 370,
      ii. a CDR2 of SEQ ID NO: 371, and
      iii. a CDR3 of SEQ ID NO: 372.

64. The nucleic acid of any one of the embodiments in paragraphs 1-5, wherein
   a. the TCR alpha chain construct comprises a variable region having at least 80% sequence identity to or 100% sequence identity to SEQ ID NO: 391; and
   b. the TCR beta chain construct comprises a variable region having at least 80% sequence identity to or 100% sequence identity to SEQ ID NO: 394.

65. The nucleic acid of any one of the embodiments in paragraphs 1-5 and 64, wherein
   a. the TCR alpha chain construct comprises
      i. a CDR1 of SEQ ID NO: 383,
      ii. a CDR2 of SEQ ID NO: 384, and
      iii. a CDR3 of SEQ ID NO: 385; and
   b. the TCR beta chain construct comprises
      i. a CDR1 of SEQ ID NO: 386,
      ii. a CDR2 of SEQ ID NO: 387, and
      iii. a CDR3 of SEQ ID NO: 388.

66. The nucleic acid of any one of the embodiments in paragraphs 1-5, wherein
   a. the TCR alpha chain construct comprises a variable region having at least 80% sequence identity to or 100% sequence identity to SEQ ID NO: 407; and
   b. the TCR beta chain construct comprises a variable region having at least 80% sequence identity to or 100% sequence identity to SEQ ID NO: 410.

67. The nucleic acid of any one of the embodiments in paragraphs 1-5 and 66, wherein
   a. the TCR alpha chain construct comprises
      i. a CDR1 of SEQ ID NO: 399,
      ii. a CDR2 of SEQ ID NO: 400, and
      iii. a CDR3 of SEQ ID NO: 401; and
   b. the TCR beta chain construct comprises
      i. a CDR1 of SEQ ID NO: 402,
      ii. a CDR2 of SEQ ID NO: 403, and
      iii. a CDR3 of SEQ ID NO: 404.

68. The nucleic acid of any one of the embodiments in paragraphs 1-5, wherein
   a. the TCR alpha chain construct comprises a variable region having at least 80% sequence identity to or 100% sequence identity to SEQ ID NO: 423; and
   b. the TCR beta chain construct comprises a variable region having at least 80% sequence identity to or 100% sequence identity to SEQ ID NO: 426.

69. The nucleic acid of any one of the embodiments in paragraphs 1-5 and 68, wherein
   a. the TCR alpha chain construct comprises
      i. a CDR1 of SEQ ID NO: 415,
      ii. a CDR2 of SEQ ID NO: 416, and
      iii. a CDR3 of SEQ ID NO: 417; and
   b. the TCR beta chain construct comprises
      i. a CDR1 of SEQ ID NO: 418,
      ii. a CDR2 of SEQ ID NO: 419, and
      iii. a CDR3 of SEQ ID NO: 420.

70. The nucleic acid of any one of the embodiments in paragraphs 1-5, wherein
   a. the TCR alpha chain construct comprises a variable region having at least 80% sequence identity to or 100% sequence identity to SEQ ID NO: 542; and
   b. the TCR beta chain construct comprises a variable region having at least 80% sequence identity to or 100% sequence identity to SEQ ID NO: 543.

71. The nucleic acid of any one of the embodiments in paragraphs 1-5 and 70, wherein
   a. the TCR alpha chain construct comprises
      i. a CDR1 of SEQ ID NO: 532,
      ii. a CDR2 of SEQ ID NO: 533, and
      iii. a CDR3 of SEQ ID NO: 534; and
   b. the TCR beta chain construct comprises
      i. a CDR1 of SEQ ID NO: 535,
      ii. a CDR2 of SEQ ID NO: 536, and
      iii. a CDR3 of SEQ ID NO: 537.
72. The nucleic acid of any one of the embodiments in paragraphs 1-5, wherein
   a. the TCR alpha chain construct comprises a variable region having at least 80% sequence identity to or 100% sequence identity to SEQ ID NO: 555; and
   b. the TCR beta chain construct comprises a variable region having at least 80% sequence identity to or 100% sequence identity to SEQ ID NO: 556.
73. The nucleic acid of any one of the embodiments in paragraphs 1-5 and 72, wherein
   a. the TCR alpha chain construct comprises
      i. a CDR1 of SEQ ID NO: 545,
      ii. a CDR2 of SEQ ID NO: 546, and
      iii. a CDR3 of SEQ ID NO: 547; and
   b. the TCR beta chain construct comprises
      i. a CDR1 of SEQ ID NO: 548,
      ii. a CDR2 of SEQ ID NO: 549, and
      iii. a CDR3 of SEQ ID NO: 550.
74. The nucleic acid of any one of the embodiments in paragraphs 1-5, wherein
   a. the TCR alpha chain construct comprises a variable region having at least 80% sequence identity to or 100% sequence identity to SEQ ID NO: 568; and
   b. the TCR beta chain construct comprises a variable region having at least 80% sequence identity to or 100% sequence identity to SEQ ID NO: 569.
75. The nucleic acid of any one of the embodiments in paragraphs 1-5 and 74, wherein
   a. the TCR alpha chain construct comprises
      i. a CDR1 of SEQ ID NO: 558,
      ii. a CDR2 of SEQ ID NO: 559, and
      iii. a CDR3 of SEQ ID NO: 560; and
   b. the TCR beta chain construct comprises
      i. a CDR1 of SEQ ID NO: 561,
      ii. a CDR2 of SEQ ID NO: 562, and
      iii. a CDR3 of SEQ ID NO: 563.
76. A nucleic acid encoding at least one T cell receptor (TCR) comprising a TCR alpha chain construct and/or TCR beta chain construct capable of specifically binding to an epitope from TMPRSS2:ERG in complex with a human MHC, wherein the TCR alpha chain construct and/or the TCR beta chain construct comprises a complementarity determining region 3 (CDR3) having at least 90% sequence identity to an amino acid sequence selected from SEQ ID NO: 144 and SEQ ID NO: 147.
77. A nucleic acid encoding at least one T cell receptor (TCR) comprising a TCR alpha chain construct and/or TCR beta chain construct capable of specifically binding to an epitope from TMPRSS2:ERG in complex with a human MHC, wherein the epitope from TMPRSS2:ERG comprises a region having at least 90% sequence identity to amino acid sequence SEQ ID NO: 156.
78. The nucleic acid of the embodiment in paragraph 76 or 77, wherein the TCR alpha chain construct comprises a variable region having at least 80% sequence identity to or 100% sequence identity to SEQ ID NO: 150.
79. The nucleic acid of the embodiment in paragraph 76 or 77, wherein the TCR beta chain construct comprises a variable region having at least 80% sequence identity to or 100% sequence identity to SEQ ID NO: 153.
80. The nucleic acid of any one of the embodiments in paragraphs 76-80, wherein the TCR alpha chain construct and/or the TCR beta chain construct comprises a complementarity determining region 1 (CDR1) having at least 90% sequence identity to or 100% sequence identity to SEQ ID NO: 142 or SEQ ID NO: 145 respectively.
81. The nucleic acid of any one of the embodiments in paragraphs 76-80, wherein the TCR alpha chain construct and/or the TCR beta chain construct comprises a complementarity determining region 2 (CDR2) having at least 90% sequence identity to or 100% sequence identity to SEQ ID NO: 143 or SEQ ID NO: 146.
82. The nucleic acid of any one of the embodiments in paragraphs 76-81, wherein
   a. the TCR alpha chain construct comprises a variable region having at least 80% sequence identity to or 100% sequence identity to SEQ ID NO: 150; and
   b. the TCR beta chain construct comprises a variable region having at least 80% sequence identity to or 100% sequence identity to SEQ ID NO: 153.
83. The nucleic acid of any one of the embodiments in paragraphs 76-82, wherein
   a. the TCR alpha chain construct comprises
      i. a CDR1 of SEQ ID NO: 142,
      ii. a CDR2 of SEQ ID NO: 143, and
      iii. a CDR3 of SEQ ID NO: 144; and
   b. the TCR beta chain construct comprises
      i. a CDR1 of SEQ ID NO: 145,
      ii. a CDR2 of SEQ ID NO: 146, and
      iii. a CDR3 of SEQ ID NO: 147.
84. A nucleic acid encoding at least one T cell receptor (TCR) comprising a TCR alpha chain construct and/or TCR beta chain construct capable of specifically binding to an epitope from GATA3 in complex with a human MHC, wherein the TCR alpha chain construct and/or the TCR beta chain construct comprises a complementarity determining region 3 (CDR3) having at least 90% sequence identity to or 100% sequence identity to an amino acid sequence selected from SEQ ID NOs: 129, 132, 191, 194, 206 and 209.
85. A nucleic acid encoding at least one T cell receptor (TCR) capable of specifically binding to a mutant GATA3 peptide in complex with a protein encoded by an HLA allele of a subject with cancer, wherein the TCR comprises
   a. a TCR alpha chain construct and/or
   b. a TCR beta chain construct.
86. A recombinant nucleic acid, or a cell comprising a recombinant nucleic acid, wherein the nucleic acid encodes a T cell receptor (TCR) comprising a TCR alpha chain construct and/or a TCR beta chain construct, wherein the TCR
   a. specifically binds to a mutant GATA3 peptide in complex with an HLA-A02:01, HLA-B07:02 or HLA-B08:01 protein;
   b. comprises an alpha chain complementarity determining region 3 (CDR3) having at least 90% sequence identity to or 100% sequence identity to SEQ ID NOs: 129, 132, 191, 194, 206 or 209; and/or c. specifically binds to a mutant GATA3 peptide comprising a region with at least 70% sequence identity to or 100% sequence identity to SEQ ID NO: 141, 203 or 218.

87. A nucleic acid encoding at least one T cell receptor (TCR) comprising a TCR alpha chain construct and/or TCR beta chain construct capable of specifically binding to an epitope from GATA3 in complex with a human MHC, wherein the epitope from GATA3 comprises a region having at least 90% sequence identity to or 100% sequence identity to amino acid sequence SEQ ID NO: 141, 203 or 218.

88. The nucleic acid of any one of the embodiments in paragraphs 84-87, wherein the TCR alpha chain construct comprises a variable region having at least 80% sequence identity to or 100% sequence identity to SEQ ID NO: 135, 197 or 212.

89. The nucleic acid of any one of the embodiments in paragraphs 84-87, wherein the TCR beta chain construct comprises a variable region having at least 80% sequence identity to or 100% sequence identity to SEQ ID NO: 138, 200 or 215.

90. The nucleic acid of any one of the embodiments in paragraphs 84-87, wherein the TCR alpha chain construct and/or the TCR beta chain construct comprises a complementarity determining region 1 (CDR1) having at least 90% sequence identity to or 100% sequence identity to an amino acid sequence selected from SEQ ID NOs: 127, 130, 189, 192, 204 and 207.

91. The nucleic acid of any one of the embodiments in paragraphs 84-87, wherein the TCR alpha chain construct and/or the TCR beta chain construct comprises a complementarity determining region 2 (CDR2) having at least 90% sequence identity to or 100% sequence identity to an amino acid sequence selected from SEQ ID NOs: 128, 131, 190, 193, 205 and 208.

92. The nucleic acid of any one of the embodiments in paragraphs 84-87, wherein
   a. the TCR alpha chain construct comprises a variable region having at least 80% sequence identity to SEQ ID NO: 135; and
   b. the TCR beta chain construct comprises a variable region having at least 80% sequence identity to SEQ ID NO: 138.

93. The nucleic acid of embodiment in paragraph 86, wherein
   a. the TCR alpha chain construct comprises
      i. a CDR1 of SEQ ID NO: 127,
      ii. a CDR2 of SEQ ID NO: 128, and
      iii. a CDR3 of SEQ ID NO: 129; and
   b. the TCR beta chain construct comprises
      i. a CDR1 of SEQ ID NO: 130,
      ii. a CDR2 of SEQ ID NO: 131, and
      iii. a CDR3 of SEQ ID NO: 132.

94. The nucleic acid of any one of the embodiments in paragraphs 84-87, wherein
   a. the TCR alpha chain construct comprises a variable region having at least 80% sequence identity to or 100% sequence identity to SEQ ID NO: 197; and
   b. the TCR beta chain construct comprises a variable region having at least 80% sequence identity to or 100% sequence identity to SEQ ID NO: 200.

95. The nucleic acid of the embodiment in paragraph 94, wherein
   a. the TCR alpha chain construct comprises
      i. a CDR1 of SEQ ID NO: 189,
      ii. a CDR2 of SEQ ID NO: 190, and
      iii. a CDR3 of SEQ ID NO: 191; and
   b. the TCR beta chain construct comprises
      i. a CDR1 of SEQ ID NO: 192,
      ii. a CDR2 of SEQ ID NO: 193, and
      iii. a CDR3 of SEQ ID NO: 194.

96. The nucleic acid of any one of the embodiments in paragraphs 78-85, wherein
   a. the TCR alpha chain construct comprises a variable region having at least 80% sequence identity to or 100% sequence identity to SEQ ID NO: 212; and
   b. the TCR beta chain construct comprises a variable region having at least 80% sequence identity to or 100% sequence identity to SEQ ID NO: 215.

97. The nucleic acid of the embodiment in paragraph 90, wherein
   a. the TCR alpha chain construct comprises
      i. a CDR1 of SEQ ID NO: 204,
      ii. a CDR2 of SEQ ID NO: 205, and
      iii. a CDR3 of SEQ ID NO: 206; and
   b. the TCR beta chain construct comprises
      i. a CDR1 of SEQ ID NO: 207,
      ii. a CDR2 of SEQ ID NO: 208, and
      iii. a CDR3 of SEQ ID NO: 209.

98. A nucleic acid encoding at least one T cell receptor (TCR) comprising a TCR alpha chain construct and/or TCR beta chain construct capable of specifically binding to an epitope from BTK in complex with a human MHC, wherein the TCR alpha chain construct comprises a complementarity determining region 3 (CDR3) having at least 90% sequence identity to or 100% sequence identity to an amino acid sequence selected from SEQ ID NO: 161 and SEQ ID NO: 176, or wherein the TCR beta chain construct comprises a complementarity determining region 3 (CDR3) having at least 90% sequence identity to or 100% sequence identity to an amino acid sequence selected from SEQ ID NO: 164 and SEQ ID NO: 179.

99. A nucleic acid encoding at least one T cell receptor (TCR) capable of specifically binding to a mutant BTK peptide in complex with a protein encoded by an HLA allele of a subject with cancer, wherein the TCR comprises
   (a) a TCR alpha chain construct and/or
   (b) a TCR beta chain construct.

100. A recombinant nucleic acid, or a cell comprising a recombinant nucleic acid, wherein the nucleic acid encodes a T cell receptor (TCR) comprising a TCR alpha chain construct and/or a TCR beta chain construct, wherein the TCR
   a. specifically binds to a mutant BTK peptide in complex with an HLA-A02:01 protein;
   b. comprises a complementarity determining region 3 (CDR3) having at least 90% sequence identity to or 100% sequence identity to SEQ ID NO: 161, 164, 176, or 179; and/or
   c. specifically binds to a mutant BTK peptide comprising a region with at least 70% sequence identity to or 100% sequence identity to SEQ ID NO: 173 or 188.

101. A nucleic acid encoding at least one T cell receptor (TCR) comprising a TCR alpha chain construct and/or TCR beta chain construct capable of specifically binding to an epitope from BTK in complex with a human MHC, wherein the epitope from BTK comprises a region having at least 90% sequence identity to or 100% sequence identity to amino acid sequence SEQ ID NO: 173 or 188.

102. The nucleic acid of any one of the embodiments in paragraphs 98-101, wherein the TCR alpha chain construct comprises a variable region having at least 80% sequence identity to or 100% sequence identity to SEQ ID NO: 167 or 182.

103. The nucleic acid of any one of the embodiments in paragraphs 98-102, wherein the TCR beta chain construct comprises a variable region having at least 80% sequence identity to or 100% sequence identity to SEQ ID NO: 170 or 185.

104. The nucleic acid of any one of the embodiments in paragraphs 98-103, wherein the TCR alpha chain construct and/or the TCR beta chain construct comprises a complementarity determining region 1 (CDR1) having at least 90% sequence identity to or 100% sequence identity to an amino acid sequence selected from SEQ ID NOs: 159, 162, 174, and 177.

105. The nucleic acid of any one of the embodiments in paragraphs 98-104, wherein the TCR alpha chain construct and/or the TCR beta chain construct comprises a complementarity determining region 2 (CDR2) having at least 90% sequence identity to or 100% sequence identity to an amino acid sequence selected from SEQ ID NOs: 160, 163, 175 and 178.

106. The nucleic acid of any one of the embodiments in paragraphs 98-105, wherein
 a. the TCR alpha chain construct comprises a variable region having at least 80% sequence identity to or 100% sequence identity to SEQ ID NO: 167 or 182; and
 b. the TCR beta chain construct comprises a variable region having at least 80% sequence identity to or 100% sequence identity to SEQ ID NO: 170 or 185.

107. The nucleic acid of any one of the embodiments in paragraphs 98-106, wherein
 a. the TCR alpha chain construct comprises
  i. a CDR1 of SEQ ID NO: 159 or 174,
  ii. a CDR2 of SEQ ID NO: 160 or 175, and
  iii. a CDR3 of SEQ ID NO: 161 or 176; and
 b. the TCR beta chain construct comprises
  i. a CDR1 of SEQ ID NO: 162 or 177,
  ii. a CDR2 of SEQ ID NO: 163 or 178, and
  iii. a CDR3 of SEQ ID NO: 164 or 179.

108. A nucleic acid encoding at least one T cell receptor (TCR) comprising a TCR alpha chain construct and/or TCR beta chain construct capable of specifically binding to an epitope from EGFR in complex with a human MHC, wherein the TCR alpha chain construct comprises a complementarity determining region 3 (CDR3) having at least 90% sequence identity to or 100% sequence identity to an amino acid sequence selected from SEQ ID NO: 449, SEQ ID NO: 466, SEQ ID NO: 483, SEQ ID NO: 500, and SEQ ID NO: 517, or wherein the TCR beta chain construct comprises a complementarity determining region 3 (CDR3) having at least 90% sequence identity to or 100% sequence identity to an amino acid sequence selected from SEQ ID NO: 452, SEQ ID NO: 469, SEQ ID NO: 486, SEQ ID NO: 503, and SEQ ID NO: 520.

109. A nucleic acid encoding at least one T cell receptor (TCR) capable of specifically binding to a mutant EGFR peptide in complex with a protein encoded by an HLA allele of a subject with cancer, wherein the TCR comprises
 a. a TCR alpha chain construct and/or
 b. a TCR beta chain construct.

110. A recombinant nucleic acid, or a cell comprising a recombinant nucleic acid, wherein the nucleic acid encodes a T cell receptor (TCR) comprising a TCR alpha chain construct and/or a TCR beta chain construct, wherein the TCR
 a. specifically binds to a mutant EGFR peptide in complex with an HLA-A02:01 protein;
 b. comprises a complementarity determining region 3 (CDR3) having at least 90% sequence identity to or 100% sequence identity to SEQ ID NO: 449, 466, 483, 500, 517, 452, 469, 486, 503, or 520; and/or
 c. specifically binds to a mutant EGFR peptide comprising a region with at least 70% sequence identity to or 100% sequence identity to SEQ ID NO: 461, 462, 463, 478, 479, 480, 495, 496, 497, 512, 513, 514, 529, 530 or 531.

111. A nucleic acid encoding at least one T cell receptor (TCR) comprising a TCR alpha chain construct and/or TCR beta chain construct capable of specifically binding to an epitope from EGFR in complex with a human MHC, wherein the epitope from EGFR comprises a region having at least 90% sequence identity to or 100% sequence identity to amino acid sequence SEQ ID NO: 461, 462, 463, 478, 479, 480, 495, 496, 497, 512, 513, 514, 529, 530 or 531.

112. The nucleic acid of any one of the embodiments in paragraphs 108-111, wherein the TCR alpha chain construct comprises a variable region having at least 80% sequence identity to or 100% sequence identity to SEQ ID NO: 455, 472, 489, 506 or 526.

113. The nucleic acid of any one of the embodiments in paragraphs 108-112, wherein the TCR beta chain construct comprises a variable region having at least 80% sequence identity to or 100% sequence identity to SEQ ID NO: 458, 475, 492, 509, or 526.

114. The nucleic acid of any one of the embodiments in paragraphs 108-113, wherein the TCR alpha chain construct and/or the TCR beta chain construct comprises a complementarity determining region 1 (CDR1) having at least 90% sequence identity to or 100% sequence identity to an amino acid sequence selected from SEQ ID NOs: 447, 464, 481, 498, 515, 450, 467, 484, 501, and 518.

115. The nucleic acid of any one of the embodiments in paragraphs 108-114, wherein the TCR alpha chain construct and/or the TCR beta chain construct comprises a complementarity determining region 2 (CDR2) having at least 90% sequence identity to or 100% sequence identity to an amino acid sequence selected from SEQ ID NOs: 448, 465, 482, 499, 516, 451, 468, 485, 502, and 519.

116. The nucleic acid of any one of the embodiments in paragraphs 108-115, wherein
 a. the TCR alpha chain construct comprises a variable region having at least 80% sequence identity to or 100% sequence identity to SEQ ID NO: 455, 472, 489, 506, or 523; and
 b. the TCR beta chain construct comprises a variable region having at least 80% sequence identity to SEQ ID NO: 458, 475, 492, 509 or 526.

117. The nucleic acid of any one of the embodiments in paragraphs 108-116, wherein
   a. the TCR alpha chain construct comprises
      i. a CDR1 of SEQ ID NO: 447, 464, 481, 498 or 515,
      ii. a CDR2 of SEQ ID NO: 448, 465, 482, 499 or 516, and
      iii. a CDR3 of SEQ ID NO: 449, 466, 483, 500 or 517; and
   b. the TCR beta chain construct comprises
      i. a CDR1 of SEQ ID NO: 450, 467, 484, 501 or 518,
      ii. a CDR2 of SEQ ID NO: 451, 468, 485, 502, or 519, and
      iii. a CDR3 of SEQ ID NO: 452, 469, 486, 503, or 520.
118. The nucleic acid of any one of the embodiments in paragraphs 1-117, wherein the epitope comprises a mutation selected from the group consisting of a point mutation, a splice-site mutation, a frameshift mutation, a read-through mutation, a resistance mutation, a gene fusion mutation and any combination thereof
119. The nucleic acid of any one of the embodiments 1-69, wherein the human MHC is encoded by either HLA-A02:01 allele, or HLA-A03:01 allele or HLA-A11:01 allele.
120. The nucleic acid of any one of the embodiments in paragraphs 1-69, wherein the epitope comprises a point mutation.
121. The nucleic acid of the embodiment in paragraph 120, wherein the point mutation is a G12V mutation.
122. The nucleic acid of the embodiment in paragraph 120, wherein the point mutation is a G12C mutation.
123. The nucleic acid of the embodiment in paragraph 120, wherein the point mutation is a G12D mutation.
124. The nucleic acid of any one of the embodiments in paragraphs 76-83, wherein the human MHC is encoded by HLA-A02:01 allele.
125. The nucleic acid of any one of the embodiments in paragraphs 76-83 and 124, wherein the epitope comprises a gene fusion mutation.
126. The nucleic acid of any one of the embodiments in paragraphs 84-97, wherein the human MHC is encoded by HLA-A02:01, HLA-B07:02 or HLA-B08:01 allele.
127. The nucleic acid of any one of the embodiments in paragraphs 84-97 and 126, wherein the epitope comprises a frameshift mutation.
128. The nucleic acid of any one of the embodiments in paragraphs 98-107, wherein the human MHC is encoded by HLA-A02:01 allele.
129. The nucleic acid of any one of the embodiments in paragraphs 98-107 and 128, wherein the epitope comprises a point mutation.
130. The nucleic acid of the embodiment in paragraph 129, wherein the point mutation is C481S mutation.
131. The nucleic acid of any one of the embodiments in paragraphs 108-117, wherein the human MHC is encoded by HLA-A02:01 allele.
132. The nucleic acid of any one of the embodiments in paragraphs 108-117, wherein the epitope comprises a point mutation.
133. The nucleic acid of embodiment in paragraph 132, wherein the point mutation is T790M.
134. The nucleic acid of any one of the embodiments in paragraphs 1-130, wherein the epitope has a length of at least 8 amino acids.
135. The nucleic acid of any one of the embodiments in paragraphs 1-134, wherein the epitope has a length of at least 16 amino acids.
136. The nucleic acid of any one of the embodiments 1-135, wherein the epitope has a length of from 8-25 amino acids.
137. The nucleic acid of any one of the embodiments 1-136, wherein the epitope has a length of from 8-12 amino acids.
138. The nucleic acid of any one of the embodiments in paragraphs 1-136, wherein the epitope has a length of from 16-25 amino acids.
139. The nucleic acid of any one of the embodiments in paragraphs 1-136, wherein the epitope has a length of 7, 8, 9, 10, 11, 12, 13, 14, 15, 16, 17, 18, 19, 20, 21, 22, 23, 24, or 25 amino acids.
140. The nucleic acid of any one of the embodiments in paragraphs 1-139, wherein the epitope binds to the human MHC with a greater affinity than a corresponding wild-type epitope.
141. The nucleic acid of any one of the embodiments in paragraphs 1-140, wherein the epitope binds to the human MHC with a $K_D$ or an $IC_{50}$ less than 500 nM, 250 nM, 150 nM, 100 nM, 50 nM, 25 nM or 10 nM.
142. The nucleic acid of any one of the embodiments 108-141, wherein the mutation is not present in non-cancer cells of a subject.
143. The nucleic acid of any one of the embodiments in paragraphs 1-142, wherein the epitope is encoded by a gene or an expressed gene of a subject's cancer cells.
144. The nucleic acid of any one of the embodiments in paragraphs 1-143, wherein the TCR binds to a MHC-peptide complex with a $K_D$ or an $IC_{50}$ of less than 500 nM, 250 nM, 150 nM, 100 nM, 50 nM, 25 nM or 10 nM.
145. The nucleic acid of any one of the embodiments in paragraphs 1-144, wherein the nucleic acid is operably linked to a promoter.
146. A vector comprising the nucleic acid of any one of the embodiments in paragraphs 1-145.
147. The vector of the embodiment in paragraph 146, wherein the vector is a self-amplifying RNA replicon, plasmid, phage, transposon, cosmid, virus, or virion.
148. The vector of the embodiment in paragraphs 146 or 147, wherein the vector is a viral vector.
149. The vector of the embodiment in paragraph 148, wherein the vector is derived from a retrovirus, lentivirus, adenovirus, adeno-associated virus, herpes virus, pox virus, alpha virus, vaccinia virus, hepatitis B virus, human papillomavirus or a pseudotype thereof.
150. The vector of the embodiment in paragraphs 146 or 147, wherein the vector is a non-viral vector.
151. The vector of the embodiment in paragraph 150, wherein the non-viral vector is a nanoparticle, a cationic lipid, a cationic polymer, a metallic nanopolymer, a nanorod, a liposome, a micelle, a microbubble, a cell-penetrating peptide, or a liposphere.
152. A protein encoded by the nucleic acid of any one of the embodiments in paragraphs 1-145.
153. A cell comprising the nucleic acid of any one embodiments in paragraphs 1-149, the vector of any one of the embodiments 144-149, or the protein of embodiment 146.
154. The cell of the embodiment 153, wherein the cell is a CD4$^+$ T cell.
155. The cell of the embodiment 153, wherein the cell is a CD8$^+$ T cell.
156. The cell of the embodiment 153, wherein the cell is an autologous cell.

157. The cell of the embodiment 153, wherein the cell is an allogeneic cell.
158. The cell of the embodiment 153, wherein the cell is a natural killer cell, a B cell, or an immortalized cell line.
159. The cell of any one of the embodiments in paragraphs 153-156, wherein the cell is a human cell.
160. A pharmaceutical composition comprising the nucleic acid of any one of the embodiments in paragraphs 1-143, the vector of any one of the embodiments in paragraphs 146-151, the protein of embodiment in paragraph 152, or the cell of any one of the embodiments in paragraphs 153-159; and a pharmaceutically acceptable excipient or diluent.
161. The pharmaceutical composition of the embodiment in paragraphs 160, further comprising an immunomodulatory agent or an adjuvant.
162. The pharmaceutical composition of the embodiment in paragraph 161, wherein the immunomodulatory agent is a cytokine.
163. The pharmaceutical composition of any one of the embodiments in paragraphs 160-162 wherein the adjuvant is poly I:C.
164. The pharmaceutical composition of any one of the embodiments in paragraphs 160-163, for use in treating an immune disease or cancer.
165. Use of the pharmaceutical composition of any one of the embodiments in paragraphs 160-164, for treating an immune disease or cancer.
166. Use of the nucleic acid of any one of the embodiments in paragraphs 1-145, the vector of any one of the embodiments in paragraphs 146-151, the protein of embodiment in paragraph 152, or the cell of any one of the embodiments 153-159, for manufacture of a medicament for treating an immune disease or cancer.
167. The use of the embodiment in paragraph 166, wherein the medicament is an adoptive T cell therapy or a TCR gene therapy.
168. A method of treating a subject with a disease or condition, comprising administering to the subject the pharmaceutical composition of any one of the embodiments in paragraphs 160-164.
169. A method of treating a subject with cancer comprising administering to the subject the pharmaceutical composition of any one of the embodiments in paragraphs 160-164.
170. A method of treating a subject with cancer comprising administering to the subject the pharmaceutical composition of any one of the embodiments in paragraphs 160-164; wherein the subject is identified as expressing or expresses a protein encoded by an HLA-A02:01 allele, an HLA-B07:02, an HLA-B08:01, an HLA-A03:01 allele, an HLA-A11:01 allele, an HLA-A03:02 allele, an HLA-A30:01 allele, an HLA-A31:01 allele, an HLA-A33:01 allele, an HLA-A33:03 allele, an HLA-A68:01 allele, or an HLA-A74:01 allele of the subject's genome.
171. A method of treating a subject with cancer comprising administering a TCR or T cell expressing the TCR to the subject, wherein the TCR specifically binds to a mutant RAS peptide in complex with a protein encoded by an HLA-A02:01, an HLA-A03:01 allele, an HLA-A11:01 allele, an HLA-A03:02 allele, an HLA-A30:01 allele, an HLA-A31:01 allele, an HLA-A33:01 allele, an HLA-A33:03 allele, an HLA-A68:01 allele, or an HLA-A74:01; wherein the subject is identified as expressing or expresses a protein encoded by an HLA-A03:01 allele, an HLA-A11:01 allele, an HLA-A03:02 allele, an HLA-A30:01 allele, an HLA-A31:01 allele, an HLA-A33:01 allele, an HLA-A33:03 allele, an HLA-A68:01 allele, or an HLA-A74:01 allele, wherein the subject expresses the HLA allele.
172. A method of treating a subject with cancer comprising administering to the subject the pharmaceutical composition of any one of the embodiments in paragraphs 154-158; wherein the TCR binds to a mutant RAS peptide comprising a mutation at G12 in complex with an HLA-A02:01. an HLA-A03:01 allele, an HLA-A11:01 allele, an HLA-A03:02 allele, an HLA-A30:01 allele, an HLA-A31:01 allele, an HLA-A33:01 allele, an HLA-A33:03 allele, an HLA-A68:01 allele, or an HLA-A74:01; wherein the subject is identified as expressing a protein encoded by an HLA-A03:01 allele, an HLA-A11:01 allele, an HLA-A03:02 allele, an HLA-A30:01 allele, an HLA-A31:01 allele, an HLA-A33:01 allele, an HLA-A33:03 allele, an HLA-A68:01 allele, or an HLA-A74:01 allele.
173. A method of treating a subject with cancer comprising administering to the subject a composition comprising a T cell receptor (TCR) specific for a mutant GATA3 peptide in complex with an HLA protein; wherein the mutant GATA3 peptide comprises at least one mutant amino acid and is fragment of at least 8 contiguous amino acids of a mutant GATA3 protein arising from a mutation in a GATA3 gene of a cancer cell; wherein the mutant GATA3 peptide binds to a protein encoded by an HLA-A02:01, HLA-B07:02 or HLA-B08:01 allele.
174. A method of treating a subject with cancer comprising administering to the subject a composition comprising a T cell receptor (TCR) specific for a mutant GATA3 peptide in complex with an HLA protein; wherein the mutant GATA3 peptide comprises one or more mutant GATA3 amino acids encoded by a GATA3 neoORF sequence, wherein the mutant GATA3 peptide binds to a protein encoded by an HLA-A02:01, HLA-B07:02 or HLA-B08:01 allele.
175. A method of treating a subject with cancer comprising administering a TCR or T cell expressing the TCR to the subject; wherein the TCR specifically binds to a mutant GATA3 peptide in complex with a protein encoded by an HLA-A02:01, HLA-B07:02 or HLA-B08:01 allele; wherein the subject is identified as expressing or expresses a protein encoded by an HLA-A02:01, HLA-B07:02 or HLA-B08:01 allele.
176. A method of treating a subject with cancer comprising administering to the subject a composition comprising a T cell receptor (TCR) specific for a mutant TMPRSS2:ERG peptide in complex with an HLA protein; wherein the mutant TMPRSS2:ERG peptide comprises at least one mutant amino acid and is a fragment of a TMPRSS2:ERG gene fusion mutation; wherein the mutant TMPRSS2:ERG peptide binds to a protein encoded by an HLA-A02:01 allele.
177. A method of treating a subject with cancer comprising administering to the subject a composition comprising a T cell receptor (TCR) specific for a mutant BTK peptide in complex with an HLA protein; wherein the mutant BTK peptide comprises at least one mutant amino acid; wherein the mutant BTK peptide binds to a protein encoded by an HLA-A02:01 allele.
178. A method of treating a subject with cancer comprising administering to the subject a composition comprising a T cell receptor (TCR) specific for a mutant BTK peptide in complex with an HLA protein; wherein the mutant BTK peptide comprises a resistance mutation or a point mutation; wherein the mutant BTK peptide binds to a protein encoded by an HLA-A02:01 allele.

179. A method of treating a subject with cancer comprising administering to the subject a composition comprising a T cell receptor (TCR) specific for a mutant BTK peptide in complex with an HLA protein; wherein the mutant BTK peptide comprises a C481S mutation; wherein the mutant BTK peptide binds to a protein encoded by an HLA-A02:01 allele.

180. A method of treating a subject with cancer comprising administering to the subject a composition comprising a T cell receptor (TCR) or a T cell expressing the TCR to the subject, wherein the TCR specifically binds to a mutant EGFR peptide in complex with a protein encoded by an HLA-A02:01;
wherein the mutant EGFR peptide comprises a resistance mutation or a point mutation, wherein the subject is identified as expressing or expresses a protein encoded by an HLA-A02:01 allele.

181. The method of embodiment in paragraph 178, wherein the mutant EGFR peptide comprises a T790M mutation.

182. A method of preventing resistance to a cancer therapy, the method comprising administering to a subject in need thereof the pharmaceutical composition of any one of the embodiments in paragraph 160-164.

183. A method of inducing an immune response, the method comprising administering to a subject in need thereof the pharmaceutical composition of any one of the embodiments in paragraphs 160-164.

184. A method of identifying a subject with cancer as a candidate for a therapeutic, the method comprising identifying the subject as a subject that expresses a protein encoded by an HLA-A02:01 allele, an HLA-A03:01 allele, an HLA-A11:01 allele, an HLA-A03:02 allele, an HLA-A30:01 allele, an HLA-A31:01 allele, an HLA-A33:01 allele, an HLA-A33:03 allele, an HLA-A68:01 allele, or an HLA-A74:01 allele, wherein the therapeutic is the pharmaceutical composition of any one of the embodiments in paragraphs 160-164.

185. A method of identifying a subject with cancer as a candidate for a therapeutic, the method comprising identifying the subject as one that expresses a protein encoded by an HLA-A02:01, HLA-B07:02 or HLA-B08:01 allele, wherein the therapeutic comprises a T cell receptor (TCR) specific for a mutant GATA3 peptide in complex with an HLA protein; wherein the mutant GATA3 peptide comprises at least one mutant amino acid and is fragment of at least 8 contiguous amino acids of a mutant GATA3 protein arising from a mutation in a GATA3 gene of a cancer cell; wherein the mutant GATA3 peptide binds to a protein encoded by an HLA-A02:01, HLA-B07:02 or HLA-B08:01 allele.

186. A method of identifying a subject with cancer as a candidate for a therapeutic, the method comprising identifying the subject as one that expresses a protein encoded by an HLA-A03:01 allele, an HLA-A11:01 allele, an HLA-A03:02 allele, an HLA-A30:01 allele, an HLA-A31:01 allele, an HLA-A33:01 allele, an HLA-A33:03 allele, an HLA-A68:01 allele, or an HLA-A74:01 allele, wherein the therapeutic comprises a T cell receptor (TCR) specific for a mutant RAS peptide comprising a mutation at G12 in complex with an HLA protein; wherein the mutant RAS peptide binds to a protein encoded by an HLA-A03:01 allele, an HLA-A11:01 allele, an HLA-A03:02 allele, an HLA-A30:01 allele, an HLA-A31:01 allele, an HLA-A33:01 allele, an HLA-A33:03 allele, an HLA-A68:01 allele, or an HLA-A74:01 allele.

187. A method of identifying a subject with cancer as a candidate for a therapeutic, the method comprising identifying the subject as one that expresses a protein encoded by an HLA-A02:01 allele, wherein the therapeutic comprises a T cell receptor (TCR) specific for a mutant TMPRSS2:ERG peptide in complex with an HLA protein; wherein the mutant TMPRSS2:ERG peptide comprises at least one mutant amino acid and is a fragment of a TMPRSS2:ERG gene fusion mutation; wherein the mutant TMPRSS2:ERG peptide binds to a protein encoded by an HLA-A02:01 allele.

188. A method of identifying a subject with cancer as a candidate for a therapeutic, the method comprising identifying the subject as one that expresses a protein encoded by an HLA-A02:01 allele, wherein the therapeutic comprises a T cell receptor (TCR) specific for a mutant BTK peptide in complex with an HLA protein; wherein the mutant BTK peptide comprises at least one mutant amino acid; wherein the mutant BTK peptide binds to a protein encoded by an HLA-A02:01 allele.

189. A method of identifying a subject with cancer as a candidate for a therapeutic, the method comprising identifying the subject as one that expresses a protein encoded by an HLA-A02:01 allele, wherein the therapeutic a T cell receptor (TCR) specific for a mutant BTK peptide in complex with an HLA protein; wherein the mutant BTK peptide comprises a resistance mutation or a point mutation; wherein the mutant BTK peptide binds to a protein encoded by an HLA-A02:01 allele.

190. A method of identifying a subject with cancer as a candidate for a therapeutic, the method comprising identifying the subject as one that expresses a protein encoded by an HLA-A02:01 allele, wherein the therapeutic a T cell receptor (TCR) specific for a mutant BTK peptide in complex with an HLA protein; wherein the mutant BTK peptide comprises a C481S mutation; wherein the mutant BTK peptide binds to a protein encoded by an HLA-A02:01 allele.

191. A method of identifying a subject with cancer as a candidate for a therapeutic, the method comprising identifying the subject as one that expresses a protein encoded by an HLA-A02:01 allele, wherein the therapeutic comprises a T cell receptor (TCR) specific for a mutant EGFR peptide in complex with an HLA protein; wherein the mutant EGFR peptide comprises at least one mutant amino acid T790M; wherein the mutant EGFR peptide binds to a protein encoded by an HLA-A02:01 allele.

192. The method of any one of the embodiments in paragraphs 162-185, wherein the cancer is selected from the group consisting of breast cancer, lung cancer, non-small cell lung cancer, pancreatic cancer, colorectal cancer, uterine cancer, melanoma, ovarian cancer, prostate cancer, endometrial cancer, chronic lymphocytic leukemia (CLL) and liver cancer.

193. The method of any one of the embodiments in paragraphs 162-185, wherein the subject has a breast cancer that is resistant to anti-estrogen therapy, is an MSI breast cancer, is a metastatic breast cancer, is a Her2 negative breast cancer, is a Her2 positive breast cancer, is an ER negative breast cancer, is an ER positive breast cancer is a recurrent breast cancer, is a metastatic breast cancer, or any combination thereof.

194. The method of the embodiment 193, wherein the breast cancer expresses an estrogen receptor with a mutation.
195. The method of any one of the embodiments in paragraphs 169-191, wherein the subject has a breast cancer that is resistant to anti-estrogen therapy.
196. The method of the embodiment in paragraph 195, wherein the breast cancer expresses an estrogen receptor with a mutation.
197. The method of any one of the embodiments in paragraphs 169-196, wherein the subject has a CLL that is resistant to ibrutinib therapy.
198. The method of the embodiment in paragraph 197, wherein the CLL expresses a Bruton tyrosine kinase (BTK) with a mutation, such as a C481S mutation.
199. The method of any one of the embodiments in paragraph 169-197, wherein the subject has a lung cancer that is resistant to a tyrosine kinase inhibitor.
200. The method of the embodiment in paragraphs 199, wherein the lung cancer expresses an epidermal growth factor receptor (EGFR) with a mutation, such as a T790M, L792F, or C797S mutation.
201. The method of any one of the embodiments in paragraphs 169-200, further comprising administering at least one additional therapeutic agent or modality.
202. The method of any one of the embodiments in paragraphs in paragraphs 168-200, wherein an immune response is elicited in the subject.
203. The method of the embodiment in paragraph 200, wherein the immune response is a humoral response.
204. The method of the embodiment in paragraph 200, wherein the immune response is a cytotoxic T cell response.
205. The method of any one of the embodiments in paragraphs 168-204, further comprising administering at least one additional therapeutic agent or modality.
206. The method of the embodiment in paragraphs 205, wherein the at least one additional therapeutic agent or modality is surgery, a checkpoint inhibitor, an antibody or fragment thereof, a chemotherapeutic agent, radiation, a vaccine, a small molecule, a T cell, a vector, and APC, a polynucleotide, an oncolytic virus or any combination thereof 207. The method of the embodiment in paragraph 206, wherein the at least one additional therapeutic agent is an anti-PD-1 agent and anti-PD-L1 agent, an anti-CTLA-4 agent, or an anti-CD40 agent.
208. The method of the embodiment in paragraph 206 or 207, wherein the additional therapeutic agent is administered before, simultaneously, or after administering the pharmaceutical composition of any one of the embodiments 160-164.
209. The method of any one of the embodiments in paragraphs 169-183, or any one of the embodiments in paragraphs 201-208 wherein administering comprises administering subcutaneously or intravenously.
210. The method of any one of the embodiments in paragraphs 169-209, wherein the subject is a subject that has had disease progression following endocrine therapy in combination with a CDK 4/6 inhibitor.
211. A method comprising:
    a. identifying neoantigen-specific T cells from a sample comprising a population of T cells;
    b. identifying one or more peptides of a peptide-MHC complex that are presented by an antigen presenting cell (APC);
    c. identifying a variable sequence of a T cell receptor (TCR) from the neoantigen-specific T cells;
    d. expressing a recombinant TCR comprising the variable sequence of the TCR identified in a TCR cell; and
    e. performing a functional assay, wherein the functional assay comprises contacting the TCR cell to a peptide-MHC complex comprising a peptide of the one or more peptides identified.
212. The method of the embodiment in paragraph 211, wherein the method comprises obtaining the sample comprising the population of cells comprising the neoantigen-specific T cells.
213. The method of the embodiment in paragraph 212, wherein obtaining the sample comprises obtaining a T cell sample from a healthy subject or from a subject with cancer.
214. The method of the embodiment in paragraph 213, wherein the T cell sample is from a healthy donor.
215. The method of the embodiment in paragraph 213 or 214, wherein the T cell sample is a peripheral blood mononuclear cell (PBMC) sample.
216. The method of any one of the embodiments in paragraphs 211-215, wherein identifying neoantigen-specific T cells comprises contacting the population of T cells to at least one peptide-MHC multimer complex comprising a neoantigen peptide.
217. The method of any one of the embodiments in paragraphs 205-209, wherein identifying neoantigen-specific T cells comprises contacting the population of T cells to a peptide-MHC complex comprising a neoantigen peptide.
218. The method of the embodiment in paragraph 211, wherein identifying neoantigen-specific T cells comprises contacting the population of T cells to an APC comprising the peptide-MHC complex.
219. The method of any one of the embodiments in paragraphs 216-218, wherein identifying neoantigen-specific T cells further comprises isolating T cells of the T cell population specific to the peptide-MHC complex.
220. The method of any one of the embodiments 216-218, wherein identifying neoantigen-specific T cells further comprises identifying or predicting T cells of the of the T cell population specific to the peptide-MHC complex based on TCR clonality.
221. The method of the embodiment in paragraphs 220, wherein identifying a variable sequence of a TCR from the neoantigen-specific T cells is performed before identifying neoantigen-specific T cells.
222. The method of any one of the embodiments in paragraphs 211-221, wherein identifying a variable sequence of a TCR from the neoantigen-specific T cells comprises sequencing DNA, RNA, or amplified products thereof from one or more neoantigen-specific T cells that encode the variable sequence.
223. The method of any one of the embodiments in paragraphs 211-222, wherein identifying a variable sequence of a TCR from the neoantigen-specific T cells comprises sequencing DNA, RNA, or amplified products thereof from a single neoantigen-specific T cell that encodes the variable sequence.
224. The method of any one of the embodiments in paragraphs 215-223, wherein identifying a variable sequence of a TCR from the neoantigen-specific T cells comprises sequencing barcoded DNA or barcoded RNA, or amplified products thereof, from one or more neoantigen-specific T cells that encode the variable sequence.

225. The method of any one of the embodiments in paragraphs 221-224, wherein identifying a variable sequence of a TCR from the neoantigen-specific T cells comprises pairing a TCR-alpha chain with a TCR-beta chain.
226. The method of any one of the embodiments in paragraphs 211-225, wherein expressing a recombinant TCR comprises expressing the variable sequence identified from a polynucleotide comprising a sequence encoding the variable sequence identified.
227. The method of the embodiment in paragraph 226, wherein the polynucleotide is a vector.
228. The method of the embodiment in paragraph 227, wherein the vector is a viral vector.
229. The method of the embodiment in paragraph 228, wherein the viral vector is a lentiviral vector.
230. The method of any one of the embodiments in paragraphs 226-229, wherein expressing a recombinant TCR comprises transducing or transfecting the polynucleotide into cells.
231. The method of embodiment in paragraph 230, wherein the cells are a T cell line or healthy donor PMBCs.
232. The method of any one of the embodiments in paragraphs 211-231, wherein identifying one or more peptides of a peptide-MHC complex that are presented by an APC comprises expressing the one or more peptides in cells.
233. The method of any one of the embodiments in paragraphs 211-231, wherein identifying one or more peptides of a peptide-MHC complex that are presented by an APC comprises loading the one or more peptides onto MHCs of cells.
234. The method of any one of the embodiments in paragraphs 211-233, wherein identifying one or more peptides of a peptide-MHC complex that are presented by an APC comprises eluting or isolating a peptide of the one or more peptides from a peptide MHC complex.
235. The method of any one of the embodiments in paragraphs 211-234, wherein identifying one or more peptides of a peptide-MHC complex that are presented by an APC comprises performing mass spectrometry on a peptide of the one or more peptides that was isolated or eluted from a peptide-MHC complex.
236. The method of any one of the embodiments in paragraphs 211-235, wherein performing a functional assay comprises determining expression of one or more cell markers.
237. The method of embodiment in paragraph 236, the one or more cell markers comprise TNF-α, IFN-γ, LAMP-1, 4-1BB, IL-2, IL-17A, Granzyme B, PD-1, CD25, CD69, TIM3, LAG3, CTLA-4, CD62L, CD45RA, CD45RO, FoxP3, or any combination thereof.

What is claimed is:

1. A recombinant nucleic acid encoding a T cell receptor (TCR) comprising a TCR beta chain construct comprising a beta chain complementarity determining region 1 (CDR1), a beta chain complementarity determining region 2 (CDR2), and a beta chain complementarity determining region 3 (CDR3); and a TCR alpha chain construct comprising an alpha chain CDR1, an alpha chain CDR2, and an alpha chain CDR3, wherein the beta chain CDR1 has an amino acid sequence set forth in SEQ ID NO: 50; the beta chain CDR2 has an amino acid sequence set forth in SEQ ID NO: 51; the beta chain CDR3 has an amino acid sequence as set forth in SEQ ID NO: 52; the alpha chain CDR1 has an amino acid sequence as set forth in SEQ ID NO: 47; the alpha chain CDR2 has an amino acid sequence as set forth in SEQ ID NO: 48; and the alpha chain CDR3 has an amino acid sequence as set forth in SEQ ID NO: 49, wherein the TCR specifically binds to a mutated RAS epitope in complex with a human MHC encoded by an HLA-A11:01 allele, wherein the mutated RAS epitope has a sequence set forth in SEQ ID NOs: 45 or 46, and wherein the recombinant nucleic acid is comprised in a vector.

2. The recombinant nucleic acid of claim 1, wherein the TCR beta chain construct comprises a variable region having an amino acid sequence with at least 80% sequence identity to an amino acid sequence as set forth in SEQ ID NO: 58.

3. The recombinant nucleic acid of claim 2, wherein the TCR beta chain construct comprises a variable region having an amino acid sequence as set forth in SEQ ID NO: 58.

4. The recombinant nucleic acid of claim 1, wherein the TCR alpha chain construct comprises a variable region having an amino acid sequence with at least 80% sequence identity to an amino acid sequence as set forth in SEQ ID NO: 55.

5. The recombinant nucleic acid of claim 4, wherein, the TCR alpha chain construct comprises a variable region having an amino acid sequence as set forth in SEQ ID NO: 55.

6. The recombinant nucleic acid of claim 1, wherein the TCR beta chain construct comprises an amino acid sequence with at least 80% sequence identity to an amino acid sequence as set forth in SEQ ID NO: 60.

7. The recombinant nucleic acid of claim 1, wherein the TCR alpha chain construct comprises an amino acid sequence with at least 80% sequence identity to an amino acid sequence as set forth in SEQ ID NO: 59.

8. The recombinant nucleic acid of claim 1, wherein the TCR comprises a TCR beta chain construct having an amino acid sequence as set forth in SEQ ID NO: 60 and a TCR alpha chain construct having an amino acid sequence as set forth in SEQ ID NO: 59.

9. A cell comprising the recombinant nucleic acid of claim 1.

10. The recombinant nucleic acid of claim 1, wherein the recombinant nucleic acid is operably linked to a promoter.

11. A recombinant nucleic acid encoding a TCR construct comprising:
   a TCR beta chain construct comprising a beta chain complementarity determining region 1 (CDR1), a beta chain complementarity determining region 2 (CDR2), and a beta chain complementarity determining region 3 (CDR3), and
   a TCR alpha chain construct comprising an alpha chain CDR1, an alpha chain CDR2, and an alpha chain CDR3, wherein:
      (a) the beta chain CDR1 has an amino acid sequence set forth in SEQ ID NO: 66, the beta chain CDR2 has an amino acid sequence set forth in SEQ ID NO: 67, the beta chain CDR3 has an amino acid sequence set forth in SEQ ID NO: 68, the alpha chain CDR1 has an amino acid sequence as set forth in SEQ ID NO: 63, the alpha chain CDR2 has an amino acid sequence as set forth in SEQ ID NO: 64, and the alpha chain CDR3 has an amino acid sequence as set forth in SEQ ID NO: 65; or
      (b) the beta chain CDR1 has an amino acid sequence set forth in SEQ ID NO: 82, the beta chain CDR2 has an amino acid sequence set forth in SEQ ID NO: 83, the beta chain CDR3 has an amino acid sequence set forth in SEQ ID NO: 84, the alpha chain CDR1 has an amino acid sequence as set forth in SEQ ID NO: 79, the alpha chain CDR2 has an amino acid sequence as set forth in SEQ ID NO: 80, and the alpha chain CDR3 has an amino acid sequence as set forth in SEQ ID NO: 81;
   wherein the TCR construct recognizes and binds to an epitope from human RAS comprising a point mutation G12V, the epitope being in a human MHC-protein complex, wherein a human MHC-protein of the human MHC-protein complex is an HLA antigen encoded by an HLA A03:01 allele, and wherein the epitope comprises a sequence set forth in SEQ ID NOs: 45 or 46.

12. The cell of claim 9, wherein the cell is a T cell.

13. The cell of claim 9, wherein the cell is from a human subject having cancer cells having a RAS G12V mutation.

14. A pharmaceutical composition comprising:
   (a) the cell of claim 9; and
   (b) a pharmaceutically acceptable excipient or diluent.

15. A method of treating cancer in a subject in need thereof comprising administering to the subject the pharmaceutical composition of claim 14.

16. A method of identifying a subject with cancer as a candidate for a therapeutic, the method comprising (a) identifying the subject as a subject that expresses a protein encoded by an HLA-A11:01 allele, and (b) administering the therapeutic, wherein the therapeutic is the pharmaceutical composition of claim 14.

17. The method of claim 15, wherein the cancer is a cancer selected from the group consisting of adenocarcinoma of the biliary tract, transitional cell carcinoma of the bladder, breast carcinoma, cervical adenocarcinoma, colon adenocarcinoma, colon adenoma, neuroblastoma (autonomic ganglia), acute myeloid leukemia, chronic myeloid leukemia, chronic myelomonocytic leukemia, juvenile myelomonocytic leukemia, acute lymphoblastic leukemia, Burkitt's lymphoma, Hodgkin's lymphoma, plasma cell myeloma, hepatocellular carcinoma, large cell carcinoma, non-small cell carcinoma, ductal carcinoma, endocrine tumor, prostate adenocarcinoma, basal cell carcinoma, squamous cell carcinoma, malignant melanoma, angiosarcoma, leiomyosarcoma, liposarcoma, rhabdomyosarcoma, myxoma, malignant fibrous histiocytoma, pleomorphic sarcoma, germinoma, seminoma, anaplastic carcinoma, follicular carcinoma, papillary carcinoma and Hurthle cell carcinoma.

\* \* \* \* \*